United States Patent
Chen et al.

(10) Patent No.: US 12,378,288 B2
(45) Date of Patent: *Aug. 5, 2025

(54) MULTIMERIC BICYCLIC PEPTIDE LIGANDS

(71) Applicant: BicycleTx Limited, Cambridge (GB)

(72) Inventors: Liuhong Chen, Cambridge (GB); Rachid Lani, Cambridge (GB); Kevin McDonnell, Lexington, MA (US); Gemma Mudd, Cambridge (GB); Peter U. Park, Lincoln, MA (US); Punit Upadhyaya, Lexington, MA (US)

(73) Assignee: BicycleTx Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,255

(22) Filed: Nov. 14, 2022

(65) Prior Publication Data

US 2023/0220008 A1 Jul. 13, 2023

Related U.S. Application Data

(62) Division of application No. 17/080,021, filed on Oct. 26, 2020, now Pat. No. 11,542,304, which is a division of application No. 16/282,877, filed on Feb. 22, 2019, now Pat. No. 10,875,894.

(30) Foreign Application Priority Data

| Feb. 23, 2018 | (GB) | ................................... | 1802931.4 |
| Apr. 9, 2018 | (GB) | ................................... | 1805848.7 |
| Nov. 7, 2018 | (GB) | ................................... | 1818158.6 |

(51) Int. Cl.
| A61K 47/64 | (2017.01) |
| A61K 47/59 | (2017.01) |
| A61K 47/60 | (2017.01) |
| A61K 47/66 | (2017.01) |
| A61P 35/00 | (2006.01) |
| C07K 2/00 | (2006.01) |
| C07K 7/08 | (2006.01) |
| C07K 7/64 | (2006.01) |
| C07K 14/705 | (2006.01) |
| C07K 17/02 | (2006.01) |
| C07K 17/14 | (2006.01) |
| A61K 47/54 | (2017.01) |

(52) U.S. Cl.
CPC .............. *C07K 7/08* (2013.01); *A61K 47/59* (2017.08); *A61K 47/60* (2017.08); *A61K 47/64* (2017.08); *A61K 47/66* (2017.08); *A61P 35/00* (2018.01); *C07K 2/00* (2013.01); *C07K 7/64* (2013.01); *C07K 14/70575* (2013.01); *C07K 17/02* (2013.01); *C07K 17/14* (2013.01); A61K 47/54 (2017.08); C07K 2319/00 (2013.01)

(58) Field of Classification Search
CPC ........ C07K 7/08; C07K 7/64; C07K 2319/00; A61K 47/64; A61K 38/10
See application file for complete search history.

(56) References Cited

U.S. PATENT DOCUMENTS

| 2,642,514 | A | 6/1953 | Herkenhoff |
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,595,756 | A | 1/1997 | Bally et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,326,144 | B1 | 12/2001 | Bawendi et al. |
| 6,468,808 | B1 | 10/2002 | Nie et al. |
| 6,552,065 | B2 | 4/2003 | Remiszewski et al. |
| 7,151,047 | B2 | 12/2006 | Chan |
| 7,192,785 | B2 | 3/2007 | Nie et al. |

(Continued)

FOREIGN PATENT DOCUMENTS

| CN | 101497878 A | 5/2009 |
| CN | 105307686 A | 2/2016 |

(Continued)

OTHER PUBLICATIONS

Adams et al., "Big Opportunities for Small Molecules in Immuno-oncology," Nature Reviews, 2015, 14:603-622.

(Continued)

*Primary Examiner* — Lianko G Garyu
*Assistant Examiner* — David Paul Bowles
(74) *Attorney, Agent, or Firm* — Wolf, Greenfield & Sacks, P.C.

(57) ABSTRACT

The present invention relates to multimers of polypeptides which are covalently bound to molecular scaffolds such that two or more peptide loops are subtended between attachment points to the scaffold. The invention also describes the multimerization of polypeptides through various chemical linkers and hinges of various lengths and rigidity using different sites of attachments within polypeptides. In particular, the invention describes multimers of peptides which are high affinity binders and activators of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

29 Claims, 15 Drawing Sheets

Specification includes a Sequence Listing.

(56) References Cited

U.S. PATENT DOCUMENTS

| | | |
|---|---|---|
| 7,390,799 B2 | 6/2008 | Bruncko et al. |
| 8,138,347 B2 | 3/2012 | Adams et al. |
| 8,680,022 B2 | 3/2014 | Gregory et al. |
| 8,685,890 B2 | 4/2014 | Winter et al. |
| 8,778,844 B2 | 7/2014 | Winter et al. |
| 8,906,682 B2 | 12/2014 | June et al. |
| 8,986,655 B2 | 3/2015 | Weiss et al. |
| 9,518,081 B2 | 12/2016 | Winter et al. |
| 9,644,201 B2 | 5/2017 | Winter et al. |
| 9,657,288 B2 | 5/2017 | Winter et al. |
| 9,670,482 B2 | 6/2017 | Winter et al. |
| 9,670,484 B2 | 6/2017 | Winter et al. |
| 9,670,521 B2 | 6/2017 | Grabstein et al. |
| 9,868,767 B2 | 1/2018 | Pei et al. |
| 9,932,367 B2 | 4/2018 | Stace et al. |
| 9,994,617 B2 | 6/2018 | Tite et al. |
| 10,118,947 B2 | 11/2018 | Teufel et al. |
| 10,294,274 B2 | 5/2019 | Teufel et al. |
| 10,441,663 B2 | 10/2019 | Bennett et al. |
| 10,532,106 B2 | 1/2020 | Teufel et al. |
| 10,624,968 B2 | 4/2020 | Bennett et al. |
| 10,626,147 B2 | 4/2020 | Pei et al. |
| 10,792,368 B1 | 10/2020 | Teufel et al. |
| 10,800,813 B2 | 10/2020 | Tite et al. |
| 10,857,196 B2 | 12/2020 | Beswick et al. |
| 10,870,679 B2 | 12/2020 | Teufel et al. |
| 10,875,894 B2 | 12/2020 | Chen et al. |
| 10,894,808 B2 | 1/2021 | Teufel et al. |
| 10,899,798 B2 | 1/2021 | Bennett et al. |
| 10,919,937 B2 | 2/2021 | Beswick et al. |
| 10,994,019 B2 | 5/2021 | Teufel et al. |
| 11,103,591 B2 | 8/2021 | Teufel et al. |
| 11,180,531 B2 | 11/2021 | Beswick et al. |
| 11,484,602 B2 | 1/2022 | Chen et al. |
| 11,261,214 B2 | 3/2022 | Chen et al. |
| 11,306,123 B2 | 4/2022 | Mudd et al. |
| 11,312,749 B2 | 4/2022 | Mudd et al. |
| 11,332,500 B2 | 5/2022 | Mudd et al. |
| 11,396,530 B2 | 7/2022 | Beswick et al. |
| 11,241,473 B2 | 8/2022 | Beswick et al. |
| 11,414,488 B2 | 8/2022 | Bennett et al. |
| 11,433,137 B2 | 9/2022 | Bennett et al. |
| 11,453,702 B2 | 9/2022 | Beswick et al. |
| 11,453,703 B2 | 9/2022 | Keen et al. |
| 11,542,304 B2 | 3/2023 | Chen et al. |
| 11,613,560 B2 | 3/2023 | Stephen et al. |
| 11,746,126 B2 | 5/2023 | Bennett et al. |
| 11,672,868 B2 | 6/2023 | Teufel et al. |
| 11,730,819 B2 | 8/2023 | Teufel et al. |
| 11,623,012 B2 | 11/2023 | Chen et al. |
| 11,696,956 B2 | 11/2023 | Chen et al. |
| 11,814,447 B2 | 11/2023 | Teufel et al. |
| 11,833,211 B2 | 12/2023 | Chen et al. |
| 11,912,792 B2 | 2/2024 | Beswick et al. |
| 11,946,041 B2 | 4/2024 | Chen et al. |
| 11,970,553 B2 | 4/2024 | Mudd et al. |
| 12,049,520 B2 | 7/2024 | Chen et al. |
| 2002/0164788 A1 | 11/2002 | Ellis et al. |
| 2005/0169931 A1 | 8/2005 | Kinch |
| 2009/0222937 A1 | 3/2009 | Arnould et al. |
| 2009/0304721 A1 | 10/2009 | Kinch et al. |
| 2012/0101253 A1 | 4/2012 | Heinis et al. |
| 2012/0172235 A1 | 5/2012 | Winter et al. |
| 2013/0064791 A1 | 3/2013 | Poelstra et al. |
| 2013/0072598 A1 | 3/2013 | Yang et al. |
| 2014/0249292 A1 | 9/2014 | Tite et al. |
| 2014/0274759 A1 | 9/2014 | Walker et al. |
| 2014/0256596 A1 | 11/2014 | Tite et al. |
| 2014/0163201 A1 | 12/2014 | Winter et al. |
| 2015/0087810 A1 | 3/2015 | Moore et al. |
| 2015/0038434 A1 | 5/2015 | Yang et al. |
| 2016/0046721 A1 | 2/2016 | Qian et al. |
| 2016/0031939 A1 | 4/2016 | Stace et al. |
| 2016/0122430 A1 | 5/2016 | Gish et al. |
| 2016/0256579 A1 | 8/2016 | Shalom |
| 2016/0326232 A1 | 10/2016 | Rosa et al. |
| 2017/0067045 A1 | 3/2017 | Winter et al. |
| 2017/0190743 A1 | 7/2017 | Pei et al. |
| 2017/0204150 A1 | 7/2017 | Liu et al. |
| 2017/0304342 A1 | 10/2017 | Cox et al. |
| 2017/0306032 A1 | 10/2017 | Gehlsen |
| 2017/0360952 A1 | 12/2017 | Schwartz et al. |
| 2018/0280525 A1 | 4/2018 | Teufel et al. |
| 2018/0169254 A1 | 6/2018 | Bennett et al. |
| 2018/0200378 A1 | 7/2018 | Bennett et al. |
| 2018/0318451 A1 | 8/2018 | Skerra et al. |
| 2018/0311300 A1 | 11/2018 | Beswick et al. |
| 2018/0362585 A1 | 12/2018 | Teufel et al. |
| 2018/0371020 A1 | 12/2018 | Bennett et al. |
| 2019/0134213 A1 | 5/2019 | Teufel et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389906 A1 | 12/2019 | Beswick et al. |
| 2019/0389907 A1 | 12/2019 | Teufel et al. |
| 2020/0129630 A1 | 4/2020 | Koehler et al. |
| 2020/0131228 A1 | 4/2020 | Beswick et al. |
| 2020/0171161 A1 | 4/2020 | Teufel et al. |
| 2020/0190213 A1 | 6/2020 | Preyer et al. |
| 2020/0215199 A1 | 7/2020 | Bennett et al. |
| 2020/0255477 A1 | 8/2020 | Chen et al. |
| 2020/0289657 A1 | 9/2020 | Teufel et al. |
| 2020/0291096 A1 | 9/2020 | Keen et al. |
| 2020/0283482 A1 | 10/2020 | Keen et al. |
| 2020/0316209 A1 | 10/2020 | Teufel et al. |
| 2020/0338203 A1 | 10/2020 | Chen et al. |
| 2020/0354406 A1 | 11/2020 | Stephen et al. |
| 2020/0354456 A1 | 11/2020 | Bennett et al. |
| 2020/0407709 A1 | 12/2020 | Chen et al. |
| 2021/0040154 A1 | 2/2021 | Mudd et al. |
| 2021/0046145 A1 | 2/2021 | Beswick et al. |
| 2021/0069287 A1 | 3/2021 | Mudd et al. |
| 2021/0079045 A1 | 3/2021 | Bennett et al. |
| 2021/0101932 A1 | 4/2021 | Chen et al. |
| 2021/0101933 A1 | 4/2021 | Chen et al. |
| 2021/0101937 A1 | 4/2021 | Mudd et al. |
| 2021/0122785 A1 | 4/2021 | Teufel et al. |
| 2021/0122804 A1 | 4/2021 | Teufel et al. |
| 2021/0147484 A1 | 5/2021 | Beswick et al. |
| 2021/0147485 A1 | 5/2021 | Teufel et al. |
| 2021/0261620 A1 | 8/2021 | Teufel et al. |
| 2021/0269480 A1 | 9/2021 | Beswick et al. |
| 2021/0299210 A2 | 9/2021 | Keen et al. |
| 2022/0023432 A1 | 1/2022 | Teufel et al. |
| 2022/0024982 A1 | 1/2022 | Chen et al. |
| 2022/0054646 A1 | 2/2022 | Chen et al. |
| 2022/0031858 A1 | 3/2022 | Mcdonnell et al. |
| 2022/0064218 A1 | 3/2022 | Baldassarre et al. |
| 2022/0064221 A1 | 3/2022 | Lani et al. |
| 2022/0088118 A1 | 3/2022 | Baldassarre et al. |
| 2022/0088207 A1 | 3/2022 | Chen et al. |
| 2022/0089643 A1 | 3/2022 | Beswick et al. |
| 2022/0119488 A1 | 4/2022 | Lani et al. |
| 2022/0133732 A1 | 5/2022 | Baldassarre et al. |
| 2022/0133733 A1 | 5/2022 | Baldassarre et al. |
| 2022/0135614 A1 | 5/2022 | Teufel |
| 2022/0184222 A1 | 6/2022 | Bennett et al. |
| 2022/0194983 A1 | 6/2022 | Teufel et al. |
| 2022/0213145 A1 | 7/2022 | Chen et al. |
| 2022/0227811 A1 | 7/2022 | Mudd et al. |
| 2022/0242911 A1 | 8/2022 | Mudd et al. |
| 2022/0257784 A1 | 8/2022 | Upadhyaya et al. |
| 2022/0281918 A1 | 8/2022 | Van Rietschoten et al. |
| 2022/0387611 A1 | 8/2022 | Bennett et al. |
| 2022/0275053 A1 | 9/2022 | Upadhyaya et al. |
| 2022/0289792 A1 | 9/2022 | Chen et al. |
| 2022/0306689 A9 | 9/2022 | Chen et al. |
| 2022/0306694 A1 | 9/2022 | Mudd et al. |
| 2022/0072140 A1 | 10/2022 | Stace et al. |
| 2022/0362390 A1 | 11/2022 | Stace et al. |
| 2023/0002596 A1 | 1/2023 | Zhang et al. |
| 2023/0008076 A1 | 1/2023 | Keen et al. |
| 2023/0025916 A1 | 1/2023 | Bennett et al. |
| 2023/0025971 A1 | 1/2023 | Bennett et al. |

(56) References Cited

U.S. PATENT DOCUMENTS

| | | | |
|---|---|---|---|
| 2023/0165966 A1 | 1/2023 | Koehler et al. |
| 2023/0086865 A1 | 3/2023 | Balmford et al. |
| 2023/0129258 A1 | 4/2023 | Upadhyaya et al. |
| 2023/0106511 A1 | 6/2023 | Balmford et al. |
| 2023/0181749 A1 | 6/2023 | Dickson et al. |
| 2023/0233698 A1 | 7/2023 | Bennett et al. |
| 2023/0287047 A1 | 9/2023 | Beswick et al. |
| 2023/0340020 A1 | 10/2023 | Teufel et al. |
| 2023/0144799 A1 | 11/2023 | Chen et al. |
| 2024/0082410 A1 | 3/2024 | Teufel et al. |
| 2024/0000957 A1 | 4/2024 | Chen et al. |
| 2024/0108738 A1 | 4/2024 | Keen et al. |
| 2024/0158444 A1 | 5/2024 | Bennett et al. |
| 2024/0173422 A1 | 5/2024 | Beswick et al. |
| 2024/0189436 A1 | 6/2024 | Chen et al. |
| 2024/0197897 A1 | 6/2024 | Keen et al. |
| 2024/0240255 A1 | 7/2024 | Blakemore et al. |
| 2024/0325554 A1 | 10/2024 | Keen et al. |
| 2024/0336656 A1 | 10/2024 | Mudd et al. |

FOREIGN PATENT DOCUMENTS

| | | | |
|---|---|---|---|
| EP | 2393520 A1 | 12/2011 |
| EP | 2970954 A1 | 1/2016 |
| EP | 3192802 A1 | 7/2017 |
| FR | 2932189 A1 | 11/2009 |
| GB | 1239978 A | 7/1971 |
| JP | 2006514104 A | 4/2006 |
| JP | 2011513298 A | 4/2011 |
| JP | 2011522794 A | 4/2011 |
| WO | WO9708320 A1 | 6/1997 |
| WO | WO9819705 A1 | 5/1998 |
| WO | WO0128683 A1 | 4/2001 |
| WO | WO0142246 A2 | 6/2001 |
| WO | WO0363794 A2 | 8/2003 |
| WO | WO2004005348 A1 | 1/2004 |
| WO | WO2004019973 A1 | 3/2004 |
| WO | WO0288112 A1 | 8/2004 |
| WO | WO-2004077062 A2 | 9/2004 |
| WO | WO2004089925 A1 | 10/2004 |
| WO | WO2004106328 A1 | 12/2004 |
| WO | WO2005007623 A1 | 1/2005 |
| WO | WO2005103083 A2 | 11/2005 |
| WO | WO2005113554 A2 | 12/2005 |
| WO | WO2006029879 A2 | 3/2006 |
| WO | WO2006078161 A1 | 7/2006 |
| WO | WO2006078846 A1 | 7/2006 |
| WO | WO2006101187 A1 | 9/2006 |
| WO | WO2006105021 A2 | 10/2006 |
| WO | WO2006122806 A2 | 11/2006 |
| WO | WO2007016176 A2 | 2/2007 |
| WO | WO2007044729 A2 | 4/2007 |
| WO | WO2007053452 A1 | 5/2007 |
| WO | WO2007070514 A1 | 6/2007 |
| WO | WO2007005874 A2 | 7/2007 |
| WO | WO2007084786 A1 | 7/2007 |
| WO | WO2007129161 A2 | 11/2007 |
| WO | WO2008033561 A2 | 3/2008 |
| WO | WO2008039218 A2 | 4/2008 |
| WO | WO2008134761 A2 | 6/2008 |
| WO | WO2008089627 A1 | 7/2008 |
| WO | WO2008109943 A1 | 9/2008 |
| WO | WO2008118802 A1 | 10/2008 |
| WO | WO2008132601 A1 | 11/2008 |
| WO | WO2008157490 A1 | 12/2008 |
| WO | WO2009009116 A2 | 1/2009 |
| WO | WO2009044273 A2 | 4/2009 |
| WO | WO2009073620 A2 | 6/2009 |
| WO | WO2009098450 A2 | 8/2009 |
| WO | WO2009114512 A1 | 9/2009 |
| WO | WO2010019570 A2 | 2/2010 |
| WO | WO2010077634 A1 | 7/2010 |
| WO | WO2010089115 A1 | 8/2010 |
| WO | WO2010089117 A1 | 12/2010 |
| WO | WO2011018227 A2 | 2/2011 |
| WO | WO2011028683 A1 | 3/2011 |
| WO | WO2011056652 A1 | 5/2011 |
| WO | WO2011070024 A1 | 6/2011 |
| WO | WO2011079015 A1 | 6/2011 |
| WO | WO2011090760 A1 | 7/2011 |
| WO | WO2011107553 A1 | 9/2011 |
| WO | WO2011109400 A2 | 9/2011 |
| WO | WO2011131407 A1 | 10/2011 |
| WO | WO2011140249 A2 | 11/2011 |
| WO | WO2012032433 A1 | 3/2012 |
| WO | WO-2012057624 A1 | 5/2012 |
| WO | WO2012142237 A1 | 10/2012 |
| WO | WO2012145493 A1 | 10/2012 |
| WO | WO2013050615 A1 | 4/2013 |
| WO | WO2013050617 A1 | 4/2013 |
| WO | WO2013079174 A1 | 6/2013 |
| WO | WO2013087699 A1 | 6/2013 |
| WO | WO2013119716 A1 | 8/2013 |
| WO | WO2013132044 A1 | 9/2013 |
| WO | WO2013050616 A1 | 11/2013 |
| WO | WO2013169264 A1 | 11/2013 |
| WO | WO2014008218 A1 | 1/2014 |
| WO | WO2014036357 A1 | 3/2014 |
| WO | WO2014044872 A1 | 3/2014 |
| WO | WO2014063012 A1 | 4/2014 |
| WO | WO2014142237 A1 | 9/2014 |
| WO | WO2014164693 A2 | 10/2014 |
| WO | WO2014167122 A1 | 10/2014 |
| WO | WO2014190257 A2 | 11/2014 |
| WO | WO2015116904 A1 | 6/2015 |
| WO | WO2015171938 A1 | 11/2015 |
| WO | WO2015179691 A2 | 11/2015 |
| WO | WO2016046574 A1 | 3/2016 |
| WO | WO2016067035 A1 | 5/2016 |
| WO | WO2016050361 A1 | 7/2016 |
| WO | WO2016171242 A1 | 10/2016 |
| WO | WO2016171272 A1 | 10/2016 |
| WO | WO2016174103 A1 | 11/2016 |
| WO | WO2017046658 A1 | 3/2017 |
| WO | WO2017102906 A1 | 6/2017 |
| WO | WO2017161069 A1 | 9/2017 |
| WO | WO2017173408 A1 | 10/2017 |
| WO | WO2017182672 A1 | 10/2017 |
| WO | WO-2017191460 A1 | 11/2017 |
| WO | WO2017205738 A1 | 11/2017 |
| WO | WO2018096365 A1 | 5/2018 |
| WO | WO2018115203 A1 | 6/2018 |
| WO | WO2018115204 A1 | 6/2018 |
| WO | WO2018222987 A1 | 6/2018 |
| WO | WO2018127699 A1 | 7/2018 |
| WO | WO2018156740 A1 | 8/2018 |
| WO | WO2018197509 A1 | 11/2018 |
| WO | WO2018197893 A1 | 11/2018 |
| WO | WO2019002842 A1 | 1/2019 |
| WO | WO-2019/025811 A1 | 2/2019 |
| WO | WO2019034866 A1 | 2/2019 |
| WO | WO2019034868 A1 | 2/2019 |
| WO | WO2019084060 A1 | 2/2019 |
| WO | WO2019094395 A2 | 5/2019 |
| WO | WO2019122860 A1 | 6/2019 |
| WO | WO2019122861 A1 | 6/2019 |
| WO | WO2019122863 A1 | 6/2019 |
| WO | WO-2019162682 A1 | 8/2019 |
| WO | WO-2019193328 A1 | 10/2019 |
| WO | WO2019136442 A1 | 11/2019 |
| WO | WO2019226617 A1 | 11/2019 |
| WO | WO2019243313 A1 | 12/2019 |
| WO | WO2019243329 A1 | 12/2019 |
| WO | WO2019243353 A1 | 12/2019 |
| WO | WO2019243455 A1 | 12/2019 |
| WO | WO2019243832 A1 | 12/2019 |
| WO | WO2019243833 A1 | 12/2019 |
| WO | WO2020084305 A1 | 4/2020 |
| WO | WO2020089627 A1 | 5/2020 |
| WO | WO2020120980 A1 | 6/2020 |
| WO | WO2020120981 A1 | 6/2020 |
| WO | WO2020120983 A1 | 6/2020 |
| WO | WO2020120984 A1 | 6/2020 |
| WO | WO2020128526 A1 | 6/2020 |

(56) References Cited

FOREIGN PATENT DOCUMENTS

| | | |
|---|---|---|
| WO | WO2020128527 A1 | 6/2020 |
| WO | WO2020148525 A1 | 7/2020 |
| WO | WO2020148526 A1 | 7/2020 |
| WO | WO2020148527 A1 | 7/2020 |
| WO | WO2020148528 A1 | 7/2020 |
| WO | WO2020148529 A1 | 7/2020 |
| WO | WO2020148530 A1 | 7/2020 |
| WO | WO2020165600 A1 | 8/2020 |
| WO | WO2020178574 A1 | 9/2020 |
| WO | WO2020201753 A1 | 10/2020 |
| WO | WO2020225577 A1 | 11/2020 |
| WO | WO2020229803 A1 | 11/2020 |
| WO | WO-2021019243 A1 | 2/2021 |
| WO | WO2021019244 A1 | 2/2021 |
| WO | WO2021019245 A1 | 2/2021 |
| WO | WO-2021019246 A1 | 2/2021 |
| WO | WO-2021028686 A1 | 2/2021 |
| WO | WO2021171028 A1 | 2/2021 |
| WO | WO2021171029 A1 | 2/2021 |
| WO | WO2021038232 A1 | 4/2021 |
| WO | WO-2021064428 A1 | 4/2021 |
| WO | WO2021074622 A1 | 4/2021 |
| WO | WO2021074647 A1 | 4/2021 |
| WO | WO2021105694 A1 | 6/2021 |
| WO | WO2021148974 A1 | 7/2021 |
| WO | WO2021234391 A1 | 11/2021 |
| WO | WO2021250418 A1 | 12/2021 |
| WO | WO2022038158 A1 | 2/2022 |
| WO | WO2022148969 A1 | 7/2022 |
| WO | WO2022148974 A2 | 7/2022 |
| WO | WO2022148975 A1 | 7/2022 |
| WO | WO2022148979 A1 | 7/2022 |
| WO | WO2022029420 A1 | 10/2022 |
| WO | WO2023089308 A1 | 5/2023 |
| WO | WO2023031623 A2 | 9/2023 |

OTHER PUBLICATIONS

Adams, "Molecular control of arterial-venous blood vessel identity," Journal of Anatomy, 2003, 202(1):105-112.

Adley et al., "Expression of membrane type 1 matrix metalloproteinase (MMP-14) in epithelial ovarian cancer: high level expression in clear cell carcinoma", Gynecologic oncology, 112(2):319-324.

Akanuma et al., "MicroRNA-133a regulates the mRNAs of two invadopodia-related proteins, FSCN1 and MMP14, in esophageal cancer," Br J Cancer. Jan. 7, 2014;110(1 ), 189-98.

Angelini et al., "Bicyclic peptide inhibitor reveals large contact interface with a protease target." ACS chemical biology 7, No. 5 (2012): 817-821.

Annunziata et al., "Phase 1, open-label study of MED1-547 in patients with relapsed or refractorysolid tumors," Invest New Druas, Feb. 2013, 31(1):77-84.

Anonymous, "Bicycle Conjugates", URL:https://web.archive.org/web/20210104063050/https://www.bicycletherapeutics.com/programs , 2021, 4 pages.

Anonymous, "Bicycle Therapeutics to Present New Translational Research for BT5528 and Preclinical Data for Tumor-targeted Immune Cell Agonists at the AACR Virtual Annual Meeting II," May 15, 2020; 2 pages. URL:https://www.businesswire.com/news/home/20200515005111/en/Bicycle-Therapeutics- to-Present-New-Translational-Research-for-BT5528-and-Preelinical-Data-for-Tumor-targeted-Immune-Cell-Aaon ists-at-the-AACR-Virtual-Ann ual-Meetina-II.

Anonymous, "Constrained Peptides Unconstrained Thinking Forward-Looking Statements", URL: https://investors.bicycletherapeutics.com/static-files/5f7f462f-2417-439d-b829-d723b3fd65f7, Aug. 2019, 26 pages.

Anthony et al., "Recapitulation of IVIG anti-inflammatory activity with a recombinant IgG Fc", Science Apr. 18, 2008;320(5874):373-376.

Arkadash et al., "Development of High Affinity and High Specificity Inhibitors of Matrix Metalloprotcinase 14 through Computational Design and Directed Evolution" J. Biol. Chem. 2017, 292(8), 3481-3495.

Arnon et al., "The mechanisms controlling the recognition of tumor- and virus-infected cells by NKp46", Blood, Jan. 15, 2004;103(2):664-672.

Arnould et al., "Trastuzumab-based treatment of HER2-positive breast cancer: an antibody-dependent cellular cytotoxicity mechanism?", Br J Cancer, 2006, 94(2):259-267.

Askoxylakis et al., "A New Peptide Ligand for Targeting Human Carbonic Anhydrase IX, Identified through the Phage Display Technology", PLoS ONE, Dec. 2010, 5(12):10 pages.

Augoff et al., "Upregulated expression and activation of membrane-associated proteases in esophageal squamous cell carcinoma." Oncology reports, 2014, 31(6):2820-2826.

Ausiello et al., "Functional topography of discrete domains of human CD38," Tissuc Antigens, Dec. 2000, 56(6):539-547.

Baek et al. "Effects of Histidine and Sucrose on the Biophysical Properties of a Monoclonal Antibody," Pharmaceutical Antibody, 2017, 34(3):629-639.

Banerji et al., "A Cancer research UK Phase I/IIA Trail of BT1718 (a first in class Bicycle Drug Conjugate) Given Intravenously in Patients with Advanced Solid Tumours," Journal of Clinical Oncology, Jan. 2018, 36(15):PS2610. (1 Page).

Banerji et al., "Preliminary pharmacokinetic assessment of BT1718: A phase I/IIa trial of BT1718 (a first in class Bicycle Toxin Conjugate) in patients with advanced solid tumours." In european journal of cancer, 2018, 103:E65-e65.

Barbas III et al., "Semisynthetic combinatorial antibody libraries: a chemical solution to the diversity problem," Proceedings of the National Academy of Sciences of the United States of America, May 1992, 89(10):4457-4461.

Barbolina et al., Microenvironmental regulation of membrane type 1 matrix metalloproteinase activity in ovarian carcinoma cells via collagen induced EGR1 expression. Journal of Biological Chemistry, 2007, 282(7):4924-4931.

Bardia et al., "Efficacy and safety of anti-trop-2 antibody drug conjugate sacituzumab govitccan (IMMU-132) in heavily pretreated patients with metastatic triple-negative breast cancer." Journal of Clinical Oncology, 2017, 35(19):2141.

Bech et al., "Chemical Strategies for Half-Life Extension of Biopharmaceuticals: Lipidation and Its Alternatives," ACS Medicinal Chemistry Letters, Jun. 2018, 9(7):577-580.

Bennett et al., "Abstract 4481: BT5528, an EphA2-targeting Bicycle Toxin Conjugate (BTC): Profound efficacy without bleeding and coagulation abnormalities in animal models", Cancer Research, 2019, 79(13 suppl):4481. 2 pages.

Bennett et al., "Abstract 5854: BT5528, a Bicycle Toxin Conjugate targeting EphA2 has potent anti-tumor activity without bleeding or coagulation abnormalities in preclinical models." Cancer Res., 2018, 78(13 suppl):5854.

Bennett et al., "Abstract 5855: Bicycle Drug Conjugates Targeting EphA2 for the Treatment of Solid Tumors: Discovery and Selection of BT5528", Cancer Research, 2018, 78(13 suppl):5855. 2 pages.

Bennett et al., "Development of BT1718, a Bicycle Drug Conjugate® (BDC) targeting MT1-MMP for treatment of solid tumours," European Journal of Cancer, Nov. 2016, 69(1):S21.

Bennett et al., "MMAE Delivery Using the Bicycle Toxin Conjugate BT5528," Mol Cancer Ther., Jul. 2020, 19(7):1385-1394.

Bennett et al., "The Mechanism of Action of BT1718, a Novel Small-Molecule Drug Conjugate for the Treatment of Solid Tumors Expressing MT1-MMP," AACR-NCI-EOrTC International Conference: Molecular Taroets and Cancer Therapeutics, Jan. 2018, 26-30.

Bennett, "BT1718, a Bicycle Drug Conjugate (BTC): Profound Efficacy Without Bleeding and Coaaulation Abnormalities in Animal Models," AACR Annual Meeting 2019, 4481, 2 pages.

Ben-Shmuel et al., "Unleashing Natural Killer Cells in the Tumor Microenvironment—The Next Generation of Immunotherapy?", Front Immunol., 2020, 11:275.

Berenson, "Multiple Myeloma," Merck Manual, Reterived from: https://www.merckmanuals.com/home/blood-disorders/plasma-cell-disorders/multiplemyeloma?query=multiple%20myeloma, Oct. 2022.

(56) References Cited

OTHER PUBLICATIONS

Berge et al., "Pharmaceutical Salts," Journal of Pharmaceutical Sciences, Jan. 1977, 66(1):1-19.
Berkel et al. "Binding of (5 S)-penicilloic acid to penicillin binding protein 3." ACS chemical biology 8, No. 10 (2013): 2112-2116.
Bernhagen et al., "Design, synthesis and characterization of different bicyclic peptides with enhanced binding and selectivity for various integrins", Retrieved form: https://ec.europa.eu/research/participants/documents/downloadPublic?documentIds=080166e5acfd6757&appId=PPGMS, Oct. 14, 2016, XP55622035:1-6.
Beswick, Paul, "Bicycles—An entirely new class of therapeutics," accessed on https://www.bicycletherapeutics.com/wp-content/uploads/RSC-02-May-2019.pdf, 2019, 21 pages.
Bicycle Therapeutics, "Bicycle Therapeutics and Cancer Research UK Announce initiation of First Clinical Study of a Bicyclic Peptide (Bicycle®)," Press Release, Feb. 13, 2018, https://investors.bicycletherapeutics.com/node/6651/pdf.
Bicycle Therapeutics, "Bicycle Therapeutics to Present New BT1718 Data in the "New Drugs on the Horizon" Session at the 2018 American Association for Cancer Rescarch Meeting," Press Release. Apr. 3, 2018.
Bicycle Therapeutics, "Bicycle Therapeutics to Present on BT5528, a Bicycle Toxin Conjugate Targeting EphA2 for the Treatment of Solid Tumors, at World ADC 2019," Business Wire Release. Mar. 5, 2019.
BicycleTx Limited, "Study BT5528-100 in Patients with Advanced Solid Tumors Associated With EphA2 Expression," ClinicalTrials.gov Identifier NCT04180371. First Posted Nov. 27, 2019; Accessed Dec. 30, 2022: https://clinicaltrials.gov/ct2/show/NCT04180371.
Bilsky, Mark H., "Gliomas", Merck Manual (https://www.merckmanuals.com/professional/neurologic-disorders/intracranial-and-spinal-tumors/gliomas), May 2023, 8 pages.
Binda et al., "The EphA2 receptor drives self-renewal and tumorigenicity in stem-like tumor-propagating cells from human glioblastomas," Cancer Cell, Dec. 11, 2012, 22(6):765-780.
Biron et al., "Improving oral bioavailability of peptides by multiple N-methylation: somatostatin analoques," Angewandte Chemie International Edition, 2008, 47(14):2595-2599.
Blank et al., "Absence of Programmed Death Receptor 1 Alters Thymic Development and Enhances Generation of CD4/CD8 Double-Negative TCR-Transgenic T Cells" in Journal of Immunology, Nov. 2003, 171(19):4574-4581.
Bogaerts et al., "Individual patient data analysis to assess modifications to the RECIST criteria." European journal of cancer, 2009, 45(2):248-260.
Bolland et al., "Spontaneous autoimmune disease in Fc(gamma)RIIB-deficient mice results from strain-specific epistasis", Immunity, Aug. 2000, 13(2):277-285.
Booth et al., "Crowd control in the crypt," Nat Med., Dec. 2002, 8(12):1360-1361.
Borghaei et al., "Nivolumab versus docetaxel in advanced nonsquamous non-small-cell lung cancer." New England Journal of Medicine, 2015, 373(17):1627-1639.
Borrelli et al., "Cell Penetrating Peptides as Molecular Carriers for Anti-Cancer Agents," Molecules, Feb. 2018, 23(2):295. (28 pages).
Boruchov et al., "Activating and inhibitory IgG Fc receptors on human DCs mediate opposing functions", The Journal of Clinical Investigation, 2005, 115(10):2914-2923.
Bouchard et al., "Antibody—drug conjugates—a new wave of cancer drugs." Bioorganic & medicinal chemistry letters, 2014, 24(23):5357-5363.
Brahmer et al., "Nivolumab versus docetaxel in advanced squamous-cell non-small-cell lung cancer." New England Journal of Medicine, 2015, 373(2):123-135.
Brannan et al., "EphA2 in the early pathogenesis and progression of non-small cell lung cancer," Cancer Prev Res (Phila)., Dec. 2009, 2(12):1039-1049.
Brantley-Sieders et al., "Eph receptor tyrosine kinases in tumor and tumor microenvironment", Current Pharmaceutical Design, 2004, 10(27):3431-3442.
Brantley-Sieders et al., "Eph/Ephrin Profiling in Human Breast Cancer Reveals Significant Associations between Expression Level and Clinical Outcome", PLOS ONE, 2011, 6(9):e24426.
Brantley-Sieders et al., "Impaired tumor microenvironment in EphA2-deficient mice inhibits tumor anaioaenesis and metastatic oroaression," FASEB J., Nov. 2005, 19(13):1884-1886.
Bristol-Myers Squibb, "An Investigational Immuno-Therapy Study to Investigate the Safety and Effectiveness of Nivolumab, and Nivolumab Combination Therapy in Virus-Associated Tumors—Full Text View—Clinicaltrials." Gov.[(accessed on Jan. 30, 2021)] (2018).
Brown et al., "Blockade of programmed death-1 ligands on dendritic cells enhances T cell activation and cytokine production", Journal of Immunolgy, Feb. 2003, 170(3):1257-1266.
Cabanillas et al., "Phase I study of maytansine using a 3-day schedule," Cancer Treat Rep., Mar. 1978, 62(3):425-428.
Cancer Research UK, "Soft tissue sarcomas," Reterived from: http://aboutcancer.cancerresearchuk.org/about-cancer/soft-tissue-sarcoma, Sep. 2022.
Cancer Research UK, "Triple Negative Breast Cancer," Reterived from: https://www.cancerresearchuk.org/about-cancer/breast-cancer/stages-typcs-grades/types/triplenegative-breast-cancer#, Sep. 2022, 6 pages.
Cancer Research UK, "Types of lung cancer," Reterived form: https://www.cancerresearchuk.org/about-cancer/lung-cancer/stages-types-grades/types#, Sep. 2022.
Cancer Research UK, "Your mouth and cancer drugs," Reterived form: https://www.cancerresearchuk.org/about-cancer/cancer-in-general/treatment/cancer-drugs/sideeffects/your-mouth, Sep. 2022, 5 pages.
Caratelli et al., "FCγ Chimeric Receptor-Engineered T Cells: Methodology, Advantages, Limitations, and Clinical Relevance", Frontiers in Immunology, Apr. 27, 2017, :8:457, 8 pages.
Center for Pancreatic and Biliary Diseases, "Bile Duct Cancer," University of Southern California,Department of Surgery. Rctreived from https://web.arch ive.org/web/20171207023733/http://www.surgery.usc.edu:80/d ivisions/tumor/PancreasDiseases/web%20pages/BILIARY%20SYSTEM/cholangiocarcinoma.html.
Centers for Discase Control and Prevention, "What Can I Do to Reduce My Risk of Ovarian Cancer?", Division of Cancer Prevention and Control, Aug. 31, 2022, 1 page.
Chabner et al., "Initial clinical trials of maytansine, an antitumor plant alkaloid." Cancer Treat Rep., 1978, 62(3):429-433.
Chahinian et al., "Phase I study of weekly maytansine given by iv bolus or 24-hour infusion," Cancer Treat Rep., Nov. 1979, 63(11-12),1953-1960.
Challita-Eid et al., "Enfortumab Vedotin Antibody-Drug Conjugate Targeting Nectin-4 Is a Highly Potent Therapeutic Agent in Multiple Preclinical Cancer Models", Cancer Research, 2016, 76(10):3003-3013.
Chan and Nic, "Quantum dot bioconjugates for ultrasensitive nonisotopic detection," Science, Sep. 25, 1998; 281(5385):2016-2018.
Chandrasekar, "Bladder Cancer," Merck Manual.; Reterived form: https://www.merckmanuals.com/professional/genitourinary-disorders/genitourinary-cancers/bladder-cancer, Sep. 2022.
Chandrasekar, "Prostate Cancer," Merck Manual. Reterived from: https://www.merckmanuals.com/professional/genitourinary-disorders/genitourinary-cancers/prostate-cancer, Sep. 2022.
Chang et al., "Five different anti-prostate-specific membrane antigen (PSMA) antibodies confirm PSMA expression in tumor-associated neovasculature," Cancer Res., Jul. 1, 1999, 59(13):3192-3198.
Chang et al., "Subtiligase: A Tool for Semisynthesis of Proteins", Proc Natl Acad Sci, 1994, 91(26):12544-12548.
Chemnitz et al., "RNA fingerprints provide direct evidence for the inhibitory role of TGFβ and PD-1 on CD4+ T cells in Hodgkin lymphoma", Blood, 2007, 110(9):3226-3233.
Chen and Harrison, "Cell-Penetrating Peptides in Drug Development: Enabling Intracellular Targets," Biochemical Society Transactions, 2007, 35(4):821-825.

(56) References Cited

OTHER PUBLICATIONS

Chen et al., "Association of FCGR3A and FCGR3B copy number variations with systemic lupus erythematosus and rheumatoid arthritis in Taiwanese patients", Arthritis & Rheumatology, 2014, 66(11):3113-3121.
Chen et al., "Structurally diverse cyclisation linkers impose different backbone conformations in bicyclic peptides," Chembiochem., May 7, 2012, 13(7):1032-1038.
Chen et al., "The Bicycle Platform: an Efficient Technology to Generate High Affinity, High Selectivity Molecules (Bicycles®) with Unique Drug Like Properties that are Amenable to Conjugation," URL:https://www.bicycletherapeutics.com/wp-content/uploads/16_PEGS-Bicycle_-30-04-2017-poster.pdf, Apr. 26, 2017, 1 page.
Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology", J Molecular Diagnostics, 2015, 17(3):251-264.
Cheng et al., "Blockade of EphA receptor tyrosine kinase activation inhibits vascular endothelial cell growth factor-induced angiogenesis," Mol Cancer Res., Nov. 2002, 1(1):2-11.
Cherney et al., "Macrocyclic Amino Carboxylates as Selective MMP-8 Inhibitors," Journal of Medicinal Chemistry, May 1998, 41(11):1749-1751.
Chiche et al., "Hypoxia-inducible carbonic anhydrases IX and XII promote tumor cell growth by counteracting acidosis through the regulation of the intracellular pH," Cancer Res., Jan. 1, 2009, 69(1):358-368.
Chinnery et al., "Viral antigen mediated NKp46 activation of NK cells results in tumor rejection via NK-DC crosstalk", Oncoimmunology, 2012, 1(6):874-883.
Christina Chun, "What are the most curable cancers?", Medical news Today (https://www.medicalnewstoday.com/articles/322700 Accessed May, 8, 2020), 2020, 8 pages.
Chung et al., "Bicycle synthesis through peptide macrocyclization using aziridine aldehydes followed by late-stage disulfide bond installation." MedChemComm, 2023, 4(7):1124-1128.
Clarkson et al., "Treatment of refractory immune thrombocytopenic purpura with an anti-Fc gamma-receptor antibody", The New England Journal of Medicine, 1986, 314(19):1236-1239.
Claus et al., "Tumor-targeted 4-1BB agonists for combination with T cell bispecific antibodies as off-the-shelf therapy", Sci Transl Med., Jun. 2019, 11(496):eaav5989. (12 Pages).
ClinicalTrials.gov, identifier NCT02426892, "Nivolumab and HPV-16 Vaccination in Patients with HPV-16 Positive Incurable Solid Tumors," https://clinicaltrials.gov/ct2/show/study/NCT02426892, 8 pages.
Clynes et al., "Inhibitory Fc receptors modulate in vivo cytotoxicity against tumor targets", Nature Medicine, Apr. 2000, 6(4):443-446.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013; EMA/749228/2013.
Connolly et al., "Complexities of TGF-β Targeted Cancer Therapy", Int'l J. Biological Sciences, 2012, 8(7):964-978.
Cook et al., "Pharmacokinetic (PK) Assessment of BT1718: A Phase 1/2a Study of BT1718, a First in Class Bicycle Toxin Conjugate (BTC), in Patients (PTS) with Advanced Solid Tumours," Annals of Oncology 2019; vol. 30, Jan. 2019, p. v174.
Cortes et al., "Phase II study of the halichondrin B analog eribulin mesylate in patients with locally advanced or metastatic breast cancer previously treated with an anthracycline, a taxane, and capecitabine." Journal of Clinical Oncology, 2010, 28(25):3922-3928.
Costello et al., "Defective expression and function of natural killer cell-triggering receptors in patients with acute myeloid leukemia", Blood, 2002, 99(10):3661-3667.
Crameri et al., "Construction and evolution of antibody-phage libraries by DNA shuffling," Nature Medicine, Jan. 1996, 2(1):100-102.

Cui, J. Jean., "A New Challenging and Promising Era of Tyrosine Kinase Inhibitors", ACS Med Chem Lett., 2014, 5(4):272-274.
Curiel et al., "Blockade of B7-H1 improves myeloid dendritic cell-mediated antitumor immunity", In Nature medicine, 2003, 9(5):562-567.
Dagher et al., "c-Kit and CD38 are expressed by long-term reconstituting hematopoietic cells present in the murine yolk sac," Biol Blood Marrow Transplant, 1998, 4(2):69-74.
Davies et al., "Antibody VH Domains as Small Recognition Units," Bio/Technology, May 13, 1995, 13(5):475-479.
Davis et al., "Natural killer cells unleashed: Checkpoint receptor blockade and BiKE/TriKE utilization in NK-mediated anti-tumor immunotherapy", Semin Immunol., 2017, 31:64-75.
Dawson et al., "Synthesis of proteins by native chemical ligation," Science, Nov. 1994, 266(5186):776-779.
De Kruif et al., "Selection and Application of Human Single Chain Fv Antibody Fragments from a Semi-synthetic Phage Antibody Display Library with Designed CDR3 Regions," Journal of Molecular Biology, Apr. 1995, 248(1):97-105.
De la Pena et al., "Expression of the matrix metalloproteases 2, 14, 24, and 25 and tissue inhibitor 3 as potential molecular markers in advanced human gastric cancer." Disease markers 2014 (2014).
Deaglio et al., "CD38 is a signaling molecule in B-cell chronic lymphocytic leukemia cells," Blood, Sep. 15, 2003, 102(6):2146-2155.
Debre et al., "Infusion of Fc gamma fragments for treatment of children with acute immune thrombocytopenic purpura", Lancet, 1993, 342(8877):945-949.
Deonarain et al., "Small-Format Drug Conjugates: A Viable Alternative to ADCs for Solid Tumours?", Antibodies (Basel), 2018, 7(2):16.
Derossi et al., "The third helix of the Antennapedia homeodomain translocates through biological membranes," Journal if Biological Chemistry, Apr. 1994, 269(14):10444-10450.
Deyle et al., "Phage Selection of Cyclic Peptides for Application in Research and Drug Development," Accounts of Chemical Research, 2017, 50(8):1866-1874.
Dharmadhikari, et al., "CD137 and CD137L signals are main drivers of type 1, cell-mediated immune responses." Oncoimmunology, 2016, 5(4):e1113367.
Di, "Strategic Approaches to Optimizing Peptide ADME Properties," AAPS J., Jan. 2015, 17(1):134-143.
Diamantis and Banerji, "Antibody-drug conjugates—an emerging class of cancer treatment." British journal of cancer, 2016, 114(4):362-367.
Diaz-Perlas et al., "Branched BBB-shuttle peptides: chemoselective modification of proteins to enhance blood-brain barrier transport," Chemical Science, Sep. 2018, 9(44):8409-8415.
Dong, et al. "Tumor-associated B7-H1 promotes T-cell apoptosis: a potential mechanism of immune evasion", Nature Medicine, 2002, 8(8):793-800.
Dorfman etal., "Programmed death-1 (PD-1) is a marker of germinal center-associated cells and angioimmunoblastic T-cell lymphoma." The American journal of surgical pathology, Jul. 2006, 30(7):802-810.
Driggers et al., "The exploration of macrocycles for drug discovery—an underexploited structural class," Nature Reviews Drug Discovery, Jul. 2008, 7(7):608-624.
Dubois et al., "New ways to image and target tumour hypoxia and its molecular responses," Radiotherapy and Oncology, Sep. 2015, 116(3):352-357.
Dufort et al, "789: Generation of a Bicycle NK-TICA(TM), a novel NK cell engaging molecule to enhance targeted tumor cytotoxicity", Nov. 10, 2021, 9(Suppl 2):A824-A824. URL:https://jitc.bmj.com/contenl/jitc/9/Suppl_2/A824.full.pdf.
Dunne et al., "EphA2 Expression Is a Key Driver of Migration and Invasion and a Poor Prognostic Marker in Colorectal Cancer," Clin Cancer Res., Jan. 1, 2016, 22(1):230-242.
Duong and Rodan, "The role of integrins in osteoclast function," J Bone Miner Metab., 1999, 17(1):1-6.
Eagan et al., "Early clinical study of an intermittent schedule for maytansine (NSC-153858): brief communication." Journal of the National Cancer Institute, 1978, 60(1):93-96.

(56) References Cited

OTHER PUBLICATIONS

Eder et al., "A phage display derived stabilised bicyclic peptide targeting MMP-14 shows high imaging contrast in small animal PET imaging." In European Journal of Nuclear Medicine and Molecular Imaging, 42:S140-S141.

Eisenhauer et al., "New response evaluation criteria in solid tumours: revised RECIST guideline (version 1.1)." European journal of cancer, 2009, 45(2):228-247.

Ellenrieder et al., "Role of MT-MMPs and MMP-2 in pancreatic cancer progression." International Journal of Cancer, 2000, 85(1):14-20.

Elson-Schwab et al., "Guanidinylated neomycin delivers large, bioactive cargo into cells through a heparan sulfate-dependent pathway." Journal of Biological Chemistry, 2007, 282(18):13585-13591.

Fauriat et al., "Deficient expression of NCR in NK cells from acute myeloid leukemia: Evolution during leukemia treatment and impact of leukemia cells in NCRdull phenotype induction", Blood, 2007, 109(1):323-330.

Fehrenbacher et al., "Atezolizumab versus docetaxel for patients with previously treated non-small-cell lung cancer (POPLAR): a multicentre, open-label, phase 2 randomised controlled trial." The Lancet, 2016, 387(10030):1837-1846.

Felices et al., "Generation of BiKEs and TriKEs to Improve NK Cell-Mediated Targeting of Tumor Cells", Methods Mol Biol., 2016, 1441:333-346.

Felices et al., "Novel CD19-targeted TriKE restores NK cell function and proliferative capacity in CLL", Blood Adv., 2019, 3(6):897-907.

Fiacco et al., "N-Methyl Scanning Mutagenesis Generates Protease-Resistant G Protein Ligands with Improved Affinity and Selectivity," ChemBioChem, Sep. 2008, 9(14):2200-2203.

Figure 3.8 of "Immunobiology: The Immune System in Health and Disease," Garland Science, 2001.

Flaherty et al., "Nonclinical evaluation of GMA161—an antihuman CD16 (FcγRIII). Monoclonal antibody for treatment of autoimmune disorders in CD16 transgenic mice", Toxicological Sciences, 2012, 125(1):299-309.

Forsberg, et al., "CD137 plays both pathogenic and protective roles in type 1 diabetes development in NOD mice." The Journal of Immunology, 2017, 198(10):3857-3868.

Francis et al., "Bone and Soft Tissue Sarcomas: UK Incidence and Survival: 1996-2010," NationalCancer Intelligence Network, Nov. 2013, v2.0.

Fumet et al. "Phase Ib/II trial evaluating the safety, tolerability and immunological activity of durvalumab (MEDI4736) (anti-PD-L1) plus tremelimumab (anti-CTLA-4) combined with FOLFOX in patients with metastatic colorectal cancer." ESMO open, 2018, 3(4):e000375.

Funaro et al., "Human CD38 is associated to distinct molecules which mediate transmembrane signaling in different lineages." European journal of immunology, Oct. 1993, 23(10):2407-2411.

Funaro et al., "Involvement of the multilineage CD38 molecule in a unique pathway of cell activation and proliferation," J Immunol., Oct. 1990, 145(8):2390-2396.

Galsky et al., "Phase I trial of the prostate-specific membrane antigen-directed immunoconjugate MLN2704 in patients with progressive metastatic castration-resistant prostate cancer." Journal of clinical oncology, 2008, 26(13):2147-2154.

Gandhi et al., "MP69-11 Carbonic Anhydrase IX Assay: A Paradigm Shift in Diagnosis of Malignant Cystic Renal Lesions," J Urol., May 18, 2015, 193(4S):e870-e871.

Garcia-Iglesias et al., "Low NKp30, NKp46 and NKG2D expression and reduced cytotoxic activity on NK cells in cervical cancer and precursor lesions", BMC Cancer, Jun. 16, 2009, 9:186, 8 pages.

Gauthier et al., "Multifunctional Natural Killer Cell Engagers Targeting NKp46 Trigger Protective Tumor Immunity", Cell, 2019, 177(7):1701-1713.

Gelb et al., "Abstract 391: Molecular-based enrichment strategy for Nectin-4 targeted Bicycle toxin conjugate BT8009," Cancer Res., Jul. 1, 2021, 81(13 suppl):391 (poster).

Gelb et al., "Abstract A047: MT1-MMP Immunohistochemistry (IHC) analysis of tumor microarrays (TMAs) using a novel scoring system guides patient selection for BT1718 expansion cohorts," In Molecular Cancer Therapeutics, 2019, 18(12_Suppl):A047.

Gen path diagnostics, "Solid Tumors", Accessed on https://genpathdiagnostics.com/patients/oncology/solid-tumors/, Jun. 30, 2023, 4 pages.

Gentilucci et al., "Chemical Modifications Designed to Improve Peptide Stability: Incorporation of Non-Natural Amino Acids, Pseudo-Peptide Bonds, and Cyclization," Current Pharmacetical Design, 2010, 16(28):3185-3203.

Gfeller et al., "Current tools for predicting cancer-specific T cell immunity," Oncoimmunology, 2016, 5(7):e1177691.

Gleason et al., "CD16xCD33 bispecific killer cell engager (BiKE) activates NK cells against primary MDS and MDSC CD33+ targets", Blood, 2014, 123(19):3016-3026.

Gokel et al., "Crown Ethers: Sensors for Ions and Molecular Scaffolds for Materials and Biological Models," Chem. Rev., 2004, 104(5):2723-2750.

Gradishar et al., "Significantly longer progression-free survival with nab-paclitaxel compared with docetaxel as first-line therapy for metastatic breast cancer." J Clin Oncol., 2009, 27(22):3611-3619.

Gresh, "Neuroblastoma," Merck Manual., Reterived form: https://www.msdmanuals.com/en-in/professional/pediatrics/pediatric-cancers/neuroblastoma, Sep. 2022, 4 pages.

Griffiths et al., "Isolation of high affinity human antibodies directly from large synthetic repertoires," EMBO Journal, Jul. 1994, 13(14):3245-3260.

Grisold et al., "Peripheral neuropathies from chemotherapeutics and targeted agents: diagnosis, treatment, and prevention." Neuro-oncology, 2012, 14(suppl_4):iv45-iv54.

Gu et al., "The influence of the penetrating peptide iRGD on the effect of paclitaxel-loaded MT1-AF7p-conjugated nanoparticles on glioma cells." Biomaterials, 2013, 34(21):5138-5148.

Guo ct al., "Prognostic significance of combinations of RNA-dependent protein kinase and EphA2 biomarkers for NSCLC," J Thorac Oncol., Mar. 2013, 8(3):301-308.

Gupta et al., "Intracellular delivery of large molecules and small particles by cell-penetrating proteins and peptides," Advanced Drug Delivery Reviews, Feb. 2005, 57(4):637-651.

Hamanishi et al. "Programmed cell death 1 ligand 1 and tumor-infiltrating CD8+ T lymphocytes are prognostic factors of human ovarian cancer", Proc. Natl. Acad. Sci. USA, 2007, 104(9):3360-3365.

Han et al., "Altered NKp30, NKp46, NKG2D, and DNAM-1 Expression on Circulating NK Cells Is Associated with Tumor Progression in Human Gastric Cancer", Journal of Immunology Research, Sep. 3, 2018, 2018:6248590, 10 pages.

Hanna et al., "Randomized phase III trial of pemetrexed versus docetaxel in patients with non-small-cell lung cancer previously treated with chemotherapy." Journal of clinical oncology, 2004, 22(9):1589-1597.

Harrison et al., "Abstract 5144: BT1718, a novel bicyclic peptide-maytansinoid conjugate targeting MT1-MMP for the treatment of solid tumors: Design of bicyclic peptide and linker selection," Cancer Res., 2017, 77(13 suppl):5144.

Hart, et al., "De novo identification of lipid II binding lipopeptides with antibacterial activity against vancomycin-resistant bacteria." Chemical Science, 2017, 8(12):7991-7997.

Hart, et al., "Cell binding and internalization by filamentous phage displaying a cyclic Arg-Gly-Aspcontaining peptide", J. Biol. Chem., 1994, 269:12468-12474.

Hasmim et al., "Critical Role of Tumor Microenvironment in Shaping NK Cell Functions: Implication of Hypoxic Stress", Frontiers in Immunology, Sep. 23, 2015, 6:482, 9 pages.

He et al., "Matrix metalloproteinase-14 is a negative prognostic marker for patients with gastric cancer." Digestive diseases and sciences, 2013, 58:1264-1270.

(56) References Cited

OTHER PUBLICATIONS

Helft et al., "A phase I study of cantuzumab mertansine administered as a single intravenous infusion once weekly in patients with advanced solid tumors." Clinical cancer research, 2004, 10(13):4363-4368.
Henriques et al., "Functional characterization of peripheral blood dendritic cells and monocytes in systemic lupus erythematosus", Rheumatology International, Apr. 2012, 32(4):863-869.
Herbst et al., "Pembrolizumab versus docetaxel for previously treated, PD-L 1-positive, advanced non-small-cell lung cancer (Keynote-010): a randomised controlled tria", Lancet, Apr. 2016, 387(10027):1540-1550.
Hershman, "Thyroid Cancers," Merck Manual, Reterived from: https://www.merckmanuals.com/professional/endocrine-and-metabolic-disorders/thyroid-disorders/thyroid-cancers, Sep. 2020.
Hess et al., "Backbone Cyclic Peptidomimetic Melanocortin-4 Receptor Agonist as a Novel Orally Administrated Drug Lead for Treating Obesity," Journal of Medicinal Chemistry, Jan. 26, 2008, 51(4):1026-1034.
Hess et al., "Molecular Regulation of Tumor Cell Vasculogenic Mimicry by Tyrosine Phosphorylation: Role of Epithelial Cell Kinasc (Eck/EphA2", Cancer Rescarch, 2001, 61(8):3250-3255.
Hikari et al., "Tags for labeling protein N-termini with subtiligase for proteomics", Bioorganic & Medicinal Chemistry Letters, Nov. 2008, 18 (22):6000-6003.
Hill et al: "Constraining Cyclic Peptides to Mimic Protein Structure Motifs". Angewandte Chemie International Edition, Nov. 24, 2014, 53(48):13020-13041.
Hinner et al., "Tumor-Localized Costimulatory T-Cell Engagement by the 4-1BB/HER2 Bispecific Antibody-Anticalin Fusion PRS-343", Clinical Cancer Research, Oct. 2019, 23(19):5878-5889.
Hirano et al. "Blockade of B7-H1 and PD-1 by monoclonal antibodies potentiates cancer therapeutic immunity," Cancer Research, 2005, 65(3):1089-1096.
Hoogenboom et al., "By-passing immunisation. Human antibodies from synthetic repertoires of germline VH gene segments rearranged in vitro," Journal of Molecular Biology, Sep. 1992, 227(2):381-388.
Hoshino et al., "Mapping of the catalytic and epitopic sites of human CD38/NAD+ glycohydrolase to a functional domain in the carboxvl terminus," J Immunol., Jan. 15, 1997, 158(2):741-747.
Hsu et al., "Efficacy of plasmin-treated intravenous gamma-globulin for therapy of Kawasaki syndrome", The Pediatric Infectious Disease Journal, Jun. 1993, 12(6):509-512.
Hu-Lieskovan and Ribas, "New Combination Strategies Using Programmed Cell Death 1/Programmed Cell Death Ligand 1 Checkpoint Inhibitors as a Backbone," Cancer J., Jan./Feb. 2017, 23(1):10-22.
Hurov et al., "BT7480, a novel fully synthetic tumor-targeted immune cell agonist (TICA™) induces tumor localized CD137 agonism", Retrieved from the Internet: URL: https://www.bicycletherapeutics.com/wp-content/uploads/2020-06-16-BT7480-AACR-2020-poster-P5552_Final_CD137-in-title-002.pdf, Jun. 20, 2020, 1 page.
Ide et al., "A novel method for artificial lipid-bilayer formation," Biosensors and Bioelectronics, 2005, 21(4):672-677.
Inman et al., "PD-L1 (B7-H1) expression by urothelial carcinoma of the bladder and BCG-induced granulomata: associations with localized stage progression", Cancer, 2007, 109(8):1499-1505.
Ip et al., "Atypical localization of membrane type 1-matrix metalloproteinase in the nucleus is associated with aggressive features of hepatocellular carcinoma." Molecular Carcinogenesis: Published in cooperation with the University of Texas MD Anderson Cancer Center, 2007, 46(3):225-230.
Izawa et al., "$H_2O_2$ production within tumor microenvironment inversely correlated with infiltration of CD56(dim) NK cells in gastric and esophageal cancer: possible mechanisms of NK cell dysfunction", Cancer Immunology, Immunotherapy, 2011, 60(12):1801-1810.
Jackson and Stover, "Using the lessons learned from the clinic to improve the preclinical development of antibody drug conjugates." Pharmaceutical research, 2015, 32(11):3458-3469.
Jackson et al., "A human antibody-drug conjugate targeting EphA2 inhibits tumor growth in vivo", Cancer Research, Nov. 15, 2008, 68(22):9367-9374.
Jespers et al., "Selection of optical biosensors from chemisynthetic antibody libraries," Protein Engineering, Design and Selection, Oct. 2004, 17(10):709-713.
Jin et al., "αVβ3 Integrin-Targeted Radionuclide Therapy with 64Cu-cyclam-RAFT-c(-RGDfK-)4," Mol Cancer Ther., Sep. 2016, 15(9):2076-2085.
Johnson et al., "Melanoma-specific MHC-II expression represents a tumour-autonomous phenotype and predicts response to anti-PD-1/PD-L1 therapy", Nature Communications, Jan. 29, 2016, 7:10582(10 pages).
Johnson et al., "Relationships between drug activity in NCI preclinical in vitro and in vivo models and early clinical trials," British Journal of Cancer, 2001, 84(10):1424-1431.
Jones et al., "Randomized phase III study of docetaxel compared with paclitaxel in metastatic breast cancer." Journal of Clinical Oncology, 2005, 23(24):5542-5551.
Jones et al., "Targeting membrane proteins for antibody discovery using phage display," Scientific Reports, May 18, 2016, 6(1):1-11.
Kamat et al., "The clinical relevance of stromal matrix metalloproteinase expression in ovarian cancer." Clinical Cancer Research, 2006, 12(6):1707-1714.
Kamijo et al., "Aberrant CD137 ligand expression induced by GATA6 overexpression promotes tumor progression in cutaneous T-cell lymphoma. " Blood, The Journal of the American Society of Hematology, 2018, 132(18): 1922-1935.
Kanazawa et al., "Non-obese-diabetic mice: immune mechanisms of pancreatic ß-cell destruction," Diabetologia, 1984, 27:113-115.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)." (2016): 5-5.
Kang, et al., "Anti-CD137 suppresses tumor growth by blocking reverse signaling by CD137 ligand." Cancer research, 2017, 77(21):5989-6000.
Keith, "Lung Carcinoma," Merck Manual, Reterived on: https://www.merckmanuals.com/professional/pulmonary-disorders/tumors-of-the- lungs/lung-carcinoma, Sep. 2021, 18 pages.
Kell, Douglas B., "The Transporter-Mediated Cellular Uptake and Efflux of Pharmaceutical Drugs and Biotechnology Projects: How and Why Phospholipid Bilayer Transport is Negligible in Real Biomembranes," Molecules, 2021, 26(5629):40 pages.
Kellog et al., "Disulfide-linked antibody- maytansinoid conjugates: Optimization of in vivo activity by varying the steric hindrance at carbon atoms adjacent to the disulfide linkage." Bioconjugate chemistry, 2011, 22(4):717-727.
Kemp and McNamara, "Conformationally restricted cyclic nonapeptides derived from L-cysteine and LL-3-amino-2- piperidone-6-carboxylic acid (LL-Acp), a potent .beta .- turn-inducing dipeptide analog." J. Org. Chem., 1985, 50(26):5834-5838.
Kerkela et al., "Differential patterns of stromelysin-2 (MMP-10) and MT1-MMP (MMP-14) expression in epithelial skin cancers." British journal of cancer, 2001, 84(5):659-669.
Kessenbrock et al., "Matrix metalloproteinases: regulators of the tumor microenvironment." Cell, 2010, 141(1):52-67.
Khan et al., "Engineering Lipid Bilayer Membranes for Protein Studies," International Journal of Molecular Sciences, Nov. 2013, 14(11):21561-21597.
Kikuchi et al., "Immunohistochemical detection of membrane-type-1-matrix metalloproteinase in colorectal carcinoma." British journal of cancer, 2000, 83(2):215-218.
Kim et al., "Synergistic signals for natural cytotoxicity are required to overcome inhibition by c-Cb1 ubiquitin ligase", Immunity, Feb. 26, 2010, 32(2):175-186.
Kim, et al., "Reverse signaling through the costimulatory ligand CD137L in epithelial cells is essential for natural killer cell-

(56) References Cited

OTHER PUBLICATIONS mediated acute tissue inflammation." Proceedings of the National Academy of Sciences, 2012, 109(1): E13-E22.
Kinch et al., "Predictive Value of the EphA2 Receptor Tyrosine Kinase in Lung Cancer Recurrence and Survival", Clin Cancer Res., 2003, 9(2):613-618.
Kitanaka et al., "CD38 ligation in human B cell progenitors triggers tyrosine phosphorylation of CD19 and association of CD19 with lyn and phosphatidylinositol 3-kinase," J Immunol., 1997, 159(1):184-192.
Kitanaka et al., "CD38-mediated signaling events in murine pro-B cells expressing human CD38 with or without its cytoplasmic domain," J Immunol., Feb. 15, 1999, 162(4):1952-1958.
Kleinau et al., "Induction and suppression of collagen-induced arthritis is dependent on distinct fcgamma receptors", J Exp Med., May 2000, 191(9):1611-1616.
Knight et al., "Three genes for lupus nephritis in NZB x NZW mice," Journal of Experimental Medicine, Jun. 1978, 147(6):1653-1660.
Konishi et al., "B7-H1 Expression on Non-Small Cell Lung Cancer Cells and Its Relationship with Tumor-Infiltrating Lymphocytes and Their PD-1 Expression", Clin Cancer Res., 2004, 10(15):5094-5100.
Konopleva et al., "Ligation of cell surface CD38 protein with agonistic monoclonal antibody induces a cell growth signal in myeloid leukemia cells," J Immunol., Nov. 1, 1998, 161(9):4702-4708.
Koo et al., "Reduction of the CD16-CD56bright NK Cell Subset Precedes NK Cell Dysfunction in Prostate Cancer", PLoS One, 2013, 8(11):e78049, 8 pages.
Kreidieh et al., "Overview, prevention and management of chemotherapy extravasation." World journal of clinical oncology, 2016, 7(1):87.
Krishnamoorthy et al., "Breaking the Permeability Barrier of *Escherichia coli* by Controlled Hyperporination of the Outer Membrane." Antimicrob Agents Chemother, 2016, 60(12):7372-7381.
Krop et al., "Trastuzumab emtansine versus treatment of physician's choice for pretreated HER2-positive advanced breast cancer (TH3RESA): a randomised, open-label, phase 3 trial." The Lancet Oncology, 2014, 15(7):689-699.
Kumagai et al., "Ligation of CD38 suppresses human B lymphopoiesis," J Exp Med., Mar. 1, 1995, 181(3):1101-1110.
Kylväjä, et al., "Penicillin binding protein 3 of *Staphylococcus aureus* NCTC 8325-4 binds and activates human plasminogen." BMC research notes, 2016, 9:1-10.
Landolt et al., "Clear cell renal cell carcinoma is linked to epithelial-to-mesenchymal transition and to fibrosis." Physiological reports, 2017, 5(11):e13305.
Lani et al., "Identification of high affinity, highly selective bicyclic peptides (Bicycles®) to transmembrane proteins using phage display screening on whole cells," Abstract, PEGS Summit, Boston, Massachusetts, May 2017, 1 page.
Lanman et al., "Analytical and Clinical Validation of a Digital Sequencing Panel for Quantitative, Highly Accurate Evaluation of Cell-Free Circulating Tumor DNA", PLoS One, 2015, 10(10):e0140712.
Lau,et al., "A penicillin-binding protein that can promote advanced-generation cephalosporin resistance and genome adaptation in the opportunistic pathogen Pseudomonas aeruginosa." International journal of antimicrobial agents, 55(3):105896.
Laudanski et al., "Increased serum level of membrane type 1-matrix metalloprotcinasc (MT1-MMP/MMP-14) in patients with breast cancer." Folia histochemica et cytobiologica, 2010, 48(1):101-103.
Lea and Simeonov, "Fluorescence polarization assays in small molecule screening," Expert Opinion in Drug Discovery, Jan. 2011, 6(1):17-32.
Lee and Aarhus, "ADP-ribosyl cyclase: an enzyme that cyclizes NAD+ into a calcium-mobilizing metabolite," Cell Regul., Mar. 1991, 2(3):203-209.
Lee et al., "ADP-ribosyl cyclase and CD38. Multi-functional enzymes in Ca+2 signaling," Adv Exp Med Biol., 1997, 419:411-419.

Lee et al., "Structural determination of a cyclic metabolite of NAD+ with intracellular Ca2+-mobilizing activity," J Biol Chem., Jan. 25, 1989, 264(3):1608-1615.
Leighton, "Pharmacology Review: Kadcyla (ado-trastuzumab emtansine)," In Center for Drug Evaluation and Research Application No. 1254270rio1 sOOO., Feb. 2020.
Levi et al., "Characterization of tumor infiltrating Natural Killer cell subset", Oncotarget, May 30, 2015, 6(15):13835-13843.
Levine et al. "Methionine residues as endogenous antioxidants in proteins", PNAS, 1996, 93(26):15036-15040.
Li et al., "Fluorescent Mu selective opioid ligands from a mixture based cyclic peptide library." ACS combinatorial science, 2012, 14(12):673-679.
Li et al., "Targeting the Fc receptor in autoimmune disease", Expert Opinion on Therapeutic Targets, 2014, 18(3):335-350.
Li et al., "The overexpression membrane type 1 matrix metalloproteinase is associated with the progression and prognosis in breast cancer." American Journal of Translational Research, 2015, 7(1):120.
Li et al., "Up-regulation of EphA2 and down-regulation of EphrinA1 are associated with the aggressive phenotype and poor prognosis of malignant glioma", Tomor Biology, 2010, 31(5):477-488.
Li, et al., "A novel strategy for in vitro selection of peptide-drug conjugates." Chemistry & biology, 2003, 10(3):233-239.
Li, et al., "Increasing the antimicrobial activity of nisin-based lantibiotics against Gram-negative pathogens." Applied and environmental microbiology, 2018, 84(12):e00052-18.
Lian at al, Screening Bicyclic Peptide Libraries for Protein-Protein Interaction Inhibitors: Discovery of Journal of the American Chemical Society, Aug. 14, 2013, 135(32):11990-11995.
Lian et al., "Cell-Permcable Bicyclic Peptide Inhibitors against Intracellular Proteins", Journal of the American Chemical Society, Jul. 2014, 136(28):9830-9833.
Lin et al., "EphA2 overexpression is associated with angiogenesis in ovarian cancer," Cancer, Jan. 15, 2007, 109(2):332-340.
Linch et al., "OX40 Agonists and Combination Immunotherapy: Putting the Pedal to the Metal," Frontiers in Oncology, Feb. 16, 2015, 5(34):1-14.
Linde et al., "Structure-Activity Relationship and Metabolic Stability Studies of Backbone Cyclization and N-Methylation of Melanocortin Peptides," Biopolymers, 2008, 90(5):671-682.
Lindstrom et al., "Myasthenia gravis," Advances in Immunology, Dec. 1988, 42:233-284.
Liu et al., "Abstract 3642: Tumor-antigen expression-dependent activation of the CD137 costimulatory pathway by bispecific DART proteins," American Association for Cancer Research, Jul. 2017, 77(supp 13):1-4.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway", Blood, 2007, 110(1):296-304.
Lopus, Manu. "Antibody-DMI conjugates as cancer therapeutics." Cancer letters, 2011, 307(2):113-118.
Lovering et al. "Escape from flatland: increasing saturation as an approach to improving clinical success." Journal of medicinal chemistry, 2009, 52(21):6752-6756.
Lovering, "Escape from Flatland 2: complexity and promiscuity," Mcducinal Chemistry Communication, Dec. 2012, 4(3):515-519.
Lund et al., "CD38 signaling in B lymphocytes is controlled by its ectodomain but occurs independently of enzymatically generated ADP-ribose or cyclic ADP-ribose," J Immunol., Mar. 1, 1999, 162(5):2693-2702.
M.D. Anderson Cancer Center, "Nivolumab and HPV-16 Vaccination in Patients With HPV-16 Positive Incurable Solid Tumors," In ClinicalTrials.gov Identifier NCT02426892. Retreived form https://clinicaltrials.gov/ct2/show/study/NCT02426892, 2015.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):e1330235.
Macheboeuf et al., "Penicillin binding proteins: key players in bacterial cell cycle and drug resistance processes", FEMS Microbiol Rev., 2006, 30(5):673-691.

(56) References Cited

OTHER PUBLICATIONS

Mallone et al., "Signaling through CD38 induces NK cell activation," Int Immunol., Apr. 1, 2001, 13(4):397-409.
Mamessier et al., "Human breast tumor cells induce self-tolerance mechanisms to avoid NKG2D-mediated and DNAM-mediated NK cell recognition", Cancer Res., 2011, 71(21):6621-6632.
Manches et al., "In vitro mechanisms of action of rituximab on primary non-Hodgkin lymphomas", Blood, 2003, 101(3):949-954.
Mark, "Renal Cell Carcinoma," Merck Manual , Reterived form : https://www.merckmanuals.com/home/kidney-and-urinary-tract-disorders/cancers-of-the-kidney-and-genitourinary-tract/kidney-cancer, Sep. 2021.
Marks et al., "By-passing immunization. Human antibodies from V-gene libraries displayed on phage," Journal of Molecular Biology, Dec. 1991, 222(3):581-597.
Marme, "VEGFs, angiopoietins, Ephrins and their receptors: putative targets for tumor therapy?" Ann Hematol., 2002, 81(Suppl 2):S66.
Maron et al., "H-2K mutation controls immune response phenotype of autoimmune thyroiditis. Critical expression of mutant gene product in both thymus and thyroid glands," Journal of Experimental Medicine, Oct. 1980, 152(4):1115-1120.
McFarlin et al., "Experimental Allergic Encephalomyelitis in the Rat: Response to Encephalitogenic Proteins and Peptides," Science, Feb. 1973, 179(4072):478-480.
Merck Manual (https://www.merckanuals.com/home/blood-disorders/plasma-celldisorders/multiple-myeloma?query=pancreaticu ltiple%20myeloma accessed Apr. 9, 2021).
Merritt et al., "Analysis of EphA2 expression and mutant p53 in ovarian carcinoma," Cancer Biol Ther., Oct. 2006, 5(10):1357-1360.
Michel, et al., "Expression of soluble CD137 correlates with activation-induced cell death of lymphocytes." Cytokine, 2000, 12(6):742-746.
Milowsky et al., Phase 1/2 multiple ascending dose trial of the prostate-specific membranc antigen-targeted antibody drug conjugate MLN2704 in metastatic castration-resistant prostate cancer. In Urologic Oncology: Seminars and Original Investigations, 2016, 34(12):530-e15.
Mitra et al., "Structure—Activity Relationship Analysis of Peptides Targeting the EphA2 Receptor," Biochemistry, 2010, 49(31):6687-6695.
Mittler, el al., "Anti-CD137 antibodies in the treatment of autoimmune disease and cancer." Immunologic research, 2004, 29:197-208.
Miyoshi and Takai, "Nectin and nectin-like molecules: biology and pathology," Am J Nephrol., 2007, 27(6):590-604.
Mohammad et al., Prognostic valuc of membrane type 1 and 2 matrix metalloprotcinasc expression and gelatinase A activity in bladder cancer. The International journal of biological markers, 2010, 25(2):69-74.
Moore et al., "A novel bispecific antibody format enables simultaneous bivalent and monovalent co-engagement of distinct target antigens", Mabs, 2011, 3(6):546-557.
Moraes et al., "Immune checkpoint inhibitors (anti PD-1 or anti PD-L1) versus chemotherapy for second- or third-line treatment of metastatic non-small cell lung cancer," Cochrane Database Syst Rev., 2017, 2017(4):CD012644.
Moretta et al., "Surface NK receptors and their ligands on tumor cells", Seminars in Immunology, 2006, 18(3):151-158.
Morgan et al., "FcgammaRIIIA-158V and rheumatoid arthritis: a confirmation study", Rheumatology (Oxford), 2003, 42(4):528-533.
Morra et al., "CD38 is functionally dependent on the TCR/CD3 complex in human T cells," FASEB J., May 1998, 12(7):581-592.
Mudali et al., "Patterns of EphA2 protein expression in primary and metastatic pancreatic carcinoma and correlation with genetic status", Clinical & Experimental Metastasis, 2006, 23(7-8):357-365.
Mudd et al., "Identification and Optimization of EphA2-Selective Bicycles for the Delivery of Cytotoxic Payloads," J Med Chem., 2020, 63(8):4107-4116.

Mugera and Ward, "Acute toxicity of maytansine in F344 rats." Cancer Treatment Reports, 1977, 61(7):1333-1338.
Mullis et al., "Specific synthesis of DNA in vitro via a polymerase-catalyzed chain reaction," Methods in Enzymology, Jan. 1987, 155:335-350.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate expression of activating Fc gamma receptors I and III and inhibiting Fc gamma receptor type II in the determination of joint inflammation and cartilage destruction during immune complex-mediated arthritis", Arthritis & Rheumatology, Jan. 2003, 48(1):255-265.
Nair et al., "Mimicry of Native Peptide Antigens by the Corresponding Retro-Inverso Analogs is Dependent on Their Intrinsic Structure and Interaction Propensities," The Journal of Immunology, 2003, 170(3):1362-1373.
Nakamoto and Bergemann, "Diverse roles for the Eph family of receptor tyrosine kinases in carcinogenesis," Microsc Res Tech., Oct. 2002, 59(1):58-67.
Nakamura et al., "EPHA2/EFNA1 expression in human gastric cancer", Cancer Science, Jan. 2005, 96(1):42-47.
Nakamura et al., "Involvement of alpha(v)beta3 integrins in osteoclast function," J Bone Miner Metab., 2007, 25(6):337-344.
Nakanishi et al., "Overexpression of B7-H1 (PD-L1) significantly associates with tumor grade and postoperative prognosis in human urothelial cancers" Cancer Immunology, Immunotherapy, 2007, 56:1173-1182.
Nam et. al., "The therapeutic potential of 4-1BB (CD137) in cancer", Current cancer drug targets, 2005, 5(5):357-363.
Nan et al., "Dual function glutamate-related ligands: discovery of a novel, potent inhibitor of glutamate carboxypeptidase II possessing mGluR3 agonist activity," J Med Chem., Mar. 9, 2000, 43(5):772-774.
National cancer institute, "Cancer prevention overview", (https://www.cancer.gov/about-cancer/causes-prevention/patient-prevention-overview-pdq accessed May 8, 2020), 2020, 12 pages.
National Cancer Institute, "What is Cancer", (https://www.cancer.gov/about-cancer/understanding/what-is-cancer, accessed Apr. 9, 2021), 10 pages.
National Cancer Institute, Understanding Cancer, and Related Topics, (https://www.cancer.gov/about-cancer/understanding/what-is-cancer, accessed Apr. 9, 2021) 63 pages.
Nayyar et al., "Overcoming Resistance to Natural Killer Cell Based Immunotherapies for Solid Tumors", Feb. 11, 2019 ;9:51, 28 pages.
Neri and Supuran, "Interfering with pH regulation in tumours as a therapeutic strategy," Nature Review Drug Discovery, Sep. 2011, 10(10):767-777.
Nestor et al., "The Medicinal Chemistry of Peptides," Curr. Medicinal Chem, 2009, 16(33):4399-4418.
Nguyen, "Colorectal Cancer," Merck Manual, Reterived from https://www.merckmanuals.com/professional/gastrointestinal-disorders/tumors-of-the-gastrointestinal-tract/colorectal-cancer, 2021.
Nguyen, "Pancreatic Cancer", Merck Manual (https://merckmanuals.com/professional/gastrointestinal-disorders/tumors-of-the-gastrointestinal-tract/pancreatic-cancer?query=adenocarcinomas), Sep. 2022, 4 pages.
NIH National Human Genome Research Institute, "Animal Model," Genome.gov., Jan. 4, 2022.
Nishiwada et al., "Nectin-4 expression contributes to tumor proliferation, angiogenesis and patient prognosis in human pancreatic cancer," Journal of Experimental & Clinical Cancer Research, 2015, 34(1):30. (9 pages.).
Nissim et al., "Antibody fragments from a 'single pot' phage display library as immunochemical reaqents," EMBO Journal, Feb. 1994, 13(3):692-698.
Nomi et al., "Clinical Significance and Therapeutic Potential of the Programmed Death-1 Ligand/Programmed Death-1 Pathway in Human Pancreatic Cancer", Clin Cancer Res., 2007, 13(7): 2151-2157.

(56) References Cited

OTHER PUBLICATIONS

Oehlke et al., "Cellular uptake of an alpha-helical amphipathic model peptide with the potential to deliver polar compounds into the cell interior non-endocytically," Biochimica et Biophysica Acta, Nov. 1998, 1414(1-2):127-139.
Okazaki et al., "A Rheostat for Immune Responses: the Unique Properties of PD-1 and Their Advantages for Clinical Application," Nat. Immunol., 2013, 14(12):1212-1218.
Okuyama et al., "Small-molecule mimics of an a-helix for efficient transport of proteins into cells," Nature Methods, Feb. 2007, 4(2):153-159.
Oliver et al., "Mouse CD38 is down-regulated on germinal center B cells and mature plasma cells," J Immunol., Feb. 1997, 158(3):1108-1115.
Ortiz et al., "Elucidating the interplay between IgG-Fc valency and FcγR activation for the design of immune complex inhibitors", Science Translational Medicine, Nov. 2016, 8(365):365ra158.
Pahwa et al., "Monitoring and inhibiting MT1-MMP during cancer initiation and progression." Cancers, 2014, 6(1):416-435.
Partida-Sanchez et al., "Cyclic ADP-ribose production by CD38 regulates intracellular calcium release, extracellular calcium influx and chemotaxis in neutrophils and is required for bacterial clearance in vivo," Nat Med., Nov. 2001, 7(11):1209-1216.
Partida-Sanchez et al., "Regulation of dendritic cell trafficking by the ADP-ribosyl cyclase CD38: impact on the development of humoral immunity," Immunity, Mar. 2004, 20(3):279-291.
Pasero et al., "Highly effective NK cells are associated with good prognosis in patients with metastatic prostate cancer", Oncotarget 6(16), Jun. 10, 2015, 14360-14373.
Pavlidou et al., "Nanodiscs Allow Phage Display Selection for Ligands to Non-Linear Epitopes on Membrane Proteins," PLoS One, Article No. e72272, Sep. 2013, 8(9):8 pages.
Pavlova et al., "A role for PVRL4-driven cell-cell interactions in tumorigenesis," Elife., Apr. 30, 2013, 2:c00358, 24 pages.
Pearson et al., "High-Level Clonal FGFR Amplification and Response to FGFR Inhibition in a Translational Clinical Trial", Cancer Discovery, 2016, 6(8):838-851.
Peng et al., Combined features based on MT1-MMP expression, CD11b+ immunocytes density and LNR predict clinical outcomes of gastric cancer. Journal of translational medicine, 2013, 11(1):1-11.
Phichith, et al., "Novel peptide inhibiting both TEM-1 β-lactamase and penicillin-binding proteins." The FEBS Journal, 2010, 277(23):4965-4972.
Pietraszek et al., "Lumican: a new inhibitor of matrix metalloproteinase-14 activity," FEBS Lett., Nov. 28, 2014, 588(23):4319-4324.
Pivot et al., "Pooled analyses of eribulin in metastatic breast cancer patients with at least one prior chemotherapy." Annals of Oncology, 2016, 27(8):1525-1531.
Platonova et al., "Profound coordinated alterations of intratumoral NK cell phenotype and function in lung carcinoma", Cancer Res., 2011, 71(16):5412-5422.
Polakis, "Antibody Drug Conjugates for Cancer Therapy," Pharmacol Rev., Jan. 2016, 68(1):3-19.
Poliakov et al., "Diverse roles of eph receptors and ephrins in the regulation of cell migration and tissue assembly", Developmental Cell, Oct. 2004;7(4):465-480.
Poon et al., Preclinical safety profile of trastuzumab emtansine (T-DM1): mechanism of action of its cytotoxic component retained with improved tolerability. Toxicology and applied pharmacology, 2013, 273(2):298-313.
Poreba, "Protease-activated prodrugs: strategies, challenges, and future directions." The FEBS Journal, 2020, 287(10):1936-1969.
Pricop et al., "Differential modulation of stimulatory and inhibitory Fc gamma receptors on human monocytes by Th1 and Th2 cytokines", Journal of Immunology, 2001, 166(1):531-537.
Purdie and Benoiton, "Piperazinedione formation from esters of dipeptides containing glycine, alanine, and sarcosine: the kinetics in aqueous solution." Journal of the Chemical Society, Perkin Transactions 2, 1973, 14: 1845-1852.

Qi et al., "Serial determination of glomerular filtration rate in conscious mice using FITC-inulin clearance," American Journal of Physiology—Renal Physiology, Mar. 2004, 286(3):F590-F596.
Ramirez et al., "Defining causative factors contributing in the activation of hedgehog signaling in diffuse large B-cell lymphoma," Leuk Res., Oct. 2012, 36(10):1267-1273.
Randall et al., "Expression of murine CD38 defines a population of long-term reconstituting hematopoietic stem cells," Blood, May 15, 1996, 87(10):4057-4067.
Rataj et al., "High-affinity CD16-polymorphism and Fc-engineered antibodies enable activity of CD16-chimeric antigen receptor-modified T cells for cancer therapy", British Journal of Cancer, 2019, 120(1):79-87.
Ravetch et al., "IgG Fc receptors", Annual Review of Immunology, 2001:19:275-290.
Reagan-Shaw et al., "Dose translation from animal to human studies revisited, " FASEB J., Mar. 2008, 22(3):659-661.
Reinertsen et al., "B-Lymphocyte Alloantigens Associated with Systemic Lupus Erythematosus," The New England Journal of Medicine, Sep. 7, 1978, 299(10):515-518.
Remacle et al., "Membrane type I-matrix metalloproteinase (MT1-MMP) is internalised by two different pathways and is recycled to the cell surface." Journal of cell science, 2003, 116(19):3905-3916.
Remacle et al., "Novel MT1-MMP small-molecule inhibitors based on insights into hemopexin domain function in tumor growth," Cancer Res., May 1, 2012, 72(9):2339-2349.
Ridderstad and Tarlinton, "Kinetics of establishing the memory B cell population as revealed by CD38 expression," J Immunol., May 15, 1998, 160(10):4688-4695.
Riddle et al., "Tumor cell surface display of immunoglobulin heavy chain Fc by gene transfer as a means to mimic antibody therapy", Human Gene Therapy, 2005, 16(7):830-844.
Robert Gale, "Cancer treatment principles", Merck Manual consumer version (https://www.merckmanuals.com/home/cancer/prevention-and-treatment-of-cancer/cancer-treatment-principles?query=Cancer%20treatment Accessed May 8, 2020), Jul. 2018, 2 pages.
Robert Gale, "Overview of Cancer therapy", Merck Manual consumer version (https://www.merckmanuals.com/professional/hematology-and-oncology/principles-of-cancer-therapy/overview-of-cancer-therapy?query=Cancer Accessed May 8, 2020), Jul. 2018, 3 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, 2016, 7:413.
Rodan and Rodan, "Integrin function in osteoclasts," J Endocrinol., Sep. 1997, 154(Suppl):S47-S56.
Rodon et al., "Cantuzumab mertansine in a three-times a week schedule: a phase I and pharmacokinetic study." Cancer chemotherapy and pharmacology, 2008, 62(5):911-919.
Ross and Christiano, "Nothing but skin and bone," J Clin Invest., May 2006, 116(5):1140-1149.
Ross et al., "Bispecific T Ccll Enager (BiTE) Antibody Constructs Can Mediate Bystander Tumor Cell Killing", PLoS ONE, Aug. 24, 2017, 12(8):1-24.
Rostovtsev et al., "A Stepwise Huisgen Cycloaddition Process: Copper(I)-Catalyzed Regioselective Ligation" of Azides and Terminal Alkynes, Angewandte Chemie, Jul. 2002, 41(14):2596-2599.
Roth et al., "Docetaxel, cisplatin, and fluorouracil; docetaxel and cisplatin; and epirubicin, cisplatin, and fluorouracil as systemic treatment for advanced gastric carcinoma: a randomized phase II trial of the Swiss Group for Clinical Cancer Research", J Clin Oncol. Aug. 1, 2007, 25(22):3217-3023.
Rothwell et al., "Utility of ctDNA to support patient selection for early phase clinical trials: the TARGET study", Nature Medicine, 2019, 25(5):738-743.
Rudgers et al., "Binding properties of a peptide derived from beta-lactamase inhibitory protein." Antimicrob Agents Chemother., 2001, 45(12):3279-3286.

(56) References Cited

OTHER PUBLICATIONS

Salmon et al., "Human receptors for immunoglobulin G: key elements in the pathogenesis of rheumatic disease", Arthritis & Rheumatology, 2001, 44(4):739-750.
Satoh et al., "Experimental allergic encephalomyelitis mediated by murine encephalitogenic T cell lines specific for myelin proteolipid apoprotein," Journal of Immunology, Jan. 1987, 138(1):179-184.
Sausville and Burger, "Contributions of Human Tumor Xenografts to Anticancer Drug Development," Cancer Res., 2006, 66(7):3351-3354.
Scagliotti et al., "Phase III study comparing cisplatin plus gemcitabine with cisplatin plus pemetrexed in chemotherapy-naive patients with advanced-stage non-small-cell lung cancer." Journal of clinical oncology, 2008, 26(21):3543-3551.
Schiller et al., "Comparison of four chemotherapy regimens for advanced non-small-cell lung cancer." New England Journal of Medicine, 2002, 346(2):92-98.
Schreiber et al., "Rapid, electrostatically assisted association of proteins," Nature Structural & Molecular Biology, May 1996, 3:427-431.
Schulke et al., "The homodimer of prostate-specific membrane antigen is a functional target for cancer therapy," Proc Natl Acad Sci U SA., Oct. 28, 2003, 100(22):12590-12595.
Seely and Frazier, "Regulatory Forum Opinion Piccc*: Dispelling Confusing Pathology Terminology: Recognition and Interpretation of Selected Rodent Renal Tubule Lesions," Toxicol Pathol., 2015, 43(4):457-463.
Segal et al., "Results from an Integrated Safety Analysis of Urelumab, an Agonist Anti-CD137 Monoclonal Antibody", clinical Cancer rescarch, 2017, 23(8):1929-1936.
Seiki et al., "Membrane-type 1 matrix metalloproteinase: a key enzyme for tumor invasion." Cancer letters, 2003, 194(1):1-11.
Sepiashvili et al., "Potentially novel candidate biomarkers for head and neck squamous cell carcinoma identified using an integrated cell line-based discovery strategy." Molecular & Cellular Proteomics, 2012, 11(11):1404-1415.
Shaabani et al., "A patent review on PD-1/PD-L 1 antagonists: small molecules, peptides, and macrocycles (2015-2018)," Expert Opinion on Therapeutic Patents, 2018, 28(9):665-678.
Shah et al., "Phase I study of IMGN901, a CD56-targeting antibody-drug conjugate, in patients with CD56-positive solid tumors." Investigational new drugs, 2016, 34:290-299.
Shah, "Update on metastatic gastric and esophageal cancers." Journal of clinical oncology 33, No. 16 (2015):1760-1769.
Shao et al., "Copy number variation is highly correlated with differential gene expression: a pan-cancer study," BMC Medical Genetics, Nov. 9, 2019, 20(1):175.
Shao et al., "CD137 ligand, a member of the tumor necrosis factor family, regulates immune responses via reverse signal transduction." Journal of leukocyte biology, 2011, 89(1):21-29.
Sharma et al., "Plasmacytoid dendritic cells from mouse tumor-draining lymph nodes directly activate mature Tregs via indoleamine 2, 3-dioxygenase", The Journal of clinical investigation, 2007, 117(9):2570-2582.
Shen et al., "Non-clinical disposition and metabolism of DM1, a Component of Trastuzumab Emtansine (T-DM1), in Sprague Dawley Rats." Drug Metabolism Letters, 2015, 9(2):119-131.
Shen, et.al., "Evaluation of phage display discovered peptides as ligands for prostate-specific membrane antigen (PSMA)." PLoS One, 2013, 8(7):e68339.
Shi et al., "One-Bead-Two-Compound Thioether Bridged Macrocyclic (gamma)-AApeptide Screening Library Against EphA2," J Med Chem., Nov. 22, 2017, 60(22):9290-9298.
Shimauchi et al., "Augmented expression of programmed death-1 in both neoplastic and non-neoplastic CD4+ T-cells in adult T-cell leukemia/lymphoma", International journal of cancer, 2007, 121(12):2585-2590.
Sibaud et al., "Pigmentary disorders induced by anticancer agents. Part I: chemotherapy." In Annales de dermatologic et de venercologic, 2013, 140(3):183-196.
Siddharth et al., "Nectin-4 is a breast cancer stem cell marker that induces WNT/β-Catenin signaling via Pi3k/Akt axis," International Journal of Biochemistry and Cell Biology, 2017, 89:85-94.
Silver, "Multi-targeting by monotherapeutic antibacterials." Nat Rev Drug Discov., 2007, 6(1):41-55.
Soderstrom, et al., "CD137: A checkpoint regulator involved in atherosclerosis." Atherosclerosis, 2018, 272:66-72.
Sordo-Bahamonde et al., "Mechanisms of Resistance to NK Cell Immunotherapy", Cancers (Basel). Apr. 7, 2020, 12(4):893.
Sounni et al. "MT1-MMP expression promotes tumor growth and angiogenesis through an up-regulation of vascular endothelial growth factor expression" FASEB J., 2002, 16(6):555-564.
Sporn et at, "Chemoprevention of cancer." Carcinogenesis, 2000, 21(3):525-530.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood, 2014, 124(21):1760.
Steck et al., "Inside-out red cell membrane vesicles: preparation and purification," Science, Apr. 10, 1970, 168(3928):255-257.
Stein et al., "Eph receptors discriminate specific ligand oligomers to determine alternative signaling complexes, attachment, and assembly responses", Genes Development, 1998, 12(5):667-678.
Stevenson et al., "Preliminary studies for an immunotherapeutic approach to the treatment of human myeloma using chimeric anti-CD38 antibody," Blood, Mar. 1, 1991, 77(5):1071-1079.
Stojanovic et al., "Natural killer cells and solid tumors", Journal of Innate Immunity, 2011, 3(4):355-364.
Stringaris et al., "Leukemia-induced phenotypic and functional defects in natural killer cells predict failure to achieve remission in acute myeloid leukemia", Haematologica, May 2014, 99(5):836-847.
Strome et al., "B7-H1 blockade augments adoptive T-cell immunotherapy for squamous cell carcinoma", Cancer Res., 2003, 63(19):6501-6505.
Stuart et al., "Collagen Autoimmunc Arthritis," Annual Review of Immunology, 1984, 2:199-218.
Sun et al., "Carbohydrate and protein immobilization onto solid surfaces by sequential Diels-Alder and azide-alkyne cycloadditions," Bioconjugate Chemistry, Jan.-Feb. 2006, 17(1):52-57.
Sun et al., "NK cell receptor imbalance and NK cell dysfunction in HBV infection and hepatocellular carcinoma", Cellular & Molecular Immunology, May 2015, 12(3):292-302.
Suojanen et al, "A novel and selective membrane type-1 matrix metalloproteinase (MT1-MMP) inhibitor reduces cancer cell motility and tumor growth," Cancer Biology & Therapy, Dec. 2009, 8(24):2362-2370.
Supuran, "Carbonic anhydrases: novel therapeutic applications for inhibitors and activators," Nature Reviews Drug Discovery, Feb. 2008, 7(2):168-181.
Tandon et al., "Emerging strategies for EphA2 receptor targeting for cancer therapeutics" Expert Opinion on Therapeutic Targets, 2011, 15(1):31-51.
Tarazona et al., "Current progress in NK cell biology and NK cell-based cancer immunotherapy", Cancer Immunol Immunother, 2020, 69(5):879-899.
Tasch et al., "A unique folate hydrolase, prostate-specific membrane antigen (PSMA): a target for immunotherapy?", Crit Rev Immunol., 2001, 21(1-3):249-261.
Teitelbaum, "Osteoclasts, integrins, and osteoporosis," J Bone Miner Metab., Oct. 2000, 18(6):344-349.
Teitelbaum, "Osteoporosis and Integrins," The Journal of Clinical Endocrinology & Metabolism, Apr. 2005, 90(4):2466-2468.
Teti et al., "The Role of the AlphaVbeta3 Integrin in the Development of Osteolytic Bone Metastases: A Pharmacological Target for Alternative Therapy?", Calcified Tissue International, Oct. 2002, 71(4):293-299.
Tetu et al., "The influence of MMP-14, TIMP-2 and MMP-2 expression on breast cancer prognosis." Breast Cancer Research, 2006, 8(3):1-9.
Teufel et al., "Backbone-driven collapse in unfolded protein chains," J Mol Biol., Jun. 3, 2011, 409(2):250-262.

(56) References Cited

OTHER PUBLICATIONS

Thake et al., "Toxicity of Maytansine (NSC 153858) in dogs and monkeys." PB-US National Technical Information Service (1975), Feb. 1975, 244628.

Thevenard et al., "The YSNSG cyclopeptide derived from tumstatin inhibits tumor angiogenesis by down-regulating endothelial cell migration." International journal of cancer, 2010, 126(5):1055-1066.

Thompson et al., "Costimulatory B7-H1 in renal cell carcinoma patients: Indicator of tumor aggressiveness and potential therapeutic target", Proceedings of the National Academy of Sciences, 2004, 101(49):17174-17179.

Timmerman et al., "Rapid and Quantitative Cyclization of Multiple Peptide Loops onto Synthetic Scaffolds for Structural Mimicry of Protein Surfaces," ChemBioChem, 2005, 6(5):821-824.

Todisco et al., "CD38 ligation inhibits normal and leukemic myelopoiesis," Blood, Jan. 2000, 95(2):535-542.

Tolcher et al., "Cantuzumab mertansine, a maytansinoid immunoconjugate directed to the CanAg antigen: a phase I, pharmacokinetic, and biologic correlative study." Journal of clinical oncology, 2003, 21(2):211-222.

Toogood, "Small Molecule Immuno-oncology Therapeutic Agents," Bioorganic & Medicinal Chemistry Letters, 2018, 28(3):319-329.

Touati et al., "Phage Selection of Bicyclic Peptide Ligands and Development of a New Peptide Cyclisation Method", Theses No. 5536, Oct. 2012, 117 pages.

Trouche et al., "Small multivalent architectures mimicking homotrimers of the TNF superfamily member CD40L: delineating the relationship between structure and effector function." Journal of the American Chemical Society, 2007, 129(44):13480-13492.

Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry." Human pathology, 2008, 39(5):731-739.

Tugyi et al, "Partial D-amino acid substitution: Improved enzymatic stability and preserved Ab recognition of a MUC2 epitope peptide," Proceedings of the National Academy of Sciences U.S.A., Jan. 2005, 102(2):413-418.

Tutt et al., "Abstract S3-01: the TNT trial: a randomized phase III trial of carboplatin (C) compared with docetaxel (D) for patients with metastatic or recurrent locally advanced triple negative or BRCA1/2 breast cancer (CRUK/07/012)." Cancer Research, May 2015, 75(9_Suppl):S3-01.

Uckun, "Regulation of human B-cell ontogeny," Blood, Nov. 1990, 76(10):1908-1923.

Ulasov et al., "Inhibition of MMP 14 potentiates the therapeutic effect of temozolomide and radiation in gliomas." Cancer medicine, 2013, 2(4):457-467.

Ün, Sanya. Charakterisierung von Peptiden für die Bindung essentieller Penicillin-bindender Proteine und die Variationen der Linkerlänge einzelkettiger TetR Varianten. Friedrich-Alexander-Universitaet Erlangen-Nuernberg (Germany), 2010. 139 pages.

Van Eden et al., "Cloning of the mycobacterial epitope recognized by T lymphocytes in adjuvant arthritis," Nature, Jan. 14, 1988, 331(6152):171-173.

Van Glabbeke et al., "Progression-free rate as the principal endpoint for phase II trials in soft-tissue sarcomas." European Journal of Cancer, 2002, 38(4):543-549.

Vandenbroucke and Libert, "Is there new hope for therapeutic matrix metalloproteinase inhibition?." Nature reviews Drug discovery, 2014, 13(12):904-927.

Walker-Daniels et al., "Overexpression of the EphA2 tyrosine kinase in prostate cancer", Prostate, 1999, 41(4):275-280.

Wallbrecher et al., "Exploration of the design principles of a cell-penetrating bicyclic peptide scaffold," Bioconjug Chem., May 21, 2014, 25(5):955-964.

Wang et al., "Co-expression of MMP-14 and MMP-19 predicts poor survival in human glioma." Clinical and Translational Oncology, 2013, 15:139-145.

Wang et al., "MMP-14 overexpression correlates with poor prognosis in non-small cell lung cancer." Tumor Biology, 2014, 35:9815-9821.

Wang et al., "Probing for Integrin $\alpha v\beta 3$ Binding of RGD Peptides Using Fluorescence Polarization," Bioconjugate Chem., May-Jun. 2005, 16(3):729-734.

Wang, "An exact mathematical expression for describing competitive binding of two different ligands to a protein molecule." FEBS letters, 1995, 360(2):111-114.

Watanabe et al., "NK cell dysfunction with down-regulated CD16 and up-regulated CD56 molecules in patients with esophageal squamous cell carcinoma", Diseases of the Esophagus, 2010, 23(8):675-681.

Waterhouse et al., "Safety profile of nivolumab administered as 30-min infusion: analysis of data from CheckMate 153," Cancer Chemother Pharmacol., Apr. 2018, 81(4):679-686.

Watts, "TNF/TNFR family members in costimulation of T cell responses", Annu. Rev, Immunol., Apr. 2005, 23:23-68.

Weber, J. "Immune Checkpoint Proteins: A New Therapeutic Paradigm for Cancer—Preclinical Background: CTLA-4 and PD-1 Blockade", Seminars in Oncology, Oct. 2010, 37(5):430-439.

Wei et al., "Discovery of Peptidomimetic Antibody—Drug Conjugate Linkers with Enhanced Protease Specificity," J. Med. Chem., 2018, 61(3):989-1000.

Wind et al., "Measuring carbonic anhydrase IX as a hypoxia biomarker: differences in concentrations in serum and plasma using a commercial enzyme-linked immunosorbent assay due to influences of metal ions," Annals of Clinical Biochemistry, Mar. 2011, 48(2):112-120.

Winter et al., "Making antibodies by phage display technology," Annual Review of Immunology, 1994, 12:433-455.

Wu et al, "Structures of the CXCR4 chemokine GPCR with small-molecule and cyclic peptide antagonists," Science, Nov. 2010, 330(6007):1066-1071.

Wu et al., "A novel polymorphism of FcgammaRIIIa (CD16) alters receptor function predisposes to autoimmune disease", The Journal of Clinical Investigation, 1997, 100(5):1059-1070.

Wu et al., "Design and Characterization of Novel EphA2 Agonists for Targeted Delivery of Chemotherapy to Cancer Cells," Chem. Biol., 2015, 22(7):876-887.

Wu et al., "Natural killer cells in cancer biology and therapy", Molecular Cancer, Aug. 6, 2020, 19(1):120, 26 pages.

Wu et al., "Immunohistochemical localization of programmed death-1 ligand-1 (PD-L1) in gastric carcinoma and its clinical significance" Acta histochemica, 2006, 108(1):19-24.

Wykosky et al., "EphA2 as a novel molecular marker and target in glioblastoma multiforme", Molecular Cancer Research, Oct. 2005, 3(10):541-551.

Xiong et al., "Crystal structure of the extracellular segment of integrin $\alpha V\beta 3$ in complex with an Arg-Gly-Asp Ligand", Science, Apr. 2002, 296(5565):151-155.

Yang et al., "Overexpression of EphA2, MMP-9, and MVD-CD34 in hepatocellular carcinoma: Implications for tumor progression and prognosis," Hepatol Res., 2009, 39(12):1169-1177.

Yardley et al., "EMERGE: a randomized phase II study of the antibody-drug conjugate glembatumumab vedotin in advanced glycoprotein NMB-expressing breast cancer." Journal of clinical oncology: official journal of the American Society of Clinical Oncology, 2015, 33(14):1609.

Yoon et al., "An efficient strategy for cell-based antibody library selection using an integrated vector system," BMC Biotechnology, 2012, 12(62):10 pages.

Yoshihara et al., "Tags for labeling protein N-termini with subtiligase for proteomics," Bioorganic & Medicinal Chemistry Letters, Nov. 2008, 18(22):6000-6003.

Yu and Taylor, "A new strategy applied to the synthesis of an $\alpha$-helical bicyclic peptide constrained by two overlapping i, i+ 7 side-chain bridges of novel design." Tetrahedron letters, 1996, 37(11):1731-1734.

Yuan et al., "Neuropilin-1 and the development progress of the same as a therapeutic target for malignant tumors," Tumor, 2016, 36:358-364.

(56) References Cited

OTHER PUBLICATIONS

Yuan et al., "Over-expression of EphA2 and EphrinA-1 in human gastric adenocarcinoma and its prognostic value for postoperative patients," Dig Dis Sci., Nov. 2009, 54(11):2410-2417.
Zarrabi et al., "Inhibition of matrix metalloproteinase 14 (MMP-14)-mediated cancer cell migration." Journal of Biological Chemistry, 2011, 286(38):33167-33177.
Zelinski et al., "EphA2 Overexpression Causes Tumorigenesis of Mammary Epithelial Cells," Cancer research, Mar. 2001, 61(5):2301-2306.
Zervosen et al., "Development of New Drugs for an Old Target—The Penicillin Binding Proteins." Molecules. 2012:17 (11);12478-12505.
Zhang et al., "A new anti-HER2 antibody that enhances the antitumor efficacy of trastuzumab and pertuzumab with a distinct mechanism of action", Mol Immunol., 2020, 119:48-58.
Zhang et al., "FCGR2A and FCGR3A Polymorphisms Associated With Clinical Outcome of Epidermal Growth Factor Receptor—Expressing Metastatic Colorectal Cancer Patients Treated With Single-Agent Cetuximab", Journal of Clinical Oncology, 2007, 25(24):3712-3718.
Zhao el al., "Structural basis of specificity of a peptidyl urokinase inhibitor, upain-1," Journal of Structural Biology, Oct. 2007, 160(1):1-10.
Zhou et al., "Significance of semaphorin-3A and MMP-14 protein expression in non-small cell lung cancer", Oncology letters, 2014, 7(5):1395-1400.
Zhu et al., "High-affinity peptide against MT1-MMP for in vivo tumor imaging." Journal of controlled release, 2011, 150(3):248-255.
Zhuang et al., "Elevation of receptor tyrosine kinase EphA2 mediates resistance to trastuzumab therapy," Cancer Res., Jan. 1, 2010, 70(1):299-308.
Zilber et al., "CD38 expressed on human monocytes: a coaccessory molecule in the superantigeninduced proliferation," Proc Natl Acad Sci US A., Mar. 14, 2000, 97(6):2840-2845.
Zou et al., "PD-L1 (B7-H1) and PD-1 Pathway Blockade for Cancer Therapy: Mechanisms, Response Biomarkers and Combinations," Sci. Transl. Med., 2016, 8(328):328rv4., 1-14.
Zubiaur et al., "CD38 Ligation Results in Activation of the Raf-1/Mitogen-Activated Protein Kinase and the CD3-zeta/zeta-Associated Protein-70 Signaling Pathways in Jurkat T Lymphocytes," J Immunol., Jul. 1, 1997, 159(1):193-205.
Zugazagoitia et al., "Current Challenges in Cancer Treatment," Clinical Therapies, 2016, 38(7):1551-1566.
Zupo et al., "CD38 signaling by agonistic monoclonal antibody prevents apoptosis of human germinal center B cells," Eur J Immunol., May 1994, 24(5):1218-1222.
PCT International Preliminary Report on Patenatbility received from PCT/GB2019/050485 dated Sep. 3, 2020, 8 pages.
PCT International Preliminary Report on Patentability received for PCT/EP2017/083953, dated Jul. 4, 2019, 7 pages.
PCT International Preliminary Report on Patentability received for PCT/EP2017/083954, dated Jul. 4, 2019, 7 pages.
PCT International Preliminary Report on Patentability received for PCT/EP2019/066010, dated Dec. 30, 2020, 9 pages.
PCT International Preliminary Report on Patentability received for PCT/EP2019/066066, dated Dec. 30, 2020, 8 pages.
PCT International Preliminary Report on Patentability received for PCT/EP2019/066273, dated Dec. 30, 2020, 8 pages.
PCT International Preliminary Report on Patentability received for PCT/EP2021/072866, dated Mar. 2, 2023, 13 pages.
PCT International Preliminary Report on Patentability received for PCT/GB2015/053247, dated May 11, 2017, 8 pages.
PCT International Preliminary Report on Patentability received for PCT/GB2018/050017, dated Jul. 18, 2019, 8 pages.
PCT International Preliminary Report on Patentability received for PCT/GB2018/052222, dated Feb. 13, 2020, 7 pages.
PCT International Preliminary Report on Patentability received for PCT/GB2019/053537, dated Jun. 24, 2021, 7 pages.
PCT International Preliminary Report on Patentability received for PCT/GB2019/053679, dated Jul. 1, 2021, 7 pages.
PCT International Preliminary Report on Patentability received for PCT/GB2019/053680, dated Jul. 1, 2021, 7 pages.
PCT International Preliminary Report on Patentability received for PCT/GB2020/050069, dated Jul. 29, 2021, 8 pages.
PCT International Preliminary Report on Patentability received for PCT/GB2020/050070, dated Jul. 29, 2021, 11 pages.
PCT International Preliminary Report on Patentability received for PCT/GB2020/050071, dated Jul. 29, 2021, 7 pages.
PCT International Preliminary Report on Patentability received for PCT/GB2020/050072, dated Jul. 29, 2021, 11 pages.
PCT International Preliminary Report on Patentability received for PCT/GB2020/050073, dated Jul. 29, 2021, 8 pages.
PCT International Preliminary Report on Patentability received for PCT/GB2020/050074, dated Jul. 29, 2021, 14 pages.
PCT International Preliminary Report on Patentability received for PCT/GB2020/052058, dated Mar. 10, 2022, 8 pages.
PCT International Preliminary Report on Patentability received for PCT/GB2020/052590, dated Apr. 28, 2022, 7 pages.
PCT International Preliminary Report on Patentability received for PCT/GB2021/050490, dated Sep. 9, 2022, 9 pages.
PCT International Preliminary Report on Patentability received for PCT/GB2021/050491, dated Sep. 9, 2022, 10 pages.
PCT International Preliminary Report on Patentability received for PCT/GB2022/050043, dated Jul. 20, 2023, 13 pages.
PCT International Preliminary Report on Patentability received for PCT/EP2018/060498, dated Nov. 7, 2019. 8 Pages.
PCT International Preliminary Report on Patentability received for PCT/EP2019/065993, dated Dec. 30, 2020, 7 pages.
PCT International Preliminary Report on Patentability received for PCT/GB2017/053560, dated Jun. 6, 2019, 7 pages.
PCT International Preliminary Report on Patentability received for PCT/GB2018/051779, dated Jan. 9, 2020, 6 pages.
PCT International Preliminary Report on Patentability received for PCT/GB2018/053676, dated Jul. 2, 2020, 7 pages.
PCT International Preliminary Report on Patentability received for PCT/GB2018/053678, dated Jul. 2, 2020, 9 pages.
PCT International Preliminary Report on Patentability received for PCT/GB2019/051740, dated Dec. 30, 2020, 8 pages.
PCT International Preliminary Report on Patentability received for PCT/GB2019/051741, dated Dec. 30, 2020, 7 pages.
PCT International Preliminary Report on Patentability received for PCT/GB2019/053020, dated May 6, 2021, 12 pages.
PCT International Preliminary Report on Patentability received for PCT/GB2019/053080, dated May 14, 2021, 16 pages.
PCT International Preliminary Report on Patentability received for PCT/GB2019/053536, dated Jun. 24, 2021, 07 pages.
PCT International Preliminary Report on Patentability received for PCT/GB2019/053539, dated Jun. 24, 2021, 7 pages.
PCT International Preliminary Report on Patentability received for PCT/GB2019/053540, dated Jun. 24, 2021, 8 pages.
PCT International Preliminary Report on Patentability received for PCT/GB2020/050505, dated Sep. 16, 2021, 7 pages.
PCT International Preliminary Report on Patentability received for PCT/GB2020/050874, dated Oct. 14, 2021, 11 pages.
PCT International Preliminary Report on Patentability received for PCT/GB2020/051140, dated Nov. 25, 2021, 8 pages.
PCT International Preliminary Report on Patentability received for PCT/GB2020/051144, dated Nov. 18, 2021, 9 pages.
PCT International Preliminary Report on Patentability received for PCT/GB2020/051827, dated Feb. 10, 2022, 8 pages.
PCT International Preliminary Report on Patentability received for PCT/GB2020/051829, dated Feb. 10, 2022 , 8 pages.
PCT International Preliminary Report on Patentability received for PCT/GB2020/051831, dated Feb. 10, 2022, 10 pages.
PCT International Preliminary Report on Patentability received for PCT/GB2020/051923, dated Feb. 24, 2022, 9 pages.
PCT International Preliminary Report on Patentability received for PCT/GB2020/052445, dated Apr. 14, 2022, 26 pages.
PCT International Preliminary Report on Patentability received for PCT/GB2020/052619, dated Apr. 28, 2022, 9 pages.

(56) References Cited

OTHER PUBLICATIONS

PCT International Preliminary Report on Patentability received for PCT/GB2020/053026, dated Jun. 9, 2022, 8 pages.
PCT International Preliminary Report on Patentability received for PCT/GB2021/051220, dated Dec. 1, 2022, 7 pages.
PCT International Preliminary Report on Patentability received for PCT/GB2021/051451, dated Dec. 22, 2022, 09 pages.
PCT International Preliminary Report on Patentability received for PCT/GB2021/052001, dated Feb. 16, 2023, 13 pages.
PCT International Preliminary Report on Patentability received for PCT/GB2022/050044, dated Jul. 20, 2023, 13 pages.
PCT International Preliminary Report on Patentability received for PCT/GB2022/050055, dated Jul. 20, 2023, 17 pages.
PCT International Preliminary Report on Patentability received for PCT/GB2017/051250, dated Nov. 15, 2018, 7 pages.
PCT International Preliminary Report on Patentability received for PCT/GB2018/051118, dated Nov. 7, 2019, 11 pages.
PCT International Search Report and Written Opinion received for PCT/EP2017/083953, dated May 9, 2018, 9 pages.
PCT International Search Report and Written Opinion received for PCT/EP2017/083954, dated May 4, 2018, 9 pages.
PCT International Search Report and Written Opinion received for PCT/EP2018/060498, dated Jul. 5, 2018, 13 pages.
PCT International Search Report and Written Opinion received for PCT/EP2019/065993, dated Sep. 24, 2019, 11 pages.
PCT International Search Report and Written Opinion received for PCT/EP2019/066010, dated Sep. 30, 2019, 12 pages.
PCT International Search Report and Written Opinion received for PCT/EP2019/066066, dated Oct. 1, 2019, 11 pages.
PCT International Search Report and Written Opinion received for PCT/EP2019/066273, dated Sep. 27, 2019, 11 pages.
PCT International Search Report and Written Opinion received for PCT/EP2021/072866, dated Dec. 21, 2021, 21 pages.
PCT International Search Report and Written Opinion received for PCT/GB2015/053247, dated Jan. 27, 2016, 12 pages.
PCT International Search Report and Written Opinion received for PCT/GB2017/051250, dated Aug. 4, 2017, 10 pages.
PCT International Search Report and Written Opinion received for PCT/GB2017/053560, dated Jul. 2, 2018, 9 pages.
PCT International Search Report and Written Opinion received for PCT/GB2018/050017, dated Mar. 23, 2018, 12 pages.
PCT International Search Report and Written Opinion received for PCT/GB2018/051118, dated Aug. 3, 2018, 20 pages.
PCT International Search Report and Written Opinion received for PCT/GB2018/051779, dated Sep. 3, 2018, 10 pages.
PCT International Search Report and Written Opinion received for PCT/GB2018/053676, dated Mar. 21, 2019, 12 pages.
PCT International Search Report and Written Opinion received for PCT/GB2018/053678, dated Mar. 20, 2019, 12 pages.
PCT International Search Report and Written Opinion received for PCT/GB2019/050951, dated Jul. 4, 2019, 11 pages.
PCT International Search Report and Written Opinion received for PCT/GB2019/051740, dated Aug. 29, 2019, 11 pages.
PCT International Search Report and Written Opinion received for PCT/GB2019/051741, dated Aug. 5, 2019, 10 pages.
PCT International Search Report and Written Opinion received for PCT/GB2019/053020, dated Jun. 23, 2020, 19 pages.
PCT International Search Report and Written Opinion received for PCT/GB2019/053080, dated Feb. 7, 2020, 19 pages.
PCT International Search Report and Written Opinion received for PCT/GB2019/053536, dated Mar. 11, 2020, 11 pages.
PCT International Search Report and Written Opinion received for PCT/GB2019/053537, dated Mar. 11, 2020, 10 pages.
PCT International Search Report and Written Opinion received for PCT/GB2019/053539, dated Mar. 11, 2020, 8 pages.
PCT International Search Report and Written Opinion received for PCT/GB2019/053540, dated Mar. 11, 2020, 10 pages.
PCT International Search Report and Written Opinion received for PCT/GB2019/053679, dated Mar. 11, 2020, 12 pages.
PCT International Search Report and Written Opinion received for PCT/GB2019/053680, dated Mar. 11, 2020, 11 pages.
PCT International Search Report and Written Opinion received for PCT/GB2020/050069, dated Apr. 15, 2020, 10 pages.
PCT International Search Report and Written Opinion received for PCT/GB2020/050070, dated Jun. 23, 2020, 16 pages.
PCT International Search Report and Written Opinion received for PCT/GB2020/050071, dated May 12, 2020, 10 pages.
PCT International Search Report and Written Opinion received for PCT/GB2020/050072, dated Jun. 30, 2020, 16 pages.
PCT International Search Report and Written Opinion received for PCT/GB2020/050073, dated Apr. 7, 2020, 11 pages.
PCT International Search Report and Written Opinion received for PCT/GB2020/050074, dated Jun. 23, 2020, 21 pages.
PCT International Search Report and Written Opinion received for PCT/GB2020/050505, dated Apr. 28, 2020, 9 pages.
PCT International Search Report and Written Opinion received for PCT/GB2020/050874, dated Jun. 17, 2020, 15 pages.
PCT International Search Report and Written Opinion received for PCT/GB2020/051140, dated Aug. 20, 2020, 10 pages.
PCT International Search Report and Written Opinion received for PCT/GB2020/051144, dated Aug. 18, 2020, 12 pages.
PCT International Search Report and Written Opinion received for PCT/GB2020/051827, dated Nov. 3, 2020, 11 pages.
PCT International Search Report and Written Opinion received for PCT/GB2020/051829, dated Oct. 30, 2020, 11 pages.
PCT International Search Report and Written Opinion received for PCT/GB2020/051831, dated Nov. 4, 2020, 13 pages.
PCT International Search Report and Written Opinion received for PCT/GB2020/052058, dated Nov. 12, 2020, 11 pages.
PCT International Search Report and Written Opinion received for PCT/GB2020/052445, dated Mar. 4, 2021, 34 pages.
PCT International Search Report and Written Opinion received for PCT/GB2020/052590, dated Jan. 28, 2021, 9 pages.
PCT International Search Report and Written Opinion received for PCT/GB2020/052619, dated Jan. 28, 2021, 12 pages.
PCT International Search Report and Written Opinion received for PCT/GB2020/053026, dated Mar. 23, 2021, 11 pages.
PCT International Search Report and Written Opinion received for PCT/GB2021/050490, dated May 19, 2021, 12 pages.
PCT International Search Report and Written Opinion received for PCT/GB2021/050491, dated May 14, 2021, 14 pages.
PCT International Search Report and Written Opinion received for PCT/GB2021/051220, dated Aug. 27, 2021, 12 pages.
PCT International Search Report and Written Opinion received for PCT/GB2021/051451, dated Sep. 22, 2021, 14 pages.
PCT International Search Report and Written Opinion received for PCT/GB2021/052001, dated Nov. 12, 2021, 11 pages.
PCT International Search Report and Written Opinion received for PCT/GB2022/050043, dated Nov. 17, 2022, 18 pages.
PCT International Search Report and Written Opinion received for PCT/GB2022/050044, dated Jun. 28, 2022, 19 pages.
PCT International Search Report and Written Opinion received for PCT/GB2022/050055, dated Apr. 19, 2022, 21 pages.
PCT International Search Report and Written Opinion received for PCT/GB2022/052249, dated Mar. 28, 2023, 14 pages.
PCT International Search Report and Written Opinion received for PCT/GB2022/052903, dated Mar. 13, 2023, 12 pages.
U.S. Appl. No. 17/769,668, filed Apr. 15, 2022.
U.S. Appl. No. 18/021,748, filed Feb. 16, 2023.
U.S. Appl. No. 18/271,360, filed Jul. 7, 2023.
U.S. Appl. No. 18/271,593, filed Jul. 10, 2023.
U.S. Appl. No. 18/313,983, filed May 8, 2023.
U.S. Appl. No. 18/345,506, filed Jun. 30, 2023.
Chen et al., "Peptide Ligands Stabilized by Small Molecules", Angew. Chem. Int. Ed. 2014, vol. 53, pp. 1602-1606.
Heinis et al., "Phage-encoded combinatorial chemical libraries based on bicyclic peptides," Nat Chem Biol. Jul. 2009;5(7):502-7.
Loktev et al., "Multicyclic Peptides as Scaffolds for the Development of Tumor Targeting Agents", Current Medicinal Chemistry, 2017, vol. 24, pp. 2141-2155.
Morrison, "Chemical Strategies for Bicyclic Peptide Formation," Univ. of Leeds, Sep. 2015, pp. 1-60.

(56) References Cited

OTHER PUBLICATIONS

Mulder et al., "Scaffold Optimization in Discontinuous Epitope Containing Protein Mimics of gp120 Using Smart Libraries," Org. Biomol. Chem. 2013, vol. 11, pp. 2676-2684.
PCT International Search Report and Written Opinion from PCT/GB2018/052222 dated Oct. 11, 2018.
PCT International Search Report and Written Opinion from PCT/GB2019/050485 dated Jun. 4, 2019.
PCT International Search Report and Written Opinion from PCT/GB2020/051923 dated Nov. 17, 2020.
Pickens et al., "Practical Considerations, Challenges, and Limitations of Bioconjugation via Azide-Alkyne Cycloaddition", Bioconjugate Chem. 2018, vol. 29, pp. 686-701.
Rhodes and Pei, "Bicyclic Peptides as Next-Generation Therapeutics," Chemistry. 2017; 23(52):12690-12703.
Smeenk et al., "Reconstructing the Discontinuous and Conformational β1/β3-Loop Binding Site on hFSH/hCG by Using Highly Constrained Multicyclic Peptides," ChemBioChem 2015, vol. 16, pp. 91-99.
U.S. Appl. No. 17/590,875 of Mudd et al., filed Feb. 2, 2022.
U.S. Appl. No. 17/592,966 of Mudd et al., filed Feb. 4, 2022.
U.S. Appl. No. 17/630,754 of McDonnell et al., filed Jan. 27, 2022.
U.S. Appl. No. 17/648,560 of Chen et al., filed Jan. 21, 2022.
Upadhyaya, "Activation of CD137 using multivalent and tumour targeted bicyclic peptides," Peptide Congress 2019, Presentation.
"Bicycle Therapeutics Investor Presentation", Retrieved from: https://investors.bicycletherapeutics.com/static-files/f456c054-95c8-4e19-a62a-fef5fcb0650b, Aug. 2024, 61 pages.
Anonymous, "Bicycle Therapeutics 2023 R&D Day Deck", Retrieved from: https://investors.bicycletherapeutics.com/static-files/46599fde-67dc-40a8-9dcb-10ed8444f31e, Dec. 14, 2023, 155 pages.
Anonymous, "Bicycle Therapeutics BT8009 Regulatory Update", Retrieved from: https://investors.bicycletherapeutics.com/static-files/265210c3-233f-4dd8-af32-d34592398d85, Sep. 11, 2023, 23 pages.
Anonymous, "UPI000011DEEB", Retrieved from: https://www.uniprot.org/uniparc/UPI000011DEEB, 2014, 2 pages.
Bader et al., "Abstract 3088: Breaking from the paradigm of antibody-drug conjugates: Evaluation of clinical pharmacokinetics and safety of Bicycle Toxin Conjugates® (BTCs)", American Society of Clinical Oncology Annual Meeting, May 31-Jun. 4, 2024, pp. 1-9.
Baldini et al., "Abstract 498: BT8009-100: A Phase I/II Study of Novel Bicyclic Peptide and MMAE Conjugate BT8009 in Patients (pts) with Advanced Malignancies Associated with Nectin-4 Expression, Including Urothelial Cancer (UC)", ASCO Genitourinary (GU) Cancers Symposium Conference, Feb. 17, 2023, pp. 1-6.
Banerji et al., "A Cancer Research UK phase I/IIa trial of BT1718 (a first in class Bicycle Toxin Conjugate) given intravenously in patients with advanced solid tumours", ASCO, Jun. 5, 2018, pp. 1-4.
Banerji et al., "A Cancer Research UK phase I/IIa trial of BT1718 (a first in class Bicycle Toxin Conjugate) given intravenously in patients with advanced solid tumours", NCRI, Oct. 1, 2018, 1 page.
Battula et al., "Abstract 4613: A novel fully synthetic dual targeted EphA2/CD137 Bicycle® peptide induces tumor localized CD137 agonism", American Association of Cancer Research, Jun. 22, 2020, pp. 1-4.
Battula et al., "Abstract P794: A novel fully synthetic dual targeted EphA2/4-1BB Bicycle® peptide induces tumor localized 4-1BB agonism", SITC, Nov. 9, 2019, pp. 1-4.
Bendell et al., "TPS3655: BT5528-100 Phase I/II Study; Safety, Pharmacokinetics & Preliminary Clinical Activity of BT5528 in Patients with Advanced Malignancies Associated with EphA2 Expression", ASCO, May 29, 2020, 1 page.
Bennett et al., "Abstract 1167/2: Development of BT1718, a novel Bicycle Drug Conjugate for the treatment of lung cancer", American Association of Cancer Research, Apr. 1, 2017, pp. 1-4.
Bennett et al., "Abstract 164: BT5528, an EphA2-targeting Bicycle Toxin Conjugate (BTC): profound efficacy without bleeding and coagulation abnormalities in animal models", EORTC, Nov. 13, 2018, pp. 1-6.
Bennett et al., "Abstract 5854: BT5528, a Bicycle Toxin Conjugate (BTC) targeting EphA2 has potent antitumour activity without bleeding or coagulation abnormalities in animal models", American Association of Cancer Research, Apr. 14, 2018, pp. 1-6.
Bennett et al., "Abstract 5855: Bicycle Toxin Conjugates (BTCs) targeting EphA2 for the treatment of solid tumours: Discovery and selection of BT5528", American Association of Cancer Research, Apr. 14, 2018, pp. 1-8.
Bennett et al., "Abstract C066: BT5528, a Bicycle Toxin Conjugate targeting EphA2: mechanism of action and clinical translation", AACR-NCI-EORTC, Oct. 29, 2019, pp. 1-6.
Bennett, "Abstract 4481: BT5528, an EphA2-targeting Bicycle® Toxin Conjugate (BTC): Profound efficacy without bleeding and coagulation abnormalities in animal models", AACR Annual Meeting, Apr. 4, 2019, 11 pages.
Bennett, "Bicycle Conjugates to Target Solid Tumors", Next Generation Conjugates Summit, Feb. 27, 2023, 23 pages.
Bennett, "BT5528: A Bicycle Toxin Conjugate Targeting EphA2 for the Treatment of Solid Tumours", 9th Annual World ADC Conference, Mar. 6, 2019, 13 pages.
Bournakas et al., "PBP inhibitors discovered using a modified phage display platform (Bicycles)", ESCMID, Oct. 11, 2022, 1 page.
Brandish, "Bicycle Therapeutics: Precision-guided immune agonism for the treatment of cancer", Immuno UK meeting, Sep. 30, 2022, 25 pages.
Campbell et al., "Poster 1197: A multi tumor survey of Nectin-4 expression to guide BT8009 indication selection", American Association of Cancer Research, Apr. 12, 2021, pp. 1-4.
Campbell et al., "Poster 5300: A survey of EphA2 expression by immunohistochemistry (IHC) in tumor tissue microarrays (TMAs) to support BT5528 indication selection", American Association of Cancer Research, Jun. 22, 2020, pp. 1-6.
Carabateas et al., "Strong Analgesics, Some 1-Substituted 4-Phenyl-4-Propionoxypiperidines", Journal of Medicinal and Pharmaceutical Chemistry, Sep. 1962, 5:913-919.
CAS No. 18226-42-1, "1,3,5-Tris(bromomethyl)benzene", Chemical Book, Retrieved from: https://www.chemicalbook.com/ProductChemicalPropertiesCB0500171_EN.htm, 2023, 2 pages.
Chen et al., "Abstract A8: Novel Multimers of Bicyclic Peptides Cluster and Activate CD137 (4-1BB): A Costimulatory T-Cell Checkpoint Receptor", PEGS, Nov. 12, 2018, pp. 1-7.
Cohen et al., "Abstract 2: Quantitation of CD137 and Nectin-4 expression across multiple tumor types to support indication selection for BT7480, a Bicycle tumor-targeted immune cell agonist™ (Bicycle TICA™)", SITC, Nov. 12, 2021, pp. 1-7.
Cohen et al., "Abstract 5555: Development of a CD137 receptor occupancy assay to support the phase I/II study of BT7480, a Bicycle® tumor-targeted immune cell agonist (Bicycle TICA™)", American Association of Cancer Research, Apr. 8, 2022, pp. 1-6.
Cohen et al., "Abstract A65: Development of a CD137 receptor occupancy assay to support the phase I/II study of BT7480, a Bicycle tumor-targeted immune cell agonist® (Bicycle TICA®)", AACR-BC-EORTC, Oct. 26, 2022, pp. 1-7.
Cohen, "Translating preclinical findings into clinical biomarker assays to support the Phase I/II study of BT7480, a Bicycle tumor-targeted immune cell agonist®", World Clinical Biomarkers & CDx Summit, Sep. 28, 2022, 21 pages.
Cohen, "Turning preclinical findings into clinic-ready biomarker assays to support BT7480 development", Markets and Markets Biomarker and Companion Diagnostics Conference, Feb. 15, 2023, 21 pages.
Cook et al., "Abstract 5764: Pharmacokinetic (PK) assessment of BT1718: A phase 1/2a study of BT1718, a first in class bicycle toxin conjugate (BTC), in patients with advanced solid tumours", EMSO, Sep. 28, 2019, pp. 1-4.
Cooke, "Bicycles as precision guided therapeutics", UK Symposium: Advancing Drug Discovery for Oncology, Mar. 13, 2023, 15 pages.
Drumm et al., "Genetic Variation and Clinical Heterogeneity in Cystic Fibrosis", Annu. Rev. Pathol. Mech. Dis., 2012, 7:267-282.
Dufort et al., "Abstract 1340: Modulation of the natural killer cell immune response to tumor with a synthetic tumor-immune cell

(56) References Cited

OTHER PUBLICATIONS agonist, NK-TICA®", American Association for Cancer Research Annual Meeting, Apr. 8, 2024, pp. 1-6.

Dufort et al., "Abstract 15699: Generation of a Bicycle NK-TICA™, a novel NK cell engaging molecule designed to induce targeted tumor cytotoxicity", SITC, Nov. 12, 2022, pp. 1-5.

Dufort et al., Abstract 1806: Modulation of the natural killer (NK) cell immune response to tumor with novel synthetic tumor-immune cell agonist, NK-TICA™, American Association for Cancer Research Annual Meeting, Apr. 17, 2023, pp. 1-7.

Dufort et al., "Abstract 4233: Generation of a Bicycle NK-TICA™, a novel NK cell engaging molecule designed to induce targeted tumor cytotoxicity", American Association for Cancer Research, Apr. 8, 2022, pp. 1-5.

Dufort, "Bicycles: Bispecific, Precision-guided NK Cell Activators for the Treatment of Solid Tumors", Innate Killer Summit, Mar. 29, 2023, 23 pages.

Eder et al., "Bicyclic Peptides as a New Modality for Imaging and Targeting of Proteins Overexpressed by Tumors", Cancer Res., Feb. 15, 2019, 79(4):841-852.

Evans et al., "Abstract CT253: Phase 1/2 study of the safety, pharmacokinetics, and preliminary clinical activity of BT7480 in patients with Nectin-4 associated advanced malignancies", American Association for Cancer Research Annual Meeting, Apr. 18, 2023, pp. 1-5.

Frigerio, "Expanding the Potential of ADCs: Bicyclic Peptide (Bicycle®) Toxin Conjugates May Offer Advancements Over Traditional ADCs", World ADC, Mar. 20, 2023, 28 pages.

Frigerio, "Targeting Tumors with Bicycle Conjugates", PEGS Boston, May 17, 2023, 31 pages.

Gelb et al., "Abstract A047: MT1-MMP Immunohistochemistry (IHC) analysis of tumor microarrays (TMAs) using a novel scoring system guides patient selection for BT1718 expansion cohorts", AACR-NCI-EORTC, Oct. 27, 2019, pp. 1-7.

GenBank Accession No. CZR33441.1, "uncharacterized protein FPRO_01747 [Fusarium proliferatum ET1]", National Center for Biotechnology Information, Retrieved from: https://www.ncbi.nlm.nih.gov/protein/1111492376, Dec. 6, 2016, 1 page.

Hacker et al., "Highly-constrained bicyclic scaffolds for the discovery of protease-stable peptides via mRNA display", ACS Chem. Biol., Mar. 17, 2017, 12(3):795-804.

Hadjicharalambous et al., "Investigating Penetration and Antimicrobial Activity of Vector Bicycle Conjugates", ACS Infectious Diseases, Jun. 12, 2024, 10(7):2381-2389.

Harrison et al., "Abstract 5144: BT1718, a novel bicyclic peptide-maytansinoid conjugate targeting MT1-MMP for the treatment of solid tumours: Design of bicyclic peptide and linker selection", AACR Annual meeting, Apr. 1, 2017, pp. 1-7.

Harrison et al., "Discovery and development of BT1718, a novel bicyclic peptidemaytansinoid conjugate targeting MT1-MMP for the treatment of solid tumours: In vitro and in vivo activities", PEGS, Apr. 30, 2017, 1 page.

Ho et al., "Expression of CD137 on Hodgkin and Reed-Sternberg Cells Inhibits T-cell Activation by Eliminating CD137 Ligand Expression", Cancer Research, Jan. 15, 2013, 73(2):652-661.

Hu et al., "Lessons Learned from Molecular Scaffold Analysis", Journal of Chemical Information and Modeling, 2011, 51(8):1742-1753.

Hurov et al., "Abstract 1340: BT7455, a fully synthetic Bicycle tumor-targeted immune cell agonist®, leads to potent EphA2-dependent CD137 agonism and robust anti-tumor efficacy", SITC, Nov. 10, 2022, pp. 1-6.

Hurov et al., "Abstract 3257: Activation of 4-1BB using multivalent and tumour targeted bicyclic peptides", American Association of Cancer Research, Apr. 2, 2019, pp. 1-4.

Hurov et al., "Abstract 3257: Activation of CD137 using multivalent and tumor targeted Bicyclic peptides", Cancer Res, Jul. 1, 2019, 79(13_Supplement):3257, 3 pages.

Hurov et al., "Abstract 700: EphA2/CD137 Bicycle® tumor-targeted immune cell agonists (TICAs™) induce tumor regressions, immunogenic memory, and reprogramming of the tumor immune microenvironment", SITC, Nov. 9, 2020, pp. 1-4.

Hurov et al., "Abstract P398: Activation of the T cell costimulatory protein CD137 using multivalent bicyclic peptides", SITC, Nov. 6, 2018, pp. 1-5.

Hurov et al., "Abstract P782: A novel fully synthetic dual targeted Nectin-4/4-1BB Bicycle® peptide induces tumor localized 4-1BB agonism", SITC, Nov. 9, 2019, pp. 1-6.

Hurov et al., "BT7480, a novel fully synthetic Bicycle tumor-targeted immune cell agonist™ (Bicycle TICA™) induces tumor localized CD137 agonism", Journal for Immuno Therapy of Cancer, 2021, 9(11):e002883, pp. 1-13.

Hurov et al., "Poster 1728: Nectin-4-dependent immune cell stimulation and anti-tumor efficacy by BT7480, a Nectin-4/CD137 Bicycle® tumor-targeted immune cell agonist (TICA™)", American Association of Cancer Research, Apr. 12, 2021, pp. 1-6.

Hurov, "BT7480, a novel and fully synthetic Bicycle tumor-targeted immune cell agonist®", Festival of Biologics, Nov. 4, 2022, 23 pages.

Kanakia et al., "Development of CD137 (4-1BB) receptor occupancy assay using fluorescently labeled Bicycles®", AACR Tumor Immunology & Immunotherapy, Oct. 19, 2020, 5 pages.

Keen, "A novel fully synthetic dual targeted Nectin-4/4-1BB Bicycle® peptide induces tumor localized 4-1BB agonism", SITC, Nov. 6-10, 2019, 19 pages.

Keen, "BT5528, an EphA2-targeting Bicycle® Toxin Conjugate", World ADC congress, Oct. 11, 2019, 24 pages.

Keen, "BT7480, a novel Nectin-4 dependent agonist of the immune cell costimulatory receptor CD137", AACR Annual Meeting, Apr. 10-15 and May 17-21, 2021, 23 pages.

Kristensson et al., "Novel Bicyclic Peptide Multimers Activate T Cell Costimulatory Protein CD137", ELRIG Drug Discovery, Oct. 9, 2018, pp. 1-7.

Kristensson et al., "Novel Bicyclic Peptide Multimers Activate T Cell Costimulatory Protein CD137", Promega Biologics, Jul. 18, 2018, pp. 1-7.

Kumara et al., "Fusarium proliferatum, an endophytic fungus from Dysoxylum binectariferum Hook.f, produces rohitukine, a chromane alkaloid possessing anti-cancer activity", Antonie van Leeuwenhoek, 2012, 101(2):323-329.

Lahdenranta et al., "Abstract 1356: Transcriptional profiling of Bicycle® tumor-targeted CD137 agonist-treated mouse tumors revealed an early and rapid activation of myeloid cells followed by infiltration of cytotoxic T cells into the tumor", SITC, Nov. 10, 2022, pp. 1-9.

Lahdenranta et al., "Abstract 5301: Tumor-targeted activation of CD137 using Bicycle® molecules: New insights into mechanism of action and discovery of BT7455, a clinical candidate for the treatment of EphA2-expressing cancers", American Association for Cancer Research Annual Meeting, Apr. 9, 2024, pp. 1-5.

Lahdenranta et al., "Abstract A067: BT7480, a synthetic Bicycle tumor-targeted immune cell agonist® (Bicycle TICA®), induces reprogramming of the tumor immune microenvironment through tumor localized CD137 agonism", CICON, Sep. 29, 2022, pp. 1-9.

Lahdenranta et al., "Poster 1319: Rapid accumulation of cytotoxic payload in tumor tissue drives BT5528 activity in tumor models", American Association for Cancer Research, Apr. 12, 2021, pp. 1-4.

Lahdenranta et al., "Poster 1724: Microinjection of Nectin-4/CD137 tumor-targeted immune cell agonist (TICA™) activates the local tumor microenvironment", American Association of Cancer Research, Apr. 12, 2021, pp. 1-4.

Lahdenranta et al., "Poster 706: BT7480, a fully synthetic tumor-targeted immune cell agonist (TICA™) induces tumor localized CD137 agonism and modulation of tumor immune microenvironment", SITC, Nov. 9, 2020, pp. 1-6.

Loriot et al., "Abstract TPS4619: A phase 2/3 study of Bicycle® Toxin Conjugate zelenectide pevedotin (BT8009) targeting Nectin-4 in patients with locally advanced or metastatic urothelial cancer (la/mUC) (Duravelo-2)", American Society of Clinical Oncology Annual Meeting, May 31-Jun. 4, 2024, 1 page.

Lowe, "Not Alphafold's Fault", blog—In the pipeline, Sep. 7, 2022, 6 pages.

(56) References Cited

OTHER PUBLICATIONS

Lowe, "The Good Sides and Bad Sides of Polar Compounds", blog—In the pipeline, Feb. 23, 2017, 15 pages.
Ludbrook, "Bicycle Toxin Conjugates to Target Solid Tumors", 3rd ADC Target Selection Summit, Dec. 6, 2023, 20 pages.
Luus et al., "Abstract 1832: EphA2-dependent CD137 agonism and anti-tumor efficacy by BT7455, a Bicycle tumor-targeted immune cell agonist®", American Association for Cancer Research Annual Meeting, Apr. 17, 2023, pp. 1-7.
McDonnell, "Bicycles for precision guided delivery", Boulder Peptide Symposium, Nov. 9, 2022, 29 pages.
McKean et al., "A Combined Phase I/II Study of BT8009 a Novel Bicycle® Toxin Conjugate with MMAE in Patients with Advanced Malignancies with Nectin-4", ASCO, Jun. 4, 2021, 1 page.
McKean et al., "BT8009-100 Phase I/II Study of Novel Bicyclic Peptide and MMAE Conjugate BT8009 in Patients with Advanced Malignancies Associated with Nectin-4 Expression", American Association for Cancer Research, Apr. 8-13, 2022, 17 pages.
McKean et al., "BT8009-100 Phase I/II Study of the Safety, Pharmacokinetics, & Preliminary Clinical Activity of BT8009 in Patients with Nectin-4 Expressing Advanced Malignancies", ESMO, Sep. 17, 2020, 1 page.
McKean, "A first in class phase I/II study of the novel bicyclic peptide and MMAE conjugate, BT5528, in patients with advanced malignancies associated with EphA2 expression", AACR-NCI-EORTC, Oct. 7-10, 2021, 19 pages.
Micoine et al., "A General Strategy for Ligation of Organic and Biological Molecules to Dawson and Keggin Polyoxotungstates", Organic Letters, Jul. 18, 2007, 9(20):3981-3984.
Mistry et al., "Abstract 15523: Establishing the preclinical/translational PK/PD relationship for BT7480, a Nectin4/CD137 Bicycle tumor-targeted immune cell agonist™ M (Bicycle TICA™)", SITC, Nov. 12, 2021, pp. 1-5.
Mistry et al., "Synthesis of Bicycle® Peptides using Gold-mediated Cysteine Arylation", European Peptide Synthesis Conference, Mar. 7, 2023, 1 page.
Mudd et al., "Bicyclic Peptides for Positron Emission Tomography (PET) Imaging of MT1-MMP Expressing tumours", PEGS, Apr. 30, 2017, 1 page.
Mudd et al., "Discovery of BT8009: A Nectin-4 Targeting Bicycle Toxin Conjugate for the Treatment of Cancer", Journal of Medicinal Chemistry, 2022, 65(21): 14261-14970.
Mudd et al., "Gold-Mediated Multiple Cysteine Arylation for the Construction of Highly Constrained Bicycle Peptides", Bioconjugate Chemistry, 2022, 33(8):1441-1445.
Mudd et al., "Potent anti-tumor activity of a Lead-212 labelled MT1-MMP targeting Bicycle Radionuclide Conjugate™", TIDES USA—Oligonucleotide, May 8, 2023, pp. 1-7.
Newman et al., "Anti-Infectives Drug Discovery at Bicycle Therapeutics", ESCMID, Oct. 11, 2022, 1 page.
Newman, "Characterisation of novel, noncovalent cyclic peptide (Bicycles®) inhibitors of PBP3s from important Gram-negative pathogens", ESCMID, Oct. 11, 2022, 18 pages.
Ngo et al., "Abstract 333: Activity of the erythropoietin-producing hepatocellular A2 Receptor (EphA2) targeting Bicycle® Toxin Conjugate (BTC™) BCY6033 in EGFR inhibitor resistant non-small cell lung cancer (NSCLC) patient derived xenografts", American Association for Cancer Research, Apr. 8, 2022, pp. 1-6.
Nguyen, "Pancreatic Cancer", Merck Manual, Retrieved from: https://www.merckmanuals.com/home/digestive-disorders/tumors-of-the-digestive-system/pancreatic-cancer?query=pancreatic%20cancer, Mar. 2021, 4 pages.
Palma et al., "CD137 and CD137 Ligand Constitutively Coexpressed on Human T and B Leukemia Cells Signal Proliferation and Survival", Int J Cancer., 2004, 108(3):390-398.
Papadopoulos et al., "Abstract TPS2689: A Combined Phase I/II Study of a Novel Bicycle Tumor-targeted Immune Cell Agonist® BT7480 in Patients with Nectin-4 Associated Advanced Malignancies", ASCO, Jun. 6, 2022, 1 page.

Park et al., "Abstract 3756: Small Synthetic, Multivalent Bicyclic Peptides That Activate T Cell Costimulatory Protein CD137", American Association of Cancer Research, Apr. 14, 2018, pp. 1-9.
Park et al., "Abstract 3756: Small Synthetic, Multivalent Bicyclic Peptides That Activate T Cell Costimulatory Protein CD137", Cancer Res., Jul. 1, 2018, 78(13_Supplement):3756, 2 pages.
Park et al., "Abstract 3756: Small Synthetic, Multivalent Bicyclic Peptides That Activate T Cell Costimulatory Protein CD137", ELRIG Drug Discovery, Oct. 9, 2018, pp. 1-9.
Rajendran et al., "CD137 signaling in Hodgkin and Reed-Sternberg cell lines induces IL-13 secretion, immune deviation and enhanced growth", Oncoimmunology, 2016, 5(6):e1160188, 7 pages.
Repash et al., "BT7480, a novel fully synthetic tumor-targeted immune cell agonist (TICA™) induces tumor localized CD137 agonism", AACR Tumor Immunology & Immunotherapy, Oct. 19, 2020, 10 pages.
Rezvaya et al., "Abstract 1207: NKp46 engaging Bicycle NK-TICA® drives tumor targeted cytotoxicity", SITC, Nov. 10, 2022, 1 page.
Rhodes et al., "Bicyclic Peptides as Next-Generation Therapeutics", Chemistry—A European Journal, 2017, 23(52):12690-12703.
Rietschoten et al., "Abstract 268: Small Synthetic, Multivalent Bicyclic Peptides That Activate T Cell Costimulatory Protein CD137", 35th European Peptide Symposium, Aug. 1, 2018, 1 page.
Rigby et al., "Abstract 4479: BT8009: A bicyclic peptide toxin conjugate targeting Nectin-4 (PVRL4) displays efficacy in preclinical tumor models", Cancer Res, 2019, 79(13_Supplement):4479, 3 pages.
Rigby et al., "Abstract C061: BT8009, a Bicycle® Toxin Conjugate targeting Nectin-4, shows target selectivity, and efficacy in preclinical large and small tumor models", AACR-NCI-EORTC, Oct. 29, 2019, pp. 1-9.
Rigby et al., "BT8009; A Nectin-4 Targeting Bicycle® Toxin Conjugate for Treatment of Solid Tumors", Molecular Cancer Therapeutics, 2022, 21(12):1-27.
Rigby, "Abstract 4479: BT8009: A bicyclic peptide toxin conjugate targeting Nectin-4 (PVRL4) displays efficacy in preclinical tumour models", AACR Annual Meeting, Apr. 2, 2019, 10 pages.
Santos et al., "Abstract 35472: Characterization of Nectin-4 protein expression in non-small cell lung cancer patients", AACR-BC-EORTC, Oct. 13, 2023, pp. 1-4.
Shah et al., "Abstract A28: Establishment of an ex vivo tissue culture platform as a preclinical model to assess the mechanism of action of Bicycle® tumor-targeted immune cell agonists in NSCLC", AACR-BC-EORTC, Oct. 26, 2022, pp. 1-8.
Singh et al., "Protein Engineering Approaches in the Post-Genomic Era", Current Protein and Peptide Science, 2017, 18(4):1-11.
Skynner et al., "BT1718, a novel Bicycle Drug Conjugate® shows potent anti-tumor activity in diverse cell-derived and patient-derived tumor xenograft models", PEGS, Apr. 30, 2017, 1 pages.
Solomons, "Organic Chemistry", 4th ed, 1988, p. 902, 3 pages.
Stanczuk et al., "Abstract 1388: Utility of humanized animal models for in vivo evaluation of NK-TICA®, novel Bicycle® tumor-targeted immune cell agonist® (Bicycle TICA®) designed to engage NK cells", SITC, Nov. 10, 2022, pp. 1-6.
Stanczuk et al., "Abstract 1826: Development of in vivo models for evaluation of NK-TICATM, novel Bicycle® tumortargeted immune cell agonist® designed to engage NK cells", American Association for Cancer Research Annual Meeting, Apr. 17, 2023, pp. 1-6.
Su, "Key DMPK Attributes of BT7480, a Bicycle Tumor-targeted Immune Cell Agonist™ Targeting Nectin-4 and Agonizing CD137", NEDMDG symposium, May 31, 2023, 20 pages.
Teufel et al., "Abstract 4920: Bicyclic Peptides for Positron Emission Tomography (PET) Imaging of MT1-MMP Expressing Tumors", American Association of Cancer Research, Apr. 1, 2017, pp. 1-8.
Thornber, "Isosterism and Molecular Modification in Drug Design", Chem. Soc. Rev, 1979, 8(4):563-580.
Tiberghien, "Highlighting the Potential of Bicycle Conjugates to Target Solid Tumours", World ADC, Mar. 20, 2023, 24 pages.
Uhlenbroich et al., "Abstract 0000: NKp46 engaging Bicycle NK-TICA™ drives tumor targeted cytotoxicity", PEGS Boston, May 17, 2023, 1 page.

(56) References Cited

OTHER PUBLICATIONS

Uhlenbroich, "Bicycles—a modality for Tumor-Targeted Immune Cell Agonism", Antibody Engineering & Therapeutics, Jun. 12, 2023, 23 pages.

Upadhyaya et al., "Abstract 888: An integrative approach to optimize a synthetic EphA2-dependent CD137 agonist: Balancing potency, physiochemical properties, and pharmacokinetics to achieve robust anti-tumor activity", SITC, Nov. 12, 2021, pp. 1-7.

Upadhyaya et al., "Anticancer immunity induced by a synthetic tumor-targeted CD137 agonist", Journal for Immunotherapy of Cancer, 2021, 9(1):e001762, pp. 1-10.

Upadhyaya et al., "Discovery and Optimization of a Synthetic Class of Nectin-4-Targeted CD137 Agonists for Immuno-oncology", Molecular Cancer Therapeutics, 2022, 65:9858-9872.

Valko et al., "Application of biomimetic HPLC to estimate lipophilicity, protein and phospholipid binding of potential peptide therapeutics", ADMET and DMPK, 2018, 6(2):162-175.

Wagstaff et al., "An Assay for Periplasm Entry Advances the Development of Chimeric Peptide Antibiotics", ACS Infectious Diseases, 2020, 6(9):2355-2361.

Wallack et al., "Abstract P05: Investigating soluble Nectin-4 and EphA2 as cancer biomarkers in plasma", Bio-IT World, May 23, 2023, pp. 1-6.

Walsh et al., "Abstract 5807: Bicycle Toxin Conjugates® for the treatment of solid tumors", American Association for Cancer Research Annual Meeting, Apr. 9, 2024, pp. 1-7.

Wang et al., "Comprehensive Surfaceome Profiling to Identify and Validate Novel Cell-Surface Targets in Osteosarcoma", Molecular Cancer Therapeutics, Jun. 2022, 21(6):903-913.

Wang et al., "Integrative surfaceome profiling identifies immunotherapeutic targets in osteosarcoma and preclinical testing of BT1769, an MT1-MMP-targeted Bicycle® toxin conjugate, in osteosarcoma by the Pediatric Preclinical Testing Consortium (PPTC)", AACR Annual Meeting, Apr. 10-15 and May 17-21, 2021, 15 pages.

Xu et al., "The application of PK/PD modelling in the clinical development of BT5528—a novel toxin delivery platform", ACoP, Oct. 30-Nov. 2, 2022, 21 pages.

Yampolsky et al., "The Exchangeability of Amino Acids in Proteins", Genetics, Aug. 2005, 170(4):1459-1472.

Zhang et al., "Characterization and application of three novel monoclonal antibodies against human 4-1BB: distinct epitopes of human 4-1BB on lung tumor cells and immune cells", Tissue Antigens, 2007, 70(6):470-479.

Zhang et al., "Propagated Perturbations from a Peripheral Mutation Show Interactions Supporting WW Domain Thermostability", Structure, Nov. 6, 2018, 26(11):1474-1485.

U.S. Appl. No. 18/427,414, Beswick et al., filed Jan. 30, 2024.
U.S. Appl. No. 18/742,691, Chen, filed Jun. 13, 2024.
U.S. Appl. No. 18/906,616, Beswick et al., filed Oct. 4, 2024.

(A)

(B)

(A)

(B)

(A)

(B)

MULTIMERIC BICYCLIC PEPTIDE LIGANDS

CROSS REFERENCE TO RELATED APPLICATIONS

This application is a divisional of U.S. patent application Ser. No. 17/080,021, filed Oct. 26, 2020 (now U.S. Pat. No. 11,542,304), which is a divisional of U.S. patent application Ser. No. 16/282,877, filed Feb. 22, 2019 (now U.S. Pat. No. 10,875,894), which claims the benefit of priority under 35 U.S.C. § 119 (a)-(d) to GB Patent Application No. 1818158.6, filed Nov. 7, 2018, GB Patent Application No. 1805848.7, filed Apr. 9, 2018, and GB Patent Application No. 1802931.4, filed Feb. 23, 2018, the contents of each of which are herein incorporated by reference in their entirety.

SEQUENCE LISTING

The instant application contains a Sequence Listing which has been submitted electronically in XML format and is hereby incorporated by reference in its entirety. Said XML copy, created on Mar. 30, 2023, is named Bicycle_194725_SL.xml and is 117,081 bytes in size.

FIELD OF THE INVENTION

The present invention relates to multimers of polypeptides which are covalently bound to molecular scaffolds such that two or more peptide loops are subtended between attachment points to the scaffold. The invention also describes the multimerization of polypeptides through various chemical linkers and hinges of various lengths and rigidity using different sites of attachments within polypeptides. In particular, the invention describes multimers of peptides which are high affinity binders and activators of CD137. The invention also includes drug conjugates comprising said peptides, conjugated to one or more effector and/or functional groups, to pharmaceutical compositions comprising said peptide ligands and drug conjugates and to the use of said peptide ligands and drug conjugates in preventing, suppressing or treating a disease or disorder mediated by CD137.

BACKGROUND OF THE INVENTION

Protein-protein interactions are important regulators of cellular functions. These interactions typically involve large surface areas and as such can neither be easily inhibited nor mimicked using typical small molecule therapeutic agents. Additionally, many important receptor classes (receptor tyrosine kinases, cytokine receptors, tumor necrosis factor (TNF) receptors, T-cell receptors and G-protein coupled receptors) require oligomerization of receptor monomer units in a particular orientation to activate the receptor signaling pathway. Recombinant proteins such as monoclonal antibodies and fusion proteins (e.g. ligand-Fc fusions) are able to bind and induce oligomerization of such receptors due to high affinity and large interaction surface areas with the potential for multivalent binding. However, large proteins are inefficient at penetrating into tissues and may not be an ideal therapeutic modality for modulating receptors, especially those found on cells that are poorly vascularized or surrounded by barriers to penetration, such as the stromal barrier found in pancreatic cancer. Small synthetic and modular therapeutic modalities with a larger interaction surface than small molecules will be ideal for bypassing the penetration barrier and activating target receptors by oligomerization.

The recent success of immune checkpoint inhibitors, such as anti-PD-1 and anti-PD-L1 antibodies in treating various types of cancers have boosted the interest in molecules that activate co-stimulatory targets, including CD137 on T cells. CD137 (4-1BB/TNFRSF9) belongs to the TNF receptor superfamily and provides costimulatory signaling for T cells.

Inducible CD137 expression is found on activated T-, B-, dendritic and natural killer (NK) cells. Stimulation of CD137 by its natural ligand, CD137L, or by agonistic antibody induces vigorous T-cell proliferation and prevents activation-induced cell death. 4-1BB forms a heterotrimer complex consisting of two TNF-receptor associated factor TRAF-2 complexes in conjunction with TRAF-1. This interaction, through leukocyte specific protein-1 (LSP-1), potentiates signaling through JNK and ERK pathways as well as through β-catenin and AKT. These signaling pathways converge on the master transcription factor NF-κB to regulate 4-1BB signaling, as well as effector immune responses.

Agonistic anti-CD137 antibodies have shown potent, often curative anti-tumor activity in mouse models. Its anti-tumor activity is even further boosted in combination with an anti-PD-1 or anti-CTLA-4 antibody. These effects are mainly mediated by cytotoxic T cells and generate long lasting, memory responses. Two human anti-CD137 antibodies are currently undergoing clinical testing: urelumab has shown single agent, partial responses in melanoma, however hepatoxicity was observed at doses 21 mg/kg and as a result, it is being combined with other immunotherapies at a suboptimal dose of 0.1 mg/kg; utolimumab is also being evaluated in solid tumors in combination with other immunotherapies, but while hepatotoxicity was not observed up to 5 mg/kg, it has little or no single agent activity.

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred-square angstrom, as for example the cyclic peptide CXCR4 antagonist CVX15 (400 Å2; Wu et al. (2007), Science 330, 1066-71), a cyclic peptide with the Arg-Gly-Asp motif binding to integrin αVβ3 (355 Å2) (Xiong et al. (2002), Science 296 (5565), 151-5) or the cyclic peptide inhibitor upain-1 binding to urokinase-type plasminogen activator (603 Å2; Zhao et al. (2007), J Struct Biol 160 (1), 1-10).

Bicycles® are a novel therapeutic class of fully synthetic, constrained bicyclic peptides that have high affinity and exquisite target specificity unachievable with conventional small molecule approaches. The Bicycle® platform uses phage display to rapidly identify and optimize binders that can then be readily chemically optimized to tune affinity and physicochemical properties. Their small size (1.5-2 kDa) delivers advantages in tumor penetration and rapid renal elimination avoids liver and gastrointestinal toxicity often associated with other drug modalities, including certain antibodies. Bicycle® CD137 agonists with rapid renal clearance and lacking Fc receptor interaction could induce anti-tumor activity while avoiding liver toxicity.

There is a need to provide alternative bicyclic peptides which bind and activate their targets with a wide range of potency and efficacy.

SUMMARY OF THE INVENTION

According to a first aspect of the invention, there is provided a multimeric binding complex which comprises at least two bicyclic peptide ligands, wherein said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

According to a further aspect of the invention, there is provided a drug conjugate comprising a multimeric binding complex as defined herein conjugated to one or more effector and/or functional groups.

According to a further aspect of the invention, there is provided a pharmaceutical composition comprising a multimeric binding complex or a drug conjugate as defined herein in combination with one or more pharmaceutically acceptable excipients.

According to a further aspect of the invention, there is provided a multimeric binding complex or drug conjugate as defined herein for use in preventing, suppressing or treating a disease or disorder, such as a disease or disorder mediated by CD137.

DETAILED DESCRIPTION OF THE INVENTION

Figure 1:
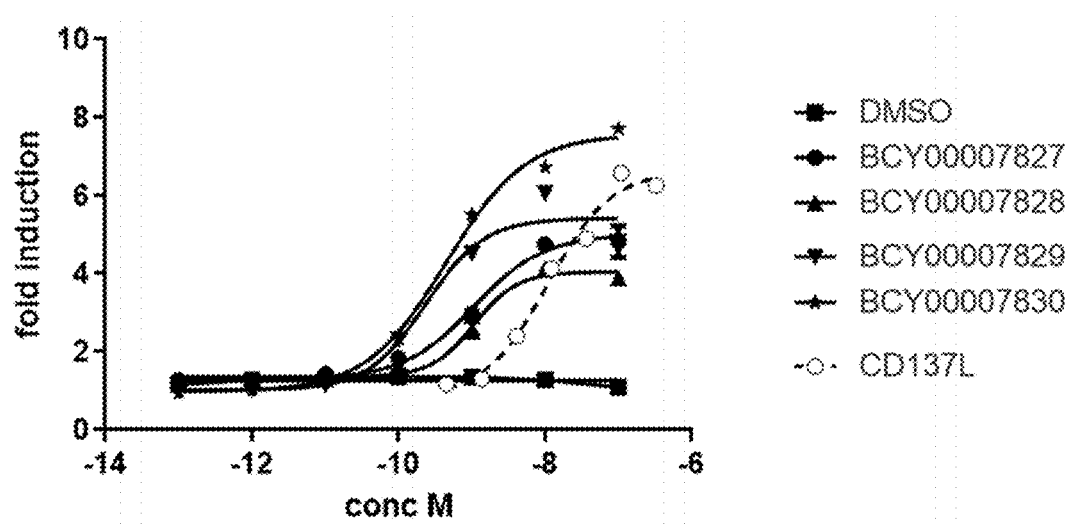
FIG. 1: Reporter cell activity assay data obtained for trimers BCY7827 and BCY7828 and tetramers BCY7829 and BCY7830 compared with CD137L.

According to a first aspect of the invention, there is provided a multimeric binding complex which comprises at least two bicyclic peptide ligands, wherein said peptide ligands may be the same or different, each of which comprises a polypeptide comprising at least three reactive groups, separated by at least two loop sequences, and a molecular scaffold which forms covalent bonds with the reactive groups of the polypeptide such that at least two polypeptide loops are formed on the molecular scaffold.

The present invention describes a series of multimerized bicyclic peptides with various chemical linkers and hinges of various lengths and rigidity using different sites of attachments within said bicyclic peptide which bind and activate targets (such as CD137) with a wide range of potency and efficacy.

It will be appreciated by the skilled person that the concept of the invention is the recognition that multiply arranged (multimeric) bicyclic peptides provide a synergistic benefit by virtue of the resultant properties of said multimeric binding complexes compared to the corresponding monomeric binding complexes which contain a single bicyclic peptide. For example, the multimeric binding complexes of the invention typically have greater levels of binding potency or avidity (as measured herein by Kd values) than their monomeric counterparts. Furthermore, the multimeric binding complexes of the invention are designed to be sufficiently small enough to be cleared by the kidneys.

The complexes of the present invention find particular utility in the treatment of cancer. Thus, in one embodiment, one of said peptide ligands is specific for an epitope present on a T cell or a cancer cell. In a further embodiment, each of said peptide ligands is specific for an epitope present on a T cell or a cancer cell.

Without being bound by theory it is believed that multimerized bicyclic peptides are able to activate receptors by homo-crosslinking more than one of the same receptor. Thus, in one embodiment, said bicyclic peptide ligands are specific for the same target. In a further embodiment, the multimeric binding complex comprises at least two identical bicyclic peptide ligands. By "identical" it is meant bicyclic peptides having the same amino acid sequence, most critically the same amino acid sequence refers to the binding portion of said bicyclic peptide (for example, the sequence may vary in attachment position). In this embodiment, each of the bicyclic peptides within the multimeric binding complex will bind exactly the same epitope upon the same target—the resultant target bound complex will therefore create a homodimer (if the multimeric complex comprises two identical bicyclic peptides), homotrimer (if the multimeric complex comprises three identical bicyclic peptides) or homotetramer (if the multimeric complex comprises four identical bicyclic peptides), etc.

In an alternative embodiment, the multimeric binding complex comprises at least two differing bicyclic peptide ligands. By "differing" it is meant bicyclic peptides having a different amino acid sequence. In this embodiment, the differing bicyclic peptide ligands within the multimeric binding complex will bind to different epitopes on the same target—the resultant target bound complex will therefore create a biparatopic (if the multimeric complex comprises two differing bicyclic peptides), triparatopic (if the multimeric complex comprises three differing bicyclic peptides) or tetraparatopic (if the multimeric complex comprises four differing bicyclic peptides), etc.

Without being bound by theory it is believed that multimerized bicyclic peptides are able to activate receptors by hetero-crosslinking differing targets, such as differing target receptors. Thus, in one embodiment, said bicyclic peptide ligands are specific for different targets. It will be appreciated that in this embodiment, the multimeric binding complex comprises at least two differing bicyclic peptide ligands (i.e. bicyclic peptide ligands having differing amino acid sequences). In this embodiment, each of the bicyclic peptides within the multimeric binding complex will bind a differing epitope upon a different target—the resultant target bound complex will therefore create a bispecific multimeric binding complex (if the multimeric complex comprises two differing bicyclic peptides), trispecific multimeric binding complex (if the multimeric complex comprises three differing bicyclic peptides), tetraspecific multimeric binding complex (if the multimeric complex comprises four differing bicyclic peptides), etc.

It will be appreciated that the multimeric binding complexes of the invention may be designed to be capable of binding to a range of different targets, such as receptors. Suitable examples include any target (i.e. receptor) involved in a cancer, such as members of the TNF receptor super-family (i.e. CD137), receptor tyrosine kinase (RTK), Ig domain receptors (immune checkpoint) etc. It will be appreciated that for the bi-, tri- and tetra-specific multimeric binding complexes referred to hereinbefore the bicyclic peptides may bind to targets on at least two differing cells (such as T, NK or other immune cells).

The bicyclic peptides within the multimeric binding complexes of the invention may be assembled via a number of differing options. For example, there may be a central hinge or branching moiety with spacer or arm elements radiating from said hinge or branch point each of which will contain a bicyclic peptide. Alternatively, it could be envisaged that a circular support member may hold a number of inwardly or outwardly projecting bicyclic peptides.

In one embodiment, each bicyclic peptide ligand is connected to a central hinge moiety by a spacer group.

It will be appreciated that the spacer group may be linear and connect a single bicyclic peptide with the central hinge moiety. Thus, in one embodiment, the multimeric binding complex comprises a compound of formula (I):

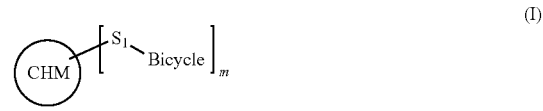

wherein CHM represents a central hinge moiety;
$S_1$ represents a spacer group;
Bicycle represents a bicyclic peptide ligand as defined herein; and
m represents an integer selected from 2 to 10.

In one embodiment, m represents an integer selected from 3 to 10. In a further embodiment, m represents an integer selected from 3 or 4. Data is presented herein which shows that optimal results were achieved with the trimers (m=3) and tetramers (m=4). When m represents 4, it will be appreciated that the central hinge moiety will require 4 points of attachment. Thus, in one embodiment, m represents 4 and CHM is a motif of formula (A):

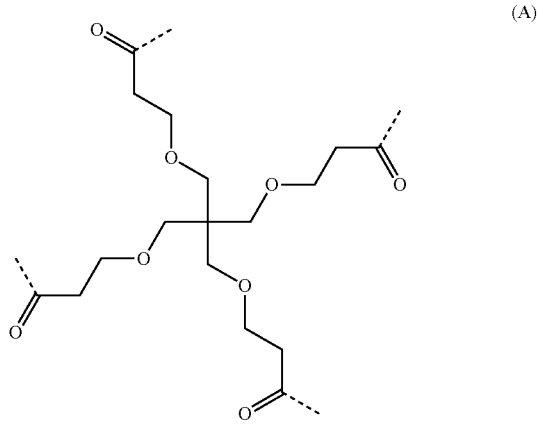

wherein "-----" represents the point of attachment to each $S_1$ group.

When m represents 3, it will be appreciated that the central hinge moiety will require 3 points of attachment. Thus, in one embodiment, m represents 3 and CHM is a motif of formula (B):

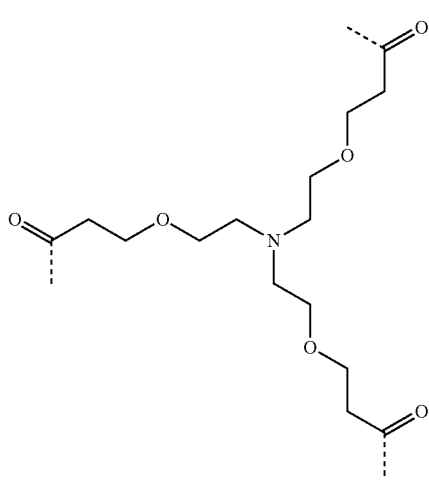

(B)

wherein "-----" represents the point of attachment to each $S_1$ group.

In an alternative embodiment, m represents 3 and CHM is a motif of formula (C):

(C)

wherein "-----" represents the point of attachment to each $S_1$ group.

In an alternative embodiment, m represents 3 and CHM is a motif of formula (D):

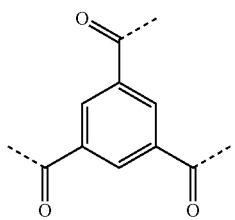

(D)

wherein "-----" represents the point of attachment to each $S_1$ group.

It will be readily apparent to the skilled person how alternative central hinge moieties may be constructed depending upon the value of m.

It will be appreciated that the spacer ($S_1$) may be any suitable construction to link the bicyclic peptide central hinge moiety to the bicyclic peptide. In one embodiment, the spacer ($S_1$) comprises a triazolyl moiety. The advantage of this embodiment is that the triazolyl moiety may be incorporated within the synthesis using commonly available "click" chemistry.

Examples of suitable spacer ($S_1$) groups include one or more PEG moieties, peptide sequences, carbohydrates, lipids and the like.

In a further embodiment, the spacer ($S_1$) comprises one or more PEG moieties. References herein to "PEG" refer to a linear polymer with a regular repeat unit of the general structure: $(CH_2CH_2O)_n$— (where n represents any number, such as 1 to 30).

Thus, in a further embodiment, the spacer ($S_1$) is selected from any one of spacers $S_1A$, $S_1B$, $S_1C$, $S_1D$, $S_1E$, $S_1F$, $S_1G$ and $S_1H$:

$S_1A$ n = 5, 10 and 23

$S_1B$ n = 5, 10

$S_1C$ $n_1 = 5, n_2 = 5$
$n_1 = 10, n_2 = 10$ $S_1D$ $n_1 = 5, n_2 = 5$
$n_1 = 10, n_2 = 10$ $S_1E$ n = 1

-continued $S_1F$

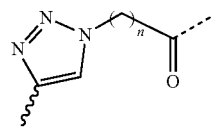

n = 1

$S_1G$

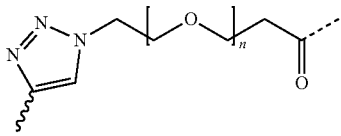

n = 5 and 10

$S_1H$

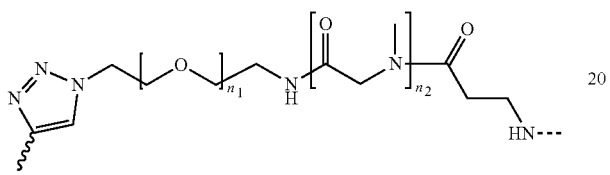

$n_1 = 5, n_2 = 5$
$n_1 = 10, n_2 = 10$ wherein "-----" represents the point of attachment to the CHM group; and "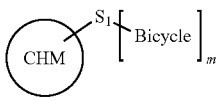" represents the point of attachment to the Bicycle group.

In a yet further embodiment, the spacer ($S_1$) is $S_1A$.

In an alternative arrangement the spacer group may be branched and thus a single spacer group may connect multiple bicyclic peptides with the central hinge moiety. Thus, in an alternative embodiment, the multimeric binding complex comprises a compound of formula (II):

$$\underset{\text{CHM}}{\bigcirc} {-} S_1 {-} [\text{Bicycle}]_m \quad (II)$$

wherein CHM represents a central hinge moiety;
$S_1$ represents a spacer group;
Bicycle represents a bicyclic peptide ligand as defined herein; and
m represents an integer selected from 2 to 10.

It will be appreciated that the bicyclic peptide ligand may be attached to the spacer via a number of means. In one embodiment, the bicyclic peptide ligand is conjugated to one half of a binding pair and said other half of said binding pair links each of the bicyclic peptides to the spacer.

In one embodiment, said binding pair comprises biotin and streptavidin. Thus, each bicyclic peptide ligand is conjugated to biotin and linked to the spacer via streptavidin.

Bicyclic Peptides

It will be appreciated that the multimeric binding complexes herein will comprise a plurality of monomeric bicyclic peptides. In one embodiment, each of said peptide ligands (i.e. monomers) is specific for CD137.

CD137 Bicyclic Peptide Monomers

In one embodiment, said loop sequences comprise 5 or 6 amino acids.

In a further embodiment, said loop sequences comprise three cysteine residues separated by two loop sequences both of which consist of 6 amino acids.

In a yet further embodiment, said peptide ligand comprises a core amino acid sequence selected from:

```
                                    (SEQ ID NO: 23)
C_iIEEGQYC_iiFADPY(Nle)C_iii;

(SEQ ID NO: 24)
C_iIKEGQYC_iiFADPY(Nle)C_iii;

(SEQ ID NO: 25)
C_iIEKGQYC_iiFADPY(Nle)C_iii;

(SEQ ID NO: 26)
C_iIEE(D-K)QYC_iiFADPY(Nle)C_iii;

(SEQ ID NO: 27)
C_iIEEGKYC_iiFADPY(Nle)C_iii;

(SEQ ID NO: 28)
C_iIEEGQYC_iiKADPY(Nle)C_iii;

(SEQ ID NO: 29)
C_iIEEGQYC_iiFADKY(Nle)C_iii;
and (SEQ ID NO: 30)
C_iIEEGQYC_iiFADPYKC_iii;
``` wherein $C_i$, $C_{ii}$ and $C_{iii}$ represent first, second and third cysteine residues, respectively and Nle represents norleucine, or a pharmaceutically acceptable salt thereof.

In a yet further embodiment, said peptide ligand comprises N and C terminal modifications and comprises an amino acid sequence selected from:

```
                    (SEQ ID NO: 31; herein referred to as
                                Monomer 1 and BCY3814)
A-C_iIEEGQYC_iiFADPY(Nle)C_iii-A;

(SEQ ID NO: 32; herein referred to as
                                Monomer 2 and BCY7732)
Ac-A-C_iIEEGQYC_iiFADPY(Nle)C_iii-Dap (SEQ ID NO: 33; herein referred to as
                                Monomer 3 and BCY7733)
Ac-A-C_iIKEGQYC_iiFADPY(Nle)C_iii-A;

(SEQ ID NO: 34; herein referred to as
                                Monomer 4 and BCY7734)
Ac-A-C_iIEKGQYC_iiFADPY(Nle)C_iii-A;

(SEQ ID NO: 35; herein referred to as
                                Monomer 5 and BCY7735)
Ac-A-C_iIEE(D-K)QYC_iiFADPY(Nle)C_iii-A;

(SEQ ID NO: 36; herein referred to as
                                Monomer 6 and BCY7736)
Ac-A-C_iIEEGKYC_iiFADPY(Nle)C_iii-A;

(SEQ ID NO: 37; herein referred to as
                                Monomer 7 and BCY7737)
Ac-A-C_iIEEGQYC_iiKADPY(Nle)C_iii-A;

(SEQ ID NO: 38; herein referred to as
                                Monomer 8 and BCY7738)
Ac-A-C_iIEEGQYC_iiFADKY(Nle)C_iii-A;

(SEQ ID NO: 39; herein referred to as
                                Monomer 9 and BCY7739)
Ac-A-C_iIEEGQYC_iiFADPYKC_iii-A;

(SEQ ID NO: 58; herein referred to as
                                Monomer 10 and BCY8217)
A-C_iIEEGQYC_iiF[D-AJDPY[Nle]C_iii-A;
```

-continued (SEQ ID NO: 59; herein referred to as
Monomer 11 and BCY8919)
Ac-C$_i$[tBuAla]PK[D-AJPYC$_{ii}$FADPY[Nle]C$_{iii}$-A;

(SEQ ID NO: 60; herein referred to as
Monomer 12 and BCY8920)
Ac-C$_i$[tBuAla]PE[D-KJPYC$_{ii}$FADPY[Nle]C$_{iii}$-A;

(SEQ ID NO: 61; herein referred to as
Monomer 13 and BCY8914)
Ac-A-C$_i$IE[D-KJGQYC$_{ii}$F[D-A]DPY[Nle]C$_{iii}$-A;

(SEQ ID NO: 62; herein referred to as
Monomer 14 and BCY8915);
Ac-A-C$_i$IE[D-K]GQYC$_{ii}$F[D-A]DPY[Nle]C$_{iii}$-A;
and (SEQ ID NO: 63; herein referred to as
Monomer 15 and BCY11072)
[Ac]-[D-A]-[D-C$_i$][D-I][D-E][D-E]K[D-Q][D-Y][D-C$_{ii}$]

[D-F][D-A][D-D][D-P][D-Y][D-Nle][D-C$_{iii}$]-[D-A];

wherein C$_i$, C$_{ii}$ and C$_{iii}$ represent first, second and third cysteine residues, respectively, Ac represents an N-terminal acetyl group, Dap represents diaminopropionic acid, tBuAla represents t-butyl-alanine and Nle represents norleucine, or a pharmaceutically acceptable salt thereof.

In a still yet further embodiment, said peptide ligand comprises N and C terminal modifications and comprises an amino acid sequence selected from:

(SEQ ID NO: 31; herein referred
to as Monomer 1 and BCY3814)
A-C$_i$IEEGQYC$_{ii}$FADPY(Nle)C$_{iii}$-A;

(SEQ ID NO: 32; herein referred
to as Monomer 2 and BCY7732)
Ac-A-C$_i$IEEGQYC$_{ii}$FADPY(Nle)C$_{iii}$-Dap;

(SEQ ID NO: 33; herein referred
to as Monomer 3 and BCY7733)
Ac-A-C$_i$IKEGQYC$_{ii}$FADPY(Nle)C$_{iii}$-A;

(SEQ ID NO: 34; herein referred
to as Monomer 4 and BCY7734)
Ac-A-C$_i$IEKGQYC$_{ii}$FADPY(Nle)C$_{iii}$-A;

(SEQ ID NO: 35; herein referred
to as Monomer 5 and BCY7735)
Ac-A-C$_i$IEE(D-K)QYC$_{ii}$FADPY(Nle)C$_{iii}$-A;

(SEQ ID NO: 36; herein referred
to as Monomer 6 and BCY7736)
Ac-A-C$_i$IEEGKYC$_{ii}$FADPY(Nle)C$_{iii}$-A;

(SEQ ID NO: 37; herein referred
to as Monomer 7 and BCY7737)
Ac-A-C$_i$IEEGQYC$_{ii}$KADPY(Nle)C$_{iii}$-A;

(SEQ ID NO: 38; herein referred
to as Monomer 8 and BCY7738)
Ac-A-C$_i$IEEGQYC$_{ii}$FADKY(Nle)C$_{iii}$-A;
and (SEQ ID NO: 39; herein referred
to as Monomer 9 and BCY7739)
Ac-A-C$_i$IEEGQYC$_{ii}$FADPYKC$_{iii}$-A;

wherein C$_i$, C$_{ii}$ and C$_{iii}$ represent first, second and third cysteine residues, respectively, Ac represents an N-terminal acetyl group, Dap represents diaminopropionic acid and Nle represents norleucine, or a pharmaceutically acceptable salt thereof.

In a yet further embodiment, said peptide ligand comprises attachment of a PYA moiety at the N-terminus, C-terminus or Lysine residues within said sequence and comprises an amino acid sequence selected from:

(SEQ ID NO: 40; herein referred to as
Monomer 1A and BCY7740)
(PYA)-A-C$_i$IEEGQYC$_{ii}$FADPY(Nle)C$_{iii}$-A;

(SEQ ID NO: 41; herein referred to as
Monomer 2A and BCY7741)
Ac-A-C$_i$IEEGQYC$_{ii}$FADPY(Nle)C$_{iii}$-Dap(PYA)

(SEQ ID NO: 42; herein referred to as
Monomer 3A and BCY7742)
Ac-A-C$_i$IK(PYA)EGQYC$_{ii}$FADPY(Nle)C$_{iii}$-A;

(SEQ ID NO: 43; herein referred to as
Monomer 4A and BCY7743)
Ac-A-C$_i$IEK(PYA)GQYC$_{ii}$FADPY(Nle)C$_{iii}$-A;

(SEQ ID NO: 44; herein referred to as
Monomer 5A and BCY7744)
Ac-A-C$_i$IEE(D-K)(PYA)QYC$_{ii}$FADPY(Nle)C$_{iii}$-A;

(SEQ ID NO: 45; herein referred to as
Monomer 6A and BCY7745)
Ac-A-C$_i$IEEGK(PYA)YC$_{ii}$FADPY(Nle)C$_{iii}$-A;

(SEQ ID NO: 46; herein referred to as
Monomer 7A and BCY7746)
Ac-A-C$_i$IEEGQYC$_{ii}$K(PYA)ADPY(Nle)C$_{iii}$-A;

(SEQ ID NO: 47; herein referred to as
Monomer 8A and BCY7747)
Ac-A-C$_i$IEEGQYC$_{ii}$FADK(PYA)Y(Nle)C$_{iii}$-A;

(SEQ ID NO: 48; herein referred to as
Monomer 9A and BCY7748)
Ac-A-C$_i$IEEGQYC$_{ii}$FADPYK(PYA)C$_{iii}$-A;

(SEQ ID NO: 64; herein referred to as
Monomer 10A and BCY8935)
(PYA)-A-C$_i$IEEGQYC$_{ii}$F[D-A]DPY[Nle]C$_{iii}$-A;

(SEQ ID NO: 65; herein referred to as
Monomer 11A and BCY8927)
Ac-C$_i$[tBuAla]PK(PYA)[D-A]PYC$_{ii}$FADPY[Nle]C$_{iii}$-A;

(SEQ ID NO: 66; herein referred to as
Monomer 12A and BCY8929)
Ac-C$_i$[tBuAla]PE[D-K(PYA)]PYC$_{ii}$FADPY[Nle]C$_{iii}$-A;

(SEQ ID NO: 67; herein referred to as
Monomer 13A and BCY8925)
Ac-A-C$_i$IE[D-K(PYA)]GQYC$_{ii}$F[D-A]DPY[Nle]C$_{iii}$-A;

(SEQ ID NO: 68; herein referred to as
Monomer 14A and BCY8926)
Ac-A-C$_i$IE[K(PYA)]GQYC$_{ii}$F[D-A]DPY[Nle]C$_{iii}$-A;
and (SEQ ID NO: 69; herein referred to as
Monomer 15A and BCY11506)
[Ac]-[D-A][D-C$_i$][D-I][D-E][D-E][K(PYA)][D-Q][D-Y]

[D-C$_{ii}$][D-F][D-A][D-D][D-P][D-Y][D-Nle][D-C$_{iii}$][D-A]

wherein C$_i$, C$_{ii}$ and C$_{iii}$ represent first, second and third cysteine residues, respectively, Ac represents an N-terminal acetyl group, Dap represents diaminopropionic acid, PYA represents propargyl-acid, tBuAla represents t-butyl-alanine and Nle represents norleucine, or a pharmaceutically acceptable salt thereof.

In a still yet further embodiment, said peptide ligand comprises attachment of a PYA moiety at the N-terminus, C-terminus or Lysine residues within said sequence and comprises an amino acid sequence selected from:

(SEQ ID NO: 40; herein referred
to as Monomer 1A and BCY7740)
(PYA)-A-C$_i$IEEGQYC$_{ii}$FADPY(Nle)C$_{iii}$-A;

(SEQ ID NO: 41; herein referred
to as Monomer 2A and BCY7741)
Ac-A-C$_i$IEEGQYC$_{ii}$FADPY(Nle)C$_{iii}$-Dap(PYA)

(SEQ ID NO: 42; herein referred
to as Monomer 3A and BCY7742)
Ac-A-C$_i$IK(PYA)EGQYC$_{ii}$FADPY(Nle)C$_{iii}$-A;

(SEQ ID NO: 43; herein referred
to as Monomer 4A and BCY7743)
Ac-A-C$_i$IEK(PYA)GQYC$_{ii}$FADPY(Nle)C$_{iii}$-A;

(SEQ ID NO: 44; herein referred
to as Monomer 5A and BCY7744)
Ac-A-C$_i$IEE(D-K)(PYA)QYC$_{ii}$FADPY(Nle)C$_{iii}$-A;

(SEQ ID NO: 45; herein referred
to as Monomer 6A and BCY7745)
Ac-A-C$_i$IEEGK(PYA)YC$_{ii}$FADPY(Nle)C$_{iii}$-A;

(SEQ ID NO: 46; herein referred
to as Monomer 7A and BCY7746)
Ac-A-C$_i$IEEGQYC$_{ii}$K(PYA)ADPY(Nle)C$_{iii}$-A;

(SEQ ID NO: 47; herein referred
to as Monomer 8A and BCY7747)
Ac-A-C$_i$IEEGQYC$_{ii}$FADK(PYA)Y(Nle)C$_{iii}$-A;

(SEQ ID NO: 48; herein referred
to as Monomer 9A and BCY7748)
Ac-A-C$_i$IEEGQYC$_{ii}$FADPYK(PYA)C$_{iii}$-A;

wherein C$_i$, C$_{ii}$ and C$_{iii}$ represent first, second and third cysteine residues, respectively, Ac represents an N-terminal acetyl group, Dap represents diaminopropionic acid, PYA represents propargyl-acid and Nle represents norleucine, or a pharmaceutically acceptable salt thereof.

In a yet further embodiment, said peptide ligand comprises attachment of a BCN moiety at the N-terminus or Lysine residues within said sequence and comprises an amino acid sequence selected from:

(SEQ ID NO: 49; herein referred
to as Monomer 1-BCN and BCY8141)
(BCN)-A-C$_i$IEEGQYC$_{ii}$FADPY(Nle)C$_{iii}$-A;

(SEQ ID NO: 50; herein referred
to as Monomer 3-BCN and BCY8095)
Ac-A-C$_i$IK(BCN)EGQYC$_{ii}$FADPY(Nle)C$_{iii}$-A;

(SEQ ID NO: 51; herein referred
to as Monomer 4-BCN and BCY8142)
Ac-A-C$_i$IEK(BCN)GQYC$_{ii}$FADPY(Nle)C$_{iii}$-A;

(SEQ ID NO: 52; herein referred
to as Monomer 5-BCN and BCY8096)
Ac-A-C$_i$IEE[(D-K)(BCN)]QYC$_{ii}$FADPY(Nle)C$_{iii}$-A;

(SEQ ID NO: 53; herein referred
to as Monomer 6-BCN and BCY8143)
Ac-A-C$_i$IEEGK(BCN)YC$_{ii}$FADPY(Nle)C$_{iii}$-A;

(SEQ ID NO: 54; herein referred
to as Monomer 7-BCN and BCY8144)
Ac-A-C$_i$IEEGQYC$_{ii}$K(BCN)ADPY(Nle)C$_{iii}$-A;
and (SEQ ID NO: 55; herein referred
to as Monomer 9-BCN and BCY8097)
Ac-A-C$_i$IEEGQYC$_{ii}$FADPYK(BCN)C$_{iii}$-A;

wherein C$_i$, C$_{ii}$ and C$_{iii}$ represent first, second and third cysteine residues, respectively, Ac represents an N-terminal acetyl group, Nle represents norleucine and BCN represents:

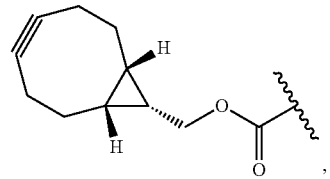 [SMILES: *C(=O)OC[C@@H]1[C@@H]2CCC#CCC[C@@H]21]

or a pharmaceutically acceptable salt thereof.

In an alternative embodiment, said loop sequences comprise three cysteine residues separated by two loop sequences one of which consists of 5 amino acids and the other of which consists of 6 amino acids.

Examples of further monomer sequences which may be used in the present invention are described in the following embodiments.

In one embodiment, said peptide ligand comprises an amino acid sequence selected from:

(SEQ ID NO: 20)
C$_i$-I-E-E-G-Q-Y-C$_{ii}$-X$_1$-X$_2$-D-X$_3$-Y/Q-X$_4$-C$_{iii}$;

(SEQ ID NO: 21)
C$_i$-D-I-G-P-P-T-C$_{ii}$-Y-R/A-D-M/P-Y-M-C$_{iii}$;

(SEQ ID NO: 22)
C$_i$-D-E-W-G-L-F/Y-C$_{ii}$-I/F-P/A-H-S/P-D-C$_{iii}$;
and (SEQ ID NO: 19)
C$_i$IEPGPFC$_{ii}$YADPYMC$_{iii}$;

wherein X$_1$-X$_4$ represent any amino acid residue and C$_i$, C$_{ii}$ and C$_{iii}$ represent first, second and third cysteine residues, respectively or a pharmaceutically acceptable salt thereof.

In one embodiment, said loop sequences comprise three cysteine residues separated by two loop sequences both of which consist of 6 amino acids, and said peptide ligand comprises an amino acid sequence selected from:

(SEQ ID NO: 20)
C$_i$-I-E-E-G-Q-Y-C$_{ii}$-X$_1$-X$_2$-D-X$_3$-Y/Q-X$_4$-C$_{iii}$;

(SEQ ID NO: 21)
C$_i$-D-I-G-P-P-T-C$_{ii}$-Y-R/A-D-M/P-Y-M-C$_{iii}$;

(SEQ ID NO: 19)
C$_i$IEPGPFC$_{ii}$YADPYMC$_{iii}$;

wherein X$_1$-X$_4$ represent any amino acid residue and C$_i$, C$_{ii}$ and C$_{iii}$ represent first, second and third cysteine residues, respectively or a pharmaceutically acceptable salt thereof.

In one embodiment, X$_1$ is selected from Y, F and H.
In one embodiment, X$_2$ is selected from R, A and S.
In one embodiment, X$_3$ is selected from M, P and H.
In one embodiment, X$_4$ is selected from M, Y, L and F.

In one embodiment, said loop sequences comprise three cysteine residues separated by two loop sequences the first of which consists of 6 amino acids and the second of which consists of 5 amino acids, and said peptide ligand comprises an amino acid sequence selected from:

(SEQ ID NO: 22)
C$_i$-D-E-W-G-L-F/Y-C$_{ii}$-I/F-P/A-H-S/P-D-C$_{iii}$;

wherein C$_i$, C$_{ii}$ and C$_{iii}$ represent first, second and third cysteine residues, respectively or a pharmaceutically acceptable salt thereof.

In a further embodiment, the peptide ligand of $C_i$-I-E-E-G-Q-Y-$C_{ii}$-$X_1$-$X_2$-D-$X_3$-Y/Q-$X_4$-$C_{iii}$ (SEQ ID NO: 20) comprises an amino acid sequence selected from:

$C_i$IEEGQYC$_{ii}$YRDMYMC$_{iii}$;  (SEQ ID NO: 1)

$C_i$IEEGQYC$_{ii}$YADPYMC$_{iii}$;  (SEQ ID NO: 2)

$C_i$IEEGQYC$_{ii}$YADPYYC$_{iii}$;  (SEQ ID NO: 3)

$C_i$IEEGQYC$_{ii}$YSDPYYC$_{iii}$;  (SEQ ID NO: 4)

$C_i$IEEGQYC$_{ii}$FADPYMC$_{iii}$;  (SEQ ID NO: 5)

$C_i$IEEGQYC$_{ii}$YADHQLC$_{iii}$;  (SEQ ID NO: 6)

$C_i$IEEGQYC$_{ii}$HADPYYC$_{iii}$;  (SEQ ID NO: 7)

$C_i$IEEGQYC$_{ii}$HADPYFC$_{iii}$;  (SEQ ID NO: 8)

$C_i$IEEGQYC$_{ii}$YADHYMC$_{iii}$;  (SEQ ID NO: 9)

$C_i$IEEGQYC$_{ii}$YADPYLC$_{iii}$;  (SEQ ID NO: 10)

$C_i$IEEGQYC$_{ii}$YSDPYLC$_{iii}$;  (SEQ ID NO: 11)

$C_i$IEEGQYC$_{ii}$FADPYLC$_{iii}$;  (SEQ ID NO: 12)

$C_i$IEEGQYC$_{ii}$HADPYMC$_{iii}$;  (SEQ ID NO: 13)
and $C_i$IEEGQYC$_{ii}$HADPQMC$_{iii}$;  (SEQ ID NO: 14)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-I-E-E-G-Q-Y-$C_{ii}$-$X_1$-$X_2$-D-$X_3$-Y/Q-$X_4$-$C_{iii}$ (SEQ ID NO: 20) comprises an amino acid sequence selected from:
A-(SEQ ID NO: 1)-A (herein referred to as 74-01-00-N004);
A-(SEQ ID NO: 2)-A (herein referred to as 74-01-01-N001);
A-(SEQ ID NO: 3)-A (herein referred to as 74-01-02-N001);
A-(SEQ ID NO: 4)-A (herein referred to as 74-01-03-N001);
A-(SEQ ID NO: 5)-A (herein referred to as 74-01-04-N001);
A-(SEQ ID NO: 6)-A (herein referred to as 74-01-05-N001);
A-(SEQ ID NO: 7)-A (herein referred to as 74-01-06-N001);
A-(SEQ ID NO: 8)-A (herein referred to as 74-01-07-N001);
A-(SEQ ID NO: 9)-A (herein referred to as 74-01-08-N001);
A-(SEQ ID NO: 10)-A (herein referred to as 74-01-09-N001);
A-(SEQ ID NO: 10)-SVG (herein referred to as 74-01-09-T03-N002);
A-(SEQ ID NO: 11)-A (herein referred to as 74-01-10-N001);
A-(SEQ ID NO: 12)-A (herein referred to as 74-01-11-N001);
A-(SEQ ID NO: 13)-A (herein referred to as 74-01-13-N001); and
A-(SEQ ID NO: 14)-A (herein referred to as 74-01-14-N001).

In a further embodiment, the peptide ligand of $C_i$-D-I-G-P-P-Y-$C_{ii}$-Y-R/A-D-M/P-Y-M-$C_{iii}$ (SEQ ID NO: 21) comprises an amino acid sequence selected from:

$C_i$DIGPPYC$_{ii}$YRDMYMC$_{iii}$;  (SEQ ID NO: 15)
and $C_i$DIGPPYC$_{ii}$YADPYMC$_{iii}$;  (SEQ ID NO: 16)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-I-G-P-P-Y-$C_{ii}$-Y-R/A-D-M/P-Y-M-$C_{iii}$ (SEQ ID NO: 21) comprises an amino acid sequence selected from:
A-(SEQ ID NO: 15)-A (herein referred to as 74-01-16-N001); and
A-(SEQ ID NO: 16)-A (herein referred to as 74-01-17-N001).

In a further embodiment, the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:

$C_i$DEWGLFC$_{ii}$IPHSDC$_{iii}$;  (SEQ ID NO: 17)
and $C_i$DEWGLYC$_{ii}$FAHPDC$_{iii}$;  (SEQ ID NO: 18)

wherein $C_i$, $C_{ii}$ and $C_{iii}$ represent first, second and third cysteine residues, respectively, or a pharmaceutically acceptable salt thereof.

In a further embodiment, the peptide ligand of $C_i$-D-E-W-G-L-F/Y-$C_{ii}$-I/F-P/A-H-S/P-D-$C_{iii}$ (SEQ ID NO: 22) comprises an amino acid sequence selected from:
Ac-A-(SEQ ID NO: 17)-A (herein referred to as 74-02-00-N004); and
A-(SEQ ID NO: 18)-A (herein referred to as 74-02-01-N001).

In one embodiment, the peptide ligand of $C_i$IEPGPFC$_{ii}$YADPYMC$_{iii}$ (SEQ ID NO: 19) comprises an amino acid sequence of:
A-(SEQ ID NO: 19)-NRV (herein referred to as 74-19-00-T01-N002).

In one embodiment, the molecular scaffold is 1,1',1"-(1,3,5-triazinane-1,3,5-triyl)triprop-2-en-1-one (TATA).

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, NY; Ausubel et al., Short Protocols in Molecular Biology (1999) 4th ed., John Wiley & Sons, Inc.), which are incorporated herein by reference.

Numbering

When referring to amino acid residue positions within peptides of the invention, cysteine residues ($C_i$, $C_{ii}$ and $C_{iii}$) are omitted from the numbering as they are invariant, therefore, the numbering of amino acid residues within the peptides of the invention is referred to as below:

(SEQ ID NO: 1)
$C_i$-I-E-E-G-Q-Y-$C_{ii}$-Y-R-D-M-Y-M-$C_{iii}$.

For the purpose of this description, all bicyclic peptides are assumed to be cyclised with TBMB (1,3,5-tris(bromomethyl)benzene) or 1,1',1''-(1,3,5-triazinane-1,3,5-triyl)triprop-2-en-1-one (TATA) and yielding a tri-substituted structure. Cyclisation with TBMB and TATA occurs on $C_i$, $C_{ii}$, and $C_{iii}$.

Molecular Format

N- or C-terminal extensions to the bicycle core sequence are added to the left or right side of the sequence, separated by a hyphen. For example, an N-terminal βAla-Sar$_{10}$-Ala tail would be denoted as:

(SEQ ID NO: X)
βAla-Sar$_{10}$-A-.

Inversed Peptide Sequences

In light of the disclosure in Nair et al (2003) J Immunol 170(3), 1362-1373, it is envisaged that the peptide sequences disclosed herein would also find utility in their retro-inverso form. For example, the sequence is reversed (i.e. N-terminus becomes C-terminus and vice versa) and their stereochemistry is likewise also reversed (i.e. D-amino acids become L-amino acids and vice versa).

Peptide Ligands

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

Multimeric Binding Complexes

Trimers

In one embodiment, the multimeric binding complex comprises a trimeric binding complex described in the following Table 1:

TABLE 1

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY7750 | BCY7741 | 3 | B (TCA) | S$_1$A: n = 10 | C-terminal Dap (PYA) |
| BCY7749 | BCY7741 | 3 | B (TCA) | S$_1$A: n = 23 | C-terminal Dap (PYA) |
| BCY7827 | BCY7740 | 3 | B (TCA) | S$_1$A: n = 10 | N-terminal PYA |
| BCY7828 | BCY7740 | 3 | B (TCA) | S$_1$A: n = 23 | N-terminal PYA |
| BCY7831 | BCY7742 | 3 | B (TCA) | S$_1$A: n = 10 | Lys(PYA)$_2$ |
| BCY7832 | BCY7742 | 3 | B (TCA) | S$_1$A: n = 23 | Lys(PYA)$_2$ |
| BCY7835 | BCY7743 | 3 | B (TCA) | S$_1$A: n = 10 | Lys(PYA)$_3$ |
| BCY7836 | BCY7743 | 3 | B (TCA) | S$_1$A: n = 23 | Lys(PYA)$_3$ |
| BCY7839 | BCY7744 | 3 | B (TCA) | S$_1$A: n = 10 | D-Lys(PYA)$_4$ |
| BCY7840 | BCY7744 | 3 | B (TCA) | S$_1$A: n = 23 | D-Lys(PYA)$_4$ |
| BCY7843 | BCY7745 | 3 | B (TCA) | S$_1$A: n = 10 | Lys(PYA)$_5$ |
| BCY7844 | BCY7745 | 3 | B (TCA) | S$_1$A: n = 23 | Lys(PYA)$_5$ |
| BCY7847 | BCY7746 | 3 | B (TCA) | S$_1$A: n = 10 | Lys(PYA)$_7$ |
| BCY7848 | BCY7746 | 3 | B (TCA) | S$_1$A: n = 23 | Lys(PYA)$_7$ |
| BCY7851 | BCY7747 | 3 | B (TCA) | S$_1$A: n = 10 | Lys(PYA)$_{10}$ |
| BCY7852 | BCY7747 | 3 | B (TCA) | S$_1$A: n = 23 | Lys(PYA)$_{10}$ |
| BCY7855 | BCY7748 | 3 | B (TCA) | S$_1$A: n = 10 | Lys(PYA)$_{12}$ |
| BCY7856 | BCY7748 | 3 | B (TCA) | S$_1$A: n = 23 | Lys(PYA)$_{12}$ |
| BCY8102 | BCY8096 | 3 | B (TCA) | S$_1$A: n = 10 | D-Lys(BCN)$_4$ |
| BCY8103 | BCY8096 | 3 | B (TCA) | S$_1$A: n = 23 | D-Lys(BCN)$_4$ |
| BCY8106 | BCY8097 | 3 | B (TCA) | S$_1$A: n = 10 | Lys(BCN)$_{12}$ |
| BCY8107 | BCY8097 | 3 | B (TCA) | S$_1$A: n = 23 | Lys(BCN)$_{12}$ |
| BCY8098 | BCY8095 | 3 | B (TCA) | S$_1$A: n = 10 | Lys(BCN)$_2$ |
| BCY8099 | BCY8095 | 3 | B (TCA) | S$_1$A: n = 23 | Lys(BCN)$_2$ |
| BCY8145 | BCY8144 | 3 | B (TCA) | S$_1$A: n = 10 | Lys(BCN)$_7$ |
| BCY8146 | BCY8144 | 3 | B (TCA) | S$_1$A: n = 23 | Lys(BCN)$_7$ |
| BCY8151 | BCY8143 | 3 | B (TCA) | S$_1$A: n = 10 | Lys(BCN)$_5$ |
| BCY8581 | BCY8935 | 3 | B (TCA) | S$_1$A: n = 10 | N-terminal PYA |
| BCY8582 | BCY8935 | 3 | B (TCA) | S$_1$A: n = 23 | N-terminal PYA |
| BCY8948 | BCY8928 | 3 | B (TCA) | S$_1$A: n = 10 | D-Lys(PYA)$_4$ |

TABLE 1-continued

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY8957 | BCY7743 | 3 | B (TCA) | $S_1B$: n = 5 | Lys(PYA)$_3$ |
| BCY8958 | BCY7743 | 3 | B (TCA) | $S_1A$: n = 5 | Lys(PYA)$_3$ |
| BCY8961 | BCY7743 | 3 | B (TCA) | $S_1C$: $n_1$ = 5, $n_2$ = 5 | Lys(PYA)$_3$ |
| BCY8962 | BCY7743 | 3 | B (TCA) | $S_1D$: $n_1$ = 5, $n_2$ = 5 | Lys(PYA)$_3$ |
| BCY8965 | BCY7743 | 3 | B (TCA) | $S_1B$: n = 10 | Lys(PYA)$_3$ |
| BCY9573 | BCY7743 | 3 | B (TCA) | $S_1C$: $n_1$ = 10, $n_2$ = 10 | Lys(PYA)$_3$ |
| BCY9595 | BCY7743 | 3 | B (TCA) | $S_1D$: $n_1$ = 10, $n_2$ = 10 | Lys(PYA)$_3$ |
| BCY9775 | BCY7744 | 3 | C (Trimesic acid) | $S_1A$: n = 10 | D-Lys(PYA)$_4$ |
| BCY9776 | BCY7744 | 3 | C (Trimesic acid) | $S_1A$: n = 23 | D-Lys(PYA)$_4$ |
| BCY10046 | BCY7744 | 3 | D (c(KGKGKG)) (cyclic (SEQ ID NO: 57)) | $S_1G$: n = 5 | D-Lys(PYA)$_4$ |
| BCY10047 | BCY7744 | 3 | D (c(KGKGKG)) (cyclic (SEQ ID NO: 57)) | $S_1G$: n = 10 | D-Lys(PYA)$_4$ |
| BCY11194 | BCY7744, BCY8928 | 2 × BCY7744 and 1 × BCY8928 | B (TCA) | $S_1A$: n = 10 | D-Lys(PYA)$_4$ |
| BCY11195 | BCY8925, BCY8928 | 2 × BCY8925 and 1 × BCY8928 | B (TCA) | $S_1A$: n = 10 | D-Lys(PYA)$_4$ |
| BCY11196 | BCY8925, BCY7744 | 2 × BCY8925 and 1 × BCY7744 | B (TCA) | $S_1A$: n = 10 | D-Lys(PYA)$_4$ |
| BCY11382 | BCY7744 | 3 | C (Trimesic acid) | $S_1E$: n = 1 | D-Lys(PYA)$_4$ |
| BCY11383 | BCY7744 | 3 | D (c(KGKGKG)) (cyclic (SEQ ID NO: 57)) | $S_1F$: n = 1 | D-Lys(PYA)$_4$ |
| BCY11450 | BCY11072 | 3 | B (TCA) | $S_1A$: n = 10 | L-Lys(PYA)$_4$ |

Data is presented herein which demonstrates that certain trimeric binding complexes of Table 1 displayed EC50 improvement relative to the CD137 ligand (see Table 4A).

In a further embodiment, the multimeric binding complex comprises a trimer comprising three bicyclic peptides each of which are BCY7741 as defined herein, which is linked via the C-terminal DAP(PYA) moiety to a spacer molecule ($S_1A$) wherein n represents 23 and wherein ($S_1A$) is linked to a central hinge moiety which is (B) as defined herein. This multimeric binding complex is referred to herein as BCY7749. Data is presented herein in FIG. 2 which shows high levels of CD137 agonism compared with the corresponding monomer (BCY7741) which demonstrated no agonism. Data is also presented in FIG. 6 which shows the stability of BCY7749 to mouse plasma.

In an alternative further embodiment, the multimeric binding complex comprises a trimer comprising three bicyclic peptides each of which are BCY7741 as defined herein, which is linked via the C-terminal DAP(PYA) moiety to a spacer molecule ($S_1A$) wherein n represents 10 and wherein ($S_1A$) is linked to a central hinge moiety which is (B) as defined herein. This multimeric binding complex is referred to herein as BCY7750. Data is presented herein in FIG. 2 which shows high levels of CD137 agonism compared with the corresponding monomer (BCY7741) which demonstrated no agonism.

In an alternative further embodiment, the multimeric binding complex comprises a trimer comprising three bicyclic peptides each of which are BCY7743 as defined herein, which is linked via a Lys(PYA)$_3$ moiety to a spacer molecule ($S_1A$) wherein n represents 10 and wherein ($S_1A$) is linked to a central hinge moiety which is (B) as defined herein. This multimeric binding complex is referred to herein as BCY7835. Data is presented in FIG. 5B which demonstrated that the multimeric bicycle conjugate BCY7835 retained the property of rapid systemic elimination characteristic of monomeric bicyclic peptides and bicyclic peptide drug conjugates (BDCs). Data is also presented in FIG. 6 which shows the stability of BCY7835 to mouse plasma. Data is also presented in FIG. 7 wherein it can be seen that BCY7835 elicits a range of anti-tumor activities as compared to a CD137 monoclonal antibody agonist that has previously been shown to elicit a CD137 dependent anti-tumour activity.

Figure 12:
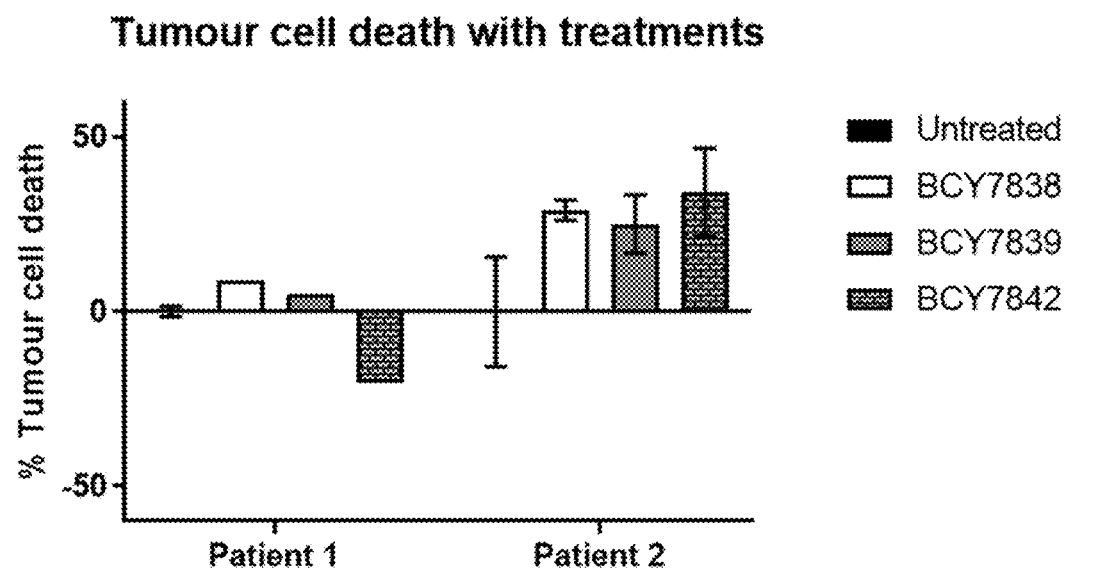
FIG. 12: Percentage of cell death, normalized to untreated control, after 2 days in 3D spheroid culture of two melanoma tumours. (A) Tumour cells are the live CD45 negative population and (B) lymphocytes are the live CD45 positive population as determined by flow cytometry. Significance is calculated using a 2-way ANOVA multiple comparison, $p<0.05$.
Figure 12:
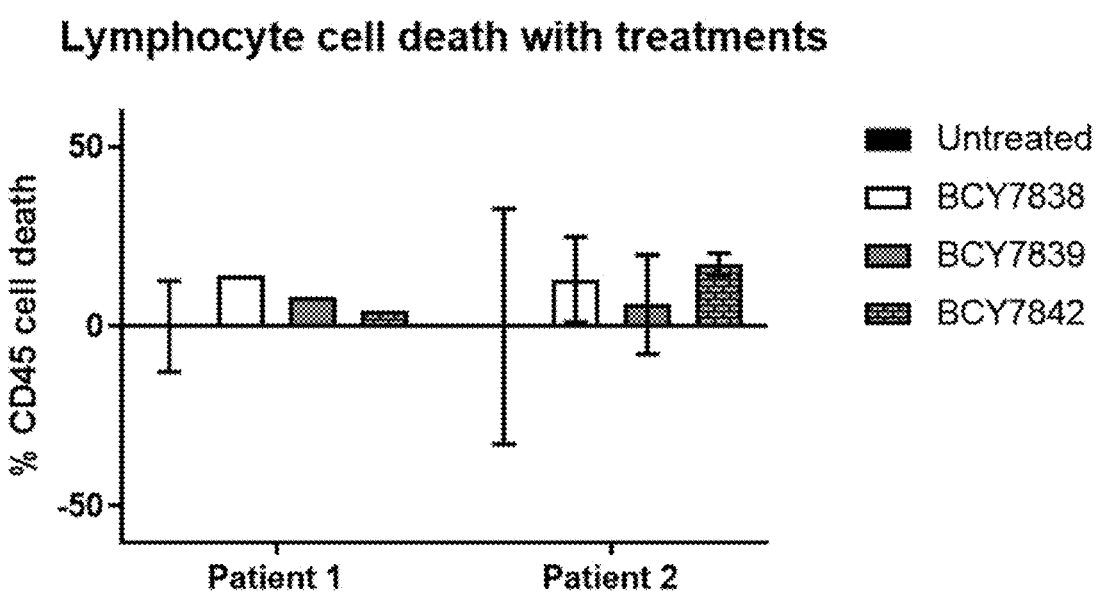

In a further alternative embodiment, the multimeric binding complex comprises a trimer comprising three bicyclic peptides each of which are BCY7744 as defined herein, which is linked via a D-Lys(PYA)$_4$ moiety to a spacer molecule (S$_1$A) wherein n represents 10 and wherein (S$_1$A) is linked to a central hinge moiety which is (B) as defined herein. This multimeric binding complex is referred to herein as BCY7839. Data is presented herein in FIG. 12 which demonstrates significant tumour cell death in response to treatment with BCY7839 in one melanoma patient sample, but not the other (FIG. 12A) and with no significant difference between treatments on lymphocyte numbers (FIG. 12B). Data is also presented herein in FIG. 13 which demonstrates that BCY7839 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY7839. Data is also presented herein in FIG. 15 which demonstrates that BCY7839 activates CD137 on the surface of Jurkat reporter cells.

In one embodiment which may be mentioned, the multimeric binding complex is a trimer selected from BCY7749, BCY7750, BCY7835 and BCY7839, such as BCY7839.

Tetramers

In one embodiment, the multimeric binding complex comprises a tetrameric binding complex described in the following Table 2:

TABLE 2

Exemplified Tetrameric Binding Complexes of the Invention

| Multimer Compound Number | Corresponding Monomer | Number of Monomers | Central Hinge Moiety | Spacer Molecule | Attachment Point |
| --- | --- | --- | --- | --- | --- |
| BCY7751 | BCY7741 | 4 | A (TET) | S$_1$A: n = 10 | C-terminal Dap(PYA) |
| BCY7752 | BCY7741 | 4 | A (TET) | S$_1$A: n = 23 | C-terminal Dap(PYA) |
| BCY7829 | BCY7740 | 4 | A (TET) | S$_1$A: n = 10 | N-terminal PYA |
| BCY7830 | BCY7740 | 4 | A (TET) | S$_1$A: n = 23 | N-terminal PYA |
| BCY7833 | BCY7742 | 4 | A (TET) | S$_1$A: n = 10 | Lys(PYA)$_2$ |
| BCY7834 | BCY7742 | 4 | A (TET) | S$_1$A: n = 23 | Lys(PYA)$_2$ |
| BCY7837 | BCY7743 | 4 | A (TET) | S$_1$A: n = 10 | Lys(PYA)$_3$ |
| BCY7838 | BCY7743 | 4 | A (TET) | S$_1$A: n = 23 | Lys(PYA)$_3$ |
| BCY7841 | BCY7744 | 4 | A (TET) | S$_1$A: n = 10 | D-Lys(PYA)$_4$ |
| BCY7842 | BCY7744 | 4 | A (TET) | S$_1$A: n = 23 | D-Lys(PYA)$_4$ |
| BCY7845 | BCY7745 | 4 | A (TET) | S$_1$A: n = 10 | Lys(PYA)$_5$ |
| BCY7846 | BCY7745 | 4 | A (TET) | S$_1$A: n = 23 | Lys(PYA)$_5$ |
| BCY7849 | BCY7746 | 4 | A (TET) | S$_1$A: n = 10 | Lys(PYA)$_7$ |
| BCY7850 | BCY7746 | 4 | A (TET) | S$_1$A: n = 23 | Lys(PYA)$_7$ |
| BCY7853 | BCY7747 | 4 | A (TET) | S$_1$A: n = 10 | Lys(PYA)$_{10}$ |
| BCY7854 | BCY7747 | 4 | A (TET) | S$_1$A: n = 23 | Lys(PYA)$_{10}$ |
| BCY7857 | BCY7748 | 4 | A (TET) | S$_1$A: n = 10 | Lys(PYA)$_{12}$ |
| BCY7858 | BCY7748 | 4 | A (TET) | S$_1$A: n = 23 | Lys(PYA)$_{12}$ |
| BCY8104 | BCY8096 | 4 | A (TET) | S$_1$A: n = 10 | D-Lys(BCN)$_4$ |
| BCY8105 | BCY8096 | 4 | A (TET) | S$_1$A: n = 23 | D-Lys(BCN)$_4$ |
| BCY8108 | BCY8097 | 4 | A (TET) | S$_1$A: n = 10 | Lys(BCN)$_{12}$ |
| BCY8109 | BCY8097 | 4 | A (TET) | S$_1$A: n = 23 | Lys(BCN)$_{12}$ |
| BCY8100 | BCY8095 | 4 | A (TET) | S$_1$A: n = 10 | Lys(BCN)$_2$ |
| BCY8101 | BCY8095 | 4 | A (TET) | S$_1$A: n = 23 | Lys(BCN)$_2$ |
| BCY8147 | BCY8144 | 4 | A (TET) | S$_1$A: n = 10 | Lys(BCN)$_7$ |
| BCY8148 | BCY8144 | 4 | A (TET) | S$_1$A: n = 23 | Lys(BCN)$_7$ |
| BCY8149 | BCY8141 | 4 | A (TET) | S$_1$A: n = 23 | N-terminal BCN |
| BCY8150 | BCY8142 | 4 | A (TET) | S$_1$A: n = 10 | Lys(BCN)$_3$ |
| BCY8583 | BCY8935 | 4 | A (TET) | S$_1$A: n = 10 | N-terminal PYA |
| BCY8584 | BCY8935 | 4 | A (TET) | S$_1$A: n = 23 | N-terminal PYA |
| BCY8937 | BCY8926 | 4 | A (TET) | S$_1$A: n = 23 | Lys(PYA)$_3$ |
| BCY8945 | BCY8927 | 4 | A (TET) | S$_1$A: n = 23 | Lys(PYA)$_3$ |
| BCY8946 | BCY8927 | 4 | A (TET) | S$_1$A: n = 10 | Lys(PYA)$_3$ |
| BCY8947 | BCY8928 | 4 | A (TET) | S$_1$A: n = 10 | D-Lys(PYA)$_4$ |
| BCY8959 | BCY7743 | 4 | A (TET) | S$_1$B: n = 5 | Lys(PYA)$_3$ |
| BCY8960 | BCY7743 | 4 | A (TET) | S$_1$A: n = 5 | Lys(PYA)$_3$ |
| BCY8963 | BCY7743 | 4 | A (TET) | S$_1$C: n$_1$ = 5, n$_2$ = 5 | Lys(PYA)$_3$ |
| BCY8964 | BCY7743 | 4 | A (TET) | S$_1$D: n$_1$ = 5, n$_2$ = 5 | Lys(PYA)$_3$ |
| BCY8966 | BCY7743 | 4 | A (TET) | S$_1$B: n = 10 | Lys(PYA)$_3$ |
| BCY9113 | BCY8926 | 4 | A (TET) | S$_1$A: n = 10 | Lys(PYA)$_3$ |
| BCY9767 | BCY7743 | 4 | A (TET) | S$_1$H: n$_1$ = 10, n$_2$ = 10 | Lys(PYA)$_3$ |
| BCY10388 | BCY8928 | 4 | A (TET) | S$_1$A: n = 23 | D-Lys(PYA)$_4$ |
| BCY11451 | BCY11506 | 4 | A (TET) | S$_1$A: n = 23 | L-Lys(PYA)$_4$ |

Data is presented herein which demonstrates that certain tetrameric binding complexes of Table 2 displayed EC50 improvement relative to the CD137 ligand (see Table 4A).

In a further embodiment, the multimeric binding complex comprises a tetramer comprising four bicyclic peptides each of which are BCY7741 as defined herein, which is linked via the C-terminal DAP(PYA) moiety to a spacer molecule $(S_1A)$ wherein n represents 10 and wherein $(S_1A)$ is linked to a central hinge moiety which is (A) as defined herein. This multimeric binding complex is referred to herein as BCY7751. Data is presented herein in FIG. 2 which shows high levels of CD137 agonism compared with the corresponding monomer (BCY7741) which demonstrated no agonism.

In a further alternative embodiment, the multimeric binding complex comprises a tetramer comprising four bicyclic peptides each of which are BCY7741 as defined herein, which is linked via the C-terminal DAP(PYA) moiety to a spacer molecule $(S_1A)$ wherein n represents 23 and wherein $(S_1A)$ is linked to a central hinge moiety which is (A) as defined herein. This multimeric binding complex is referred to herein as BCY7752. Data is presented herein in FIG. 2 which shows high levels of CD137 agonism compared with the corresponding monomer (BCY7741) which demonstrated no agonism.

In a further alternative embodiment, the multimeric binding complex comprises a tetramer comprising four bicyclic peptides each of which are BCY7745 as defined herein, which is linked via the Lysine5 amino acid residue to a spacer molecule $(S_1A)$ wherein n represents 10 and wherein $(S_1A)$ is linked to a central hinge moiety which is (A) as defined herein. This multimeric binding complex is referred to herein as BCY7845. Data is presented herein in FIG. 3 which shows high levels of CD137 agonism compared with the corresponding monomer (BCY7741) which demonstrated no agonism. Data is also presented in FIG. 6 which shows the stability of BCY7845 to mouse plasma.

In a further alternative embodiment, the multimeric binding complex comprises a tetramer comprising four bicyclic peptides each of which are BCY7745 as defined herein, which is linked via the Lysine5 amino acid residue to a spacer molecule $(S_1A)$ wherein n represents 23 and wherein $(S_1A)$ is linked to a central hinge moiety which is (A) as defined herein. This multimeric binding complex is referred to herein as BCY7846. Data is presented herein in FIG. 3 which shows high levels of CD137 agonism compared with the corresponding monomer (BCY7741) which demonstrated no agonism.

In a further alternative embodiment, the multimeric binding complex comprises a tetramer comprising four bicyclic peptides each of which are BCY7740 as defined herein, which is linked via an N-terminal PYA moiety to a spacer molecule $(S_1A)$ wherein n represents 10 and wherein $(S_1A)$ is linked to a central hinge moiety which is (A) as defined herein. This multimeric binding complex is referred to herein as BCY7829. Data is presented herein in FIG. 1 which shows high levels of CD137 agonism. Data is also presented herein in FIG. 4 which shows the stability of BCY7829 to human, cyno, rat and mouse plasma. Data is also presented in FIG. 5A which demonstrated that the multimeric bicycle conjugate BCY7829 retained the property of rapid systemic elimination characteristic of monomeric bicyclic peptides and bicyclic peptide drug conjugates (BDCs). Data is also presented in FIG. 6 which shows the stability of BCY7829 to mouse plasma. Data is also presented in FIG. 7 wherein it can be seen that BCY7829 elicits a range of anti-tumor activities as compared to a CD137 monoclonal antibody agonist that has previously been shown to elicit a CD137 dependent anti-tumour activity.

In a further alternative embodiment, the multimeric binding complex comprises a tetramer comprising four bicyclic peptides each of which are BCY7743 as defined herein, which is linked via a $Lys(PYA)_3$ moiety to a spacer molecule $(S_1A)$ wherein n represents 23 and wherein $(S_1A)$ is linked to a central hinge moiety which is (A) as defined herein. This multimeric binding complex is referred to herein as BCY7838. Data is presented herein in FIG. 5B which demonstrated that the multimeric bicycle conjugate BCY7838 retained the property of rapid systemic elimination characteristic of monomeric bicyclic peptides and bicyclic peptide drug conjugates (BDCs). Data is also presented in FIG. 6 which shows the stability of BCY7838 to mouse plasma. Data is also presented in FIG. 7 wherein it can be seen that BCY7838 elicits a range of anti-tumor activities as compared to a CD137 monoclonal antibody agonist that has previously been shown to elicit a CD137 dependent anti-tumour activity. Data is also presented herein in FIG. 12 which demonstrates significant tumour cell death in response to treatment with BCY7838 in one melanoma patient sample, but not the other (FIG. 12A) and with no significant difference between treatments on lymphocyte numbers (FIG. 12B). Data is also presented herein in FIG. 13 which demonstrates that BCY7838 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY7838.

In a further alternative embodiment, the multimeric binding complex comprises a tetramer comprising four bicyclic peptides each of which are BCY7744 as defined herein, which is linked via a $D-Lys(PYA)_4$ moiety to a spacer molecule $(S_1A)$ wherein n represents 23 and wherein $(S_1A)$ is linked to a central hinge moiety which is (A) as defined herein. This multimeric binding complex is referred to herein as BCY7842. Data is presented in FIG. 8 wherein it can be seen that BCY7842 elicits anti-tumour activity in syngeneic mouse models. Data is also presented in FIGS. 9 and 10 wherein it can be seen that BCY7842 elicits a range of increase in T-cell and CD8+ T-cell percentage, respectively, in the tumor tissue as compared to the CD137 monoclonal antibody agonist. Data is also presented in FIG. 11 wherein it can be seen that BCY7842 elicits a range of decease in T-cell percentage in the tumor tissue as compared to the CD137 monoclonal antibody agonist that has previously been shown to elicit a CD137 dependent anti-tumour activity. Data is also presented herein in FIG. 12 which demonstrates significant tumour cell death in response to treatment with BCY7842 in one melanoma patient sample, but not the other (FIG. 12A) and with no significant difference between treatments on lymphocyte numbers (FIG. 12B). Data is also presented herein in FIG. 13 which demonstrates that BCY7842 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY7842. Data is also presented herein in FIG. 15 which demonstrates that BCY7842 activates CD137 on the surface of Jurkat reporter cells.

In a further alternative embodiment, the multimeric binding complex comprises a tetramer comprising four bicyclic peptides each of which are BCY8927 as defined herein, which is linked via a $Lys(PYA)_3$ moiety to a spacer molecule ($S_1A$) wherein n represents 23 and wherein ($S_1A$) is linked to a central hinge moiety which is (A) as defined herein. This multimeric binding complex is referred to herein as BCY8945. Data is presented in FIG. 8 wherein it can be seen that BCY8945 elicits anti-tumour activity in syngeneic mouse models. Data is also presented in FIGS. 9 and 10 wherein it can be seen that BCY8945 elicits a range of increase in T-cell and CD8+ T-cell percentage, respectively, in the tumor tissue as compared to the CD137 monoclonal antibody agonist. Data is also presented in FIG. 11 wherein it can be seen that BCY8945 elicits a range of decease in T-cell percentage in the tumor tissue as compared to the CD137 monoclonal antibody agonist that has previously been shown to elicit a CD137 dependent anti-tumour activity. Data is also presented herein in FIG. 13 which demonstrates that BCY8945 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY8945. Data is also presented herein in FIG. 15 which demonstrates that BCY8945 activates CD137 on the surface of Jurkat reporter cells.

In a further alternative embodiment, the multimeric binding complex comprises a tetramer comprising four bicyclic peptides each of which are BCY8928 as defined herein, which is linked via a D-Lys(PYA)$_4$ moiety to a spacer molecule ($S_1A$) wherein n represents 10 and wherein ($S_1A$) is linked to a central hinge moiety which is (A) as defined herein. This multimeric binding complex is referred to herein as BCY8947. Data is presented in FIG. 8 wherein it can be seen that BCY8947 elicits anti-tumour activity in syngeneic mouse models. Data is also presented in FIGS. 9 and 10 wherein it can be seen that BCY8947 elicits a range of increase in T-cell and CD8+ T-cell percentage, respectively, in the tumor tissue as compared to the CD137 monoclonal antibody agonist. Data is also presented in FIG. 11 wherein it can be seen that BCY8947 elicits a range of decease in T-cell percentage in the tumor tissue as compared to the CD137 monoclonal antibody agonist that has previously been shown to elicit a CD137 dependent anti-tumour activity. Data is also presented herein in FIG. 13 which demonstrates that BCY8947 maintains cell activity after washout which is consistent with a molecule having high avidity to the trimeric CD137 receptor complex. Data is also presented herein in FIG. 14 which demonstrates that T-cells secrete pro-inflammatory cytokines in response to BCY8947. Data is also presented herein in FIG. 15 which demonstrates that BCY8947 activates CD137 on the surface of Jurkat reporter cells.

In one embodiment, the multimeric binding complex is a tetramer selected from BCY7751, BCY7752, BCY7845, BCY7846, BCY7829, BCY7838, BCY7842, BCY8945 and BCY8947. In one embodiment which may be mentioned, the multimeric binding complex is a tetramer selected from BCY7751, BCY7752, BCY7845, BCY7846, BCY7829, BCY7838 and BCY7842.

In a further embodiment, the multimeric binding complex is as a tetramer selected from BCY7842, BCY8945 and BCY8947.

Pharmaceutically Acceptable Salts

It will be appreciated that salt forms are within the scope of this invention, and references to peptide ligands include the salt forms of said ligands.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the peptides of the invention contain an amine function, these may form quaternary ammonium salts, for example by reaction with an alkylating agent according to methods well known to the skilled person. Such quaternary ammonium compounds are within the scope of the peptides of the invention.

Modified Derivatives

It will be appreciated that modified derivatives of the peptide ligands as defined herein are within the scope of the present invention. Examples of such suitable modified derivatives include one or more modifications selected from:

N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyne-group bearing amino acids that allow functionalisation with alkyne or azide-bearing moieties, respectively.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as $C_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target.

In a further embodiment, the modified derivative comprises a C-terminal modification. In a further embodiment, the C-terminal modification comprises an amide group. In this embodiment, the C-terminal cysteine group (the group referred to herein as $C_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise p-turn conformations (Tugyi et al (2005) PNAS, 102(2), 413-418).

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labelled peptide ligands of the invention, wherein one or more atoms are replaced by atoms having the same atomic number, but an atomic mass or mass number different from the atomic mass or mass number usually found in nature, and peptide ligands of the invention, wherein metal chelating groups are attached (termed "effector") that are capable of holding relevant (radio)isotopes, and peptide ligands of the invention, wherein certain functional groups are covalently replaced with relevant (radio) isotopes or isotopically labelled functional groups.

Examples of isotopes suitable for inclusion in the peptide ligands of the invention comprise isotopes of hydrogen, such as $^2$H (D) and $^3$H (T), carbon, such as $^{11}$C, $^{13}$C and $^{14}$C, chlorine, such as $^{31}$C, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulphur, such as $^{31}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled peptide ligands of the invention, for example, those incorporating a radioactive isotope, are useful in drug and/or substrate tissue distribution studies, and to clinically assess the presence and/or absence of the CD137 target on diseased tissues. The peptide ligands of the invention can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labelled compounds of peptide ligands of the invention can generally be prepared by conventional techniques known to those skilled in the art or by processes analogous to those described in the accompanying Examples using an appropriate isotopically-labeled reagent in place of the non-labeled reagent previously employed.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of hexahydro-1,3,5-triazine, especially 1,3,5-triacryloylhexahydro-1,3,5-triazine ('TATA'), or a derivative thereof.

In one embodiment, the molecular scaffold is 2,4,6-tris (bromomethyl)mesitylene. This molecule is similar to 1,3, 5-tris(bromomethyl)benzene (TBMB) but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene or iodoacetamide. Other scaffold reactive groups that are used to selectively couple compounds to cysteines in proteins are maleimides, αβ unsaturated carbonyl containing compounds and α-halomethylcarbonyl containing compounds. Examples of maleimides which may be used as molecular scaffolds in the invention include: tris-(2-maleimidoethyl) amine, tris-(2-maleimidoethyl)benzene, tris-(maleimido) benzene. An example of an αβ unsaturated carbonyl containing compound is 1,1',1"-(1,3,5-triazinane-1,3,5-triyl) triprop-2-en-1-one (TATA) (Angewandte Chemie, International Edition (2014), 53(6), 1602-1606). An example of an α-halomethylcarbonyl containing compound is N,N',N"-(benzene-1,3,5-triyl)tris(2-bromoacetamide). Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Effector and Functional Groups

According to a further aspect of the invention, there is provided a drug conjugate comprising a peptide ligand as defined herein conjugated to one or more effector and/or functional groups.

Effector and/or functional groups can be attached, for example, to the N and/or C termini of the polypeptide, to an amino acid within the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of Drosophila (Antennapedia), e.g. as described in Chen and Harrison, Biochemical Society Transactions (2007) Volume 35, part 4, p 821; Gupta et al. in Advanced Drug Discovery Reviews (2004) Volume 57 9637. Examples of short peptides which have been shown to be efficient at translocation through plasma membranes include the 16 amino acid penetratin peptide from Drosophila Antennapedia protein (Derossi et al (1994) J Biol. Chem. Volume 269 p 10444), the 18 amino acid 'model amphipathic peptide' (Oehlke et al (1998) Biochim Biophys Acts Volume 1414 p 127) and arginine rich regions of the HIV TAT protein. Non peptidic approaches include the use of small molecule mimics or SMOCs that can be easily attached to biomolecules (Okuyama et al (2007) Nature Methods Volume 4 p 153). Other chemical strategies to add guanidinium groups to molecules also enhance cell penetration (Elson-Scwab et al (2007) J Biol Chem Volume 282 p 13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half-life in the range 12 to 60 hours. In a further embodiment, it will have a tβ half-life of a day or more. In a further embodiment still, it will be in the range 12 to 26 hours.

In one particular embodiment of the invention, the functional group is selected from a metal chelator, which is suitable for complexing metal radioisotopes of medicinal relevance.

Possible effector groups also include enzymes, for instance such as carboxypeptidase G2 for use in enzyme/prodrug therapy, where the peptide ligand replaces antibodies in ADEPT.

In one embodiment, the multimeric binding complexes of the invention contain a cleavable bond, such as a disulphide bond or a protease sensitive bond. Without being bound by theory it is believed that such a cleavable moiety deactivates the complex until it reaches the tumour microenvironment. The benefit of this embodiment provides for the complex to be reduced in size following binding to the target. In a further embodiment, the groups adjacent to the disulphide bond are modified to control the hindrance of the disulphide bond, and by this the rate of cleavage and concomitant release of the binding agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on the targeting entity (here, the bicyclic peptide).

Synthesis

The peptides of the present invention may be manufactured synthetically by standard techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to the manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994.

Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TATA) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulphide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

Pharmaceutical Compositions

According to a further aspect of the invention, there is provided a pharmaceutical composition comprising a multimeric binding complex or a drug conjugate as defined herein in combination with one or more pharmaceutically acceptable excipients.

Generally, the present peptide ligands will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cyclosporine, methotrexate, adriamycin or cisplatinum and immunotoxins. Pharmaceutical compositions can include "cocktails" of various cytotoxic or other agents in conjunction with the protein ligands of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, the peptide ligands of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. Preferably, the pharmaceutical compositions according to the invention will be administered by inhalation. The dosage and frequency of administration will depend on the age, sex and condition of the patient, concurrent administration of other drugs, counter indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the peptide ligands described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

Therapeutic Uses

The bicyclic peptides of the invention have specific utility as CD137 binding agents.

CD137 is a member of the tumour necrosis factor (TNF) receptor family. Its alternative names are tumour necrosis factor receptor superfamily member 9 (TNFRSF9), 4-1BB and induced by lymphocyte activation (ILA). CD137 can be expressed by activated T cells, but to a larger extent on CD8+ than on CD4+ T cells. In addition, CD137 expression is found on dendritic cells, follicular dendritic cells, natural killer cells, granulocytes and cells of blood vessel walls at sites of inflammation. One characterized activity of CD137 is its costimulatory activity for activated T cells. Crosslinking of CD137 enhances T cell proliferation, IL-2 secretion, survival and cytolytic activity. Further, it can enhance immune activity to eliminate tumours in mice.

CD137 is a T-cell costimulatory receptor induced on TCR activation (Nam et al., Curr. Cancer Drug Targets, 5:357-363 (2005); Waits et al., Annu. Rev, Immunol., 23:23-68 (2005)). In addition to its expression on activated CD4+ and CD8+ T cells, CD137 is also expressed on CD4+CD25+ regulatory T cells, natural killer (NK) and NK-T cells, monocytes, neutrophils, and dendritic cells. Its natural ligand, CD137L, has been described on antigen-presenting cells including B cells, monocyte/macrophages, and dendritic cells (Watts et al. Annu. Rev. Immunol, 23:23-68 (2005)). On interaction with its ligand, CD137 leads to increased TCR-induced T-cell proliferation, cytokine production, functional maturation, and prolonged CD8+ T-cell survival (Nam et al, Curr. Cancer Drug Targets, 5:357-363 (2005), Watts et al., Annu. Rev. Immunol, 23:23-68 (2005)).

Signalling through CD137 by either CD137L or agonistic monoclonal antibodies (mAbs) against CD137 leads to increased TCR-induced T cell proliferation, cytokine production and functional maturation, and prolonged CD8+ T cell survival. These effects result from: (1) the activation of the NF-κB, c-Jun $NH_2$-terminal kinase/stress-activated protein kinase (JNK/SAPK), and p38 mitogen-activated protein kinase (MAPK) signalling pathways, and (2) the control of anti-apoptotic and cell cycle-related gene expression.

Experiments performed in both CD137 and CD137L-deficient mice have additionally demonstrated the importance of CD137 costimulation in the generation of a fully competent T cell response. IL-2 and IL-15 activated NK cells express CD137, and ligation of CD137 by agonistic mAbs stimulates NK cell proliferation and IFN-γ secretion, but not their cytolytic activity.

Furthermore, CD137-stimulated NK cells promote the expansion of activated T cells in vitro.

In accordance with their costimulatory function, agonist mAbs against CD137 have been shown to promote rejection of cardiac and skin allografts, eradicate established tumours, broaden primary antiviral CD8+ T cell responses, and increase T cell cytolytic potential. These studies support the view that CD137 signalling promotes T cell function which may enhance immunity against tumours and infection.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a multimeric binding complex or a drug conjugate as defined herein, for use in preventing, suppressing or treating a disease or disorder mediated by CD137.

According to a further aspect of the invention, there is provided a method of preventing, suppressing or treating a disease or disorder mediated by CD137, which comprises administering to a patient in need thereof an effector group and drug conjugate of the multimeric binding complex as defined herein.

In one embodiment, the CD137 is mammalian CD137. In a further embodiment, the mammalian CD137 is human CD137 (hCD137).

In one embodiment, the disease or disorder mediated by CD137 is selected from cancer, infection and inflammation. In a further embodiment, the disorder or disease mediated by CD137 is selected from cancer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the oesophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukaemias, lymphomas) and pre-malignant haematological disorders and disorders of borderline malignancy including haematological malignancies and related conditions of lymphoid lineage (for example acute lymphocytic leukaemia [ALL], chronic lymphocytic leukaemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukaemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In a further embodiment, the cancer is selected from a hematopoietic malignancy such as selected from: non-Hodgkin's lymphoma (NHL), Burkitt's lymphoma (BL), multiple myeloma (MM), B chronic lymphocytic leukaemia (B-CLL), B and T acute lymphocytic leukaemia (ALL), T cell lymphoma (TCL), acute myeloid leukaemia (AML), hairy cell leukaemia (HCL), Hodgkin's Lymphoma (HL), and chronic myeloid leukaemia (CML).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with 1,3,5-Triacryloylhexahydro-1,3,5-triazine (TATA, Sigma). For this, linear peptide was diluted with 50:50 MeCN:H$_2$O up to ~35 mL, ~500 μL of 100 mM TATA in acetonitrile was added, and the reaction was initiated with 5 mL of 1 M NH$_4$HCO$_3$ in H$_2$O. The reaction was allowed to proceed for ~30-60 min at RT, and lyophilised once the reaction had completed (judged by MALDI-MS). Once completed, 1 ml of 1M L-cysteine hydrochloride monohydrate (Sigma) in H$_2$O was added to the reaction for ~60 min at RT to quench any excess TATA.

Following lyophilisation, the modified peptide was purified as above, while replacing the Luna C8 with a Gemini C18 column (Phenomenex), and changing the acid to 0.1% trifluoroacetic acid. Pure fractions containing the correct TATA-modified material were pooled, lyophilised and kept at −20° C. for storage.

All amino acids, unless noted otherwise, were used in the L-configurations.

Multimer Synthesis
General Procedure for Preparation of Compound 3

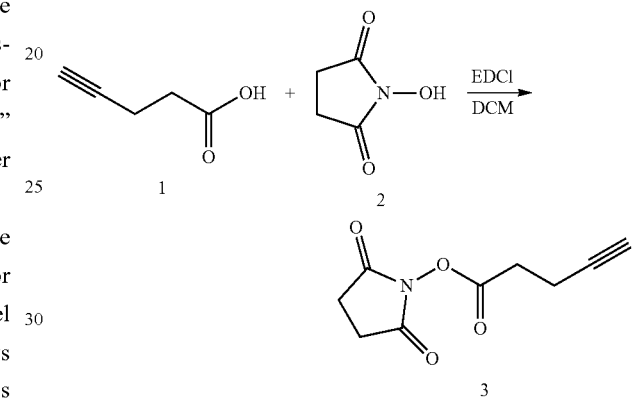

To a solution of compound 1 (500 mg, 5.10 mmol, 1.0 eq) in DCM (25 mL) were added compound 2 (645.2 mg, 5.61 mmol, 1.1 eq) and EDC; (1.95 g, 10.19 mmol, 2.0 eq). The mixture was stirred at 20° C. for 1 hr. TLC (PE:DCM=0:1, R$_f$=0.43, Color Developing Reagent: Bromocresol green) indicated compound 1 was consumed completely and one new spot was formed. The reaction was clean according to TLC. The reaction mixture was concentrated under reduced pressure to give a residue. The residue was purified by column chromatography (SiO$_2$, Petroleum ether/Ethyl acetate=2/1 to 1:1) to give compound 3 (620 mg, 3.18 mmol, 62.33% yield) as a white solid.

$^1$H NMR: 400 MHz CDCl$_3$

δ 2.80~2.95 (m, 6H), 2.55~2.70 (m, 2H), 2.05~2.10 (t, 1H)

General Procedure for Preparation of Compound 5

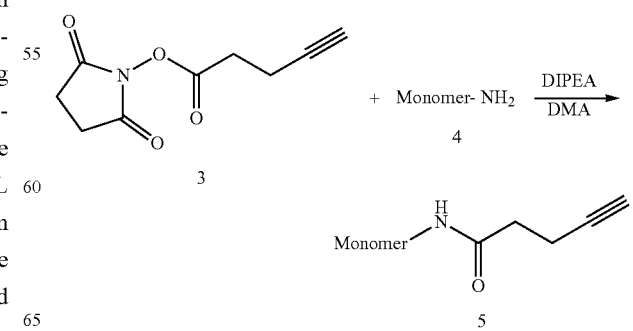

Monomer-NH₂:
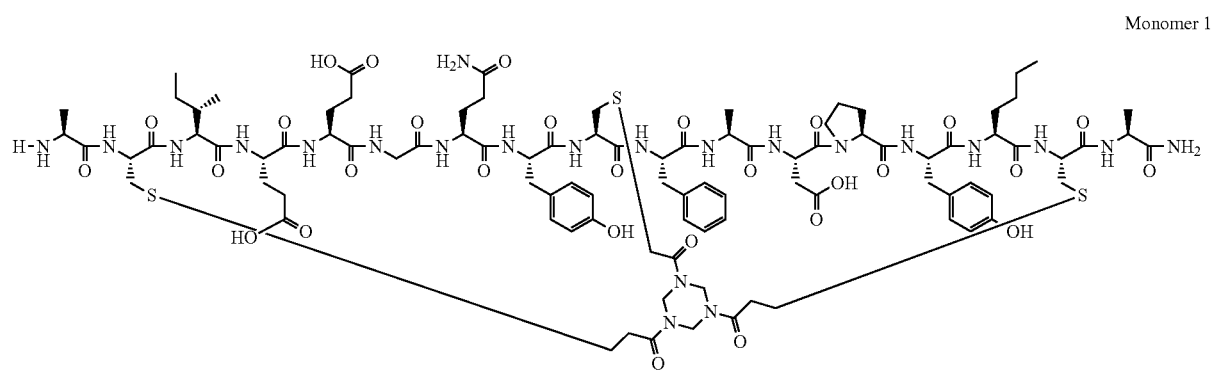
Monomer 1
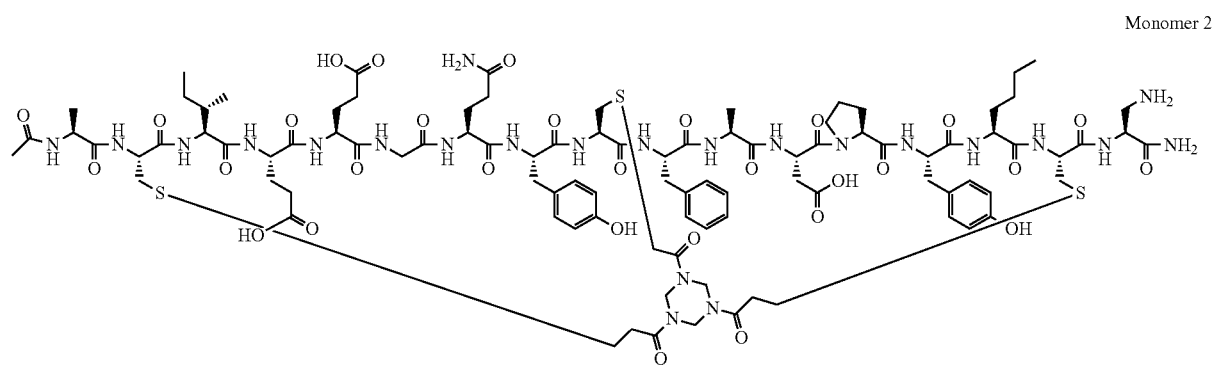
Monomer 2
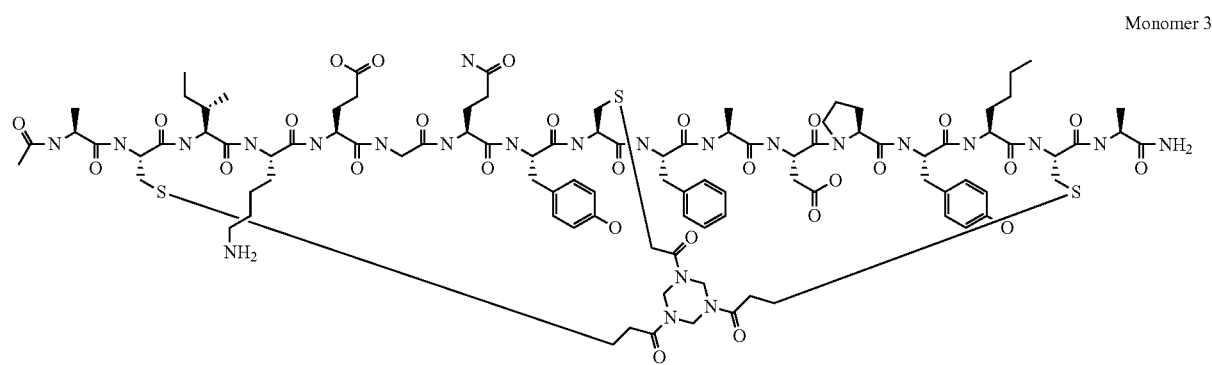
Monomer 3
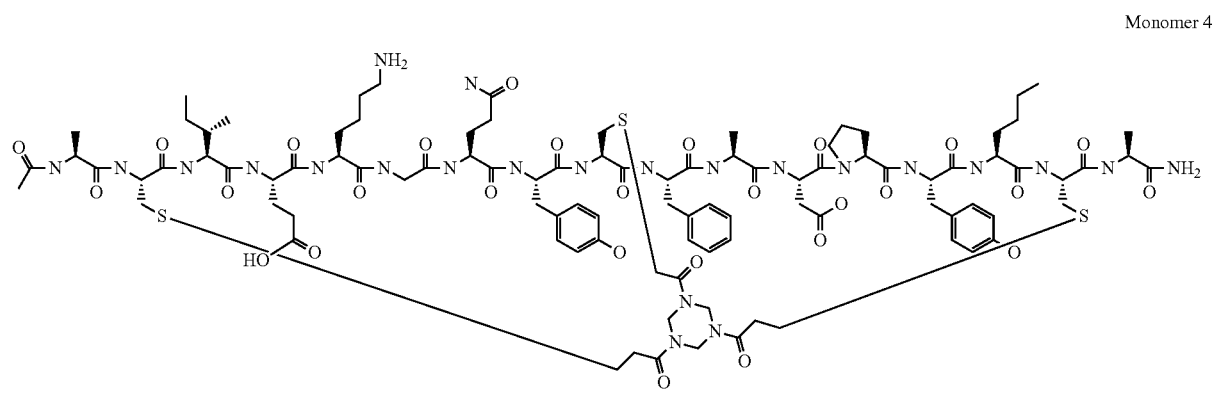
Monomer 4

Monomer 5
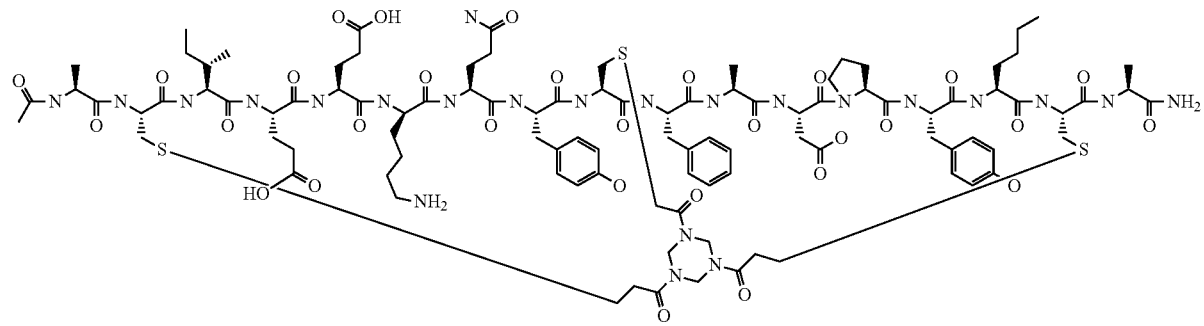
Monomer 6
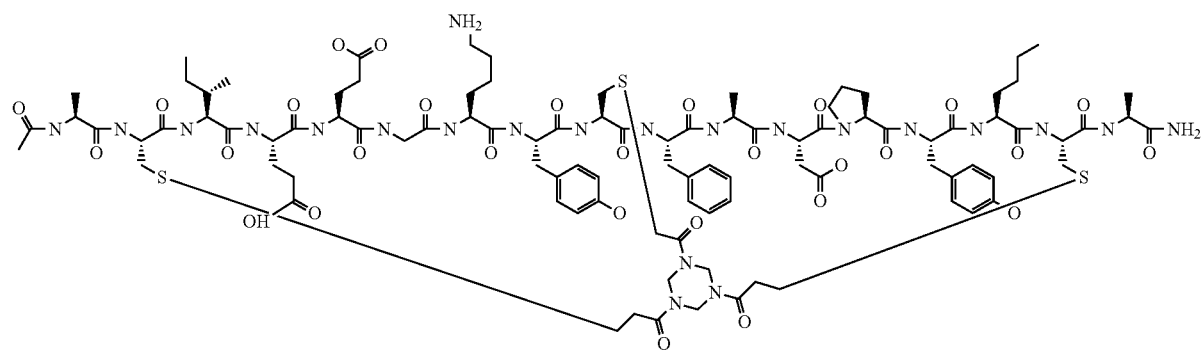
Monomer 7
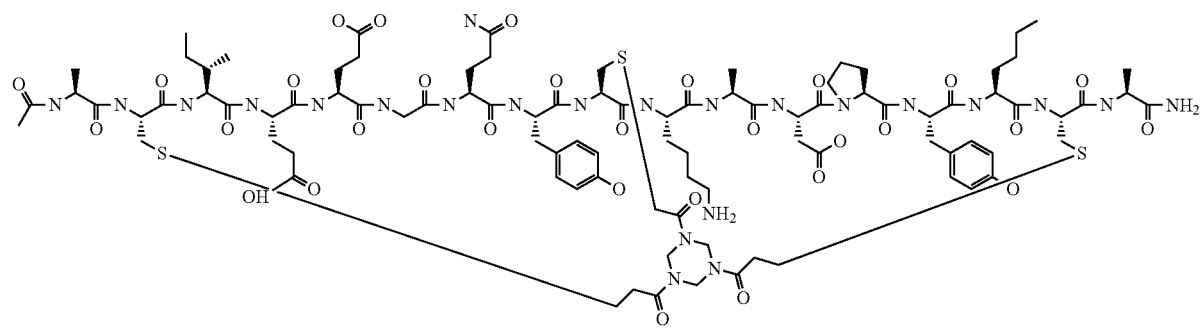
Monomer 8
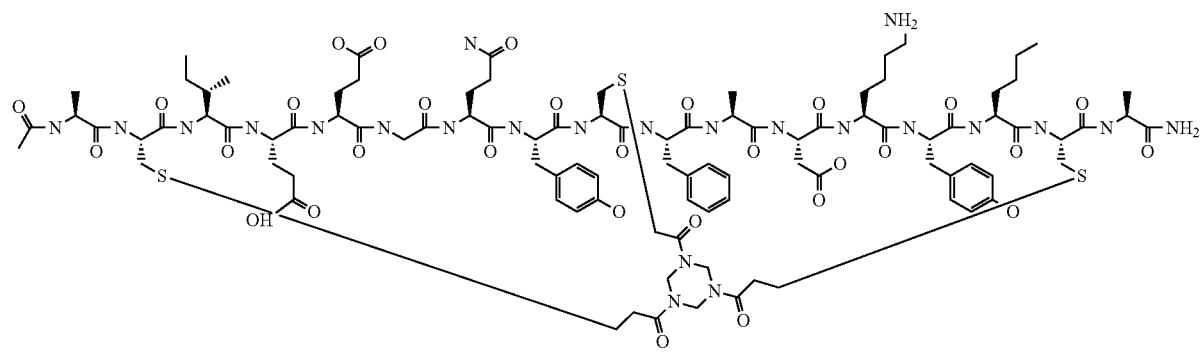

Monomer 9
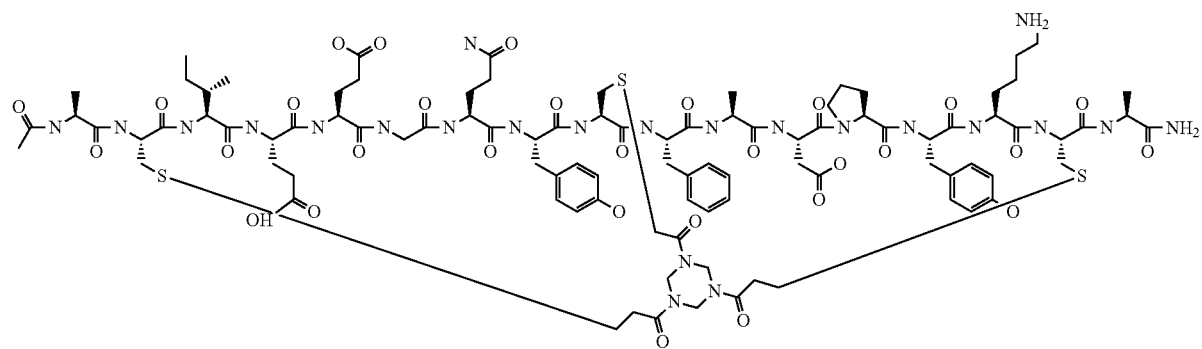
Monomer 10
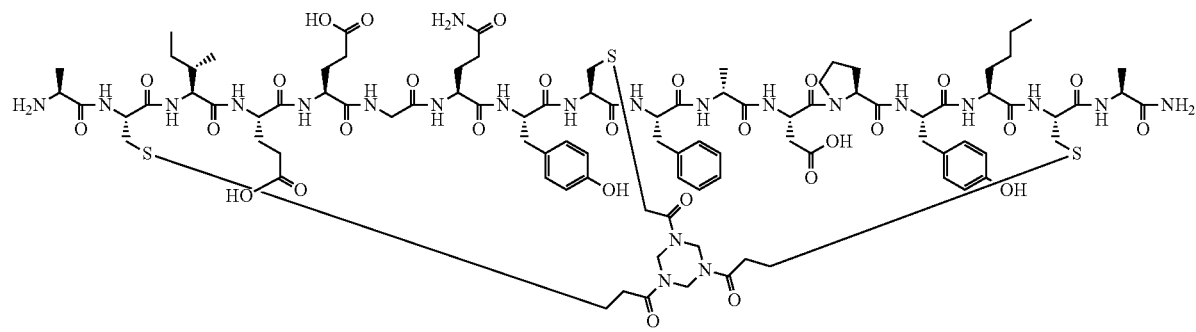
Monomer 11
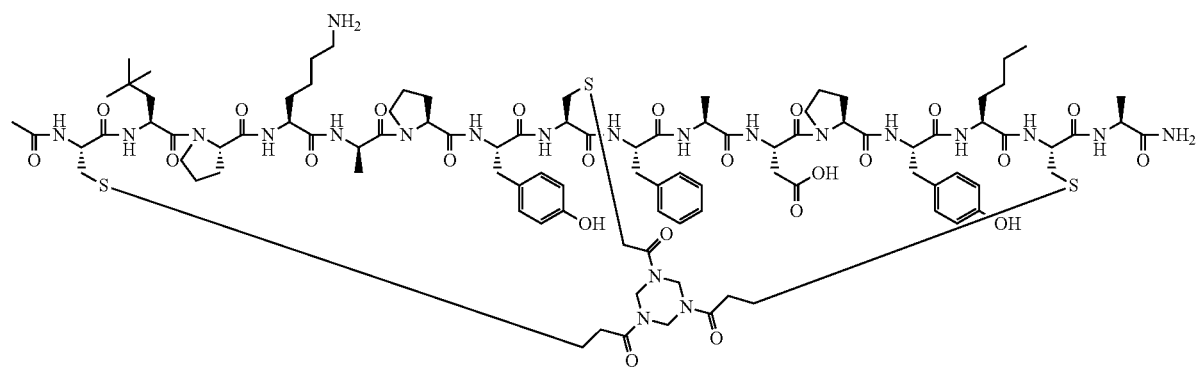
Monomer 12
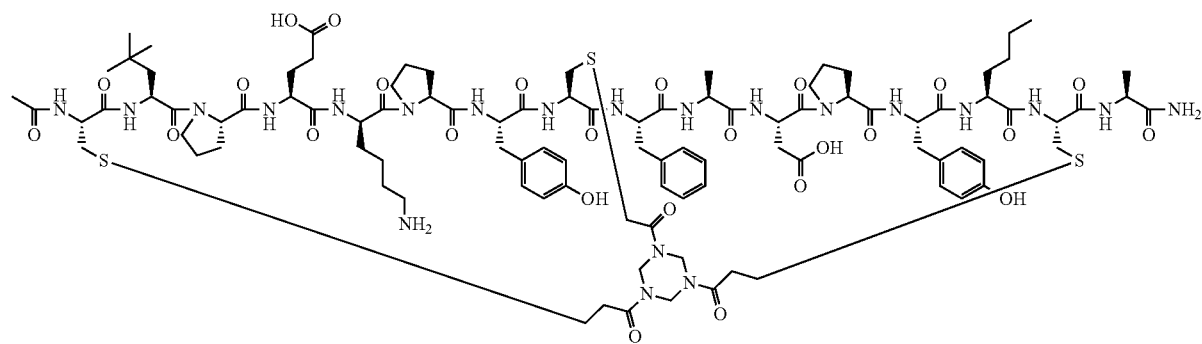

Monomer 13
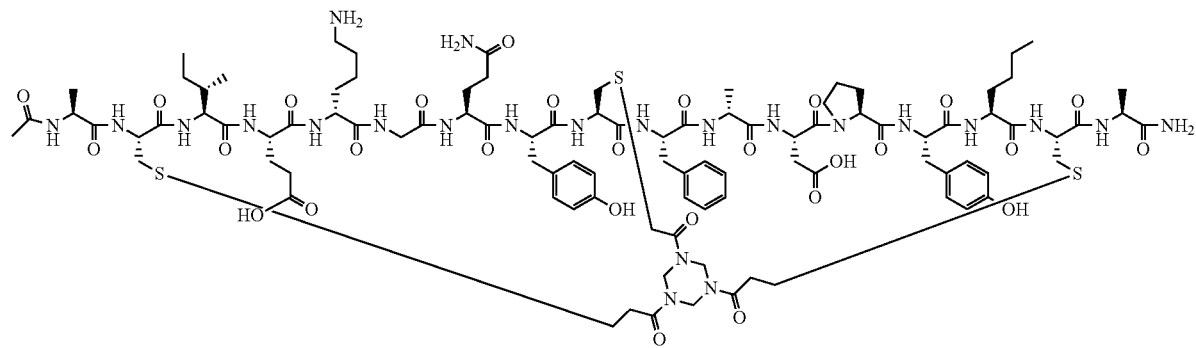
Monomer 14
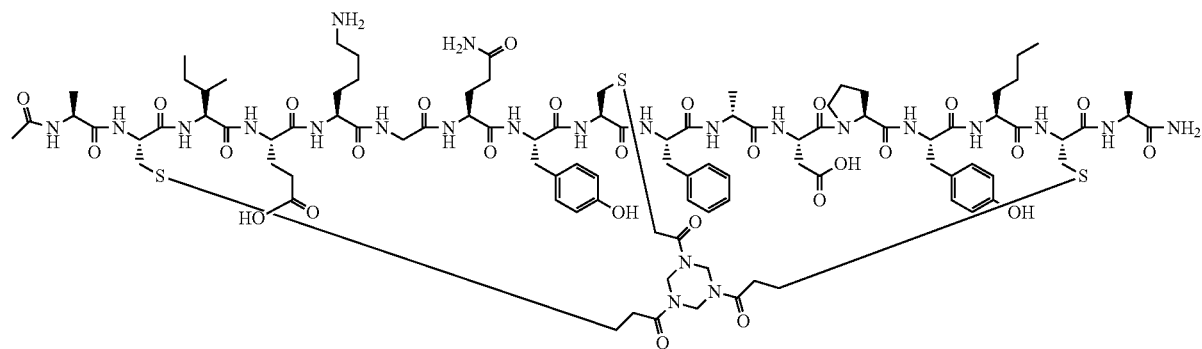
Monomer 15
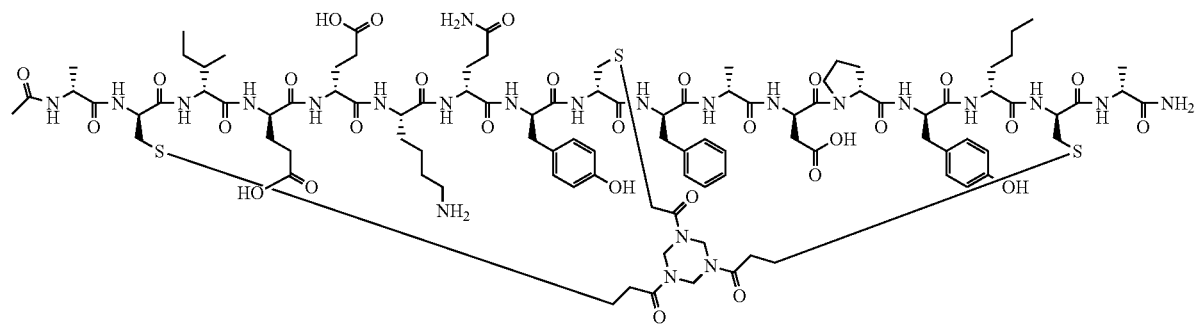
Compound 5:
Monomer 1A
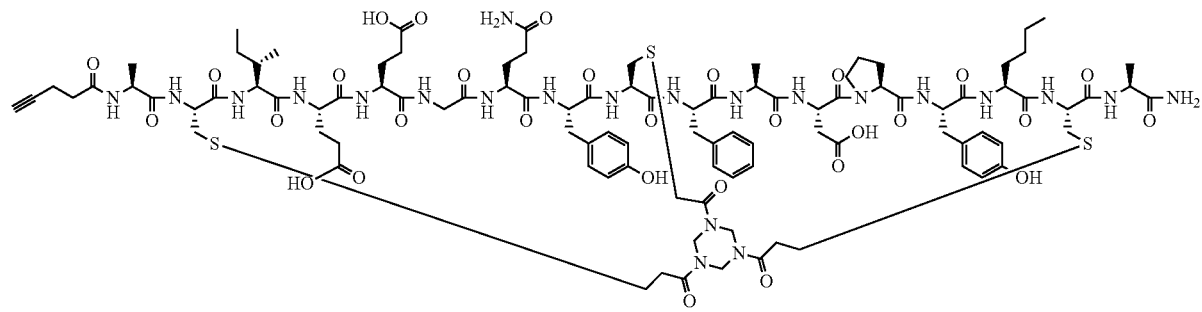

-continued
Monomer 2A
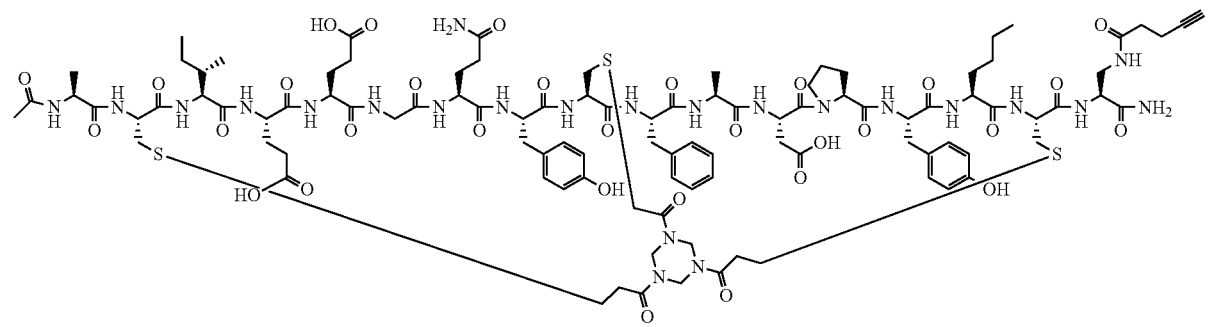
Monomer 3A
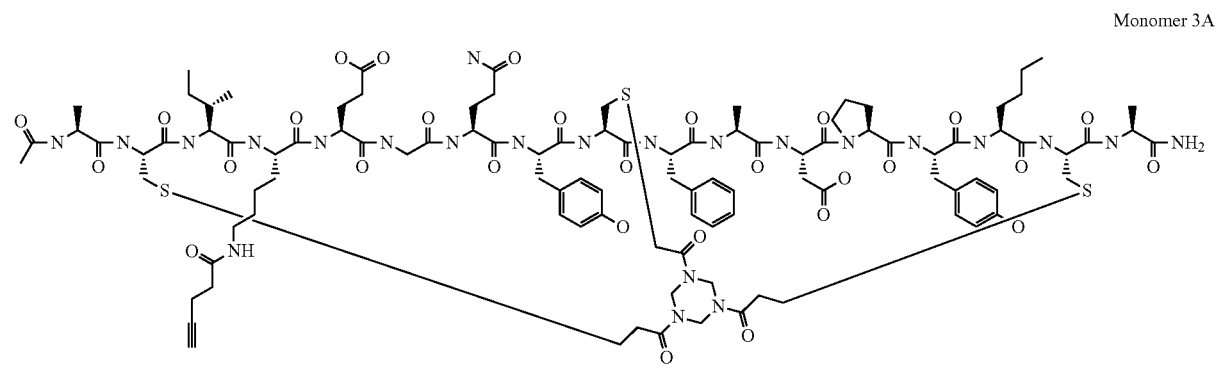
Monomer 4A
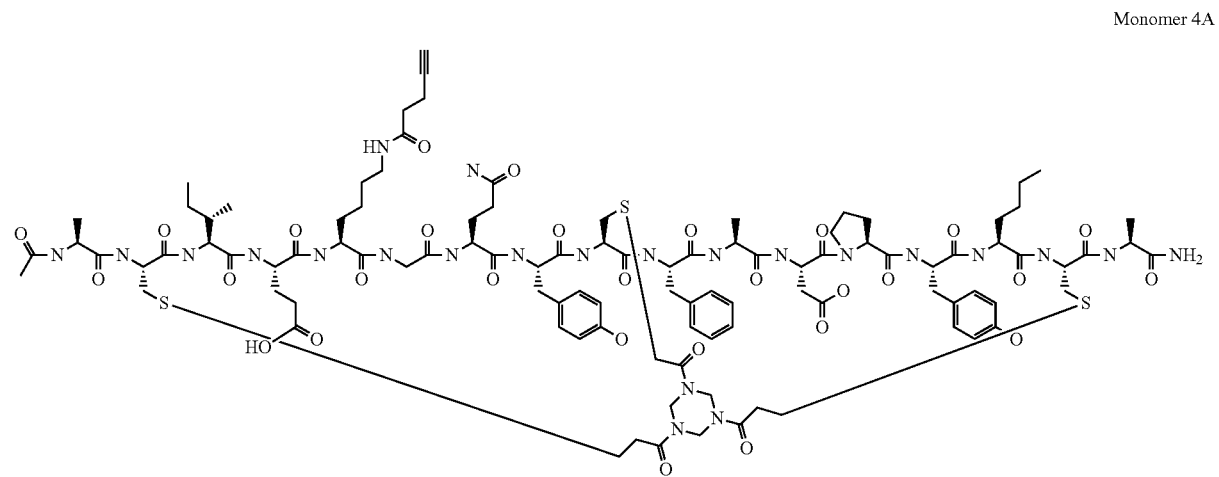
Monomer 5A
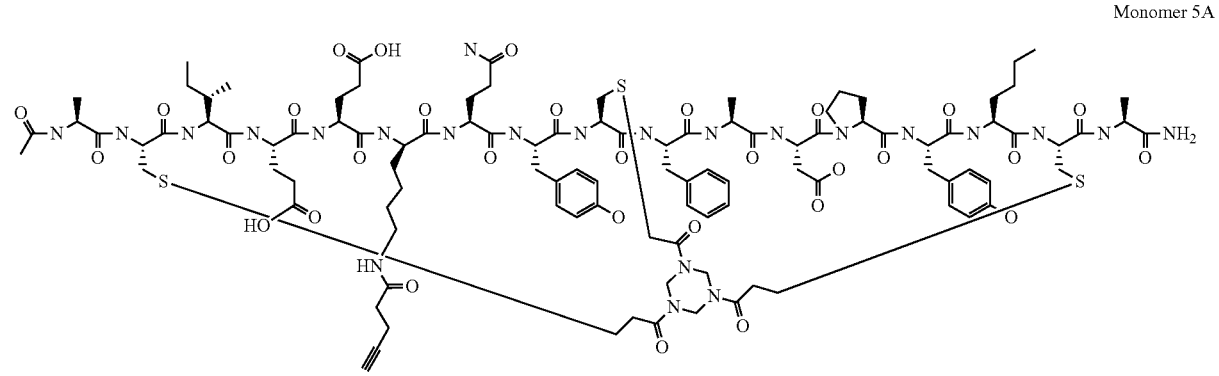

-continued
Monomer 6A
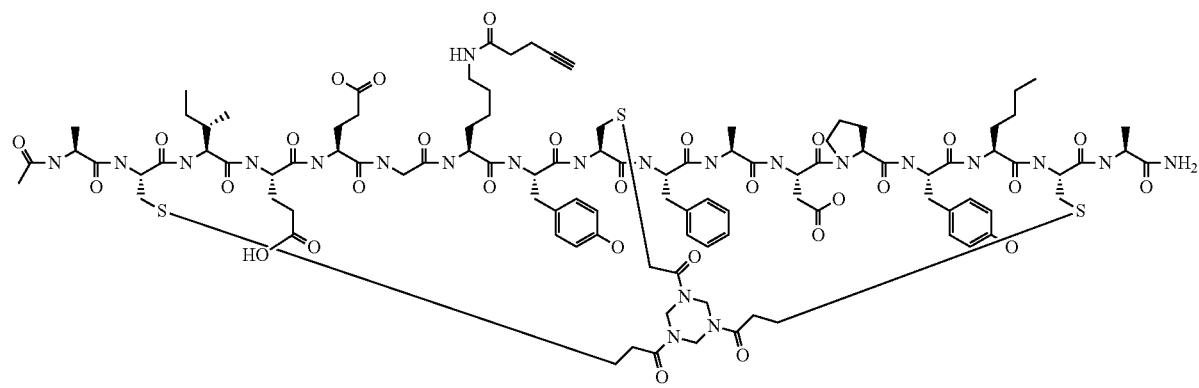
Monomer 7A
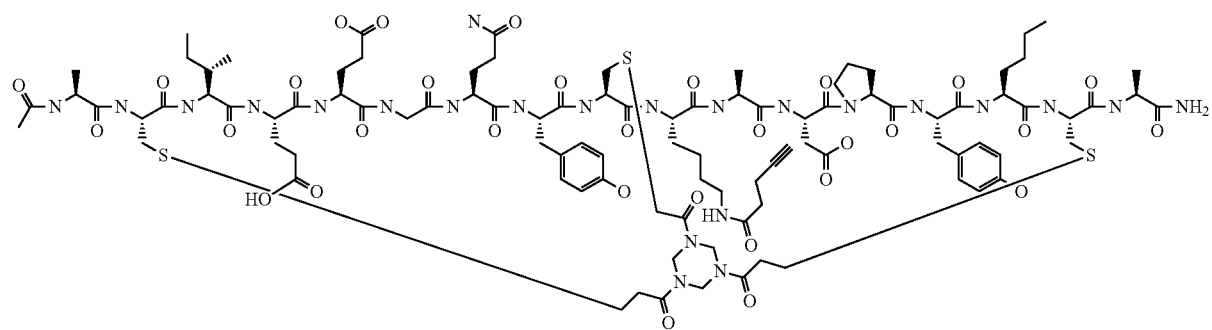
Monomer 8A
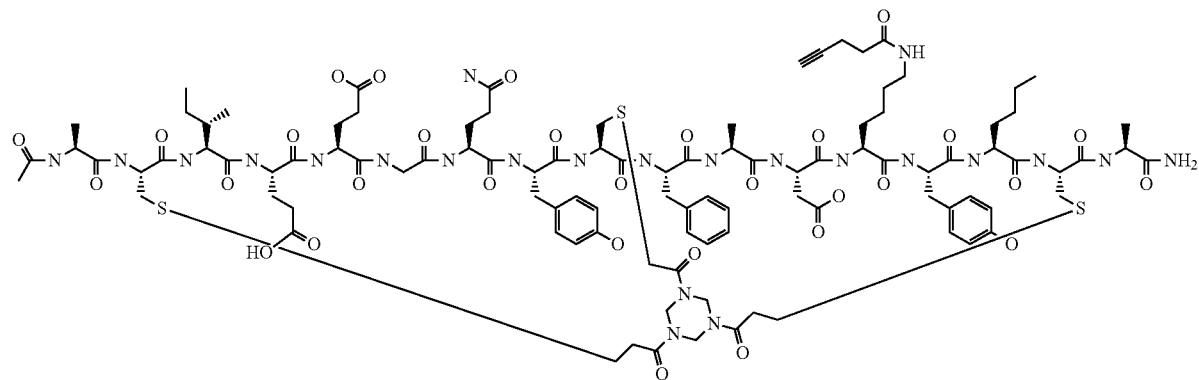
Monomer 9A
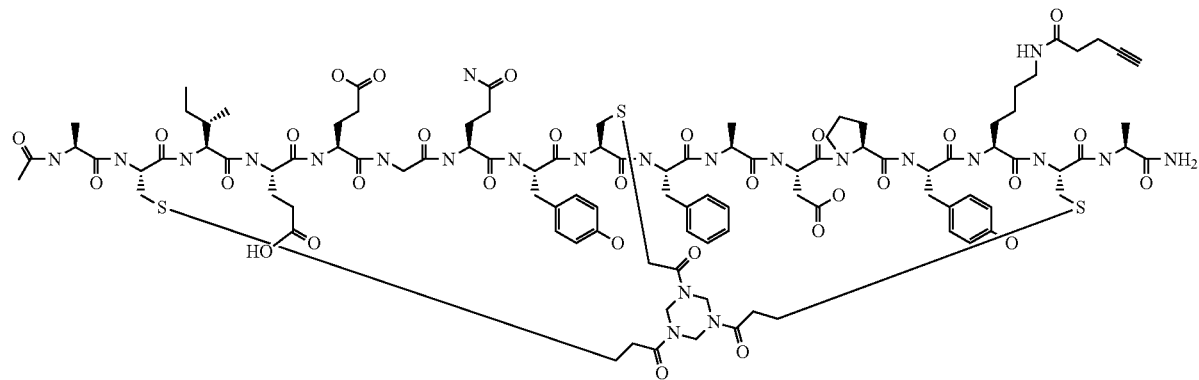

Monomer 10A
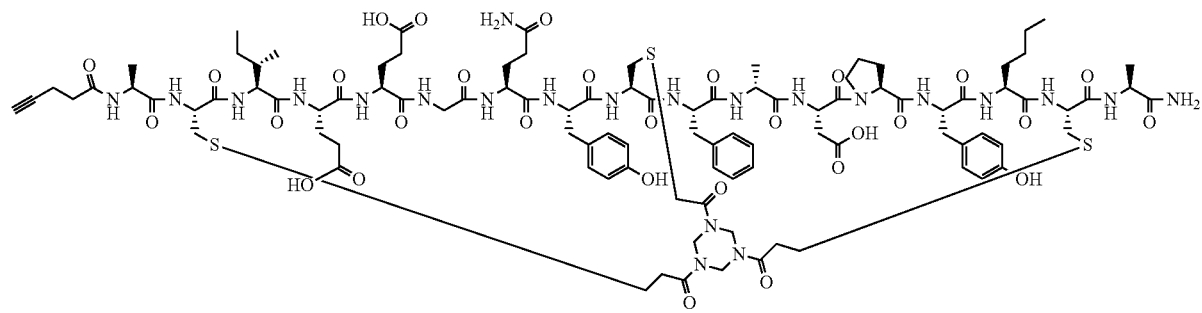
Monomer 11A
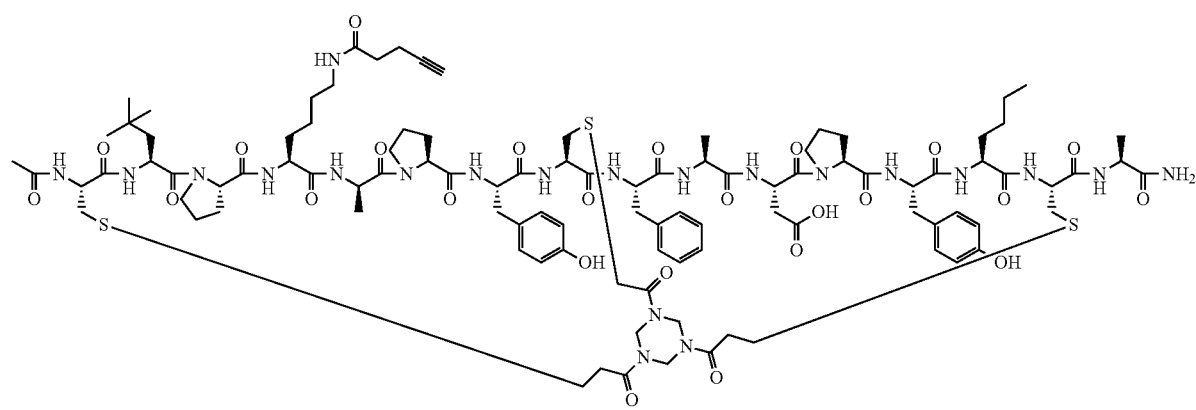
Monomer 12A
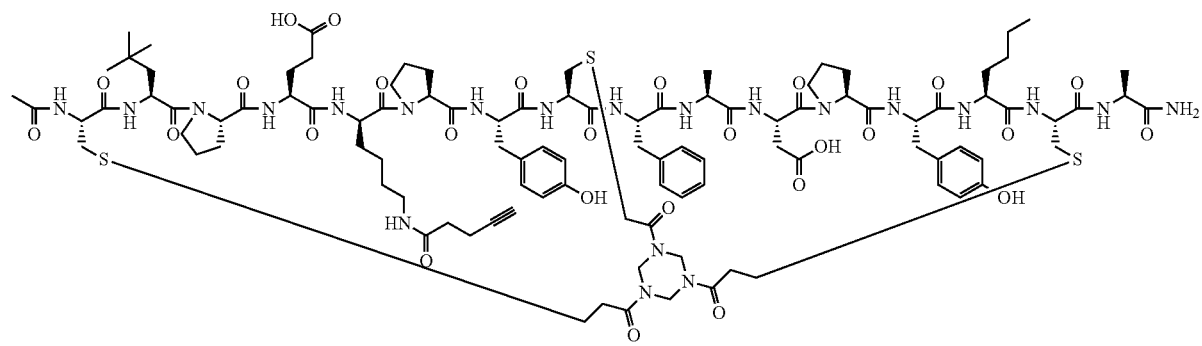
Monomer 13A
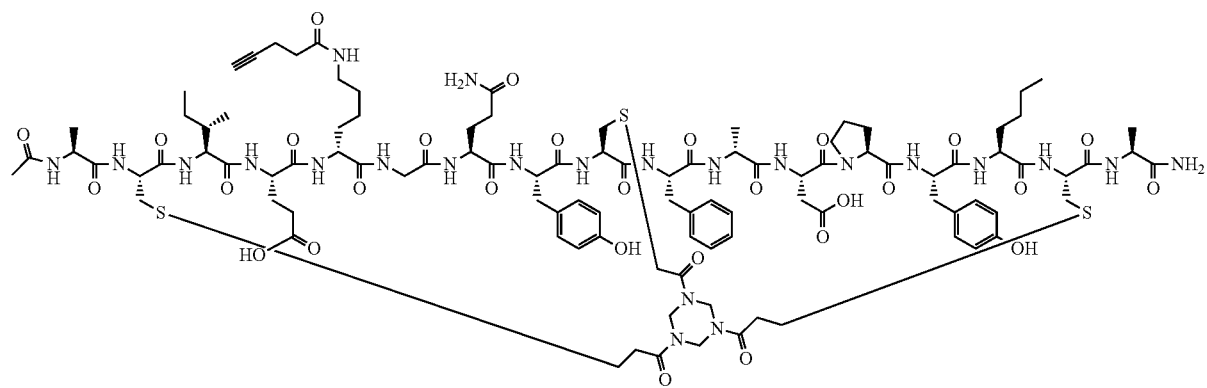

Monomer 14A

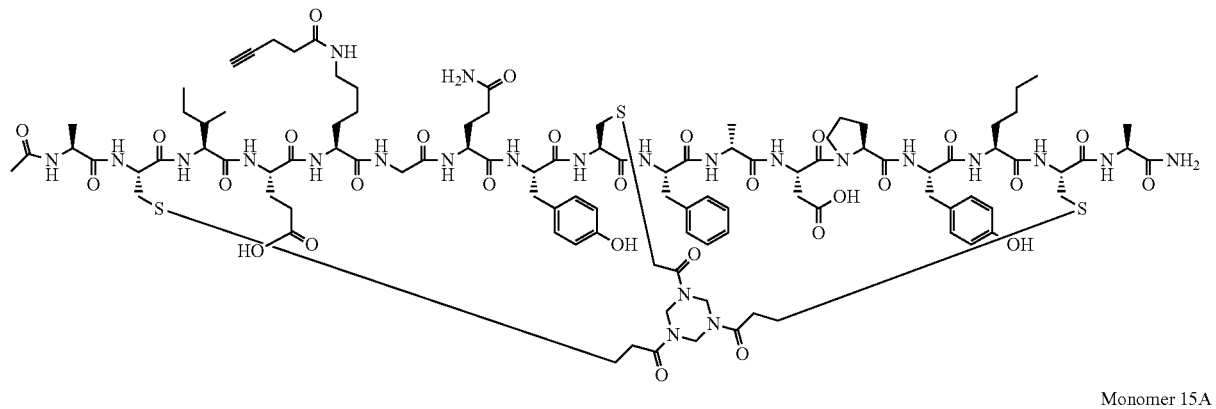

Monomer 15A

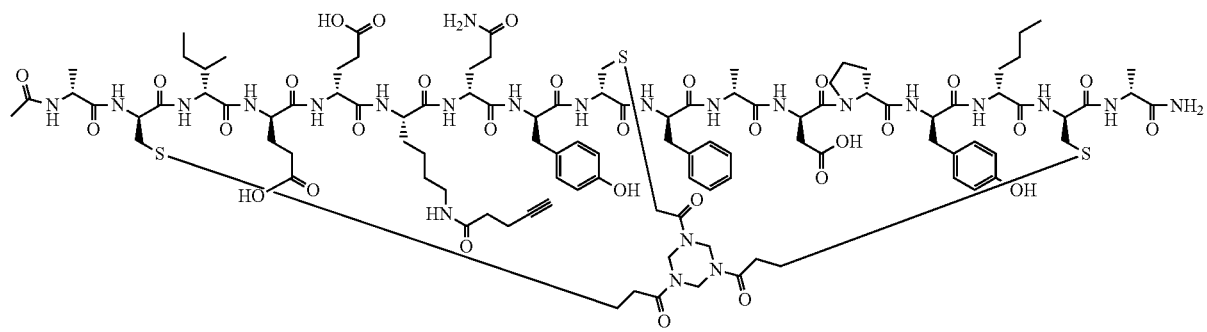

Monomer 1A:
To a solution of Monomer 1 (350.0 mg, 163.22 μmol, 1.0 eq) and compound 3 (63.71 mg, 326.43 μmol, 2.0 eq) in DMA (10 mL) was added DIPEA (105.47 mg, 816.08 μmol, 142.15 μL, 5.0 eq). The mixture was stirred at 20° C. for 2 hr. LC-MS showed Monomer 1 was consumed completely and one main peak with desired MS was detected. The mixture was purified by prep-HPLC (neutral condition) to give Monomer 1A (254 mg, 69.96% yield) as a white solid.

Monomer 2A:
To a solution of Monomer 2 (350 mg, 158.99 μmol, 1 eq) and compound 3 (62.0 mg, 317.97 μmol, 2 eq) in DMA (3 mL) was added DIPEA (103.0 mg, 794.93 μmol, 138.46 μL, 5 eq). The mixture was stirred at 20° C. for 2 hr. LC-MS showed Monomer 2 was consumed completely and one main peak with desired MS was detected. The mixture was purified by prep-HPLC (neutral condition) to give Monomer 2A (304 mg, 130.58 μmol, 82.13% yield, 98% purity) as a white solid.

Monomer 3A:
To a solution of Monomer 3 (0.3 g, 137.27 μmol, 1.0 eq) and compound 3 (54 mg, 276.68 μmol, 2.0 eq) in DMA (3 mL) was added DIPEA (89 mg, 688.63 μmol, 119.95 μL, 5.0 eq). The mixture was stirred at 25~30° C. for 2 hr. LC-MS and HPLC showed Monomer 3 was consumed completely and one main peak with desired MS was detected. The mixture was purified by prep-HPLC (neutral condition) to give Monomer 3A (272 mg, 110.21 μmol, 80.29% yield, 91.8% purity) as a white solid.

Monomer 4A:
To a solution of Monomer 4 (0.3 g, 137.27 μmol, 1 eq) and compound 3 (54 mg, 276.68 μmol, 2.02 eq) in DMA (3 mL) was added DIPEA (89 mg, 688.63 μmol, 119.95 μL, 5.02 eq). The mixture was stirred at 25~30° C. for 2 hr. LC-MS and HPLC showed Monomer 4 was consumed completely and one main peak with desired MS was detected. The mixture was purified by prep-HPLC (neutral condition) to give Monomer 4A (204 mg, 85.36 μmol, 62.19% yield, 94.8% purity) as a white solid.

Monomer 5A:
To a solution of Monomer 5 (0.3 g, 132.89 μmol, 1 eq) and compound 3 (52.0 mg, 266.43 μmol, 2.0 eq) in DMA (3 mL) was added DIPEA (86.0 mg, 665.41 μmol, 115.90 μL, 5.0 eq). The mixture was stirred at 25~30° C. for 2 hr. LC-MS and HPLC showed Monomer 5 was consumed completely and one main peak with desired MS was detected. The mixture was purified by prep-HPLC (neutral condition) to give Monomer 5A (194 mg, 74.69 μmol, 56.21% yield, 90.0% purity) as a white solid.

Monomer 6A:
To a solution of Monomer 6 (0.3 g, 137.21 μmol, 1.0 eq) and compound 3 (54 mg, 276.68 μmol, 2.0 eq) in DMA (3 mL) was added DIPEA (89 mg, 688.63 μmol, 119.95 μL, 5.02 eq). The mixture was stirred at 25~30° C. for 2 hr. LC-MS and HPLC showed Monomer 6 was consumed completely and one main peak with desired MS was detected. The mixture was purified by prep-HPLC (neutral condition) to give Monomer 6A (204 mg, 83.25 μmol, 60.68% yield, 92.5% purity) as a white solid.

Monomer 7A:
To a solution of Monomer 7 (0.3 g, 138.41 μmol, 1.0 eq) and compound 3 (54.00 mg, 276.82 μmol, 2.0 eq) in DMA (3 mL) was added DIPEA (89 mg, 688.63 μmol, 119.95 μL, 5.0 eq). The mixture was stirred at 25~30° C. for 2 hr. LC-MS and HPLC showed Monomer 7 was consumed completely and one main peak with desired MS was detected. The mixture was purified by prep-HPLC (neutral condition) to give Monomer 7A (183 mg, 73.69 µmol, 53.24% yield, 90.5% purity) as a white solid.

Monomer 8A:

A mixture of Monomer 8 (400 mg, 180.38 µmol, 1.0 eq), compound 3 (70.41 mg, 360.77 µmol, 2.0 eq) and DIPEA (118.72 mg, 918.58 µmol, 160.00 µL, 5.0 eq) in DMSO (5 mL) was degassed and purged with $N_2$ for 3 times. And then the mixture was stirred at 30° C. for 2 hrs under $N_2$ atmosphere. LC-MS and HPLC showed Monomer 8 was consumed completely and one main peak with desired MS was detected. The mixture was purified by prep-HPLC (neutral condition) to give Monomer 8A (300 mg, 118.82 µmol, 65.87% yield, 91.74% purity) as a white solid.

Monomer 9A:

To a solution of Monomer 9 (0.3 g, 136.27 µmol, 1.0 eq) and compound 3 (53.0 mg, 272.55 µmol, 2.0 eq) in DMA (3 mL) was added DIPEA (88.0 mg, 681.37 µmol, 118.68 µL, 5.0 eq). The mixture was stirred at 25-30° C. for 2 hr. LC-MS and HPLC showed Monomer 9 was consumed completely and one main peak with desired MS was detected. The mixture was purified by prep-HPLC (neutral condition) to give Monomer 9A (249 mg, 100.41 µmol, 73.68% yield, 92.0% purity) as a white solid.

Monomer 10A (260 mg, 90% Purity), Monomer 11A (123 mg, 97.10% Purity), Monomer 12A (131 mg, 97.5% Purity), Monomer 13A (780 mg, 98.0% Purity), Monomer 14A (710 mg, 92.40% Purity) and Monomer 15A (820 mg, 96.9% Purity) was Synthesized as Described Above and Purified Using Prep-HPLC to Give a White Solid.

General Procedure for Preparation of Compound 7

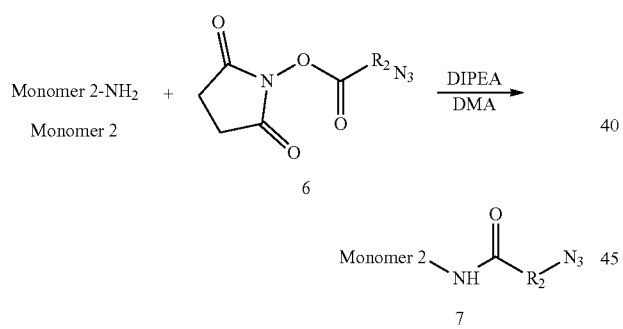

Compound 6:

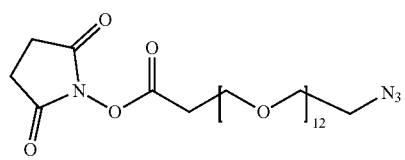

6A

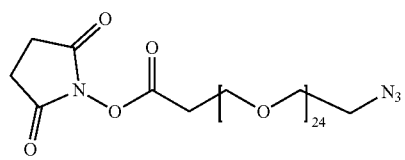

6B

Compound 7:

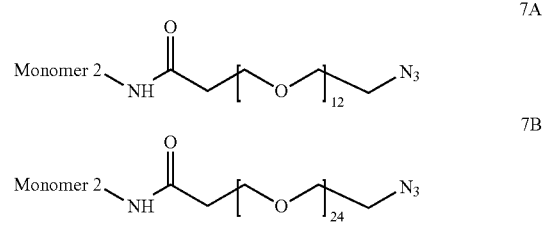

7A

7B

Compound 7A:

To a solution of Monomer 2 (120 mg, 54.51 µmol, 1.0 eq) in DMA (4 mL) was added compound 6A (40.38 mg, 54.51 µmol, 1.0 eq) and DIPEA (35.22 mg, 272.55 µmol, 47.47 µL, 5 eq). The mixture was stirred at 20° C. for 12 hrs. LC-MS showed no Monomer 2 was remained. Several new peaks were shown on LC-MS and ~80% of desired compound was detected. The mixture was purified by prep-HPLC (TFA condition) to give compound 7A (89 mg, 31.48 µmol, 57.75% yield) as a white solid.

Compound 7B:

To a solution of Monomer 2 (75.0 mg, 34.07 µmol, 1.0 eq) in DMA (3 mL) was added compound 6B (43.25 mg, 34.07 µmol, 1.0 eq) and DIPEA (22.02 mg, 170.34 µmol, 29.67 µL, 5.0 eq). The mixture was stirred at 20° C. for 12 hrs. LC-MS showed no Monomer 2 was remained. Several new peaks were shown on LC-MS and ~80% of desired compound was detected. The mixture was purified by prep-HPLC (TFA condition) to give compound 7B about (73 mg, 21.75 µmol, 63.85% yield) as a white solid.

General Procedure for Preparation of Dimeric Bicycle Conjugates:

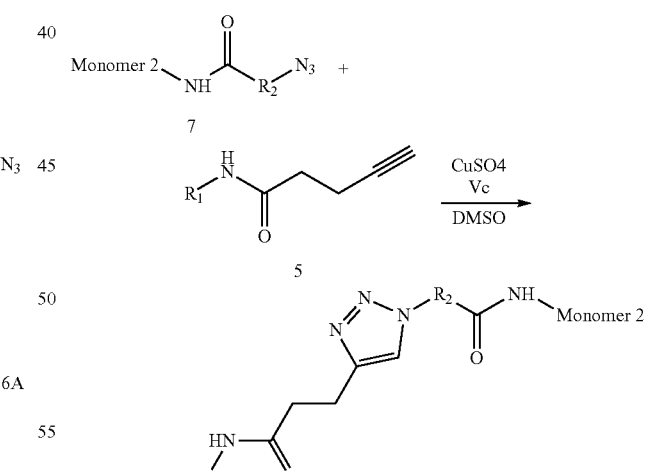

Compound 7:

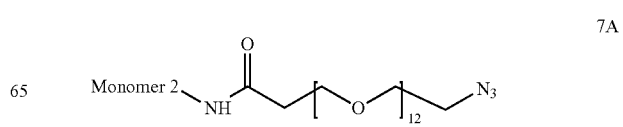

7A

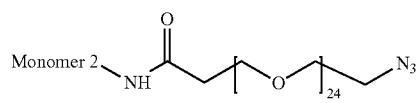
7B
Compound 5:
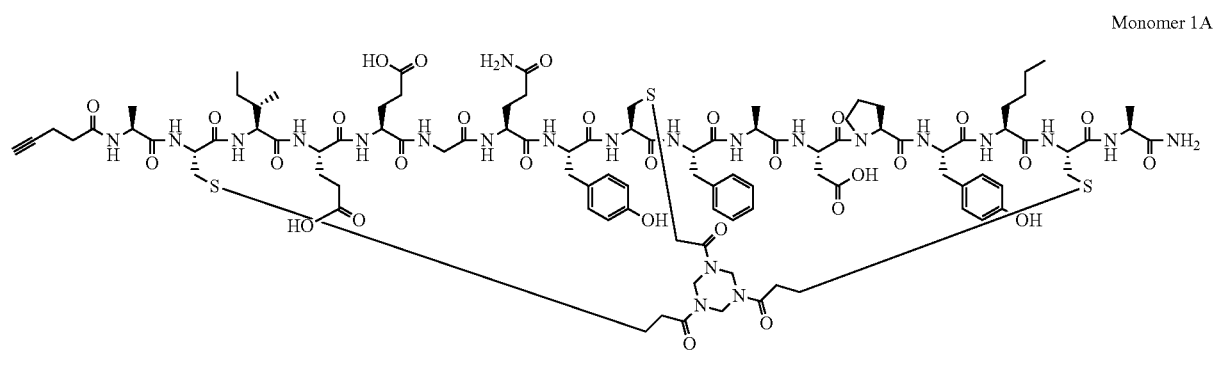
Monomer 1A
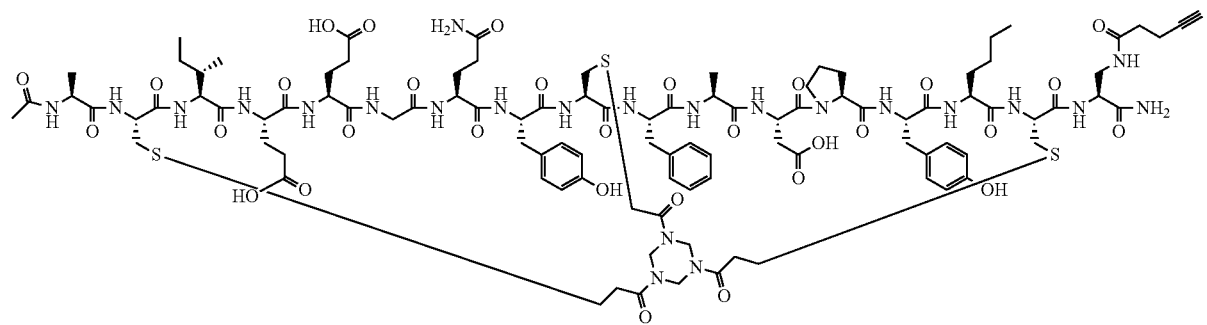
Monomer 2A
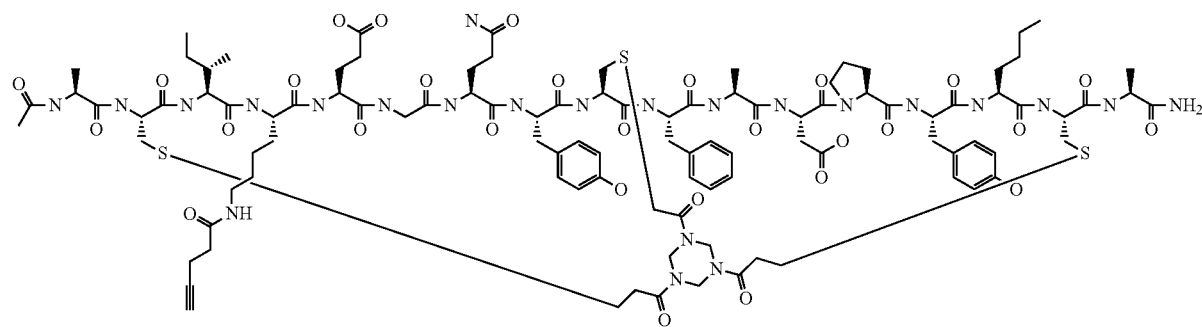
Monomer 3A Monomer 4A
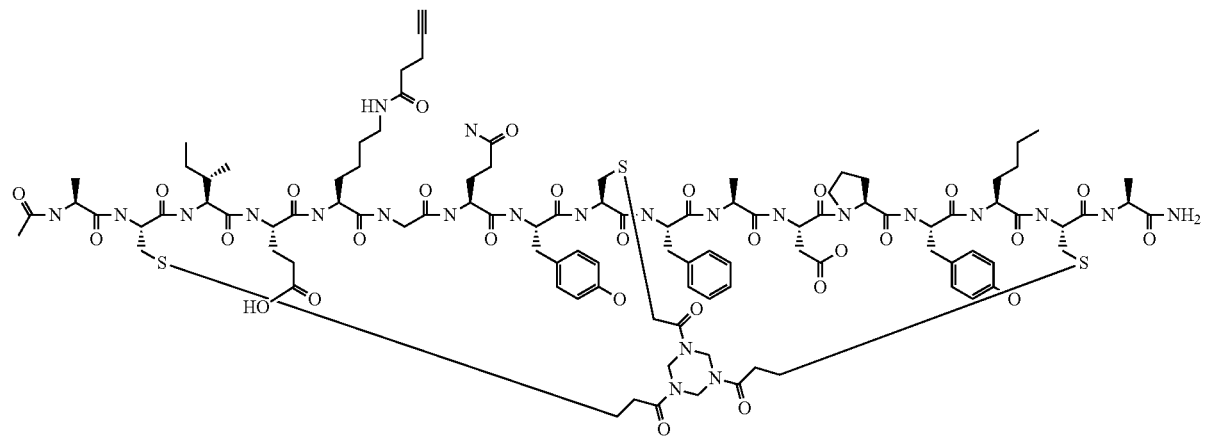
Monomer 5A
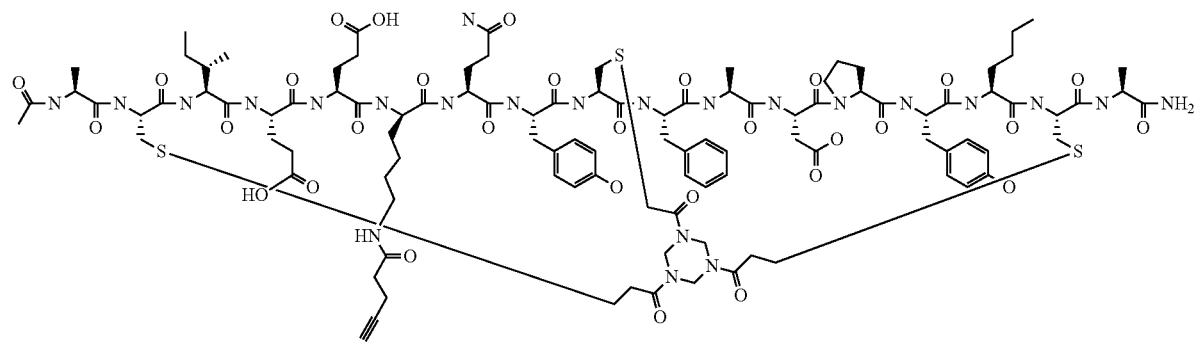
Monomer 6A
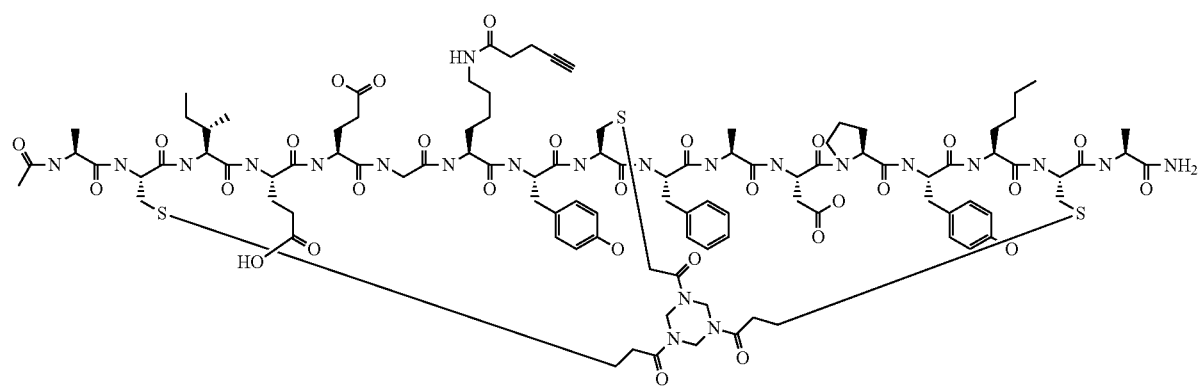
Monomer 7A
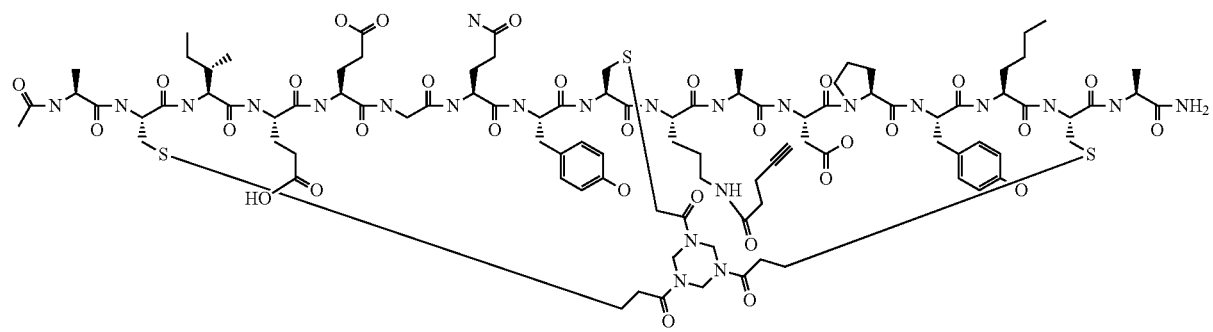

Monomer 8A

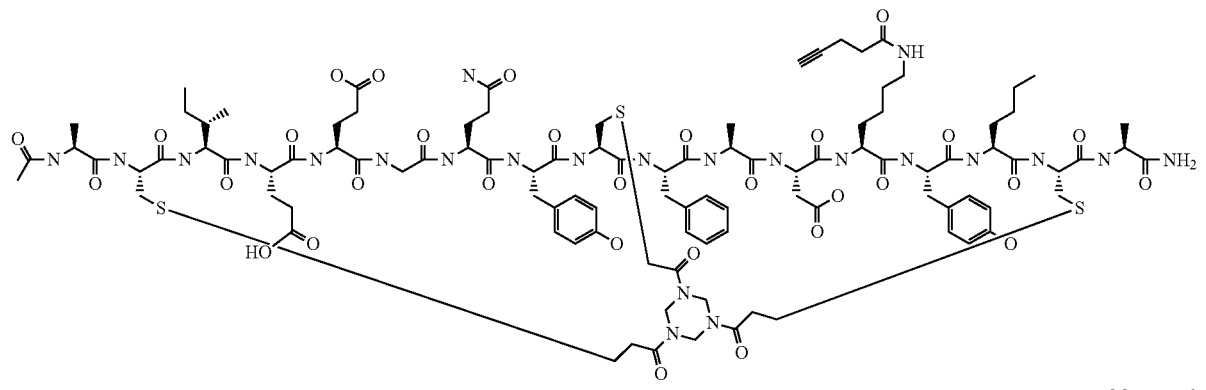

Monomer 9A

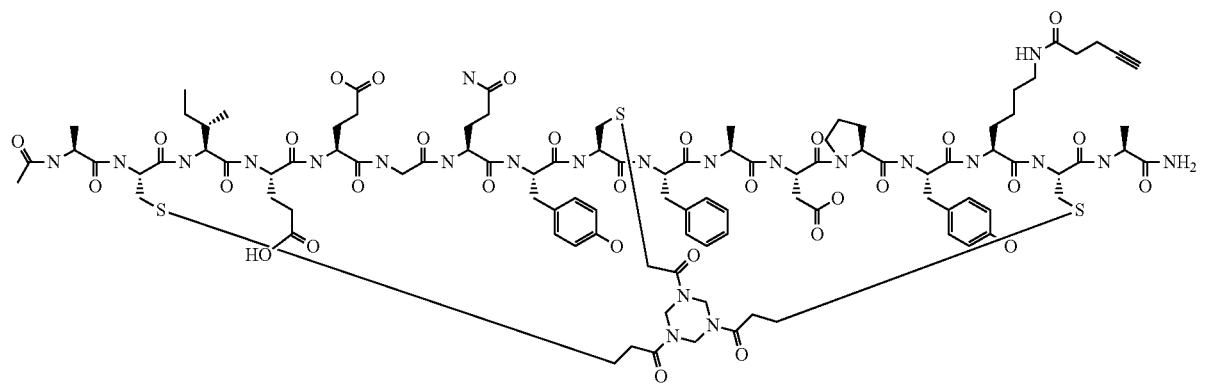

Compound 8:

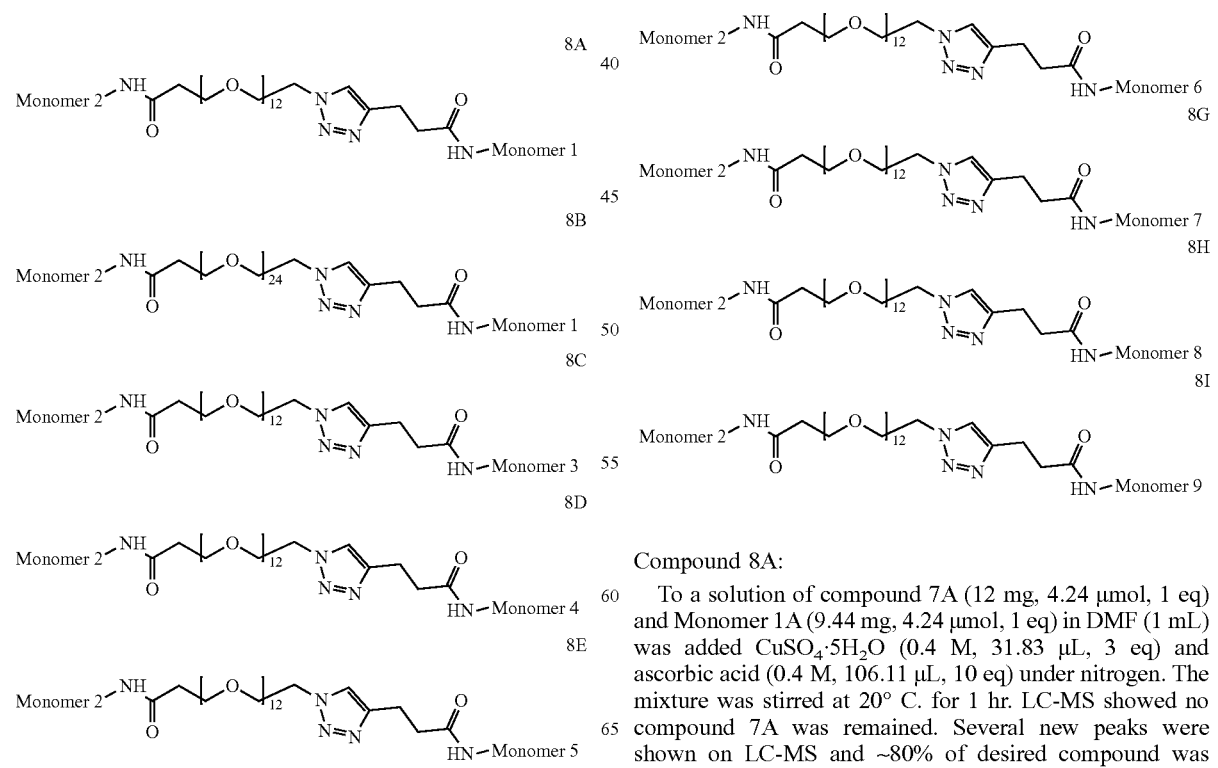

Compound 8A:

To a solution of compound 7A (12 mg, 4.24 μmol, 1 eq) and Monomer 1A (9.44 mg, 4.24 μmol, 1 eq) in DMF (1 mL) was added CuSO$_4$·5H$_2$O (0.4 M, 31.83 μL, 3 eq) and ascorbic acid (0.4 M, 106.11 μL, 10 eq) under nitrogen. The mixture was stirred at 20° C. for 1 hr. LC-MS showed no compound 7A was remained. Several new peaks were shown on LC-MS and ~80% of desired compound was detected. The residue was purified by prep-HPLC (TFA condition) to give compound 8A (8.1 mg, 1.49 μmol, 35.11% yield, 92.94% purity) as a white solid.

Compound 8B:

To a solution of compound 7B (14 mg, 4.17 μmol, 1 eq) and Monomer 1A (9.28 mg, 4.17 μmol, 1 eq) in DMF (1 mL) was added CuSO$_4$·5H$_2$O (0.4 M, 31.29 μL, 3 eq) and ascorbic acid (0.4 M, 104.30 μL, 10 eq) under nitrogen. The mixture was stirred at 20° C. for 1 hr. LC-MS showed no compound 7B was remained. Several new peaks were shown on LC-MS and ~80% of desired compound was detected. The residue was purified by prep-HPLC (TFA condition) to give compound 8B (5.2 mg, 0.86 μmol, 20.62% yield, 92.31% purity) as a white solid.

Compound 8C:

To a solution of compound 7A (10 mg, 3.54 μmol, 1 eq) and Monomer 3A (12.02 mg, 5.31 μmol, 1.5 eq) in DMF (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to give compound 8C (2.8 mg, 5.04e-1 μmol, 14.24% yield, 91.6% purity) as a white solid.

Compound 8D:

To a solution of compound 7A (10 mg, 3.54 μmol, 1 eq) and Monomer 4A (12.02 mg, 5.31 μmol, 1.5 eq) in DMF (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to give compound 8D (2.1 mg, 3.76e-1 μmol, 10.62% yield, 91.1% purity) as a white solid.

Compound 8E:

To a solution of compound 7A (10 mg, 3.54 μmol, 1 eq) and Monomer 5A (12.40 mg, 5.31 μmol, 1.5 eq) in DMF (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 20° C. for 1 hr. LC-MS showed no compound 7A was remained. Several new peaks were shown on LC-MS and ~20% of desired compound was detected. The residue was purified by prep-HPLC (TFA condition) to give compound 8E (1.2 mg, 2.01e-1 μmol, 5.69% yield, 86.6% purity) as a white solid.

Compound 8F:

To a solution of compound 7A (10 mg, 3.54 μmol, 1 eq) and Monomer 6A (12.03 mg, 5.31 μmol, 1.5 eq) in DMF (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to give compound 8F (3.4 mg, 3.93e-1 μmol, 11.12% yield, 58.9% purity) as a white solid.

Compound 8G:

To a solution of compound 7A (10 mg, 3.54 μmol, 1 eq) and Monomer 7A (11.92 mg, 5.31 μmol, 1.5 eq) in DMSO (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 25-30° C. for 1 hr. LC-MS showed no compound 7A was remained. Several new peaks were shown on LC-MS and ~40% of desired compound was detected. The residue was purified by prep-HPLC (TFA condition) to give compound 8G (7.2 mg, 1.33 mmol, 37.78% yield, 94.2% purity) as a white solid.

Compound 8H:

To a solution of compound 7A (10 mg, 3.54 μmol, 1 eq) and Monomer 8A (11.19 mg, 5.31 μmol, 1.5 eq) in DMSO (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 25-30° C. for 1 hr. LC-MS showed no compound 7A was remained. Several new peaks were shown on LC-MS and ~40% of desired compound was detected. The residue was purified by prep-HPLC (TFA condition) to give compound 8H (9.0 mg, 1.73 mmol, 49.15% yield, 99.0% purity) as a white solid.

Compound 8I:

To a solution of compound 7A (10 mg, 3.54 μmol, 1 eq) and Monomer 9A (12.11 mg, 5.31 μmol, 1.5 eq) in DMF (1 mL) was added CuSO$_4$·5H$_2$O (0.4 M, 26.53 μL, 3 eq) and ascorbic acid (0.4 M, 88.43 μL, 10 eq) under nitrogen. The mixture was stirred at 20° C. for 1 hr. LC-MS showed no compound 7A was remained. Several new peaks were shown on LC-MS and ~40% of desired compound was detected. The residue was purified by prep-HPLC (TFA condition) to afford compound 8I (3.8 mg, 6.81e-1 μmol, 19.24% yield, 91.5% purity) as a white solid.

General Procedure for Preparation of Trimeric Azide Linker

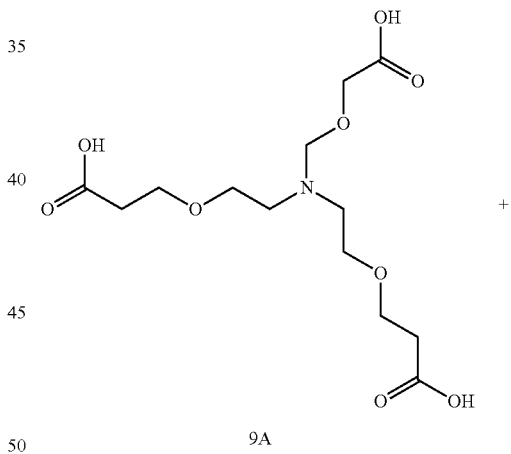

9A

+

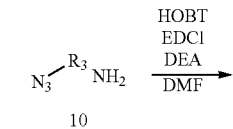

10

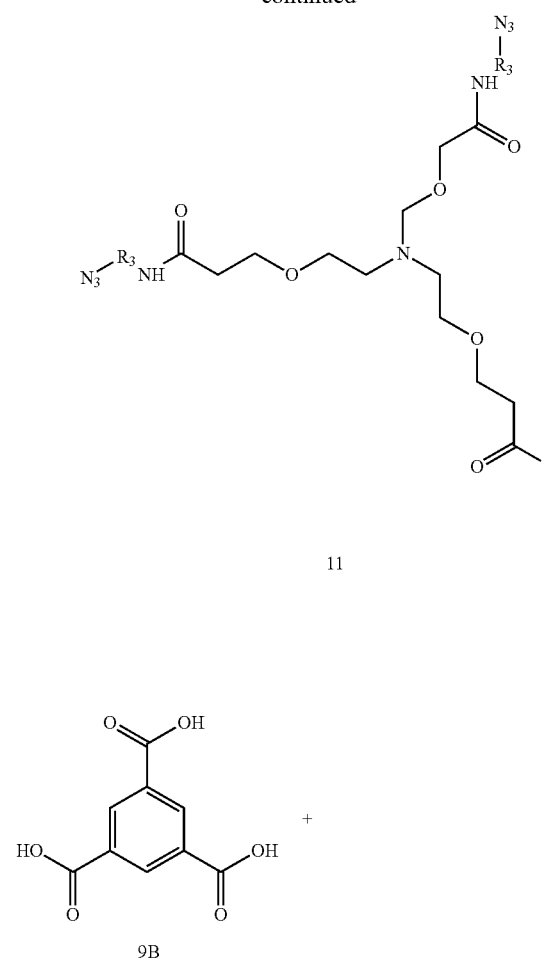

11

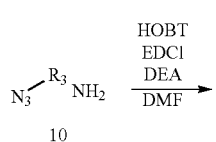

9B

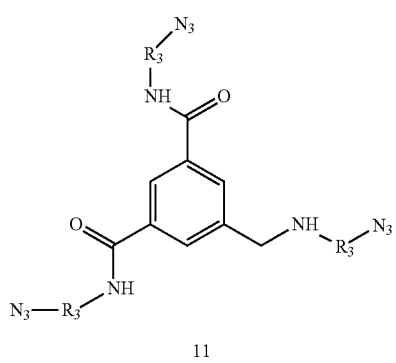

11

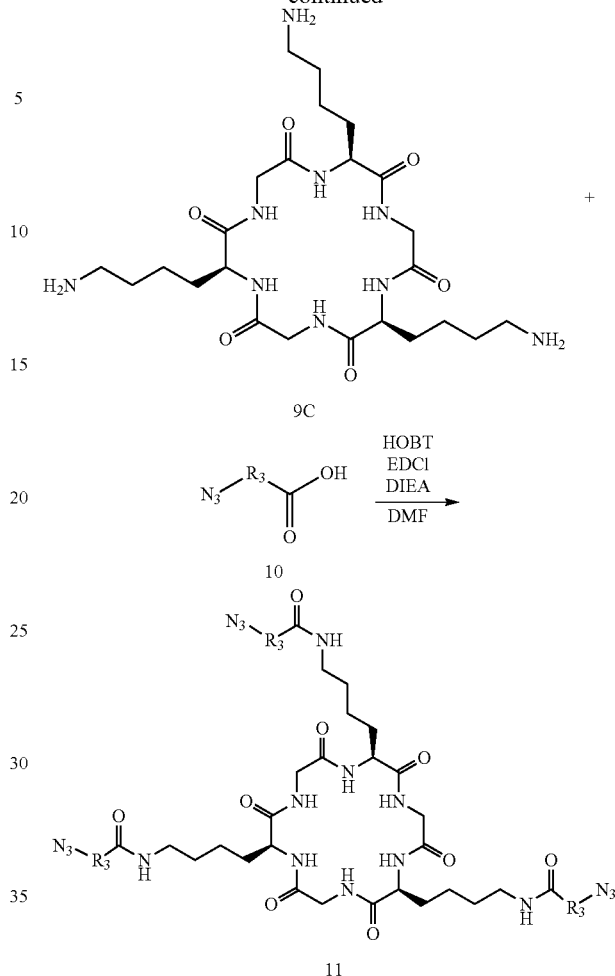

9C

Compound 9C: c(KGKGKG) (cyclic (SEQ ID NO: 57))

Linear peptide NH$_2$-Lys-Gly-Lys-Gly-Lys-Gly-COOH (NH$_2$-(SEQ ID NO: 57)-COOH) was synthesized on 2-Cl-Trt chloride resin (CTC resin) using standard Fmoc chemistry. The peptide was then cleaved by treatment with 20% HFIP in DCM (30 min×2), and the solution was combined, evaporated under vacuum, and lyophilized to dry, resulting in linear crude product. The crude peptide was then dissolved in DMF, following by addition of coupling reagents (DIC and HOAt, 1 eq and 1 eq, respectively). The mixture was stirred at room temperature for 16 hr, until LCMS indicated no linear peptide remained. Subsequently, the cyclisation crude was dried under vacuum and purified by FLASH C18 chromatography. The purified cyclic peptide was then lyophilized, and all protecting groups were removed by treatment with HCl/dioxane (4 M, 1 hour, room temperature). The precipitates were collected, washed with methyl tert-butyl ether, and dried under vacuum to give final product as a white solid (HCl salt).

Compound 10:

10A

Compound 10D:

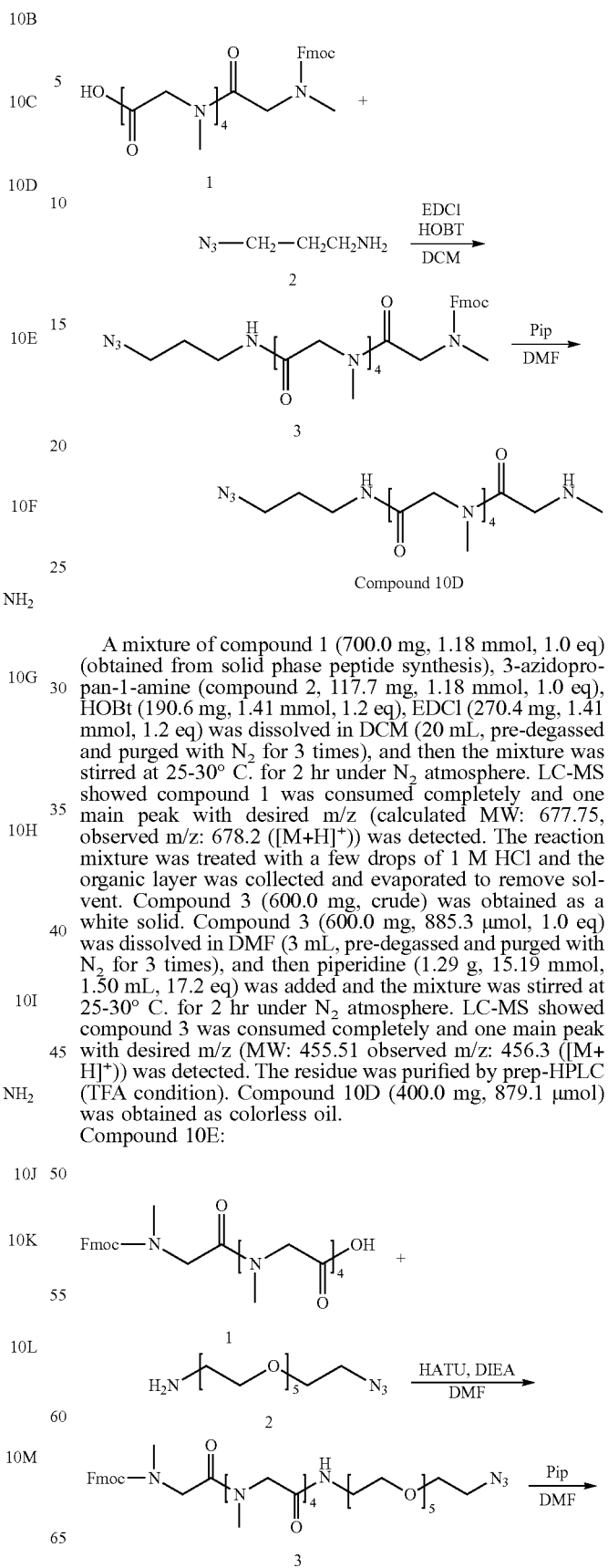

A mixture of compound 1 (700.0 mg, 1.18 mmol, 1.0 eq) (obtained from solid phase peptide synthesis), 3-azidopropan-1-amine (compound 2, 117.7 mg, 1.18 mmol, 1.0 eq), HOBt (190.6 mg, 1.41 mmol, 1.2 eq), EDCl (270.4 mg, 1.41 mmol, 1.2 eq) was dissolved in DCM (20 mL, pre-degassed and purged with $N_2$ for 3 times), and then the mixture was stirred at 25-30° C. for 2 hr under $N_2$ atmosphere. LC-MS showed compound 1 was consumed completely and one main peak with desired m/z (calculated MW: 677.75, observed m/z: 678.2 ([M+H]$^+$)) was detected. The reaction mixture was treated with a few drops of 1 M HCl and the organic layer was collected and evaporated to remove solvent. Compound 3 (600.0 mg, crude) was obtained as a white solid. Compound 3 (600.0 mg, 885.3 µmol, 1.0 eq) was dissolved in DMF (3 mL, pre-degassed and purged with $N_2$ for 3 times), and then piperidine (1.29 g, 15.19 mmol, 1.50 mL, 17.2 eq) was added and the mixture was stirred at 25-30° C. for 2 hr under $N_2$ atmosphere. LC-MS showed compound 3 was consumed completely and one main peak with desired m/z (MW: 455.51 observed m/z: 456.3 ([M+H]$^+$)) was detected. The residue was purified by prep-HPLC (TFA condition). Compound 10D (400.0 mg, 879.1 µmol) was obtained as colorless oil.

Compound 10E:

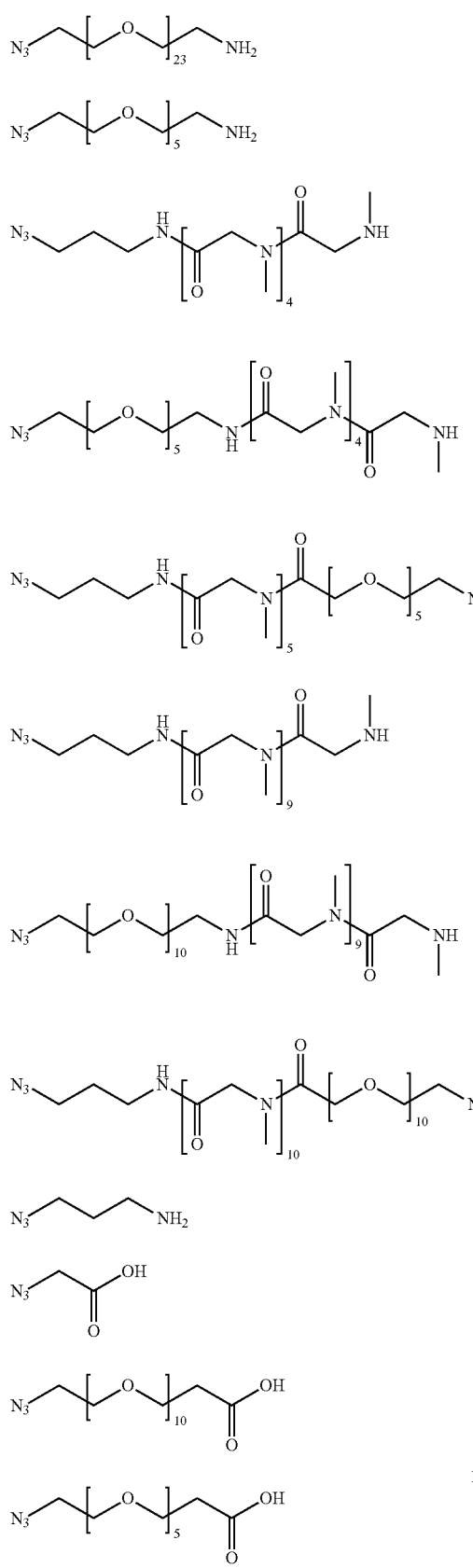

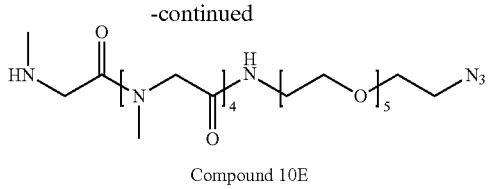

Compound 10E

A mixture of compound 1 (1 g, 1.68 mmol, 1.0 eq), compound 2 (411.5 mg, 1.34 mmol, 0.8 eq) and DIEA (217.0 mg, 1.68 mmol, 292.4 μL, 1.0 eq) was dissolved in DMF (2 mL), following by addition of HATU (638.4 mg, 1.68 mmol, 1.0 eq) as one portion at 25° C. The mixture was stirred at 25° C. for 30 min. TLC (DCM: $CH_3OH=10:1$, $R_f=0.18$) showed compound 1 was consumed completely and one new spot formed. The solvent was evaporated to produce compound 3 (1 g, 1.13 mmol, 67.38% yield) as a white solid, which was directly used in next step without further purification. Compound 3 (1 g, 1.13 mmol, 1.0 eq) was dissolved in DMF (8 mL), following by addition of piperidine (2 mL). The mixture was stirred for 15 mins at 25° C. LC-MS showed compound 3 was consumed completely and one main peak with desired m/z (calculated MW: 661.75, observed m/z: 663.1 ([M+H]$^+$)) was detected. The residue was purified by prep-HPLC (TFA condition). Compound 10E (800 mg, 1.09 mmol, 96.18% yield,) was obtained as colorless oil.

Compound 10F:

showed compound 1 was consumed completely and one main peak with desired m/z (calculated MW: 677.75, observed m/z: 678.2 ([M+H]$^+$)) was detected. The reaction mixture was treatment with a few drops of 1 M HCl, and the organic layer was collected and evaporated under reduced pressure. Compound 2 (600.0 mg, crude) was obtained as a white solid. Compound 2 (600.0 mg, 885.2 μmol, 1.0 eq) was dissolved in DMF (3 mL, pre-degassed and purged with $N_2$ for 3 times), and then piperidine (1.29 g, 15.19 mmol, 1.50 mL, 17.2 eq) was added and the mixture was stirred at 25-30° C. for 2 hr under $N_2$ atmosphere. LC-MS showed compound 2 was consumed completely and one main peak with desired m/z (calculated MW: 455.51 observed m/z: 456.3 ([M+H]$^+$)) was detected. The reaction mixture was purified by prep-HPLC (TFA condition), and compound 3 (400.0 mg, 879.1 μmol) was obtained as colorless oil.

A mixture of compound 3 (250.0 mg, 548.83 μmol, 1.0 eq), compound 4 (284.1 mg, 548.83 μmol, 1 eq), HATU (229.6 mg, 603.72 μmol, 1.1 eq), DIEA (141.9 mg, 1.10 mmol, 191.19 μL, 2.0 eq) in DCM (20 mL, pre-degassed and purged with $N_2$ for 3 times), and then the mixture was stirred at 25-30° C. for 2 hr under $N_2$ atmosphere. LC-MS showed compound 3 was consumed completely and one main peak with desired m/z (calculated MW: 955.06, observed m/z: 955.6 ([M+H]$^+$)) was detected. The residue was purified by prep-HPLC (TFA condition). Compound 5 (400.0 mg, 419.1 μmol) was obtained as a white solid.

A mixture of Compound 5 (400.0 mg, 418.82 μmol, 1.0 eq) was dissolved in DMF (4 mL, pre-degassed and purged

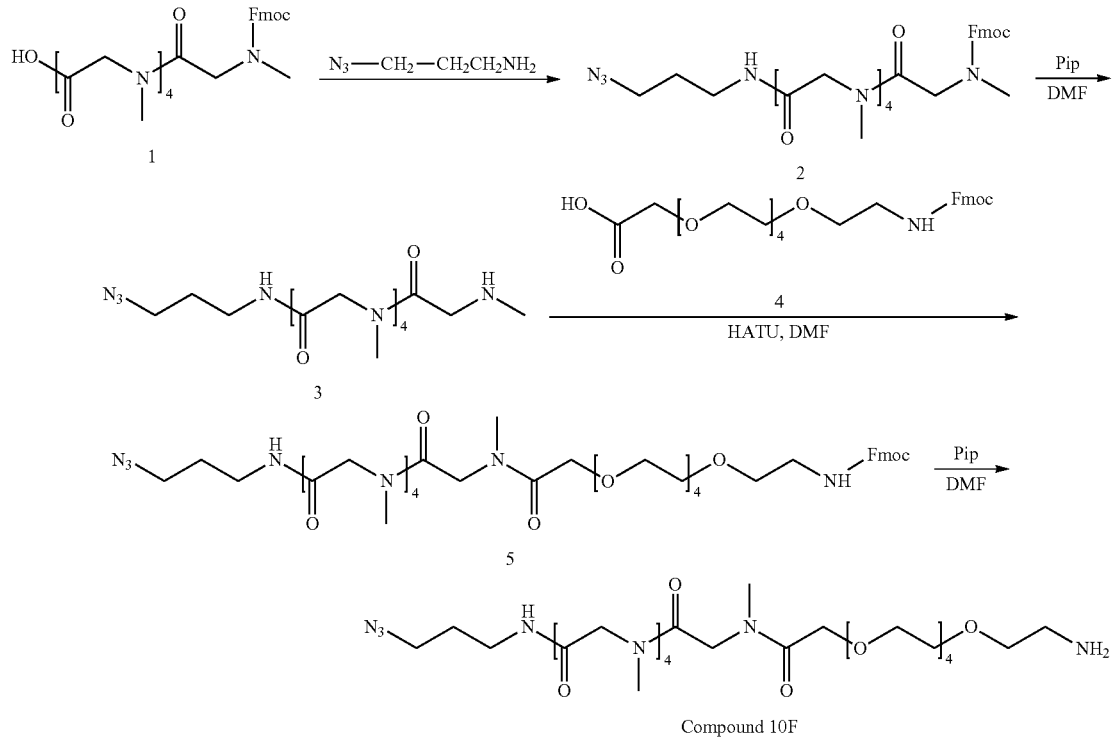

Compound 10F

A mixture of compound 1 (700.0 mg, 1.18 mmol, 1.0 eq), 3-azidopropan-1-amine (117.7 mg, 1.18 mmol, 1.0 eq), HOBt (190.6 mg, 1.41 mmol, 1.2 eq), EDCl (270.4 mg, 1.41 mmol, 1.2 eq) was dissolved in DCM (20 mL, pre-degassed and purged with $N_2$ for 3 times), and then the mixture was stirred at 25-30° C. for 2 hr under $N_2$ atmosphere. LC-MS with $N_2$ for 3 times), and then piperidine (862.2 mg, 10.13 mmol, 1 mL, 24.2 eq) was added and the mixture was stirred at 25-30° C. for 2 hr under $N_2$ atmosphere. LC-MS showed Compound 5 was consumed completely and one main peak with desired m/z (MW: 732.83 observed m/z: 733.3 ([M+H]$^+$)) was detected. The residue was purified by prep-HPLC (TFA condition). Compound 10F (200 mg, 272.9 μmol) was obtained as colorless oil.

Compound 10G:

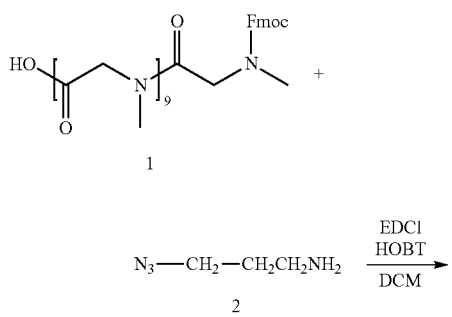

and purged with N₂ for 3 times), and then the mixture was stirred at 25-30° C. for 2 hr under N₂ atmosphere. LC-MS showed compound 1 was consumed completely and one main peak with desired (calculated MW: 1033.14, observed m/z: 1033.2 ([M+H]⁺)) was detected. The reaction mixture was treated with a few drops of 1 M HCl, and the organic layer was collected and evaporated under reduced pressure to remove solvent. Compound 3 (700.0 mg, crude) was obtained as a white solid.

A mixture of compound 3 (700.0 mg, 677.6 μmol, 1.0 eq), N-ethylethanamine (2.48 g, 33.88 mmol, 3.49 mL, 50.0 eq) was dissolved in DCM (5 mL, pre-degassed and purged with N₂ for 3 times), and then the mixture was stirred at 25-30° C. for 2 hr under N₂ atmosphere. LC-MS showed compound 3 was consumed completely and one main peak with desired m/z (calculated MW: 810.90, observed m/z: 811.1 ([M+H]⁺)) was detected. The reaction mixture was concentrated under reduced pressure to remove solvent. Compound 10G (400.0 mg, crude) was obtained as a white solid.

Compound 10H:

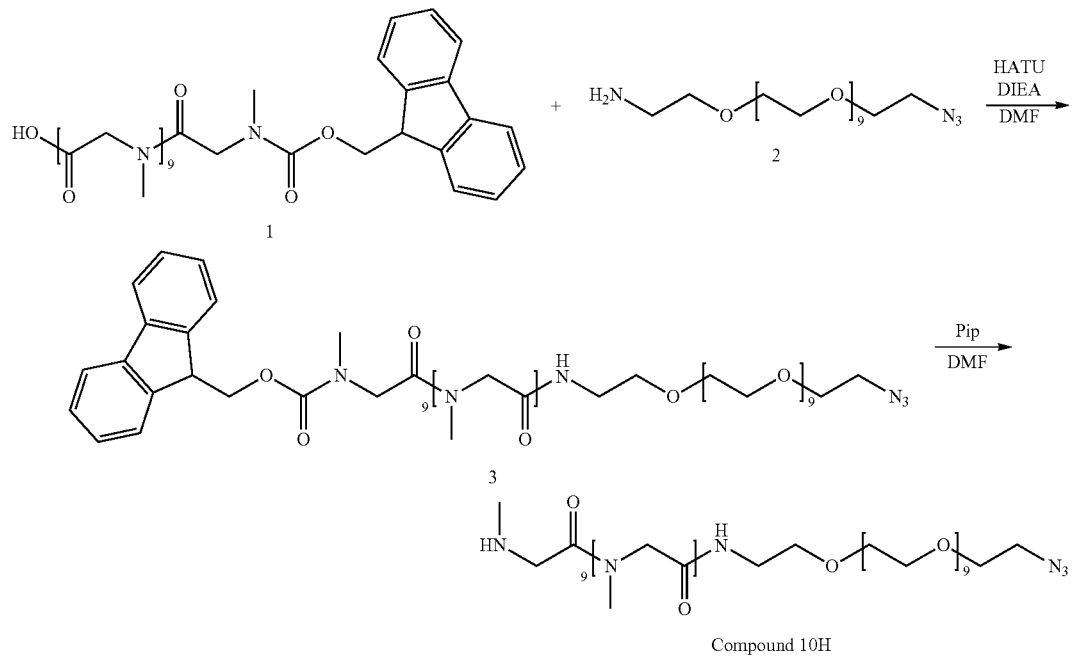

Compound 10H

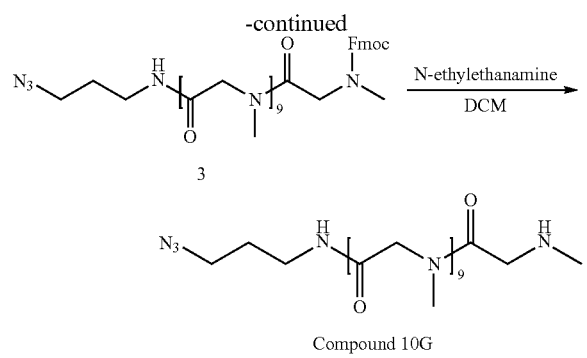

Compound 10G

A mixture of compound 1 (700.0 mg, 736.04 μmol, 1.0 eq) (obtained from solid phase peptide synthesis), 3-azidopropan-1-amine (73.7 mg, 736.04 μmol, 1.0 eq), EDCl (282.2 mg, 1.47 mmol, 2.0 eq), HOBt (119.4 mg, 883.25 μmol, 1.2 eq) was dissolved in DCM (5 mL, pre-degassed A mixture of compound 1 (1 g, 1.05 mmol, 1.0 eq) (obtained from solid phase peptide synthesis), compound 2 (553.7 mg, 1.05 mmol, 1.0 eq) was dissolved in DMF (2 mL), following by addition of HATU (399.8 mg, 1.05 mmol, 1.0 eq) and DIEA (135.9 mg, 1.05 mmol, 183.2 μL, 1.0 eq). The mixture was stirred at 25-30° C. for 2 hr under N₂ atmosphere. TLC (Dichloromethane:Methanol=10:1, $R_f$=0.28) showed the compound 1 was consumed completely. The crude product was then directly used for next step without purification. To a solution of compound 3 (1 g, 685.11 μmol, 1 eq) in DMF (8 mL) was added piperidine (2 mL, 714.05 μmol, 24 eq) in one portion at 25° C. The mixture was stirred for 15 mins at 25° C. LC-MS showed compound 3 was consumed completely and one main peak with desired m/z (calculated MW: 1237.4, observed m/z: 1238.4 ([M+H]⁺)) was detected. The reaction mixture was purified by prep-HPLC (TFA condition). Compound 10H (757 mg, 611.77 μmol, 89.30% yield) was obtained as a white solid.

Compound 10I:

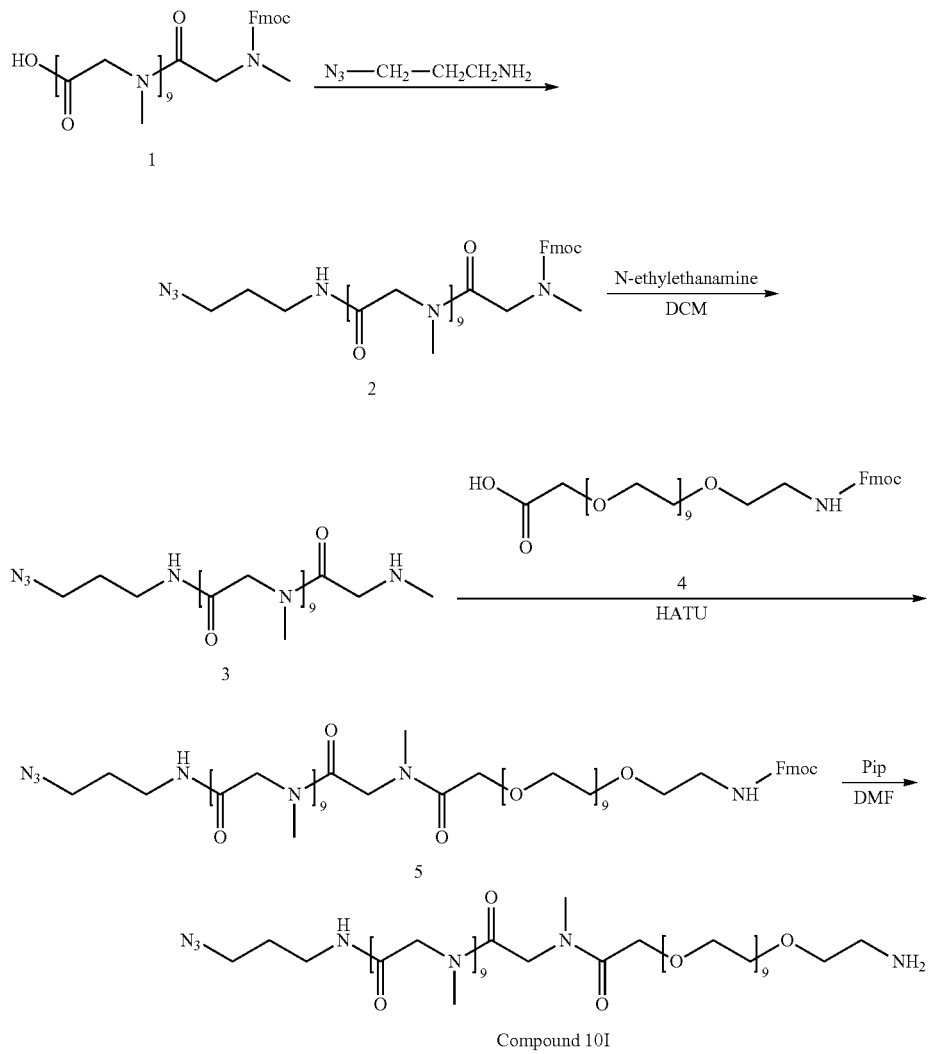

Compound 10I

A mixture of compound 1 (1.4 g, 1.47 mmol, 1.0 eq), 3-azidopropan-1-amine (162.1 mg, 1.62 mmol, 1.1 eq), EDCl (338.6 mg, 1.77 mmol, 1.2 eq), HOBt (238.7 mg, 1.77 mmol, 1.2 eq) was dissolved in DCM (5 mL, pre-degassed and purged with $N_2$ for 3 times), and then the mixture was stirred at 20-25° C. for 1 hr under $N_2$ atmosphere. LC-MS showed compound 1 was consumed completely and one main peak with desired m/z (calculated MW: 1033.14, observed m/z: 1033.2 ([M+H]$^+$)) was detected. The reaction mixture was treated with a few drops of 1 M HCl, and the organic layer was evaporated under reduced pressure to remove solvent. Compound 2 (1.1 g, crude) was obtained as yellow oil.

A mixture of compound 2 (1.1 g, 1.06 mmol, 1 eq), N-ethylethanamine (3.89 g, 53.24 mmol, 5.48 mL, 50 eq) was dissolved in DCM (5 mL, pre-degassed and purged with $N_2$ for 3 times), and then the mixture was stirred at 20-25° C. for 1 hr under $N_2$ atmosphere. LC-MS showed compound 2 was consumed completely and one main peak with desired m/z (calculated MW: 810.90, observed m/z: 810.9 ([M+H]$^+$)) was detected. The reaction mixture was evaporated under reduced pressure and compound 3 (810 mg, crude) was obtained as a white solid.

A mixture of compound 3 (810.0 mg, 998.9 μmol, 1.0 eq), compound 4 (810.7 mg, 1.10 mmol, 1.1 eq), HATU (455.8 mg, 1.20 mmol, 1.2 eq), DIEA (258.2 mg, 2.00 mmol, 348.0 μL, 2.0 eq) was dissolved in DMF (2 mL, pre-degassed and purged with $N_2$ for 3 times), and then the mixture was stirred at 25-30° C. for 2 under $N_2$ atmosphere. LC-MS showed compound 3 was consumed completely and one main peak with desired m/z (calculated MW: 1530.72, observed m/z: 765.5 ([M/2+H]$^+$)) was detected. The reaction mixture was treated with a few drops of 1 M HCl, and the organic layer was collected and evaporated under reduced pressure to remove solvent. Compound 5 (1.1 g, crude) was obtained as a yellow solid.

Compound 5 (1 g, 653.29 μmol, 1 eq) was dissolved in DCM (10 mL, pre-degassed and purged with $N_2$ for 3 times), following by addition of piperidine (2.39 g, 32.66 mmol, 3.36 mL, 50 eq), and then the mixture was stirred at 25-30° C. for 2 hr under $N_2$ atmosphere. LC-MS showed Compound 5 was consumed completely and one main peak with desired m/z (calculated MW: 1308.47, observed m/z: 1308.4 ([M+H]$^+$)) was detected. The residue was purified by prep-HPLC (TFA condition). Compound 10I (700 mg, 463.72 μmol, 70.98% yield) was obtained as a yellow solid.

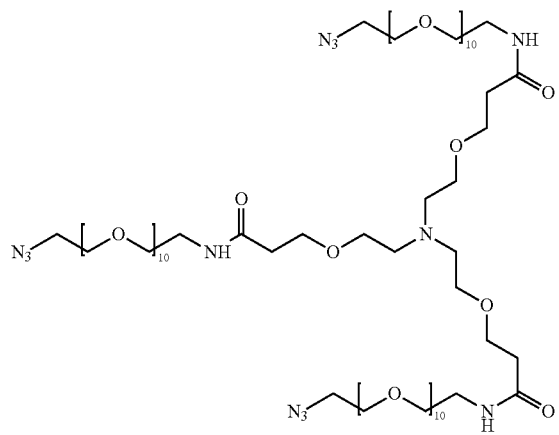
11A
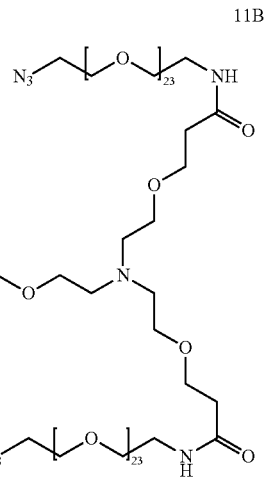
11B
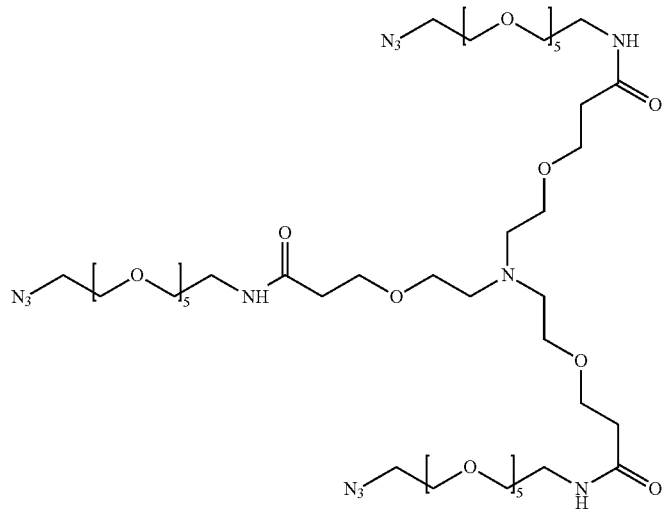
11C
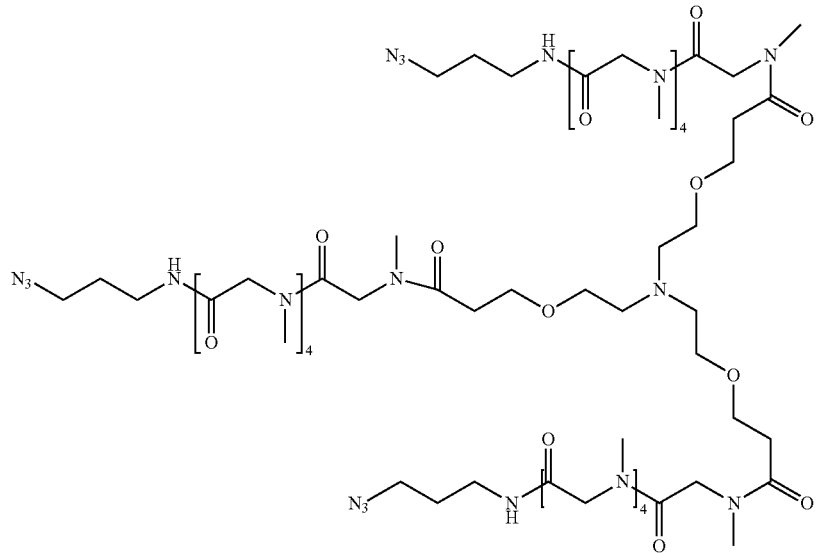
11D

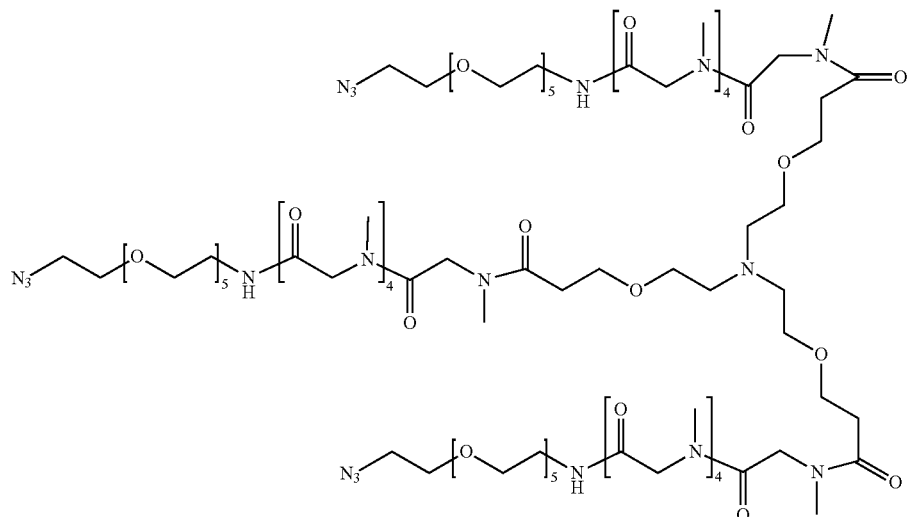
11E
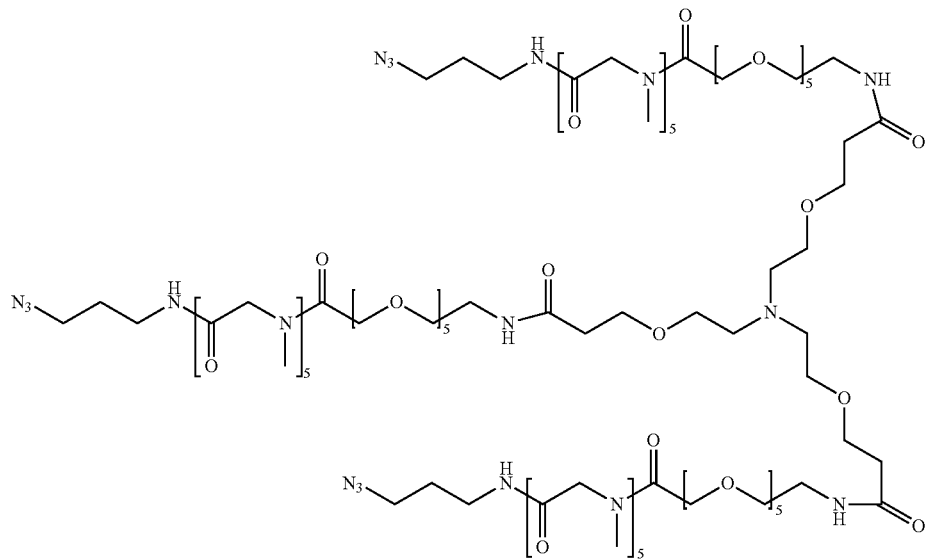
11F
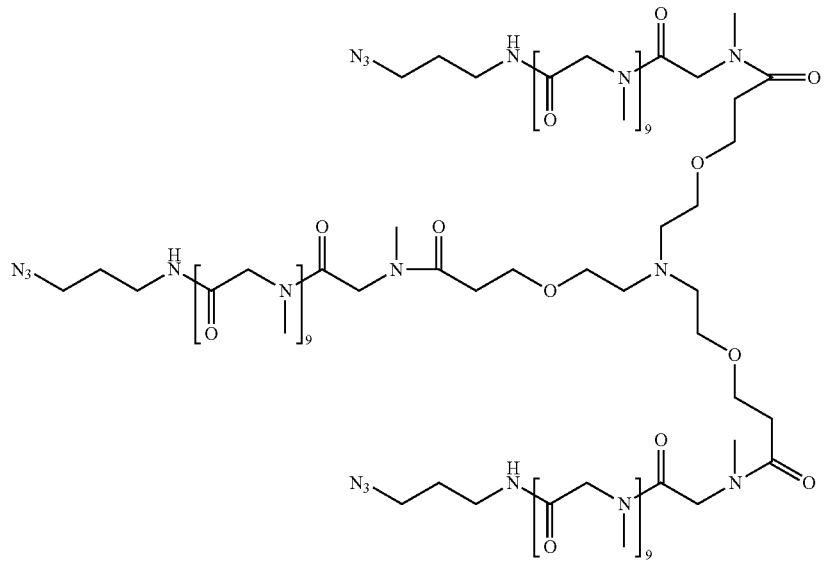
11G

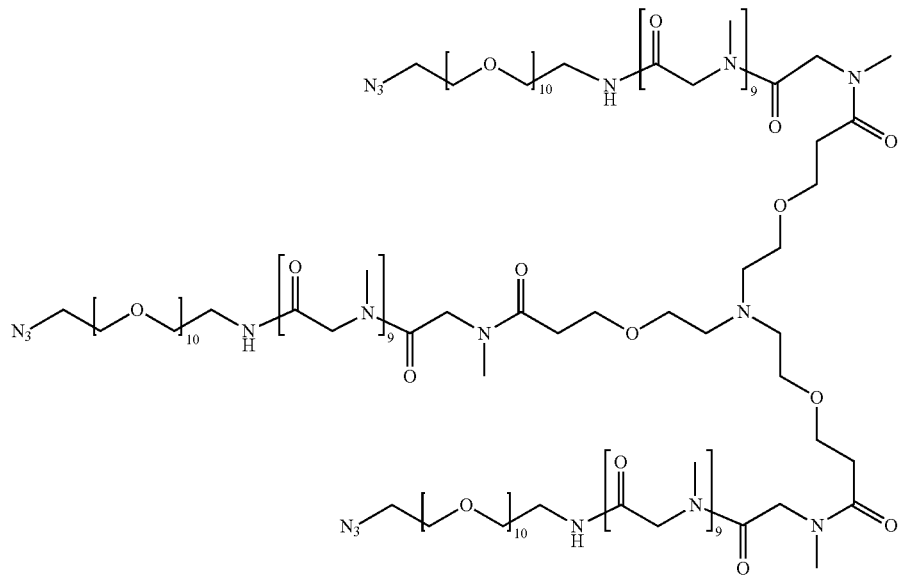
11H
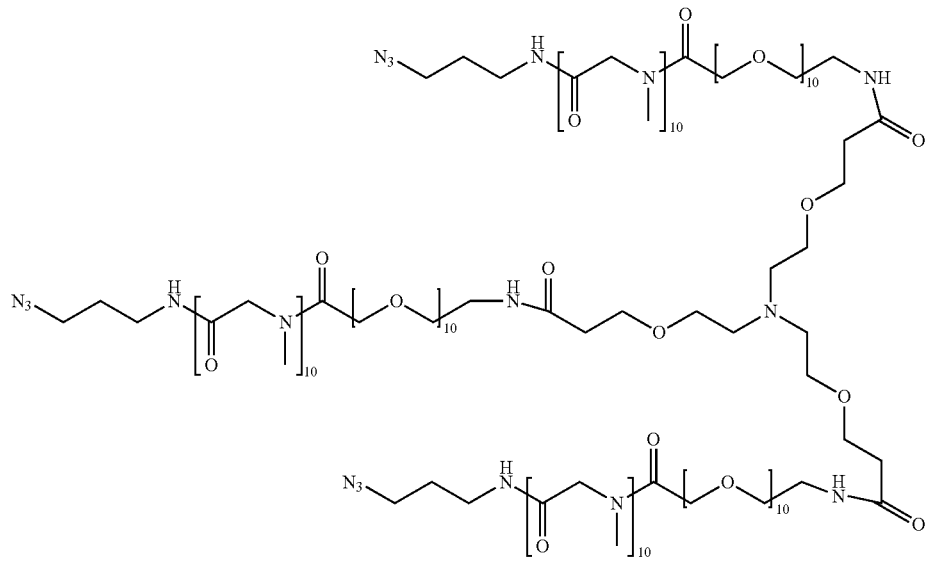
11I
11J
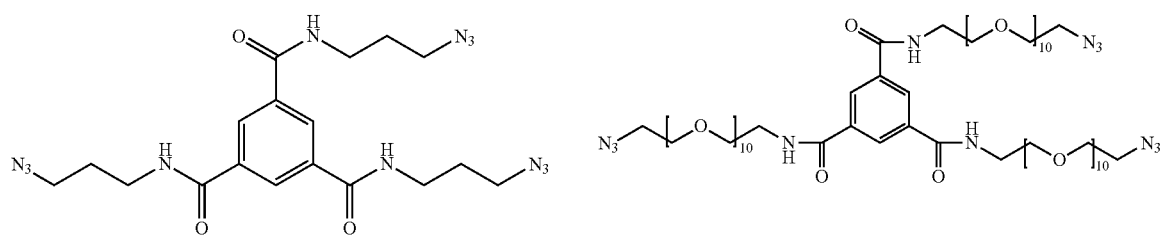
11K
11L

11M
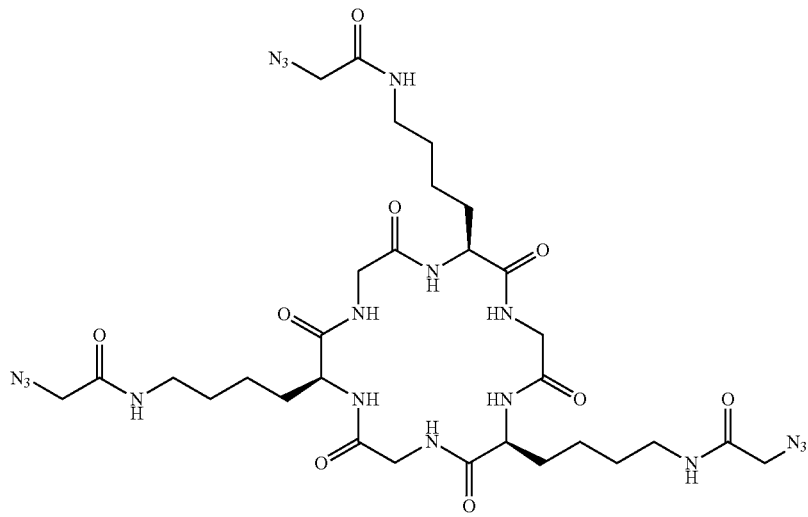
11N
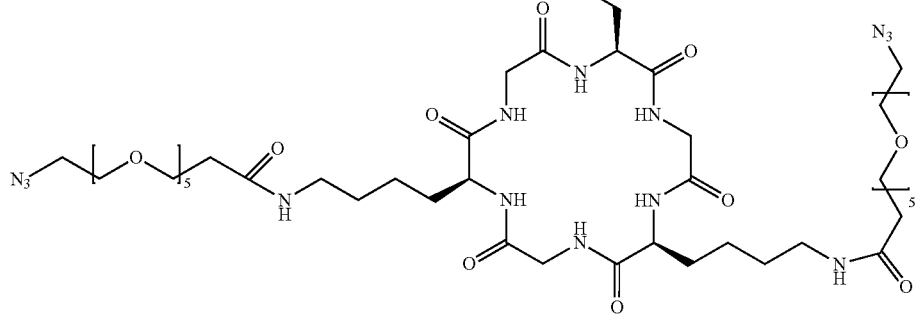
11O
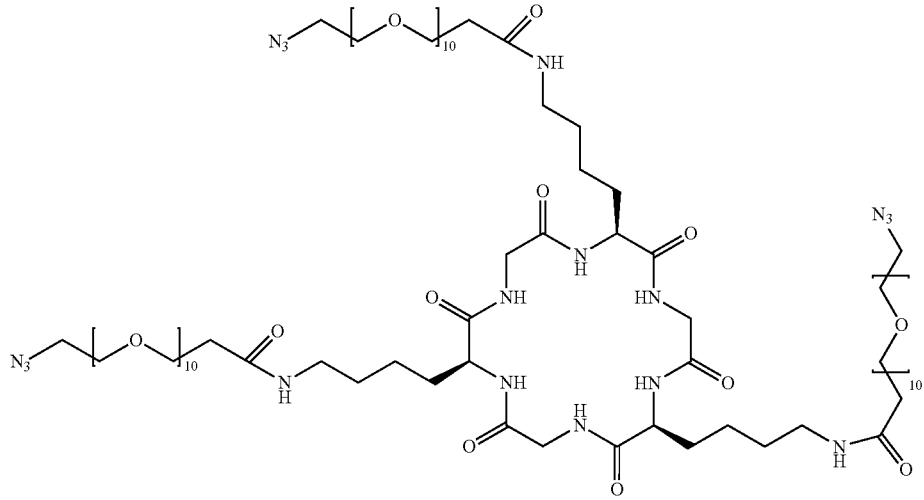
Compound 11A:
To a solution of compound 9A (100 mg, 248.86 μmol, 1 eq, HCl) in DMF (1 mL) was added EDCl (160 mg, 834.63 μmol, 3.35 eq) and HOBt (110 mg, 814.07 μmol, 3.27 eq) and DIPEA (192.98 mg, 1.49 mmol, 260.08 μL, 6.0 eq), then compound 10A (400 mg, 759.56 μmol, 3.05 eq) in DMF (1 mL) was added dropwise. The mixture was stirred at 25-30° C. for 12 hrs. LC-MS showed Reactant 1 was consumed completely and one main peak with desired m/z was detected. The reaction mixture was purified by prep-HPLC (TFA condition) to give compound 11A (128 mg, 64.30 µmol, 25.84% yield, 95% purity) as a colorless oil.

Compound 11B:

To a solution of compound 9A (50 mg, 124.43 µmol, 1.0 eq, HCl) in DMF (1 mL) was added HOBt (56 mg, 414.44 µmol, 3.33 eq), EDCl (80 mg, 417.31 µmol, 3.35 eq) and DIPEA (96.49 mg, 746.57 µmol, 130.04 µL, 6.0 eq) then compound 10B (420 mg, 382.06 µmol, 3.07 eq) in DMF (1 mL) was added dropwise. The mixture was stirred at 25-30° C. for 12 hrs. LC-MS showed Reactant 1 was consumed completely and one main peak with desired m/z was detected. The reaction mixture was purified by prep-HPLC (TFA condition) to give compound 11B (257 mg, 67.65 µmol, 54.37% yield, 95.0% purity) as a colorless oil.

Compounds 11C, 11D, 11E, 11F, 11G, 11H and 11I were synthesized in an analogous manner to that described above for Compound 11B using Compound 9A and one of Compounds 10C, 10D, 10E, 1° F., 10G, 10H and 10I as starting materials, EDCl as the coupling reagent and DIPEA as the base.

Compound 11K:

To a solution of compound 9B (20.0 mg, 95.2 µmol, 1.0 eq), compound 10A (320.0 mg, 291.1 µmol, 3.06 eq) in DMF (5 mL) was added EDCl (60.0 mg, 313.0 µmol, 3.29 eq), HOBt (40.0 mg, 296.0 µmol, 3.11 eq), DMAP (10.0 mg, 81.8 µmol, 0.86 eq) and DIEA (44.5 mg, 344.5 µmol, 60 µL, 3.62 eq). The mixture was stirred at 30° C. for 12 hr. LC-MS showed compound 9B was consumed completely and one main peak with desired m/z (calculated MW: 3454.01, observed m/z: 1168.4000 ([M/3+H$_2$O]$^+$)) was detected. The reaction mixture was concentrated under reduced pressure to remove solvent to give a residue. The residue was purified by prep-HPLC (TFA condition). Compound 11K (200.0 mg, 57.9 µmol, 60.84% yield, 100% purity) was obtained as a white solid.

Compound 11J was synthesized in an analogous manner to that described above for Compound 11K using Compound 9B and Compound 10J as starting materials, EDCl as coupling reagent and DIPEA as base.

Compound 11L:

To a solution of compound 9B (20.0 mg, 95.2 µmol, 1.0 eq), compound 10B (152.0 mg, 288.6 µmol, 3.03 eq) in DMF (5 mL) was added EDCl (60.0 mg, 313.0 µmol, 3.29 eq), HOBt (40.0 mg, 296.0 µmol, 3.11 eq), DMAP (12.0 mg, 98.2 µmol, 1.03 eq) and DIEA (41.6 mg, 321.5 µmol, 56 µL, 3.38 eq). The mixture was stirred at 30° C. for 12 hr. LC-MS showed compound 9B was consumed completely and one main peak with desired m/z (calculated MW: 1735.96, observed m/z: 867.87 ([M/2+H]$^+$)) was detected. The reaction mixture was concentrated under reduced pressure to remove solvent to give a residue. The residue was purified by prep-HPLC (TFA condition). Compound 11L (140.0 mg, 79.8 µmol, 83.86% yield, 98.97% purity) was obtained as a colorless oil.

Compound 11M was synthesized in an analogous manner to that described below for Compound 11N using Compound 9C and Compound 10M as starting materials, EDCl as coupling reagent and DIPEA as base.

Compound 11N:

To a solution of compound 9C (20.0 mg, 36.0 µmol, 1.0 eq), compound 10M (40.0 mg, 119.3 µmol, 3.3 eq) in DMF (2 mL) was added EDCl (26.0 mg, 135.6 µmol, 3.8 eq), HOBt (18.0 mg, 133.2 µmol, 3.7 eq), DMAP (4.4 mg, 36.0 µmol, 1.0 eq) and DIEA (23.7 mg, 183.7 µmol, 32 µL, 5.1 eq). The mixture was stirred at 30° C. for 12 hr. LC-MS showed compound 9C was consumed completely and one main peak with desired m/z (calculated MW: 1507.68, observed m/z: 753.77 ([M/2+H]$^+$)) was detected. The reaction mixture was concentrated under reduced pressure to remove solvent to give a residue. The residue was purified by prep-HPLC (TFA condition). Compound 11N (40.0 mg, 26.5 µmol, 73.71% yield, 100% purity) was obtained as a colorless oil.

Compound 11O:

To a solution of compound 9C (10.0 mg, 18.0 µmol, 1.0 eq), compound 10L (30.0 mg, 54.0 µmol, 3.0 eq) in DMF (2 mL) was added EDCl (28.0 mg, 144.0 µmol, 8.0 eq), HOBt (13.0 mg, 90.0 µmol, 5.0 eq), DMAP (5.0 mg, 36.0 µmol, 2.0 eq) and DIEA (19 mg, 144.0 µmol, 25 µL, 8.0 eq). The mixture was stirred at 30° C. for 12 hr. LC-MS showed compound 9C was consumed completely and one main peak with desired m/z (calculated MW: 2168.47, observed m/z: 1183.88 ([M/2+H]$^+$)) was detected. The reaction mixture was concentrated under reduced pressure to remove solvent to give a residue. The residue was purified by prep-HPLC (TFA condition). Compound 11O (17.8 mg, 8.2 µmol, 45.61% yield, 100% purity) was obtained as a white oil.

General Procedure for Preparation of Tetrameric Azide Linker

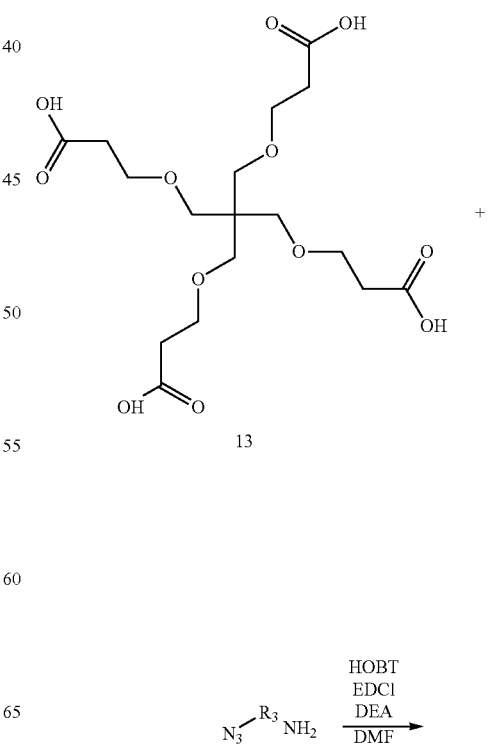

-continued

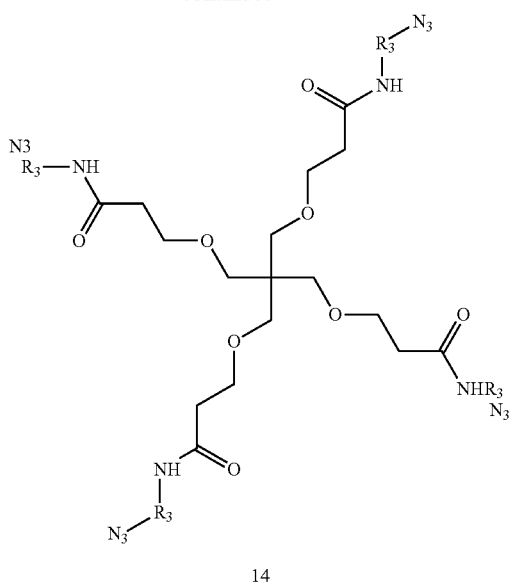

14

Compound 10:

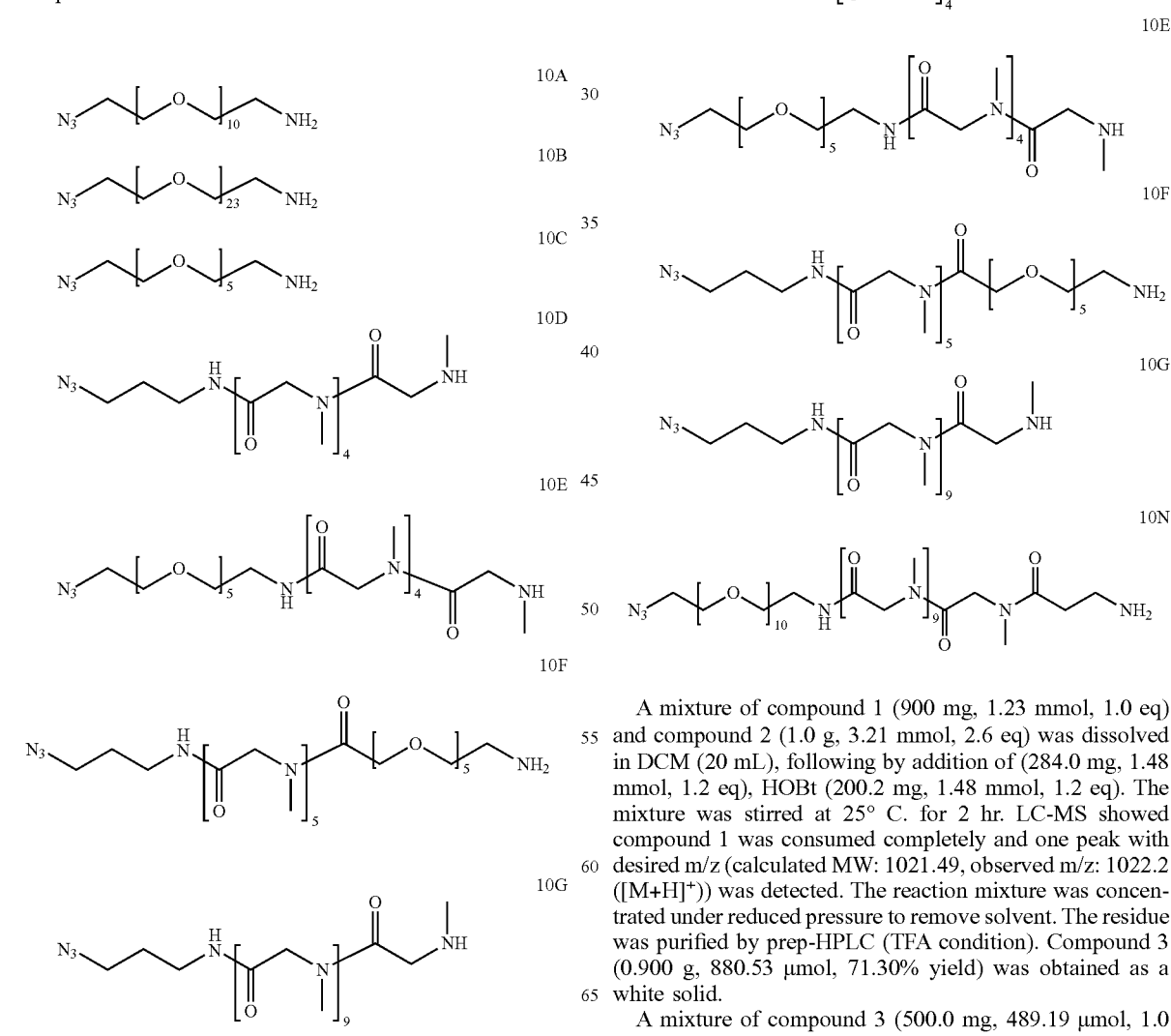

Compound 10 N:

A mixture of compound 1 (900 mg, 1.23 mmol, 1.0 eq) and compound 2 (1.0 g, 3.21 mmol, 2.6 eq) was dissolved in DCM (20 mL), following by addition of (284.0 mg, 1.48 mmol, 1.2 eq), HOBt (200.2 mg, 1.48 mmol, 1.2 eq). The mixture was stirred at 25° C. for 2 hr. LC-MS showed compound 1 was consumed completely and one peak with desired m/z (calculated MW: 1021.49, observed m/z: 1022.2 ([M+H]$^+$)) was detected. The reaction mixture was concentrated under reduced pressure to remove solvent. The residue was purified by prep-HPLC (TFA condition). Compound 3 (0.900 g, 880.53 μmol, 71.30% yield) was obtained as a white solid.

A mixture of compound 3 (500.0 mg, 489.19 μmol, 1.0 eq), compound 4 (257.6 mg, 489.19 μmol, 1.0 eq) was dissolved in DCM (5 mL), following by addition of HOBt (132.2 mg, 978.37 μmol, 2.0 eq), EDCl (187.6 mg, 978.37 μmol, 2.0 eq). The mixture was stirred at 25-30° C. for 2 hrs. LC-MS showed compound 3 was consumed completely and one main peak with desired m/z (MW: 1529.80 observed m/z: 765.9 ([M/2+H]$^+$) was detected. The reaction mixture was concentrated under reduced pressure to remove solvent to give a residue. The residue was purified by prep-HPLC (neutral condition). Compound 3 (420 mg, 246.94 μmol, 50.48% yield) was obtained as colorless oil.

Compound 5 (420 mg, 274.38 μmol, 1.0 eq) was dissolved in DMF (4 mL), following by addition of piperidine (865.2 mg, 10.16 mmol, 1 mL, 37 eq). The mixture was stirred at 25-30° C. for 2 hr. LC-MS showed compound 5 was consumed completely and one main peak with desired m/z (calculated MW: 1308.48, observed m/z: 654.8 ([M/2+H]$^+$) was detected. The crude product was purified by prep-HPLC (TFA condition). Compound 10N (386 mg, 265.50 μmol, 96.76% yield) was obtained as colorless oil. Compound 14:

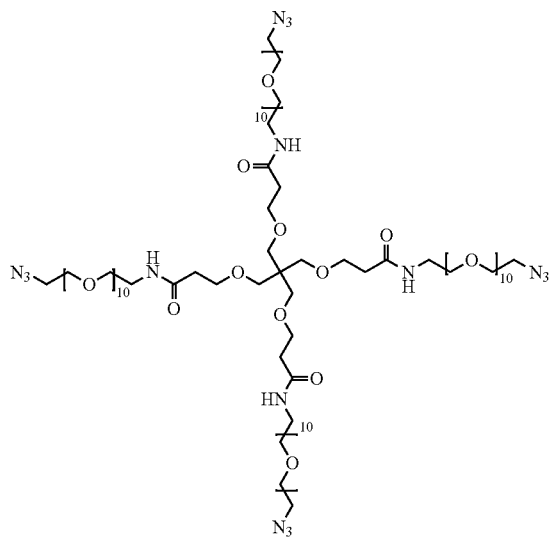

14A

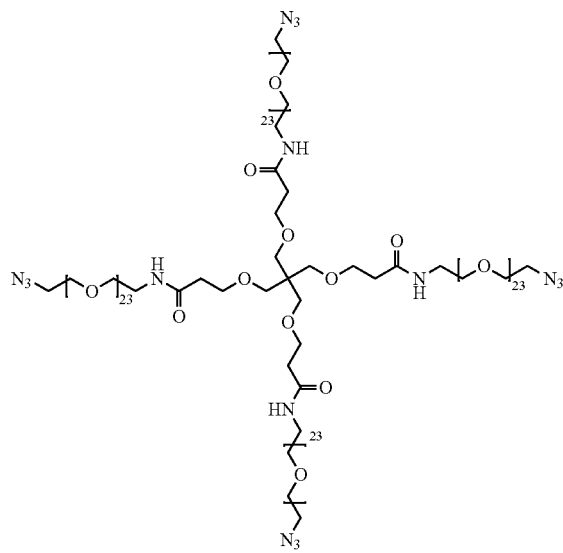

14B

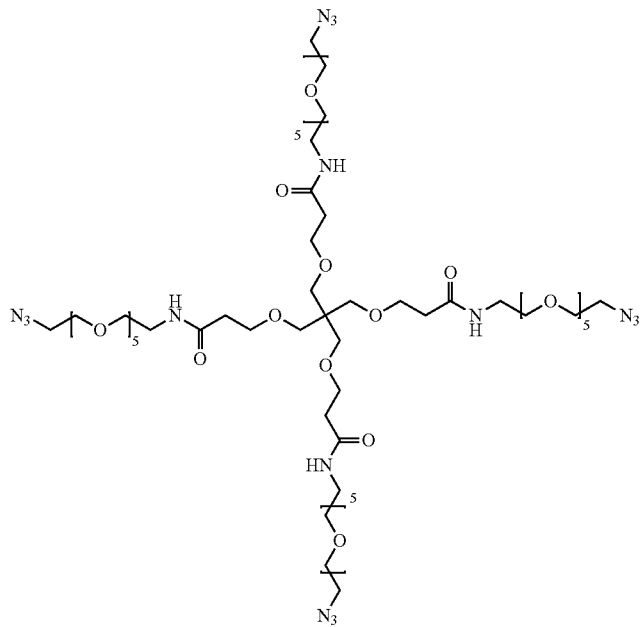

14C

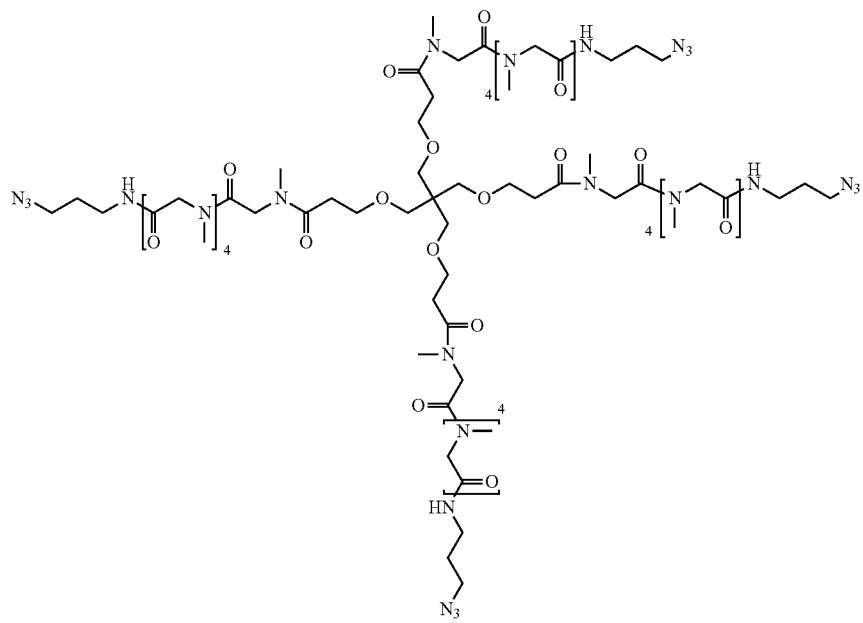
14D
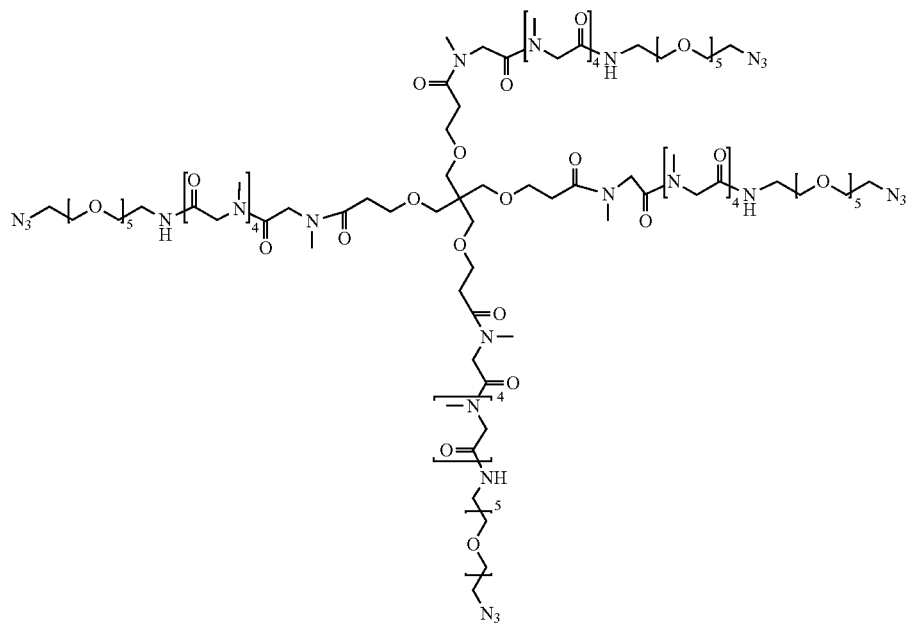
14E

-continued
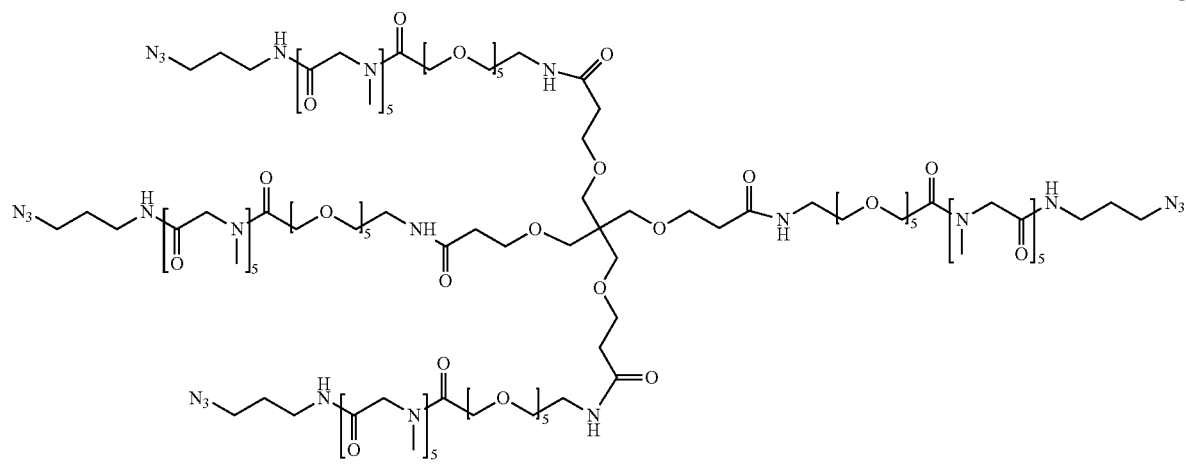
14F
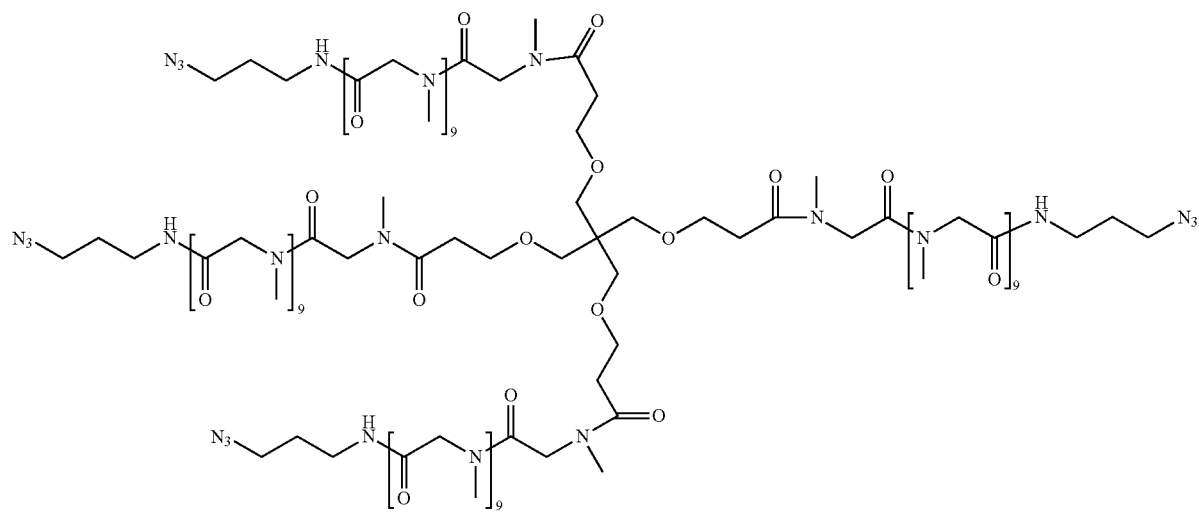
14G
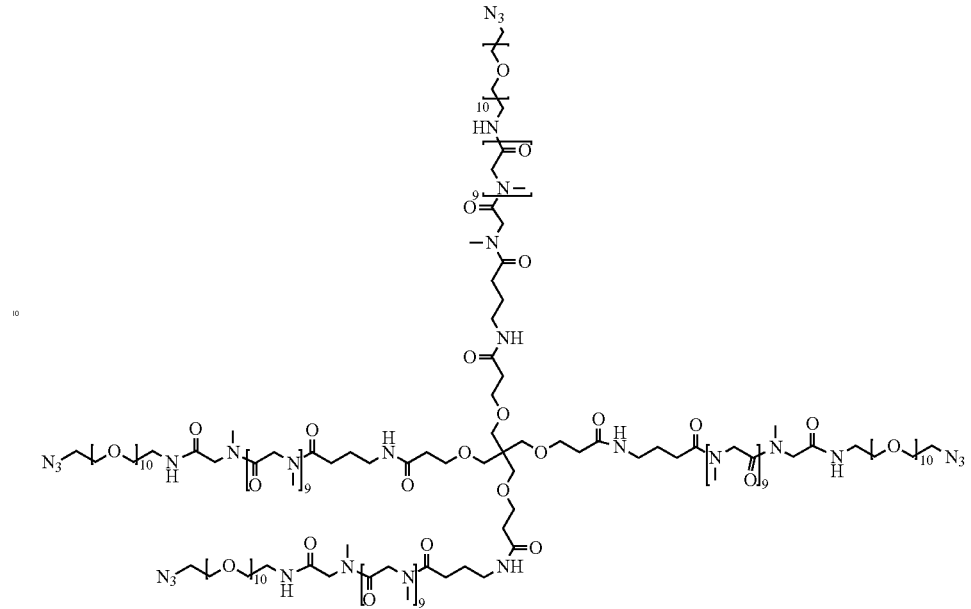
14H

Compound 14A:

To a solution of compound 13 (100 mg, 235.63 µmol, 1 eq) in DMF (1 mL) was added EDCl (200 mg, 1.04 mmol, 4.43 eq) and HOBt (140 mg, 1.04 mmol, 4.4 eq) and DIPEA (185.50 mg, 1.44 mmol, 0.25 mL, 6.09 eq), then compound 10A (500 mg, 949.45 µmol, 4.03 eq) in DMF (1 mL) was added dropwise. The mixture was stirred at 25-30° C. for 12 hrs. LC-MS showed LC-MS showed no Reactant 1 was remained. Several new peaks were shown on LC-MS and ~50% of desired compound was detected. The reaction mixture was purified by prep-HPLC (TFA condition) to give compound 14A (385 mg, 148.75 µmol, 63.13% yield, 95% purity) as a light yellow oil.

Compound 14B:

To a solution of compound 13 in DMF (1 mL) was added HOBt (56 mg, 414.45 µmol, 4.40 eq) and EDCl (80 mg, 417.32 µmol, 4.43 eq) and DIEA (73.09 mg, 565.51 µmol, 98.50 µL, 6.0 eq) then compound 10B (420 mg, 382.06 µmol, 4.05 eq) in DMF (1 mL) was added dropwise. The mixture was stirred at 20° C. for 12 hrs. LC-MS showed no compound 13 was remained. Several new peaks were shown on LC-MS and 50% of desired compound was detected. The mixture was purified by prep-HPLC (TFA condition) to give compound 14B (225 mg, 47.37 µmol, 50.26% yield, 100% purity) as a white solid.

Compounds 14C, 14D, 14E, 14F, 14G, and 14H were synthesized in an analogous manner to that described above for Compound 14B using Compound 13, and one of Compounds 10A, 10B, 10C, 10D, 10E, 10F, 10G and 10N as starting materials, EDCl as the coupling reagent and DIPEA as the base.

General Procedure for Preparation of Compound Trimeric Bicycle Conjugates

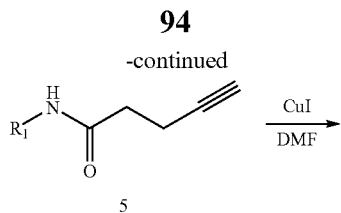

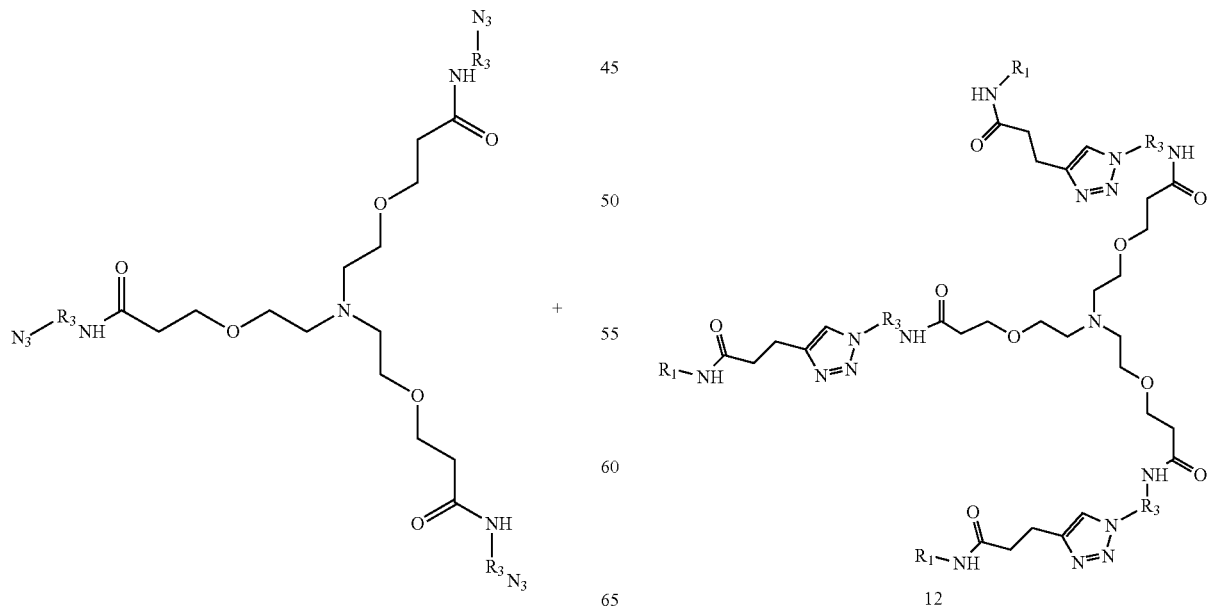

Compound 11:
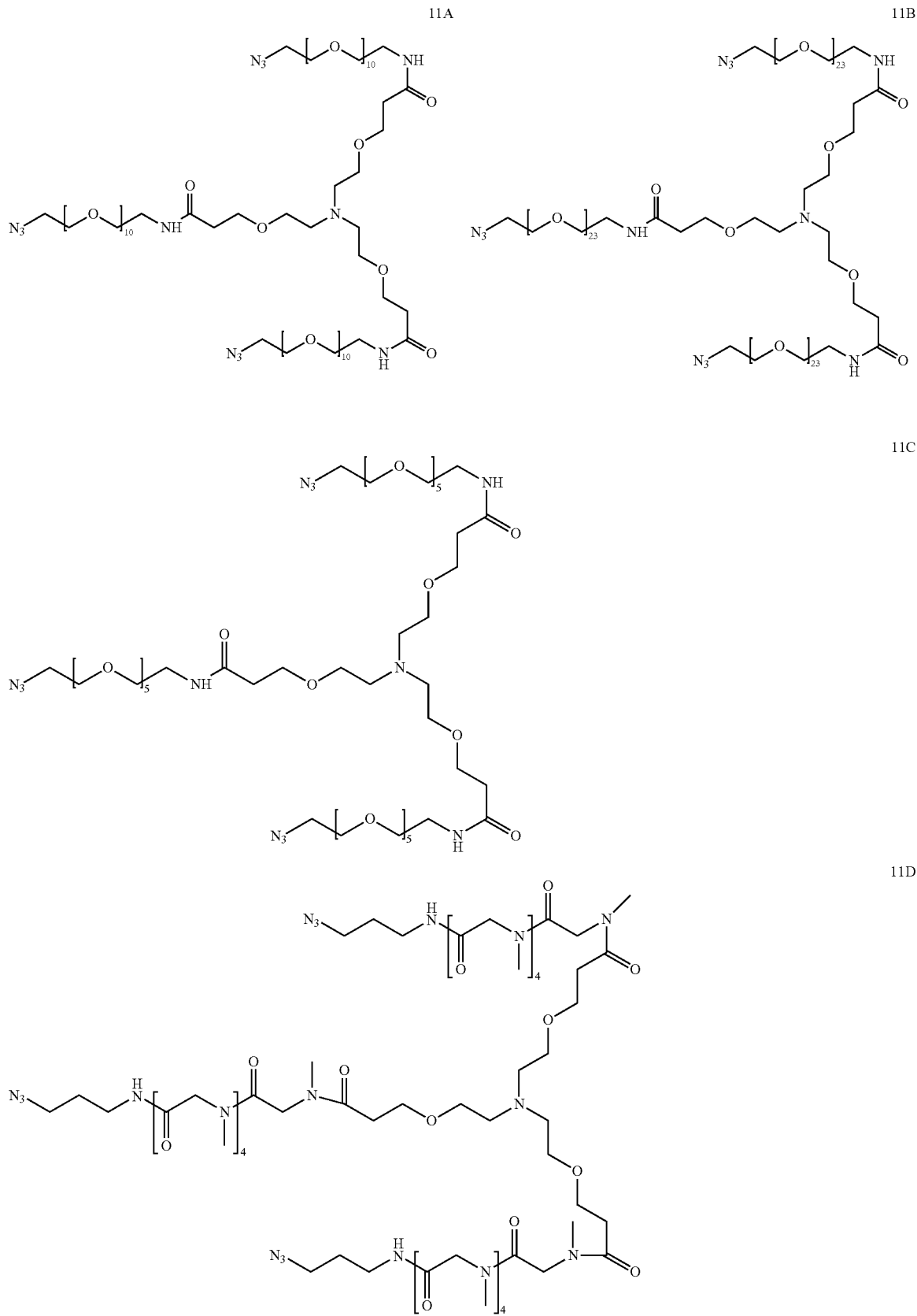

-continued
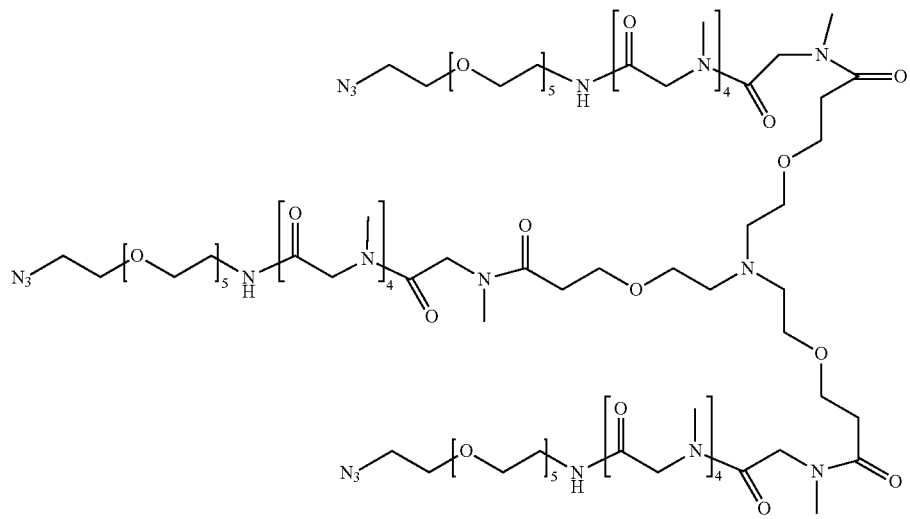
11E
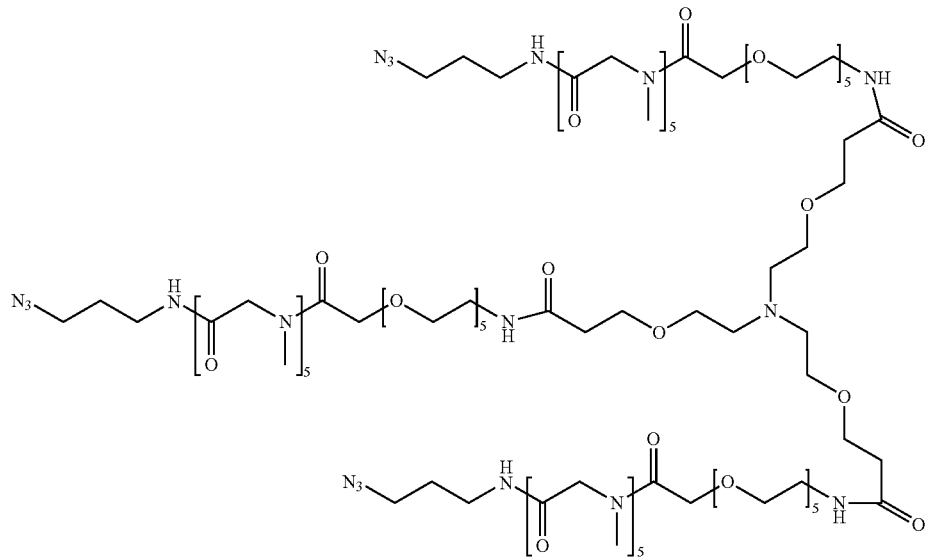
11F
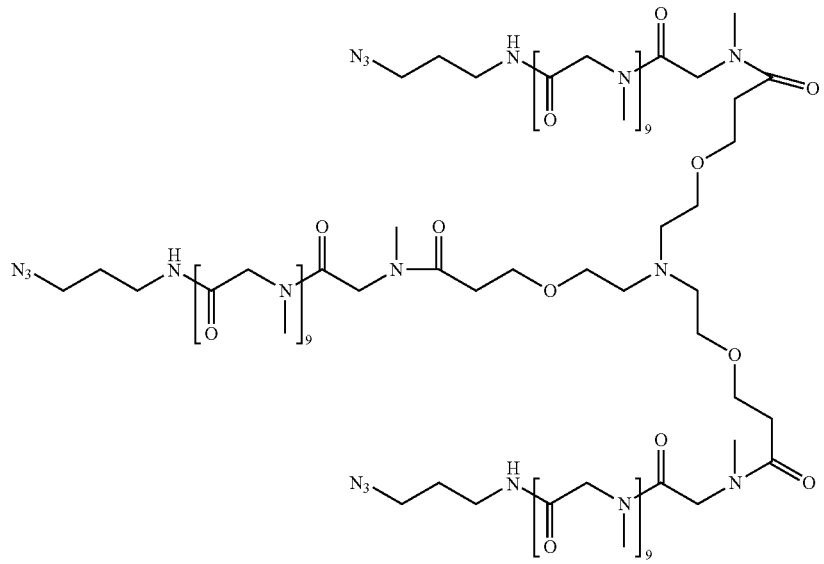
11G

-continued
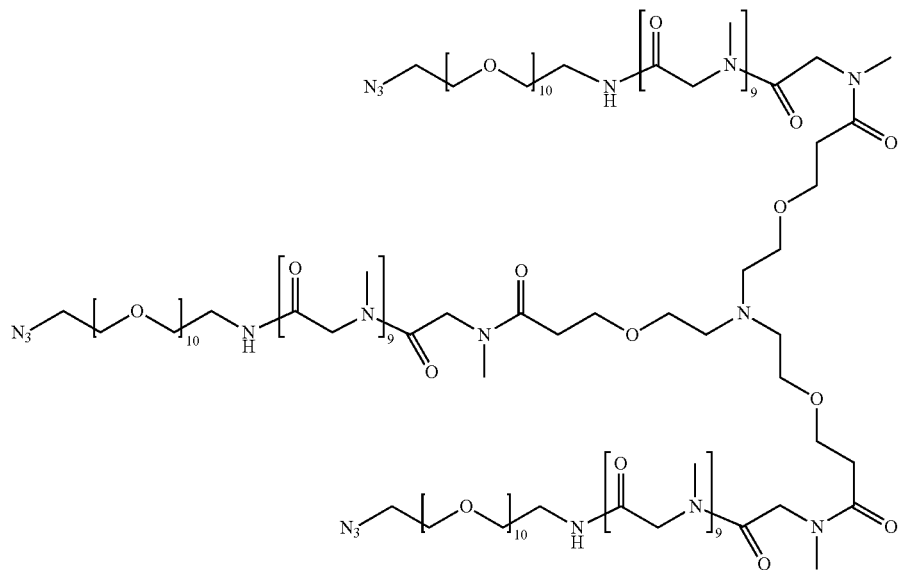
11H
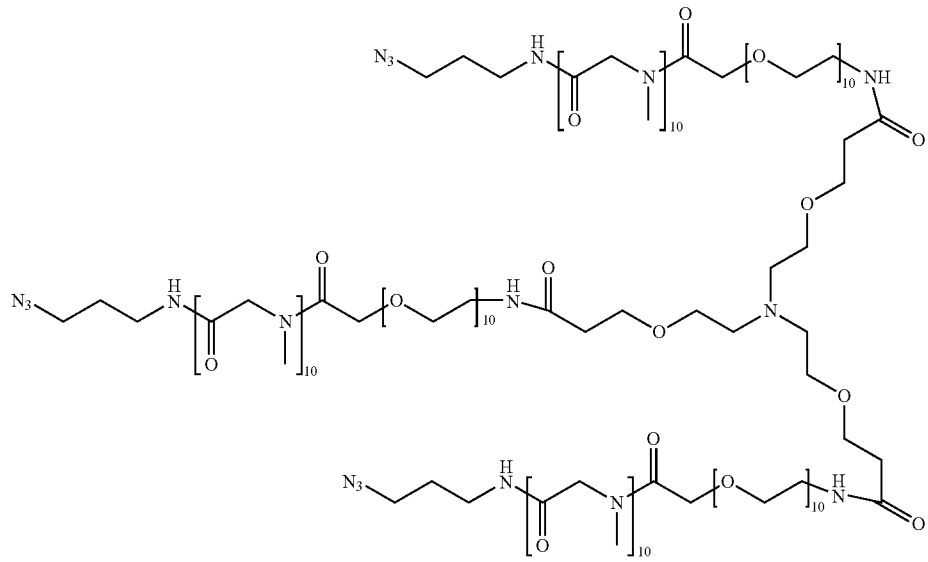
11I
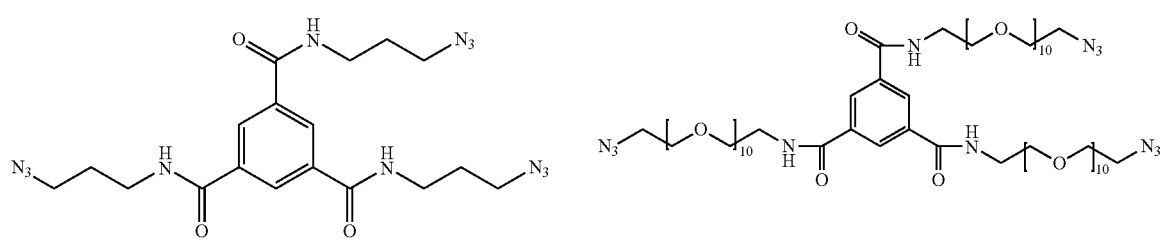
11J 11K
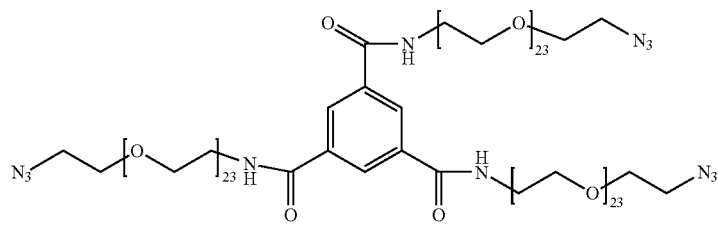
11L

-continued
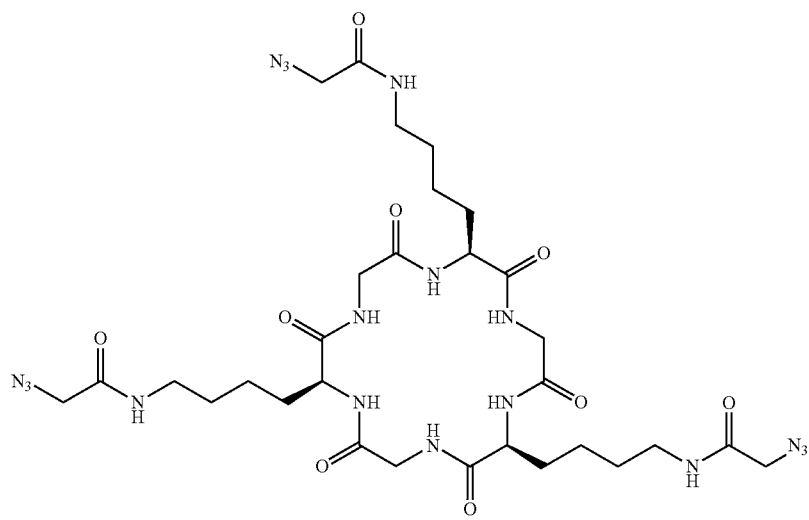
11M
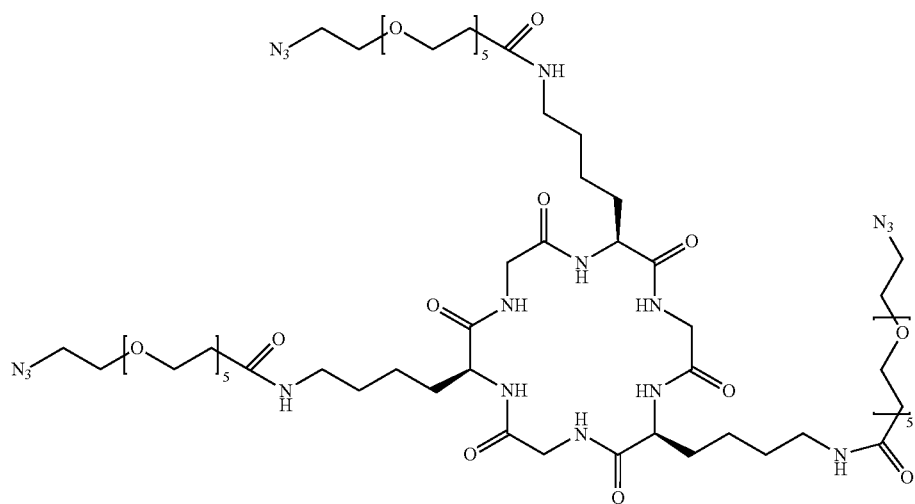
11N
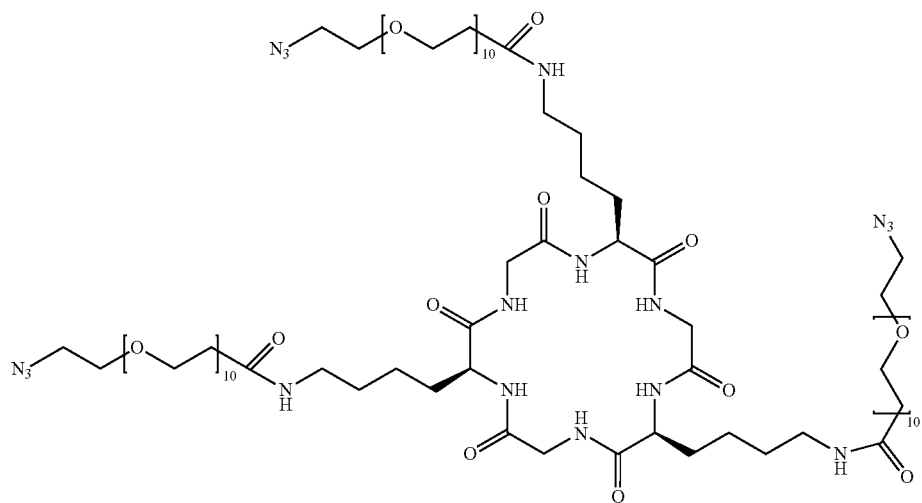
11O

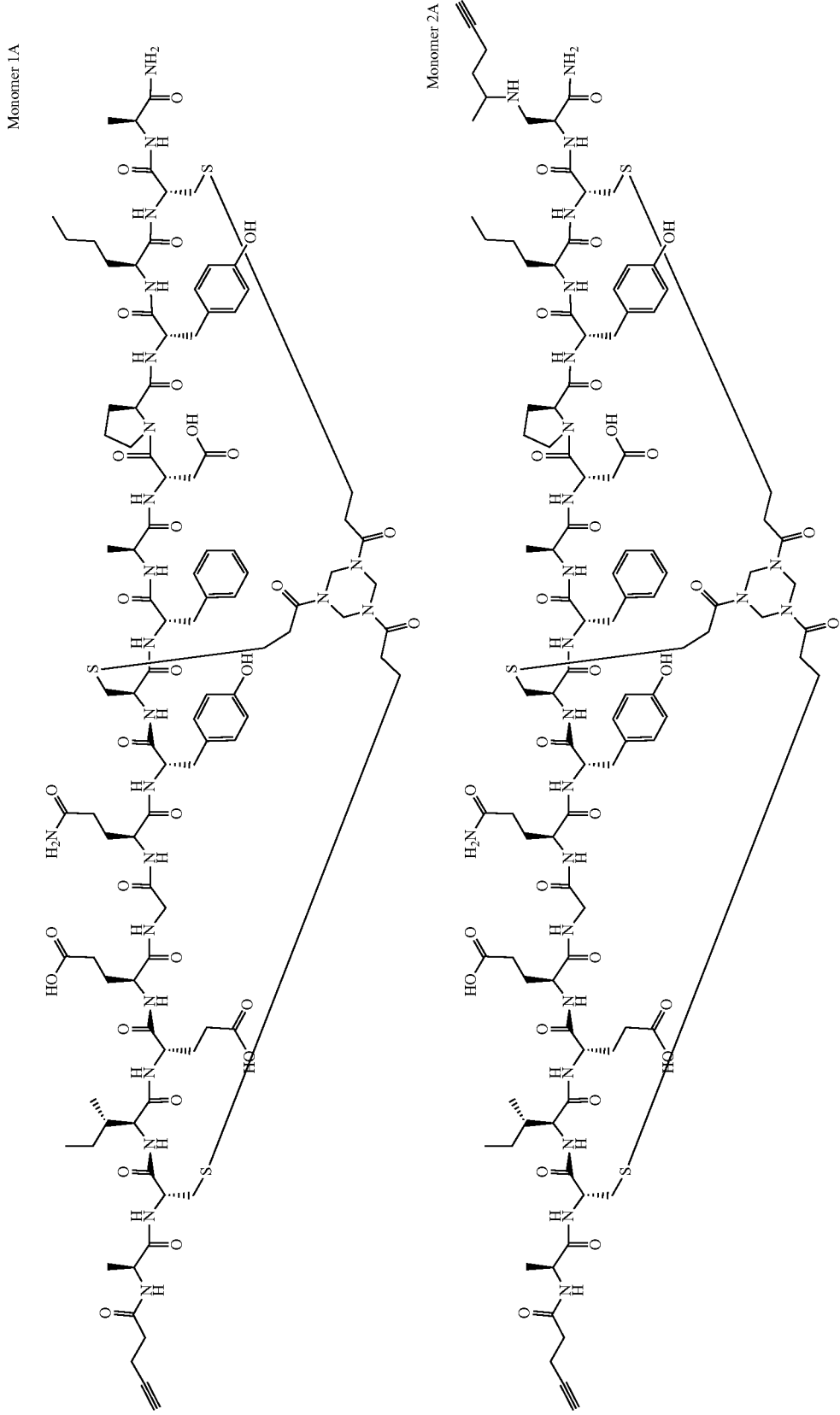

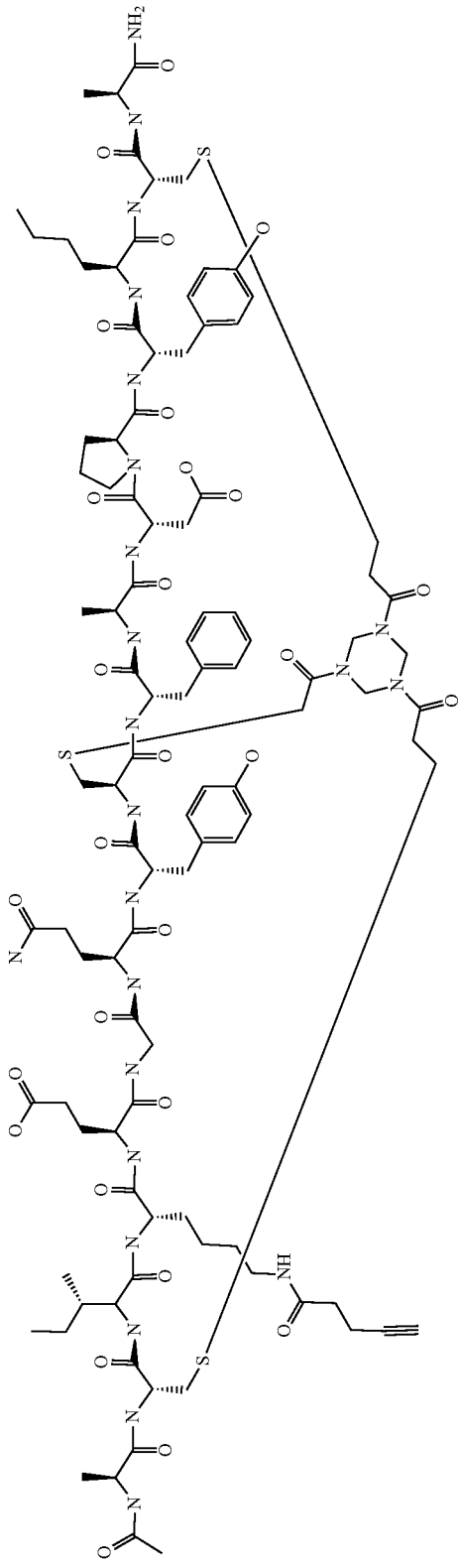

-continued
Monomer 4A
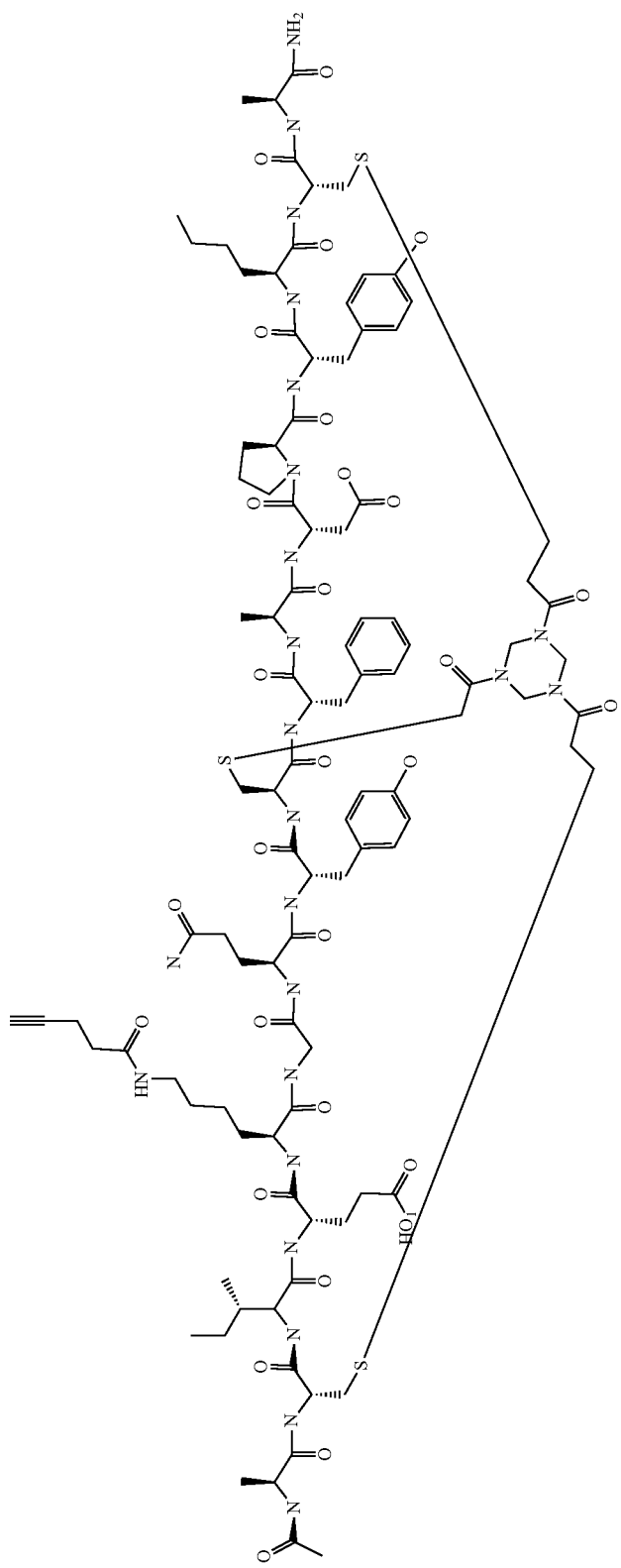

-continued
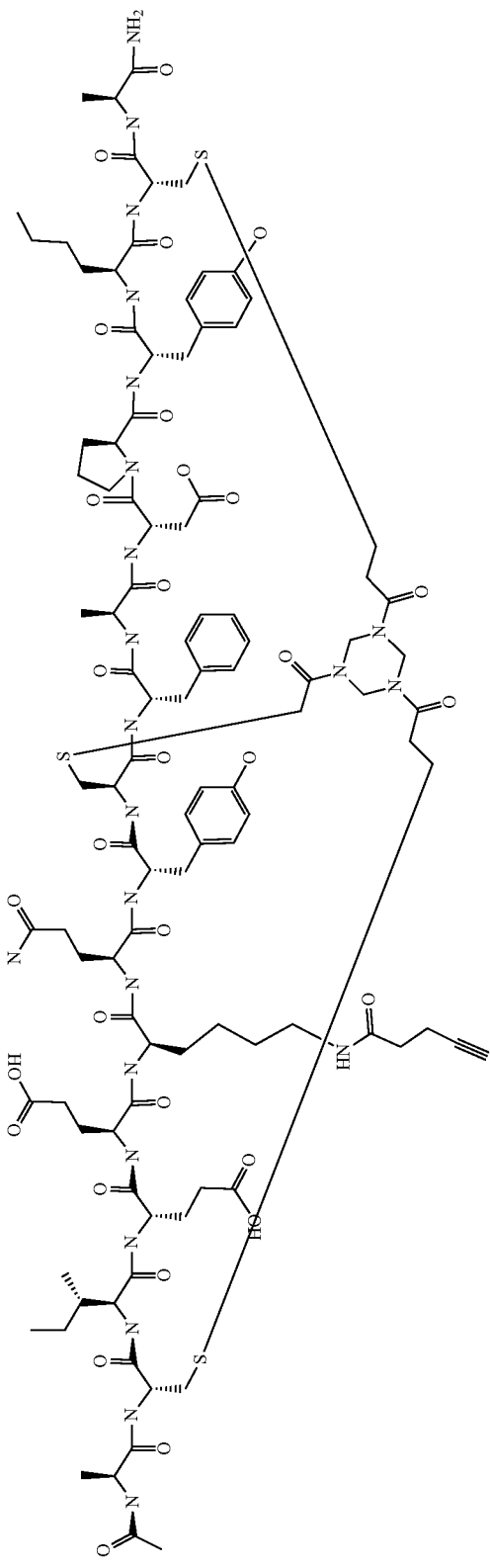
Monomer 5A
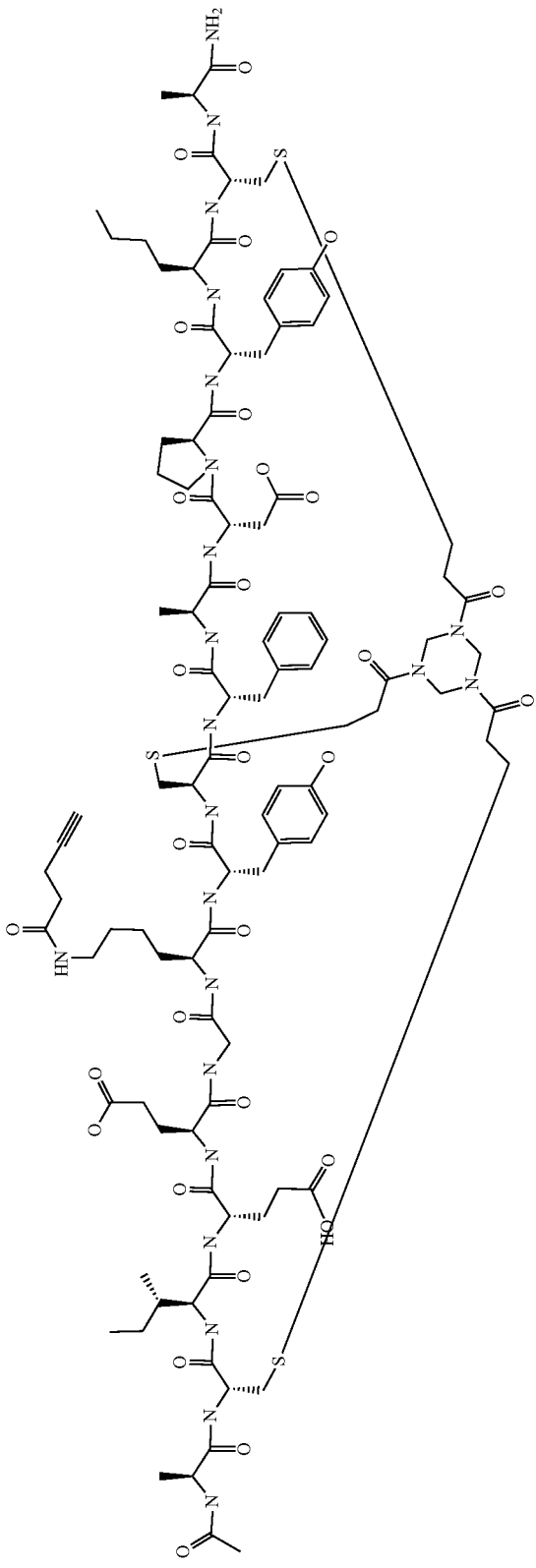
Monomer 6A

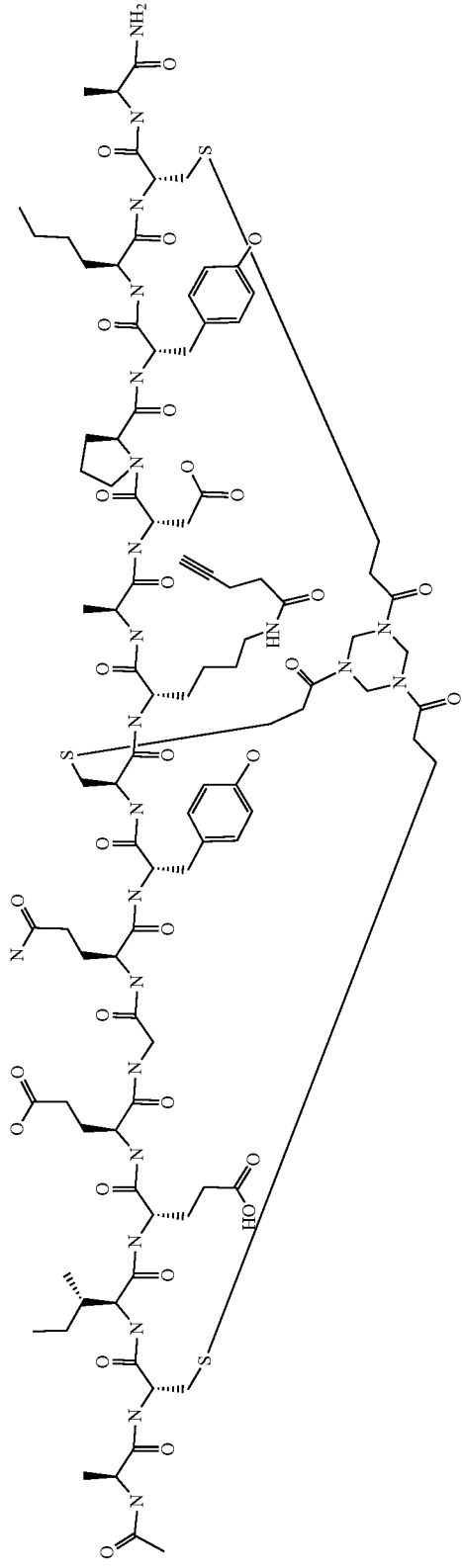
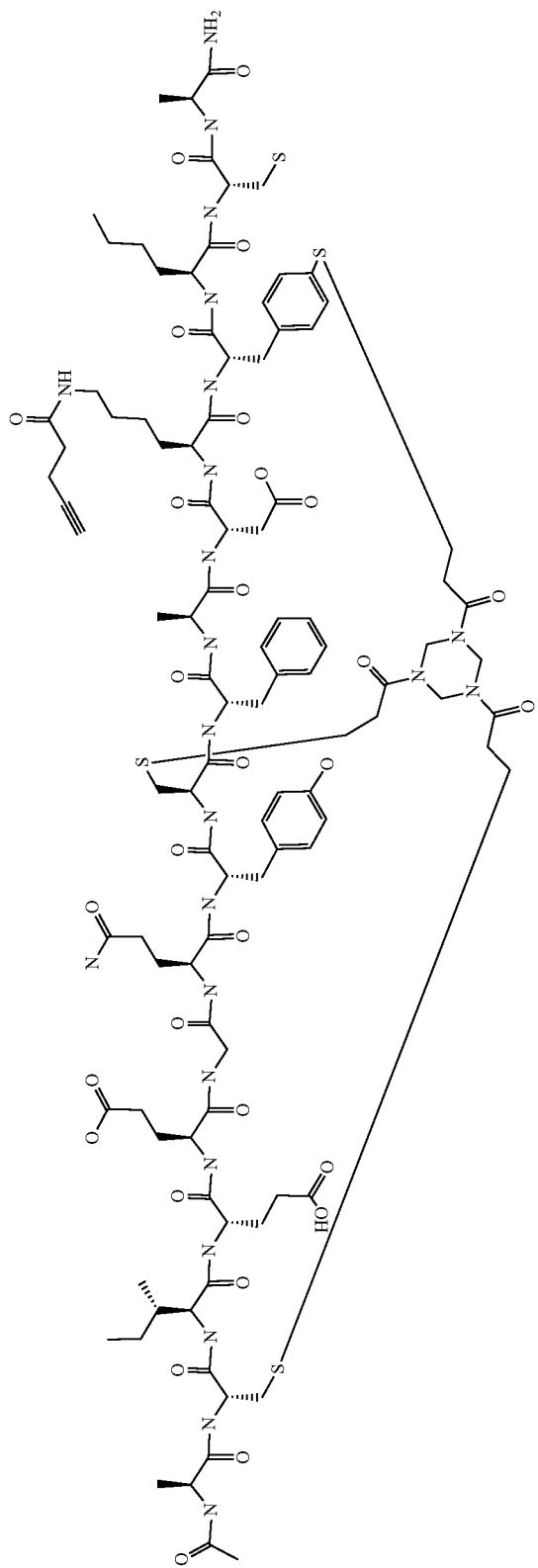

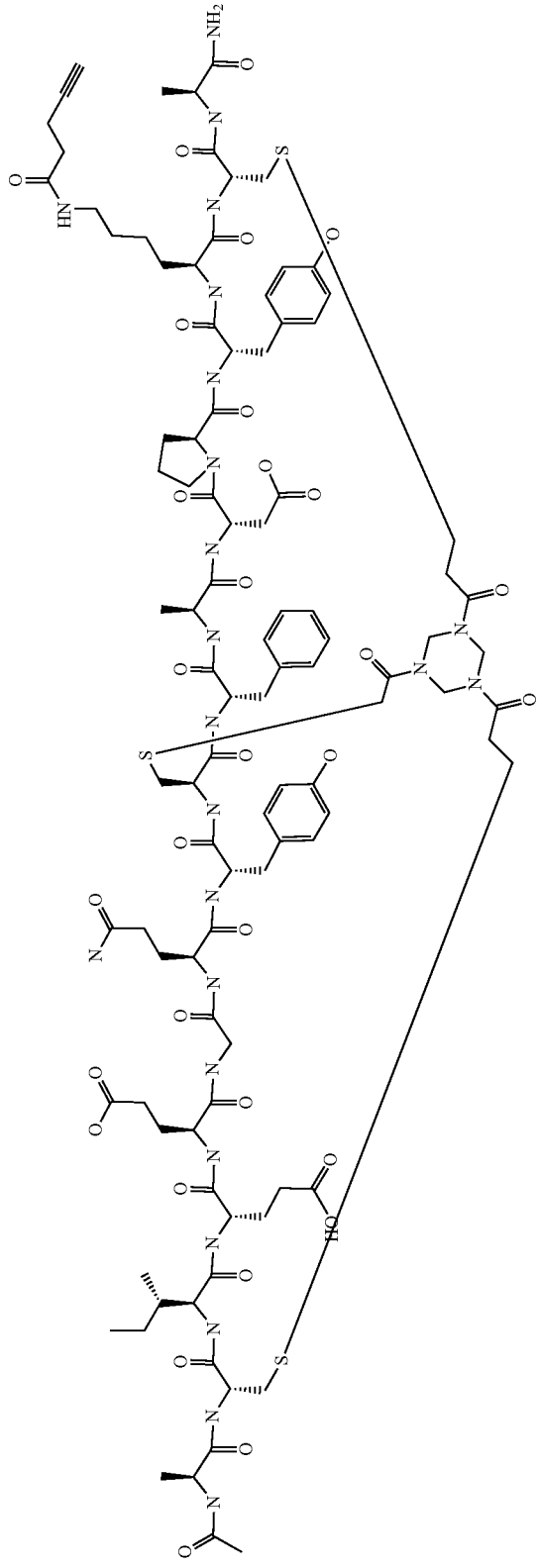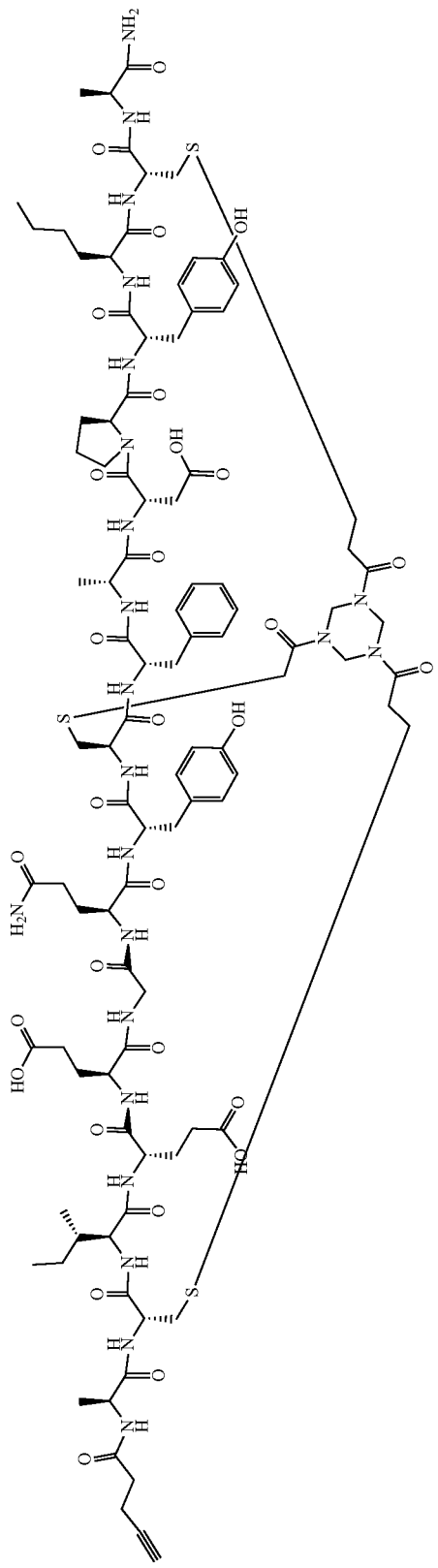

-continued
Monomer 11A
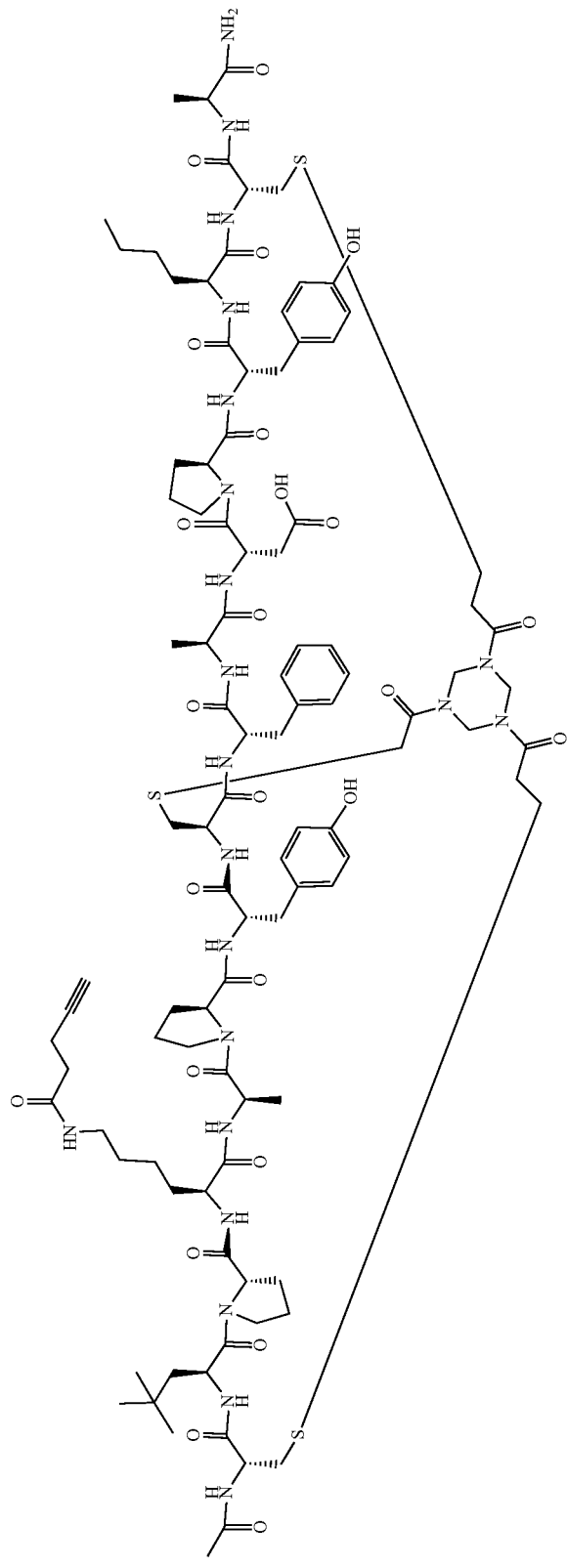
Monomer 12A
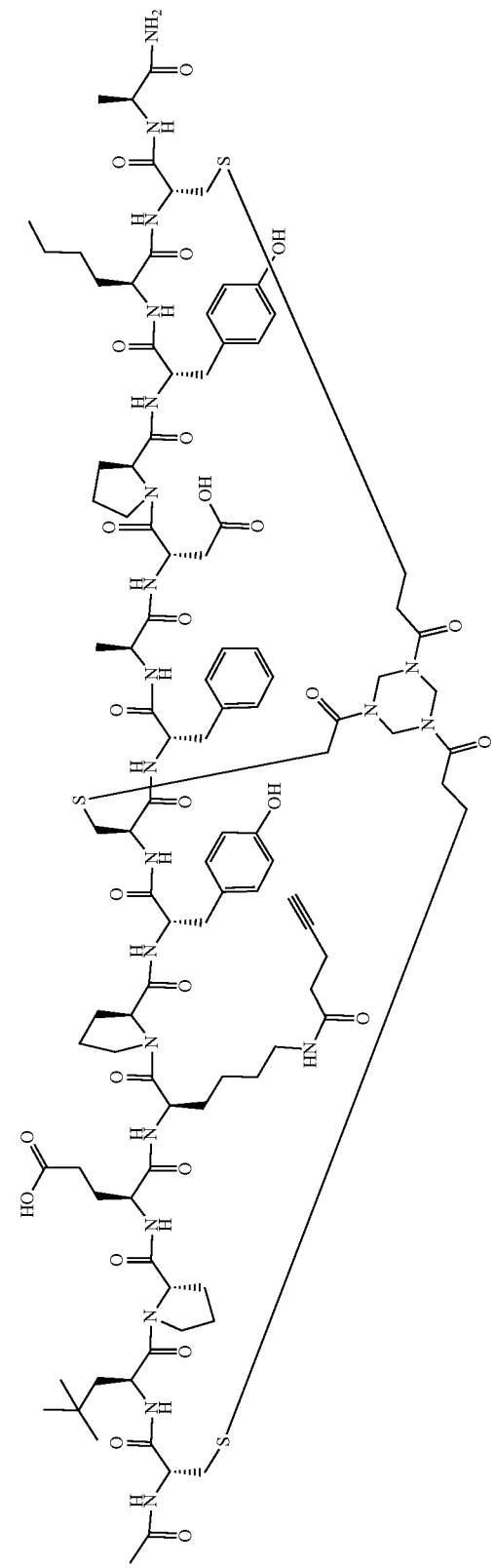

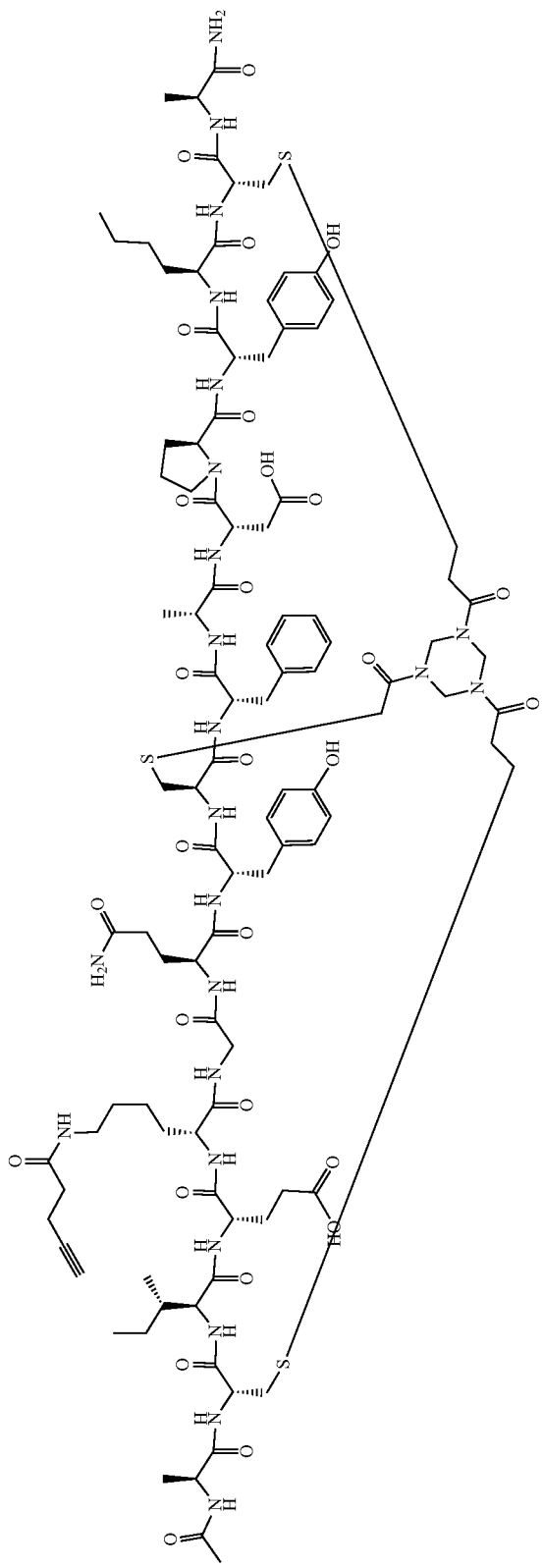

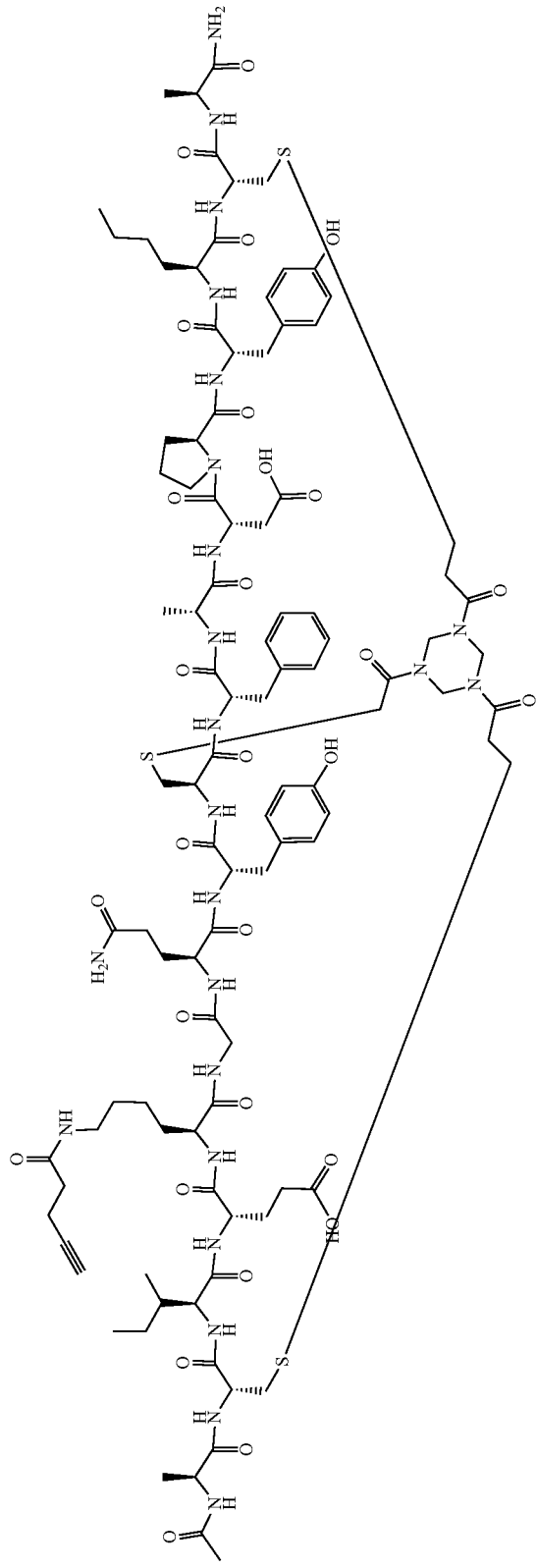
Monomer 14A
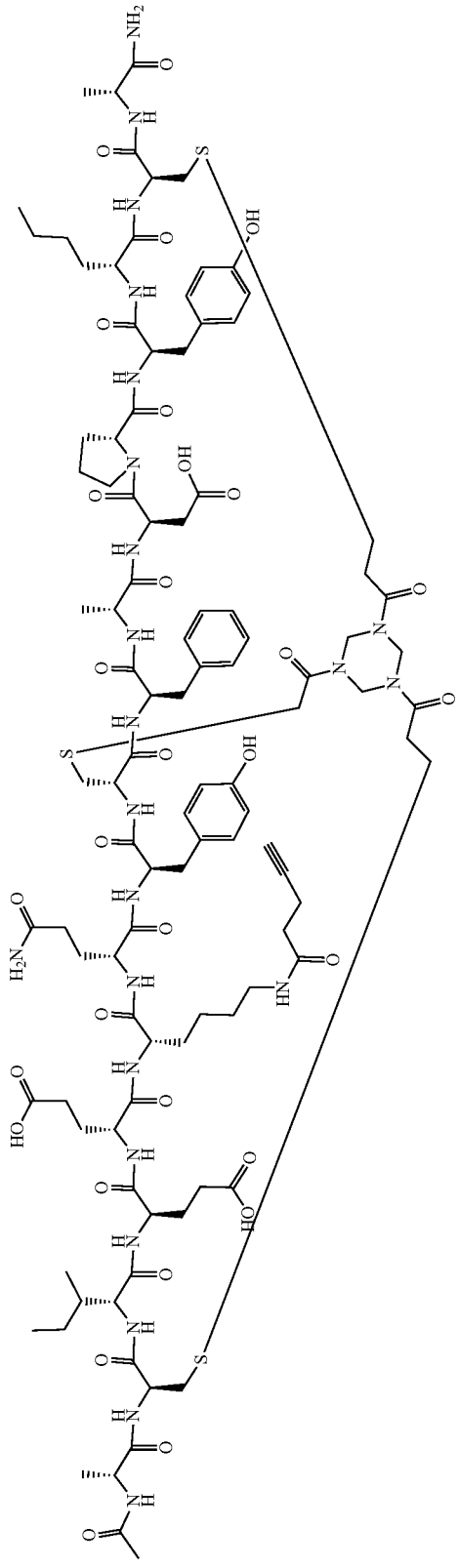
Monomer 15A

121
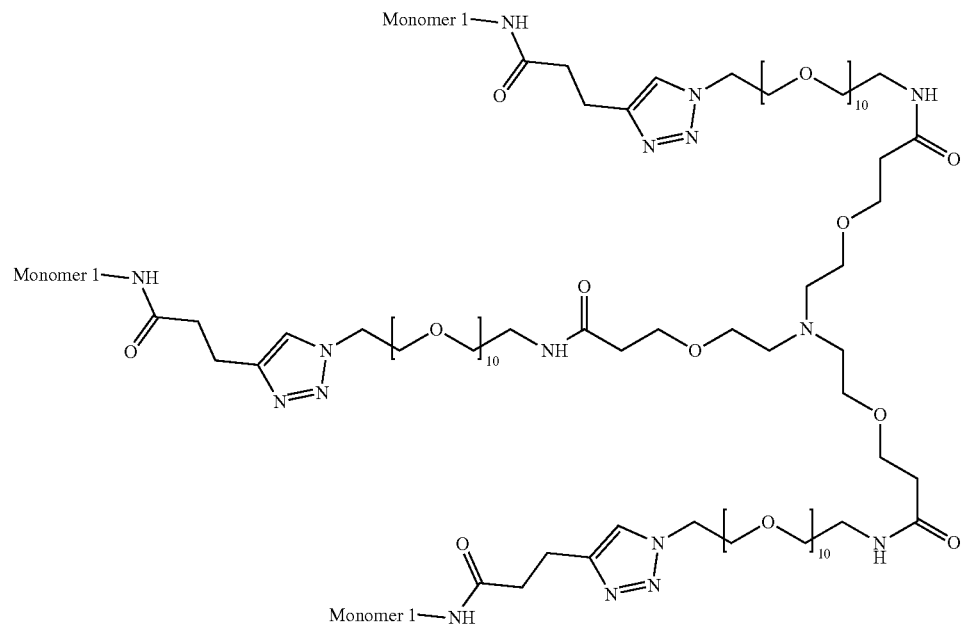
BCY7827
122
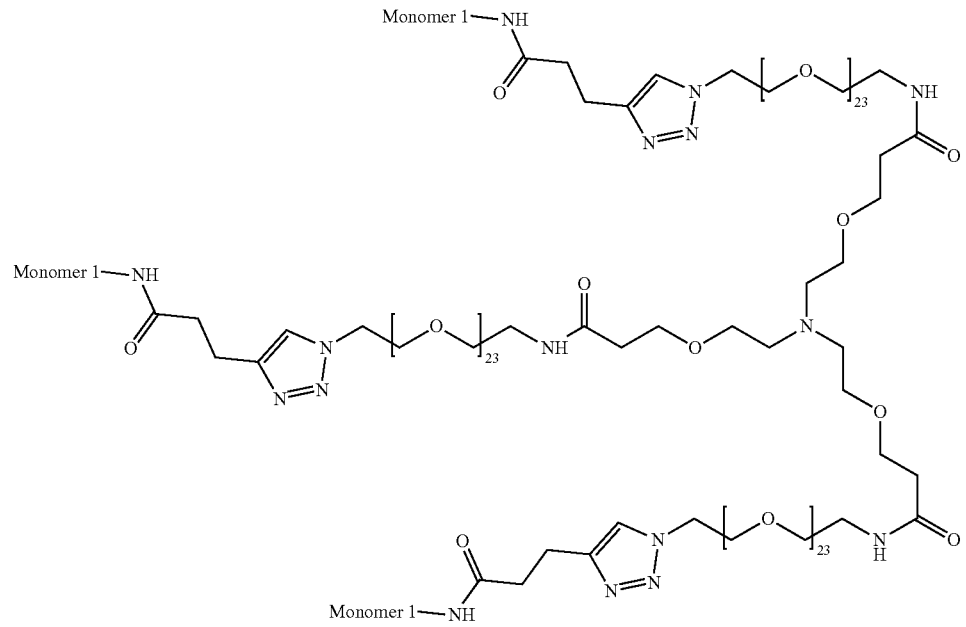
BCY7828

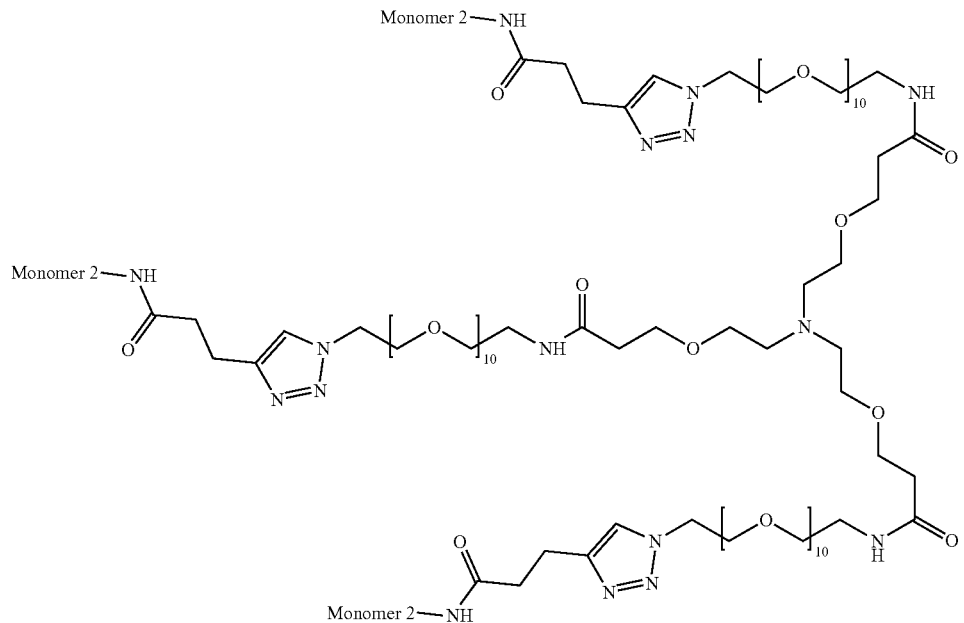
BCY7750
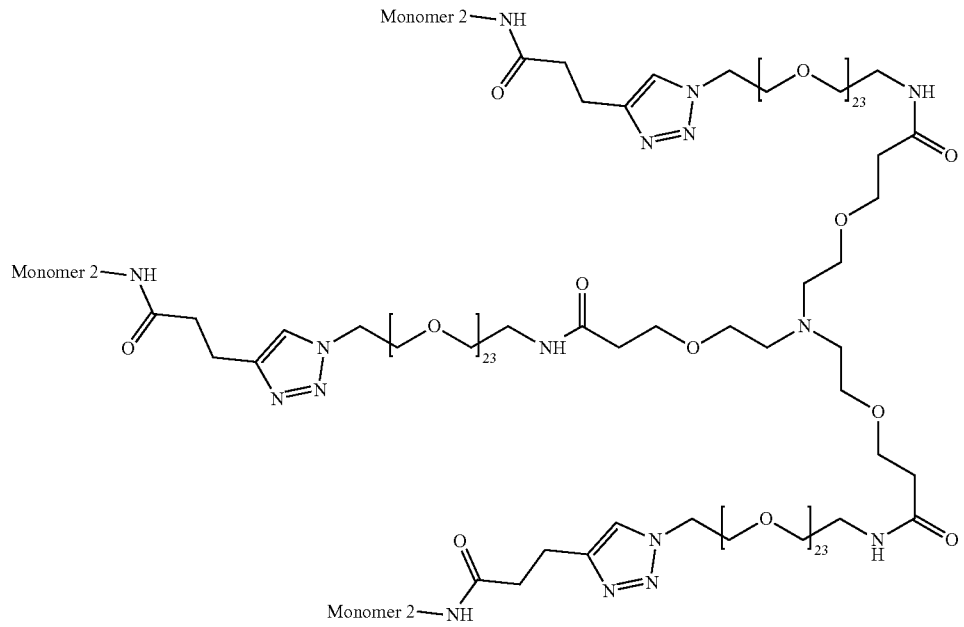
BCY7749

-continued
BCY7831
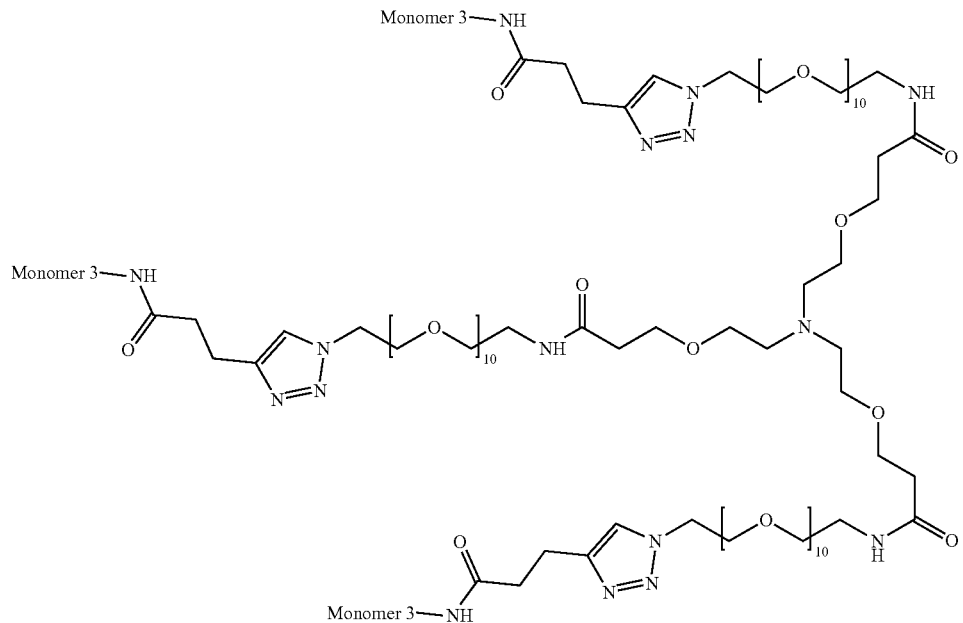
BCY7832
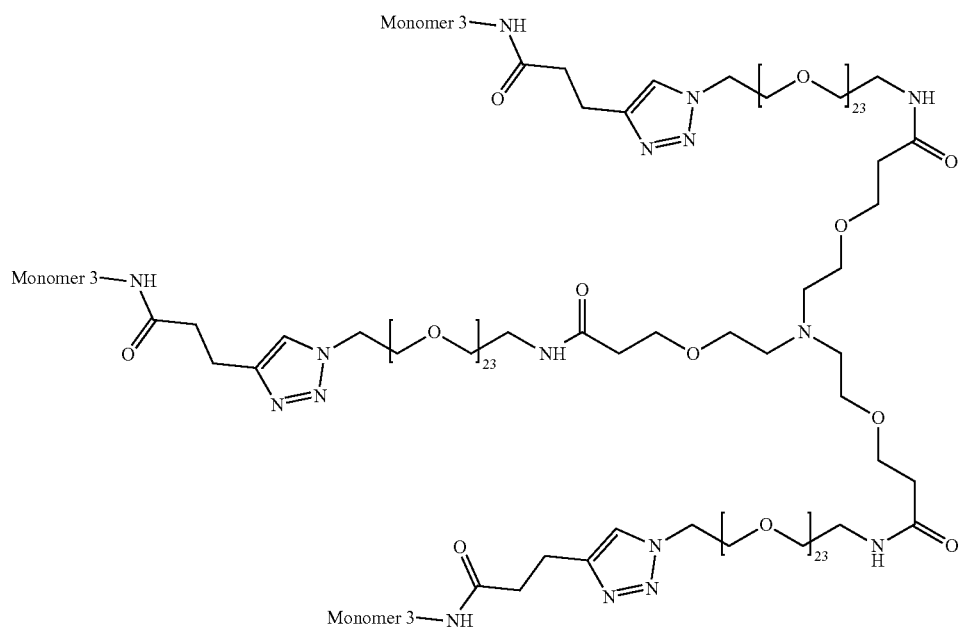

-continued
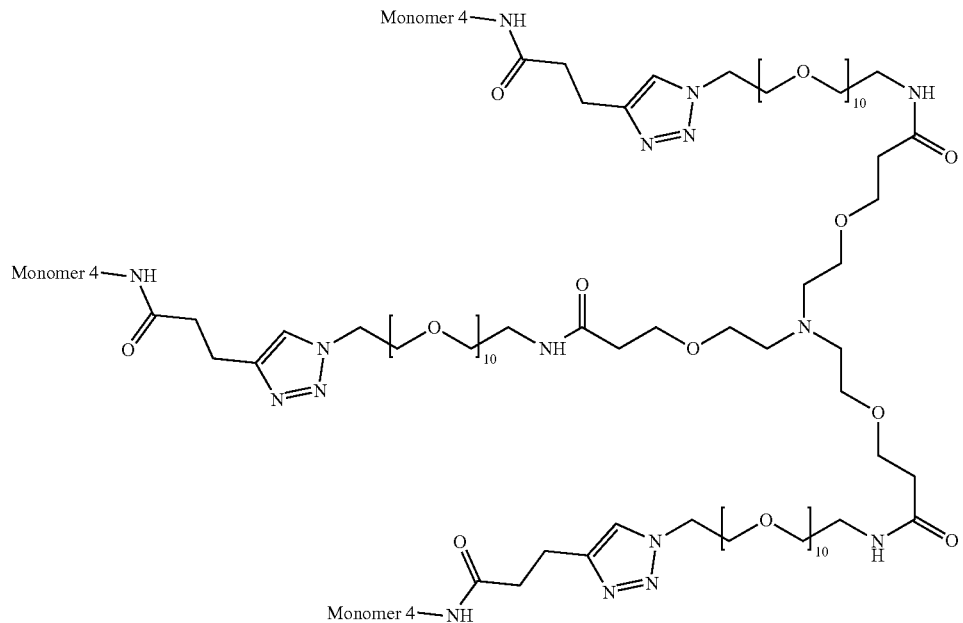
BCY7835
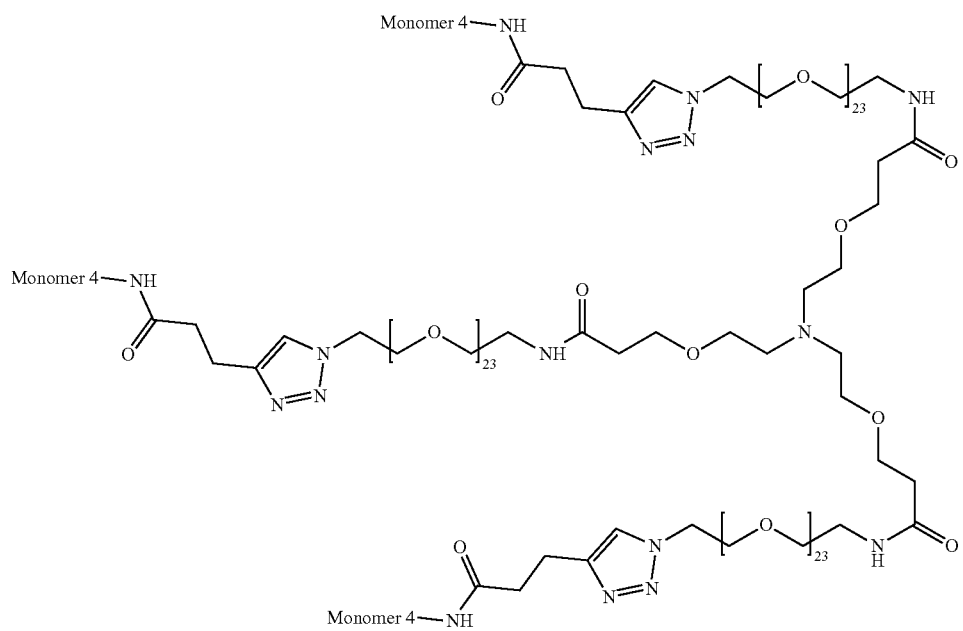
BCY7836

-continued
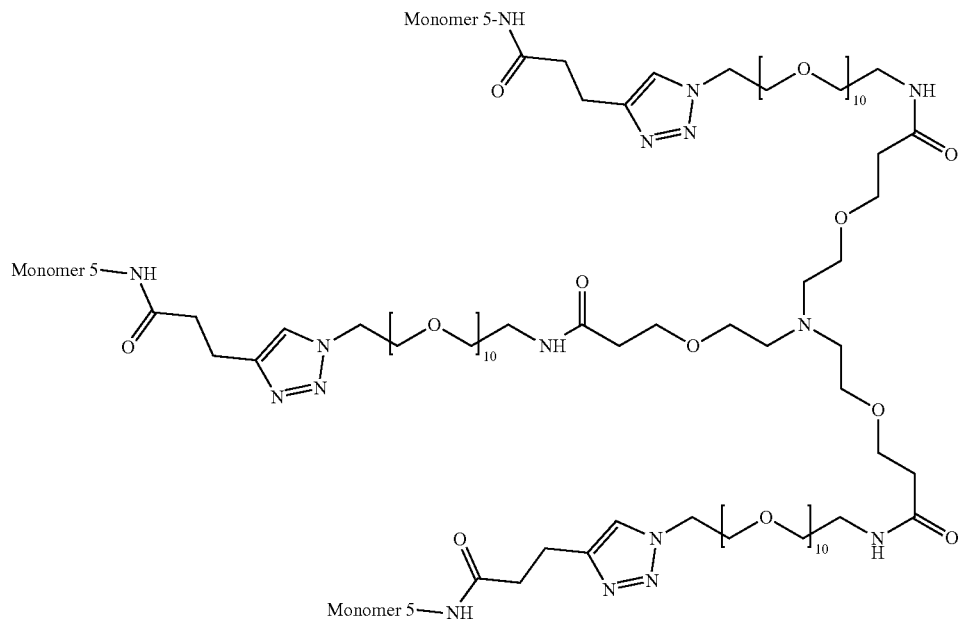
BCY7839
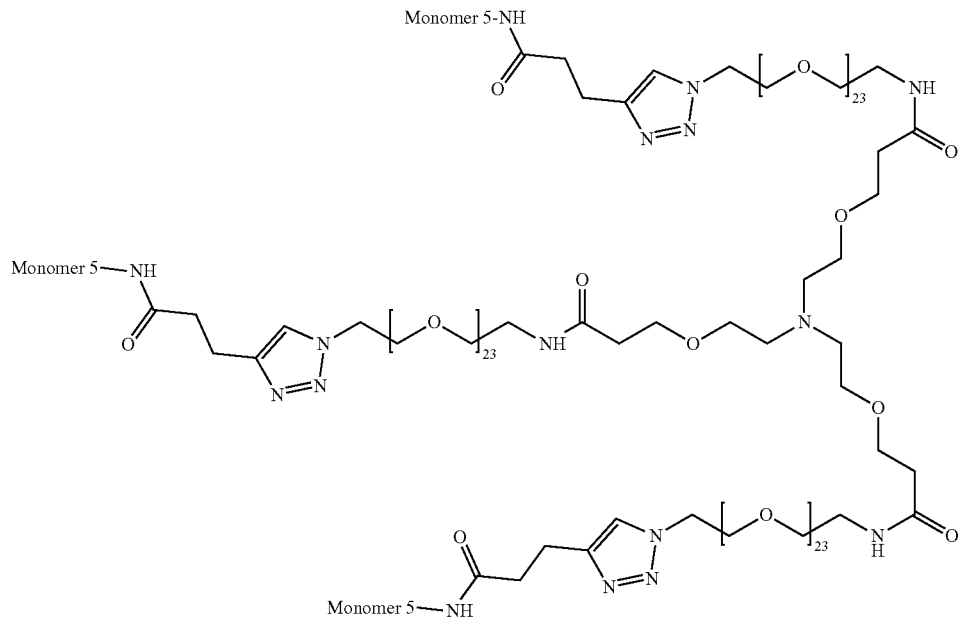
BCY7840

-continued
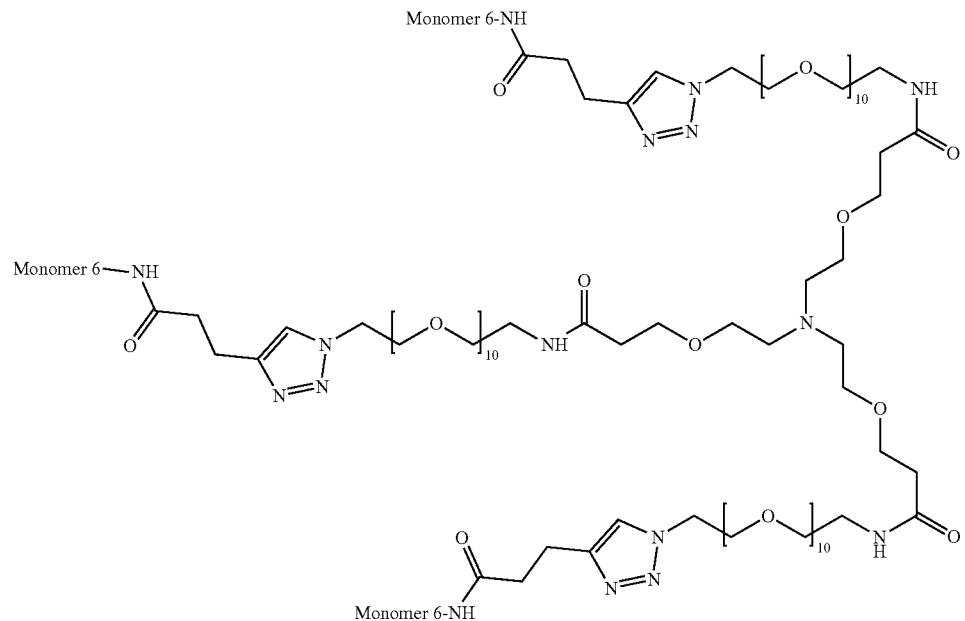
BCY7743
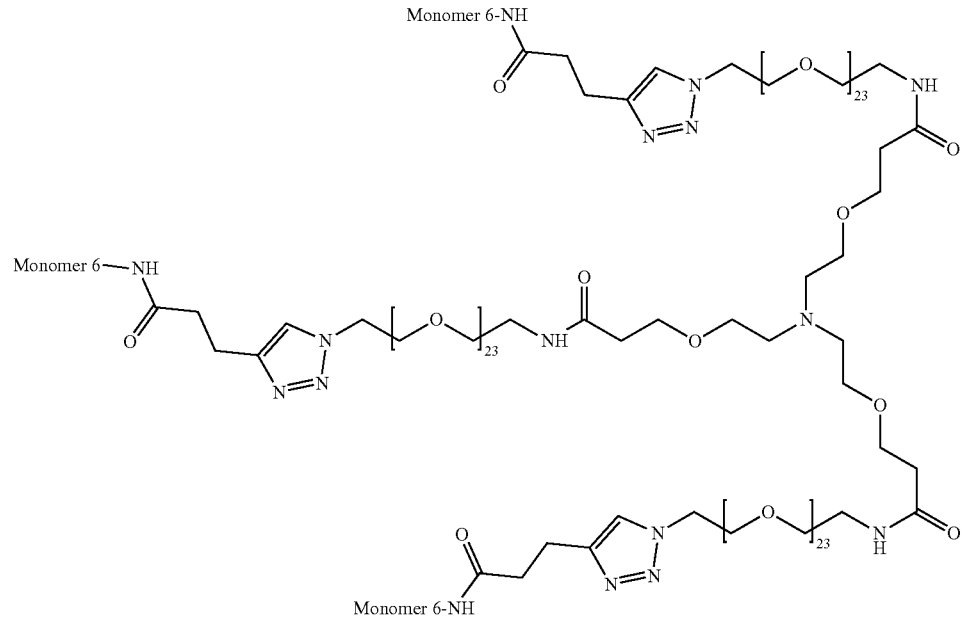
BCY7744

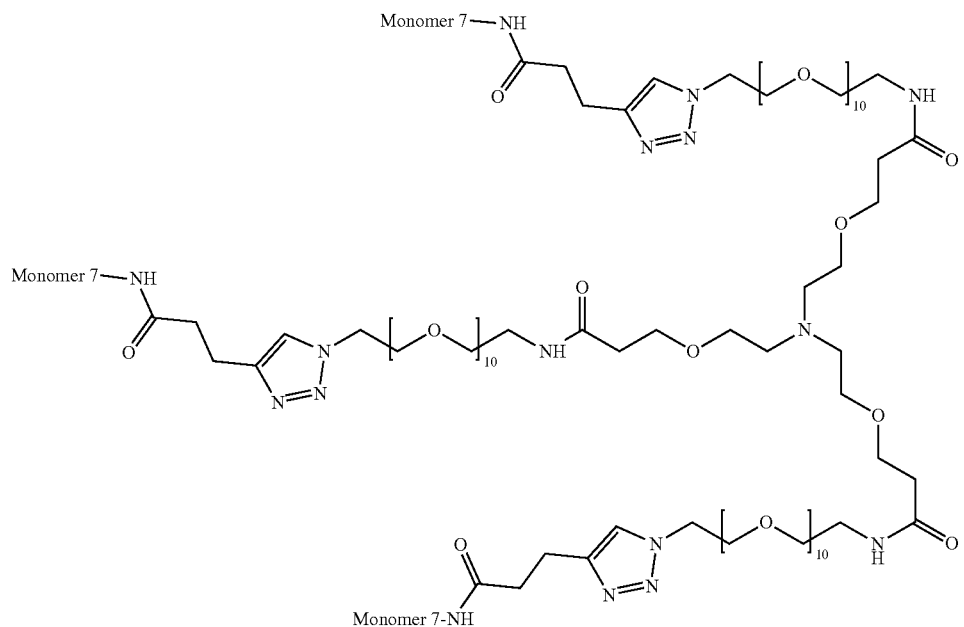
BCY7847
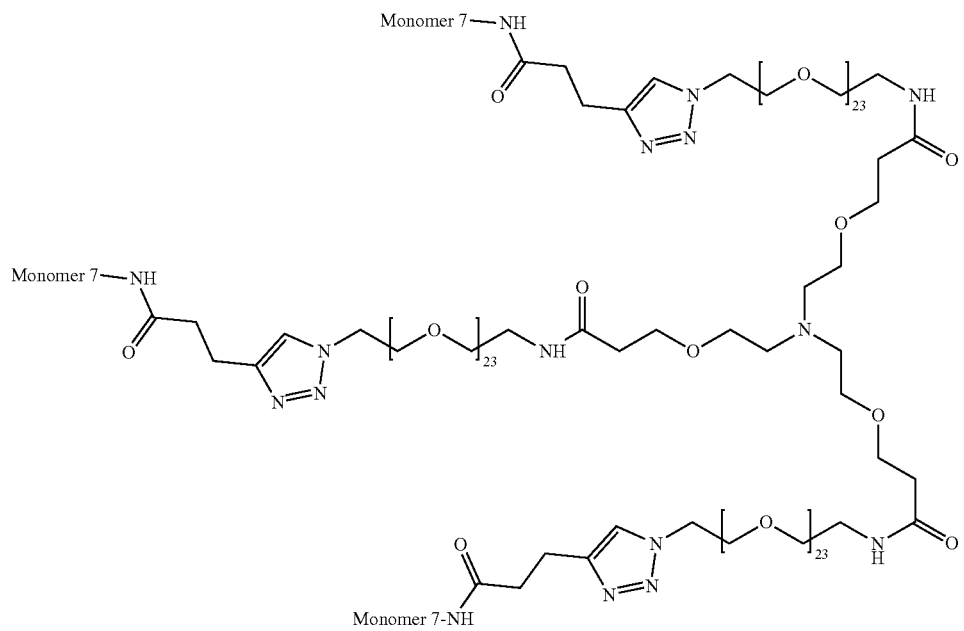
BCY7848

-continued
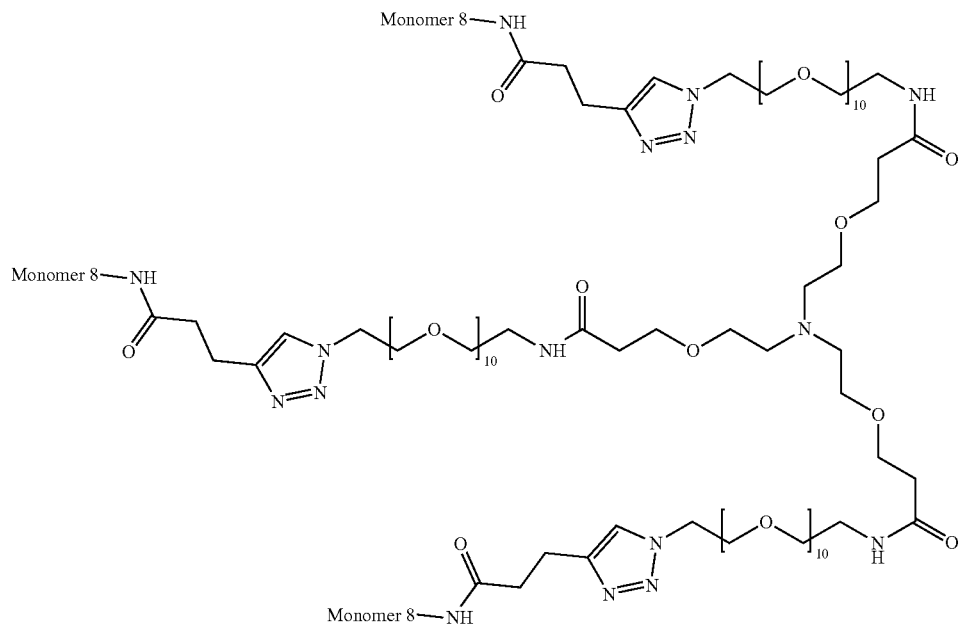
BCY7851
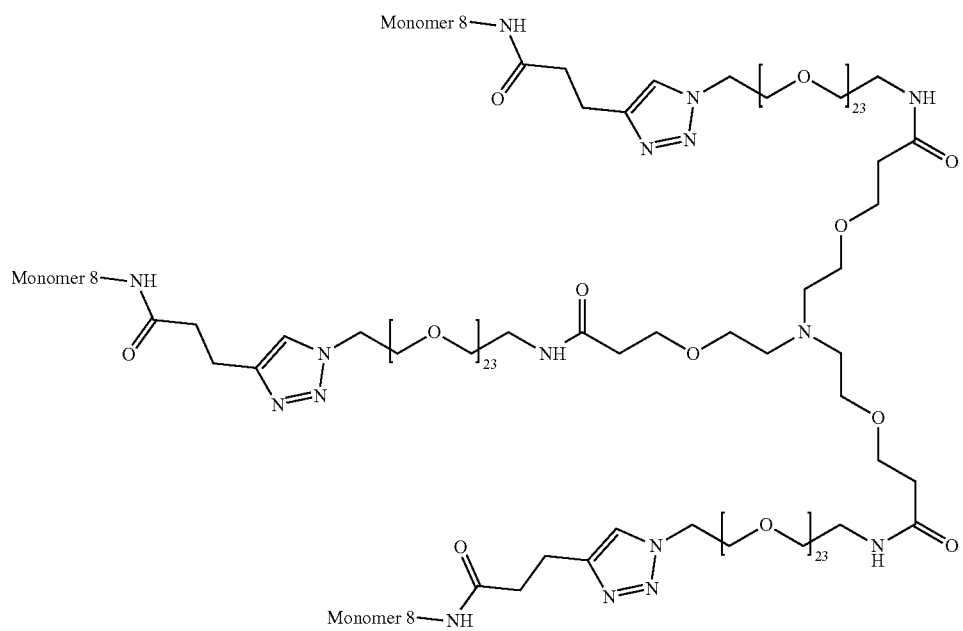
BCY7852

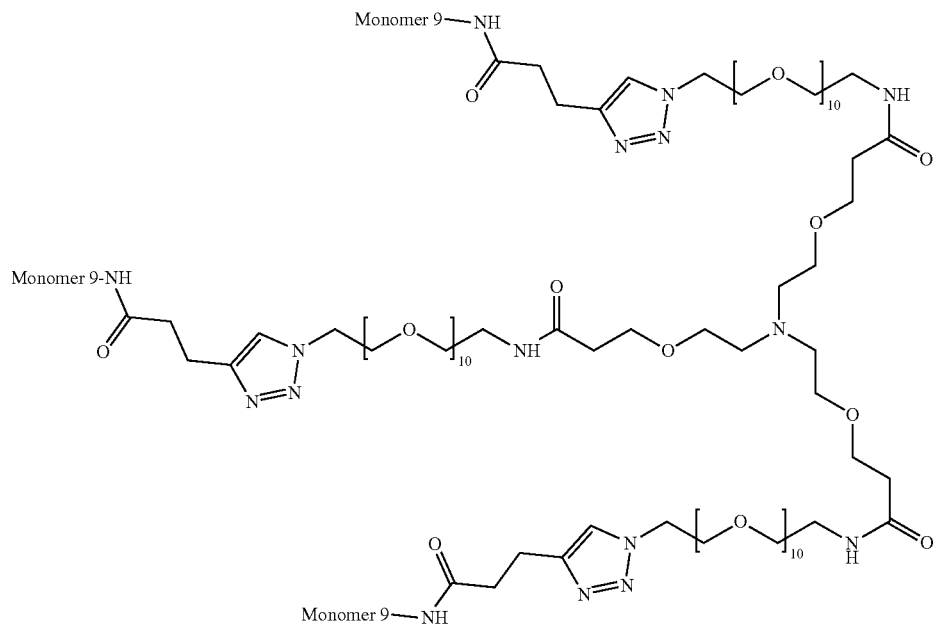
BCY7855
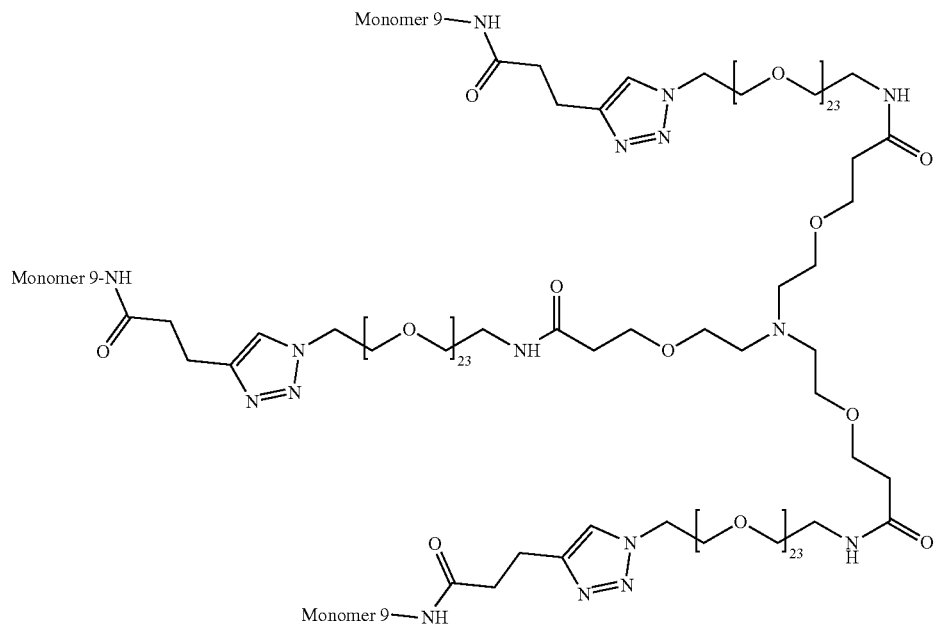
BCY7856

-continued
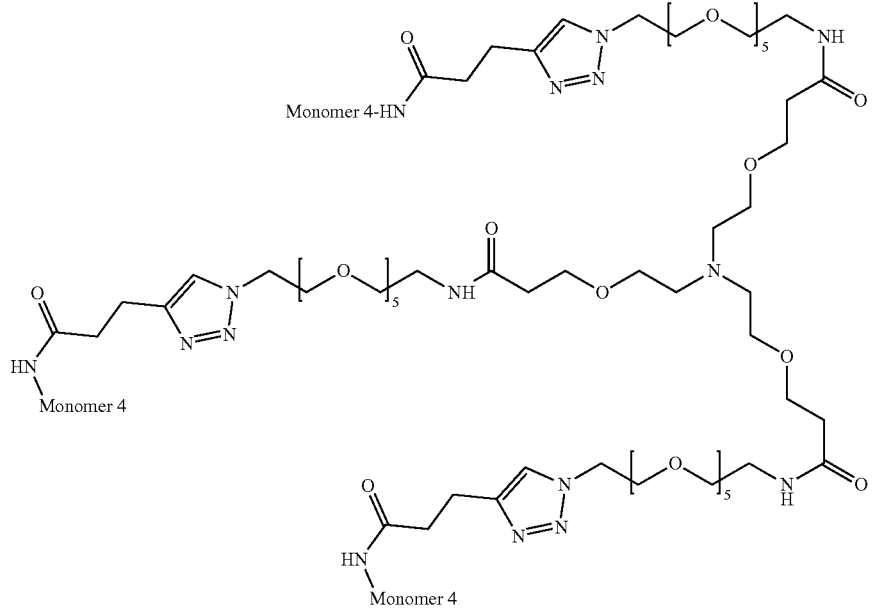
BCY8958
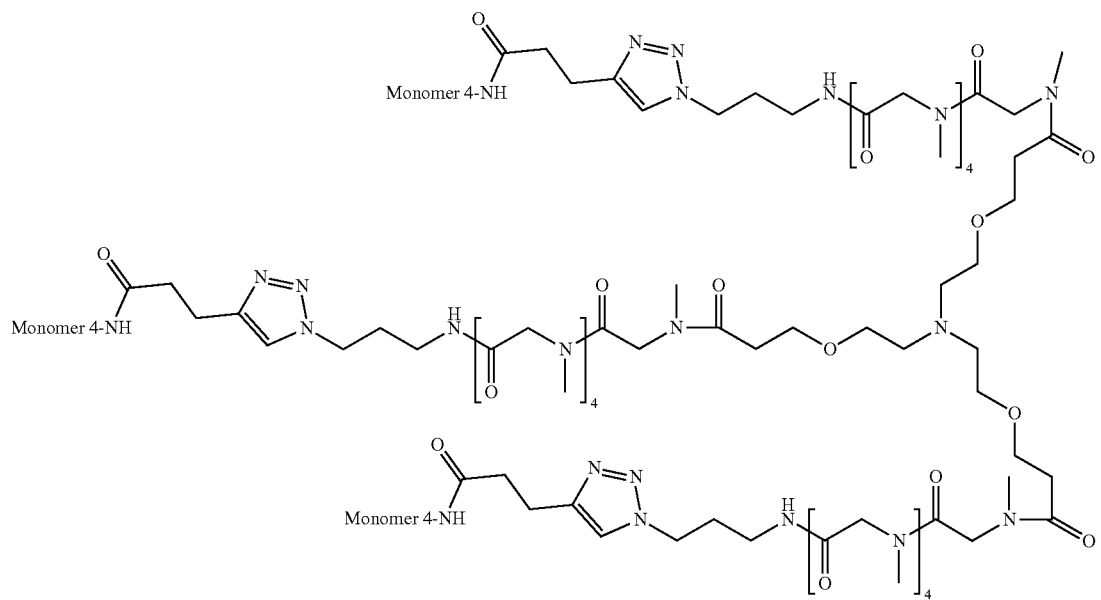
BCY8957

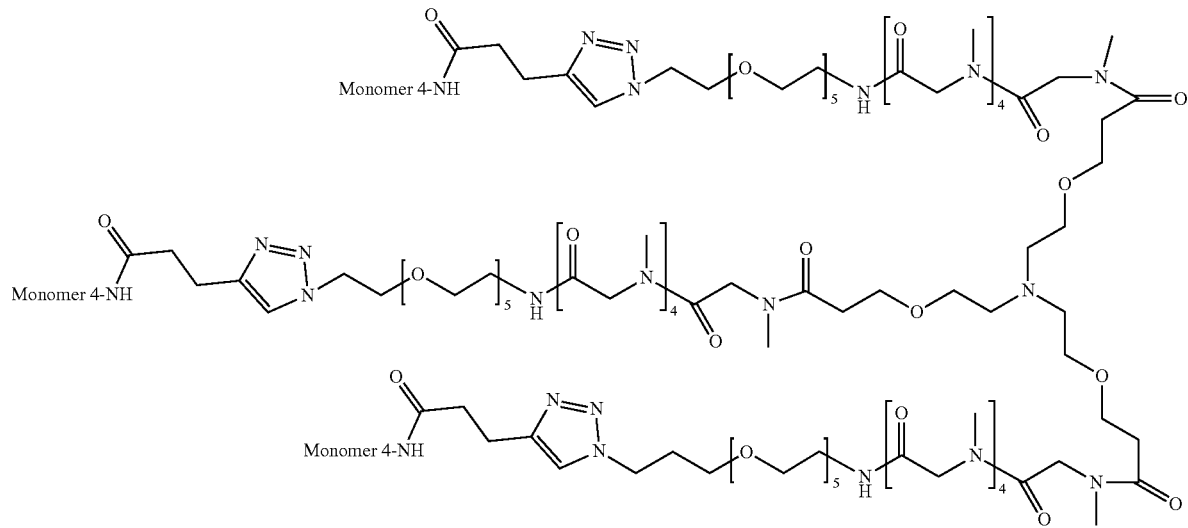
BCY8961
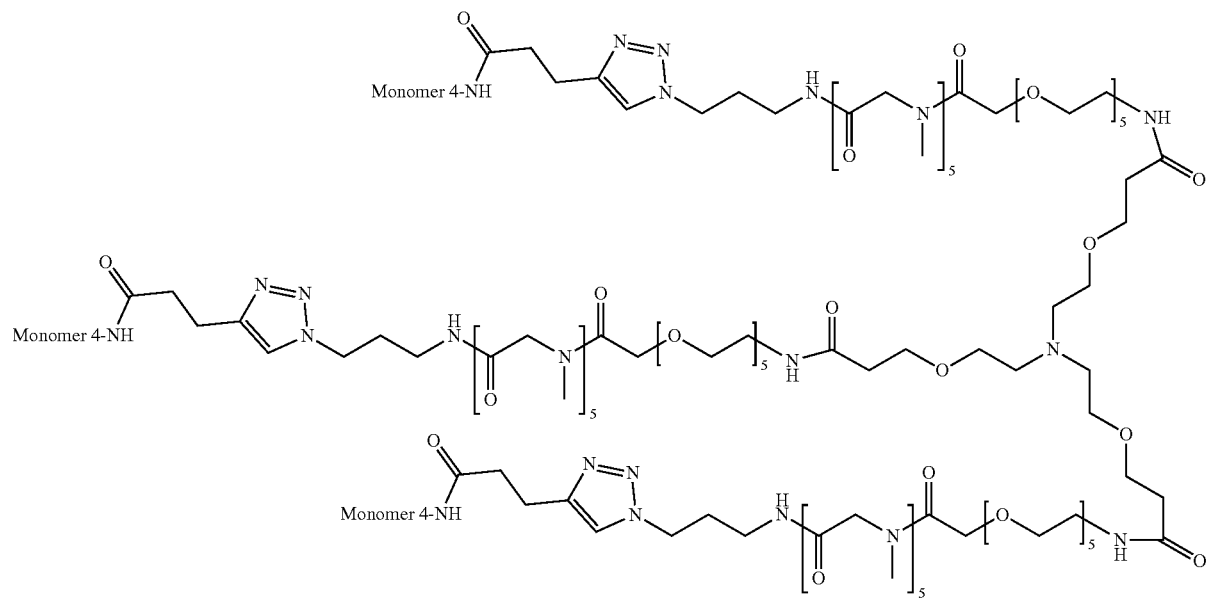
BCY8962

-continued
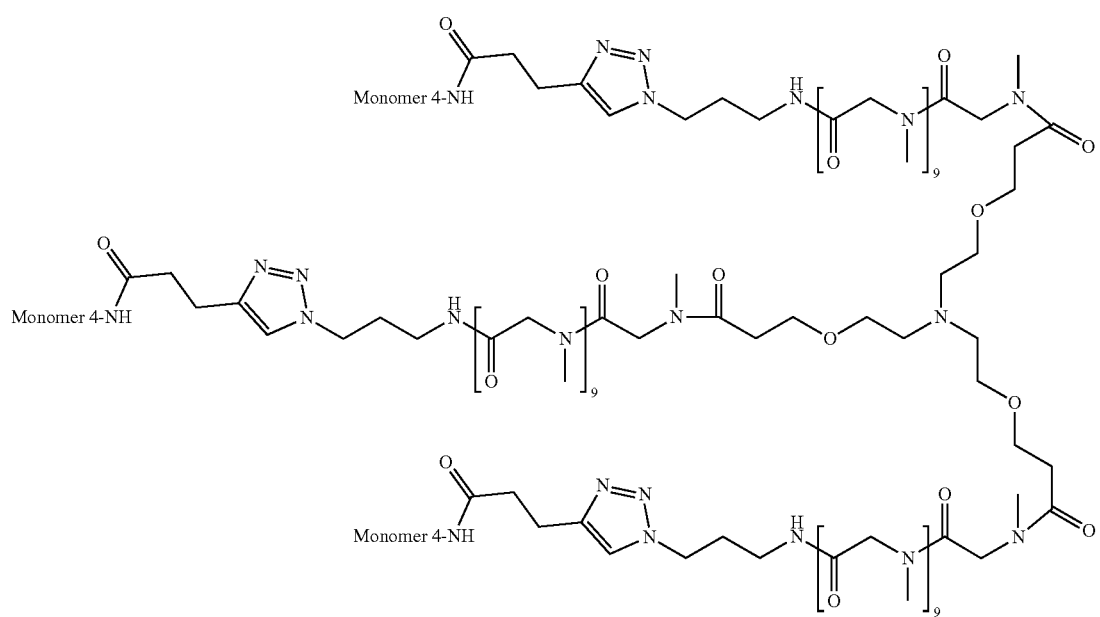
BCY8965
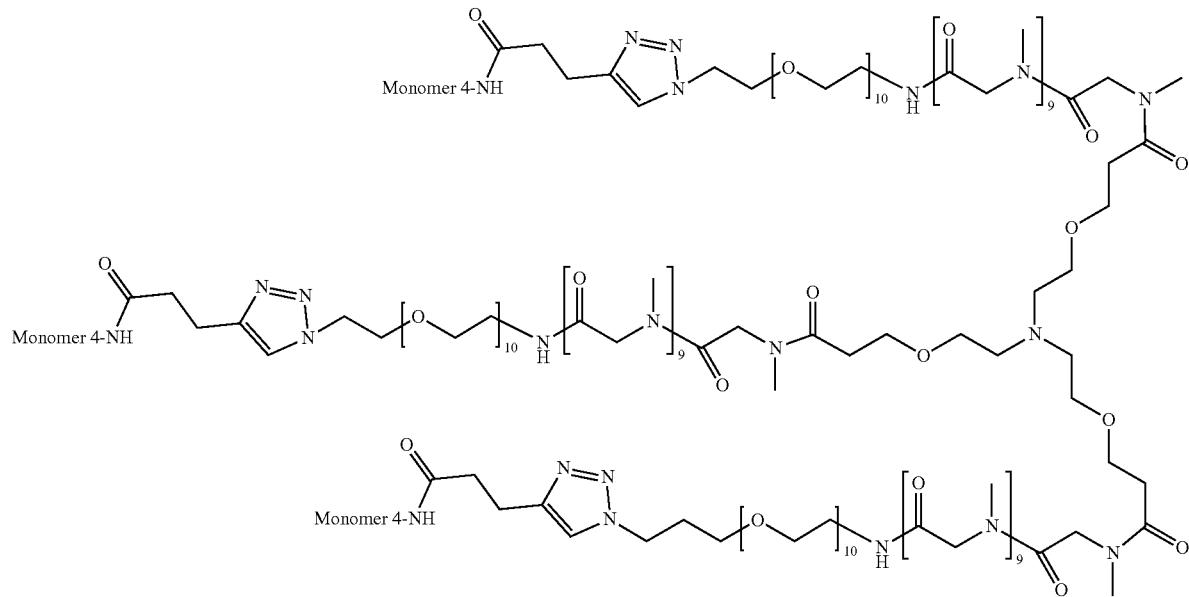
BCY9573

-continued
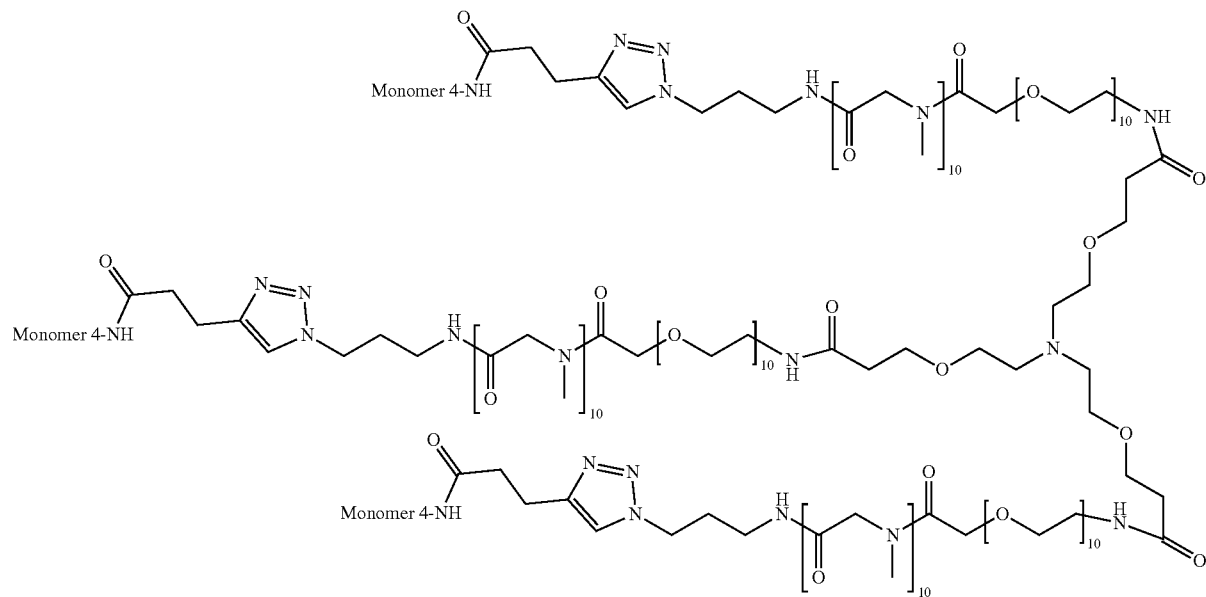
BCY9595
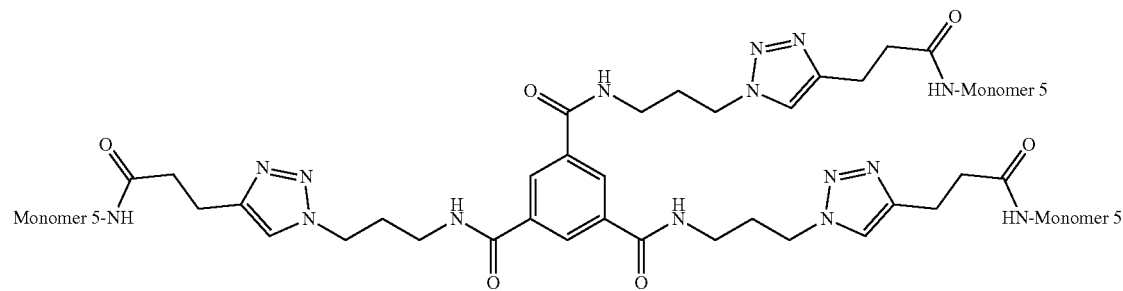
BCY11382
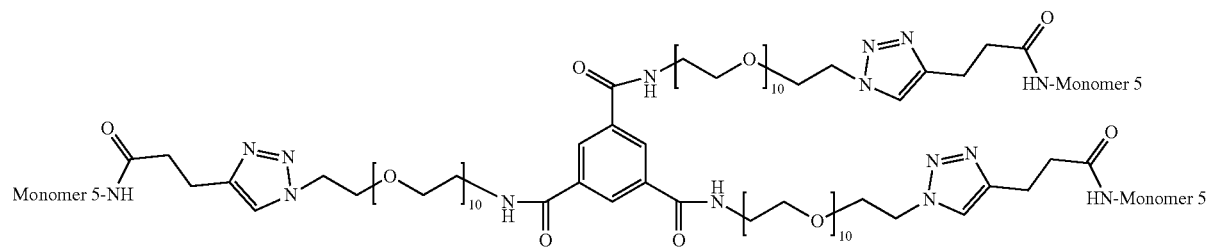
BCY9775
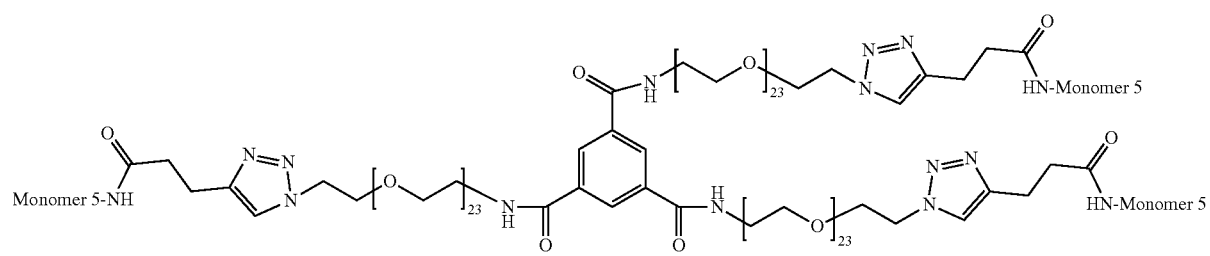
BCY9776

BCY11383
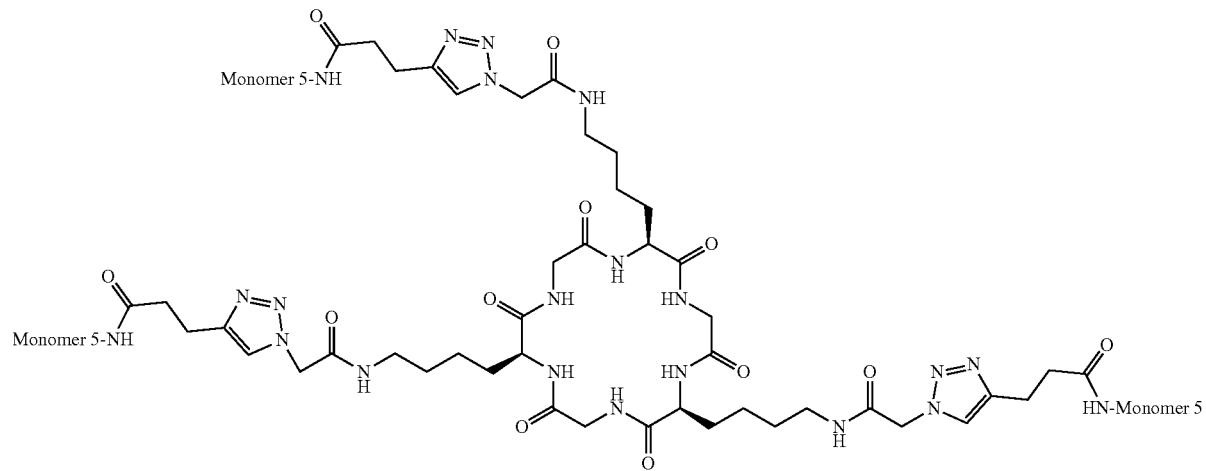
BCY10046
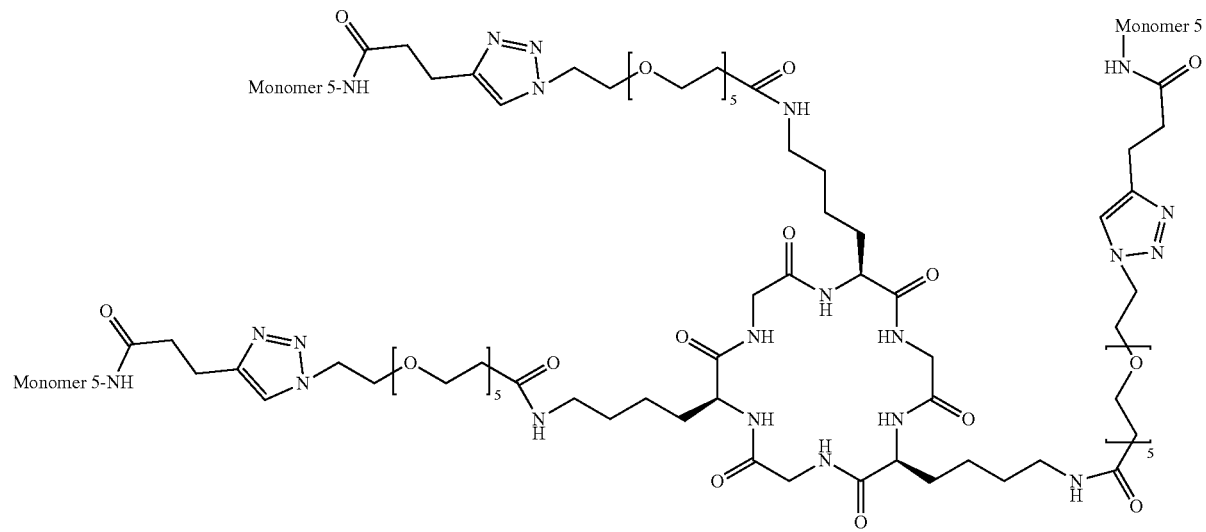
BCY10047
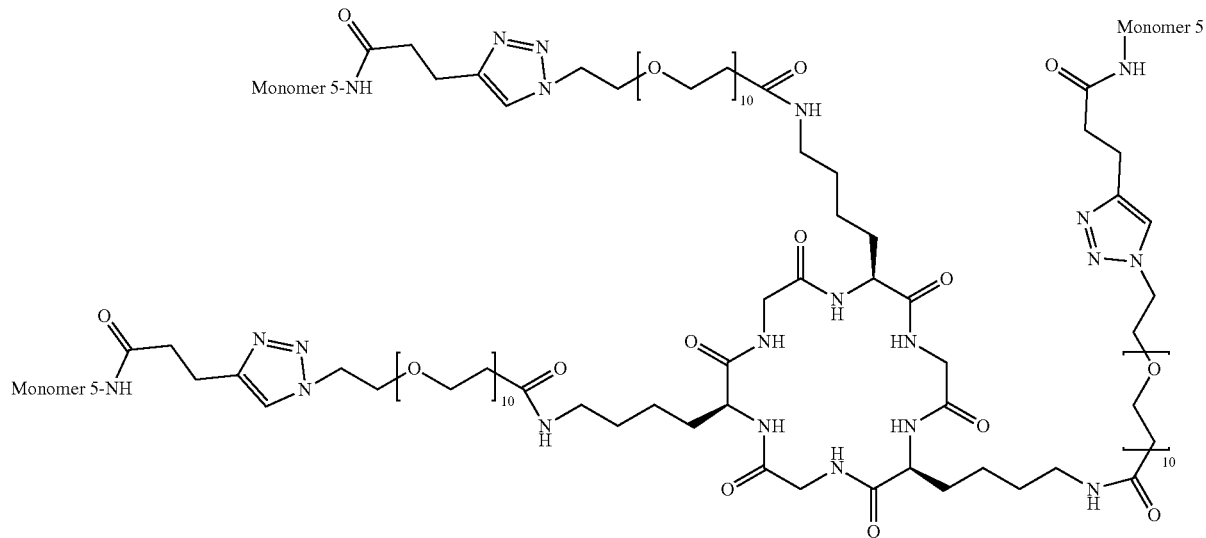

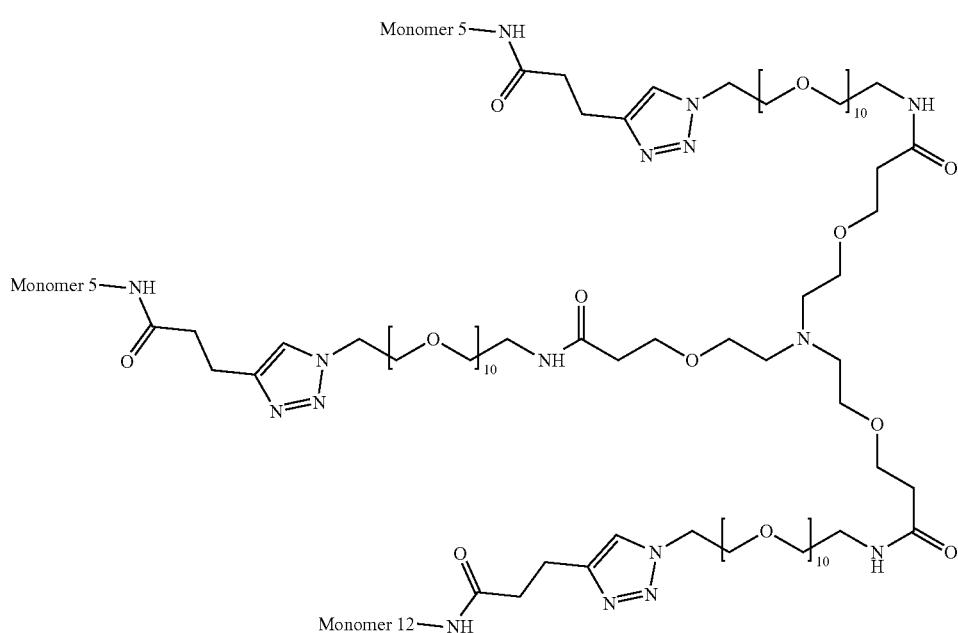

BCY7827:

To a solution of compound 11A (4 mg, 2.12 µmol, 1 eq) and Monomer 1A (28.2 mg, 12.69 µmol, 6.0 eq) in DMF (1 mL) was added a solution of CuSO$_4$ (0.8 M, 23.79 µL, 9.0 eq) and (2R)-2-[(1S)-1, 2-dihydroxyethyl]-3, 4-dihydroxy-2H-furan-5-one (0.8 M, 158.63 µL, 60 eq). The mixture was stirred at 25-30° C. for 1 hr under N$_2$ atmosphere. LC-MS showed Reactant 1 was consumed completely. The reaction mixture was filtered and concentrated under reduced pressure to give a residue. The residue was purified by prep-HPLC (TFA condition) to give BCY7827 (9.1 mg, 0.96 µmol, 45.37% yield, 90.3% purity) as a white solid.

BCY7828:

To a solution of compound 11B (4 mg, 1.11 µmol, 1 eq) and Monomer 1A (15 mg, 6.74 µmol, 6.08 eq) in DMF (1 mL) was added a solution of CuSO$_4$ (0.8 M, 12.47 µL, 9.0 eq) and (2R)-2-[(1S)-1, 2-dihydroxyethyl]-3, 4-dihydroxy-2H-furan-5-one (0.8 M, 83.12 µL, 60 eq). The mixture was stirred at 25-30° C. for 1 hr under N$_2$ atmosphere. LC-MS showed Reactant 1 was consumed completely. The reaction mixture was filtered and concentrated under reduced pressure to give a residue. The residue was purified by prep-HPLC (TFA condition) to give BCY7828 (5.7 mg, 5.05e-1 µmol, 45.60% yield, 91.17% purity) as a white solid.

BCY7750:

To a solution of compound 11A (4 mg, 2.12 µmol, 1 eq) and Monomer 2A (30 mg, 13.15 µmol, 6.22 eq) in DMF (1 mL) was added CuI (6.00 mg, 31.73 µmol, 15 eq). The mixture was stirred at 25-30° C. for 1 hr under N$_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7750 (7.3 mg, 6.85e-1 µmol, 32.41% yield, 82.02% purity) as a white solid.

BCY7749:

To a solution of compound 11B (48 mg, 13.30 µmol, 1 eq) and Monomer 2A (136.54 mg, 59.85 µmol, 4.5 eq) in DMF (6 mL) was added CuI (38.0 mg, 199.49 µmol, 15 eq). The mixture was stirred at 25-30° C. for 1 hr under N$_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7749 (22.4 mg, 1.39 µmol, 10.43% yield, 64.72% purity) as a white solid.

BCY7831:

To a solution of compound 11A (4 mg, 2.12 µmol, 1 eq) and Monomer 3A (21.56 mg, 9.52 µmol, 4.5 eq) in DMF (1 mL) was added CuI (6.00 mg, 31.73 µmol, 15 eq). The mixture was stirred at 25-30° C. for 2 hrs under N$_2$ atmosphere. LC-MS showed Reactant 1 was consumed completely. The reaction mixture was filtered and concentrated under reduced pressure to give a residue. The residue was purified by prep-HPLC (TFA condition) to give BCY7831 (1.4 mg, 1.48e-1 µmol, 6.98% yield, 91.6% purity) as a white solid.

BCY7832:

To a solution of compound 11B (4 mg, 1.11 µmol, 1 eq) and Monomer 3A (11.30 mg, 4.99 µmol, 4.5 eq) in DMF (1 mL) was added CuI (3.17 mg, 16.62 µmol, 15 eq). The mixture was stirred at 25-30° C. for 2 hrs under N$_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7832 (1.5 mg, 9.40e-2 µmol, 8.49% yield, 65.24% purity) as a white solid.

BCY7835:

To a solution of compound 11A (32 mg, 16.92 µmol, 1 eq) and Monomer 4A (172.51 mg, 76.14 µmol, 4.5 eq) in DMF (4 mL) was added CuI (48.34 mg, 253.81 µmol, 15 eq). The mixture was stirred at 25-30° C. for 2 hrs under N$_2$ atmosphere. LC-MS showed Reactant 1 was consumed completely. The reaction mixture was filtered and concentrated under reduced pressure to give a residue. The residue was purified by prep-HPLC (TFA condition) to give BCY7835 (19.8 mg, 2.08 µmol, 12.28% yield, 91.16% purity) as a white solid.

BCY7836:

To a solution of compound 11B (4 mg, 1.11 µmol, 1 eq) and Monomer 4A (15.07 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3, 4-dihydroxy-2H-furan-5-one (0.8 M, 83.12 µL, 60 eq). The mixture was stirred at 25-30° C. for 2 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7836 (2 mg, 1.15e-1 µmol, 10.40% yield, 59.97% purity) as a white solid.

BCY7839:

A mixture of compound 11A (0.2 g, 105.75 µmol, 1 eq.), Monomer 5A (750 mg, 320.8 µmol, 3.03 eq.), and THPTA (0.4 M, 264.4 µL, 1 eq.) was dissolved in t-BuOH/H2O (1:1, 12 mL, pre-degassed and purged with $N_2$ for 3 times), and then $CuSO_4$ (0.4 M, 265 µL, 1 eq.) and VcNa (0.4 M, 529 µL, 2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25-30° C. for 12 hr under $N_2$ atmosphere. LC-MS showed compound 11A was consumed completely and one main peak with desired m/z [MW: 8904.11, observed m/z: 1271.92 ([M/7+H+]), 1113.07 ([M/8+H+]), and 989.65 ([M/9+H+])] was detected. The reaction mixture was directly purified by prep-HPLC (TFA condition). BCY7839 (283.7 mg, 30.40 µmol, 28.74% yield, 95.40% purity) was obtained as a white solid.

BCY7840:

To a solution of compound 11B (4 mg, 1.11 µmol, 1 eq) and Monomer 5A (11.66 mg, 4.99 µmol, 4.5 eq) in DMF (0.5 mL) was added CuI (3.17 mg, 16.62 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7840 (2.9 mg, 2.54e-1 µmol, 22.91% yield, 93.00% purity) as a white solid.

BCY7743:

To a solution of compound 11A (4 mg, 2.12 µmol, 1 eq) and Monomer 6A (19.18 mg, 8.46 µmol, 4.5 eq) in DMF (1 mL) was added CuI (6.04 mg, 31.73 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7743 (4 mg, 3.85e-1 µmol, 18.19% yield, 83.56% purity) as a white solid.

BCY7744:

To a solution of compound 11B (4 mg, 1.11 µmol, 1 eq) and Monomer 6A (11.30 mg, 4.99 µmol, 4.5 eq) in DMF (1 mL) was added CuI (3.17 mg, 16.62 µmol, 15 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7744 (4.2 mg, 1.79e-1 µmol, 16.17% yield, 44.40% purity) as a white solid.

BCY7847:

To a solution of compound 11A (4 mg, 2.12 µmol, 1 eq) and Monomer 7A (28.52 mg, 12.69 µmol, 6 eq) in DMF (1 mL) was added a solution of $CuSO_4$ (0.8 M, 23.79 µL, 9.0 eq) and (2R)-2-[(1S)-1, 2-dihydroxyethyl]-3, 4-dihydroxy-2H-furan-5-one (0.8 M, 158.63 µL, 60 eq). The mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7847 (1.3 mg, 5.63e-2 µmol, 2.66% yield, 37.4% purity) as a white solid.

BCY7848:

To a solution of compound 11B (4 mg, 1.11 µmol, 1 eq) and Monomer 7A (14.95 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3, 4-dihydroxy-2H-furan-5-one (0.8 M, 83.12 µL, 60 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7848 (2.7 mg, 2.46e-1 µmol, 22.23% yield, 94.47% purity) as a white solid.

BCY7851:

To a solution of compound 11A (4 mg, 2.12 µmol, 1 eq) and Monomer 8A (21.87 mg, 9.52 µmol, 4.5 eq) in DMF (1 mL) was added CuI (6.0 mg, 31.73 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7851 (2.5 mg, 8.64e-2 µmol, 4.08% yield, 30.35% purity) as a white solid.

BCY7852:

To a solution of compound 11B (4 mg, 1.11 µmol, 1 eq) and Monomer 8A (15.28 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3, 4-dihydroxy- 2H-furan-5-one (0.8 M, 83.12 µL, 60 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7852 (1.2 mg, 9.85e-2 µmol, 8.89% yield, 86.2% purity) as a white solid.
BCY7855:

To a solution of compound 11A (4 mg, 2.12 µmol, 1 eq) and Monomer 9A (21.72 mg, 9.52 µmol, 4.5 eq) in DMF (1 mL) was added CuI (6.04 mg, 31.73 µmol, 15 eq). The mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7855 (3.8 mg, 0.28 µmol, 13.25% yield, 64.45% purity) as a white solid.
BCY7856:

To a solution of compound 11B (4 mg, 1.11 µmol, 1 eq) and Monomer 9A (15.17 mg, 6.65 µmol, 6.0 eq) in DMF (1 mL) was added a solution of $CuSO_4$ (0.8 M, 12.47 µL, 9.0 eq) and (2R)-2-[(1S)-1, 2-dihydroxyethyl]-3,4-dihydroxy-2H-furan-5-one (0.8 M, 83.12 µL, 60 eq). The mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7856 (5.7 mg, 5.05e-1 µmol, 45.60% yield, 91.17% purity) as a white solid.

BCY8958 (15.8 mg, 93.9% purity, 22.7% yield), BCY8957 (15.1 mg, 90.4% purity, 18% yield), BCY8961 (3.1 mg, 93.3% purity, 5.4% yield), BCY8962 (12.8 mg, 89.6% purity, 20.6% yield), BCY8965 (17.8 mg, 92.9% purity, 41.4% yield), BCY9573 (6.2 mg, 92.50% purity, 5.50% yield), BCY9595 (5.4 mg, 95.50% purity, 6.60% yield), BCY11382 (81 mg, 89.04% purity, 26.1% yield), BCY9775 (55.1 mg, 95.01% purity, 51.93% yield), BCY9776 (11.5 mg, 99.70% purity, 18.92% yield), BCY11383 (5.1 mg, 85.46% purity, 8.97% yield), BCY10046 (12.6 mg, 95.10% purity, 10.59% yield), BCY10047 (19.5 mg, 94.69% purity, 25.65% yield) were each synthesized in an analogous manner to that described above for BCY7839 using one of Compounds 11A, 11B, 11C, 11D, 11E, 11F, 11G, 11H, 11I, 11J, 11K, 11L, 11M, 11N and 11O; and one of Monomer 4A, Monomer 5A; and $CuSO_4$, (2R)-2-[(1S)-1, 2-dihydroxyethyl]-3,4-dihydroxy-2H-furan-5-one and THPTA.
BCY11194:

A mixture of Compound 11A (30 mg, 15.86 µmol, 1 eq), Monomer 12A (31.6 mg, 14.28 µmol, 0.9 eq), and THPTA (8.0 mg, 1 eq) was dissolved in t-BuOH/$H_2O$ (1:1, 2 mL, pre-degassed and purged with $N_2$ for 3 times), followed by addition of $CuSO_4$ (0.4 M, 40.0 µL, 1 eq) and VcNa (0.4 M, 80.0 µL, 2 eq) under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25° C. for 4 hr under $N_2$ atmosphere. LC-MS showed Monomer 12A was consumed completely and one main peak with desired m/z (MS: 4108.77, observed m/z: 1369.8 ([M/3+H]$^+$)) was detected. The reaction mixture was filtered and concentrated under reduced pressure to give a residue. The crude product was purified by prep-HPLC (TFA condition), and desired fractions were combine and lyophilized, resulting in Intermediate 1 (9.2 mg, 2.16 µmol, 13.63% yield, 96.56% purity) as a white solid. A mixture of Intermediate 1 (5 mg, 1.22 µmol, 1 eq), Monomer 5A (5.7 mg, 2.43 µmol, 2 eq), and THPTA (1.1 mg, 2 eq) was dissolved in t-BuOH/$H_2O$ (1:1, 2 mL, pre-degassed and purged with $N_2$ for 3 times), and then $CuSO_4$ (0.4 M, 6.1 µL, 2 eq) and VcNa (0.4 M, 12.2 µL, 4 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25° C. for 4 hr under $N_2$ atmosphere. LC-MS showed Monomer 5A was consumed completely and one main peak with desired m/z (calculated MW: 8784.05, observed m/z: 1236.5 ([M/7-$H_2O$+H$^+$]), 1077.8 ([M/8-$H_2O$+H$^+$])) was detected. The reaction mixture was filtered and concentrated under reduced pressure to give a residue. The crude product was purified by prep-HPLC (TFA condition). BCY11194 (3.4 mg, 29.01% yield, 91.2% purity) was obtained as a white solid.

General Procedure for Preparation of Compound 15

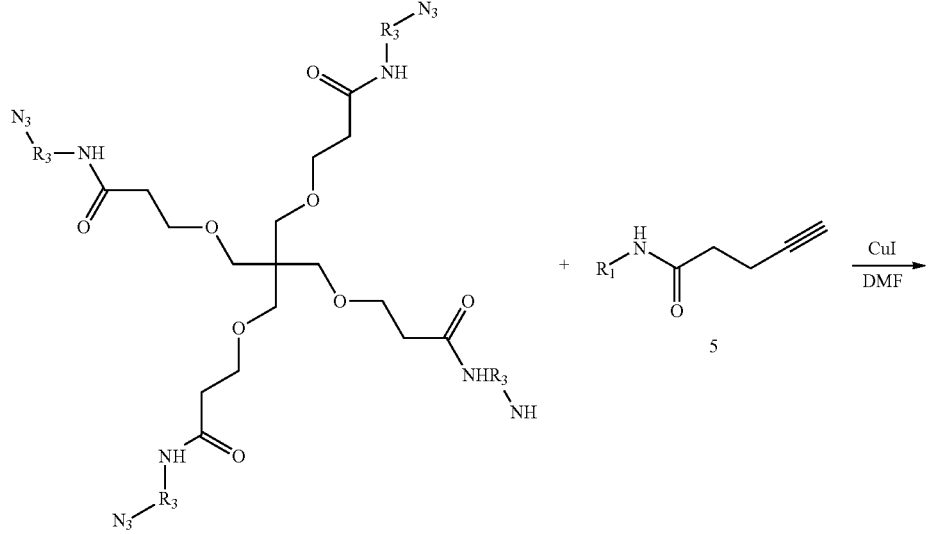

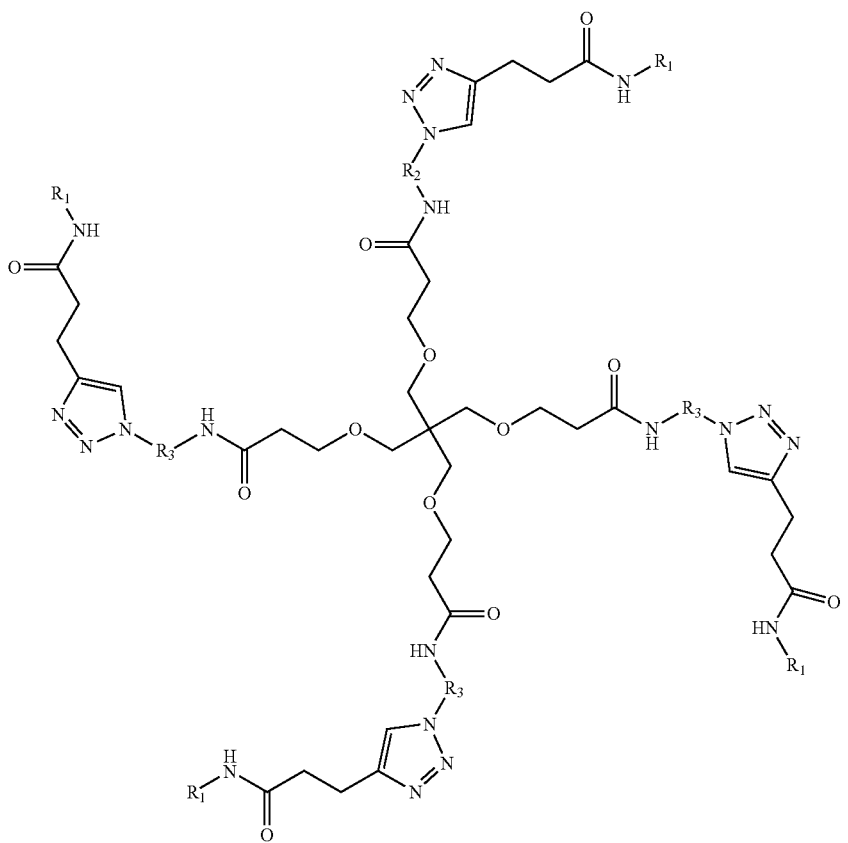
15

Compound 14:
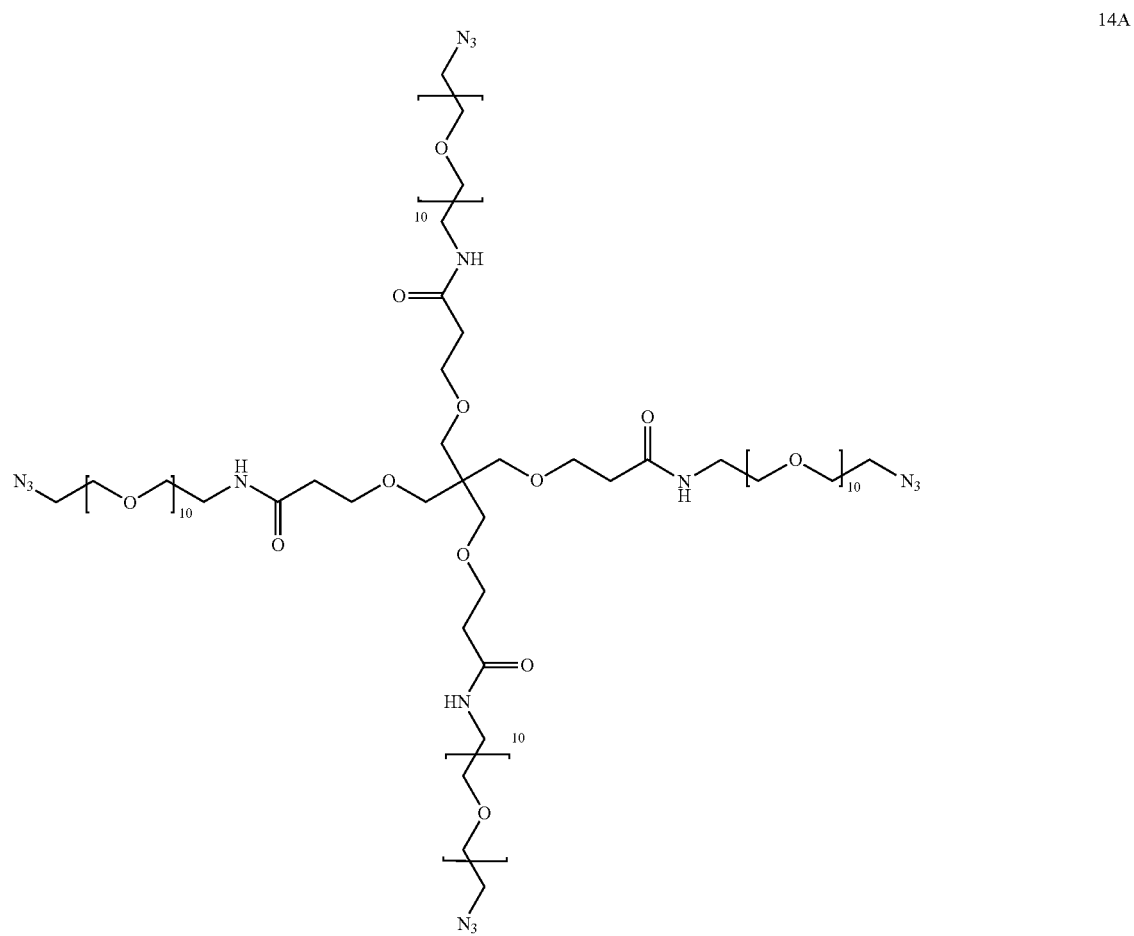
14A

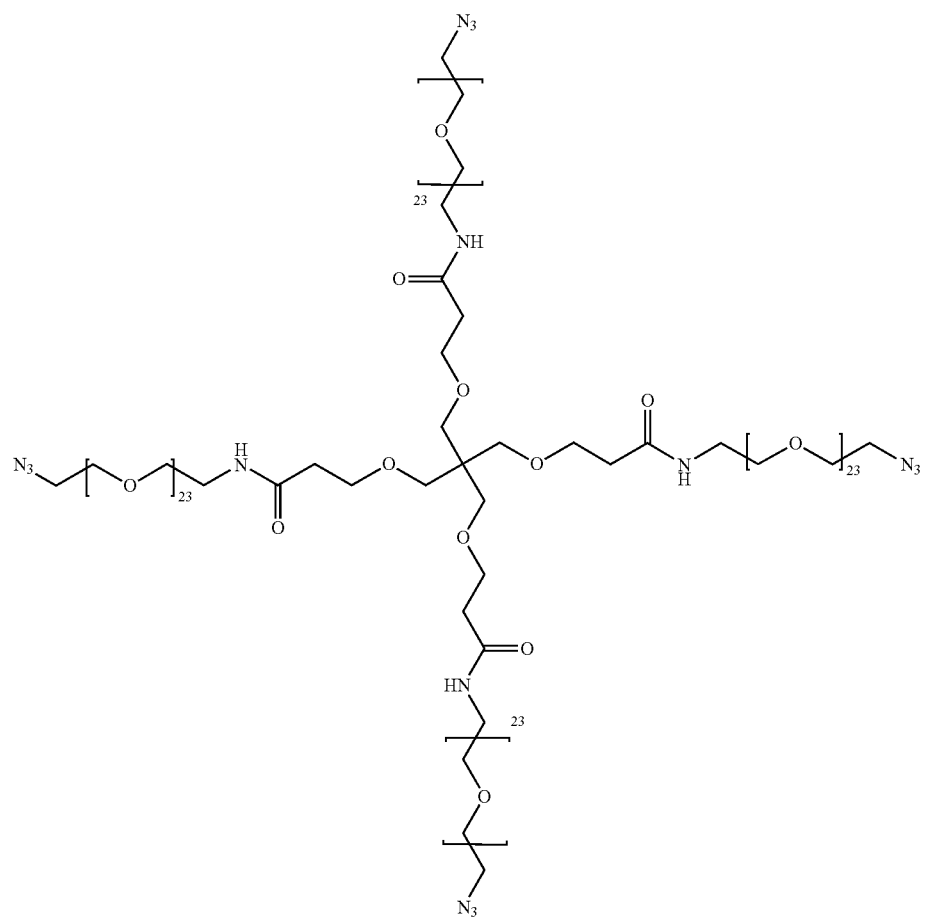
14B

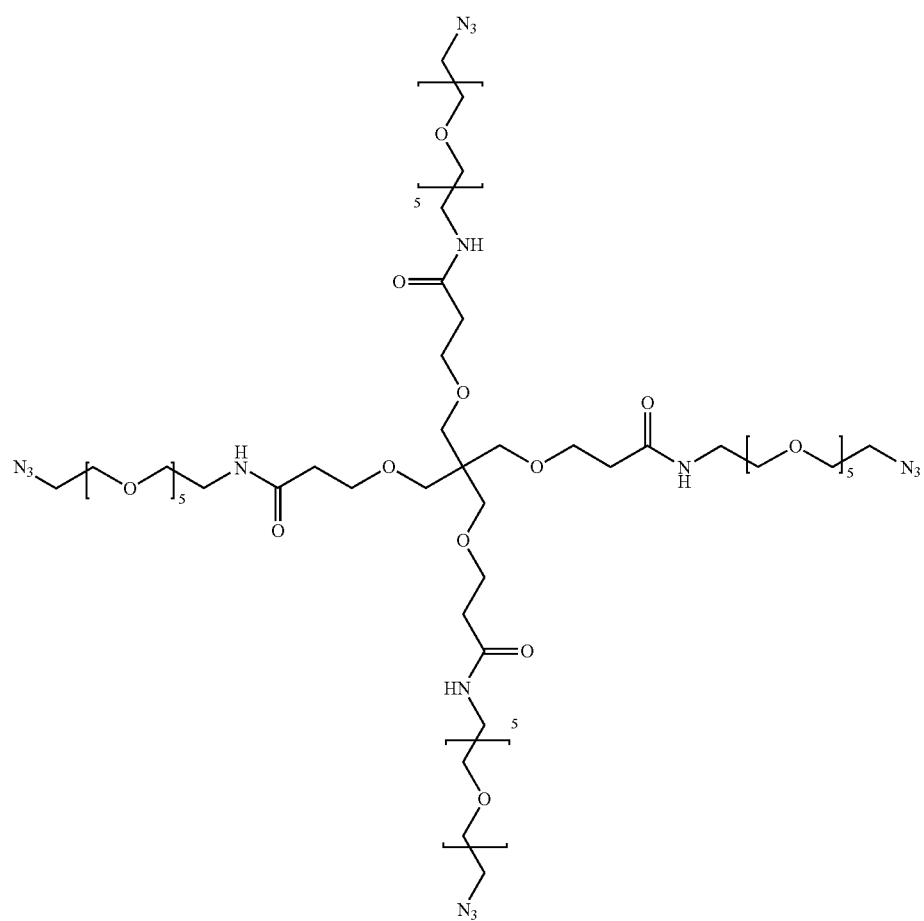
14C

-continued
14D
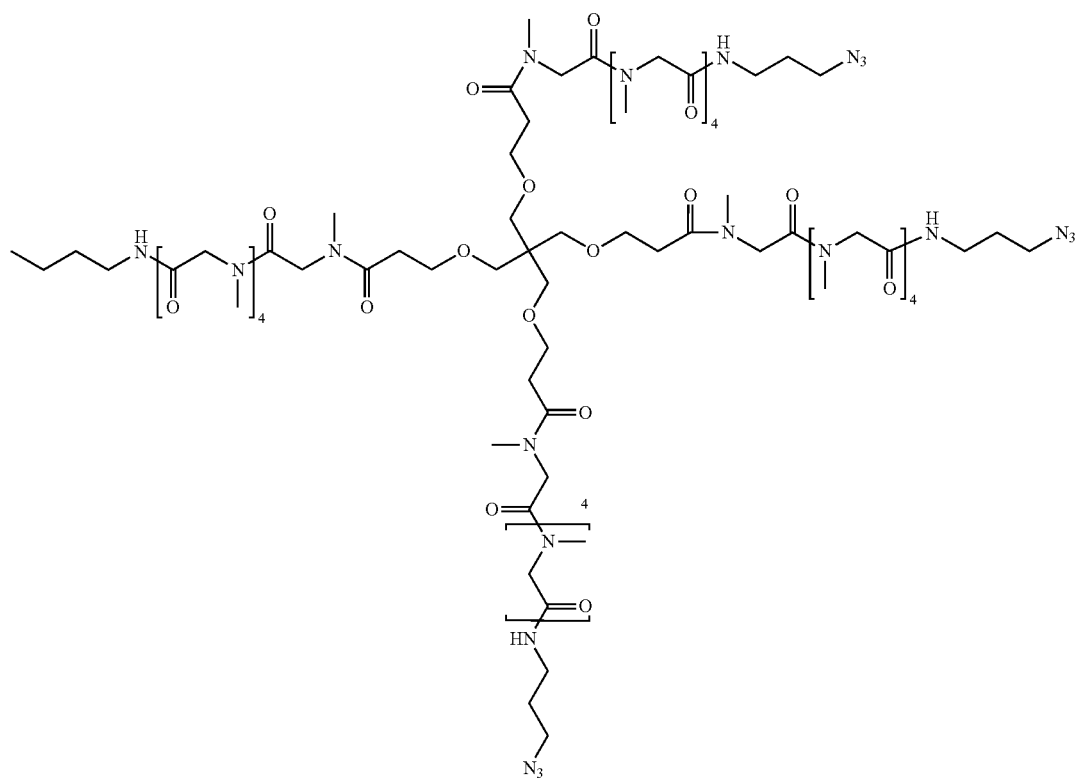
Compound 5:

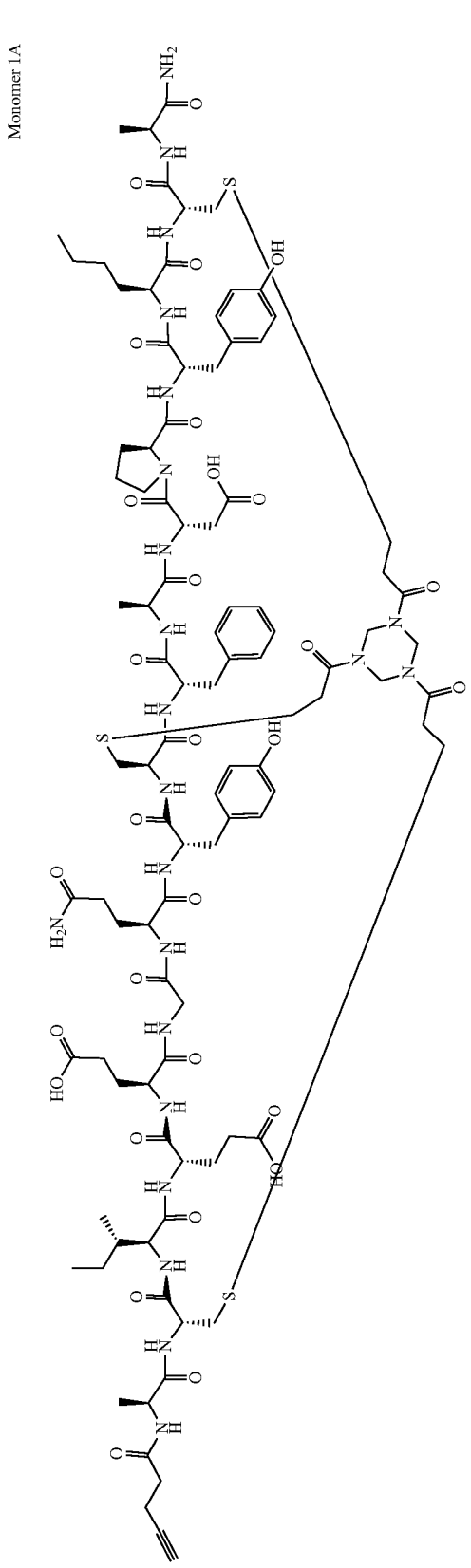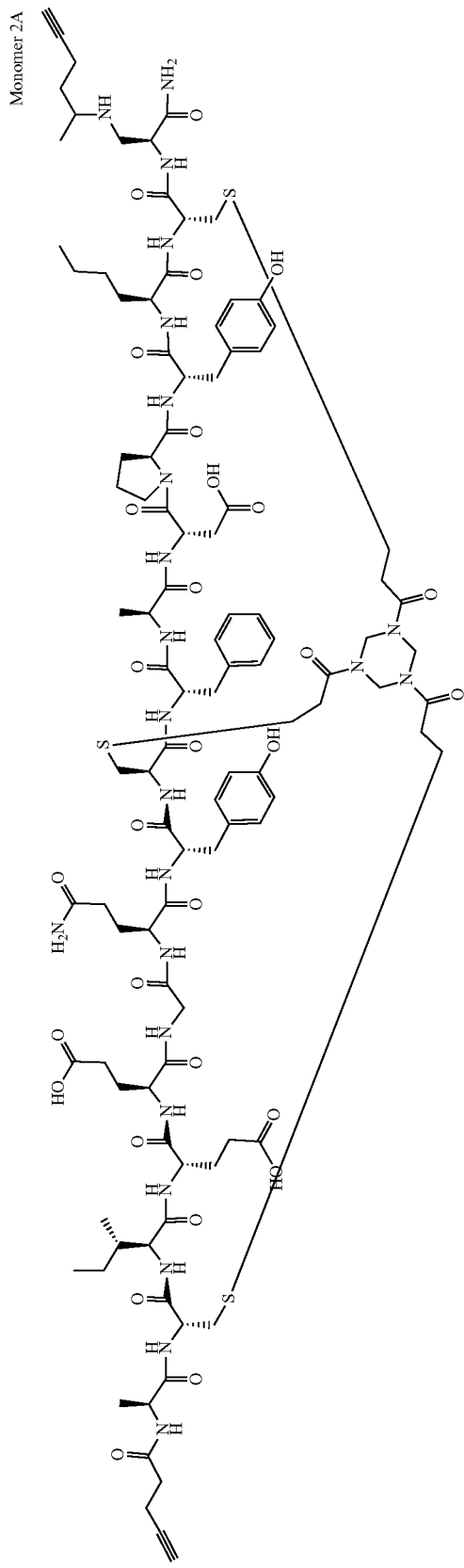

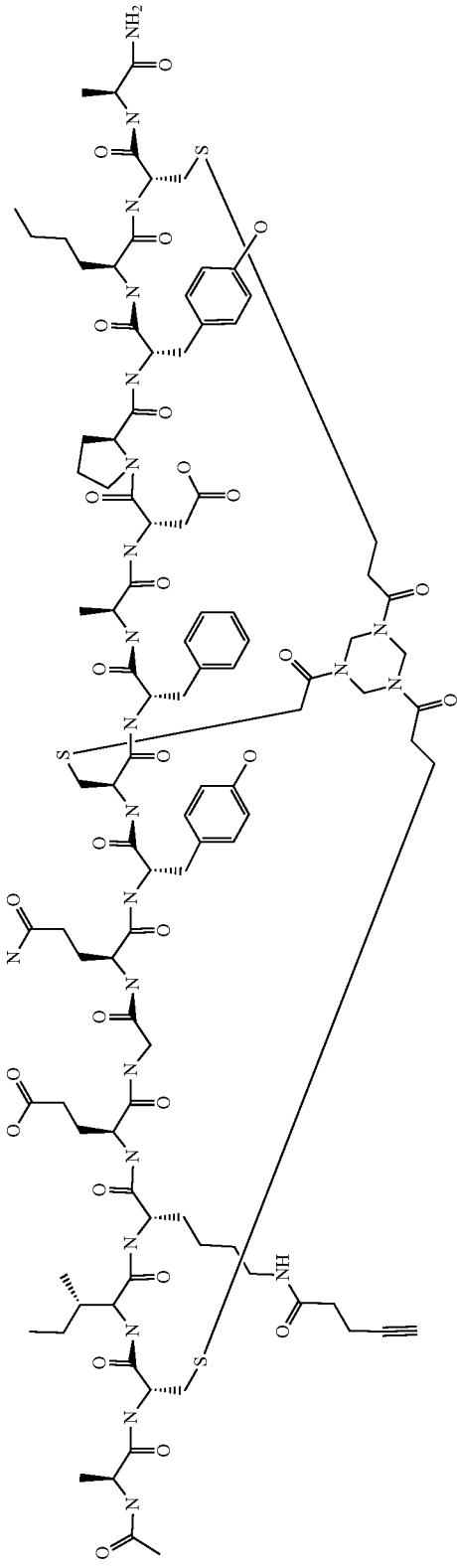

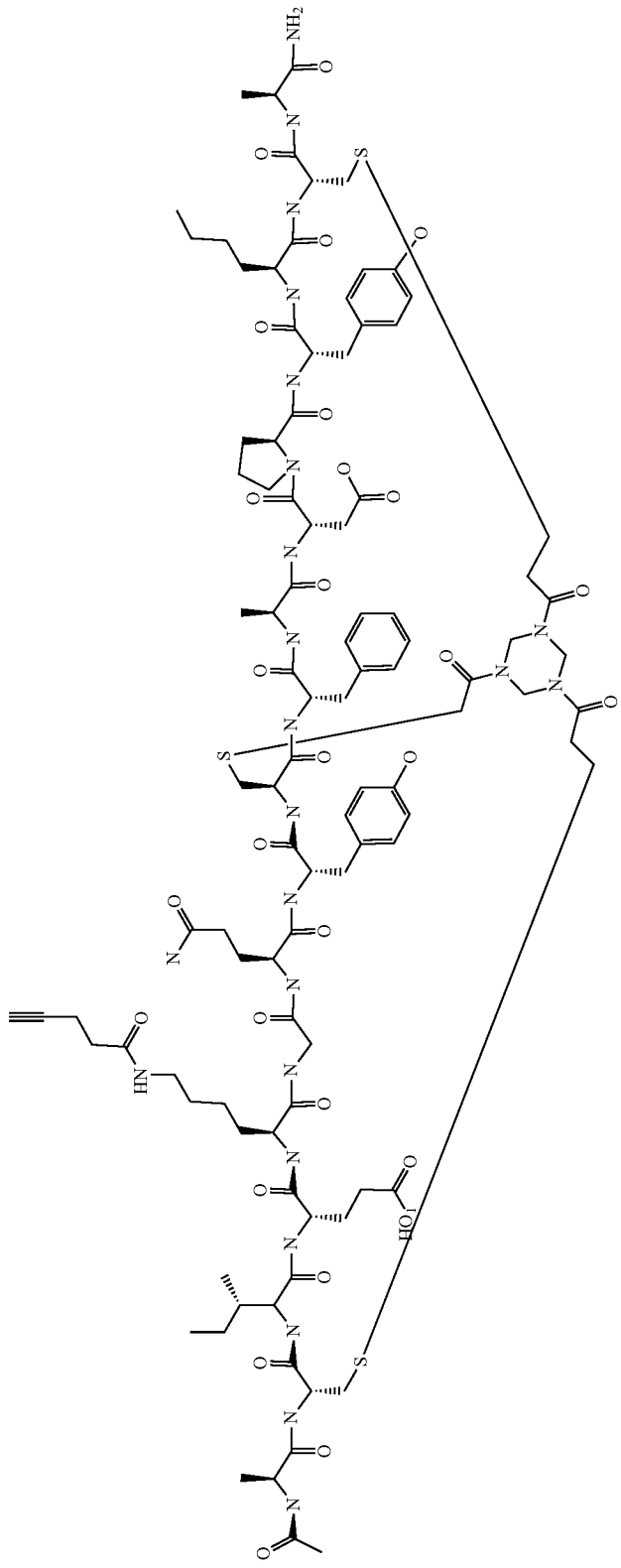
Monomer 4A

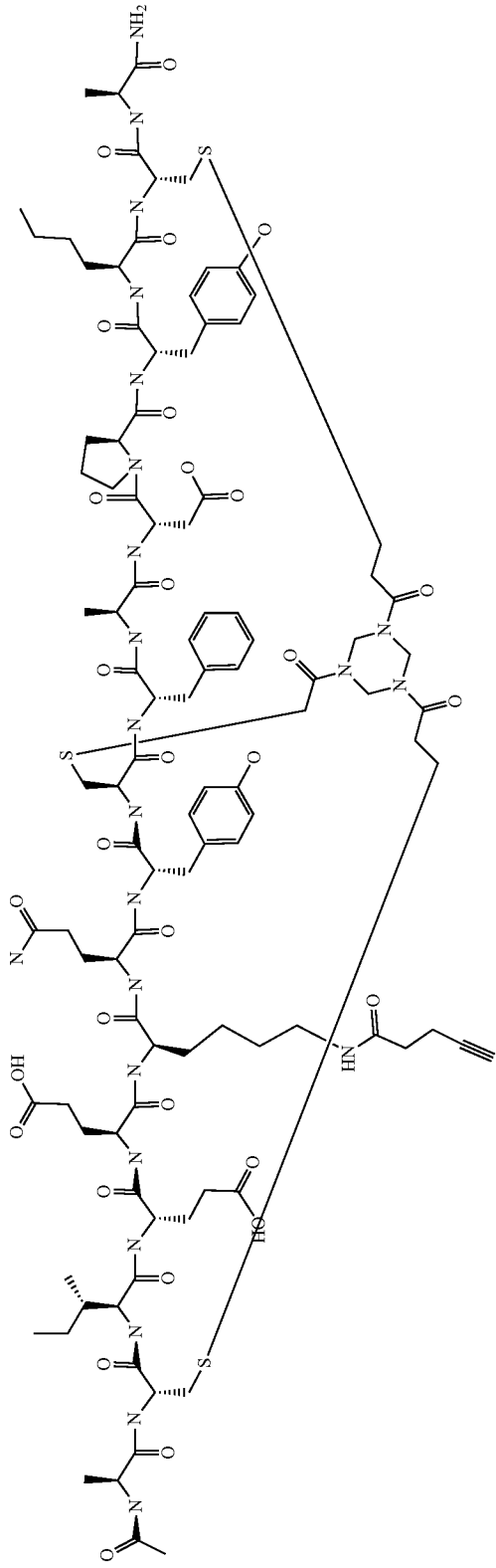
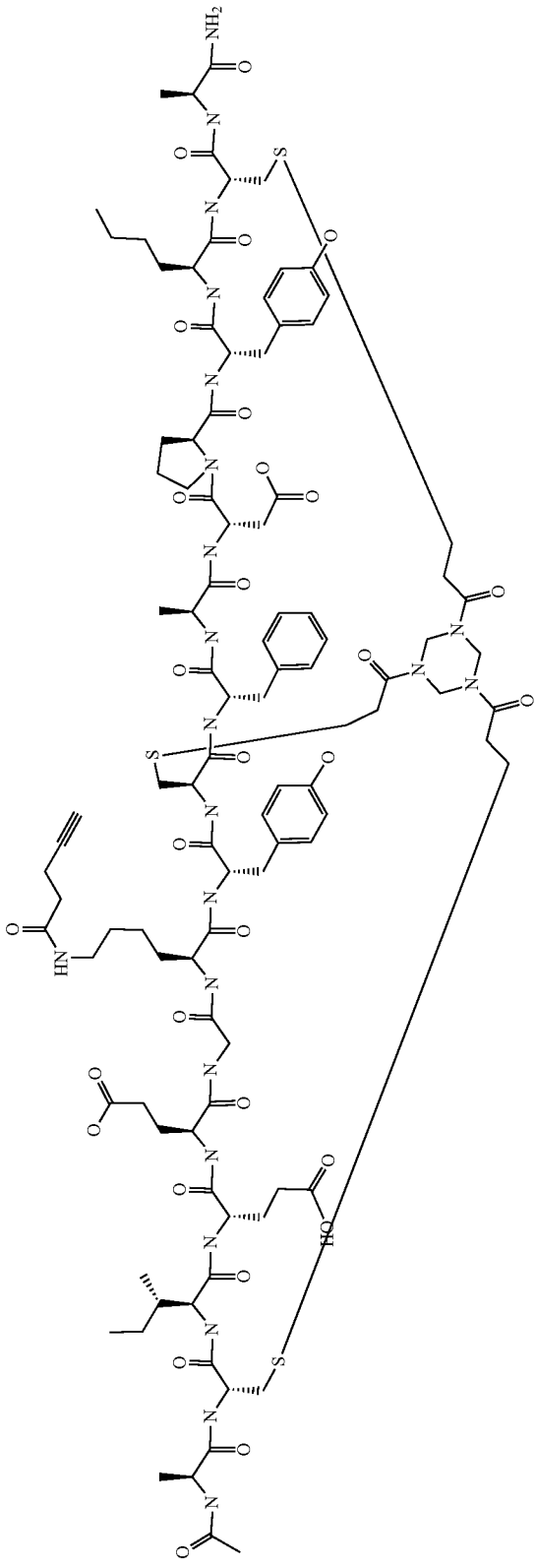

-continued
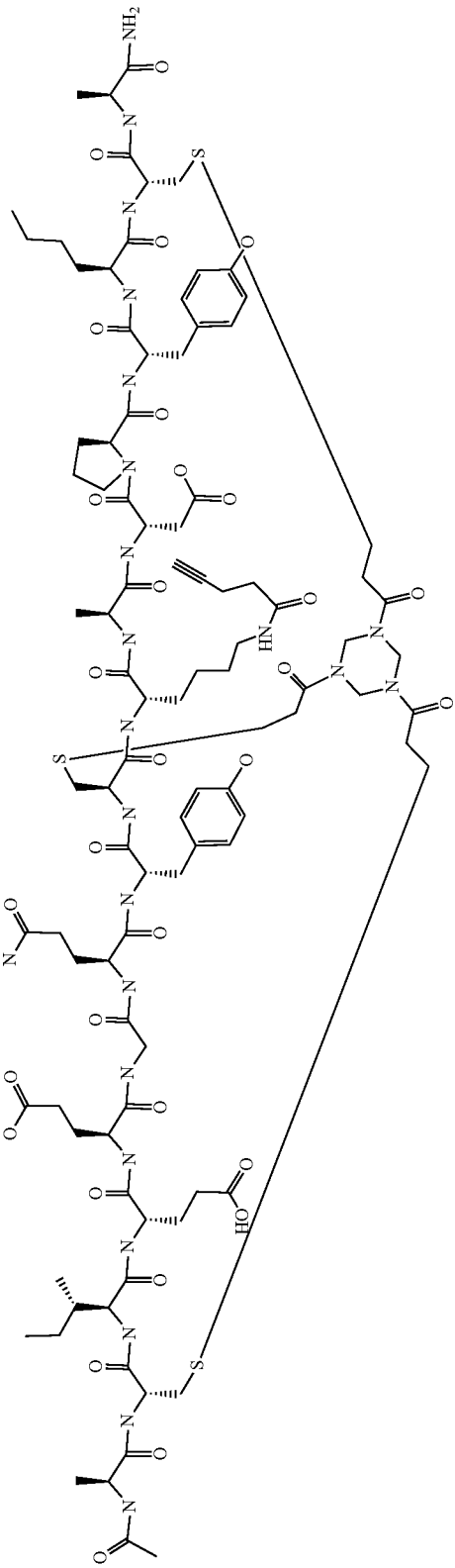
Monomer 7A
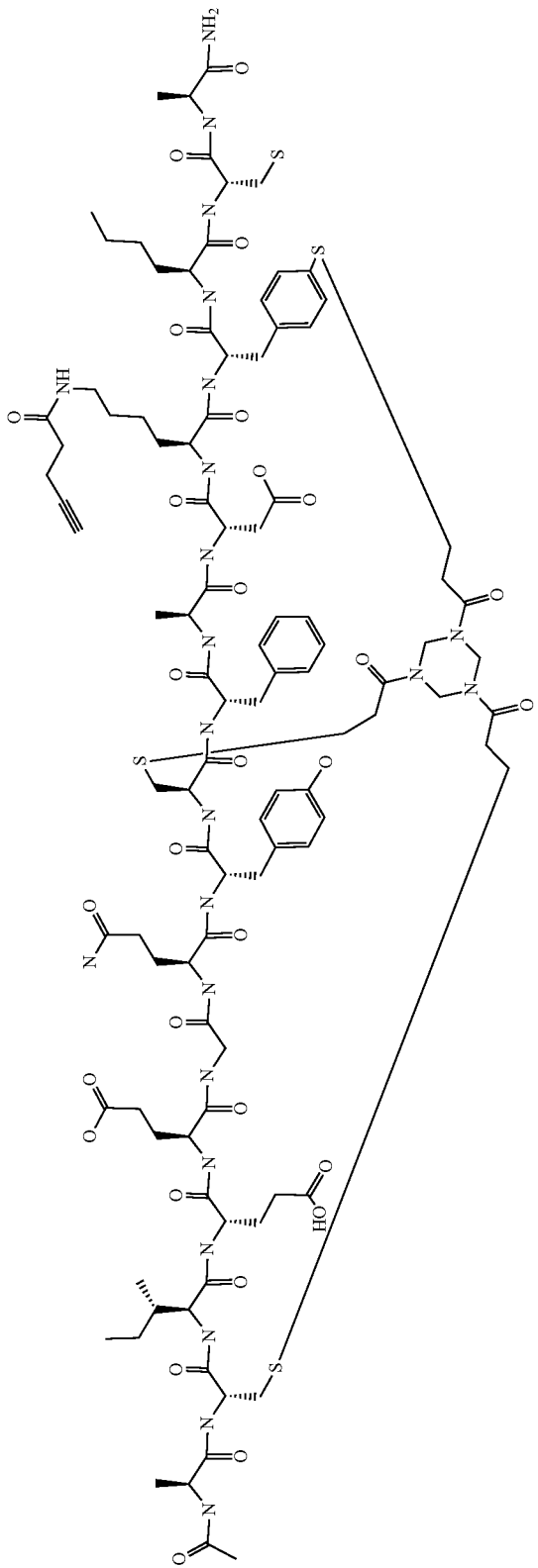
Monomer 8A

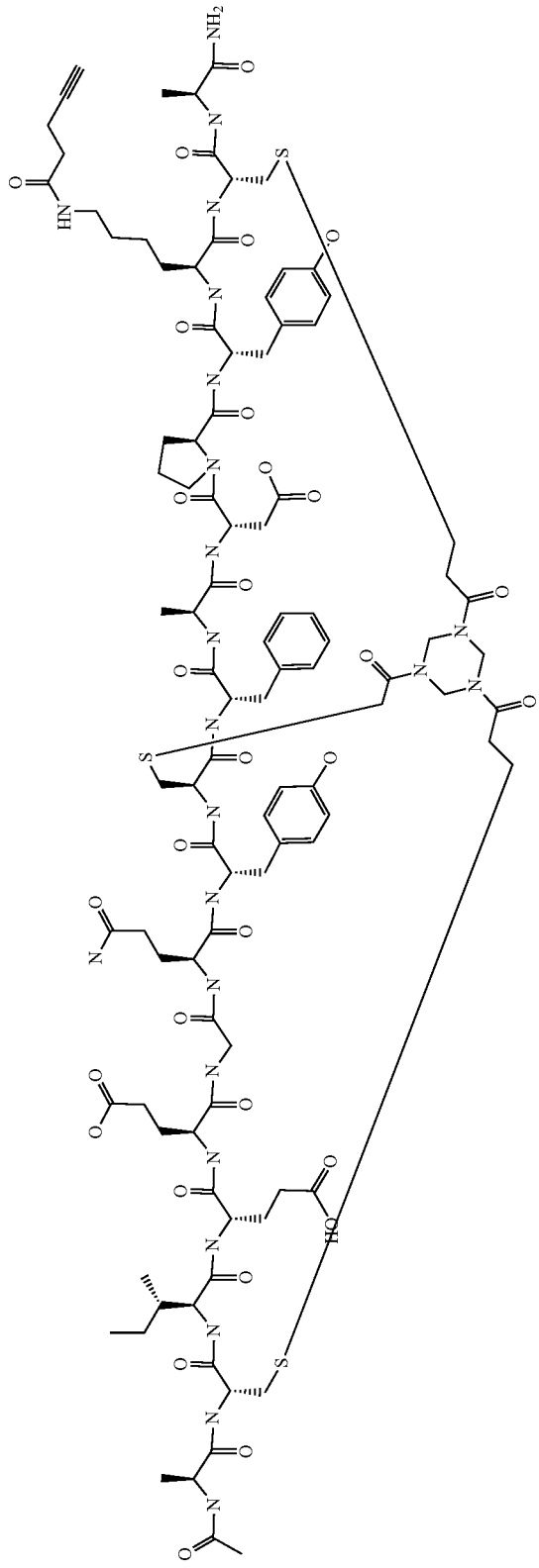
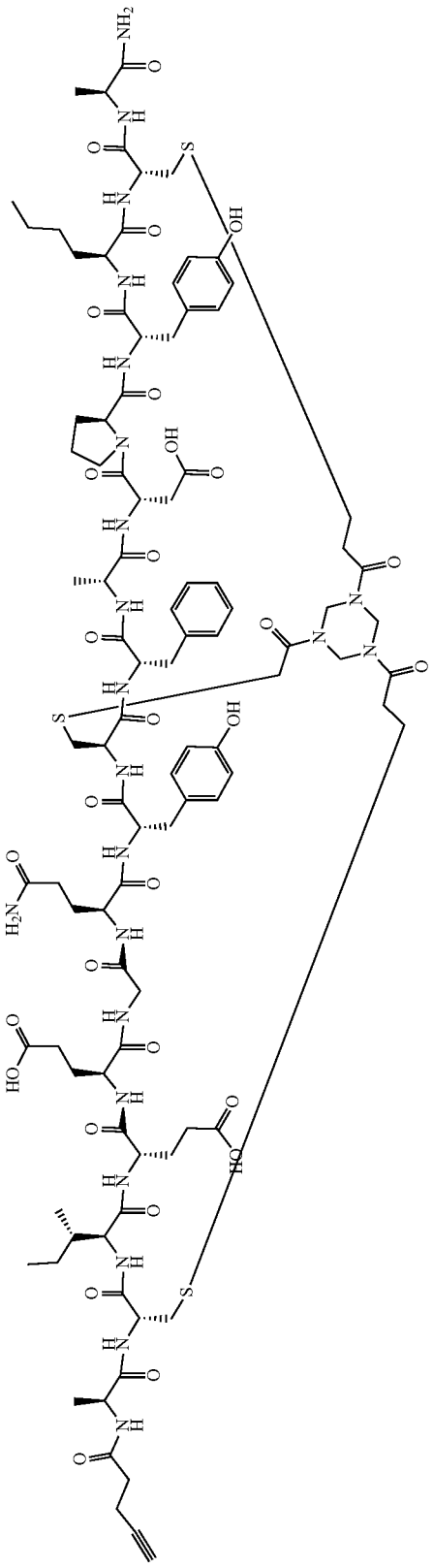

Monomer 11A
Monomer 12A
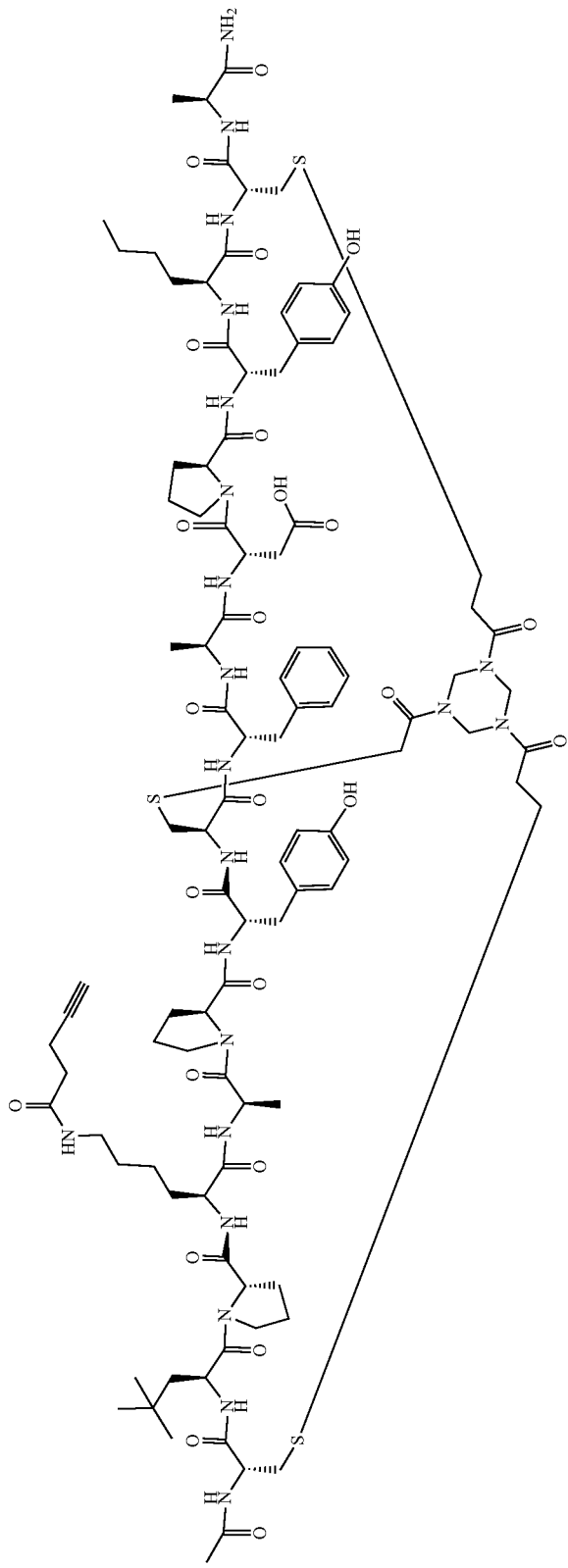
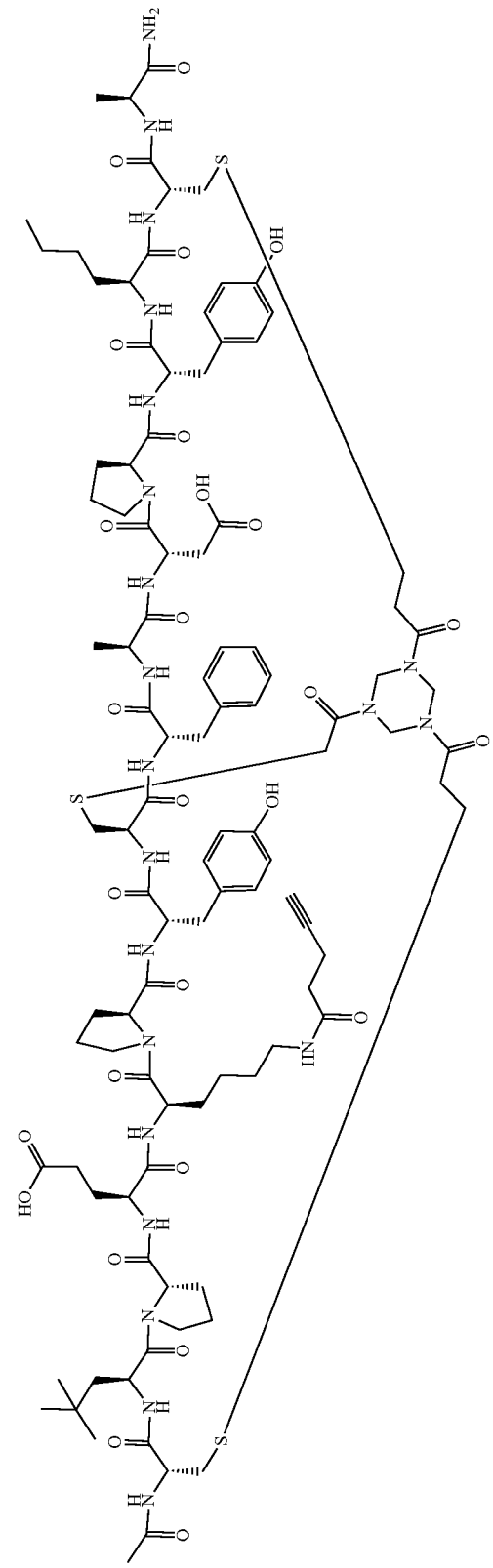

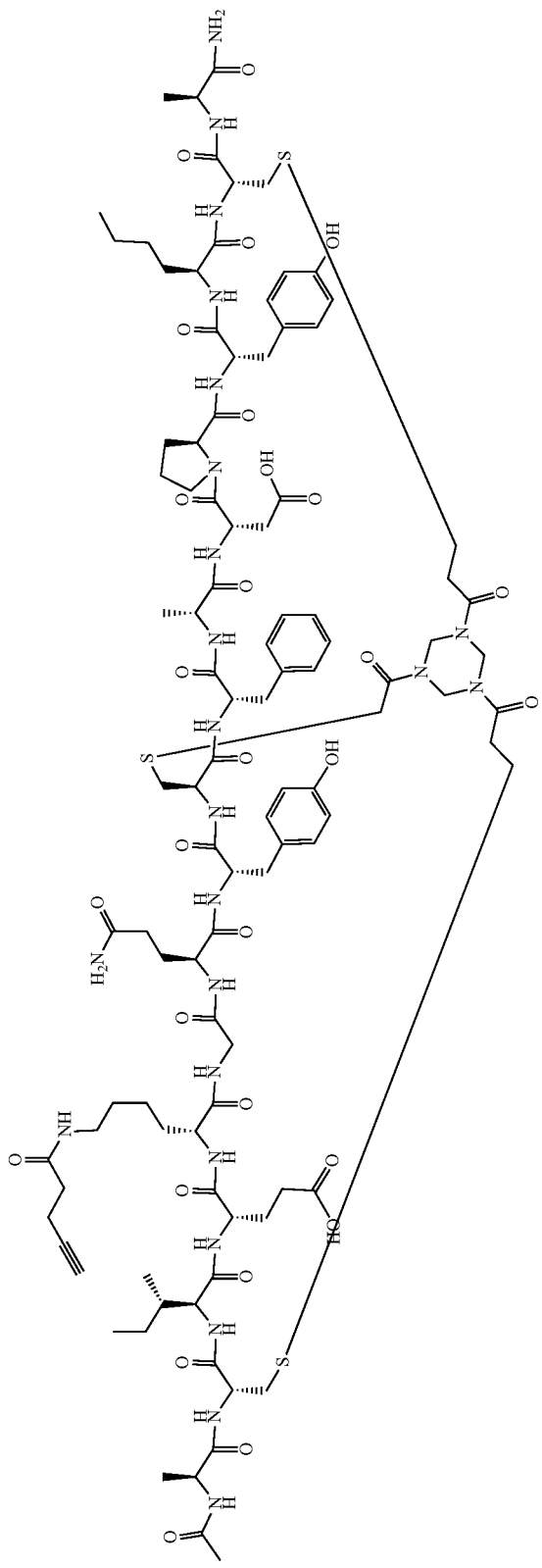
Monomer 13A

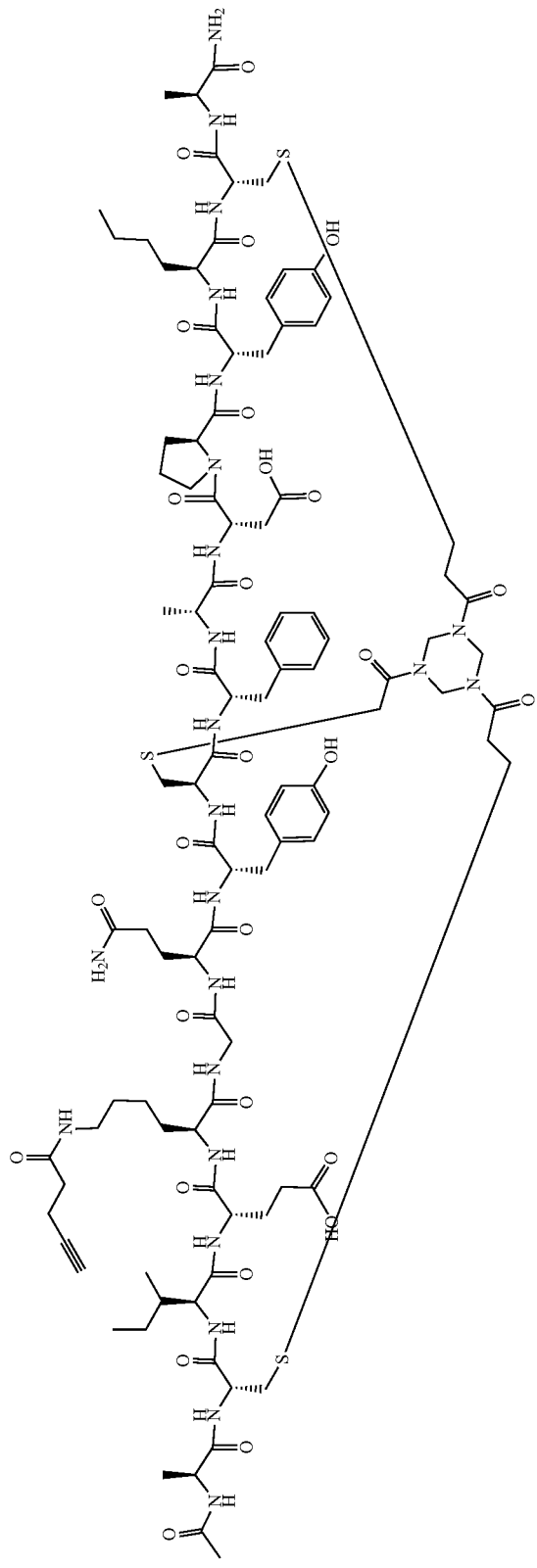
Monomer 14A
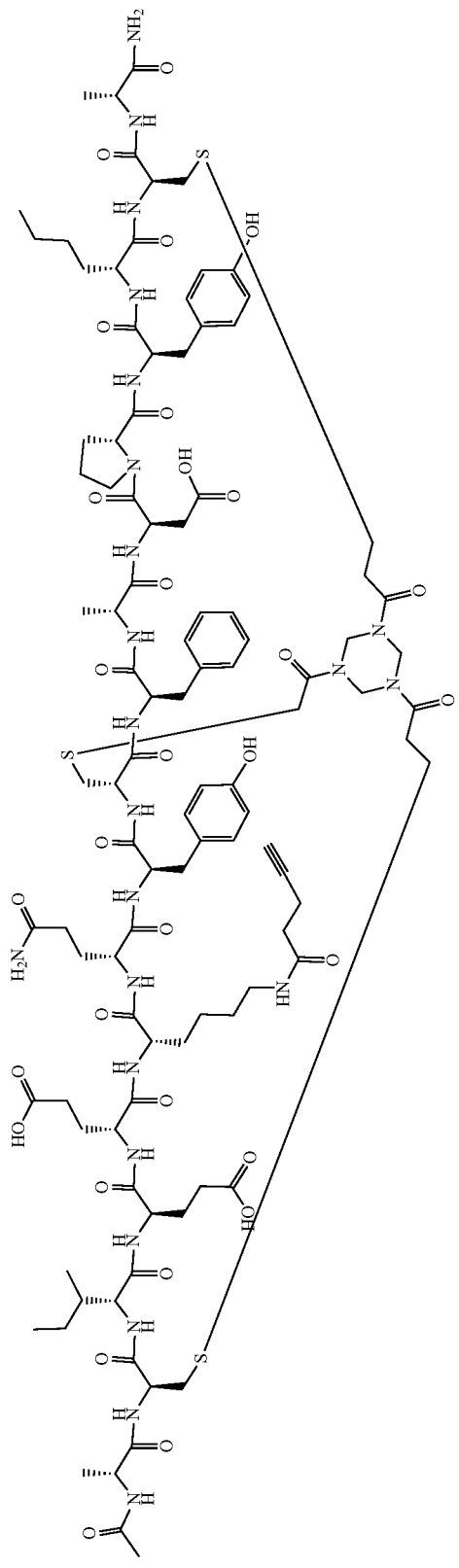
Monomer 15A

Compound 15:

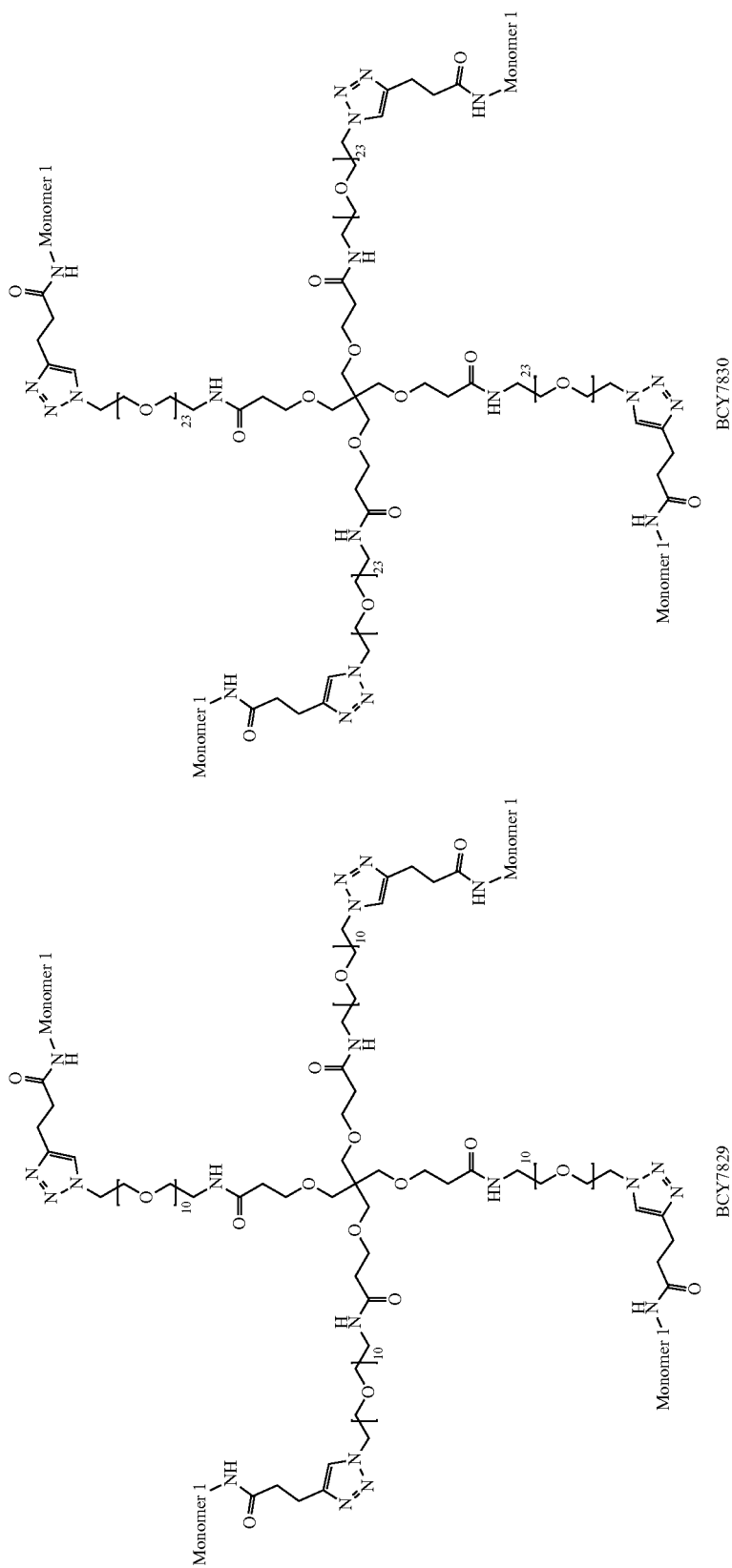

-continued
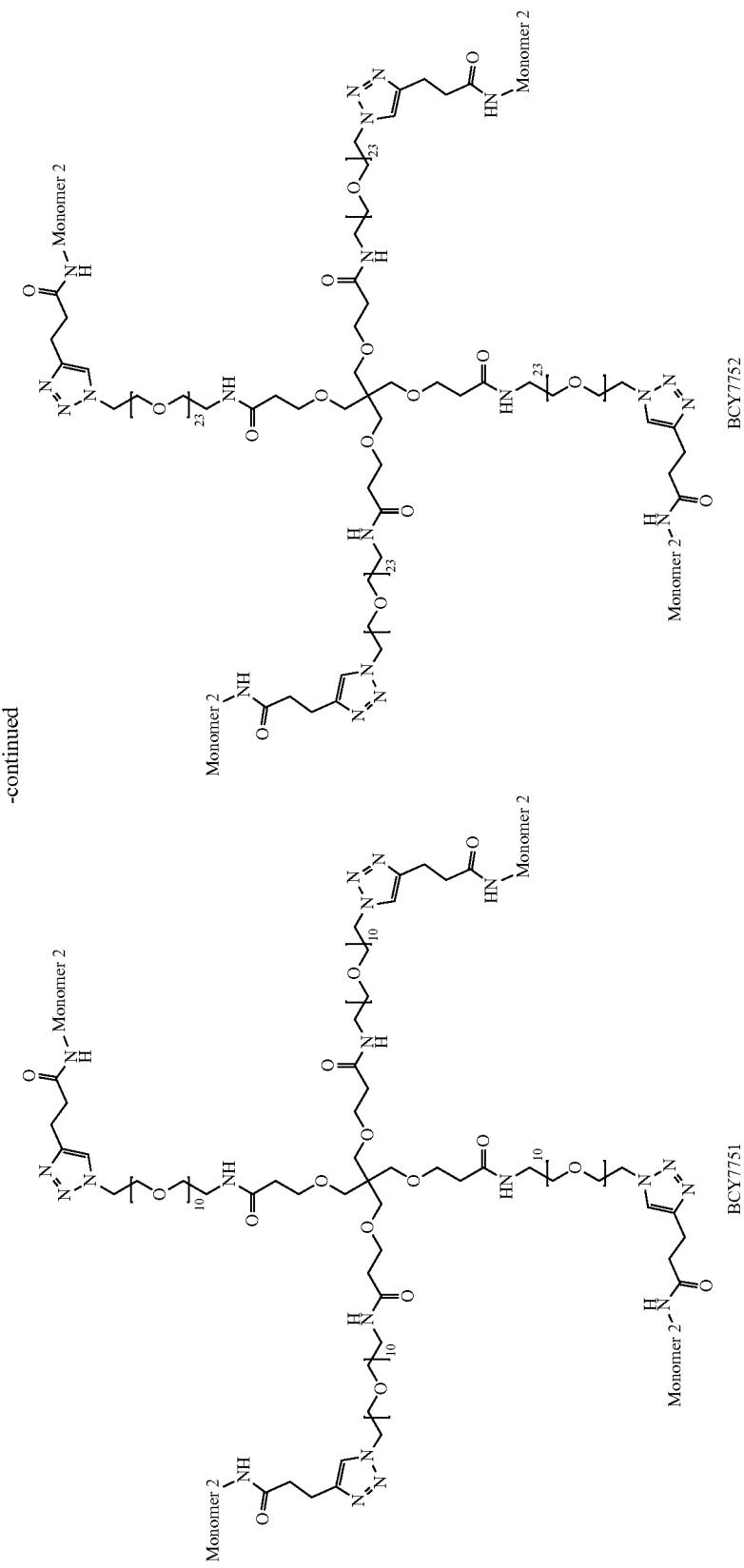

-continued
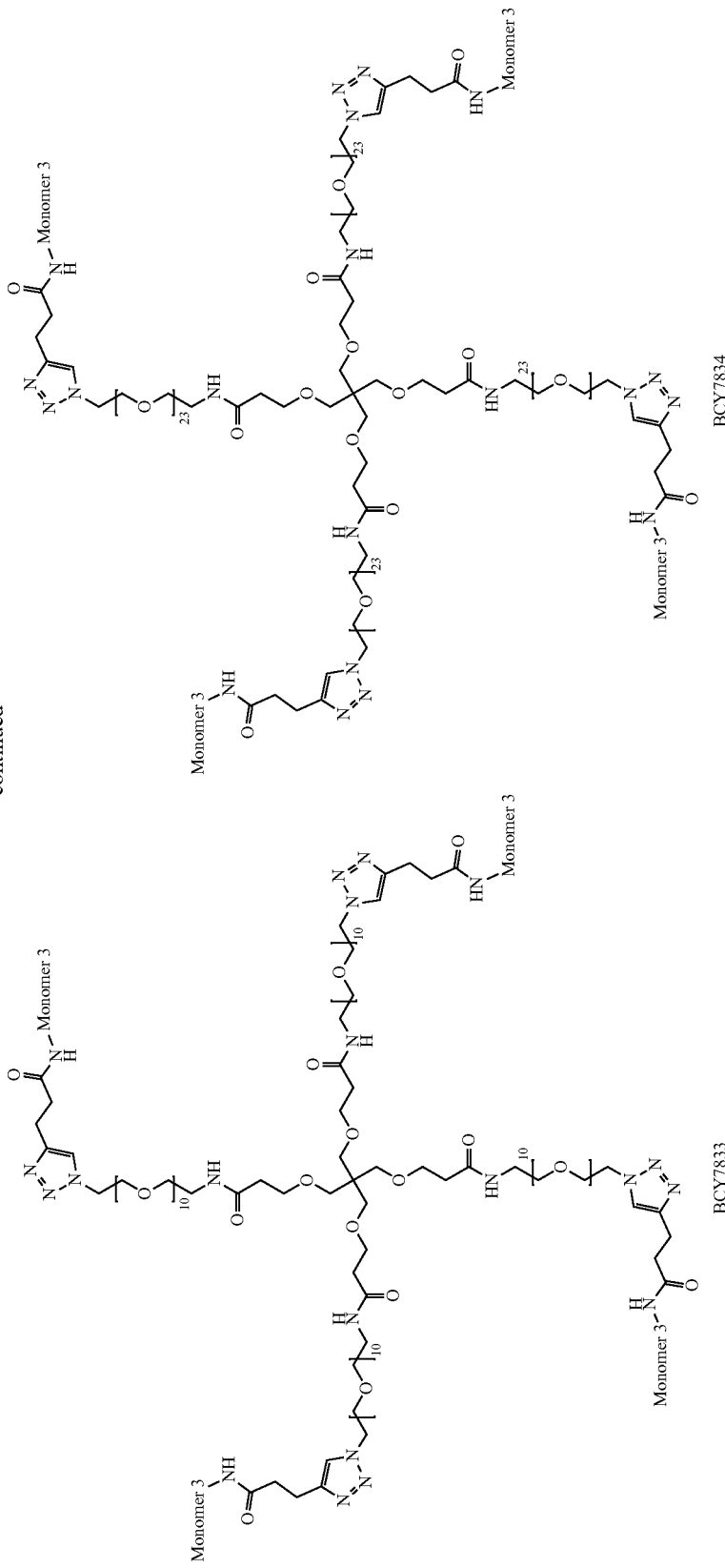

-continued
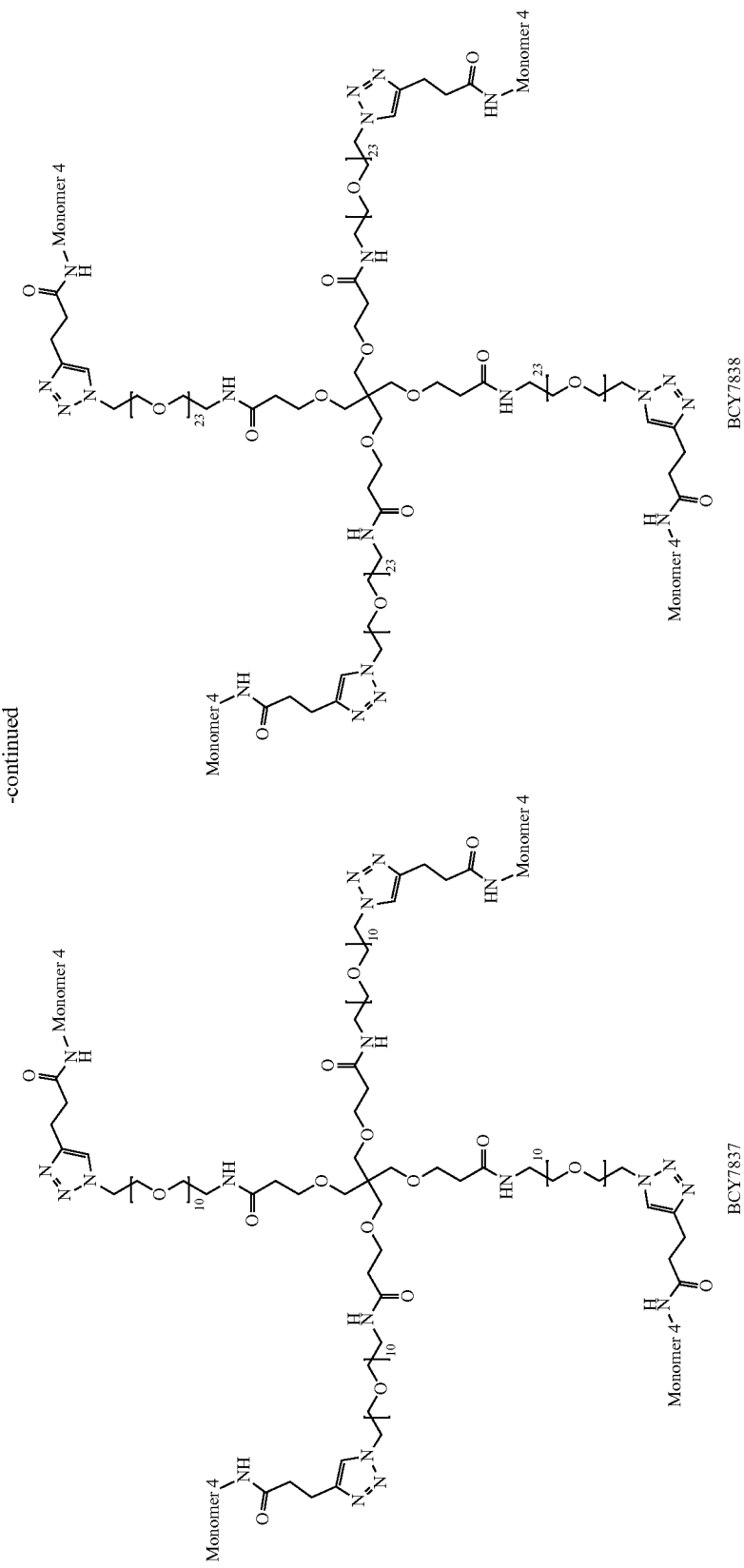

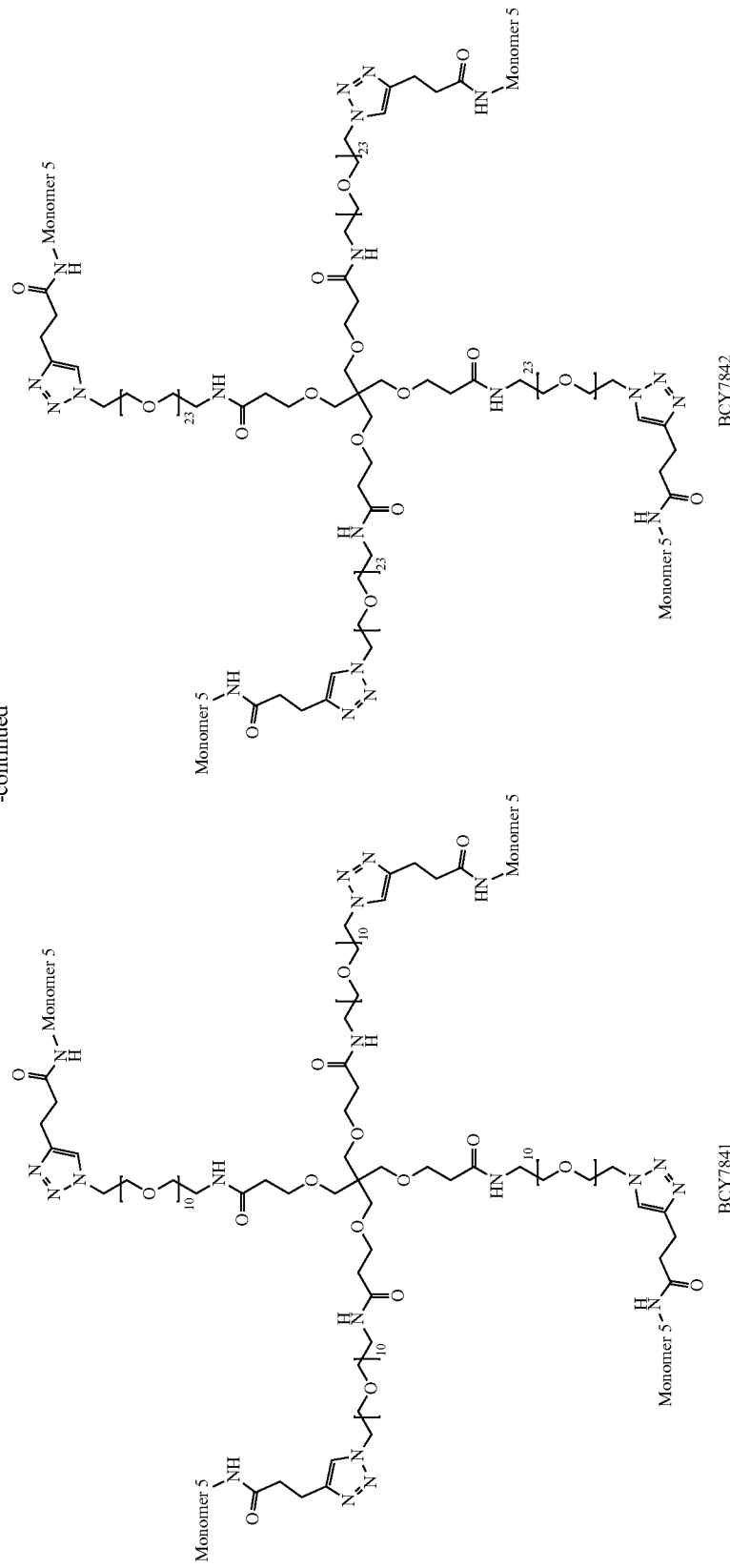

-continued
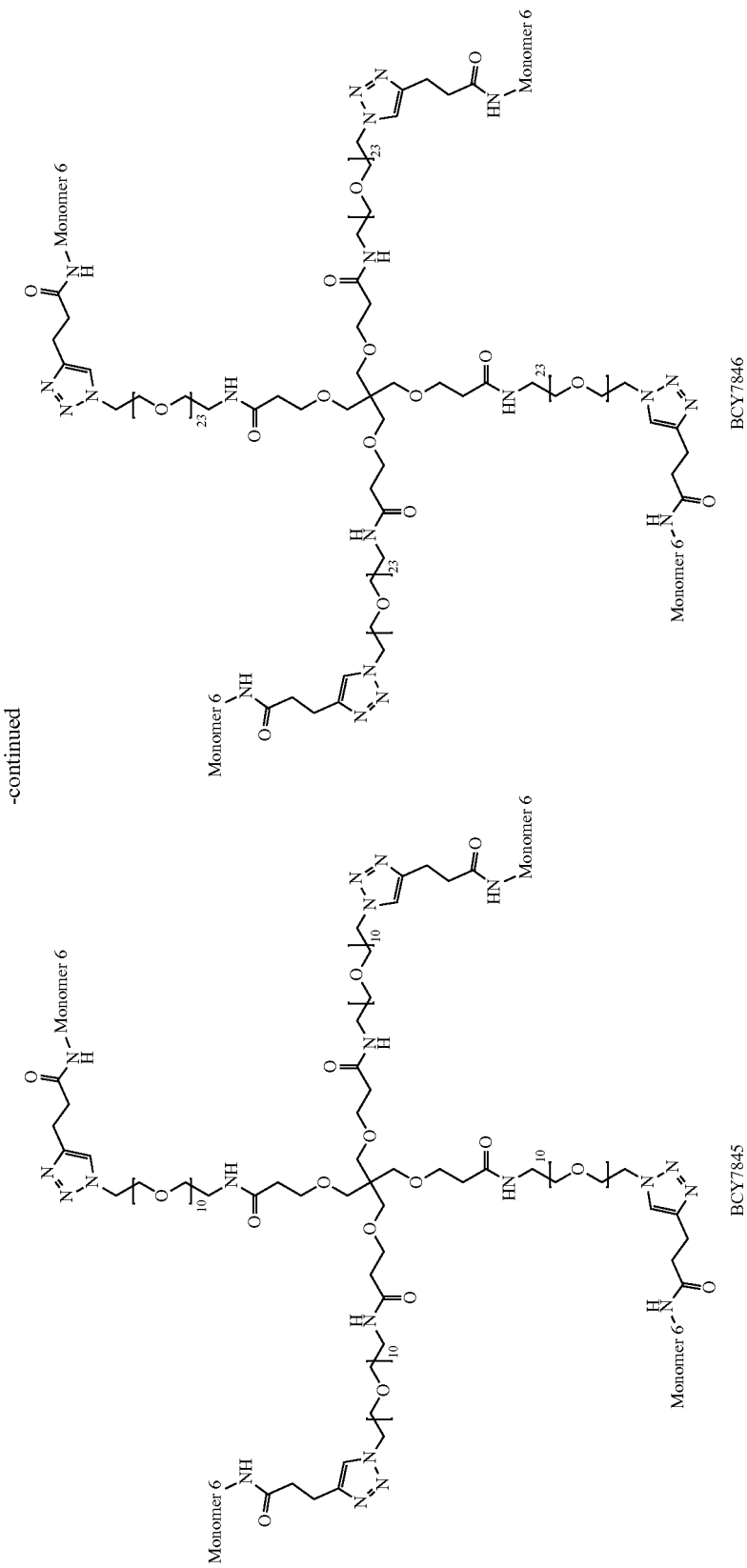

-continued
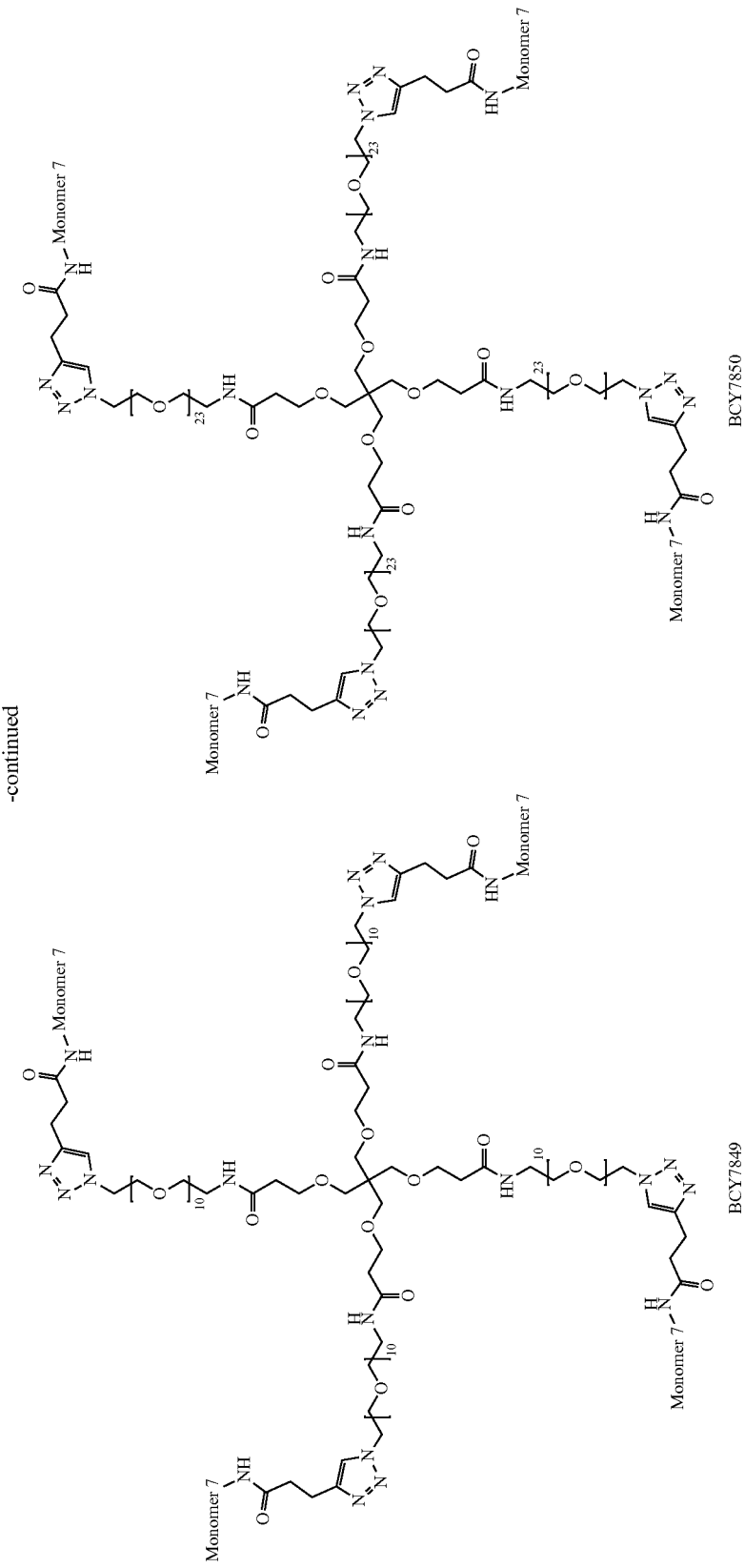

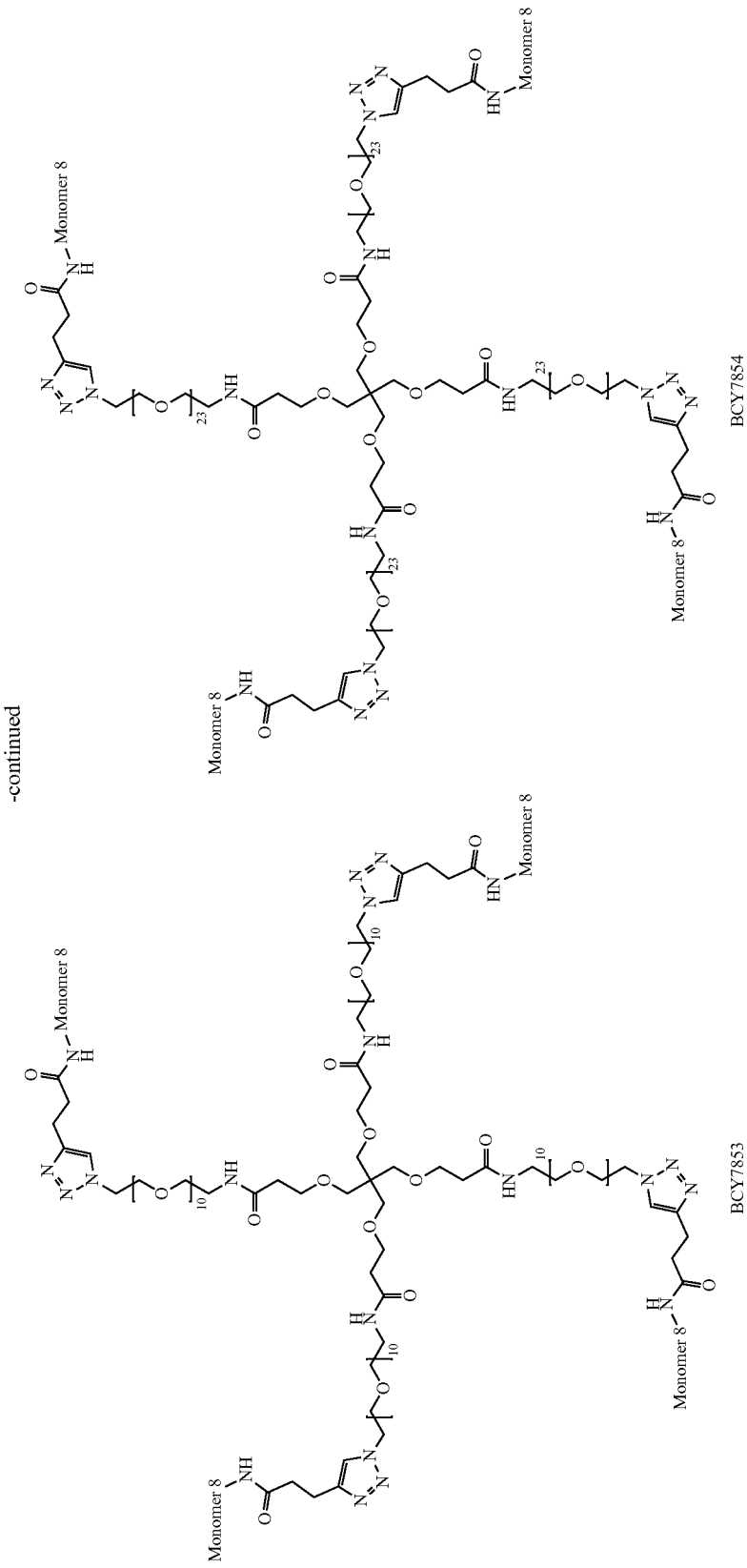

-continued
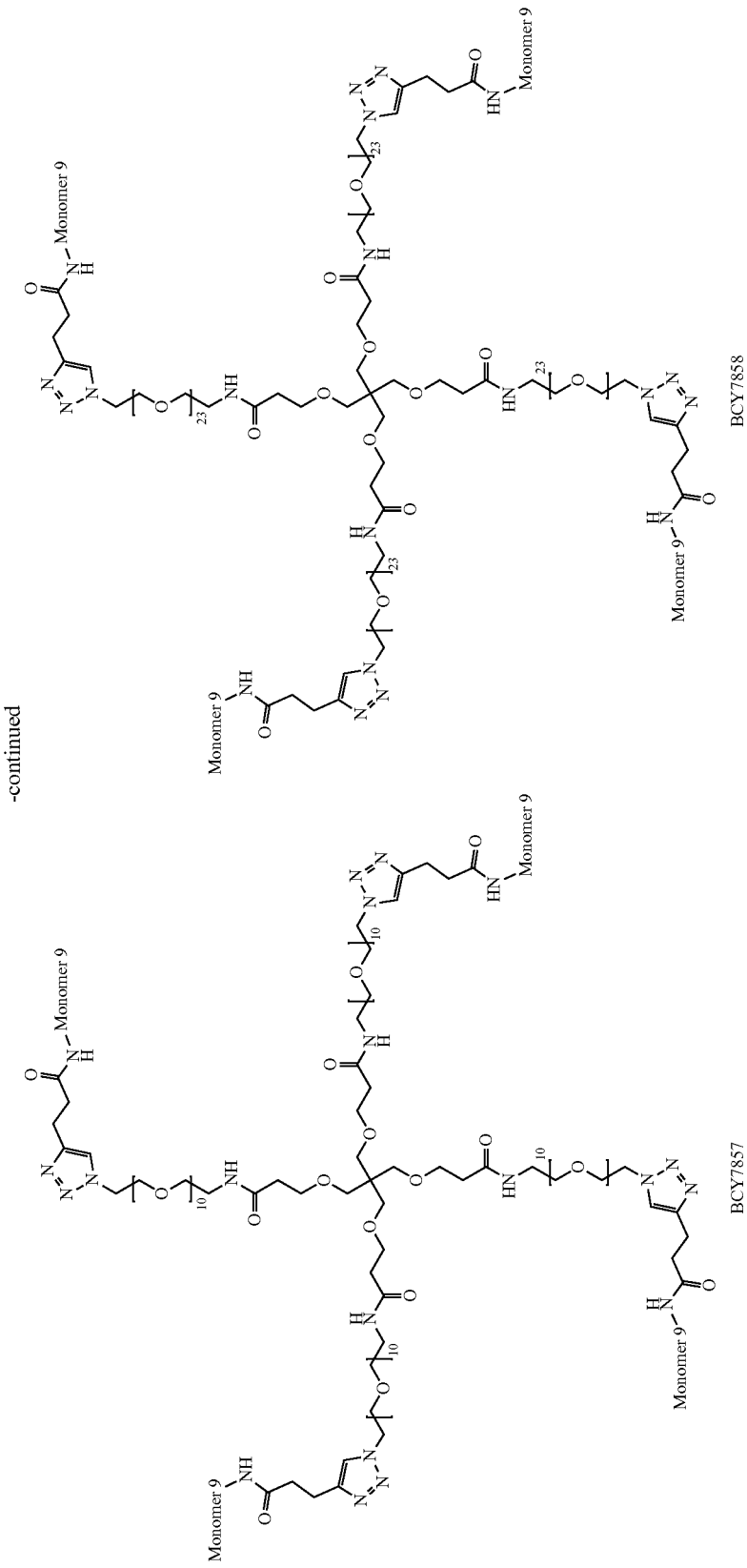

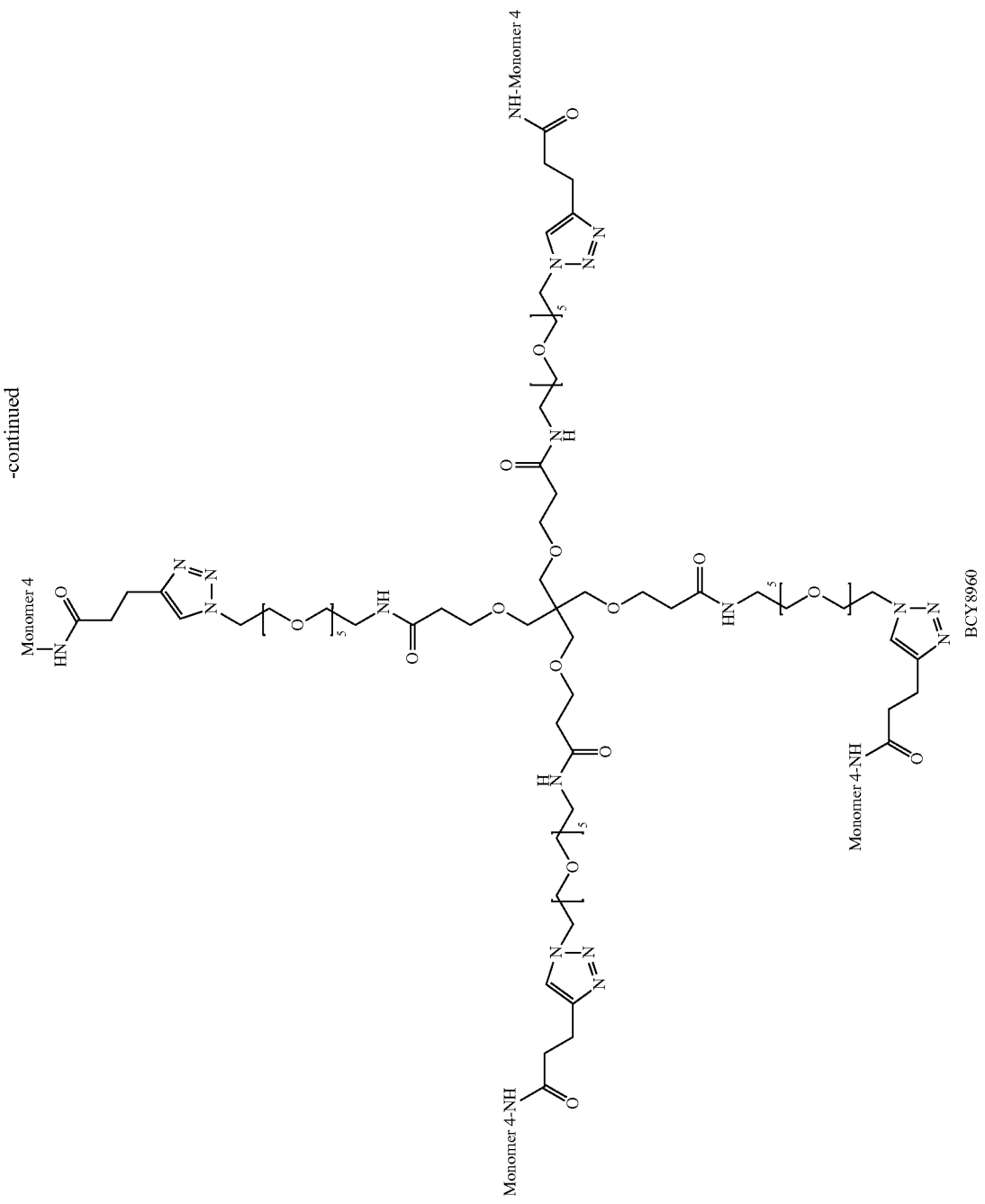

-continued
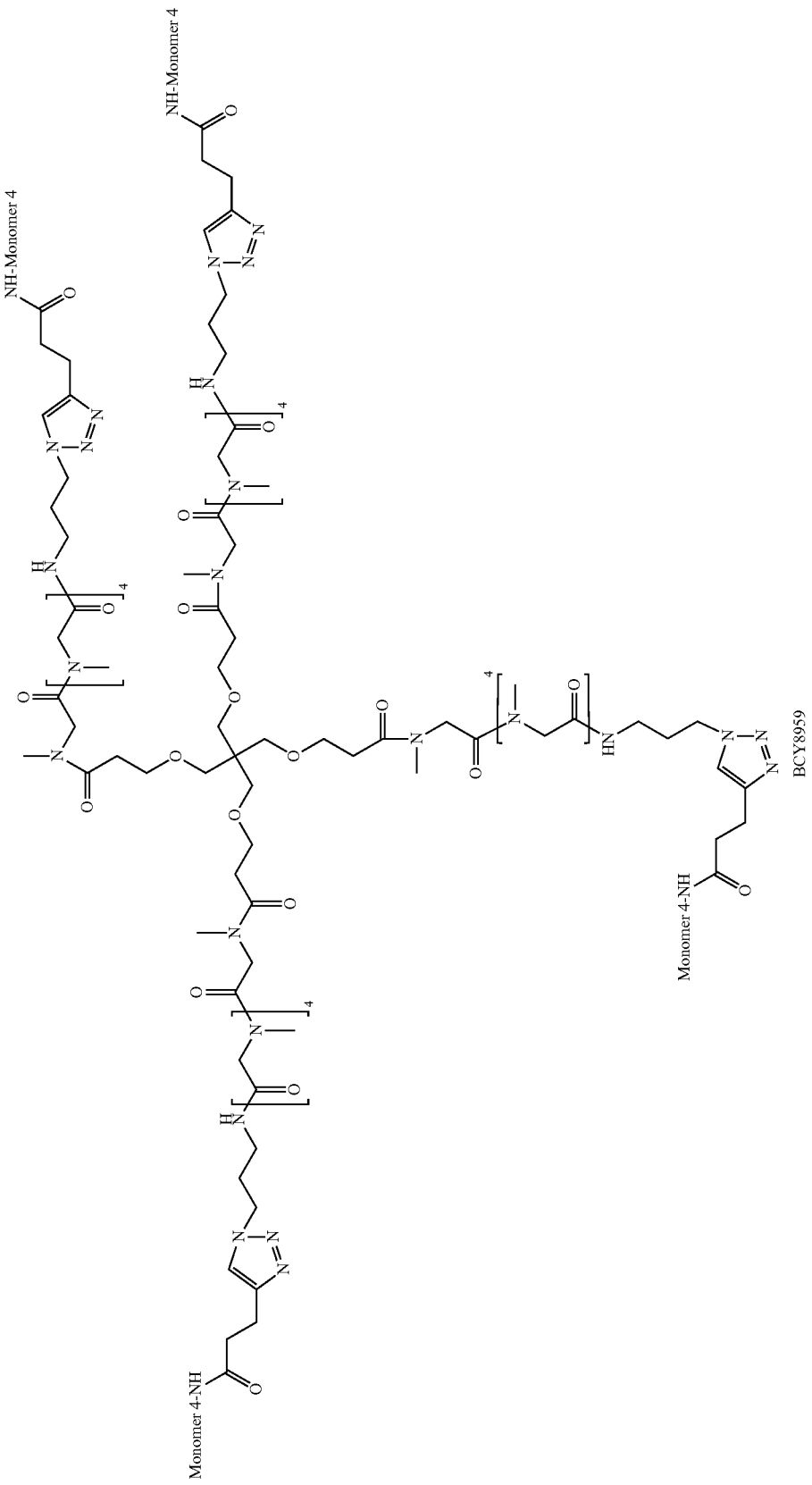

-continued
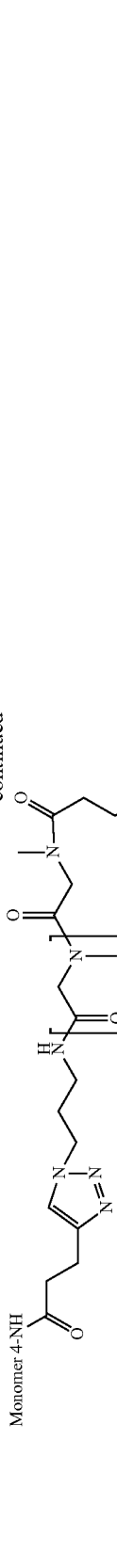
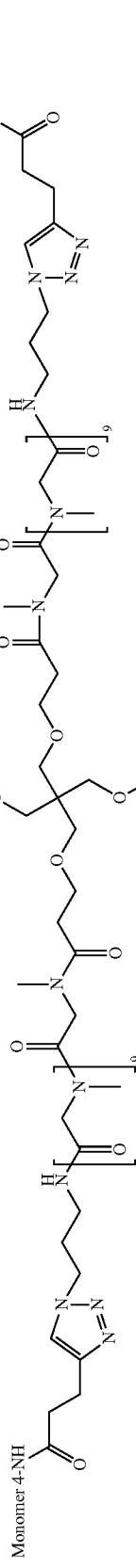
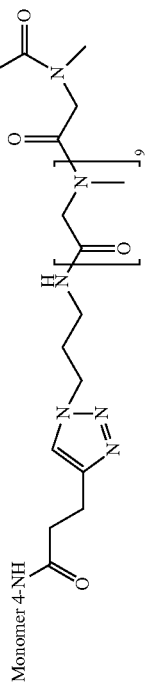
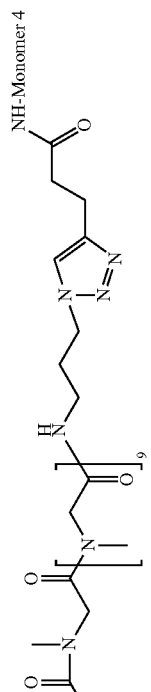
BCY8966

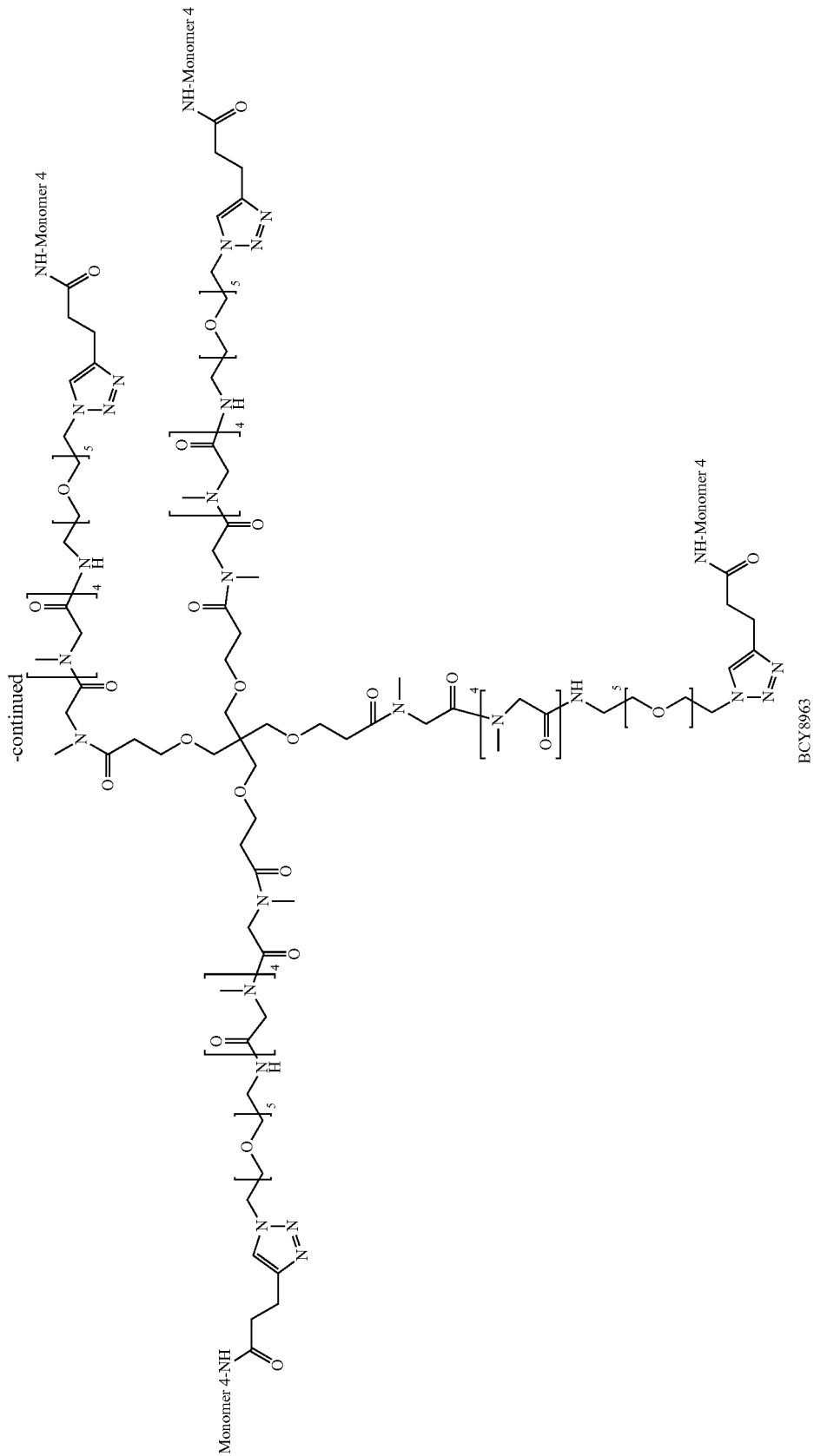

-continued
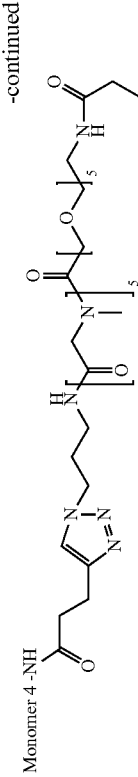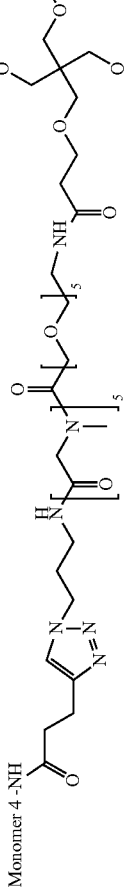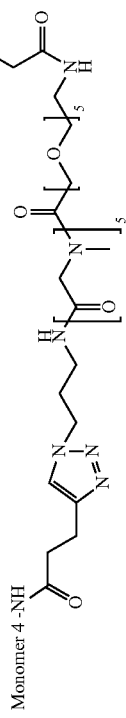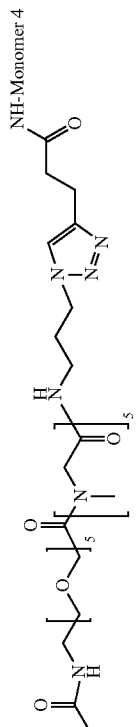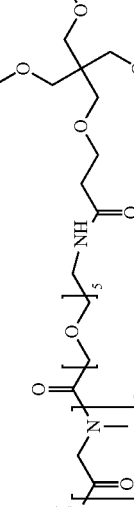
BCY8964

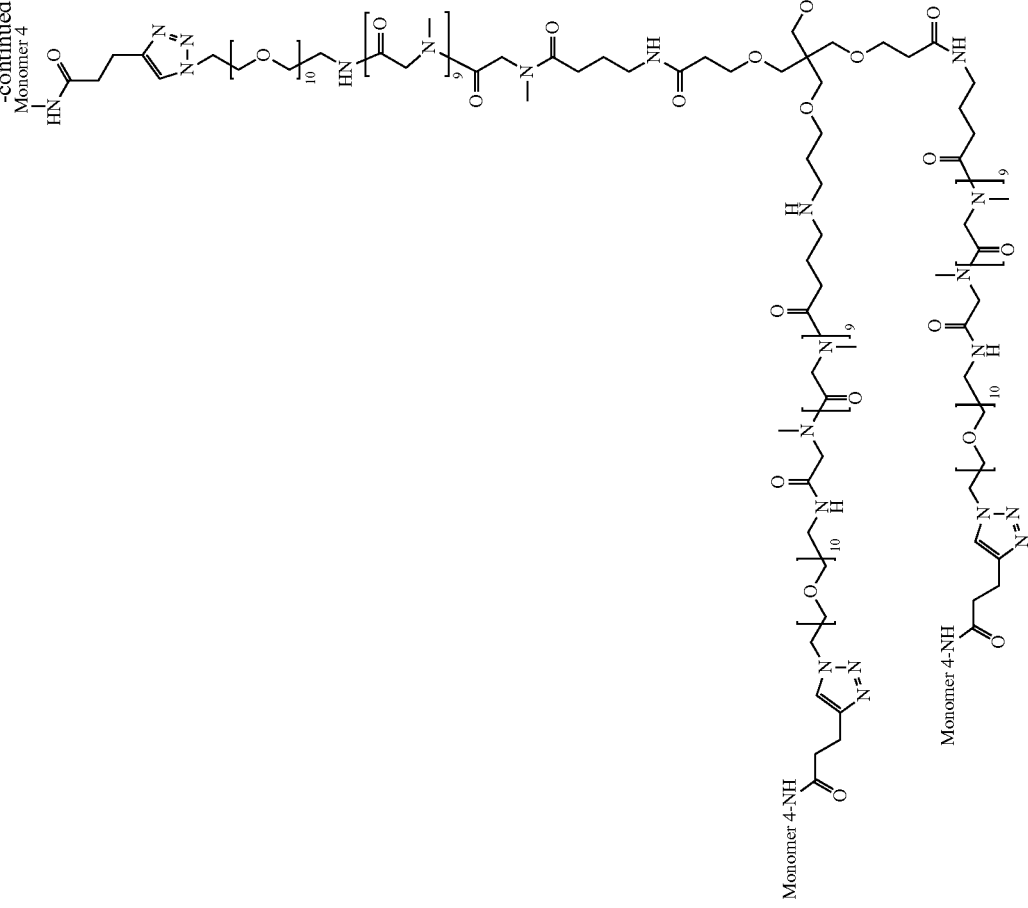

BCY7829:

A mixture of compound 14A (24 mg, 9.76 µmol, 1 eq), Monomer 1A (130.28 mg, 58.56 µmol, 6 eq), CuI (37.18 mg, 195.22 µmol, 20 eq) in DMF (3 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7829 (39.4 mg, 3.19 µmol, 32.64% yield, 91.83% purity) as a white solid.

BCY7830:

To a solution of compound 14B (4 mg, 8.42e-1 µmol, 1 eq) and Monomer 1A (14.99 mg, 6.74 µmol, 8 eq) in DMF (1 mL) was added $CuSO_4 \cdot 5H_2O$ (0.8 M, 12.63 µL, 12 eq) and ascorbic acid (0.8 M, 84.22 µL, 80 eq) under $N_2$ atmosphere. The mixture was stirred at 30° C. for 1 hr. LC-MS and HPLC showed Reactant 1 was consumed completely. The reaction mixture was filtered and concentrated under reduced pressure to give a residue. The residue was purified by prep-HPLC (TFA condition) to give BCY7830 (6 mg, 3.69e-1 µmol, 36.79% yield, 70.48% purity) as a white solid.

BCY7751:

To a mixture of compound 14A (4 mg, 1.63 µmol, 1 eq), Monomer 2A (29.67 mg, 13.00 µmol, 7.99 eq) in DMF (0.5 mL) was added CuI (6.2 mg, 32.6 µmol, 20 eq) and the mixture was degassed and purged with $N_2$ for 3 times, and then the mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7751 (5 mg, 1.74e-1 µmol, 22.85% yield, 86.1% purity) as a white solid.

BCY7752:

A mixture of compound 14B (24 mg, 5.05 µmol, 1 eq), Monomer 2A (69.17 mg, 30.32 µmol, 6 eq), CuI (11.55 mg, 60.64 µmol, 12 eq) in DMF (3 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7752 (21.7 mg, 1.41 µmol, 27.97% yield, 90.38% purity) as a white solid.

BCY7833:

To a mixture of compound 14A (4 mg, 1.63 µmol, 1 eq), Monomer 3A (44.23 mg, 19.52 µmol, 12.0 eq) in DMF (1 mL) was added a solution of $CuSO_4$ (0.4 M, 48.80 µL, 12.0 eq) and (2R)-2-[(1S)-1,2-dihydroxyethyl]-3,4-dihydroxy-2H-furan-5-one (0.4 M, 162.68 µL, 40.0 eq) and the mixture was degassed and purged with $N_2$ for 3 times, and then the mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7833 (4.2 mg, 1.86e-1 µmol, 11.43% yield, 51.00% purity) as a white solid.

BCY7834:

To a mixture of compound 14B (4 mg, 8.42e-1 µmol, 1 eq), Monomer 3A (22.90 mg, 10.11 µmol, 12.0 eq) in DMF (1 mL) was added a solution of $CuSO_4 \cdot 5H_2O$ (0.4 M, 18.95 µL, 9.0 eq) and (2R)-2-[(1S)-1,2-dihydroxy-2H-furan-5-one (0.4 M, 84.22 µL, 40 eq) in H2O (0.11 mL) and the mixture was degassed and purged with $N_2$ for 3 times, and then the mixture was stirred at 25-30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7834 (2.3 mg, 1.40e-1 µmol, 16.64% yield, 84.14% purity) as a white solid.

BCY7837:

To a mixture of compound 14A (4 mg, 1.63 µmol, 1 eq), Monomer 4A (22.11 mg, 9.76 µmol, 6 eq) in DMF (1 mL) was added CuI (6.20 mg, 32.54 µmol, 20 eq) and the mixture was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7837 (11.4 mg, 6.16e-1 µmol, 37.86% yield, 62.25% purity) as a white solid.

BCY7838:

A mixture of compound 14B (40 mg, 8.42 µmol, 1 eq), Monomer 4A (114.48 mg, 50.53 µmol, 6 eq), CuI (32.08 mg, 168.44 µmol, 20 eq) in DMF (5 mL) was degassed and purged with $N_2$ for 3 times, and then the mixture was stirred at 25-30° C. for 2 hrs under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7838 (51 mg, 3.33 µmol, 39.49% yield, 90.08% purity) as a white solid.

BCY7841:

A mixture of compound 14A (4 mg, 1.63 µmol, 1 eq), Monomer 5A (23 mg, 9.84 µmol, 6.05 eq), CuI (309.82 µg, 1.63 µmol, 1 eq) in DMF (0.5 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7841 (8.3 mg, 4.47e-1 µmol, 27.45% yield, 63.54% purity) as a white solid.

BCY7842:

The click reaction was performed in 3 containers in parallel. In each reaction container, a mixture of compound 14B (170.0 mg, 35.8 µmol, 1.0 eq), Monomer 5A (340.0 mg, 145.4 µmol, 4.06 eq), and THPTA (0.4 M, 89.5 µL, 1.0 eq) was dissolved in t-BuOH/H2O (1:1, 6 mL, pre-degassed and purged with $N_2$ for 3 times), and then $CuSO_4$ (0.4 M, 89.5 µL, 1.0 eq) and VcNa (0.4 M, 179.0 µL, 2.0 eq) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 40° C. for 16 hr under $N_2$ atmosphere. LC-MS showed compound 14B was consumed completely and one main peak with desired m/z (MW: 14100.11, observed m/z: 1007.5400 ([M/14+H+])) was detected. The reaction mixture was combined, filtered, and concentrated under reduced pressure to give a residue. The crude product was then purified by prep-HPLC (TFA condition), resulting in BCY7842 (1.03 g, 69.25 µmol, 64.49% yield, 94.34% purity) was obtained as a white solid.

BCY7845:

A mixture of compound 14A (40 mg, 16.27 µmol, 1 eq), Monomer 6A (221.23 mg, 97.61 µmol, 6 eq), CuI (62 mg, 325.36 µmol, 20 eq) in DMF (4 mL) was degassed and purged with $N_2$ for 3 times, and then the mixture was stirred at 25-30° C. for 2 hrs under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7845 (49 mg, 3.02 µmol, 18.57% yield, 71.06% purity) as a white solid.

BCY7846:

To a solution of compound 14B (4 mg, 8.42e-1 µmol, 1 eq) and Monomer 6A (15.27 mg, 6.74 µmol, 8.0 eq) in DMF (1 mL) was added $CuSO_4 \cdot 5H_2O$ (0.8 M, 12.63 µL, 12 eq) and ascorbic acid (0.8 M, 84.22 µL, 80 eq). The mixture was degassed and purged with $N_2$ for 3 times, and then the mixture was stirred at 30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7846 (4.8 mg, 1.52e-1 µmol, 18.03% yield, 43.7% purity) as a white solid.

BCY7849:

To a solution of compound 14A (4 mg, 1.63 µmol, 1 eq) and Monomer 7A (29.25 mg, 13.01 µmol, 8 eq) in DMF (1 mL) was added $CuSO_4$ (0.8 M, 24.40 µL, 12 eq) and (2R)-2-[(1S)-1,2-dihydroxyethyl]-3,4-dihydroxy-2H-furan-5-one (0.8 M, 81.34 µL, 40 eq). The mixture was stirred at 30° C. for 1 hrs. LC-MS showed Reactant 1 was consumed completely. The reaction mixture was filtered and concentrated under reduced pressure to give a residue. The residue was purified by prep-HPLC (TFA condition) to give BCY7849 (8.5 mg, 4.72e-1 µmol, 29.03% yield, 63.6% purity) as a white solid.

BCY7850:

To a solution of compound 14B (4 mg, 8.42e-1 µmol, 1 eq) and Monomer 7A (15.14 mg, 6.74 µmol, 8 eq) in DMF (1 mL) was added $CuSO_4 \cdot 5H_2O$ (0.8 M, 12.63 µL, 12 eq) and ascorbic acid (0.8 M, 84.22 µL, 80 eq) under $N_2$ atmosphere. The mixture was stirred at 30° C. for 1 hr. LC-MS and HPLC showed Reactant 1 was consumed completely. The reaction mixture was filtered and concentrated under reduced pressure to give a residue. The residue was purified by prep-HPLC (TFA condition) to give BCY7850 (2.5 mg, 0.18 µmol, 21.41% yield, 99.09% purity) as a white solid.

BCY7853:

To a solution of compound 14A (4 mg, 1.63 µmol, 1 eq) and Monomer 8A (29.90 mg, 13.01 µmol, 8 eq) in DMF (1 mL) was added $CuSO_4$ (0.8 M, 24.40 µL, 12 eq) and (2R)-2-[(1S)-1, 2-dihydroxyethyl]-3, 4-dihydroxy-2H-furan-5-one (0.8 M, 81.34 µL, 40 eq). The mixture was stirred at 30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7853 (0.7 mg, 4.20e-2 µmol, 2.58% yield, 69.882% purity) as a white solid.

BCY7854:

To a solution of compound 14B (4 mg, 8.42e-1 µmol, 1 eq) and Monomer 8A (15.48 mg, 6.74 µmol, 8 eq) in DMF (1 mL) was added $CuSO_4$ (0.8 M, 12.63 µL, 12 eq) and ascorbic acid (0.8 M, 84.22 µL, 80 eq). The mixture was stirred at 30° C. for 1 hr under $N_2$ atmosphere. LC-MS showed Reactant 1 was consumed completely. The reaction mixture was filtered and concentrated under reduced pressure to give a residue. The residue was purified by prep-HPLC (TFA condition) to give BCY7854 (0.6 mg, 3.02e-2 µmol, 3.59% yield, 70.227% purity) as a white solid.

BCY7857:

To a solution of compound 14A (4 mg, 1.63 µmol, 1 eq) and Monomer 9A (22.27 mg, 9.76 µmol, 6 eq) in DMF (1 mL) was added CuI (6.20 mg, 32.54 µmol, 20 eq). The mixture was stirred at 25-30° C. for 1 hr under $N_2$ atmosphere. LC-MS and HPLC showed Reactant 1 was consumed completely. The reaction mixture was filtered and concentrated under reduced pressure to give a residue. The residue was purified by prep-HPLC (TFA condition) to give BCY7857 (1.3 mg, 8.28e-2 µmol, 5.09% yield, 73.80% purity) as a white solid.

BCY7858:

To a solution of compound 14B (4 mg, 8.42e-1 µmol, 1 eq) and Monomer 9A (15.37 mg, 6.74 µmol, 8 eq) in DMF (1 mL) was added $CuSO_4$ (0.8 M, 12.63 µL, 12 eq) and ascorbic acid (0.8 M, 84.22 µL, 80 eq) under $N_2$ atmosphere. The mixture was stirred at 30° C. for 1 hr. LC-MS and HPLC showed Reactant 1 was consumed completely. The reaction mixture was filtered and concentrated under reduced pressure to give a residue. The residue was purified by prep-HPLC (TFA condition) to give BCY7858 (2.0 mg, 1.19e-1 µmol, 14.13% yield, 82.55% purity) as a white solid.

BCY8945:

A mixture of compound 14B (105 mg, 22.11 µmol, 1 eq.), Monomer 11A (200 mg, 92.61 µmol, 4.2 eq.), and THPTA (9.6 mg, 1 eq.) was dissolved in $t$-BuOH/$H_2O$ (1:1, 6 mL, pre-degassed and purged with $N_2$ for 3 times), and then $CuSO_4$ (0.4 M, 55 µL, 1 eq.) and VcNa (0.4 M, 110 µL, 2 eq.) were added under $N_2$. The pH of this solution was adjusted to 8 by dropwise addition of 0.2 M $NH_4HCO_3$ (in 1:1 t-BuOH/$H_2O$), and the solution turned to light yellow. The reaction mixture was stirred at 25° C. for 2 hr under $N_2$ atmosphere. LC-MS showed compound 14B was consumed completely and one main peak with desired m/z (MS: 13378.66, observed m/z: 1030.6 ([M/13+H+]), 956.9 ([M/14+H+])) was detected. The reaction mixture was filtered and concentrated under reduced pressure to give a residue. The crude product was purified by prep-HPLC (TFA condition). BCY8945 (120 mg, 8.37 µmol, 37.86% yield, 91.11% purity) was obtained as a white solid.

BCY8947:

To a solution of compound 14A (150.0 mg, 61.0 µmol, 1.0 eq), Monomer 12A (543.8 mg, 245.2 µmol, 4.02 eq), and THPTA (26.5 mg, 61.0 µmol, 1.0 eq) was dissolved in t-BuOH/H2O (1:1, 6 mL, pre-degassed and purged with N2 for 3 times), and then CuSO4 (9.8 mg, 61.0 µmol, 1.0 eq) and VcNa (24.2 mg, 122.0 µmol, 2.0 eq) were added under N2. The pH of this solution was adjusted to 8 by dropwise addition of 0.2 M NH4HCO3 (in 1:1 t-BuOH/H2O), and the solution turned to light yellow. The reaction mixture was stirred at 40° C. for 16 hr under N2 atmosphere. LC-MS showed compound 14A was consumed completely and one main peak with desired m/z (calculated MW: 11329.12, observed m/z: 1133.6 ([M/10+H+]), 1029.2 ([M/11+H+]), m/z=1109 corresponds to extra compound 4) was detected. The reaction mixture was filtered and concentrated under reduced pressure to give a residue. The crude product was purified by prep-HPLC (TFA condition), resulting in BCY8947 (230 mg, 18.28 µmol, 29.96% yield, 95.82% purity) was obtained as a white solid. Furthermore, 200 mg was subjected to sodium salt exchange, and 150.3 mg (97.16% purity) was obtained.

BCY8960 (122.1 mg, 91.90% purity, 16.80% yield), BCY8959 (21.3 mg, 91.49% purity, 25.14% yield), BCY8966 (20.5 mg, 90.04% purity, 45.90% yield), BCY8963 (17.1 mg, 96.70% purity, 9.4% yield), BCY8964 (27.8 mg, 90.41% purity, 11.5% yield) and BCY9767 (6.1 mg, 89.40% purity, 6.12% yield) were synthesized in an analogous manner to that described above for BCY8945 using one of Compounds 14C, 14D, 14E, 14F, 14G or 14H;

monomer 4A; and CuSO$_4$,(2R)-2-[(1S)-1, 2-dihydroxyethyl]-3,4-dihydroxy-2H-furan-5-one and THPTA.

Production of CD137 Monoclonal Antibody Agonist:

The sequence of the CD137 monoclonal antibody agonist that was used for comparison to CD137 multimers in the experiments presented herein was disclosed in U.S. Pat. No. 7,288,638. The IgG4 isotype antibody was expressed using the ExpiCHO Expression System (Thermo Fisher Scientific) following transient transfection of the DNA expression construct. The antibody was purified by Protein A affinity chromatography and formulated in phosphate-buffered solution (PBS) pH 7.2. Purity analysis using HPLC-SEC (column GF-250, Agilent) indicated that the monomer rate of CD137 monoclonal antibody is approximately 95%. Binding activity analysis indicated that the CD137 monoclonal antibody with a concentration higher than 1 μg/ml can bind to CHO cells expressing CD137. Endotoxin analysis using the ToxinSensor™ Chromogenic LAL Endotoxin Assay Kit (Genscript) indicated that the CD137 monoclonal antibody preparation contained <7 EU/mg of endotoxin.

Biological Data

1. CD137 Biacore Experimental Description

Biacore experiments were performed to determine $k_a$ (M$^{-1}$ s$^{-1}$), $k_d$ (s$^{-1}$), $K_D$ (nM) values of monomeric peptides binding to human CD137 protein. Recombinant human CD137 (R&D systems) was resuspended in PBS and biotinylated using EZ-Link™ Sulfo-NHS-LC-LC-Biotin reagent (Thermo Fisher) as per the manufacturer's suggested protocol. The protein was desalted to remove uncoupled biotin using spin columns into PBS.

For analysis of peptide binding, a Biacore T200 or a Biacore 3000 instrument was used with a XanTec CMD500D chip. Streptavidin was immobilized on the chip using standard amine-coupling chemistry at 25° C. with HBS-N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μl/min. For capture of streptavidin, the protein was diluted to 0.2 mg/ml in 10 mM sodium acetate (pH 4.5) and captured by injecting 120 μl of onto the activated chip surface. Residual activated groups were blocked with a 7 min injection of 1 M ethanolamine (pH 8.5) and biotinylated CD137 captured to a level of 270-1500 RU. Buffer was changed to PBS/0.05% Tween 20 and a dilution series of the peptides was prepared in this buffer with a final DMSO concentration of 0.5%. The top peptide concentration was 500 nM with 6 further 2-fold or 3-fold dilutions. The SPR analysis was run at 25° C. at a flow rate of 90 μl/min with 60 seconds association and 900 seconds dissociation. After each cycle a regeneration step (10 μl of 10 mM glycine pH 2) was employed. Data were corrected for DMSO excluded volume effects as needed. All data were double-referenced for blank injections and reference surface using standard processing procedures and data processing and kinetic fitting were performed using Scrubber software, version 2.0c (BioLogic Software). Data were fitted using simple 1:1 binding model allowing for mass transport effects where appropriate.

Certain monomeric peptides were tested in this assay and the results are shown in Table 3:

TABLE 3

CD137 Biacore Assay Data with Monomeric Peptides

| Monomer Number | Kd (nM) |
|---|---|
| BCY3814 | 33.3 |
| BCY7740 | 88 |
| BCY7741 | 122 |
| BCY7742 | 855 |
| BCY7743 | 101 |
| BCY7744 | 92 |
| BCY7745 | 63.1 |
| BCY7746 | 260 |
| BCY7747 | 361 |
| BCY7748 | 264 |
| BCY8935 | NB |
| BCY8927 | 12.3 |
| BCY8928 | 11.4 |
| BCY8925 | NB |
| BCY8926 | NB |
| BCY8141 | 57.8 |
| BCY8095 | 0.685 |
| BCY8142 | 321 |
| BCY8096 | 26 |
| BCY8143 | 112 |
| BCY8144 | 66.7 |
| BCY8097 | 99.4 |

NB: No binding up to 5 μM

2. CD137 Promega Assay Experimental Description

CD137 binding multimers were evaluated for CD137 using a Reporter cell activity assay that uses NF-κB luciferase luminescence as a read-out of CD137 activation in Jurkat cells. Medium was prepared by thawing FBS and adding 1% FBS to RPMI-1640 (Promega kit CS196005). Samples were diluted at concentration expected to give the maximum fold induction and then titrated down in 1/3 dilution series or 1/10 dilution series in a sterile 96 well-plate. CD137 Jurkat cells were thawed in a water-bath and then 500 μl cells were added to 9.5 ml pre-warmed 1% FBS RPMI-1640 medium. 50 μl cells were added per well to white cell culture plates. 25 μl of samples were added as duplicate samples or 1% FBS RPMI-1640 alone as background control.

Cells were co-incubated together with agonists for 6 h at 37° C., 5% CO$_2$. After 6 h Bio-Glo™ was thawed and the assay developed at room-temperature. 75 ul Bio-Glo™ was added per well and incubated for 5-10 min. Luciferase signal was read on a Pherastar plate-reader using MARS program. Data was analysed by transforming the data to x=log (X), then plotting log (agonist) vs. response variable slope (4 parameters) to calculate EC$_{50}$ values.

Figure 2:
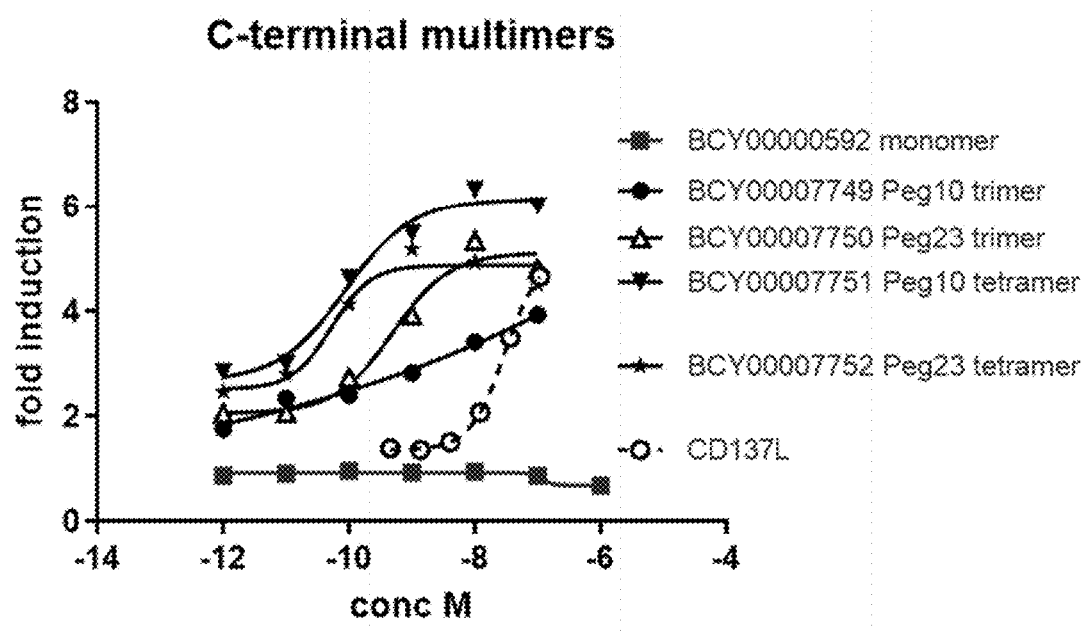
FIG. 2: Reporter cell activity assay data obtained for trimers BCY7749 and BCY7750 and tetramers BCY7751 and BCY7752 compared with monomer BCY592 and the CD137 ligand.
Figure 3:
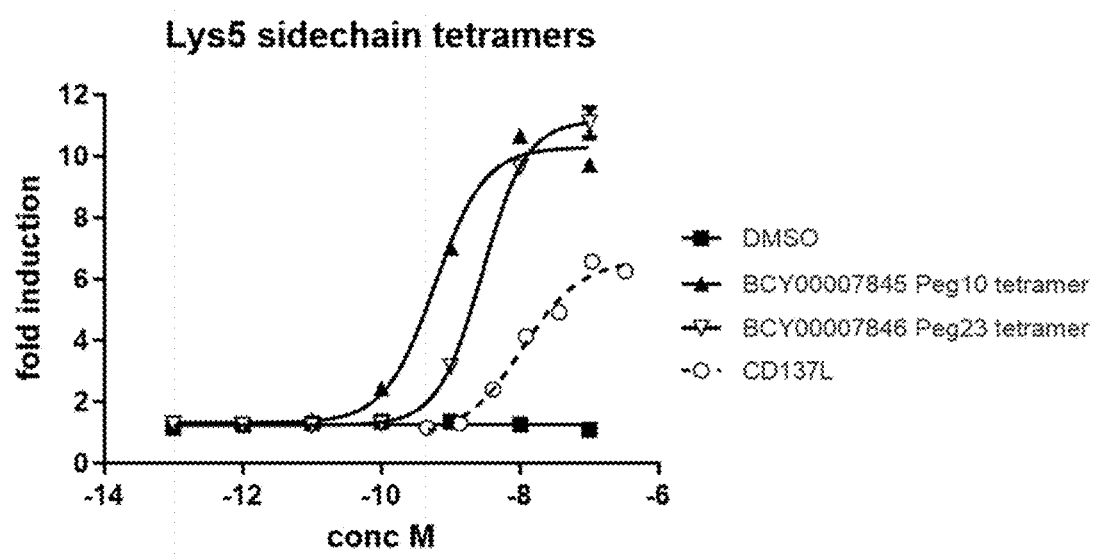
FIG. 3: Reporter cell activity assay data obtained for tetramers BCY7845 and BCY7846 compared with DMSO control and the CD137 ligand.

Data is presented in FIGS. 1 to 3 which shows that the multivalent CD137 bicyclic peptides exhibit a range of properties when compared to the natural ligand (CD137L) for activation of CD137. In FIG. 1, N and C-terminal conjugated trimers and tetramers are compared. A monomeric CD137 binding bicycle peptide (ACIEEGQYCFADPYMCA (SEQ ID NO: 56); BCY592) is included and has no detectable activity in the assay. In FIG. 2, activity for multimers with different PEG chain lengths are compared. Various attachment points for the multimers were explored and FIG. 3 shows the activation data for Lys5 conjugated tetramers as compared to CD137L. DMSO control is included to demonstrate that the inclusion of DMSO in the sample stocks has no influence on the observed activity. Table 4 details the average fold induction and fold improvement in EC50 for each multimer relative to CD137L.

TABLE 4A

CD137 Promega Assay Data with Multimeric Binding Peptides

| Multimer Number | Average Fold EC50 Improvement relative to CD137L* | Average Relative Fold Induction relative to CD137L** |
|---|---|---|
| BCY7750 | 16.13 | 0.90 |
| BCY7749 | 2.08 | 0.88 |
| BCY7827 | 10.86 | 0.76 |
| BCY7828 | 9.72 | 0.65 |
| BCY7831 | 0.56 | 1.01 |
| BCY7832 | 0.15 | 0.68 |
| BCY7835 | 0.50 | 1.04 |
| BCY7836 | 3.18 | 0.32 |
| BCY7839 | 188.19 | 0.56 |
| BCY7840 | 1.58 | 0.55 |
| BCY7843 | 47.73 | 0.68 |
| BCY7844 | 43.07 | 0.57 |
| BCY7847 | 2.91 | 0.59 |
| BCY7848 | 6.60 | 0.55 |
| BCY7851 | 1.43 | 0.64 |
| BCY7852 | 1.36 | 0.58 |
| BCY7855 | 0.66 | 1.12 |
| BCY7856 | 1.07 | 0.67 |
| BCY8102 | 41.27 | 0.91 |
| BCY8103 | 188.34 | 0.91 |
| BCY8106 | 1.26 | 0.94 |
| BCY8107 | 64.33 | 0.64 |
| BCY8145 | 5.93 | 0.95 |
| BCY8146 | 5.11 | 0.83 |
| BCY8151 | 213.05 | 0.49 |
| BCY7751 | 120.52 | 1.32 |
| BCY7752 | 177.8 | 1.18 |
| BCY7829 | 186.8 | 1.12 |
| BCY7830 | 31.31 | 1.48 |
| BCY7833 | 0.07 | 1.03 |
| BCY7837 | 28.99 | 0.97 |
| BCY7838 | 0.73 | 2.19 |
| BCY7841 | 306.76 | 1.14 |
| BCY7842 | 237.56 | 1.22 |
| BCY7845 | 17.78 | 1.54 |
| BCY7846 | 3.39 | 1.92 |
| BCY7849 | 4.91 | 1.50 |
| BCY7850 | 6.35 | 1.21 |
| BCY7853 | 3.46 | 1.02 |
| BCY7854 | 2.35 | 1.16 |
| BCY7857 | 6.66 | 0.86 |
| BCY7858 | 0.60 | 0.91 |
| BCY8104 | 103.27 | 1.65 |
| BCY8105 | 296.56 | 1.09 |
| BCY8108 | 34.03 | 0.79 |
| BCY8147 | 50.58 | 1.04 |
| BCY8148 | 18.71 | 1.20 |
| BCY8149 | 140.06 | 0.93 |
| BCY8150 | 4.14 | 0.77 |
| BCY8581 | — | <2 Fold induction over background at up to 1 μM |
| BCY8582 | — | <2 Fold induction over background at up to 1 μM |
| BCY8583 | 0.031 | 3.14 |
| BCY8584 | — | <2 Fold induction over background at up to 1 μM |
| BCY8937 | — | <2 Fold induction over background at up to 1 μM |

*Average EC50 for CD137L = 14.2 nM
**Average fold induction for CD137L = 4.0

Table 4B

CD137 Promega Assay Data with Multimeric Binding Peptides

| Multimer Number | Average Fold EC50 Improvement relative to BCY7845* | Average Relative Fold Induction relative to BCY7845** |
|---|---|---|
| BCY8948 | — | <2 Fold Induction over Background at concentrations up to 100 nM |
| BCY8957 | — | <2 Fold Induction over Background at concentrations up to 100 nM |
| BCY8958 | 0.96 | 0.39 |
| BCY8961 | — | <2 Fold Induction over Background at concentrations up to 100 nM |
| BCY8962 | — | <2 Fold Induction over Background at concentrations up to 100 nM |
| BCY8965 | — | <2 Fold Induction over Background at concentrations up to 100 nM |
| BCY9573 | 0.01 | 0.57 |
| BCY9595 | 0.03 | 0.52 |
| BCY9775 | 0.89 | 0.45 |
| BCY9776 | 0.13 | 0.87 |
| BCY10046 | 0.41 | 0.63 |
| BCY10047 | 0.52 | 0.53 |
| BCY8945 | 0.13 | 1.23 |
| BCY8946 | 5.22 | 0.41 |
| BCY8947 | 1.33 | 0.62 |
| BCY8959 | — | <2 Fold Induction over Background at concentrations up to 100 nM |
| BCY8960 | 0.41 | 0.68 |
| BCY8963 | 1.61 | 0.84 |
| BCY8964 | 2.37 | 1.13 |
| BCY8966 | 5.88 | 0.56 |
| BCY9113 | — | <2 Fold Induction over Background at concentrations up to 100 nM |
| BCY9767 | 0.02 | 0.74 |

*Average EC50 for BCY7845 = 0.57 nM
**Average fold induction for BCY7845 = 6.3
ND: Not determined 3. Plasma Stability Analysis Multimer stability in plasma was assessed in human, cyno, rat and mouse plasma as follows. Plasma Sources

TABLE 5

| Species / Matrix | Minimum No. of Individuals | Anticoagulant Used | Vendor | Cat# | Batch |
|---|---|---|---|---|---|
| CD-1 Mouse Plasma | 20 Male | EDTA-K2 | Bioreclamation IVT | MSEPLEDTA2-M | MSE261221 |

TABLE 5-continued

| Species / Matrix | Minimum No. of Individuals | Anticoagulant Used | Vendor | Cat# | Batch |
|---|---|---|---|---|---|
| SD Rat Plasma | 10 Male | EDTA-K2 | Bioreclamation IVT | RATPLEDTA2-M | RAT326207 |
| Cynomolgus Monkey Plasma | 10 Male | EDTA-K2 | Suzhou Research | CYNOMOLGUS MONKEY PLASMA | SZ20170317 |
| Human Plasma | 3 Male & 3 Female | EDTA-K2 | Bioreclamation IVT | HMPLEDTA2 | BRH1412539 |

Propantheline bromide was used as reference compound in this assay.

EXPERIMENTAL

The pooled frozen plasma was thawed in a water bath at 37° C. prior to experiment. Plasma was centrifuged at 4000 rpm for 5 min and the clots were removed if any. The pH was be adjusted to 7.4±0.1 if required. 1 mM intermediate solutions of test compounds was prepared with DMSO. For positive control Propantheline: a 1 mM intermediate solution was prepared by diluting 5 µL of the stock solution with 45 µL ultra pure water. 100 µM dosing solution was prepared by diluting 20 µL of the intermediate solution (1 mM) with 180 µL DMSO. For positive control Propantheline: 100 µM intermediate solution was prepared by diluting 20 µL of the stock solution with 180 µL 45% MeOH/$H_2O$. 196 µL of blank plasma was spiked with 4 µL of dosing solution (100 µM) to achieve 2 µM of the final concentration in duplicate and samples were Incubated at 37° C. in a water bath. At each time point (0, 1, 2, 4, 6 and 24 hr), 800 µL of stop solution (100 ng/mL tolbutamide Labetalol, Dexamethasone, propranolol, Diclofenac, Celecoxib in 100% MeOH) was added to precipitate protein and mixed thoroughly. Sample plates were centrifuged at 4,000 rpm for 10 min. An aliquot of supernatant (200 µL) was transferred from each well before submitting to LC-MS/MS analysis.

Data Analysis:

The % remaining of test compound after incubation in plasma was calculated using following equation:

% Remaining=100×(PAR at appointed incubation time/PAR at T0 time)

where PAR is the peak area ratio of analyte versus internal standard (IS)

The appointed incubation time points are T0 (0 hr), Tn (n=0, 1, 2, 4, 6, 24 hr)

Figure 4:
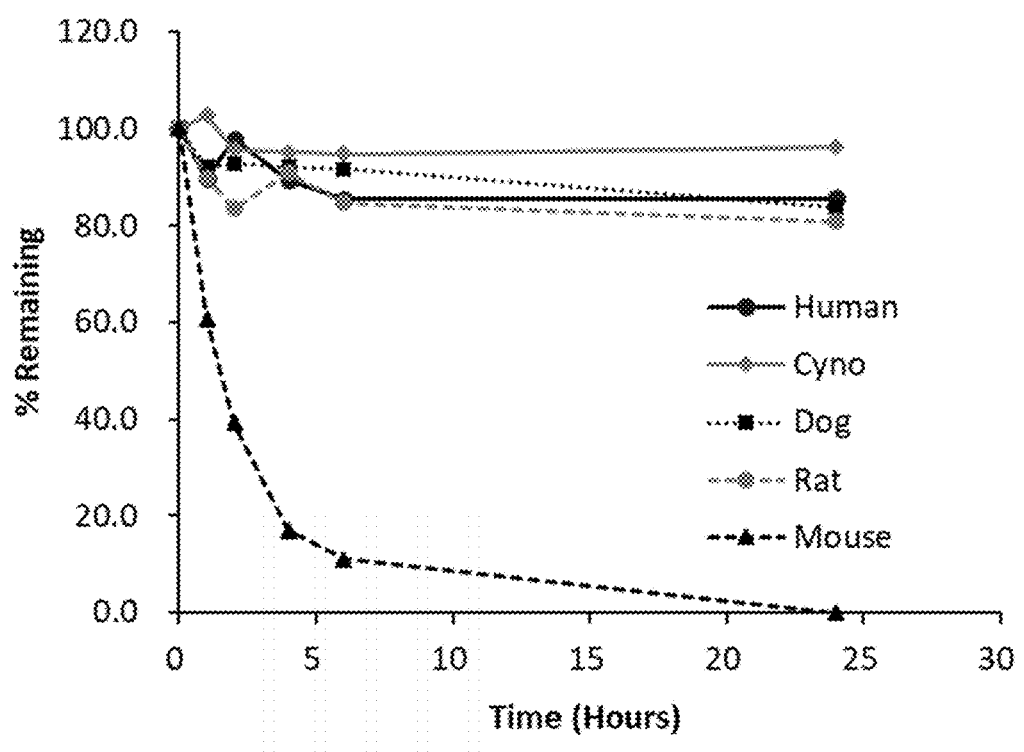
FIG. 4: Data showing plasma stability of BCY7829.

FIG. 4 shows the stability to human, cyno, rat and mouse plasma of BCY7829.

Figure 6:
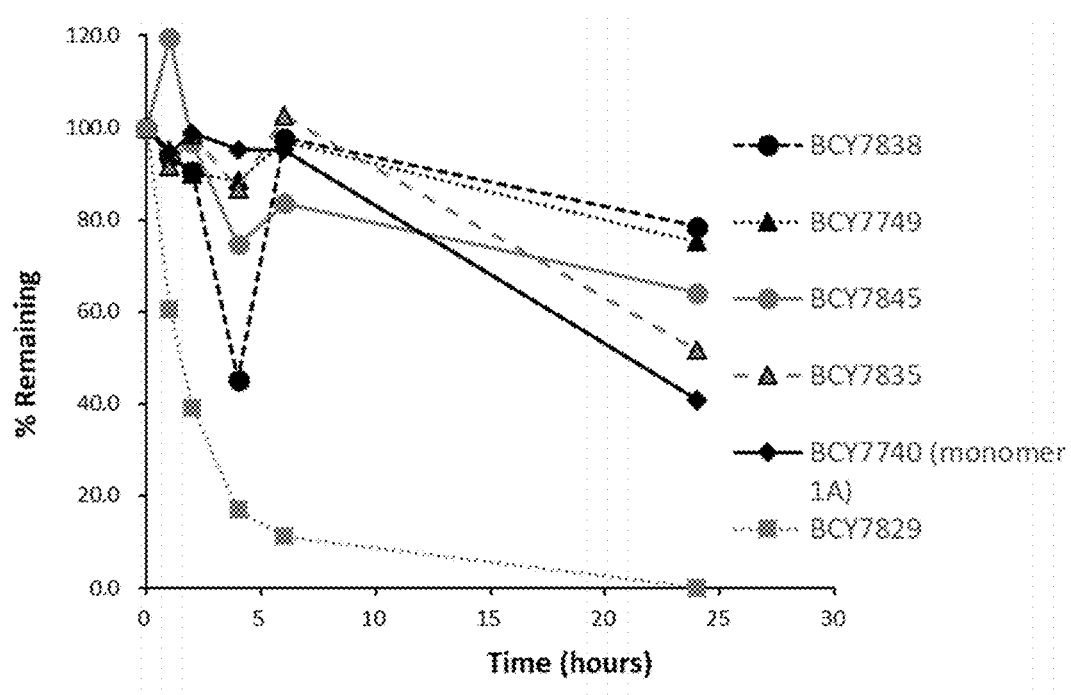
FIG. 6: Data showing stability of CD137 multimers in mouse plasma.

FIG. 6 shows the stability of several multimers and monomer 1A (BCY 7741) to mouse plasma.

4. In Vivo Efficacy Test of Bicycle Multimers Targeting CD137 in Treatment of MC38 Syngeneic Tumors in C57BL/6J B-h4-1BB Humanized Mice Experimental Methods and Procedures The MC38 murine colon carcinoma cell line was purchased from Shunran Shanghai Biological Technology Co., Ltd. The cells will be maintained in vitro as monolayer culture in Dulbecco's Modified Eagle's medium (DMEM) supplemented with 10% heat inactivated fetal calf serum, 100 U/mL penicillin and 100 µg/mL streptomycin at 37° C. in an atmosphere of 5% $CO_2$. The tumor cells will be routinely subcultured twice weekly by trypsin-EDTA treatment. Cells growing in an exponential growth phase will be harvested and counted for tumor inoculation. 6-8 week old female C57BL/6J B-h4-1BB humanized mice were subcutaneously injected (in the flank) with MC38 tumor cells ($5\times10^5$) with 0.1 mL PBS for tumor development. Tumor-bearing animals were randomly enrolled into six study groups when the mean tumor size reached approximately 113 $mm^3$ (Study 1) or 107 $mm^3$ (Study 2). The test and positive control articles were administrated to the tumor-bearing mice according to predetermined regimens as shown below.

Test articles were formulated in aqueous vehicle (25 mM Histidine, 10% sucrose pH=7) and administered intravenously or intraperitoneally. CD137 monoclonal antibody agonist was administered by intraperitoneal injection in 0.9% saline.

Tumor volume was measured three times a week in two dimensions using a caliper, and the volume was expressed in mm3 using the formula: V=0.5 a×b2 where a and b were the long and short diameters of the tumor, respectively. Results are represented by mean and the standard deviation (Mean±SD).

In study 2, mice were sacrificed 21 days after treatment initiation and tumors were harvested for T-cell analysis by flow cytometry. Tumor were cut into small pieces and filtered through a 70 micrometer filter. Lymphocytes were isolated using Histopaque 1083 and resuspended in RPMI 1640 supplemented with 10% fetal bovine serum. Lymphocytes were stained with a cell viability dye (Zombie NIR, Biolegend, #423106) and a panel of antibodies including anti-mouse CD45 (Biolegend, #103138), anti-mouse CD3 (Biolegend, #100328), anti-mouse CD4 (Biolegend, #100438), anti-mouse CD8 (Biolegend, #100759). Stained cells were analysed by Attune N×T Flow Cytometer. T-cell results are expressed as % of CD3+ cells among CD45+ cells. CD8+ T-cell results are expressed as % of CD8+ cells among CD45+CD3+ cells. CD4+ T-cell results are expressed as % of CD4+ cells among CD45+CD3+ cells. Results are represented by mean and the standard deviation (Mean±SD) and the individual values.

Statistical analysis: Data was analyzed using 2 way ANOVA or ordinary One-way ANOVA with Dunnett's test for multiple comparisons, and P<0.05 was considered to be statistically significant. Both statistical analysis and biological observations are taken into consideration. * $p<0.001$,  $p<0.01$, * $p<0.05$.

Experimental Design

TABLE 6

Dosing Regimen

| Study | No. Of Animals | Treatment | Dosages (mg/kg) | Dosing Route | Schedule |
|---|---|---|---|---|---|
| 1 | 5 | BCY7829 | 20 | i.v. | QAD × 6 |
| 1 | 5 | BCY7835 | 20 | i.v. | QAD × 6 |
| 1 | 5 | BCY7838 | 30 | i.v. | QAD × 6 |
| 1 | 5 | Anti-CD137 mAb Agonist | 3 | i.p. | BIW × 4 |
| 1 | 5 | Vehicle | — | i.v. | QAD × 6 |
| 2 | 5 | Vehicle | — | i.v. | QD × 20 |
| 2 | 5 | Anti-CD137 mAb Agonist | 3 | i.p. | BIW × 6 |
| 2 | 5 | BCY8945 | 30 | i.p. | QD × 20 |
| 2 | 5 | BCY8945 | 30 | s.c. | QD × 20 |
| 2 | 5 | BCY8947 | 30 | i.p. | QD × 20 |
| 2 | 5 | BCY7842 | 30 | i.p. | QD × 20 |

Notes:
Dosing volume was adjusted based on body weight (10 µL/g).
QAD refers to every other days,
BIW refers to twice per week,
QD refers to once a day.
i.v. refers to intravenous injection.
i.p. refers to intraperitoneal injection.
s.c. refers to subcutaneous injection.

Figure 7:
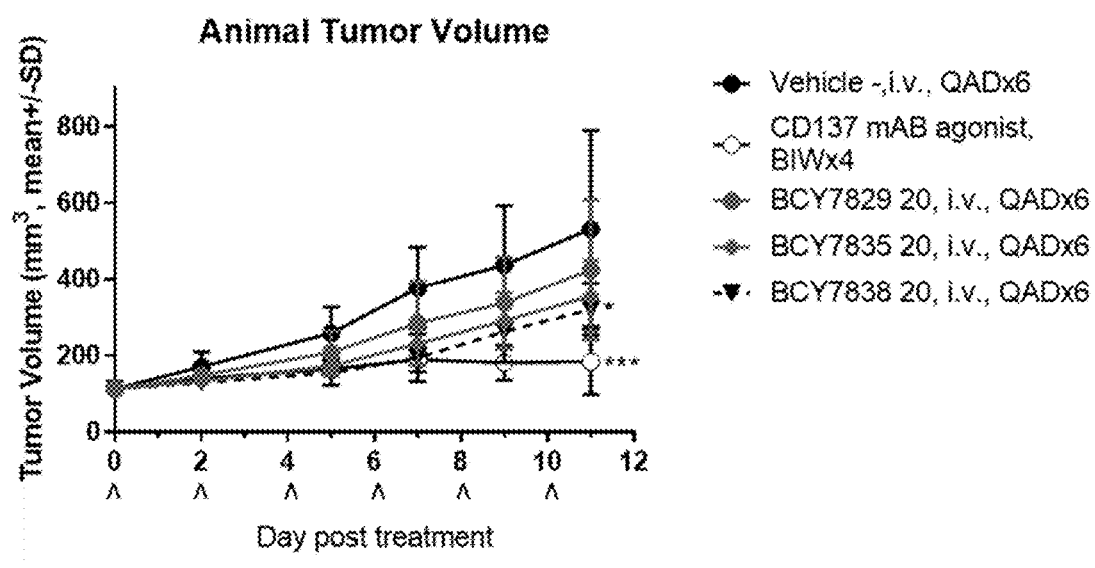
FIG. 7: Tumor volume trace after administering CD137 multimers to C57BL/6J B-h4-1BB humanized mice bearing MC38 syngeneic tumors. Data points represent group mean tumor volumes. Error bars represent standard deviation (SD).
Figure 8:
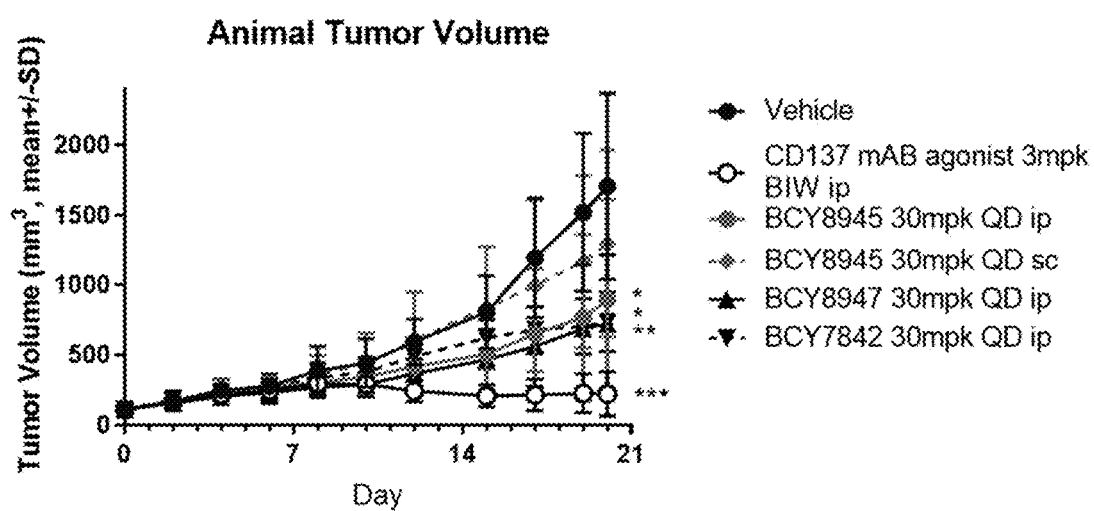
FIG. 8: Tumor volume trace after administering multimeric bicyclic peptides to C57BL/6J B-h4-1BB humanized mice bearing MC38 syngeneic tumors. Data points represent group mean tumor volumes. Error bars represent standard deviation (SD). * $p<0.001$, $p<0.01$, * $p<0.05$, 2 way ANOVA with Dunnett's test for multiple comparisons.
Figure 9:
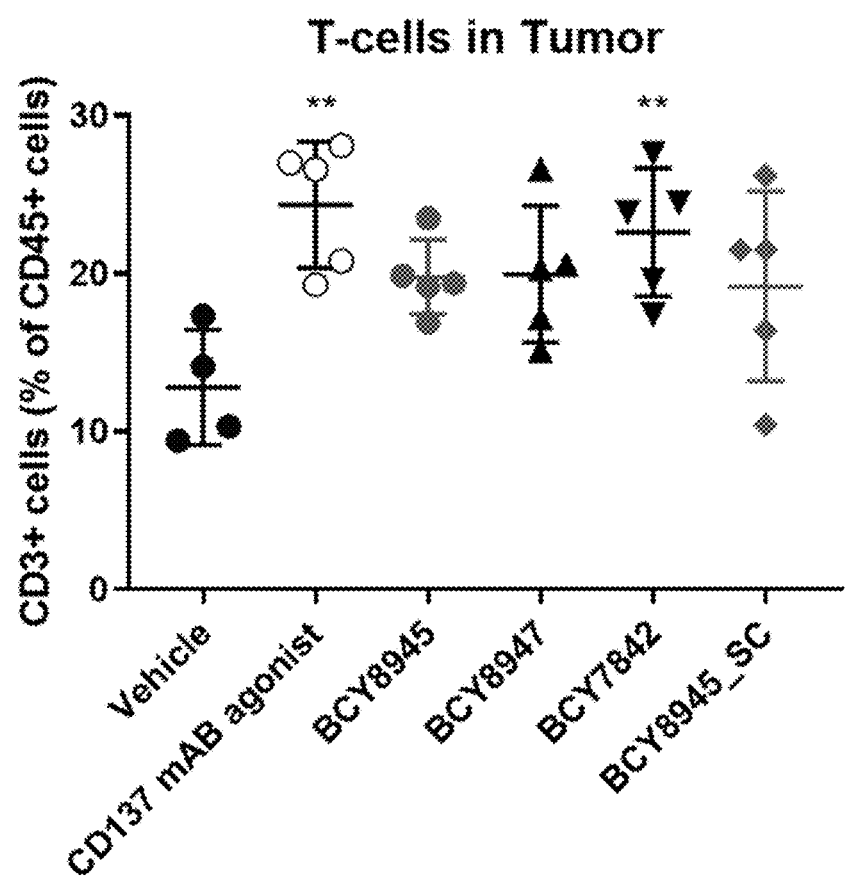
FIG. 9: Percentage of CD3+ cells among CD45+ cells in the tumor tissue after administering multimeric bicyclic peptides to C57BL/6J B-h4-1BB humanized mice bearing MC38 syngeneic tumors for a treatment period of 21 days. Data points represent cell population percentage from individual mice and line and error bars represent mean and standard deviation (SD). **$p<0.01$, one-way ANOVA with Dunnett's test for multiple comparisons.
Figure 10:
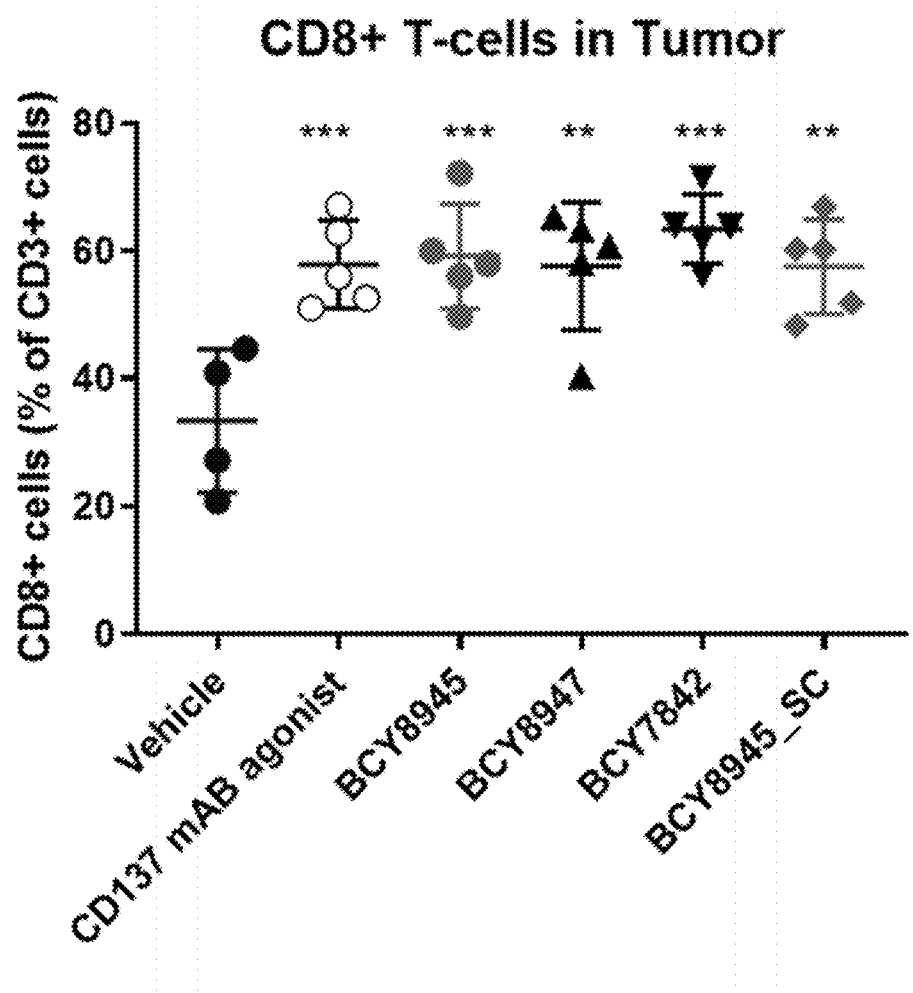
FIG. 10: Percentage of CD8+ cells among CD45+CD3+ cells in the tumor tissue after administering multimeric bicyclic peptides to C57BL/6J B-h4-1BB humanized mice bearing MC38 syngeneic tumors for a treatment period of 21 days. Data points represent cell population percentage from individual mice and line and error bars represent mean and standard deviation (SD). * $p<0.001$, $p<0.01$, one-way ANOVA with Dunnett's test for multiple comparisons.
Figure 11:
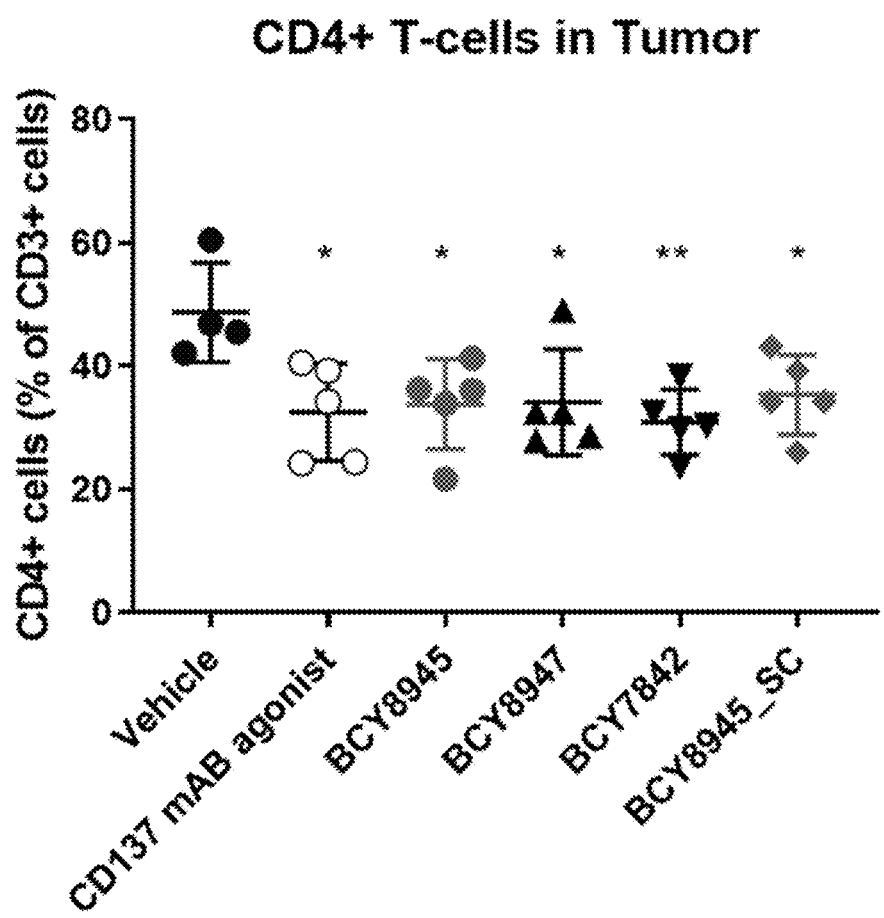
FIG. 11: Percentage of CD4+ cells among CD45+CD3+ cells in the tumor tissue after administering multimeric bicyclic peptides to C57BL/6J B-h4-1BB humanized mice bearing MC38 syngeneic tumors for a treatment period of 21 days. Data points represent cell population percentage from individual mice and line and error bars represent mean and standard deviation (SD). **$p<0.01$, * $p<0.05$, one-way ANOVA with Dunnett's test for multiple comparisons.

The results from Study 1 are shown in FIG. 7 wherein it can be seen that the multimeric bicyclic peptides elicit a range of anti-tumor activities as compared to the CD137 monoclonal antibody agonist. The results from Study 2 are shown in FIG. 8 wherein it can be seen that the multimeric bicyclic peptides elicit a range of anti-tumor activities as compared to the CD137 monoclonal antibody agonist. The results of Tumor T-cell analysis from Study 2 are shown in FIG. 9 wherein it can be seen that the multimeric bicyclic peptides elicit a range of increase in T-cell percentage in the tumor tissue as compared to the CD137 monoclonal antibody agonist. The results of CD8+ Tumor T-cell analysis from Study 2 are shown in FIG. 10 wherein it can be seen that the multimeric bicyclic peptides elicit a range of increase in CD8+ T-cell percentage in the tumor tissue as compared to the CD137 monoclonal antibody agonist. The results of CD4+ Tumor T-cell analysis from Study 2 are shown in FIG. 11 wherein it can be seen that the multimeric bicyclic peptides elicit a range of decease in T-cell percentage in the tumor tissue as compared to the CD137 monoclonal antibody agonist that has previously been shown to elicit a CD137 dependent anti-tumour activity.

5. Pharmacokinetics of Bicycle Multimers in CD-1 Mice

Male CD-1 mice were dosed with 5 mg/kg of each Bicycle multimer formulated in 25 mM Histidine HCl, 10% sucrose pH 7 via tail vein injection. Serial bleeding (about 80 µL blood/time point) was performed via submadibular or saphenous vein at each time point. All blood samples were immediately transferred into prechilled microcentrifuge tubes containing 2 µL K2-EDTA (0.5M) as anti-coagulant and placed on wet ice. Blood samples were immediately processed for plasma by centrifugation at approximately 4° C., 3000 g. The precipitant including internal standard was immediately added into the plasma, mixed well and centrifuged at 12,000 rpm, 4° C. for 10 minutes. The supernatant was transferred into pre-labeled polypropylene microcentrifuge tubes, and then quick-frozen over dry ice. The samples were stored at 70° C. or below as needed until analysis. 7.5 µL of the supernatant samples were directly injected for LC-MS/MS analysis using an Orbitrap Q Exactive in positive ion mode to determine the concentrations of Bicycle multimer. Plasma concentration versus time data were analyzed by non-compartmental approaches using the Phoenix WinNonlin 6.3 software program. $C_0$, Cl, $Vd_{ss}$, $T_{1/2}$, $AUC_{(0-last)}$, $AUC_{(0-inf)}$, $MRT_{(0-last)}$, $MRT_{(0-inf)}$ and graphs of plasma concentration versus time profile were reported.

Figure 5:
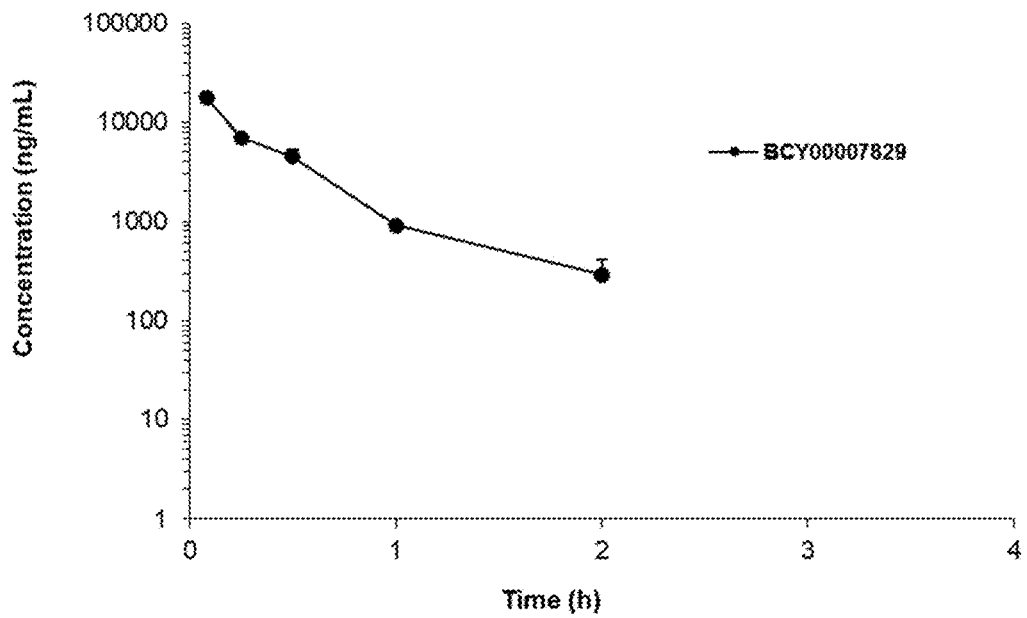
FIG. 5: (A): Data showing mean plasma concentration of BCY7829 after IV Dosing 5 mg/kg (6.35 mg/kg measured) in CD-1 mice; (B): Data showing mean plasma concentration of BCY7835 and BCY7838 after IV Dosing in CD-1 mice.
Figure 5:
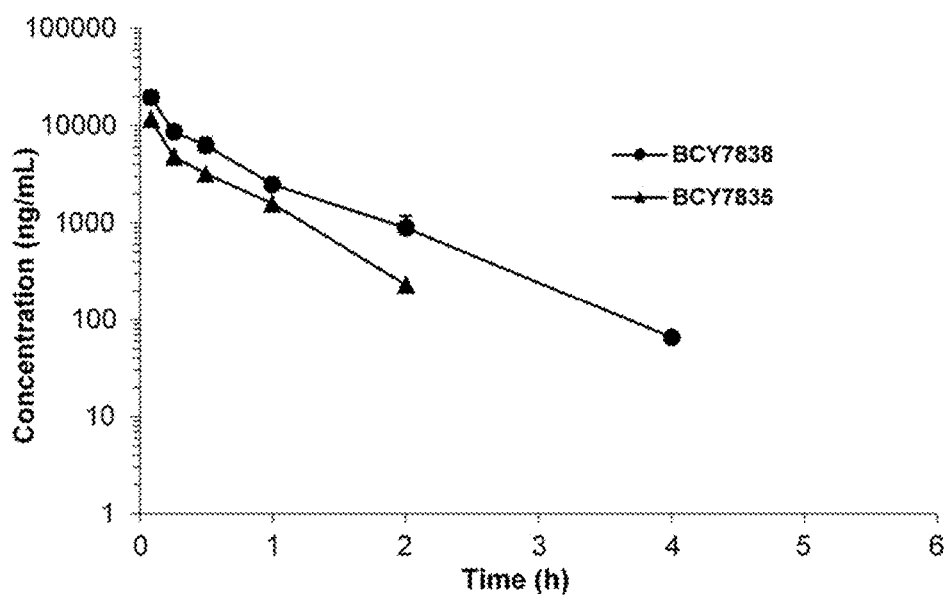

The results of the plasma concentration analysis in male CD-1 mice is shown in FIGS. 5A and 5B where it can be seen that the pharmacokinetic data show that the multimeric bicycle conjugates (in particular BCY7829, BCY7835 and BCY7838) retain the property of rapid systemic elimination characteristic of monomeric bicyclic peptides and bicyclic peptide drug conjugates (BDCs).

6. Ex Vivo Human Tumour Cell Kill Assay

Two frozen, dissociated melanoma patient tumour samples were purchased from Folio Conversant. Cells were thawed quickly at 37° C. and pipetted into 10 mL of Wash Medium [DMEM/F12+1× Penicillin/Streptomycin+50 µg/mL Gentamycin+100 µg/mL G418+100 µg/mL Hygromycin+1× Insulin-Transferrin-Selenium (ITS)+10 mM HEPES] with 1 mg/mL DNaseI added fresh. Cell counts were performed using a haemocytometer and a 1:2 dilution with 0.04% Trypan blue. Cells were spun down and resuspended in Growth Medium [EmbryoMax DMEM+10% heat-inactivated FBS+1× Penicillin/Streptomycin+50 µg/mL Gentamycin+1× GlutaMAX+1 mM Sodium pyruvate+1×ITS+0.4% BSA+4.5 g/L glucose+2.3 g/L sodium bicarbonate+10 mM HEPES+10 ng/mL basic fibroblast growth factor (bFGF)+20 ng/mL epidermal growth factor (EGF)] at $5 \times 10^5$ cells/mL. Cells were magnetized as described in the N3D Biosciences manufacturer's protocol. Briefly, NanoShuttle (NS) is added at 1 µL to $1 \times 10^4$ cells and mixed in by pipetting. Cells and NS are spun down at 100×g for 5 minutes, mixed by pipetting, and spun down again until the cell pellet acquires an even brown colour—approximately 3 to 5 cycles of spinning and mixing. Cells were then added to a cell-repellent 96-well plate at 50,000 cells/well in 100 µL of Growth Medium—one aliquot of 50,000 cells were reserved for a Day 0 flow cytometry panel. CD137 multimers (BCY7838, BCY7839 and BCY7842) and control compounds were added in 100 µL of 2× final concentration also in Growth Medium to the plated cells. The cell-repellent dish was then placed on top of the magnetic spheroid plate and incubated at 37° C. for 48 hours. At the end of 48 hours, cells were harvested, stained with the appropriate flow cytometry antibodies and a fixable viability stain (BD), and fixed in 2% paraformaldehyde before being run on the BD FACS Celesta. Data analysis was performed using FlowJo, Microsoft Excel, and GraphPad Prism software. Flow cytometry panels used in this experiment analysed the number of lymphocytes and tumour cells present on Days 0 and 2. Tumour cell killing was determined by the decrease in the number of CD45 negative cells in the treated wells versus the untreated control (FIG. 12)—significance was calculated using a 2-way ANOVA.

The data presented in FIG. 12 demonstrates significant tumour cell death in response to CD137 multimer treatment (BCY7838, BCY7839 and BCY7842) in one melanoma patient sample, but not the other (FIG. 12A). Though cell numbers changed from Day 0 to Day 2 (data not shown), there was no significant difference between treatments on lymphocyte numbers (FIG. 12B).

7. CD137 Reporter Cell Activity Washout Assay

Jurkat cells engineered to overexpress CD137 and express a luciferase gene under the NF-κB promoter were purchased from Promega. The reporter cells were incubated with 10 nM of CD137 agonists for the indicated times at 37° C. in RPMI1640 media with 1% FBS. After either 30, 60, or 120 minutes, cells were washed in an excess of culture media and resuspended in 75 μL of fresh media. A no washout condition was also included. All washout conditions were performed in duplicate. Cells then continued to incubate for a total of 6 hours (an additional 5.5, 5, or 4 hours respective to exposure times). After incubation, 75 μL of Bio-Glo reagent (Promega) was added to each well and allowed to equilibrate for 10 minutes at room temperature. Luminescence was read on the Clariostar plate reader (BMG LabTech). Fold induction was calculated by dividing the luminescence signal by background wells (reporter cells with no agonist added). The percent of the maximum fold induction was calculated by dividing the fold induction of the washout time by the fold induction of the no washout condition and multiplying by 100. Data was graphed in Prism and is displayed as a bar graph of the means or replicates with standard deviation error bars.

Figure 13:
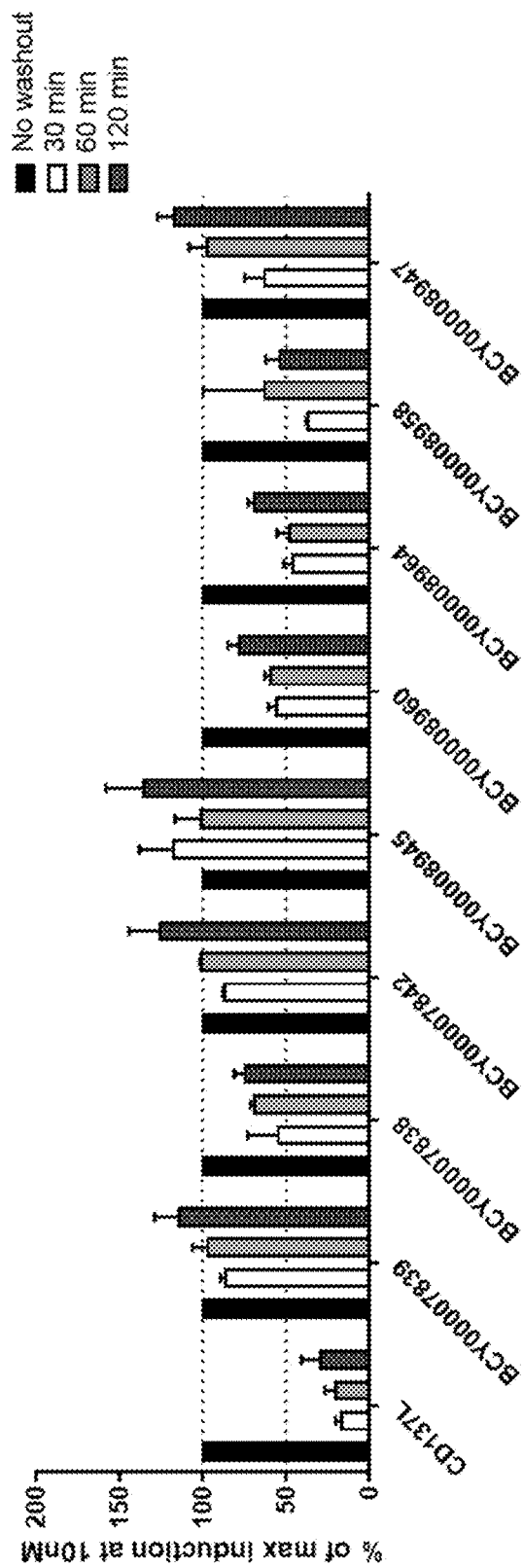
FIG. 13: CD137 multimers maintain activity after washout. CD137 reporter cells are exposed to compound for 30, 60, or 120 minutes prior to washout of the compound and activity is measured 5.5, 5, or 4 hours later, respectively. In the 'no washout' conditions, cells are exposed to the compound for the full 6 hour incubation.

The data presented in FIG. 13 demonstrates that CD137 multimers (BCY7838, BCY7839 and BCY7842) maintain cell activity after washout consistent with high avidity to the trimeric CD137 receptor complex.

8. T-Cell Cytokine Release Assay

Healthy human buffy coat was purchased from the Sylvan N. Goldman Oklahoma Blood Institute and shipped fresh. Peripheral blood mononuclear cells (PBMCs) were isolated by Ficoll density gradient centrifugation. Red blood cells were lysed with ACK (Ammonium-Chloride-Potassium) lysis buffer. Pan T-cells were then isolated from total PBMCs using negative magnetic bead selection (Miltenyi MACS human Pan-T cell isolation kit). Pan T-cells were then plated on anti-CD3 coated 96-well plates (0.5 μg/mL) in culture media (RPMI1640 with 10% FBS) plus or minus compounds. Supernatant from cultures was collected after 24 and 48 hours. Cytokine [i.e., interleukin-2 (IL-2), interferon gamma (IFNγ)] release in supernatant was measured by HTRF assay (CisBio) according to the kit's instructions. HTRF assay plates were read on a Clariostar plate reader (BMG Labtech) at 665 nm and 620 nm. Data was analyzed and extrapolated to a standard curve according to the HTRF kit instruction in Prism and Excel. Cytokine release fold change was calculated by dividing the pg/mL of cytokine detected by background cytokine released (CD3 stimulation alone). Data was graphed in Prism as the mean of replicates with standard deviation error bars.

Figure 14:
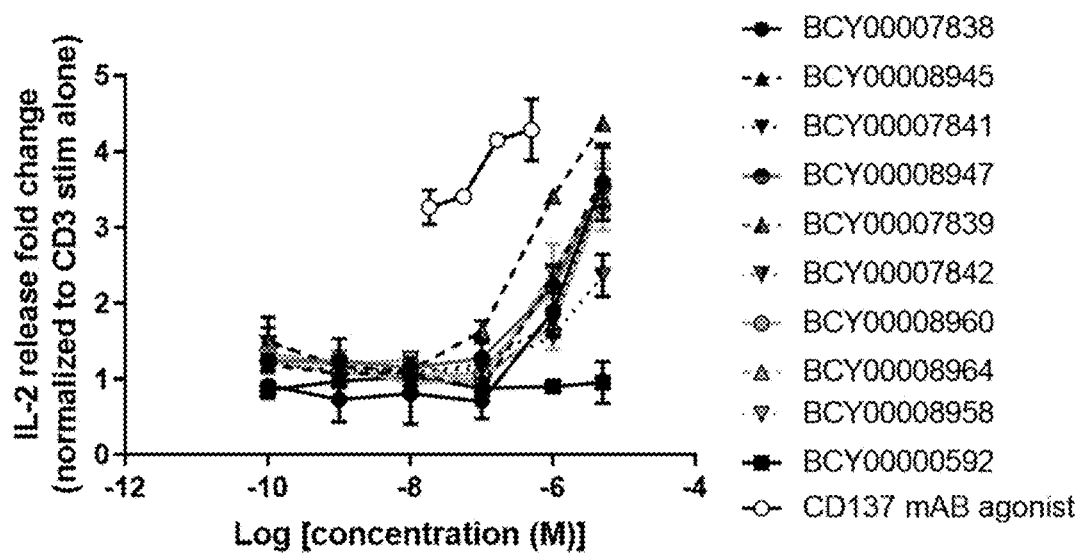
FIG. 14: CD137 multimers lead to increased cytokine secretion in a primary T cell assay. CD137 expression is induced in T cells (isolated from human PBMCs) using anti-CD3 antibody. T cells are then treated with CD137 multimers, CD137 monomer (negative control), or a CD137 monoclonal antibody agonist for 48 hours and IL-2 levels (A) and IFNγ (B) were measured in the supernatant using a HTRF assay.
Figure 14:
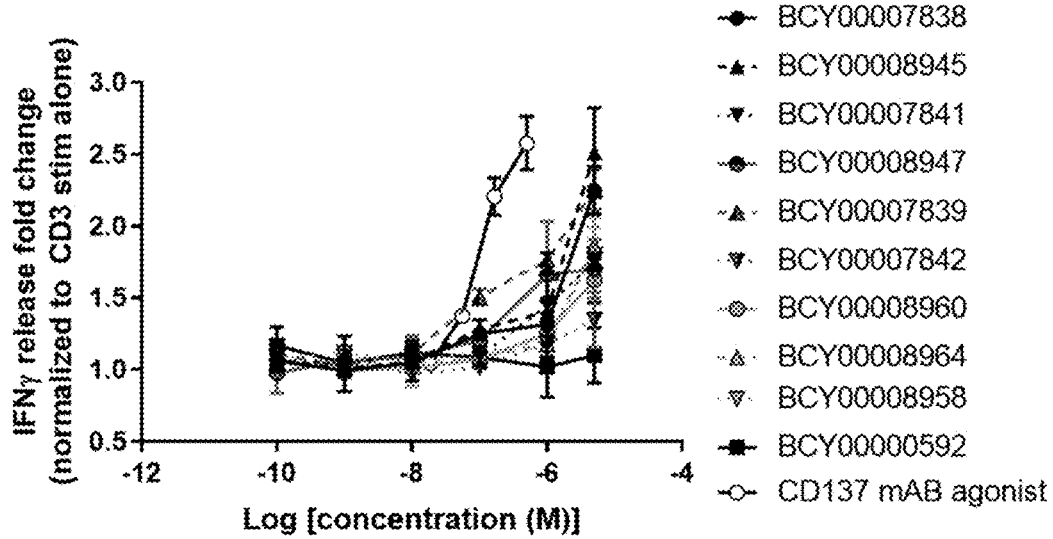
Figure 15:
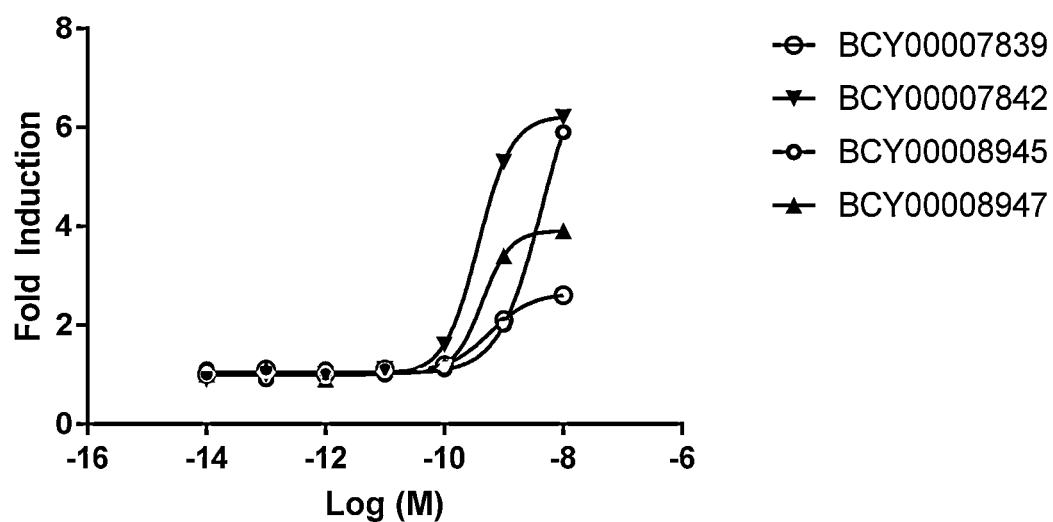
FIG. 15: Reporter cell activity assay data obtained for BCY7839, BCY7842, BCY8945 and BCY8947.

The data presented in FIG. 14 demonstrates that T-cells secrete pro-inflammatory cytokines in response to CD137 multimers BCY7838, BCY8945, BCY7841, BCY8947, BCY7839, BCY7842, BCY8960, BCY8964 and BCY8958 but not with monomer control BCY0592.

The invention claimed is:

1. A multimeric binding complex comprising at least two bicyclic peptide ligands, wherein said bicyclic peptide ligands may be the same or different, each of which comprises a polypeptide comprising at least three reactive groups, separated by at least two loop sequences, and a molecular scaffold which forms covalent bonds with the reactive groups of the polypeptide, such that at least two polypeptide loops are formed on the molecular scaffold, wherein the multimeric binding complex comprises a compound of formula (I):

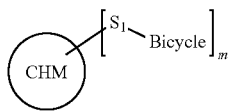
(I)

wherein:
CHM represents a central hinge moiety;
$S_1$ represents a spacer group;
Bicycle represents the bicyclic peptide ligand; and
m represents an integer selected from 2 to 10;

wherein each of said at least two bicyclic peptide ligands is specific for CD137 and independently comprises an amino acid sequence selected from:

$C_i$IEEGQYC$_{ii}$YRDMYMC$_{iii}$; (SEQ ID NO: 1)

$C_i$IEEGQYC$_{ii}$YADPYMC$_{iii}$; (SEQ ID NO: 2)

$C_i$IEEGQYC$_{ii}$YADPYYC$_{iii}$; (SEQ ID NO: 3)

$C_i$IEEGQYC$_{ii}$YSDPYYC$_{iii}$; (SEQ ID NO: 4)

$C_i$IEEGQYC$_{ii}$FADPYMC$_{iii}$; (SEQ ID NO: 5)

$C_i$IEEGQYC$_{ii}$YADHQLC$_{iii}$; (SEQ ID NO: 6)

$C_i$IEEGQYC$_{ii}$HADPYYC$_{iii}$; (SEQ ID NO: 7)

$C_i$IEEGQYC$_{ii}$HADPYFC$_{iii}$; (SEQ ID NO: 8)

$C_i$IEEGQYC$_{ii}$YADHYMC$_{iii}$; (SEQ ID NO: 9)

$C_i$IEEGQYC$_{ii}$YADPYLC$_{iii}$; (SEQ ID NO: 10)

$C_i$IEEGQYC$_{ii}$YSDPYLC$_{iii}$; (SEQ ID NO: 11)

$C_i$IEEGQYC$_{ii}$FADPYLC$_{iii}$; (SEQ ID NO: 12)

$C_i$IEEGQYC$_{ii}$HADPYMC$_{iii}$; (SEQ ID NO: 13)

$C_i$IEEGQYC$_{ii}$HADPQMC$_{iii}$; (SEQ ID NO: 14)

$C_i$DIGPPYC$_{ii}$YRDMYMC$_{iii}$; (SEQ ID NO: 15)

$C_i$DIGPPYC$_{ii}$YADPYMC$_{iii}$; (SEQ ID NO: 16)

$C_i$DEWGLFC$_{ii}$IPHSDC$_{iii}$; (SEQ ID NO: 17)

$C_i$DEWGLYC$_{ii}$FAHPDC$_{iii}$; (SEQ ID NO: 18)

$C_i$EPGPFC$_{ii}$YADPYMC$_{iii}$; (SEQ ID NO: 19)

$C_i$IEEGQYC$_{ii}$FADPY(Nle)C$_{iii}$; (SEQ ID NO: 23)

$C_i$IKEGQYC$_{ii}$FADPY(Nle)C$_{iii}$; (SEQ ID NO: 24)

$C_i$IEKGQYC$_{ii}$FADPY(Nle)C$_{iii}$; (SEQ ID NO: 25)

$C_i$IEE(D-K)QYC$_{ii}$FADPY(Nle)C$_{iii}$; (SEQ ID NO: 26)

$C_i$IEEGKYC$_{ii}$FADPY(Nle)C$_{iii}$; (SEQ ID NO: 27)

$C_i$IEEGQYC$_{ii}$KADPY(Nle)C$_{iii}$; (SEQ ID NO: 28)

$C_i$IEEGQYC$_{ii}$FADKY(Nle)C$_{iii}$; (SEQ ID NO: 29)

$C_i$IEEGQYC$_{ii}$FADPYKC$_{iii}$; (SEQ ID NO: 30)

A-$C_i$IEEGQYC$_{ii}$FADPY(Nle)C$_{iii}$-A; (SEQ ID NO: 31)

Ac-A-$C_i$IEEGQYC$_{ii}$FADPY(Nle)C$_{iii}$-Dap; (SEQ ID NO: 32)

Ac-A-$C_i$IKEGQYC$_{ii}$FADPY(Nle)C$_{iii}$-A; (SEQ ID NO: 33)

Ac-A-$C_i$IEKGQYC$_{ii}$FADPY(Nle)C$_{iii}$-A; (SEQ ID NO: 34)

Ac-A-$C_i$IEE(D-K)QYC$_{ii}$FADPY(Nle)C$_{iii}$-A; (SEQ ID NO: 35)

Ac-A-$C_i$IEEGKYC$_{ii}$FADPY(Nle)C$_{iii}$-A; (SEQ ID NO: 36)

Ac-A-$C_i$IEEGQYC$_{ii}$KADPY(Nle)C$_{iii}$-A; (SEQ ID NO: 37)

Ac-A-$C_i$IEEGQYC$_{ii}$FADKY(Nle)C$_{iii}$-A; (SEQ ID NO: 38)

Ac-A-$C_i$IEEGQYC$_{ii}$FADPYKC$_{iii}$-A; (SEQ ID NO: 39)

(PYA)-A-$C_i$IEEGQYC$_{ii}$FADPY(Nle)C$_{iii}$-A; (SEQ ID NO: 40)

Ac-A-$C_i$IEEGQYC$_{ii}$FADPY(Nle)C$_{iii}$-Dap(PYA); (SEQ ID NO: 41)

Ac-A-$C_i$IK(PYA)EGQYC$_{ii}$FADPY(Nle)C$_{iii}$-A; (SEQ ID NO: 42)

Ac-A-$C_i$IEK(PYA)GQYC$_{ii}$FADPY(Nle)C$_{iii}$-A; (SEQ ID NO: 43)

Ac-A-$C_i$IEE(D-K)(PYA)QYC$_{ii}$FADPY(Nle)C$_{iii}$-A; (SEQ ID NO: 44)

Ac-A-$C_i$IEEGK(PYA)YC$_{ii}$FADPY(Nle)C$_{iii}$-A; (SEQ ID NO: 45)

Ac-A-$C_i$IEEGQYC$_{ii}$K(PYA)ADPY(Nle)C$_{iii}$-A; (SEQ ID NO: 46)

Ac-A-$C_i$IEEGQYC$_{ii}$FADK(PYA)Y(Nle)C$_{iii}$-A; (SEQ ID NO: 47)

Ac-A-$C_i$IEEGQYC$_{ii}$FADPYK(PYA)C$_{iii}$-A; (SEQ ID NO: 48)

(BCN)-A-$C_i$IEEGQYC$_{ii}$FADPY(Nle)C$_{iii}$-A; (SEQ ID NO: 49)

Ac-A-$C_i$IK(BCN)EGQYC$_{ii}$FADPY(Nle)C$_{iii}$-A; (SEQ ID NO: 50)

Ac-A-$C_i$IEK(BCN)GQYC$_{ii}$FADPY(Nle)C$_{iii}$-A; (SEQ ID NO: 51)

Ac-A-$C_i$IEE[(D-K)(BCN)]QYC$_{ii}$FADPY(Nle)C$_{iii}$-A; (SEQ ID NO: 52)

Ac-A-$C_i$IEEGK(BCN)YC$_{ii}$FADPY(Nle)C$_{iii}$-A; (SEQ ID NO: 53)

Ac-A-$C_i$IEEGQYC$_{ii}$K(BCN)ADPY(Nle)C$_{iii}$-A; (SEQ ID NO: 54)

Ac-A-$C_i$IEEGQYC$_{ii}$FADPYK(BCN)C$_{iii}$-A; (SEQ ID NO: 55)

ACIEEGQYCFADPYMCA; (SEQ ID NO: 56)

A-$C_i$IEEGQYC$_{ii}$F[D-A]DPY[Nle]C$_{iii}$-A; (SEQ ID NO: 58)

Ac-$C_i$[tBuAla]PK[D-A]PYC$_{ii}$FADPY[Nle]C$_{iii}$-A; (SEQ ID NO: 59)

Ac-$C_i$[tBuAla]PE[D-K]PYC$_{ii}$FADPY[Nle]C$_{iii}$-A; (SEQ ID NO: 60)

Ac-A-$C_i$IE[D-K]GQYC$_{ii}$F[D-A]DPY[Nle]C$_{iii}$-A; (SEQ ID NO: 61)

Ac-A-$C_i$IE[D-K]GQYC$_{ii}$F[D-A]DPY[Nle]C$_{iii}$-A; (SEQ ID NO: 62)

[Ac]-[D-A]-[D-$C_i$][D-I][D-E][D-E]K[D-Q][D-Y][D-$C_{ii}$]D-F][D-A][D-D][D-P][D-Y][D-Nle][D-$C_{iii}$]-[D-A]; (SEQ ID NO: 63)

(PYA)-A-$C_i$IEEGQYC$_{ii}$F[D-A]DPY[Nle]C$_{iii}$-A; (SEQ ID NO: 64)

Ac-$C_i$[tBuAla]PK(PYA)[D-A]PYC$_{ii}$FADPY[Nle]C$_{iii}$-A; (SEQ ID NO: 65)

Ac-$C_i$[tBuAla]PE[D-K(PYA)]PYC$_{ii}$FADPY[Nle]C$_{iii}$-A; (SEQ ID NO: 66)

Ac-A-$C_i$IE[D-K(PYA)]GQYC$_{ii}$F[D-A]DPY[Nle]C$_{iii}$-A; (SEQ ID NO: 67)

Ac-A-$C_i$IE[K(PYA)]GQYC$_{ii}$F[D-A]DPY[Nle]C$_{iii}$-A; (SEQ ID NO: 68)
and

[Ac]-[D-A]-[D-$C_i$][D-I][D-E][D-E][K(P YA)][D-Q][D-Y][D-$C_{ii}$][D-F][D-A][D-D][D-P][D-Y][D-Nle][D-$C_{iii}$]-[D-A], (SEQ ID NO: 69)

wherein $C_i$, $C_{ii}$ and $C_{iii}$ represent, respectively, first, second, and third cysteine residues, Ac represents an N-terminal acetyl group, Dap represents diaminopropionic acid, tBuAla represents tert-butyl-alanine, Nle represents norleucine, PYA represents pent-4-ynoyl, and BCN represents:

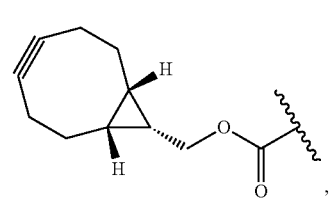 [SMILES: *C(=O)OC[C@@H]1[C@@H]2CCC#CCC[C@@H]21]

2. The multimeric binding complex of claim 1, wherein the spacer group is $S_1A$:

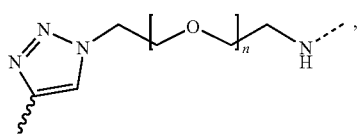

n = 5, 10, or 23 wherein:
"-----" represents a point of attachment to the central hinge moiety (CHM); and
"∼∼∼" represents a point of attachment to the Bicycle.

3. The multimeric binding complex of claim 1, wherein the spacer group is $S_1B$:

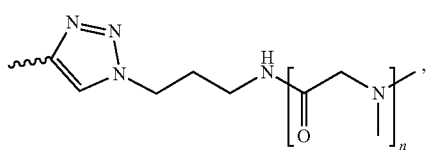

n = 5 or 10 wherein:
"-----" represents a point of attachment to the central hinge moiety (CHM); and
"∼∼∼" represents a point of attachment to the Bicycle.

4. The multimeric binding complex of claim 1, wherein the spacer group is $S_1C$:

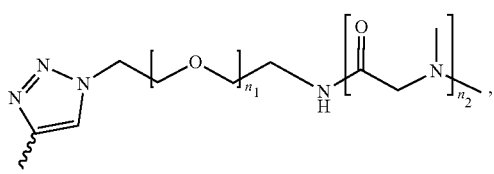

$n_1 = 5$ and $n_2 = 5$
or
$n_1 = 10$ and $n_2 = 10$ wherein:
"-----" represents a point of attachment to the central hinge moiety (CHM); and
"∼∼∼" represents a point of attachment to the Bicycle.

5. The multimeric binding complex of claim 1, wherein the spacer group is $S_1D$:

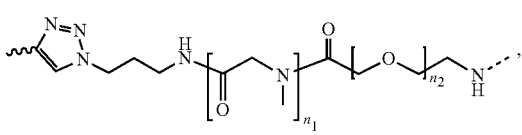

$n_1 = 5$ and $n_2 = 5$
or
$n_1 = 10$ and $n_2 = 10$ wherein:
"-----" represents a point of attachment to the central hinge moiety (CHM); and
"∼∼∼" represents a point of attachment to the Bicycle.

6. The multimeric binding complex of claim 1, wherein the spacer group is $S_1E$:

$S_1E$ n = 1 wherein:
"-----" represents a point of attachment to the central hinge moiety (CHM); and
"∼∼∼" represents a point of attachment to the Bicycle.

7. The multimeric binding complex of claim 1, wherein the spacer group is $S_1F$:

$S_1F$ n = 1 wherein:
"-----" represents a point of attachment to the central hinge moiety (CHM); and
"∼∼∼" represents a point of attachment to the Bicycle.

8. The multimeric binding complex of claim 1, wherein the spacer group is $S_1G$:

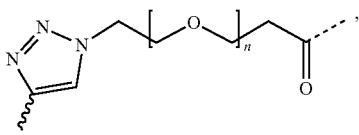

n = 5 or 10 wherein:
 "-----" represents a point of attachment to the central hinge moiety (CHM); and
 "∼∼∼" represents a point of attachment to the Bicycle.

9. The multimeric binding complex of claim 1, wherein the spacer group is $S_1H$:

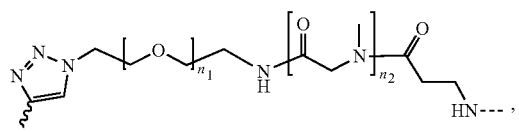

$n_1 = 5$ and $n_2 = 5$
or
$n_1 = 10$ and $n_2 = 10$ wherein:
 "-----" represents a point of attachment to the central hinge moiety (CHM); and
 "∼∼∼" represents a point of attachment to the Bicycle.

10. The multimeric binding complex of claim 1, wherein the central hinge moiety is central hinge moiety A:

(A)

[structure A]

wherein "-----" represents the point of attachment to each $S_1$ group.

11. The multimeric binding complex of claim 1, wherein the central hinge moiety is central hinge moiety B:

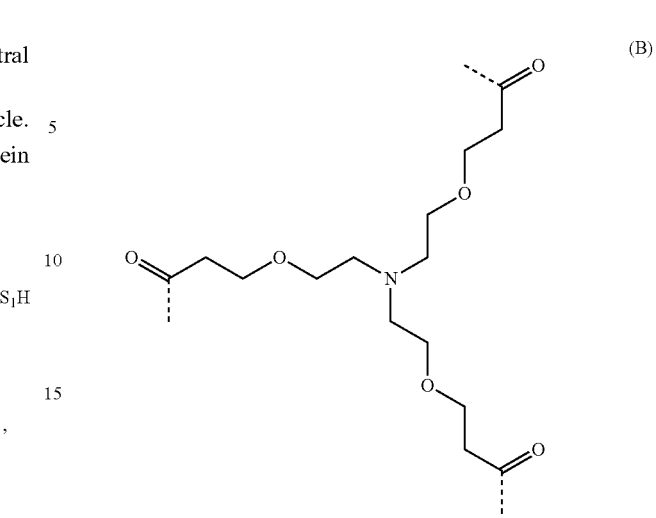

wherein "-----" represents the point of attachment to each $S_1$ group.

12. The multimeric binding complex of claim 1, wherein the central hinge moiety is central hinge moiety C:

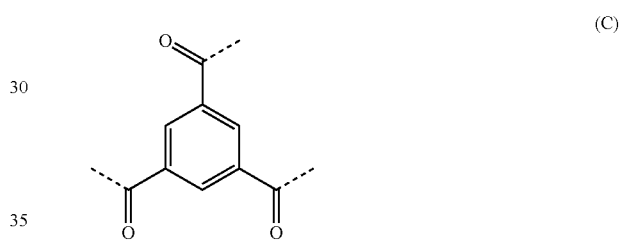

wherein "-----" represents the point of attachment to each $S_1$ group.

13. The multimeric binding complex of claim 1, wherein the central hinge moiety is central hinge moiety D:

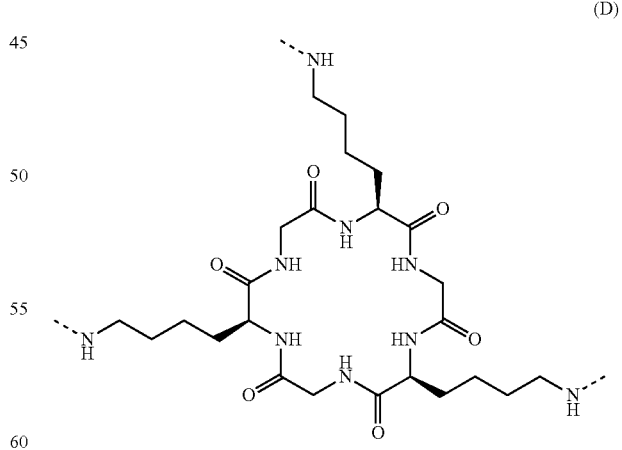

wherein "-----" represents the point of attachment to each $S_1$ group.

14. The multimeric binding complex of claim 1, wherein m is 3.

15. The multimeric binding complex of claim 14, wherein the multimeric binding complex is selected from BCY7750, BCY7749, BCY7827, BCY7828, BCY7831, BCY7832, BCY7835, BCY7836, BCY7839, BCY7840, BCY7843, BCY7844, BCY7847, BCY7848, BCY7851, BCY7852, BCY7855, BCY7856, BCY8102, BCY8103, BCY8106, BCY8107, BCY8098, BCY8099, BCY8145, BCY8146, BCY8151, BCY8581, BCY8582, BCY8948, BCY8957, BCY8958, BCY8961, BCY8962, BCY8965, BCY9573, BCY9595, BCY9775, BCY9776, BCY10046, BCY10047, BCY11194, BCY11195, BCY11196, BCY11382, BCY11383, and BCY11450 in Table A below:

TABLE 1

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY7750 | BCY7741 | 3 | B (TCA) | $S_1A$: n = 10 | C-terminal Dap(PYA) |
| BCY7749 | BCY7741 | 3 | B (TCA) | $S_1A$: n = 23 | C-terminal Dap(PYA) |
| BCY7827 | BCY7740 | 3 | B (TCA) | $S_1A$: n = 10 | N-terminal PYA |
| BCY7828 | BCY7740 | 3 | B (TCA) | $S_1A$: n = 23 | N-terminal PYA |
| BCY7831 | BCY7742 | 3 | B (TCA) | $S_1A$: n = 10 | Lys(PYA)$_2$ |
| BCY7832 | BCY7742 | 3 | B (TCA) | $S_1A$: n = 23 | Lys(PYA)$_2$ |
| BCY7835 | BCY7743 | 3 | B (TCA) | $S_1A$: n = 10 | Lys(PYA)$_3$ |
| BCY7836 | BCY7743 | 3 | B (TCA) | $S_1A$: n = 23 | Lys(PYA)$_3$ |
| BCY7839 | BCY7744 | 3 | B (TCA) | $S_1A$: n = 10 | D-Lys(PYA)$_4$ |
| BCY7840 | BCY7744 | 3 | B (TCA) | $S_1A$: n = 23 | D-Lys(PYA)$_4$ |
| BCY7843 | BCY7745 | 3 | B (TCA) | $S_1A$: n = 10 | Lys(PYA)$_5$ |
| BCY7844 | BCY7745 | 3 | B (TCA) | $S_1A$: n = 23 | Lys(PYA)$_5$ |
| BCY7847 | BCY7746 | 3 | B (TCA) | $S_1A$: n = 10 | Lys(PYA)$_7$ |
| BCY7848 | BCY7746 | 3 | B (TCA) | $S_1A$: n = 23 | Lys(PYA)$_7$ |
| BCY7851 | BCY7747 | 3 | B (TCA) | $S_1A$: n = 10 | Lys(PYA)$_{10}$ |
| BCY7852 | BCY7747 | 3 | B (TCA) | $S_1A$: n = 23 | Lys(PYA)$_{10}$ |
| BCY7855 | BCY7748 | 3 | B (TCA) | $S_1A$: n = 10 | Lys(PYA)$_{12}$ |
| BCY7856 | BCY7748 | 3 | B (TCA) | $S_1A$: n = 23 | Lys(PYA)$_{12}$ |
| BCY8102 | BCY8096 | 3 | B (TCA) | $S_1A$: n = 10 | D-Lys(BCN)$_4$ |
| BCY8103 | BCY8096 | 3 | B (TCA) | $S_1A$: n = 23 | D-Lys(BCN)$_4$ |
| BCY8106 | BCY8097 | 3 | B (TCA) | $S_1A$: n = 10 | Lys(BCN)$_{12}$ |
| BCY8107 | BCY8097 | 3 | B (TCA) | $S_1A$: n = 23 | Lys(BCN)$_{12}$ |
| BCY8098 | BCY8095 | 3 | B (TCA) | $S_1A$: n = 10 | Lys(BCN)$_2$ |
| BCY8099 | BCY8095 | 3 | B (TCA) | $S_1A$: n = 23 | Lys(BCN)$_2$ |
| BCY8145 | BCY8144 | 3 | B (TCA) | $S_1A$: n = 10 | Lys(BCN)$_7$ |
| BCY8146 | BCY8144 | 3 | B (TCA) | $S_1A$: n = 23 | Lys(BCN)$_7$ |
| BCY8151 | BCY8143 | 3 | B (TCA) | $S_1A$: n = 10 | Lys(BCN)$_5$ |
| BCY8581 | BCY8935 | 3 | B (TCA) | $S_1A$: n = 10 | N-terminal PYA |
| BCY8582 | BCY8935 | 3 | B (TCA) | $S_1A$: n = 23 | N-terminal PYA |
| BCY8948 | BCY8928 | 3 | B (TCA) | $S_1A$: n = 10 | D-Lys(PYA)$_4$ |
| BCY8957 | BCY7743 | 3 | B (TCA) | $S_1B$: n = 5 | Lys(PYA)$_3$ |
| BCY8958 | BCY7743 | 3 | B (TCA) | $S_1A$: n = 5 | Lys(PYA)$_3$ |
| BCY8961 | BCY7743 | 3 | B (TCA) | $S_1C$: $n_1$ = 5, $n_2$ = 5 | Lys(PYA)$_3$ |
| BCY8962 | BCY7743 | 3 | B (TCA) | $S_1D$: $n_1$ = 5, $n_2$ = 5 | Lys(PYA)$_3$ |
| BCY8965 | BCY7743 | 3 | B (TCA) | $S_1B$: n = 10 | Lys(PYA)$_3$ |
| BCY9573 | BCY7743 | 3 | B (TCA) | $S_1C$: $n_1$ = 10, $n_2$ = 10 | Lys(PYA)$_3$ |
| BCY9595 | BCY7743 | 3 | B (TCA) | $S_1D$: $n_1$ = 10, $n_2$ = 10 | Lys(PYA)$_3$ |
| BCY9775 | BCY7744 | 3 | C (Trimesic acid) | $S_1A$: n = 10 | D-Lys(PYA)$_4$ |
| BCY9776 | BCY7744 | 3 | C (Trimesic acid) | $S_1A$: n = 23 | D-Lys(PYA)$_4$ |
| BCY10046 | BCY7744 | 3 | D (c(KGKGKG)) (cyclic (SEQ ID NO: 57)) | $S_1G$: n = 5 | D-Lys(PYA)$_4$ |
| BCY10047 | BCY7744 | 3 | D (c(KGKGKG)) (cyclic (SEQ ID NO: 57)) | $S_1G$: n = 10 | D-Lys(PYA)$_4$ |
| BCY11194 | BCY7744, BCY8928 | 2 × BCY7744 and 1 × BCY8928 | B (TCA) | $S_1A$: n = 10 | D-Lys(PYA)$_4$ |

TABLE 1-continued

Exemplified Trimeric Binding Complexes of the Invention

| Multimer Compound Number | Corresponding Monomer | Number of Monomers | Central Hinge Moiety | Spacer Molecule | Attachment Point |
|---|---|---|---|---|---|
| BCY11195 | BCY8925, BCY8928 | 2 × BCY8925 and 1 × BCY8928 | B (TCA) | $S_1A$: n = 10 | D-Lys(PYA)$_4$ |
| BCY11196 | BCY8925, BCY7744 | 2 × BCY8925 and 1 × BCY7744 | B (TCA) | $S_1A$: n = 10 | D-Lys(PYA)$_4$ |
| BCY11382 | BCY7744 | 3 | C (Trimesic acid) | $S_1E$: n = 1 | D-Lys(PYA)$_4$ |
| BCY11383 | BCY7744 | 3 | D (c(KGKGKG)) (cyclic (SEQ ID NO: 57)) | $S_1F$: n = 1 | D-Lys(PYA)$_4$ |
| BCY11450 | BCY11072 | 3 | B (TCA) | $S_1A$: n = 10 | L-Lys(PYA)$_4$ | wherein:

(SEQ ID NO: 40)
monomer BCY7740 is (PYA)-A-$C_i$IEEGQYC$_{ii}$FADPY(Nle)C$_{iii}$-A;

(SEQ ID NO: 41)
monomer BCY7741 is Ac-A-$C_i$IEEGQYC$_{ii}$FADPY(Nle)C$_{iii}$-Dap(PYA);

(SEQ ID NO: 42)
monomer BCY7742 is Ac-A-$C_i$IK(PYA)EGQYC$_{ii}$FADPY(Nle)C$_{iii}$-A;

(SEQ ID NO: 43)
monomer BCY7743 is Ac-A-CHIEK(PYA)GQYC$_{ii}$FADPY(Nle)C$_{iii}$-A;

(SEQ ID NO: 44)
monomer BCY7744 is Ac-A-$C_i$IEE(D-K)(PYA)QYC$_{ii}$FADPY(Nle)C$_{iii}$-A;

(SEQ ID NO: 45)
monomer BCY7745 is Ac-A-$C_i$IEEGK(PYA)YC$_{ii}$FADPY(Nle)C$_{iii}$-A;

(SEQ ID NO: 46)
monomer BCY7746 is Ac-A-$C_i$IEEGQYC$_{ii}$K(PYA)ADPY(Nle)C$_{iii}$-A;

(SEQ ID NO: 47)
monomer BCY7747 is Ac-A-$C_i$IEEGQYC$_{ii}$FADK(PYA)Y(Nle)C$_{iii}$-A;

(SEQ ID NO: 48)
monomer BCY7748 is Ac-A-$C_i$IEEGQYC$_{ii}$FADPYK(PYA)C$_{iii}$-A;

(SEQ ID NO: 50)
monomer BCY8095 is Ac-A-$C_i$IK(BCN)EGQYC$_{ii}$FADPY(Nle)C$_{iii}$-A;

(SEQ ID NO: 52)
monomer BCY8096 is Ac-A-$C_i$IEE[(D-K)(BCN)]QYC$_{ii}$FADPY(Nle)C$_{iii}$-A;

(SEQ ID NO: 53)
monomer BCY8143 is Ac-A-$C_i$IEEGK(BCN)YC$_{ii}$FADPY(Nle)C$_{iii}$-A;

(SEQ ID NO: 54)
monomer BCY8144 is Ac-A-$C_i$IEEGQYC$_{ii}$K(BCN)ADPY(Nle)C$_{iii}$-A;

(SEQ ID NO: 55)
monomer BCY8097 is Ac-A-$C_i$IEEGQYC$_{ii}$FADPYK(BCN)C$_{iii}$-A;

(SEQ ID NO: 63)
monomer BCY11072 is [Ac]-[D-A]-[D-$C_i$][D-I][D-E][D-E]K[D-Q][D-Y][D-$C_{ii}$][D-F][D-A][D-D][D-P][D-Y][D-Nle][D-$C_{iii}$]-[D-A];

(SEQ ID NO: 64)
monomer BCY8935 is (PYA)-A-$C_i$IEEGQYC$_{ii}$F[D-A]DPY[Nle]C$_{iii}$-A;

(SEQ ID NO: 66)
monomer BCY8928 is Ac-C$_i$[tBuAla]PE[D-K(PYA)]PYC$_{ii}$FADPY[Nle]C$_{iii}$-A;
and (SEQ ID NO: 67)
monomer BCY8925 is Ac-A-C$_i$IE[D-K(PYA)]GQYC$_{ii}$F[D-A]DPY[Nle]C$_{iii}$-A;

wherein:

S$_1$A has a structure:

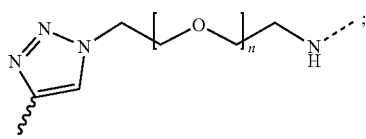

S$_1$A n = 5, 10, or 23

S$_1$B has a structure:

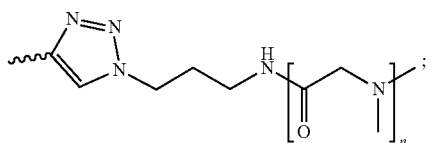

S$_1$B n = 5 or 10

S$_1$C has a structure:

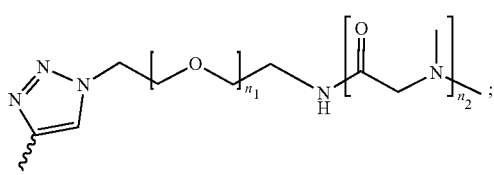

S$_1$C n$_1$ = 5 and n$_2$ = 5
or
n$_1$ = 10 and n$_2$ = 10

S$_1$D has a structure:

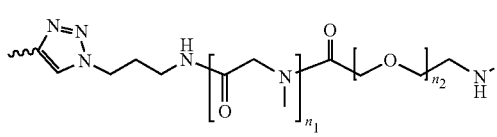

S$_1$D n$_1$ = 5 and n$_2$ = 5
or
n$_1$ = 10 and n$_2$ = 10

S$_1$E has a structure:

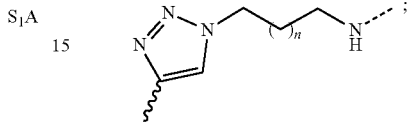

S$_1$E n = 1

S$_1$F has a structure:

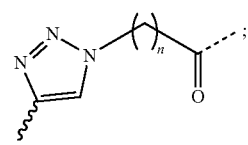

S$_1$F n = 1

S$_1$G has a structure:

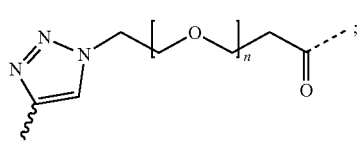

S$_1$G n = 5 or 10 wherein:

"-----" represents a point of attachment to the central hinge moiety (CHM); and

"∼∼∼" represents a point of attachment to the Bicycle;

wherein:
central hinge moiety B has a structure:

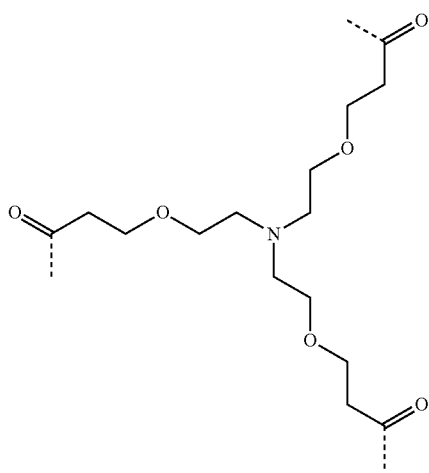

(B)

central hinge moiety C has a structure:

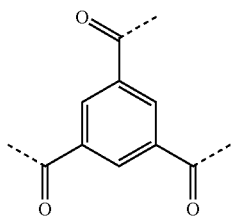

(C)

and
central hinge moiety D has a structure:

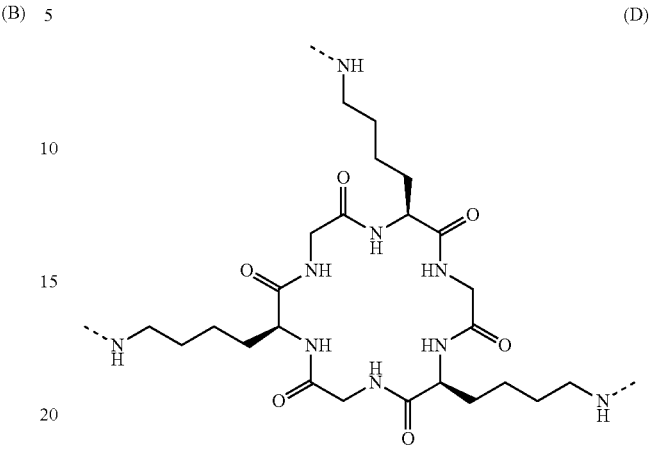

(D)

wherein "-----" represents the point of attachment to each $S_1$ group.

16. The multimeric binding complex of claim 1, wherein m is 4.

17. The multimeric binding complex of claim 16, wherein the multimeric binding complex is selected from BCY7751, BCY7752, BCY7829, BCY7830, BCY7833, BCY7834, BCY7837, BCY7838, BCY7841, BCY7842, BCY7845, BCY7846, BCY7849, BCY7850, BCY7853, BCY7854, BCY7857, BCY7858, BCY8104, BCY8105, BCY8108, BCY8109, BCY8100, BCY8101, BCY8147, BCY8148, BCY8149, BCY8150, BCY8583, BCY8584, BCY8937, BCY8945, BCY8946, BCY8947, BCY8959, BCY8960, BCY8963, BCY8964, BCY8966, BCY9113, BCY9767, BCY10388, and BCY11451 as shown in Table B below:

TABLE B

| Multimer Compound Number | Corresponding Monomer | Number of Monomers | Central Hinge Moiety | Spacer Molecule | Attachment Point |
| --- | --- | --- | --- | --- | --- |
| BCY7751 | BCY7741 | 4 | A (TET) | $S_1A$: n = 10 | C-terminal Dap(PYA) |
| BCY7752 | BCY7741 | 4 | A (TET) | $S_1A$: n = 23 | C-terminal Dap(PYA) |
| BCY7829 | BCY7740 | 4 | A (TET) | $S_1A$: n = 10 | N-terminal PYA |
| BCY7830 | BCY7740 | 4 | A (TET) | $S_1A$: n = 23 | N-terminal PYA |
| BCY7833 | BCY7742 | 4 | A (TET) | $S_1A$: n = 10 | Lys(PYA)$_2$ |
| BCY7834 | BCY7742 | 4 | A (TET) | $S_1A$: n = 23 | Lys(PYA)$_2$ |
| BCY7837 | BCY7743 | 4 | A (TET) | $S_1A$: n = 10 | Lys(PYA)$_3$ |
| BCY7838 | BCY7743 | 4 | A (TET) | $S_1A$: n = 23 | Lys(PYA)$_3$ |
| BCY7841 | BCY7744 | 4 | A (TET) | $S_1A$: n = 10 | D-Lys(PYA)$_4$ |
| BCY7842 | BCY7744 | 4 | A (TET) | $S_1A$: n = 23 | D-Lys(PYA)$_4$ |
| BCY7845 | BCY7745 | 4 | A (TET) | $S_1A$: n = 10 | Lys(PYA)$_5$ |
| BCY7846 | BCY7745 | 4 | A (TET) | $S_1A$: n = 23 | Lys(PYA)$_5$ |
| BCY7849 | BCY7746 | 4 | A (TET) | $S_1A$: n = 10 | Lys(PYA)$_7$ |
| BCY7850 | BCY7746 | 4 | A (TET) | $S_1A$: n = 23 | Lys(PYA)$_7$ |
| BCY7853 | BCY7747 | 4 | A (TET) | $S_1A$: n = 10 | Lys(PYA)$_{10}$ |
| BCY7854 | BCY7747 | 4 | A (TET) | $S_1A$: n = 23 | Lys(PYA)$_{10}$ |
| BCY7857 | BCY7748 | 4 | A (TET) | $S_1A$: n = 10 | Lys(PYA)$_{12}$ |
| BCY7858 | BCY7748 | 4 | A (TET) | $S_1A$: n = 23 | Lys(PYA)$_{12}$ |
| BCY8104 | BCY8096 | 4 | A (TET) | $S_1A$: n = 10 | D-Lys(BCN)$_4$ |
| BCY8105 | BCY8096 | 4 | A (TET) | $S_1A$: n = 23 | D-Lys(BCN)$_4$ |
| BCY8108 | BCY8097 | 4 | A (TET) | $S_1A$: n = 10 | Lys(BCN)$_{12}$ |
| BCY8109 | BCY8097 | 4 | A (TET) | $S_1A$: n = 23 | Lys(BCN)$_{12}$ |
| BCY8100 | BCY8095 | 4 | A (TET) | $S_1A$: n = 10 | Lys(BCN)$_2$ |
| BCY8101 | BCY8095 | 4 | A (TET) | $S_1A$: n = 23 | Lys(BCN)$_2$ |
| BCY8147 | BCY8144 | 4 | A (TET) | $S_1A$: n = 10 | Lys(BCN)$_7$ |
| BCY8148 | BCY8144 | 4 | A (TET) | $S_1A$: n = 23 | Lys(BCN)$_7$ |

TABLE B-continued

| Multimer Compound Number | Corresponding Monomer | Number of Monomers | Central Hinge Moiety | Spacer Molecule | Attachment Point |
|---|---|---|---|---|---|
| BCY8149 | BCY8141 | 4 | A (TET) | $S_1A: n = 23$ | N-terminal BCN |
| BCY8150 | BCY8142 | 4 | A (TET) | $S_1A: n = 10$ | $Lys(BCN)_3$ |
| BCY8583 | BCY8935 | 4 | A (TET) | $S_1A: n = 10$ | N-terminal PYA |
| BCY8584 | BCY8935 | 4 | A (TET) | $S_1A: n = 23$ | N-terminal PYA |
| BCY8937 | BCY8926 | 4 | A (TET) | $S_1A: n = 23$ | $Lys(PYA)_3$ |
| BCY8945 | BCY8927 | 4 | A (TET) | $S_1A: n = 23$ | $Lys(PYA)_3$ |
| BCY8946 | BCY8927 | 4 | A (TET) | $S_1A: n = 10$ | $Lys(PYA)_3$ |
| BCY8947 | BCY8928 | 4 | A (TET) | $S_1A: n = 10$ | $D\text{-}Lys(PYA)_4$ |
| BCY8959 | BCY7743 | 4 | A (TET) | $S_1B: n = 5$ | $Lys(PYA)_3$ |
| BCY8960 | BCY7743 | 4 | A (TET) | $S_1A: n = 5$ | $Lys(PYA)_3$ |
| BCY8963 | BCY7743 | 4 | A (TET) | $S_1C: n_1 = 5, n_2 = 5$ | $Lys(PYA)_3$ |
| BCY8964 | BCY7743 | 4 | A (TET) | $S_1D: n_1 = 5, n_2 = 5$ | $Lys(PYA)_3$ |
| BCY8966 | BCY7743 | 4 | A (TET) | $S_1B: n = 10$ | $Lys(PYA)_3$ |
| BCY9113 | BCY8926 | 4 | A (TET) | $S_1A: n = 10$ | $Lys(PYA)_3$ |
| BCY9767 | BCY7743 | 4 | A (TET) | $S_1H: n_1 = 10, n_2 = 10$ | $Lys(PYA)_3$ |
| BCY10388 | BCY8928 | 4 | A (TET) | $S_1A: n = 23$ | $D\text{-}Lys(PYA)_4$ |
| BCY11451 | BCY11506 | 4 | A (TET) | $S_1A: n = 23$ | $L\text{-}Lys(PYA)_4$ | wherein:

(SEQ ID NO: 40)
monomer BCY7740 is (PYA)-A-$C_i$IEEGQY$C_{ii}$FADPY(Nle)$C_{iii}$-A;

(SEQ ID NO: 41)
monomer BCY7741 is Ac-A-$C_i$IEEGQY$C_{ii}$FADPY(Nle)$C_{iii}$-Dap(PYA);

(SEQ ID NO: 42)
monomer BCY7742 is Ac-A-$C_i$IK(PYA)EGQY$C_{ii}$FADPY(Nle)$C_{iii}$-A;

(SEQ ID NO: 43)
monomer BCY7743 is Ac-A-$C_i$IEK(PYA)GQY$C_{ii}$FADPY(Nle)$C_{iii}$-A;

(SEQ ID NO: 44)
monomer BCY7744 is Ac-A-$C_i$IEE(D-K)(PYA)QY$C_{ii}$FADPY(Nle)$C_{iii}$-A;

(SEQ ID NO: 45)
monomer BCY7745 is Ac-A-$C_i$IEEGK(PYA)Y$C_{ii}$FADPY(Nle)$C_{iii}$-A;

(SEQ ID NO: 46)
monomer BCY7746 is Ac-A-$C_i$IEEGQY$C_{ii}$K(PYA)ADPY(Nle)$C_{iii}$-A;

(SEQ ID NO: 47)
monomer BCY7747 is Ac-A-$C_i$IEEGQY$C_{ii}$FADK(PYA)Y(Nle)$C_{iii}$-A;

(SEQ ID NO: 48)
monomer BCY7748 is Ac-A-$C_i$IEEGQY$C_{ii}$FADPYK(PYA)$C_{iii}$-A;

(SEQ ID NO: 49)
monomer BCY8141 is (BCN)-A-$C_i$IEEGQY$C_{ii}$FADPY(Nle)$C_{iii}$-A;

(SEQ ID NO: 50)
monomer BCY8095 is Ac-A-$C_i$IK(BCN)EGQY$C_{ii}$FADPY(Nle)$C_{iii}$-A;

(SEQ ID NO: 51)
monomer BCY8142 is Ac-A-$C_i$IEK(BCN)GQY$C_{ii}$FADPY(Nle)$C_{iii}$-A;

(SEQ ID NO: 52)
monomer BCY8096 is Ac-A-$C_i$IEE[(D-K)(BCN)]QY$C_{ii}$FADPY(Nle)$C_{iii}$-A;

(SEQ ID NO: 55)
monomer BCY8097 is Ac-A-$C_i$IEEGQY$C_{ii}$FADPYK(BCN)$C_{iii}$-A;

(SEQ ID NO: 64)
monomer BCY8935 is (PYA)-A-$C_i$IEEGQY$C_{ii}$F[D-A]DPY[Nle]$C_{iii}$-A;

(SEQ ID NO: 65)
monomer BCY8927 is Ac-$C_i$[tBuAla]PK(PYA)[D-A]PY$C_{ii}$FADPY[Nle]$C_{iii}$-A;

(SEQ ID NO: 66)
monomer BCY8928 is Ac-$C_i$[tBuAla]PE[D-K(PYA)]PY$C_{ii}$FADPY[Nle]$C_{iii}$-A;

(SEQ ID NO: 68)
monomer BCY8926 is Ac-A-$C_i$IE[K(PYA)]GQY$C_{ii}$F[D-A]DPY[Nle]$C_{iii}$-A;
and (SEQ ID NO: 69)
monomer BCY11506 is [Ac]-[D-A]-[D-$C_i$][D-I][D-E][D-E][K(PYA)][D-Q][D-Y][D-$C_{ii}$][D-F][D-A][D-D][D-P][D-Y][D-Nle][D-$C_{iii}$]-[D-A];

wherein:

$S_1A$ has a structure:

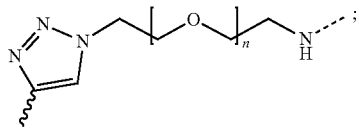

n = 5, 10, or 23

$S_1B$ has a structure:

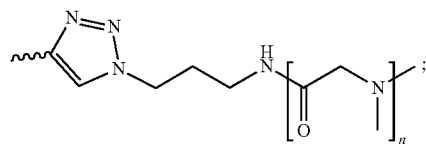

n = 5 or 10

$S_1C$ has a structure:

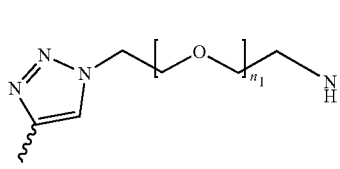

$n_1 = 5$ and $n_2 = 5$
or
$n_1 = 10$ and $n_2 = 10$ $S_1D$ has a structure:

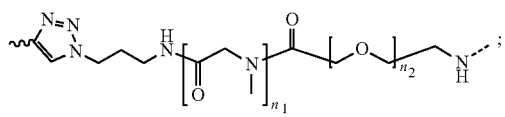

$n_1 = 5$ and $n_2 = 5$
or
$n_1 = 10$ and $n_2 = 10$ $S_1H$ has a structure:

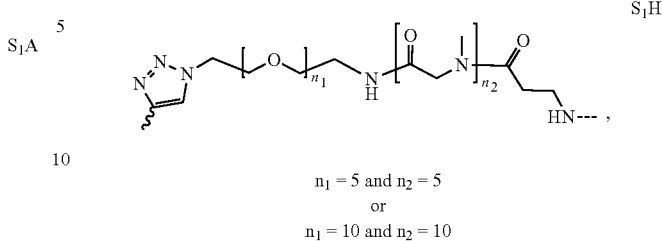

$n_1 = 5$ and $n_2 = 5$
or
$n_1 = 10$ and $n_2 = 10$ wherein:
"-----" represents a point of attachment to the central hinge moiety (CHM); and
"∼∼∼" represents a point of attachment to the Bicycle;
wherein:
central hinge moiety A has a structure:

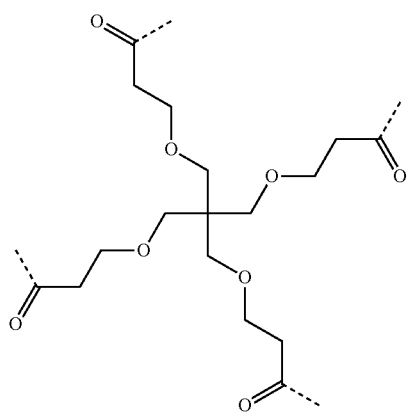

(A)

wherein "-----" represents the point of attachment to each $S_1$ group.

18. The multimeric binding complex of claim 1, wherein the molecular scaffold is 1,1',1"-(1,3,5-triazinane-1,3,5-triyl)triprop-2-en-1-one (TATA).

19. The multimeric binding complex of claim 1, wherein the multimeric binding complex is selected from:

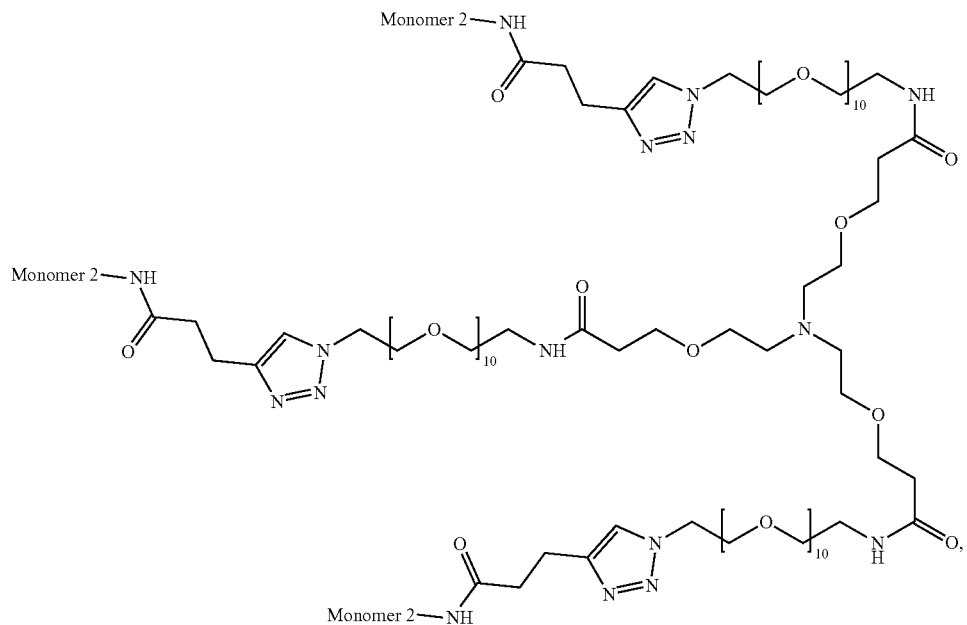
BCY7750
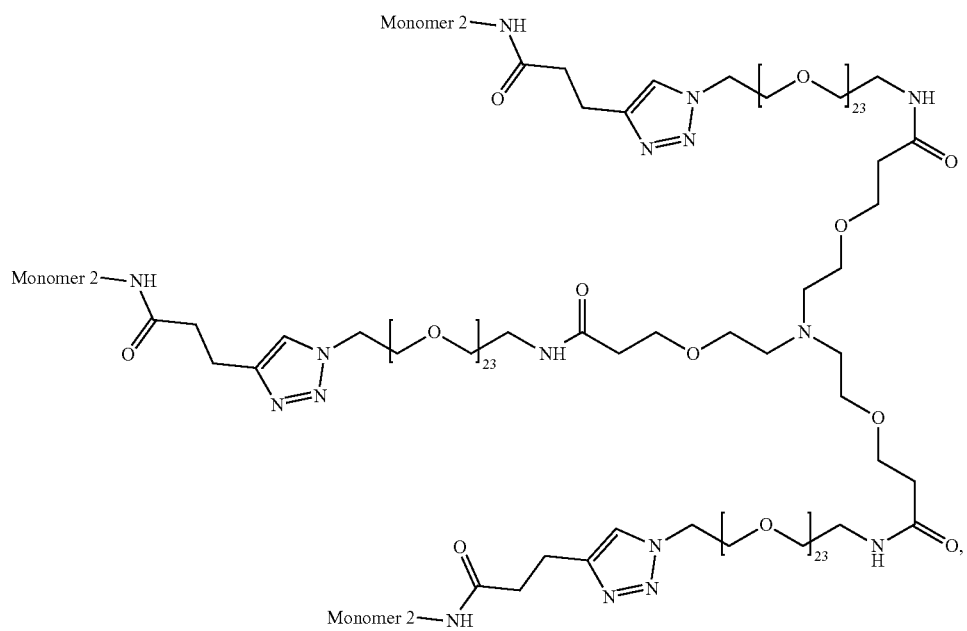
BCY7749

-continued
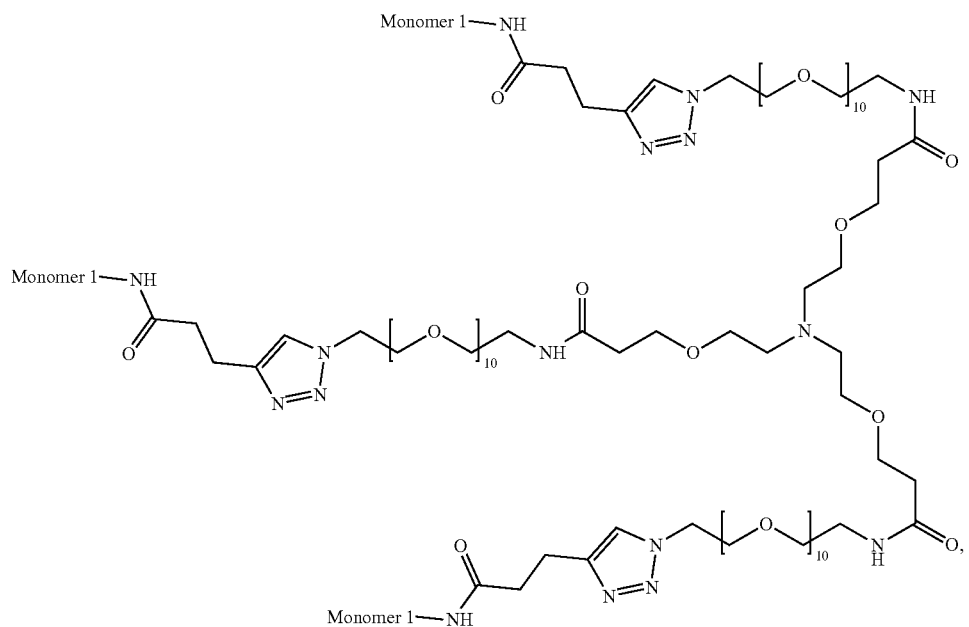
BCY7827
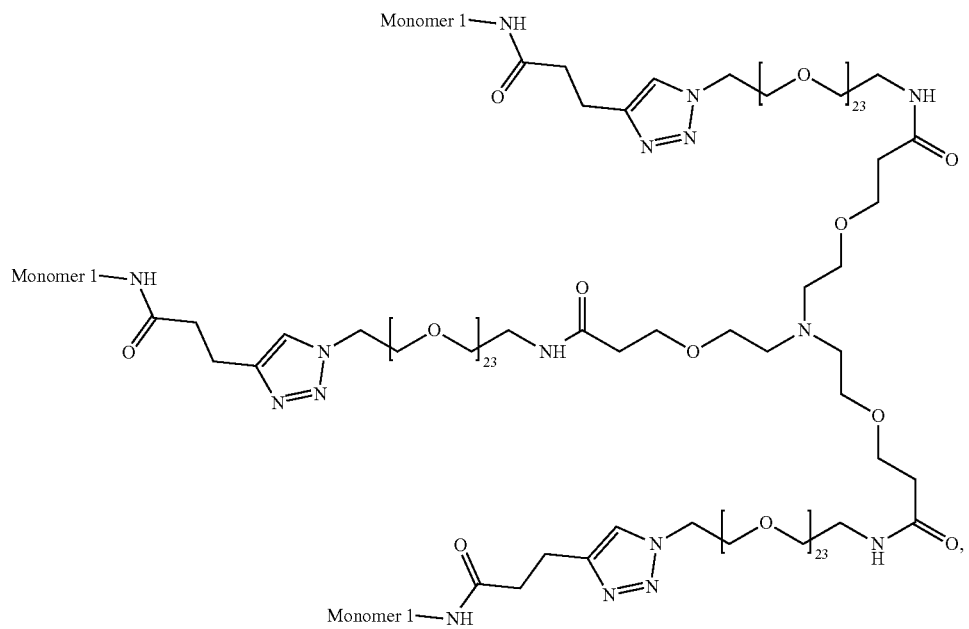
BCY7828

-continued
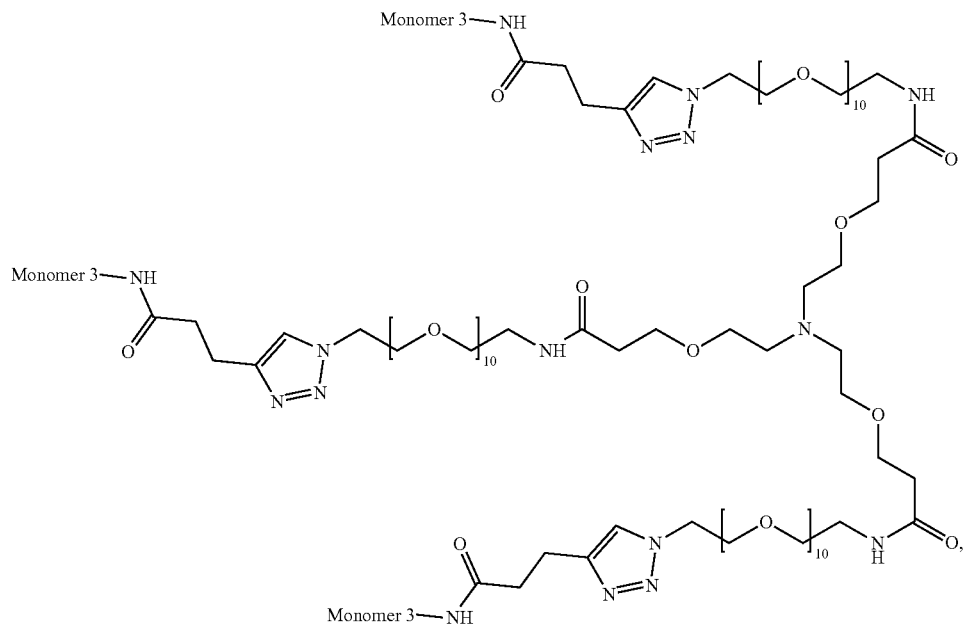
BCY7831
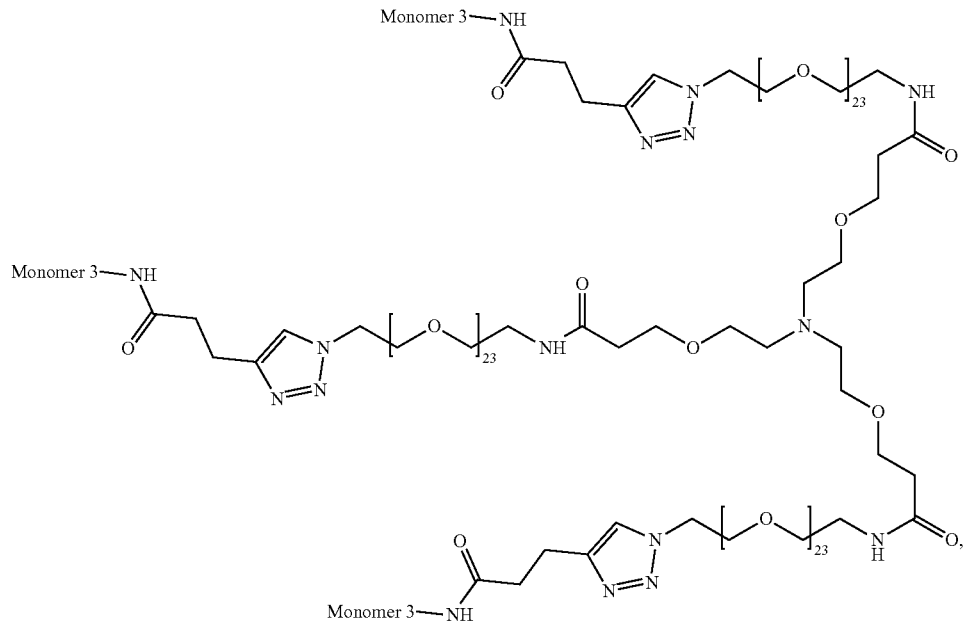
BCY7832

BCY7835
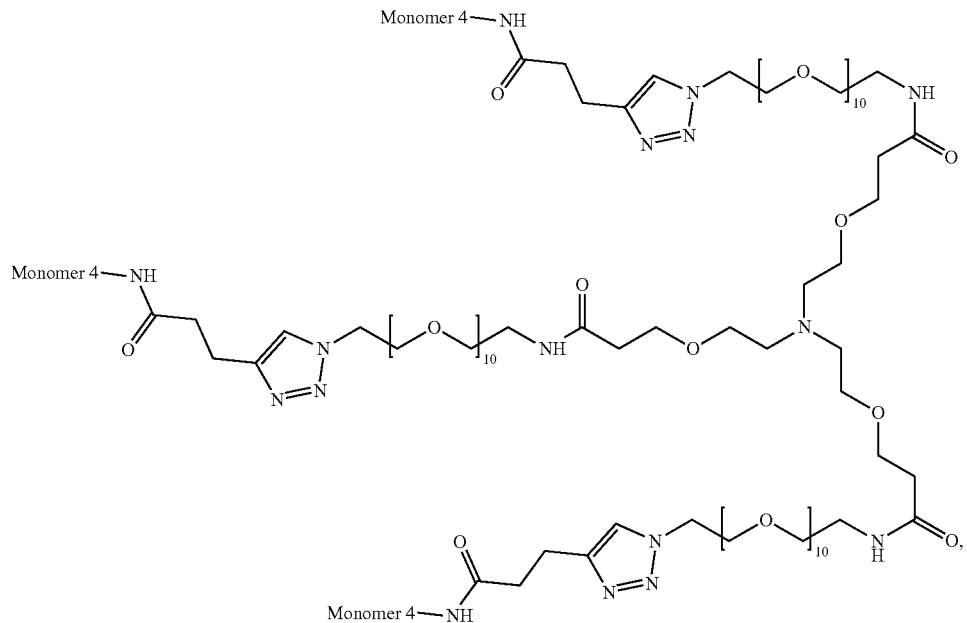
BCY7836
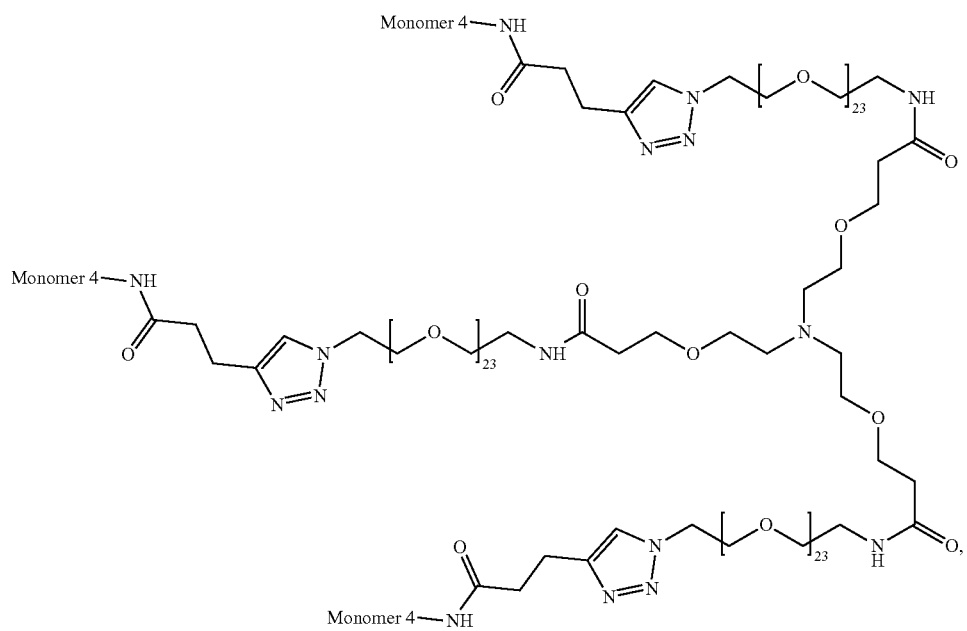

-continued
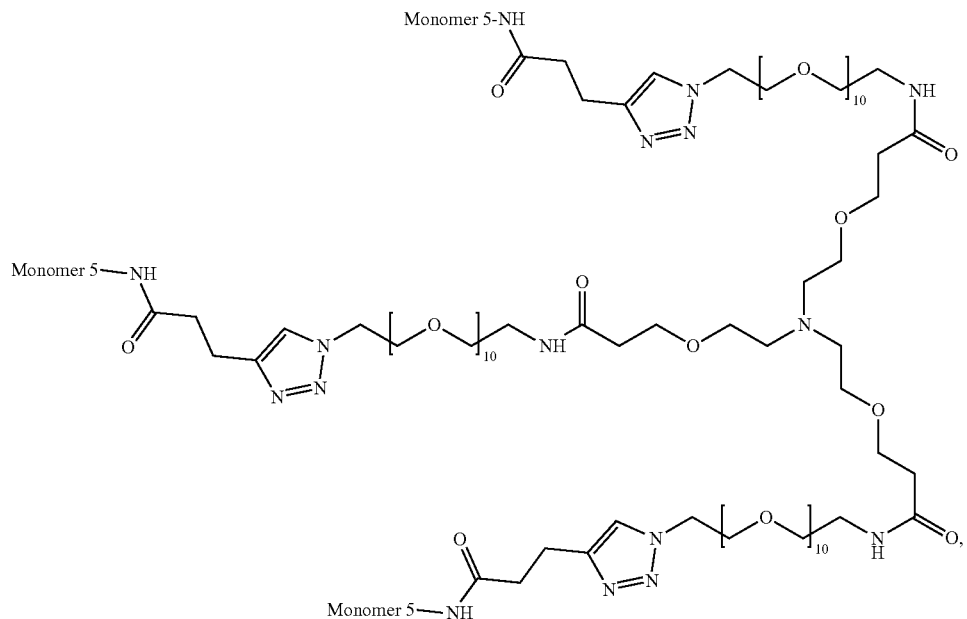
BCY7839
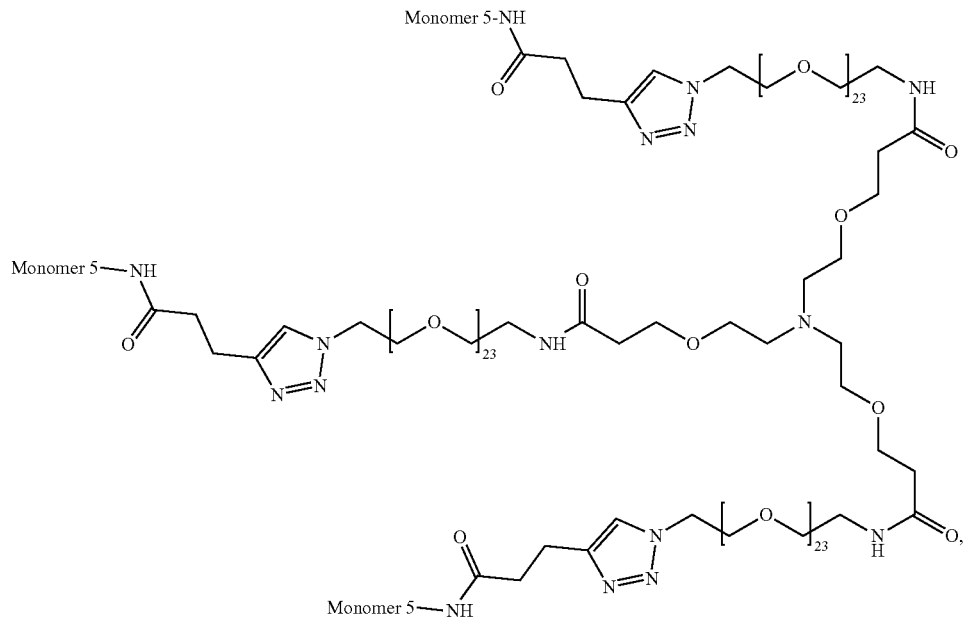
BCY7840

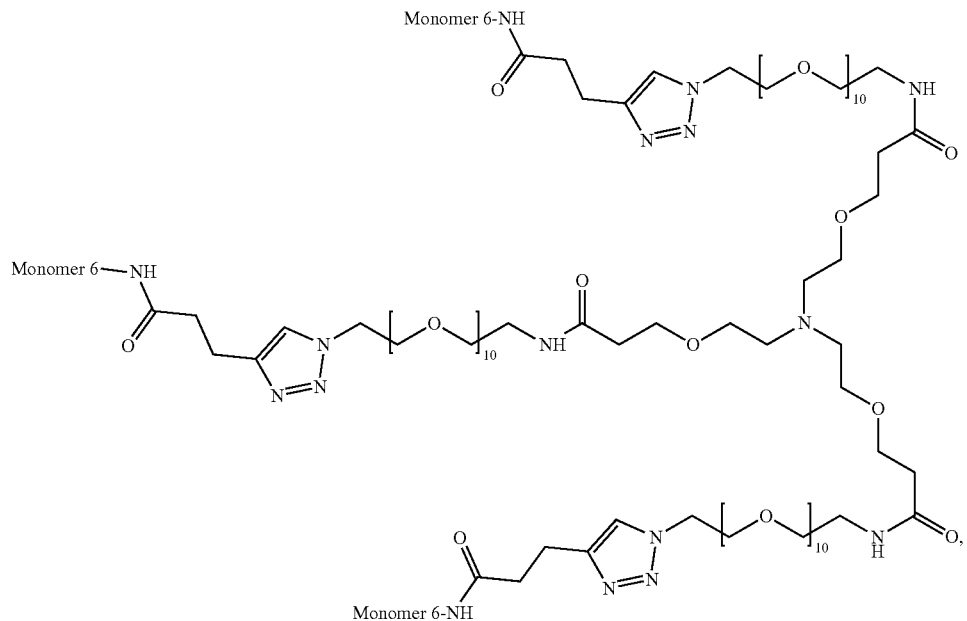
BCY7743
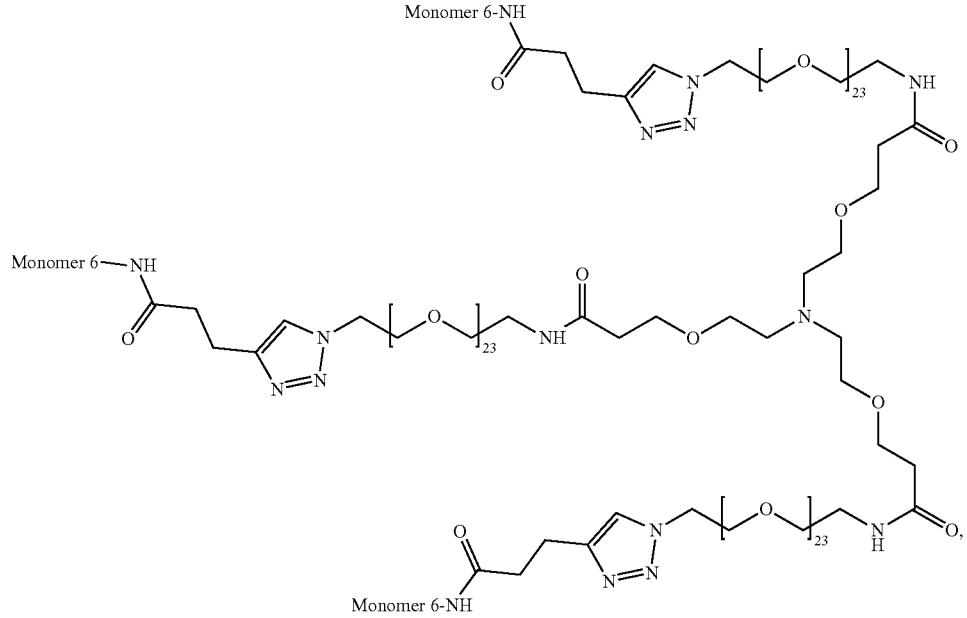
BCY7744

-continued
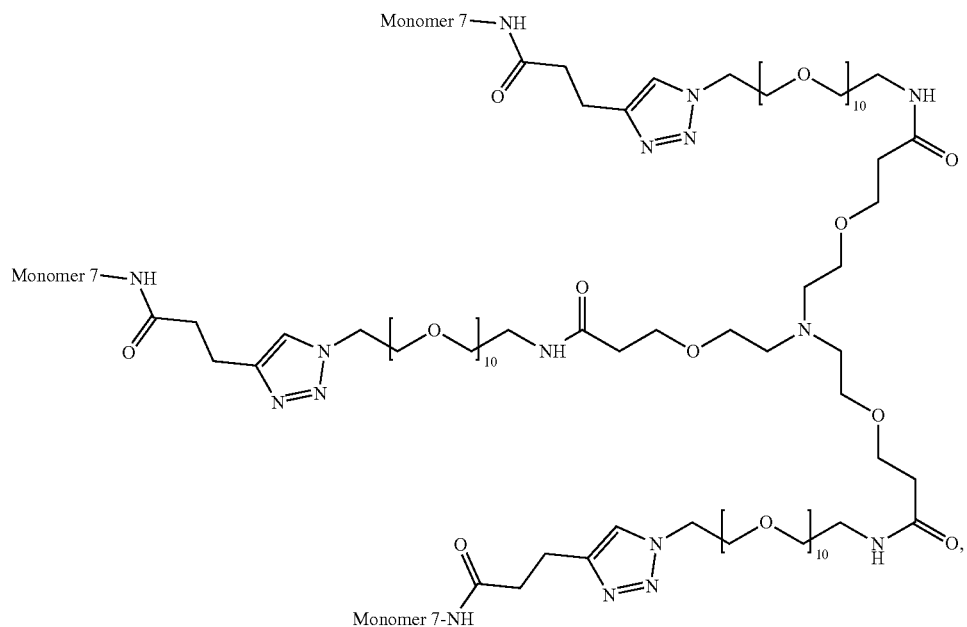
BCY7847
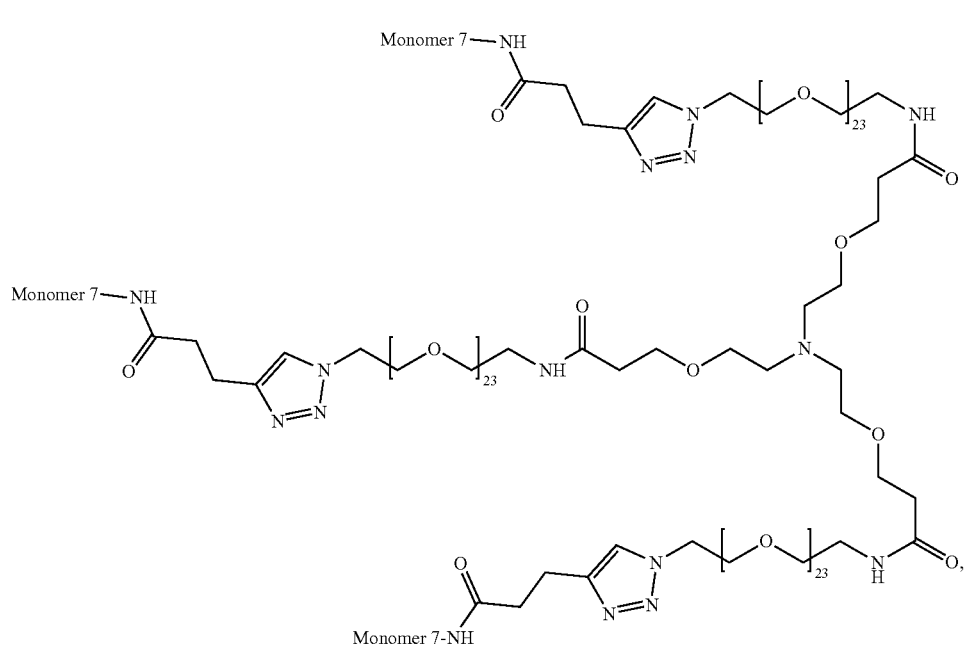
BCY7848

-continued
BCY7851
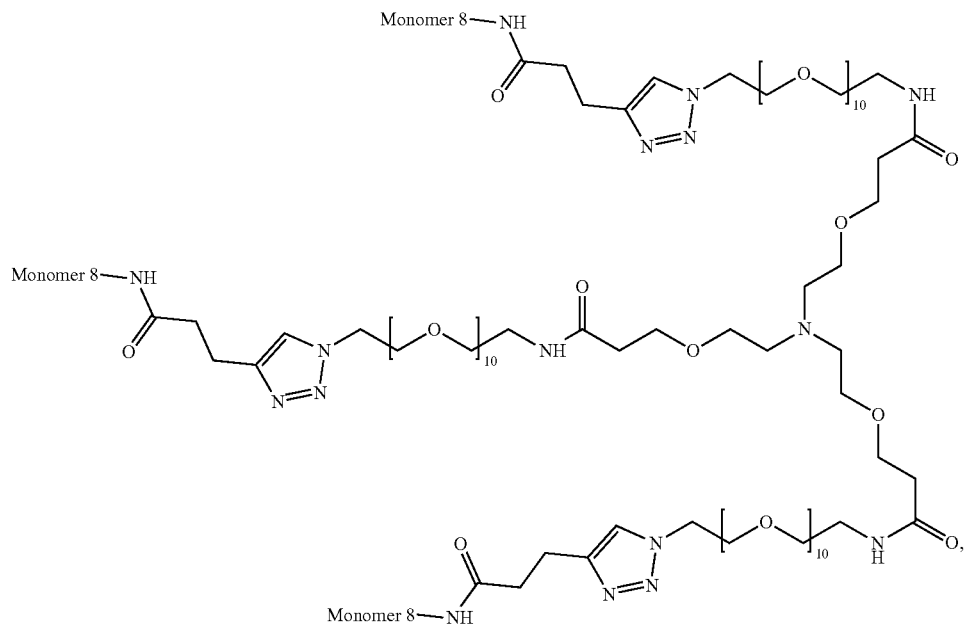
BCY7852
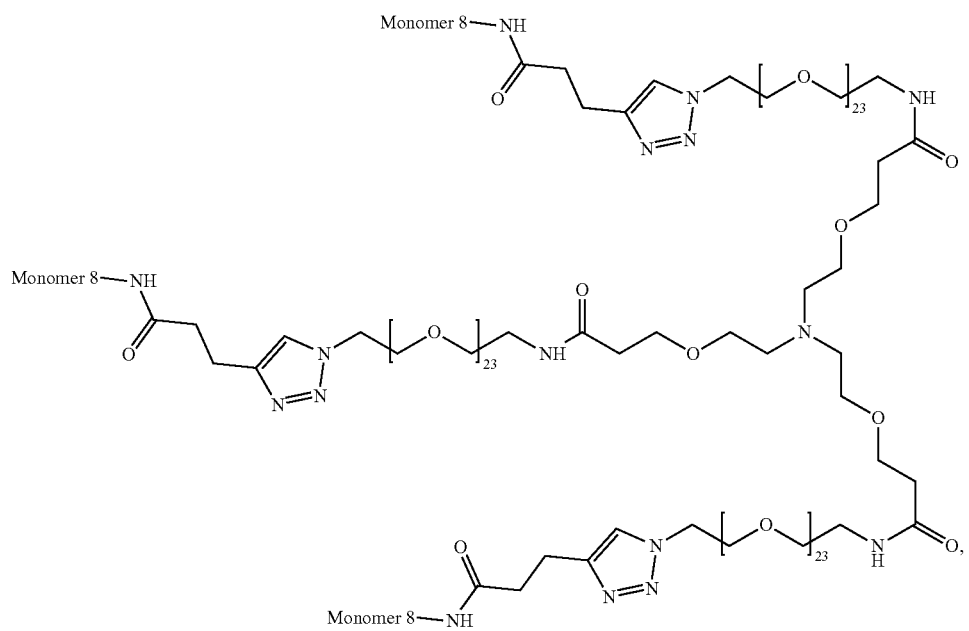

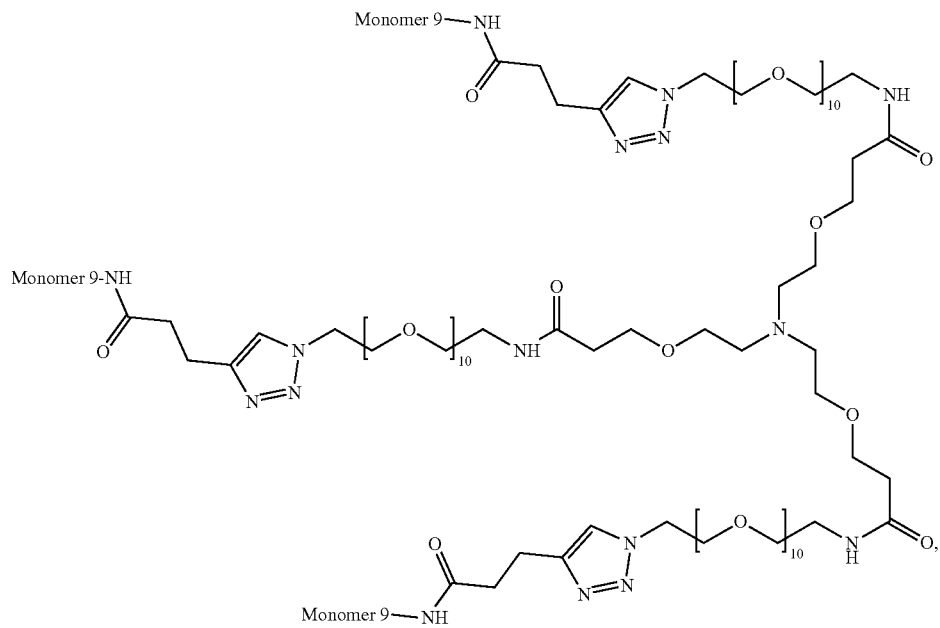
BCY7855
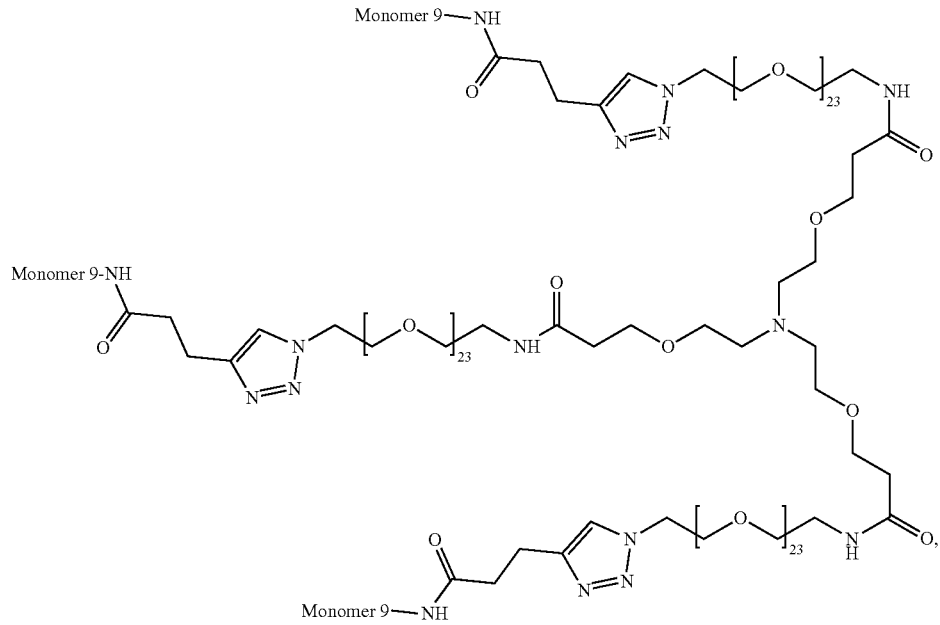
BCY7856

287                                                      288
-continued
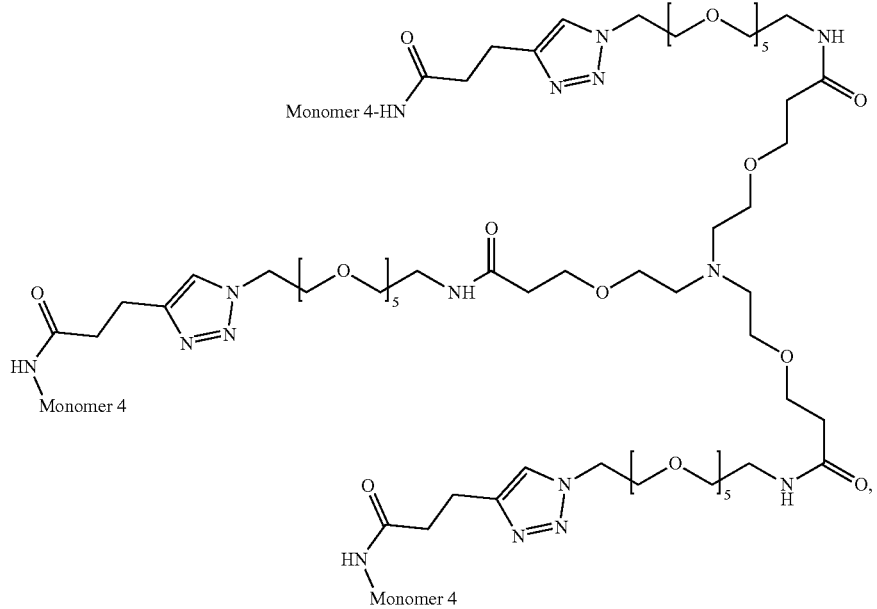
BCY8958
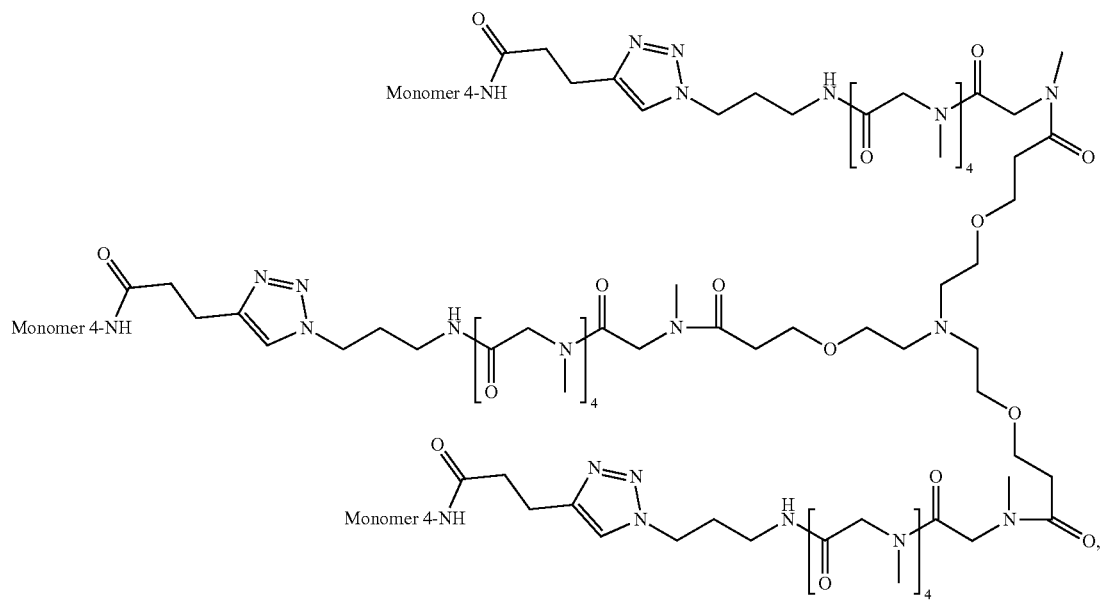
BCY8957

-continued
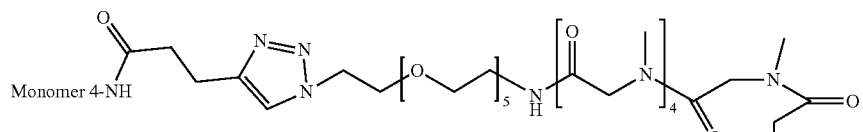
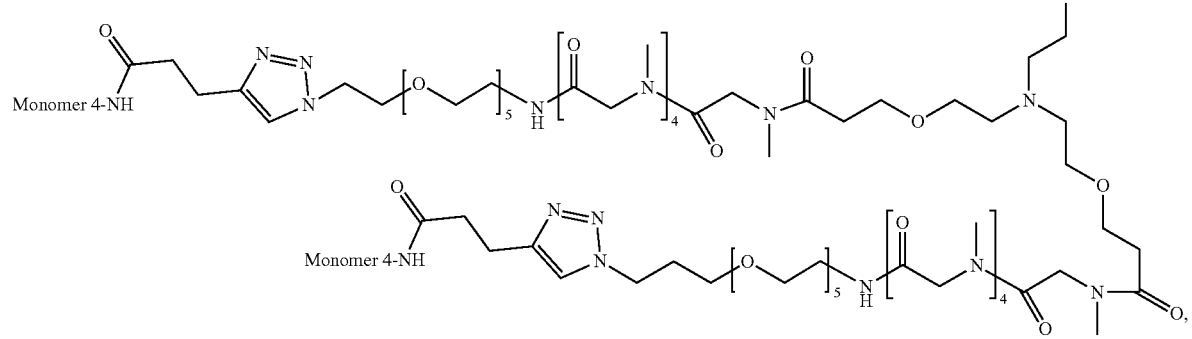
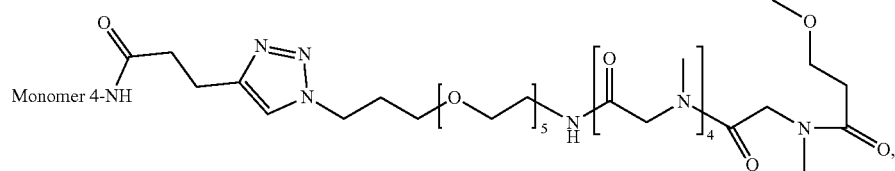
BCY8961
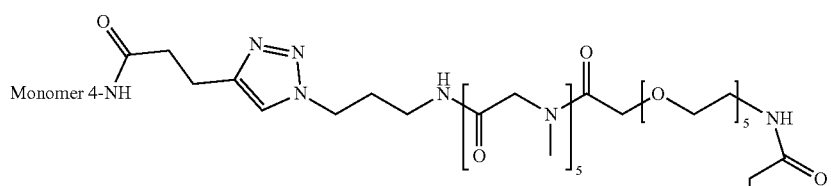
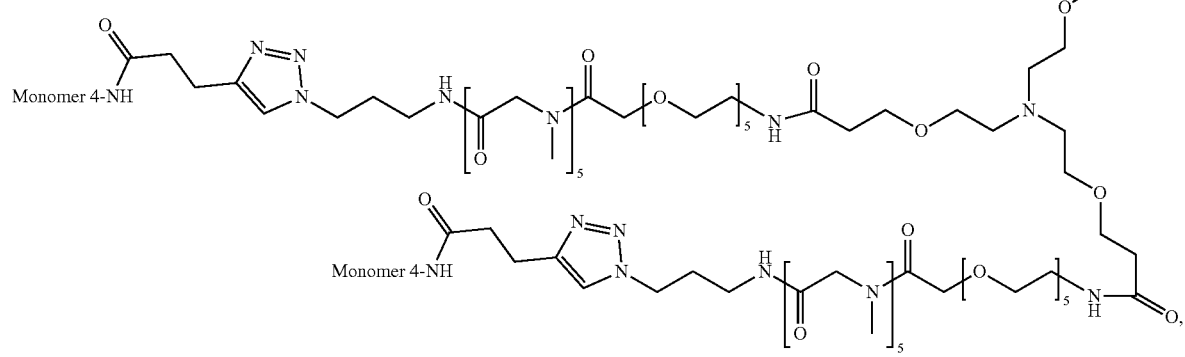
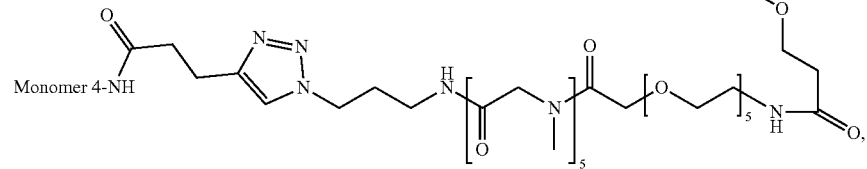
BCY8962

-continued
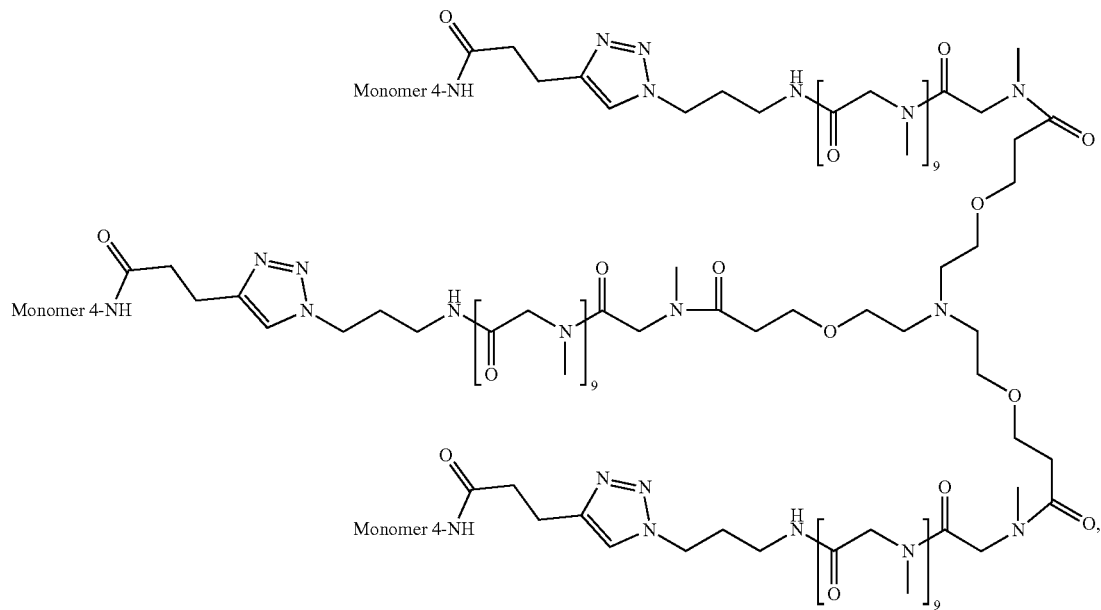
BCY8965
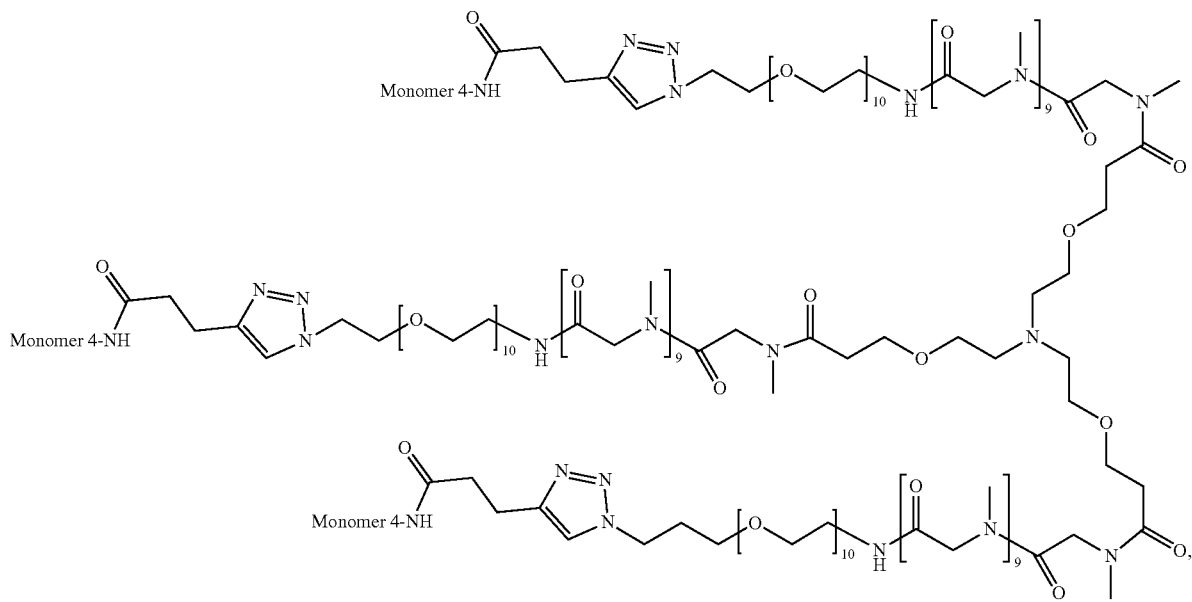
BCY9573

-continued
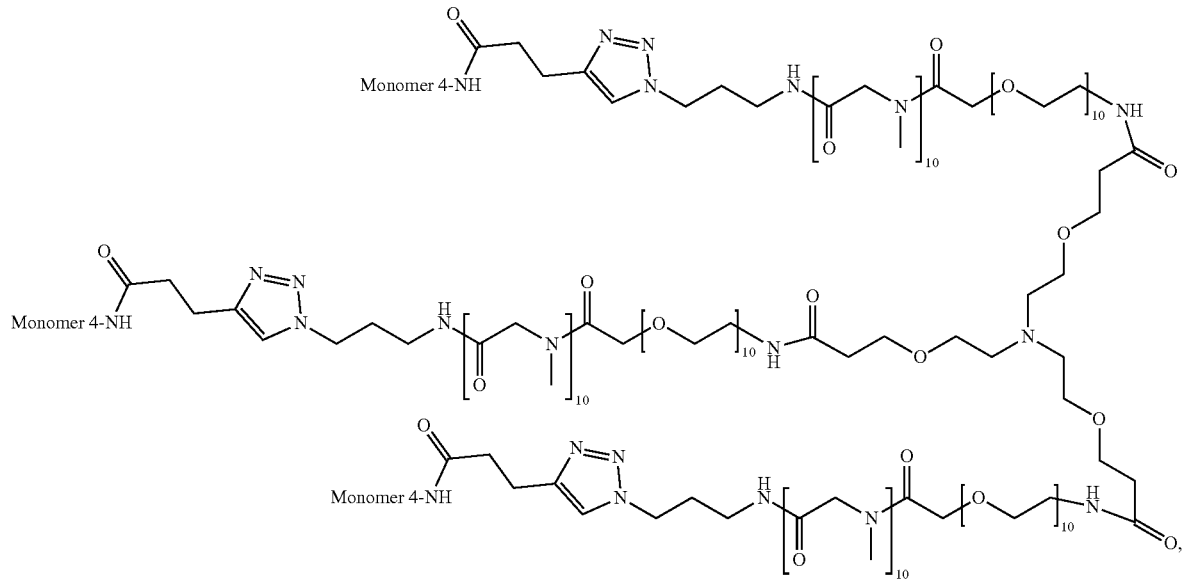
BCY9595
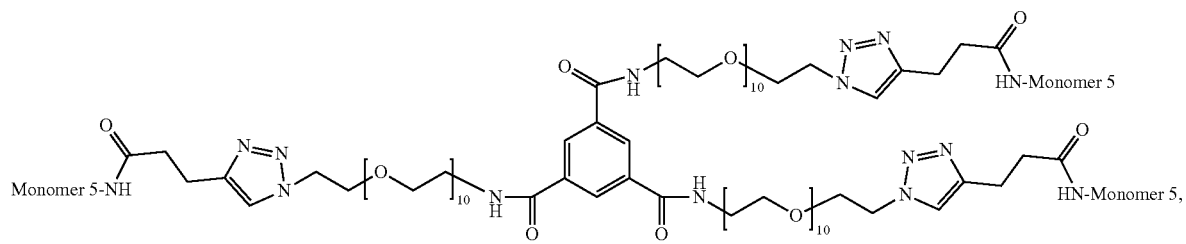
BCY9775
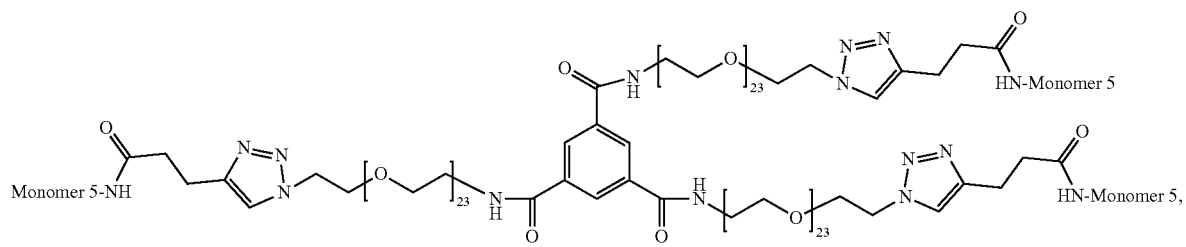
BCY9776
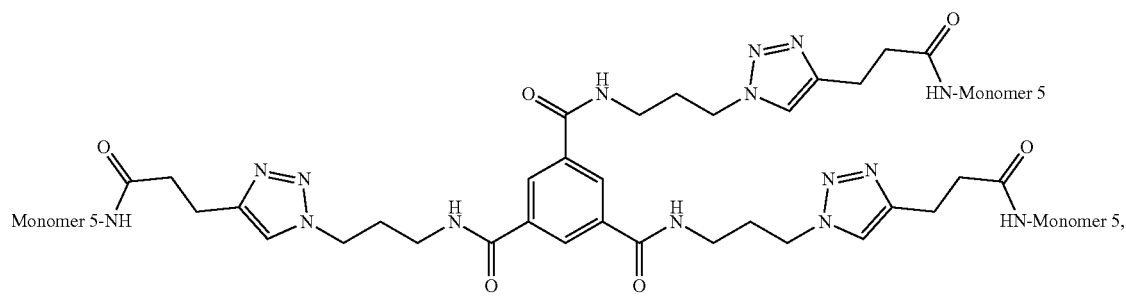
BCY11382

BCY11383
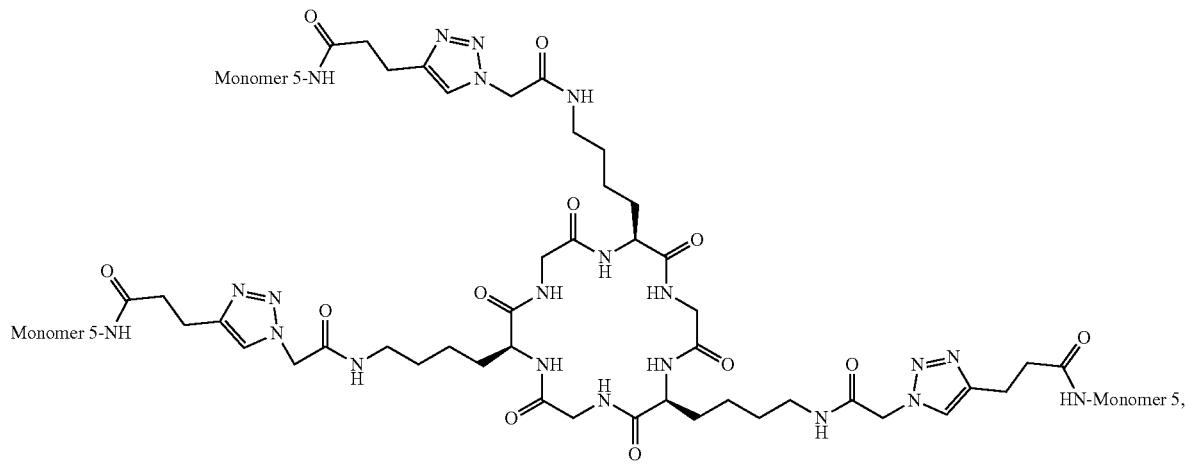
BCY10046
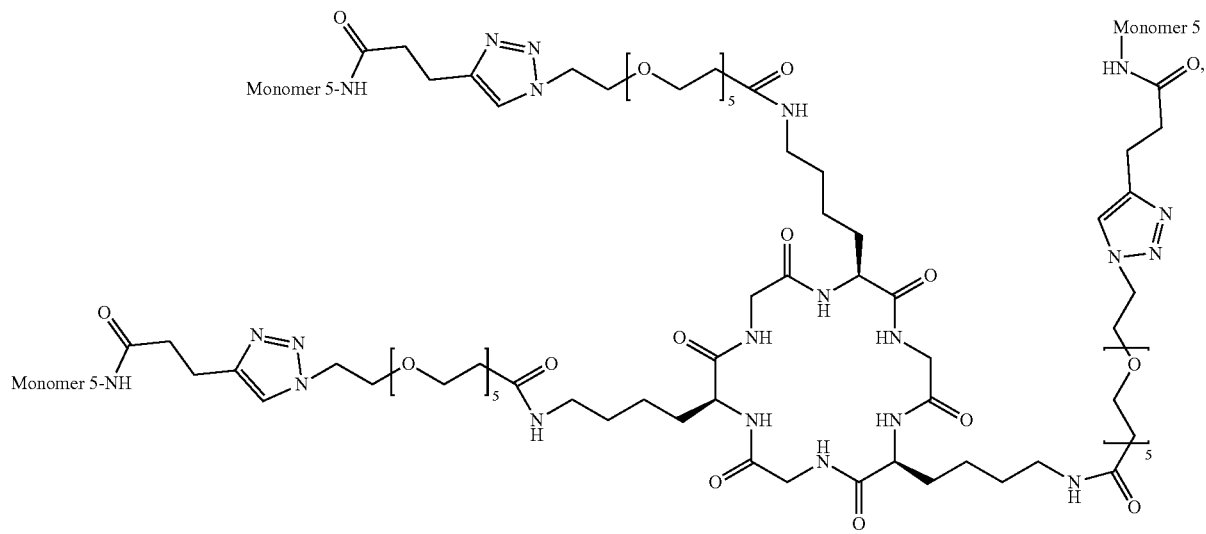
BCY10047
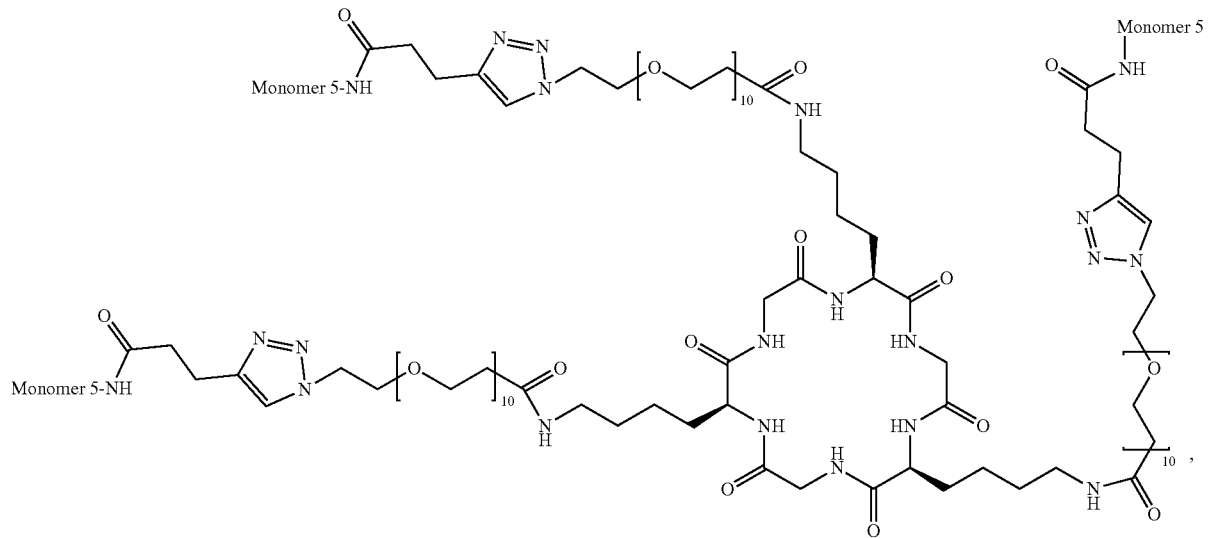
and

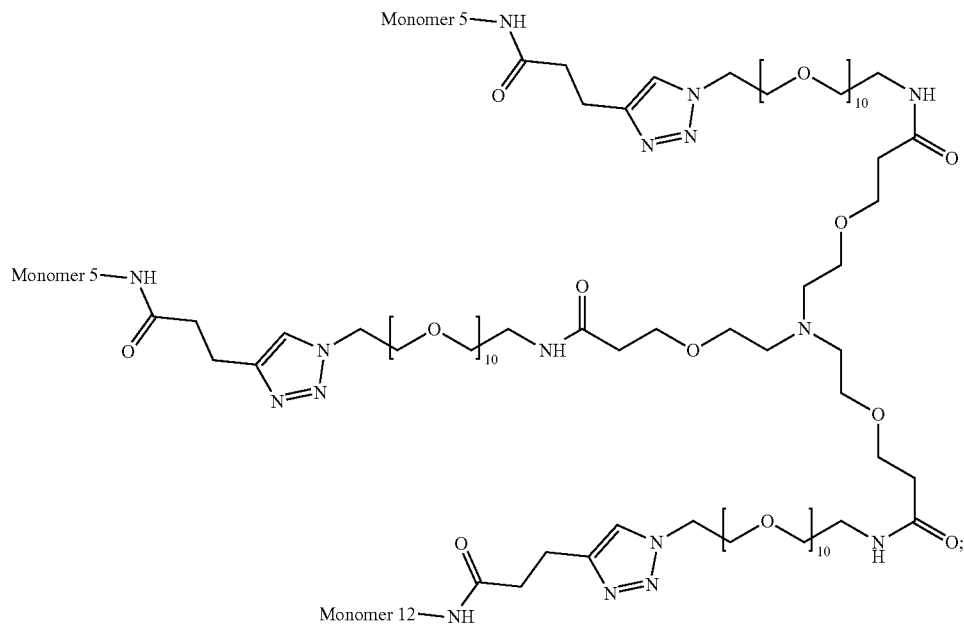
wherein Monomer 1 has a structure:
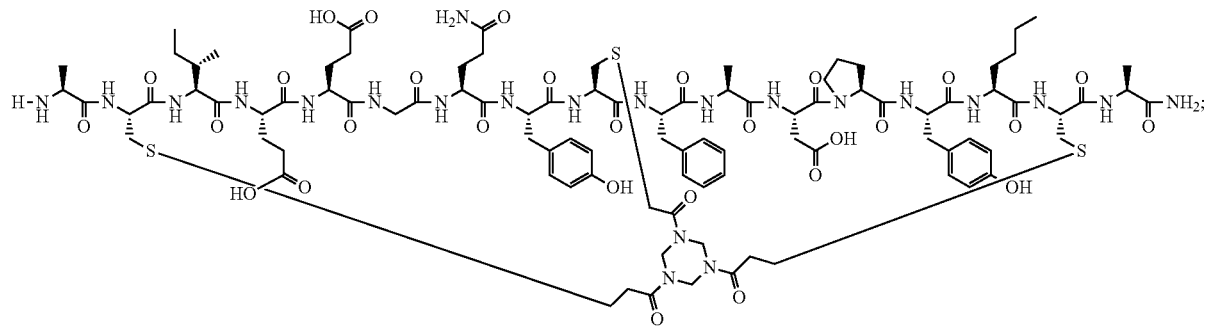 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)N)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 2 has a structure:
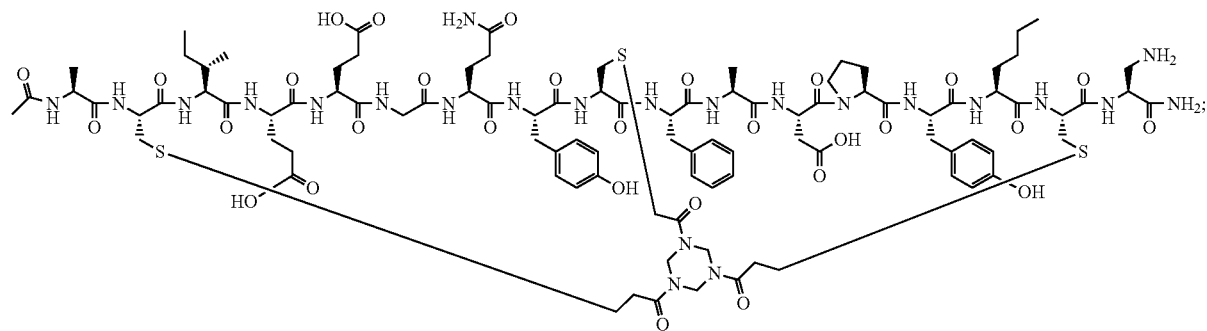 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](CN)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]

wherein Monomer 3 has a structure:
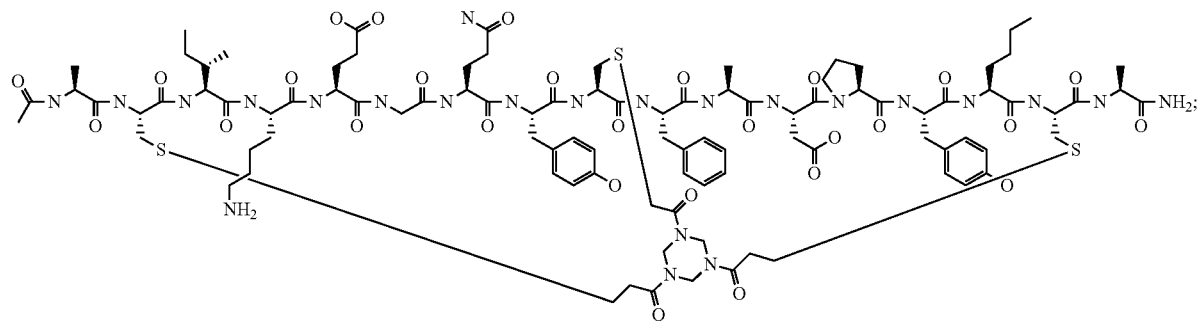 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCCCN)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 4 has a structure:
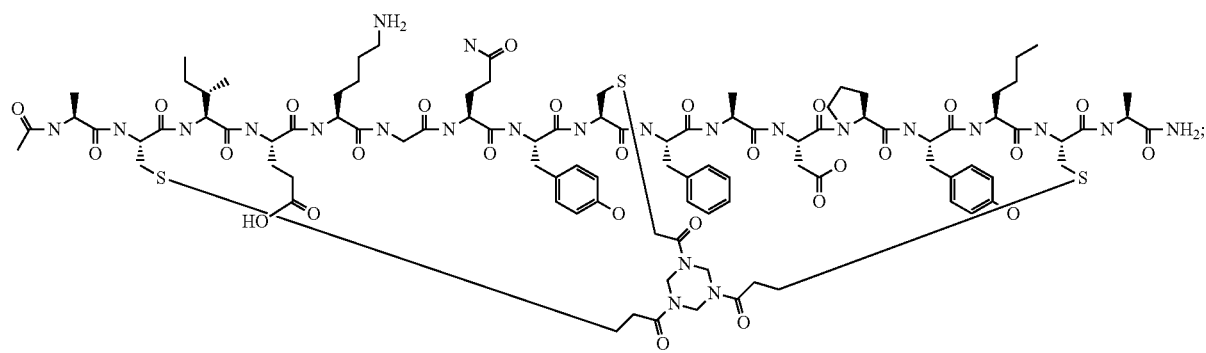 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCCCN)C(=O)NCC(=O)N[C@@H](CCC(N)=O)C(=O)N[C@@H](Cc1ccc(O)cc1)C(=O)N2]
wherein Monomer 5 has a structure:
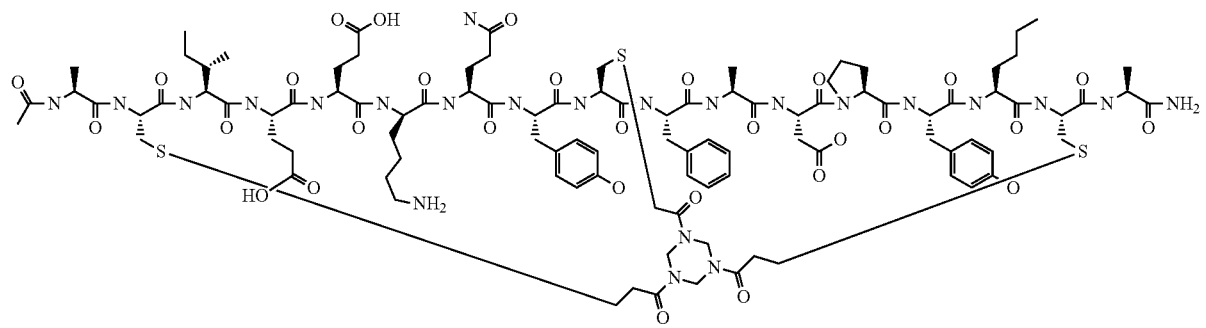 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)N[C@H](CCCCN)C(=O)N[C@@H](CCC(N)=O)C(=O)N[C@@H](Cc1ccc(O)cc1)C(=O)N2]
wherein Monomer 6 has a structure:
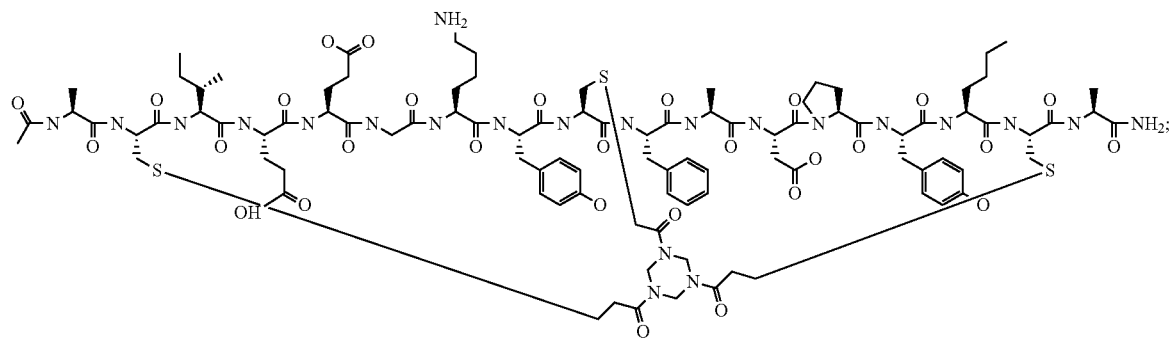 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCCCN)C(=O)N[C@@H](Cc1ccc(O)cc1)C(=O)N2]

wherein Monomer 7 has a structure:
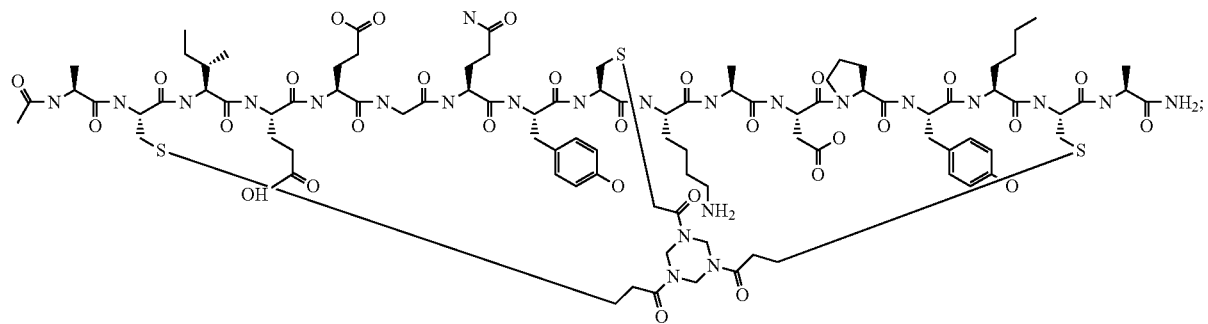 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](CCCCN)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 8 has a structure:
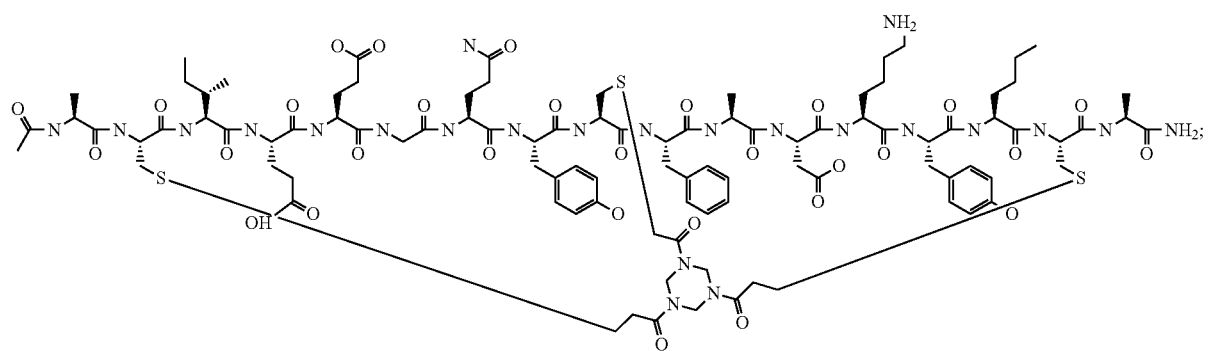 [SMILES: CCCC[C@@H]1NC(=O)[C@H](Cc2ccc(O)cc2)NC(=O)[C@H](CCCCN)NC(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 9 has a structure:
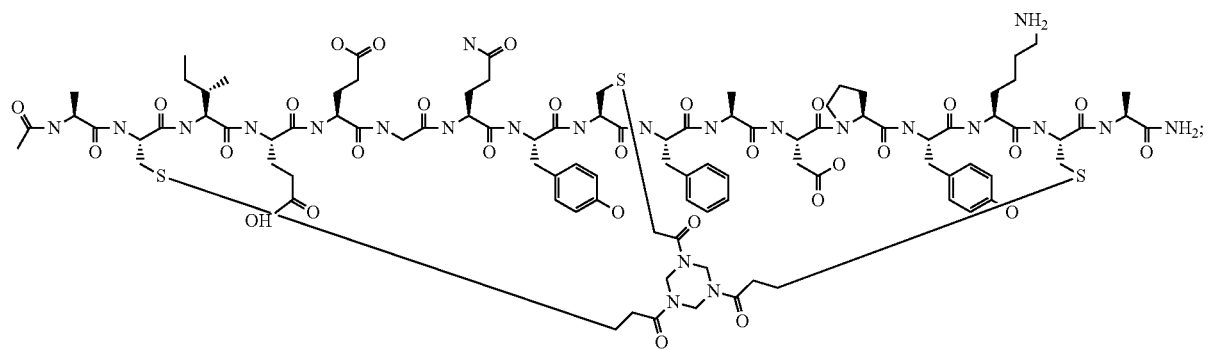 [SMILES: CC[C@H](C)[C@@H]1NC(=O)[C@@H](NC(=O)[C@H](C)NC(C)=O)CSCCC(=O)N2CN3CN(C2)C(=O)CSC[C@H](NC(=O)[C@H](Cc2ccc(O)cc2)NC(=O)[C@H](CCC(N)=O)NC(=O)CNC(=O)[C@H](CCC(=O)O)NC(=O)[C@H](CCC(=O)O)NC1=O)C(=O)N[C@@H](Cc1ccccc1)C(=O)N[C@@H](C)C(=O)N[C@@H](CC(=O)O)C(=O)N1CCC[C@H]1C(=O)N[C@@H](Cc1ccc(O)cc1)C(=O)N[C@@H](CCCCN)C(=O)N[C@H](C(=O)N[C@@H](C)C(N)=O)CSCCC3=O]

and
wherein Monomer 12 has a structure:ke
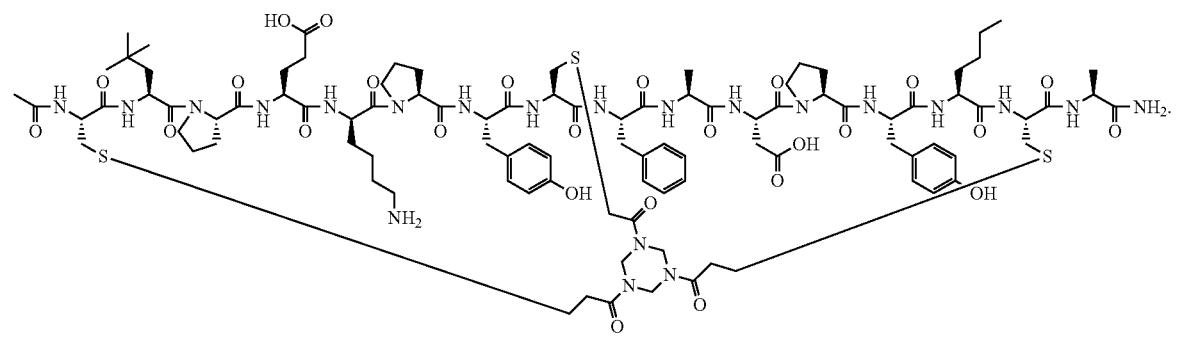 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(C)=O)C(=O)N[C@@H](CC(C)(C)C)C(=O)N1CCC[C@H]1C(=O)N[C@@H](CCC(=O)O)C(=O)N[C@H](CCCCN)C(=O)N1CCC[C@H]1C(=O)N[C@@H](Cc1ccc(O)cc1)C(=O)N2]
20. The multimeric binding complex of claim 1, wherein the multimeric binding complex is selected from:

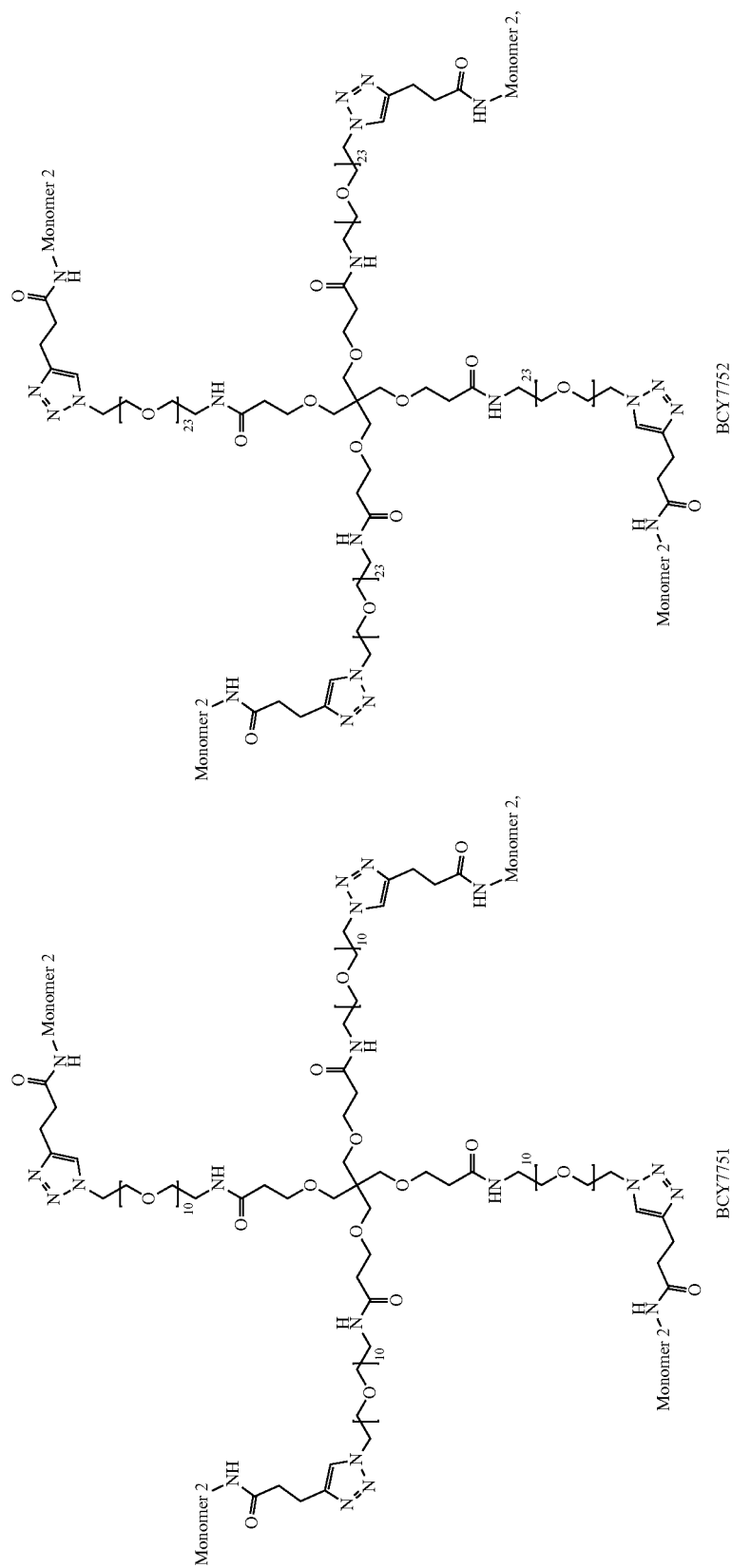

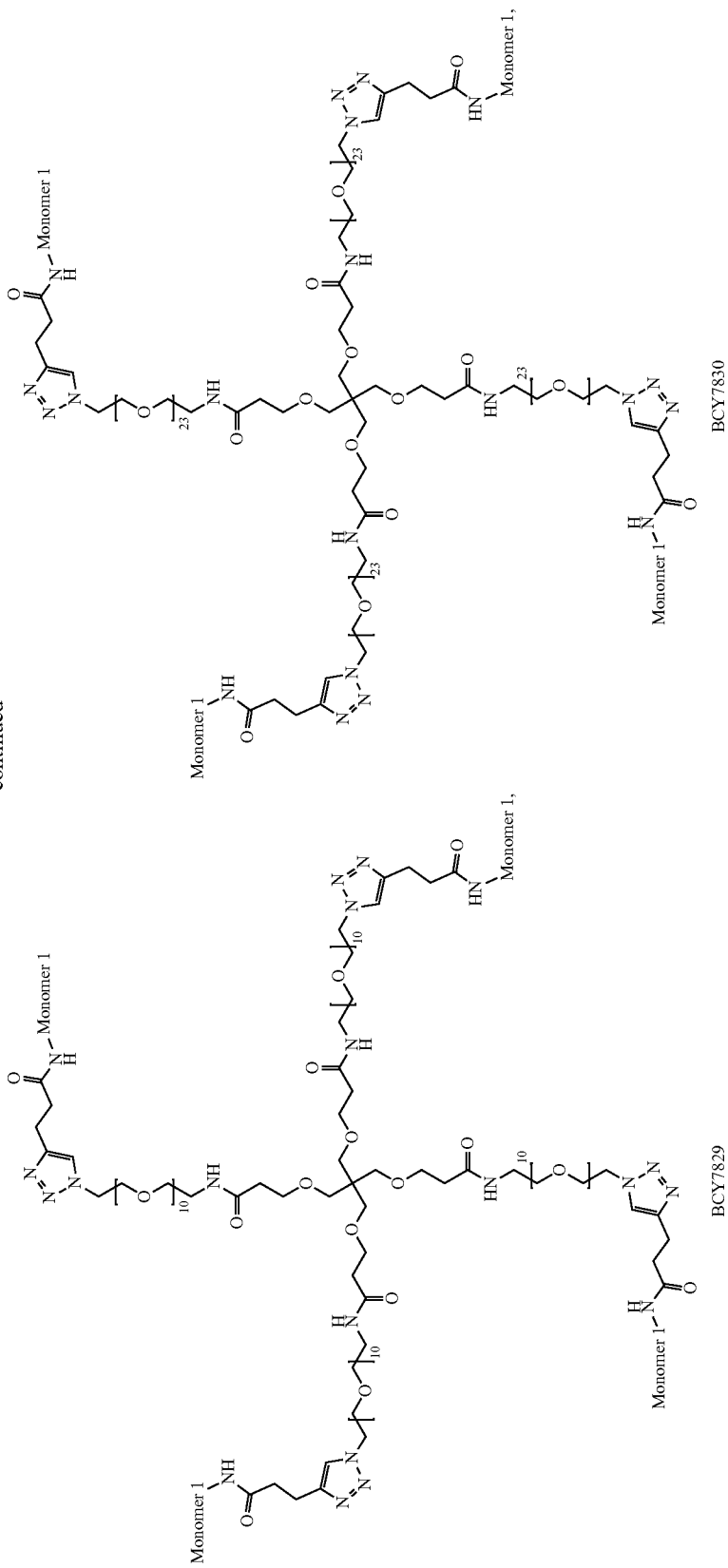

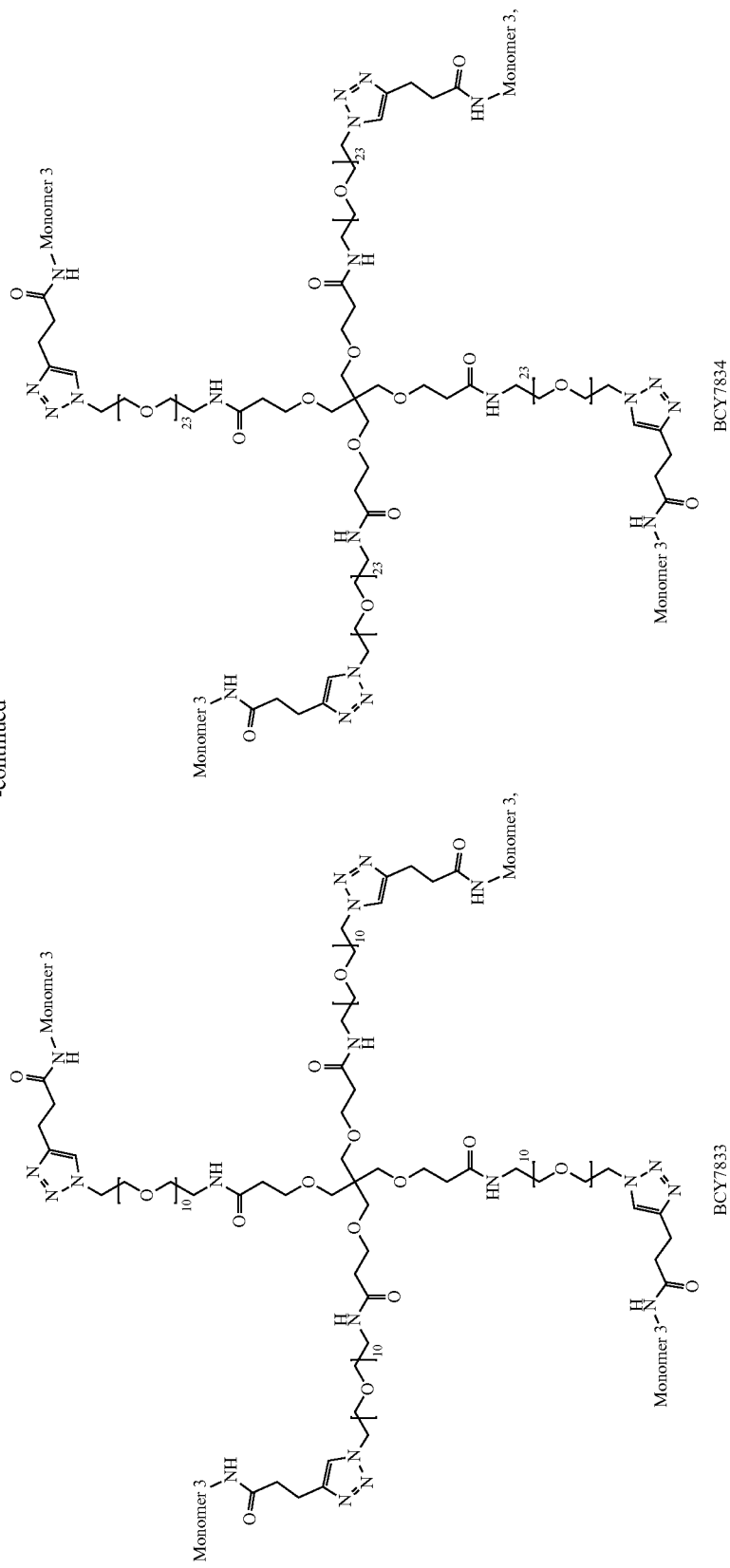

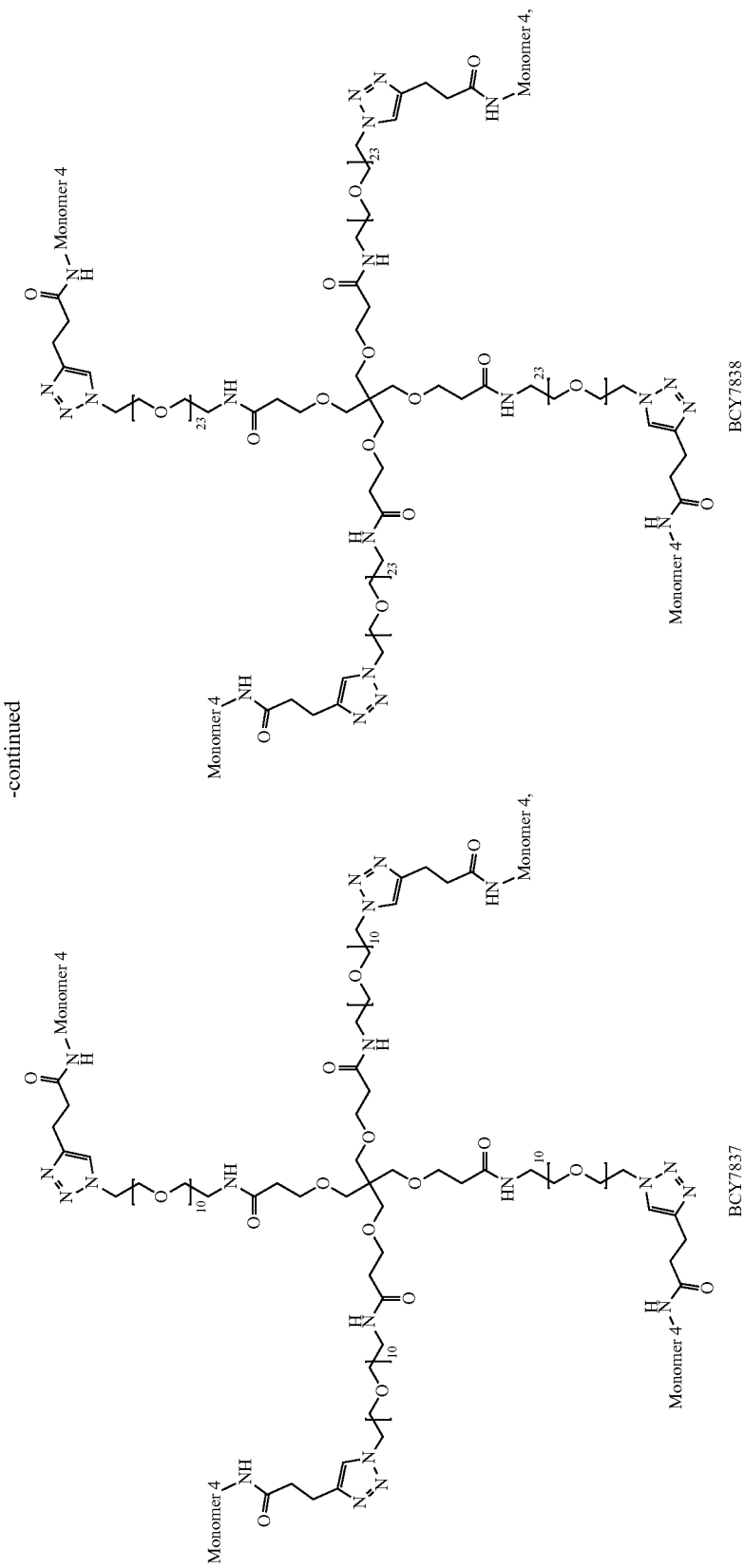

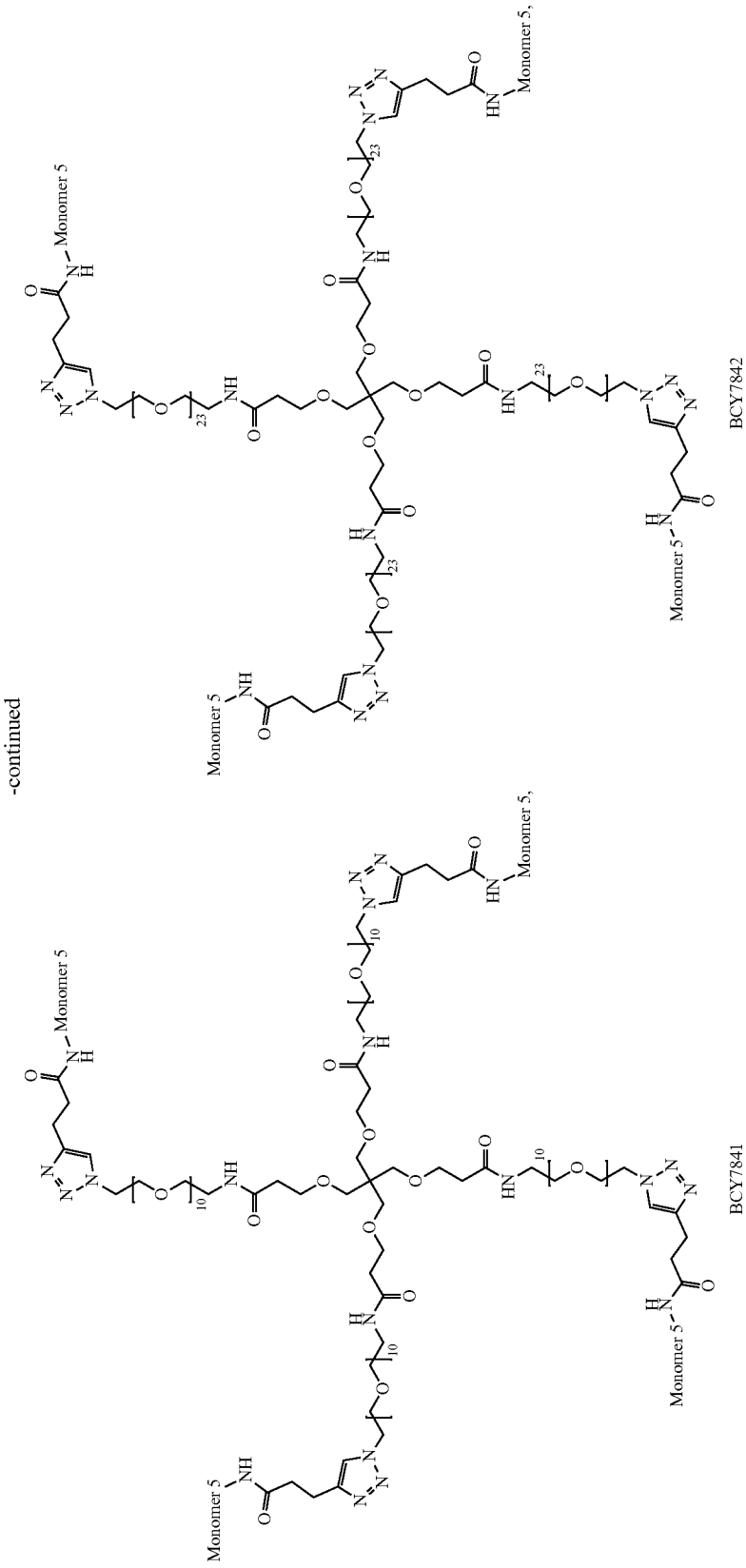

-continued
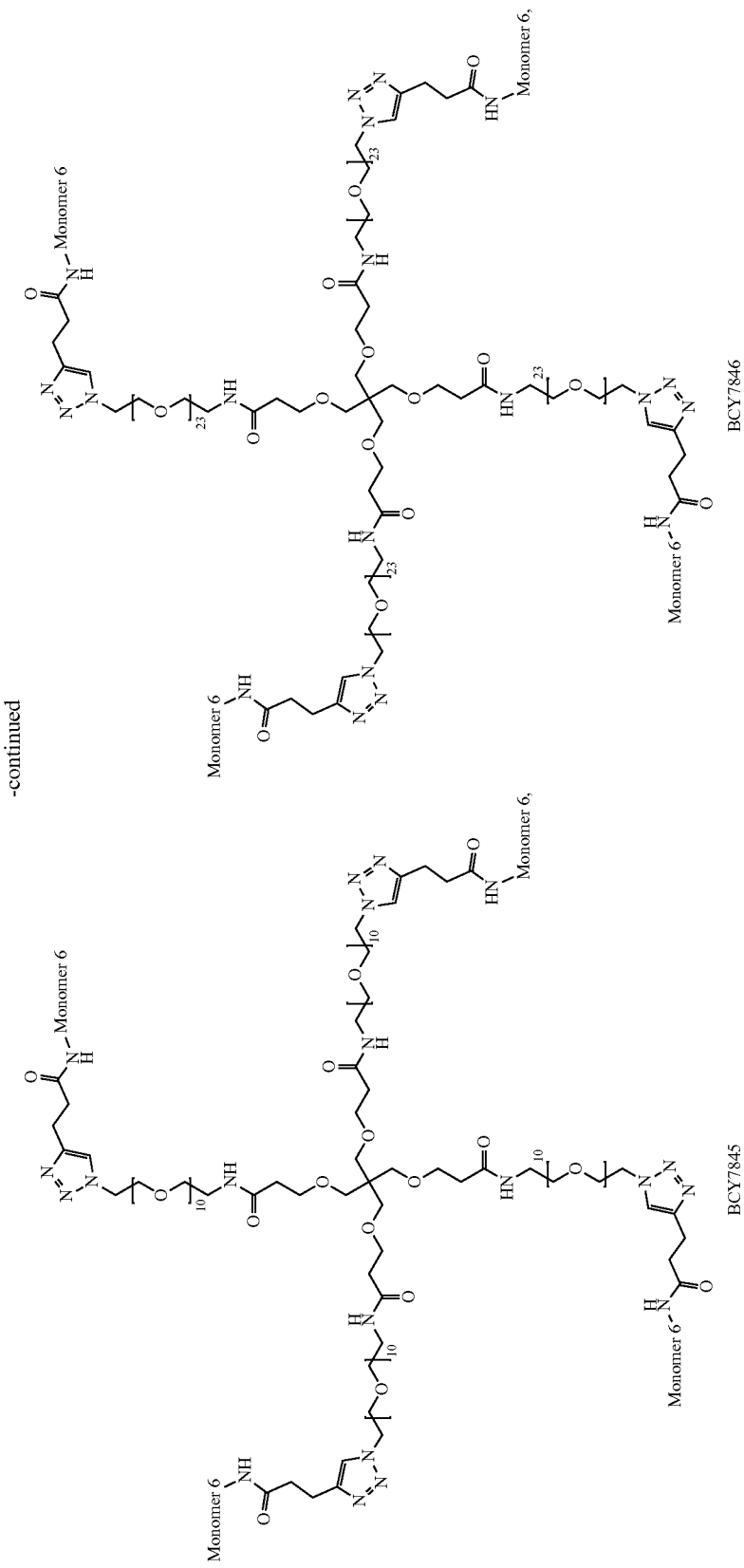

-continued
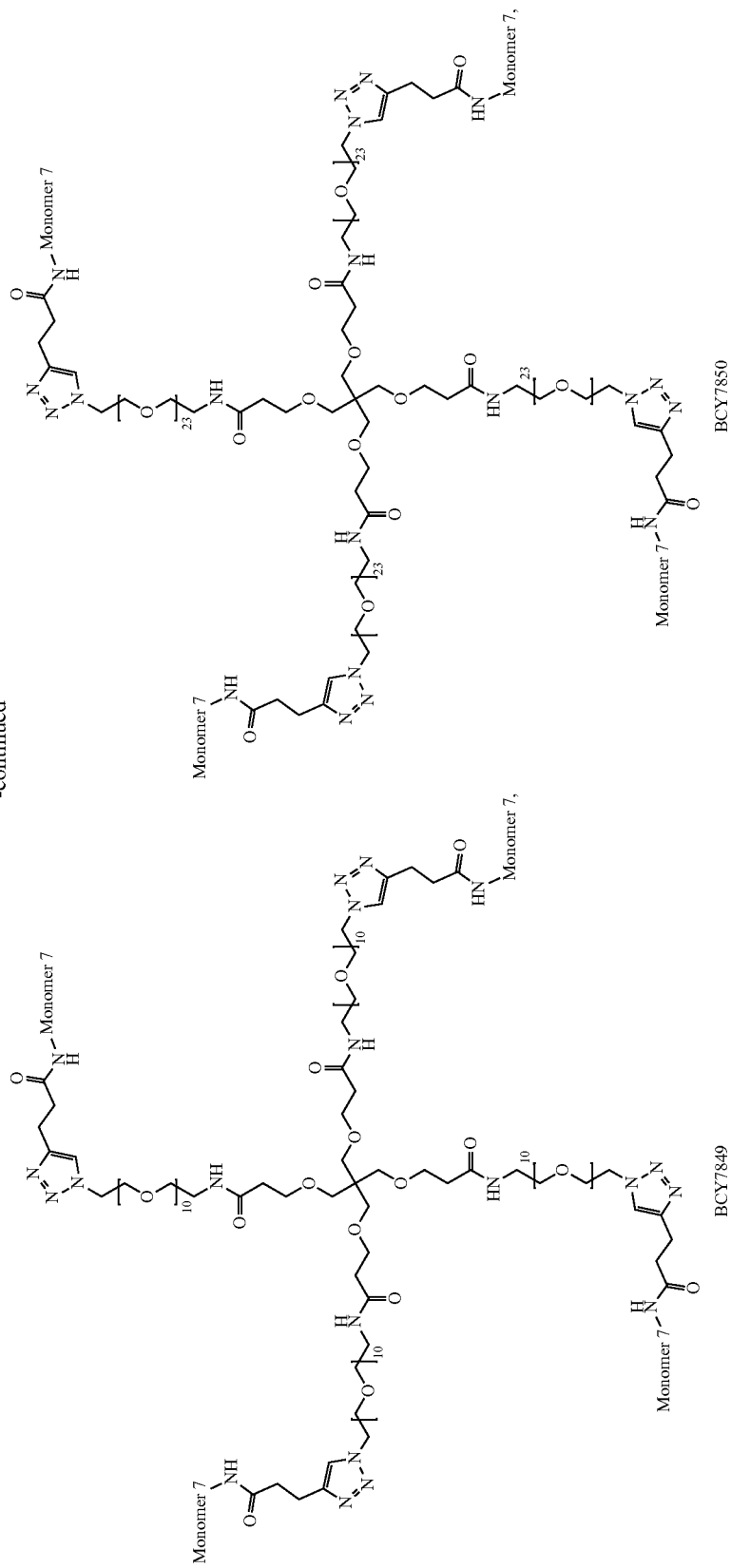

-continued
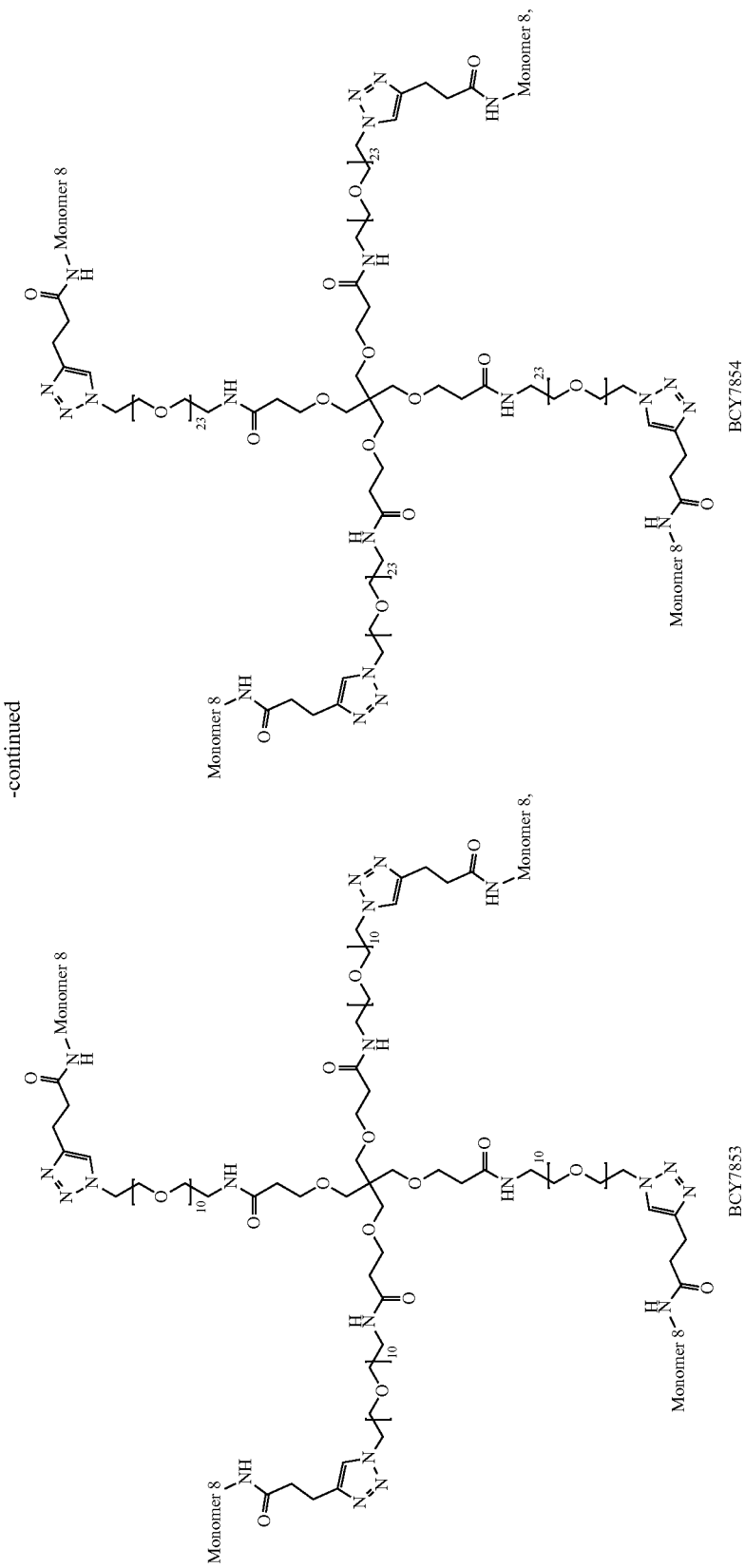

-continued
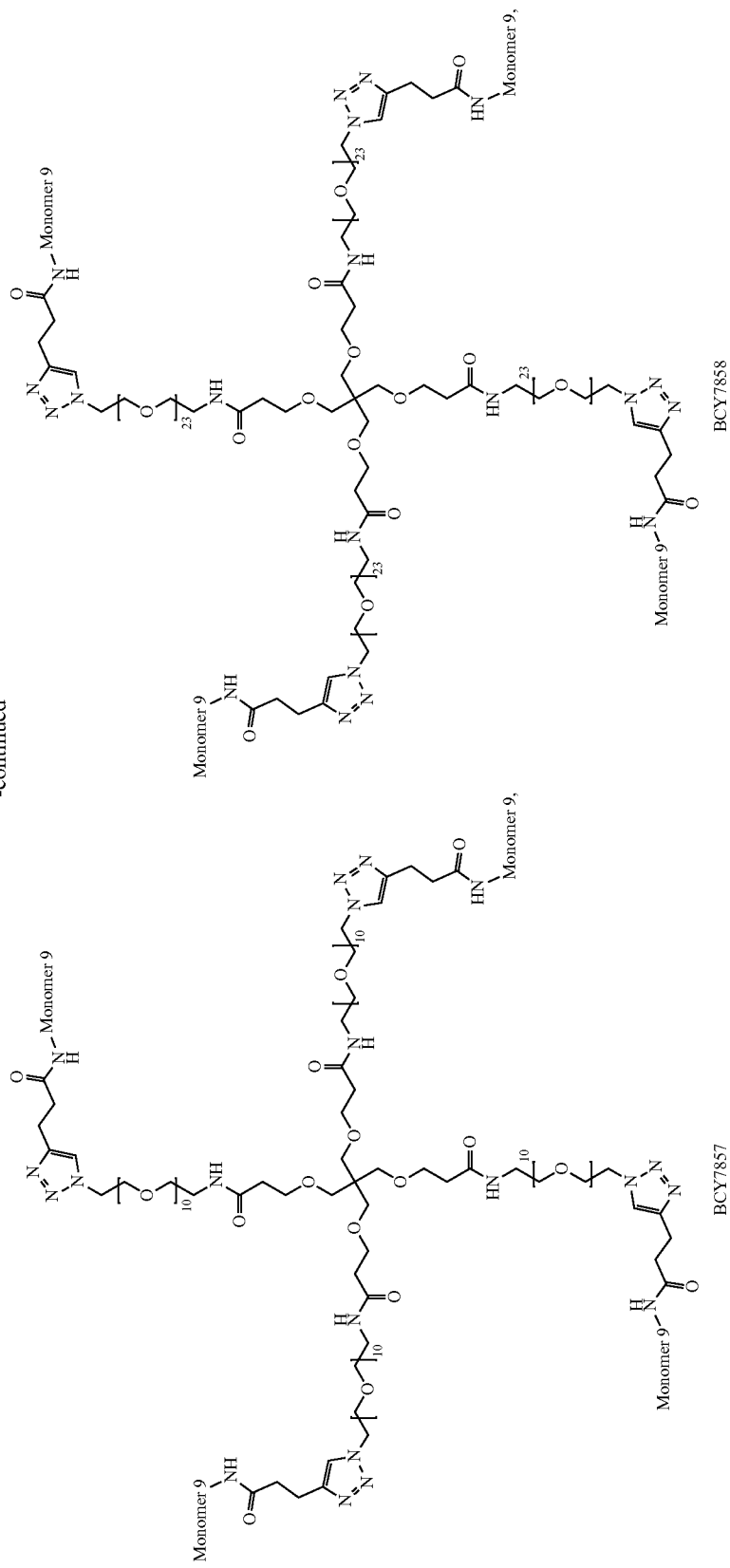

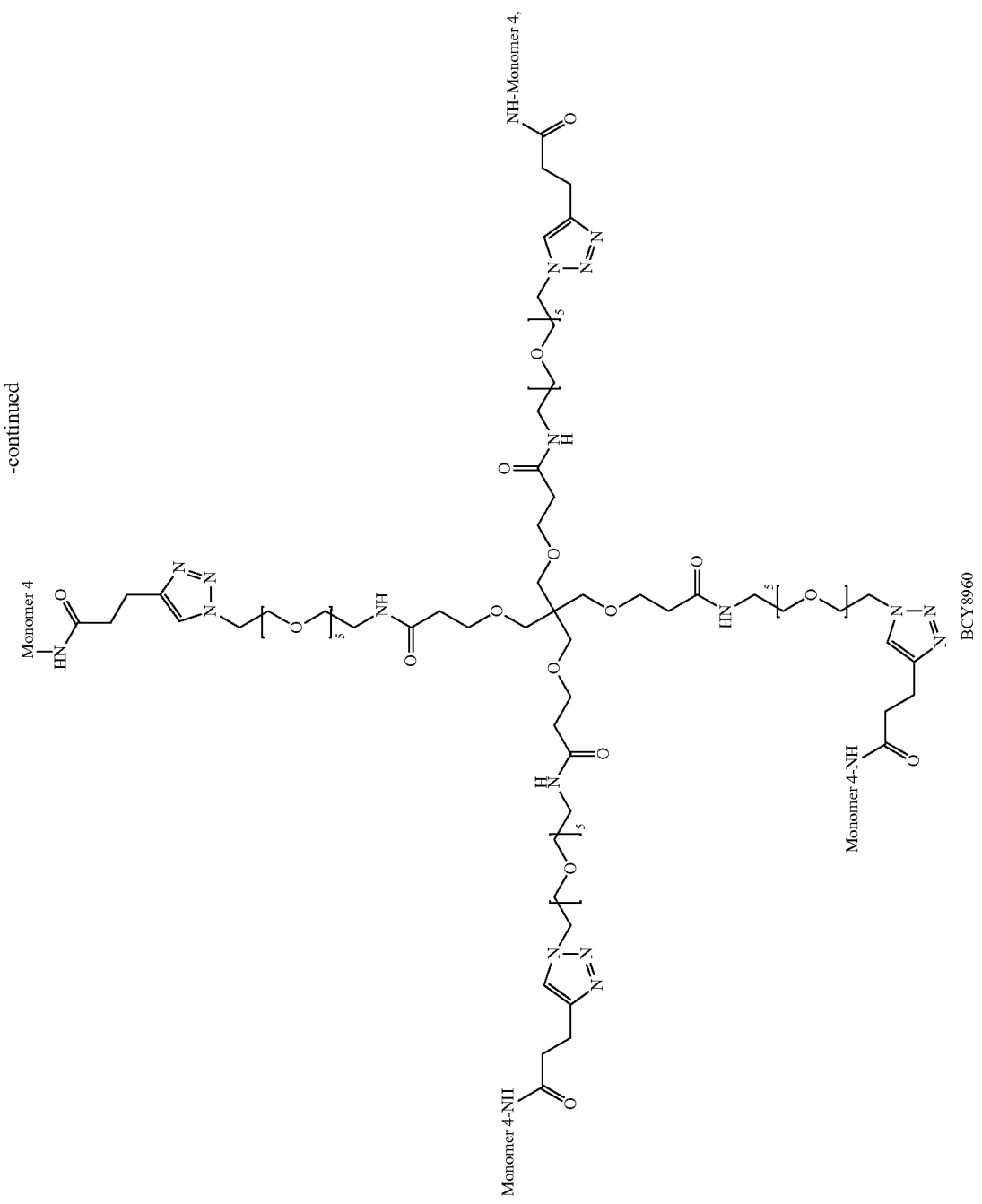

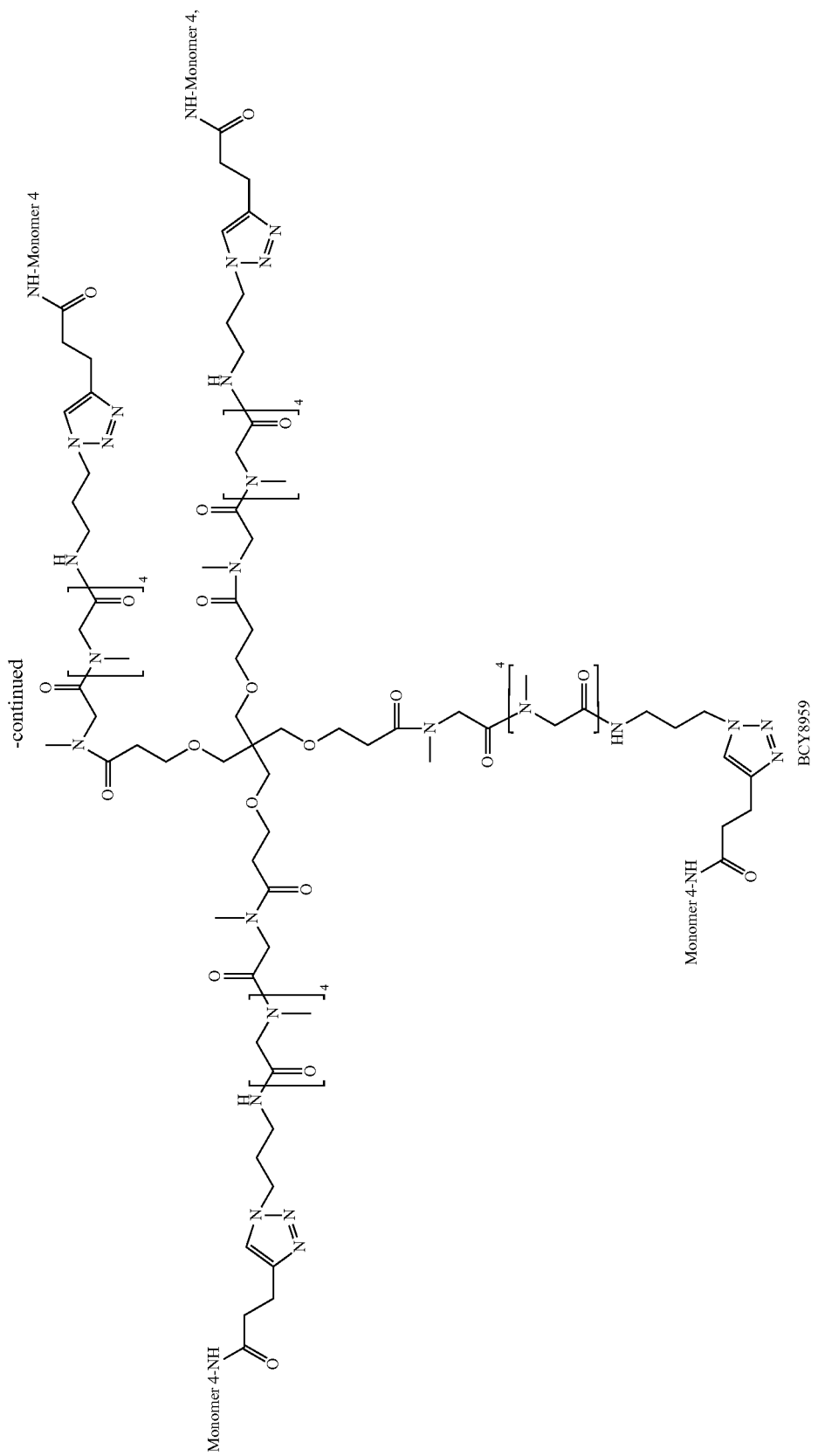

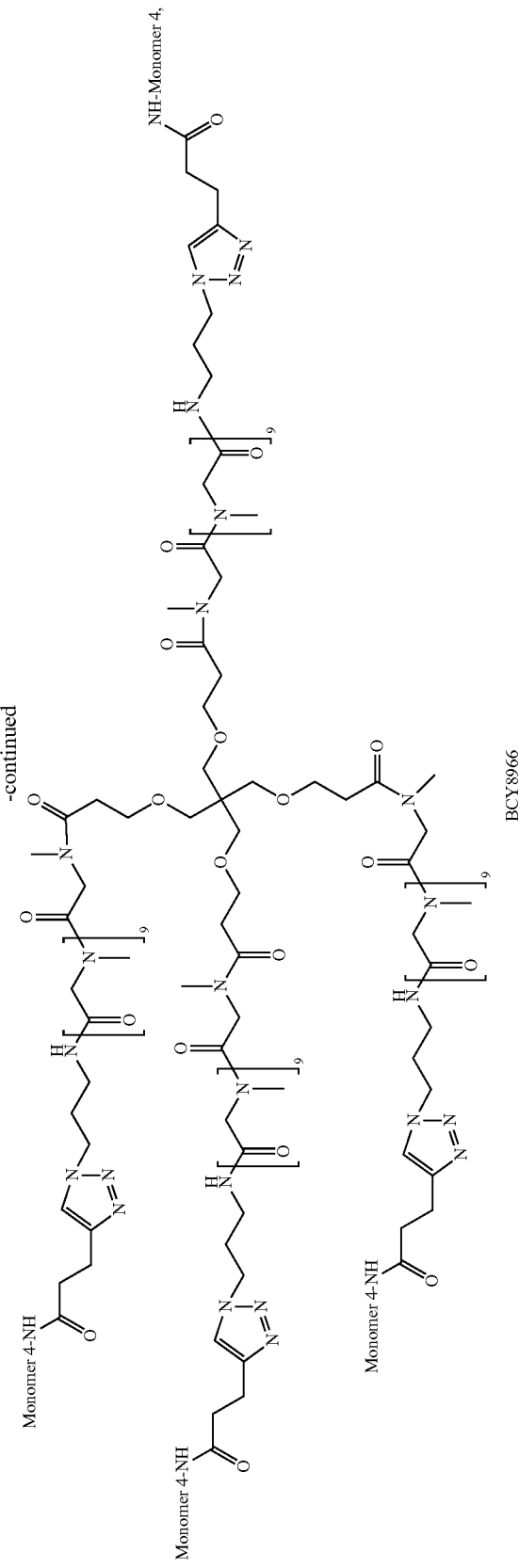

-continued
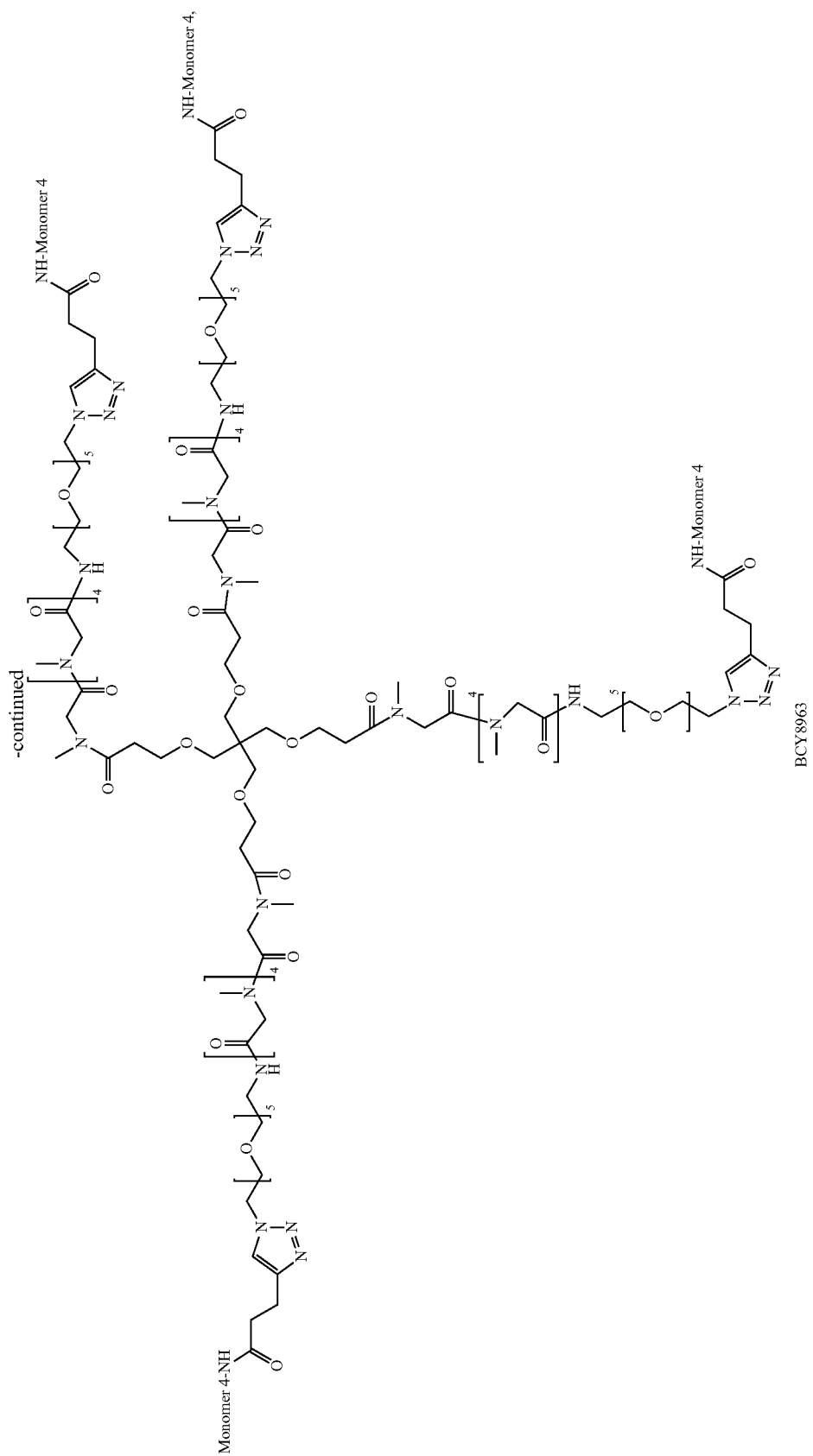

-continued
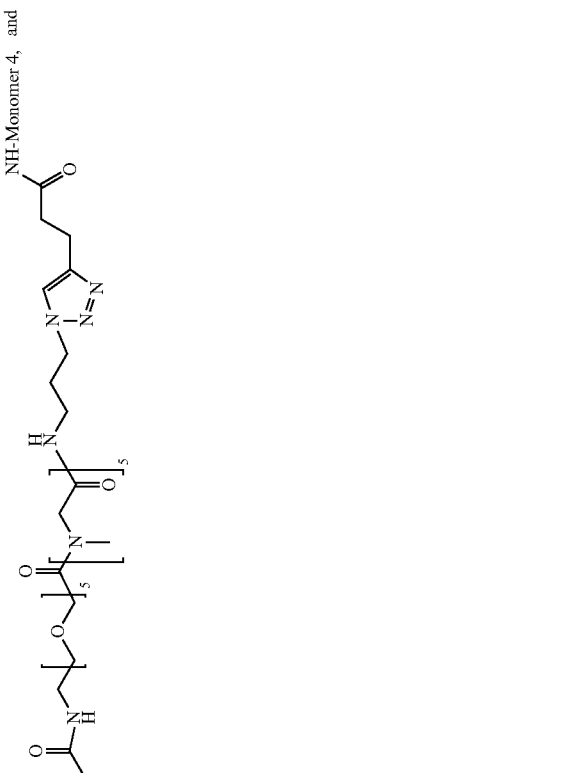
BCY8964

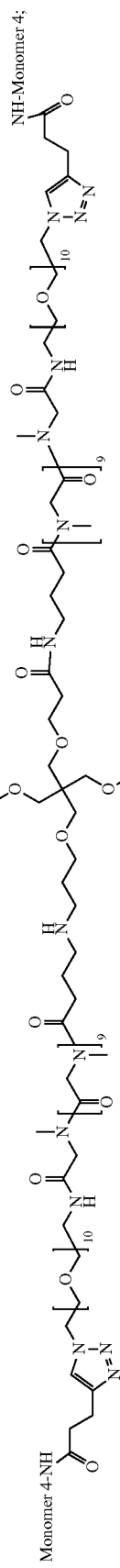

wherein Monomer 1 has a structure:
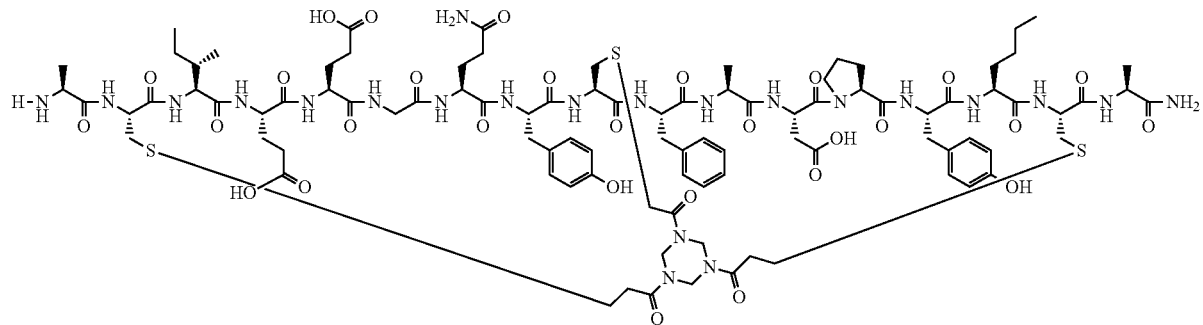 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)N)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 2 has a structure:
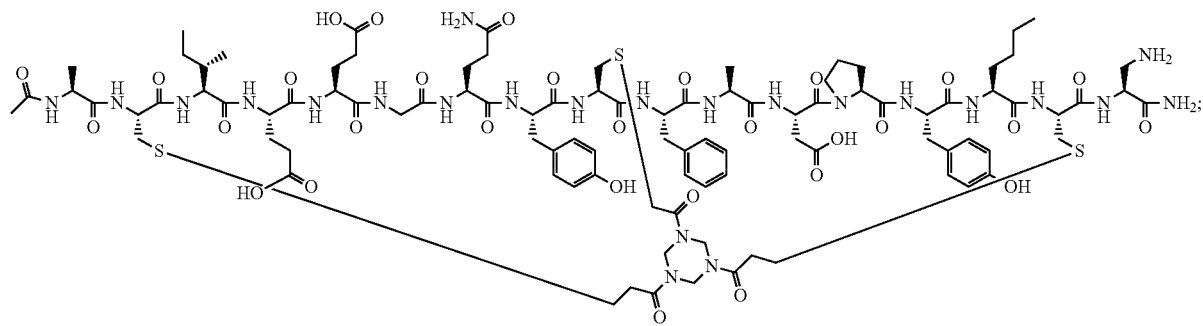 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](CN)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 3 has a structure:
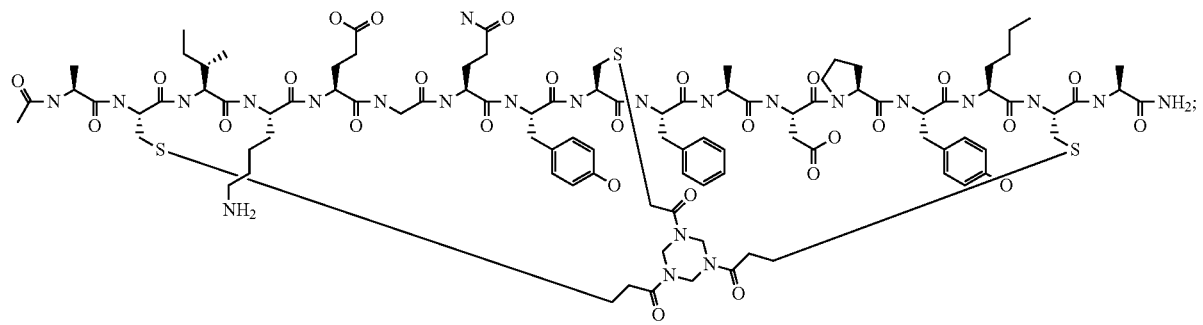 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCCCN)C(=O)N[C@@H](CCC(=O)O)C(=O)NCC(=O)N[C@@H](CCC(N)=O)C(=O)N[C@@H](Cc1ccc(O)cc1)C(=O)N2]
wherein Monomer 4 has a structure:
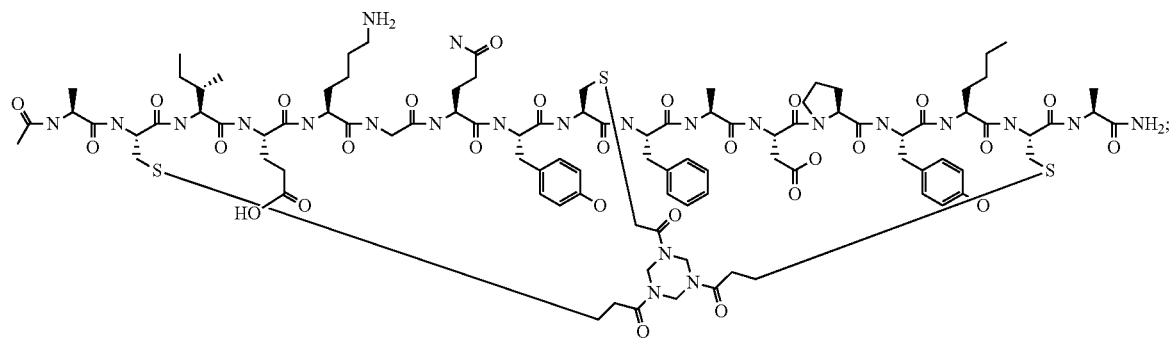 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCCCN)C(=O)NCC(=O)N[C@@H](CCC(N)=O)C(=O)N[C@@H](Cc1ccc(O)cc1)C(=O)N2]

wherein Monomer 5 has a structure:
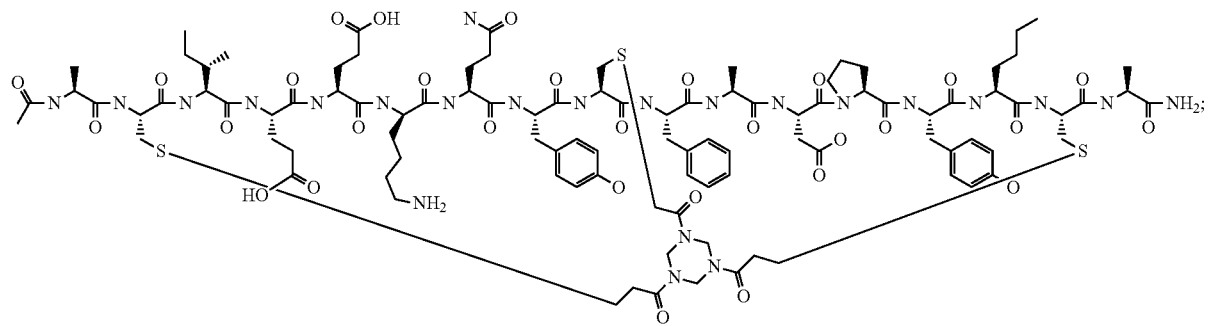 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)N[C@H](CCCCN)C(=O)N[C@@H](CCC(N)=O)C(=O)N[C@@H](Cc1ccc(O)cc1)C(=O)N2]
wherein Monomer 6 has a structure:
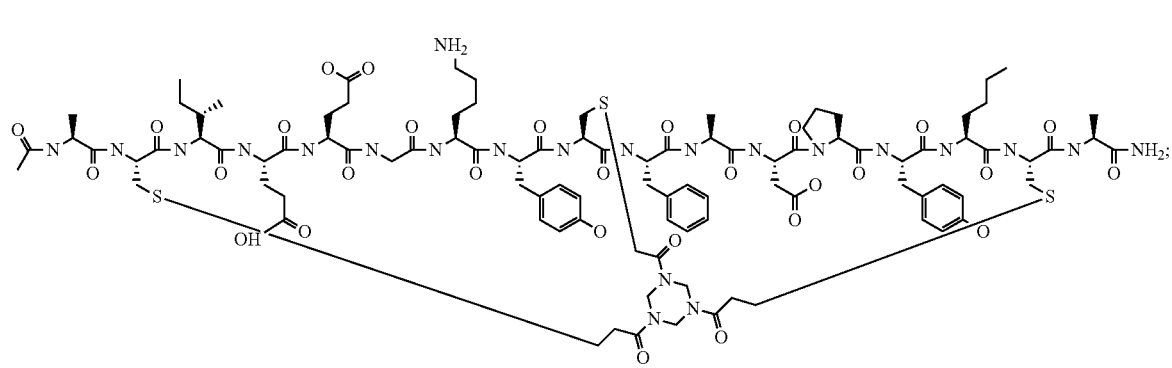 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCCCN)C(=O)N[C@@H](Cc1ccc(O)cc1)C(=O)N2]
wherein Monomer 7 has a structure:
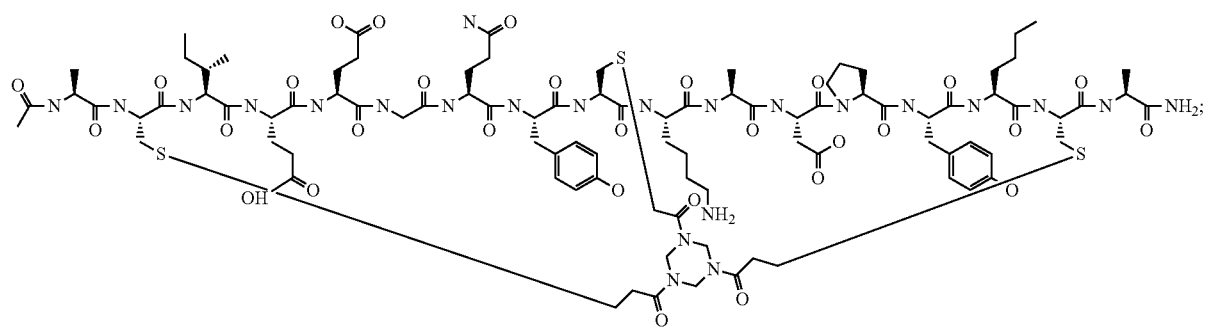 [SMILES: CCCC[C@@H]1NC(=O)[C@H](Cc2ccc(O)cc2)NC(=O)[C@@H]2CCCN2C(=O)[C@H](CC(=O)O)NC(=O)[C@H](C)NC(=O)[C@H](CCCCN)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]
wherein monomer 8 has a structure:
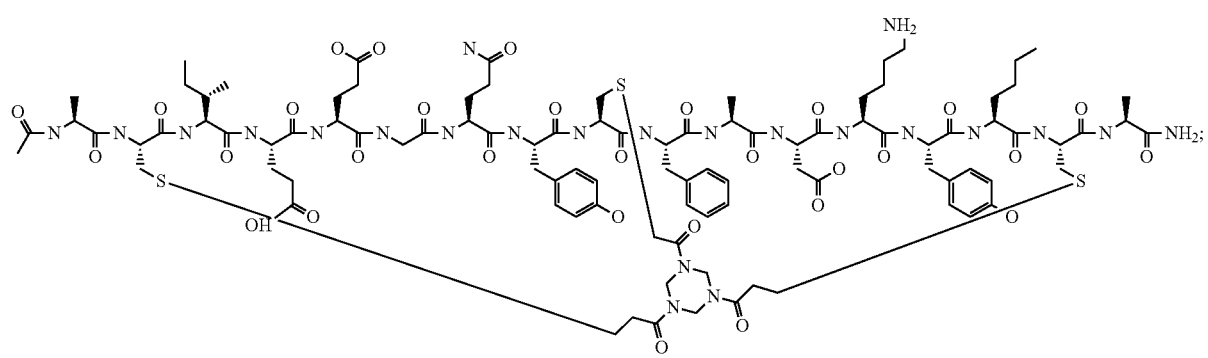 [SMILES: CCCC[C@@H]1NC(=O)[C@H](Cc2ccc(O)cc2)NC(=O)[C@H](CCCCN)NC(=O)[C@H](CC(=O)O)NC(=O)[C@H](C)NC(=O)[C@H](Cc2ccccc2)NC(=O)[C@@H]2CSCC(=O)N3CN(CN(C3)C(=O)CCSC[C@@H](C(=O)N[C@@H](C)C(N)=O)NC1=O)C(=O)CCSC[C@H](NC(=O)[C@H](C)NC(C)=O)C(=O)N[C@@H]([C@@H](C)CC)C(=O)N[C@@H](CCC(=O)O)C(=O)N[C@@H](CCC(=O)O)C(=O)NCC(=O)N[C@@H](CCC(N)=O)C(=O)N[C@@H](Cc1ccc(O)cc1)C(=O)N2]

and
wherein Monomer 9 has a structure:

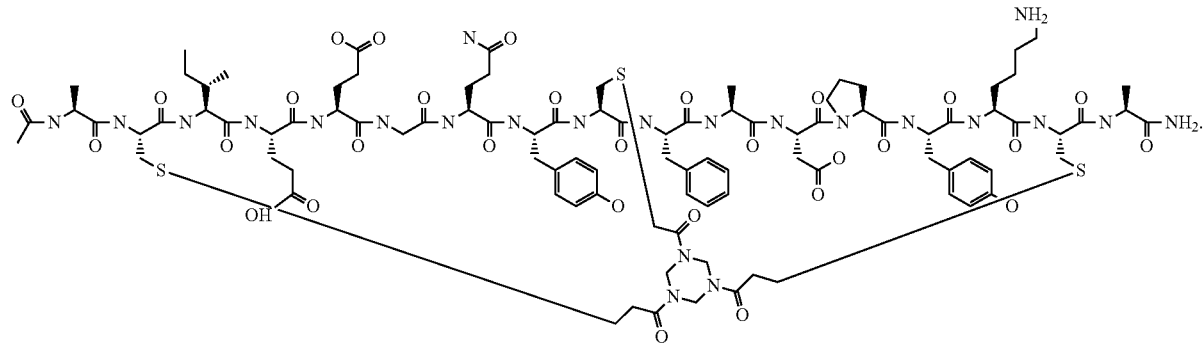 [SMILES: CC[C@H](C)[C@@H]1NC(=O)[C@@H](NC(=O)[C@H](C)NC(C)=O)CSCCC(=O)N2CN3CN(C2)C(=O)CSC[C@H](NC(=O)[C@H](Cc2ccc(O)cc2)NC(=O)[C@H](CCC(N)=O)NC(=O)CNC(=O)[C@H](CCC(=O)O)NC(=O)[C@H](CCC(=O)O)NC1=O)C(=O)N[C@@H](Cc1ccccc1)C(=O)N[C@@H](C)C(=O)N[C@@H](CC(=O)O)C(=O)N1CCC[C@H]1C(=O)N[C@@H](Cc1ccc(O)cc1)C(=O)N[C@@H](CCCCN)C(=O)N[C@H](C(=O)N[C@@H](C)C(N)=O)CSCCC3=O]

21. A pharmaceutical composition comprising the multimeric binding complex of claim 1 in combination with one or more pharmaceutically acceptable excipients.

22. The multimeric binding complex of claim 1, wherein the multimeric binding complex comprises an amino acid sequence selected from: Ac-C$_i$[tBuAla]PK(PYA)[D-A]PYC$_{ii}$FADPY[Nle]C$_{iii}$-A (SEQ ID NO: 65) and Ac-A-C$_i$IEE(D-K)(PYA)QYC$_{ii}$FADPY(Nle)C$_{iii}$-A (SEQ ID NO: 44).

23. The multimeric binding complex of claim 1, wherein the multimeric binding complex comprises the following amino acid sequence: Ac-C$_i$[tBuAla]PK(PYA)[D-A]PYC$_{ii}$FADPY[Nle]C$_{iii}$-A (SEQ ID NO: 65).

24. The multimeric binding complex of claim 1, wherein the multimeric binding complex comprises the following amino acid sequence: Ac-A-C$_i$IEE(D-K)(PYA)QYC$_{ii}$FADPY(Nle)C$_{iii}$-A (SEQ ID NO: 44).

25. The multimeric binding complex of claim 1, wherein all bicyclic peptide ligands in the multimeric binding complex are the same.

26. The multimeric binding complex of claim 1, wherein the multimeric binding complex comprises four bicyclic peptide ligands.

27. The multimeric binding complex of claim 1, wherein the spacer group is S$_1$A:

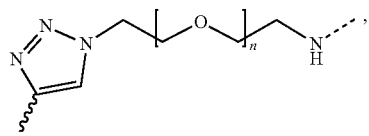

n = 5, 10, or 23 wherein:
"-----" represents a point of attachment to the central hinge moiety (CHM); and
"∿∿∿" represents a point of attachment to the Bicycle;
and wherein the central hinge moiety is central hinge moiety A:

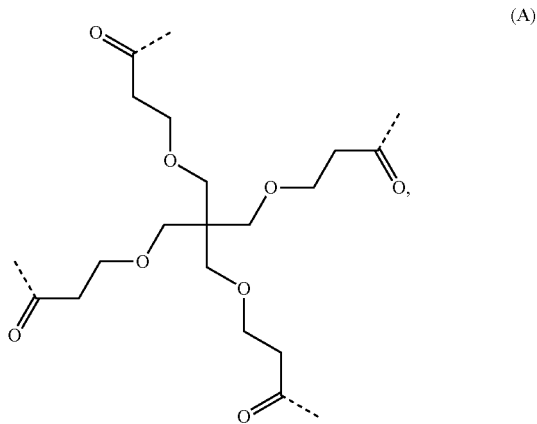

(A)

wherein "-----" represents the point of attachment to each S$_1$ group.

28. A conjugate comprising the multimeric binding complex of claim 1 conjugated to one or more effector and/or functional groups.

29. The conjugate of claim 28, wherein the effector group is a cytotoxic agent, a radiochelator or a chromophore, and/or wherein the functional group is a metal chelator.

* * * * *

SEQUENCE LISTING

```
Sequence total quantity: 69
SEQ ID NO: 1            moltype = AA  length = 15
FEATURE                 Location/Qualifiers
REGION                  1..15
                        note = Synthetic peptide
source                  1..15
                        mol_type = protein
                        organism = synthetic construct
SEQUENCE: 1
CIEEGQYCYR DMYMC                                                         15

SEQ ID NO: 2            moltype = AA  length = 15
FEATURE                 Location/Qualifiers
REGION                  1..15
                        note = Synthetic peptide
source                  1..15
                        mol_type = protein
                        organism = synthetic construct
SEQUENCE: 2
CIEEGQYCYA DPYMC                                                         15

SEQ ID NO: 3            moltype = AA  length = 15
FEATURE                 Location/Qualifiers
REGION                  1..15
                        note = Synthetic peptide
source                  1..15
                        mol_type = protein
                        organism = synthetic construct
SEQUENCE: 3
CIEEGQYCYA DPYYC                                                         15

SEQ ID NO: 4            moltype = AA  length = 15
FEATURE                 Location/Qualifiers
REGION                  1..15
                        note = Synthetic peptide
source                  1..15
                        mol_type = protein
                        organism = synthetic construct
SEQUENCE: 4
CIEEGQYCYS DPYYC                                                         15

SEQ ID NO: 5            moltype = AA  length = 15
FEATURE                 Location/Qualifiers
REGION                  1..15
                        note = Synthetic peptide
source                  1..15
```

```
                        mol_type = protein
                        organism = synthetic construct
SEQUENCE: 5
CIEEGQYCFA DPYMC                                                         15

SEQ ID NO: 6            moltype = AA   length = 15
FEATURE                 Location/Qualifiers
REGION                  1..15
                        note = Synthetic peptide
source                  1..15
                        mol_type = protein
                        organism = synthetic construct
SEQUENCE: 6
CIEEGQYCYA DHQLC                                                         15

SEQ ID NO: 7            moltype = AA   length = 15
FEATURE                 Location/Qualifiers
REGION                  1..15
                        note = Synthetic peptide
source                  1..15
                        mol_type = protein
                        organism = synthetic construct
SEQUENCE: 7
CIEEGQYCHA DPYYC                                                         15

SEQ ID NO: 8            moltype = AA   length = 15
FEATURE                 Location/Qualifiers
REGION                  1..15
                        note = Synthetic peptide
source                  1..15
                        mol_type = protein
                        organism = synthetic construct
SEQUENCE: 8
CIEEGQYCHA DPYFC                                                         15

SEQ ID NO: 9            moltype = AA   length = 15
FEATURE                 Location/Qualifiers
REGION                  1..15
                        note = Synthetic peptide
source                  1..15
                        mol_type = protein
                        organism = synthetic construct
SEQUENCE: 9
CIEEGQYCYA DHYMC                                                         15

SEQ ID NO: 10           moltype = AA   length = 15
FEATURE                 Location/Qualifiers
REGION                  1..15
                        note = Synthetic peptide
source                  1..15
                        mol_type = protein
                        organism = synthetic construct
SEQUENCE: 10
CIEEGQYCYA DPYLC                                                         15

SEQ ID NO: 11           moltype = AA   length = 15
FEATURE                 Location/Qualifiers
REGION                  1..15
                        note = Synthetic peptide
source                  1..15
                        mol_type = protein
                        organism = synthetic construct
SEQUENCE: 11
CIEEGQYCYS DPYLC                                                         15

SEQ ID NO: 12           moltype = AA   length = 15
FEATURE                 Location/Qualifiers
REGION                  1..15
                        note = Synthetic peptide
source                  1..15
                        mol_type = protein
                        organism = synthetic construct
SEQUENCE: 12
CIEEGQYCFA DPYLC                                                         15

SEQ ID NO: 13           moltype = AA   length = 15
FEATURE                 Location/Qualifiers
REGION                  1..15
                        note = Synthetic peptide
```

```
source                  1..15
                        mol_type = protein
                        organism = synthetic construct
SEQUENCE: 13
CIEEGQYCHA DPYMC                                                          15

SEQ ID NO: 14           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 14
CIEEGQYCHA DPQMC                                                          15

SEQ ID NO: 15           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 15
CDIGPPYCYR DMYMC                                                          15

SEQ ID NO: 16           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 16
CDIGPPYCYA DPYMC                                                          15

SEQ ID NO: 17           moltype = AA  length = 14
FEATURE                 Location/Qualifiers
REGION                  1..14
                        note = Synthetic peptide
source                  1..14
                        mol_type = protein
                        organism = synthetic construct
SEQUENCE: 17
CDEWGLFCIP HSDC                                                           14

SEQ ID NO: 18           moltype = AA  length = 14
FEATURE                 Location/Qualifiers
REGION                  1..14
                        note = Synthetic peptide
source                  1..14
                        mol_type = protein
                        organism = synthetic construct
SEQUENCE: 18
CDEWGLYCFA HPDC                                                           14

SEQ ID NO: 19           moltype = AA  length = 15
FEATURE                 Location/Qualifiers
REGION                  1..15
                        note = Synthetic peptide
source                  1..15
                        mol_type = protein
                        organism = synthetic construct
SEQUENCE: 19
CIEPGPFCYA DPYMC                                                          15

SEQ ID NO: 20           moltype = AA  length = 15
FEATURE                 Location/Qualifiers
REGION                  1..15
                        note = Synthetic peptide
VARIANT                 9..10
                        note = X is any amino acid residue
VARIANT                 12
                        note = X is any amino acid residue
VARIANT                 13
                        note = X is Y or Q
VARIANT                 14
                        note = X is any amino acid residue
source                  1..15
```

```
SEQUENCE: 20
CIEEGQYCXX DXXXC                                               15

SEQ ID NO: 21         moltype = AA  length = 15
FEATURE               Location/Qualifiers
REGION                1..15
                      note = Synthetic peptide
VARIANT               10
                      note = X is R or A
VARIANT               12
                      note = X is M or P
source                1..15
                      mol_type = protein
                      organism = synthetic construct
SEQUENCE: 21
CDIGPPYCYX DXYMC                                               15

SEQ ID NO: 22         moltype = AA  length = 14
FEATURE               Location/Qualifiers
REGION                1..14
                      note = Synthetic peptide
VARIANT               7
                      note = X is F or Y
VARIANT               9
                      note = X is I or F
VARIANT               10
                      note = X is P or A
VARIANT               12
                      note = X is S or P
source                1..14
                      mol_type = protein
                      organism = synthetic construct
SEQUENCE: 22
CDEWGLXCXX HXDC                                                14

SEQ ID NO: 23         moltype = AA  length = 15
FEATURE               Location/Qualifiers
REGION                1..15
                      note = Synthetic peptide
SITE                  14
                      note = Nle
source                1..15
                      mol_type = protein
                      organism = synthetic construct
SEQUENCE: 23
CIEEGQYCFA DPYXC                                               15

SEQ ID NO: 24         moltype = AA  length = 15
FEATURE               Location/Qualifiers
REGION                1..15
                      note = Synthetic peptide
SITE                  14
                      note = Nle
source                1..15
                      mol_type = protein
                      organism = synthetic construct
SEQUENCE: 24
CIKEGQYCFA DPYXC                                               15

SEQ ID NO: 25         moltype = AA  length = 15
FEATURE               Location/Qualifiers
REGION                1..15
                      note = Synthetic peptide
SITE                  14
                      note = Nle
source                1..15
                      mol_type = protein
                      organism = synthetic construct
SEQUENCE: 25
CIEKGQYCFA DPYXC                                               15

SEQ ID NO: 26         moltype = AA  length = 15
FEATURE               Location/Qualifiers
REGION                1..15
                      note = Synthetic peptide
SITE                  5
                      note = X is D-Lysine
```

```
SITE                      14
                          note = Nle
source                    1..15
                          mol_type = protein
                          organism = synthetic construct
SEQUENCE: 26
CIEEXQYCFA DPYXC                                                                    15

SEQ ID NO: 27             moltype = AA  length = 15
FEATURE                   Location/Qualifiers
REGION                    1..15
                          note = Synthetic peptide
SITE                      14
                          note = Nle
source                    1..15
                          mol_type = protein
                          organism = synthetic construct
SEQUENCE: 27
CIEEGKYCFA DPYXC                                                                    15

SEQ ID NO: 28             moltype = AA  length = 15
FEATURE                   Location/Qualifiers
REGION                    1..15
                          note = Synthetic peptide
SITE                      14
                          note = Nle
source                    1..15
                          mol_type = protein
                          organism = synthetic construct
SEQUENCE: 28
CIEEGQYCKA DPYXC                                                                    15

SEQ ID NO: 29             moltype = AA  length = 15
FEATURE                   Location/Qualifiers
REGION                    1..15
                          note = Synthetic peptide
SITE                      14
                          note = Nle
source                    1..15
                          mol_type = protein
                          organism = synthetic construct
SEQUENCE: 29
CIEEGQYCFA DKYXC                                                                    15

SEQ ID NO: 30             moltype = AA  length = 15
FEATURE                   Location/Qualifiers
REGION                    1..15
                          note = Synthetic peptide
source                    1..15
                          mol_type = protein
                          organism = synthetic construct
SEQUENCE: 30
CIEEGQYCFA DPYKC                                                                    15

SEQ ID NO: 31             moltype = AA  length = 17
FEATURE                   Location/Qualifiers
REGION                    1..17
                          note = Synthetic peptide
SITE                      15
                          note = Nle
source                    1..17
                          mol_type = protein
                          organism = synthetic construct
SEQUENCE: 31
ACIEEGQYCF ADPYXCA                                                                  17

SEQ ID NO: 32             moltype = AA  length = 17
FEATURE                   Location/Qualifiers
REGION                    1..17
                          note = Synthetic peptide
SITE                      15
                          note = Nle
SITE                      17
                          note = diaminopropionic acid
source                    1..17
                          mol_type = protein
                          organism = synthetic construct
SEQUENCE: 32
ACIEEGQYCF ADPYXCX                                                                  17
```

```
SEQ ID NO: 33           moltype = AA   length = 17
FEATURE                 Location/Qualifiers
REGION                  1..17
                        note = Synthetic peptide
SITE                    15
                        note = Nle
source                  1..17
                        mol_type = protein
                        organism = synthetic construct
SEQUENCE: 33
ACIKEGQYCF ADPYXCA                                                  17

SEQ ID NO: 34           moltype = AA   length = 17
FEATURE                 Location/Qualifiers
REGION                  1..17
                        note = Synthetic peptide
SITE                    15
                        note = Nle
source                  1..17
                        mol_type = protein
                        organism = synthetic construct
SEQUENCE: 34
ACIEKGQYCF ADPYXCA                                                  17

SEQ ID NO: 35           moltype = AA   length = 17
FEATURE                 Location/Qualifiers
REGION                  1..17
                        note = Synthetic peptide
SITE                    6
                        note = X is D-Lysine
SITE                    15
                        note = Nle
source                  1..17
                        mol_type = protein
                        organism = synthetic construct
SEQUENCE: 35
ACIEEXQYCF ADPYXCA                                                  17

SEQ ID NO: 36           moltype = AA   length = 17
FEATURE                 Location/Qualifiers
REGION                  1..17
                        note = Synthetic peptide
SITE                    15
                        note = Nle
source                  1..17
                        mol_type = protein
                        organism = synthetic construct
SEQUENCE: 36
ACIEEGKYCF ADPYXCA                                                  17

SEQ ID NO: 37           moltype = AA   length = 17
FEATURE                 Location/Qualifiers
REGION                  1..17
                        note = Synthetic peptide
SITE                    15
                        note = Nle
source                  1..17
                        mol_type = protein
                        organism = synthetic construct
SEQUENCE: 37
ACIEEGQYCK ADPYXCA                                                  17

SEQ ID NO: 38           moltype = AA   length = 17
FEATURE                 Location/Qualifiers
REGION                  1..17
                        note = Synthetic peptide
SITE                    15
                        note = Nle
source                  1..17
                        mol_type = protein
                        organism = synthetic construct
SEQUENCE: 38
ACIEEGQYCF ADKYXCA                                                  17

SEQ ID NO: 39           moltype = AA   length = 17
FEATURE                 Location/Qualifiers
REGION                  1..17
                        note = Synthetic peptide
```

```
source                   1..17
                         mol_type = protein
                         organism = synthetic construct
SEQUENCE: 39
ACIEEGQYCF ADPYKCA                                                17

SEQ ID NO: 40            moltype = AA  length = 18
FEATURE                  Location/Qualifiers
REGION                   1..18
                         note = Synthetic peptide
SITE                     1
                         note = X is propargyl-acid
SITE                     16
                         note = Nle
source                   1..18
                         mol_type = protein
                         organism = synthetic construct
SEQUENCE: 40
XACIEEGQYC FADPYXCA                                               18

SEQ ID NO: 41            moltype = AA  length = 17
FEATURE                  Location/Qualifiers
REGION                   1..17
                         note = Synthetic peptide
SITE                     15
                         note = Nle
SITE                     17
                         note = diaminopropionic acid
source                   1..17
                         mol_type = protein
                         organism = synthetic construct
SEQUENCE: 41
ACIEEGQYCF ADPYXCX                                                17

SEQ ID NO: 42            moltype = AA  length = 17
FEATURE                  Location/Qualifiers
REGION                   1..17
                         note = Synthetic peptide
SITE                     4
                         note = X is Lysine(propargyl-acid)
SITE                     15
                         note = Nle
source                   1..17
                         mol_type = protein
                         organism = synthetic construct
SEQUENCE: 42
ACIXEGQYCF ADPYXCA                                                17

SEQ ID NO: 43            moltype = AA  length = 17
FEATURE                  Location/Qualifiers
REGION                   1..17
                         note = Synthetic peptide
SITE                     5
                         note = X is Lysine(propargyl-acid)
SITE                     15
                         note = Nle
source                   1..17
                         mol_type = protein
                         organism = synthetic construct
SEQUENCE: 43
ACIEXGQYCF ADPYXCA                                                17

SEQ ID NO: 44            moltype = AA  length = 17
FEATURE                  Location/Qualifiers
REGION                   1..17
                         note = Synthetic peptide
SITE                     6
                         note = X is D-Lysine(propargyl-acid)
SITE                     15
                         note = Nle
source                   1..17
                         mol_type = protein
                         organism = synthetic construct
SEQUENCE: 44
ACIEEXQYCF ADPYXCA                                                17

SEQ ID NO: 45            moltype = AA  length = 17
FEATURE                  Location/Qualifiers
REGION                   1..17
```

```
                        note = Synthetic peptide
SITE                    7
                        note = X is Lysine(propargyl-acid)
SITE                    15
                        note = Nle
source                  1..17
                        mol_type = protein
                        organism = synthetic construct
SEQUENCE: 45
ACIEEGXYCF ADPYXCA                                                         17

SEQ ID NO: 46           moltype = AA  length = 17
FEATURE                 Location/Qualifiers
REGION                  1..17
                        note = Synthetic peptide
SITE                    10
                        note = X is Lysine(propargyl-acid)
SITE                    15
                        note = Nle
source                  1..17
                        mol_type = protein
                        organism = synthetic construct
SEQUENCE: 46
ACIEEGQYCX ADPYXCA                                                         17

SEQ ID NO: 47           moltype = AA  length = 17
FEATURE                 Location/Qualifiers
REGION                  1..17
                        note = Synthetic peptide
SITE                    13
                        note = X is Lysine(propargyl-acid)
SITE                    15
                        note = Nle
source                  1..17
                        mol_type = protein
                        organism = synthetic construct
SEQUENCE: 47
ACIEEGQYCF ADXYXCA                                                         17

SEQ ID NO: 48           moltype = AA  length = 17
FEATURE                 Location/Qualifiers
REGION                  1..17
                        note = Synthetic peptide
SITE                    15
                        note = X is Lysine(propargyl-acid)
source                  1..17
                        mol_type = protein
                        organism = synthetic construct
SEQUENCE: 48
ACIEEGQYCF ADPYXCA                                                         17

SEQ ID NO: 49           moltype = AA  length = 18
FEATURE                 Location/Qualifiers
REGION                  1..18
                        note = Synthetic peptide
SITE                    1
                        note = X is ((1R,8S,9s)-bicyclo[6.1.0]non-4-yn-9-yl)methyl
                         hydrogen carbonate
SITE                    16
                        note = Nle
source                  1..18
                        mol_type = protein
                        organism = synthetic construct
SEQUENCE: 49
XACIEEGQYC FADPYXCA                                                        18

SEQ ID NO: 50           moltype = AA  length = 17
FEATURE                 Location/Qualifiers
REGION                  1..17
                        note = Synthetic peptide
SITE                    4
                        note = X is
                         Lysine(((1R,8S,9s)-bicyclo[6.1.0]non-4-yn-9-yl)methyl
                         hydrogen carbonate)
SITE                    15
                        note = Nle
source                  1..17
                        mol_type = protein
                        organism = synthetic construct
```

```
SEQUENCE: 50
ACIXEGQYCF ADPYXCA                                                          17

SEQ ID NO: 51           moltype = AA  length = 17
FEATURE                 Location/Qualifiers
REGION                  1..17
                        note = Synthetic peptide
SITE                    5
                        note = X is
                         Lysine(((1R,8S,9s)-bicyclo[6.1.0]non-4-yn-9-yl)methyl
                         hydrogen carbonate)
SITE                    15
                        note = Nle
source                  1..17
                        mol_type = protein
                        organism = synthetic construct
SEQUENCE: 51
ACIEXGQYCF ADPYXCA                                                          17

SEQ ID NO: 52           moltype = AA  length = 17
FEATURE                 Location/Qualifiers
REGION                  1..17
                        note = Synthetic peptide
SITE                    6
                        note = X is
                         D-Lysine(((1R,8S,9s)-bicyclo[6.1.0]non-4-yn-9-yl)methyl
                         hydrogen carbonate)
SITE                    15
                        note = Nle
source                  1..17
                        mol_type = protein
                        organism = synthetic construct
SEQUENCE: 52
ACIEEXQYCF ADPYXCA                                                          17

SEQ ID NO: 53           moltype = AA  length = 17
FEATURE                 Location/Qualifiers
REGION                  1..17
                        note = Synthetic peptide
SITE                    7
                        note = X is
                         Lysine(((1R,8S,9s)-bicyclo[6.1.0]non-4-yn-9-yl)methyl
                         hydrogen carbonate)
SITE                    15
                        note = Nle
source                  1..17
                        mol_type = protein
                        organism = synthetic construct
SEQUENCE: 53
ACIEEGXYCF ADPYXCA                                                          17

SEQ ID NO: 54           moltype = AA  length = 17
FEATURE                 Location/Qualifiers
REGION                  1..17
                        note = Synthetic peptide
SITE                    10
                        note = X is
                         Lysine(((1R,8S,9s)-bicyclo[6.1.0]non-4-yn-9-yl)methyl
                         hydrogen carbonate)
SITE                    15
                        note = Nle
source                  1..17
                        mol_type = protein
                        organism = synthetic construct
SEQUENCE: 54
ACIEEGQYCX ADPYXCA                                                          17

SEQ ID NO: 55           moltype = AA  length = 17
FEATURE                 Location/Qualifiers
REGION                  1..17
                        note = Synthetic peptide
SITE                    15
                        note = X is
                         Lysine(((1R,8S,9s)-bicyclo[6.1.0]non-4-yn-9-yl)methyl
                         hydrogen carbonate)
source                  1..17
                        mol_type = protein
                        organism = synthetic construct
SEQUENCE: 55
```

```
ACIEEGQYCF ADPYXCA                                                    17

SEQ ID NO: 56           moltype = AA  length = 17
FEATURE                 Location/Qualifiers
REGION                  1..17
                        note = Synthetic peptide
source                  1..17
                        mol_type = protein
                        organism = synthetic construct SEQUENCE: 56
ACIEEGQYCF ADPYMCA                                                    17

SEQ ID NO: 57           moltype = AA  length = 6
FEATURE                 Location/Qualifiers
REGION                  1..6
                        note = Synthetic peptide
source                  1..6
                        mol_type = protein
                        organism = synthetic construct SEQUENCE: 57
KGKGKG                                                                 6

SEQ ID NO: 58           moltype = AA  length = 17
FEATURE                 Location/Qualifiers
REGION                  1..17
                        note = Synthetic peptide
SITE                    15
                        note = Nle
source                  1..17
                        mol_type = protein
                        organism = synthetic construct SEQUENCE: 58
ACIEEGQYCF ADPYXCA                                                    17

SEQ ID NO: 59           moltype = AA  length = 16
FEATURE                 Location/Qualifiers
REGION                  1..16
                        note = Synthetic Peptide
SITE                    2
                        note = X is tert-butyl-alanine
SITE                    14
                        note = Nle
source                  1..16
                        mol_type = protein
                        organism = synthetic construct SEQUENCE: 59
CXPKAPYCFA DPYXCA                                                     16

SEQ ID NO: 60           moltype = AA  length = 16
FEATURE                 Location/Qualifiers
REGION                  1..16
                        note = Synthetic peptide
SITE                    2
                        note = X is tert-butyl-alanine
SITE                    14
                        note = Nle
source                  1..16
                        mol_type = protein
                        organism = synthetic construct SEQUENCE: 60
CXPEKPYCFA DPYXCA                                                     16

SEQ ID NO: 61           moltype = AA  length = 17
FEATURE                 Location/Qualifiers
REGION                  1..17
                        note = Synthetic peptide
SITE                    15
                        note = Nle
source                  1..17
                        mol_type = protein
                        organism = synthetic construct SEQUENCE: 61
ACIEKGQYCF ADPYXCA                                                    17

SEQ ID NO: 62           moltype = AA  length = 17
FEATURE                 Location/Qualifiers
REGION                  1..17
                        note = Synthetic peptide
SITE                    15
```

```
                         note = Nle
source                   1..17
                         mol_type = protein
                         organism = synthetic construct
SEQUENCE: 62
ACIEKGQYCF ADPYXCA                                                      17

SEQ ID NO: 63            moltype = AA  length = 17
FEATURE                  Location/Qualifiers
REGION                   1..17
                         note = Synthetic peptide
SITE                     15
                         note = Nle
source                   1..17
                         mol_type = protein
                         organism = synthetic construct
SEQUENCE: 63
ACIEEKQYCF ADPYXCA                                                      17

SEQ ID NO: 64            moltype = AA  length = 18
FEATURE                  Location/Qualifiers
REGION                   1..18
                         note = Synthetic peptide
SITE                     1
                         note = X is propargyl-acid
SITE                     16
                         note = Nle
source                   1..18
                         mol_type = protein
                         organism = synthetic construct
SEQUENCE: 64
XACIEEGQYC FADPYXCA                                                     18

SEQ ID NO: 65            moltype = AA  length = 16
FEATURE                  Location/Qualifiers
REGION                   1..16
                         note = Synthetic peptide
SITE                     2
                         note = X is tert-butyl-alanine
SITE                     4
                         note = X is D-Lysine(propargyl-acid)
SITE                     14
                         note = Nle
source                   1..16
                         mol_type = protein
                         organism = synthetic construct
SEQUENCE: 65
CXPXAPYCFA DPYXCA                                                       16

SEQ ID NO: 66            moltype = AA  length = 16
FEATURE                  Location/Qualifiers
REGION                   1..16
                         note = Synthetic peptide
SITE                     2
                         note = X is tert-butyl-alanine
SITE                     5
                         note = X is D-Lysine(propargyl-acid)
SITE                     14
                         note = Nle
source                   1..16
                         mol_type = protein
                         organism = synthetic construct
SEQUENCE: 66
CXPEXPYCFA DPYXCA                                                       16

SEQ ID NO: 67            moltype = AA  length = 17
FEATURE                  Location/Qualifiers
REGION                   1..17
                         note = Synthetic peptide
SITE                     5
                         note = X is D-Lysine(propargyl-acid)
SITE                     15
                         note = Nle
source                   1..17
                         mol_type = protein
                         organism = synthetic construct
SEQUENCE: 67
ACIEXGQYCF ADPYXCA                                                      17
```

```
SEQ ID NO: 68          moltype = AA  length = 17
FEATURE                Location/Qualifiers
REGION                 1..17
                       note = Synthetic peptide
SITE                   5
                       note = X is Lysine(propargyl-acid)
SITE                   15
                       note = Nle
source                 1..17
                       mol_type = protein
                       organism = synthetic construct
SEQUENCE: 68
ACIEXGQYCF ADPYXCA                                              17

SEQ ID NO: 69          moltype = AA  length = 17
FEATURE                Location/Qualifiers
REGION                 1..17
                       note = Synthetic peptide
SITE                   6
                       note = X is Lysine(propargyl-acid)
SITE                   15
                       note = Nle
source                 1..17
                       mol_type = protein
                       organism = synthetic construct
SEQUENCE: 69
ACIEEXQYCF ADPYXCA                                              17
```